United States Patent
Alphey

(10) Patent No.: US 10,844,402 B2
(45) Date of Patent: *Nov. 24, 2020

(54) EXPRESSION SYSTEMS

(71) Applicant: Oxitec Limited, Abingdon, Oxfordshire (GB)

(72) Inventor: Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 5 days.

This patent is subject to a terminal disclaimer.

(21) Appl. No.: 16/035,530

(22) Filed: Jul. 13, 2018

(65) Prior Publication Data

US 2018/0312870 A1  Nov. 1, 2018

Related U.S. Application Data

(63) Continuation of application No. 14/839,683, filed on Aug. 28, 2015, now Pat. No. 10,059,961, which is a continuation of application No. 11/352,177, filed on Feb. 10, 2006, now Pat. No. 9,133,477, which is a continuation-in-part of application No. 10/566,448, filed as application No. PCT/GB2004/003263 on Jul. 28, 2004, now Pat. No. 9,121,036.

(30) Foreign Application Priority Data

Jul. 28, 2003 (GB) .................................. 0317656.7

(51) Int. Cl.
*C12N 15/85* (2006.01)
*A01K 67/033* (2006.01)

(52) U.S. Cl.
CPC .......... *C12N 15/85* (2013.01); *A01K 67/0333* (2013.01); *C12N 15/8509* (2013.01); *A01K 2217/05* (2013.01); *A01K 2217/20* (2013.01); *A01K 2227/70* (2013.01); *A01K 2227/706* (2013.01); *A01K 2267/02* (2013.01); *C12N 2830/007* (2013.01); *C12N 2830/008* (2013.01)

(58) Field of Classification Search
CPC .................................................. C12N 15/8509
See application file for complete search history.

(56) References Cited

U.S. PATENT DOCUMENTS

| | | | |
|---|---|---|---|
| 5,254,801 A | 10/1993 | Dotson et al. |
| 5,278,057 A | 1/1994 | Jorgensen |
| 5,670,353 A | 9/1997 | Ahlquist et al. |
| 5,674,747 A | 10/1997 | Hammock et al. |
| 5,773,697 A | 6/1998 | Tomes et al. |
| 5,851,796 A | 12/1998 | Schatz |
| 5,977,441 A | 11/1999 | Oliver et al. |
| 6,200,800 B1 | 3/2001 | Choulika et al. |
| 6,235,278 B1 | 5/2001 | Miller et al. |
| 6,338,040 B1 | 1/2002 | Buman et al. |
| 6,962,810 B2 | 11/2005 | Fraser et al. |
| 7,998,475 B2 | 8/2011 | Alphey |
| 8,124,404 B2 | 2/2012 | Alphey |
| 8,704,041 B2 | 4/2014 | Gordon-Kamm |
| 9,121,036 B2 | 9/2015 | Alphey |
| 9,125,388 B2 | 9/2015 | Alphey |
| 9,133,477 B2 | 9/2015 | Alphey |
| 9,487,801 B2 | 11/2016 | Alphey et al. |
| 2003/0015007 A1 | 8/2003 | Savakis et al. |
| 2003/0213005 A1 | 11/2003 | Alphey et al. |
| 2004/0082032 A1 | 4/2004 | Bovi et al. |
| 2005/0221430 A1 | 10/2005 | Prentice |
| 2006/0212949 A1 | 9/2006 | Alphey |
| 2006/0242717 A1 | 10/2006 | Alphey |
| 2006/0275276 A1 | 12/2006 | Alphey |
| 2007/0056051 A1 | 3/2007 | Alphey |
| 2008/0115233 A1 | 5/2008 | Alphey et al. |
| 2009/0170793 A1 | 7/2009 | Gaur |
| 2009/0183269 A1 | 7/2009 | Alphey |
| 2013/0298266 A1 | 11/2013 | Alphey et al. |

FOREIGN PATENT DOCUMENTS

| | | |
|---|---|---|
| EP | 0 636 310 | 2/1995 |
| EP | 0 955 364 | 11/1999 |
| GB | 2 355 459 | 4/2001 |
| GB | 2 404 382 | 2/2005 |
| GB | 2 443 186 | 4/2008 |
| GB | 2 500 113 | 9/2013 |
| JP | 2008-067678 | 3/2008 |
| WO | WO-90/08830 | 8/1990 |
| WO | WO-94/03619 | 2/1994 |
| WO | WO-96/04393 | 2/1996 |
| WO | WO-96/24605 | 8/1996 |
| WO | WO-97/30162 | 8/1997 |

(Continued)

OTHER PUBLICATIONS

Adelman et al., "Formation and loss of large, unstable tandem arrays of the piggyBac transposable element in the yellow fever mosquito, *Aedes aegypti*," Transgenic Res (2004) 13(5):411-425.

(Continued)

*Primary Examiner* — Thaian N. Ton
*Assistant Examiner* — David A. Montanari

(57) ABSTRACT

A gene expression system is provided. The system comprises at least one coding sequence to be expressed in an organism, and at least one promoter operably linked thereto. It further comprises at least one splice control sequence which, in cooperation with a spliceosome, mediates alternative splicing of RNA transcripts of the coding sequence. The mediation of alternative splicing is in a sex-specific, stage-specific, germline-specific and tissue-specific manner.

23 Claims, 48 Drawing Sheets

Specification includes a Sequence Listing.

(56) References Cited

FOREIGN PATENT DOCUMENTS

| WO | WO-98/08960 | 3/1998 |
|---|---|---|
| WO | WO-99/10488 | 3/1999 |
| WO | WO-00/73510 | 12/2000 |
| WO | WO-01/39599 | 6/2001 |
| WO | WO-01/59088 | 8/2001 |
| WO | WO-01/91802 | 12/2001 |
| WO | WO-020/46444 | 6/2002 |
| WO | WO-02/101061 | 12/2002 |
| WO | WO-04/044150 | 5/2004 |
| WO | WO-04/098278 | 11/2004 |
| WO | WO-04/108933 | 12/2004 |
| WO | WO-05/003364 | 1/2005 |
| WO | WO-05/012534 | 2/2005 |
| WO | WO-07/091099 | 8/2007 |
| WO | WO-08/134068 | 11/2008 |
| WO | WO-09/016627 | 2/2009 |
| WO | WO-09/115569 | 9/2009 |
| WO | WO-09/157771 | 12/2009 |
| WO | WO-13/131920 | 9/2013 |

OTHER PUBLICATIONS

Alignment of SEQ ID No. 22 of D1 (WO 2005/012534) with tTAV, Jul. 4, 2014.

Alphey et al. "Managing Insecticide Resistance by Mass Release of Engineered Insects" J. Econ. Entomol. (2007) 100(5):1642-1649.

Alphey et al. "Dominant Lethality and Insect Population Control," Mol Biochem Parasitol (2002)121(2):173-178.

Alphey et al., "Modeling resistance to genetic control of insects," Journal of Theoretical Biology (2011) 270:42-55.

Arribas et al., Biochimica et Biophysica Acta (1986) 868:119-127.

Atkinson et al. "Hermes and Other hAT Elements as Gene Vectors in Insects," Insect Transgenesis: Methods and Applications (2000) pp. 219-236.

Atkinson et al., "Genetic transformation systems in insects," Annu Rev Entomol (2001) 46:317-346.

Bello et al., "Spatial and temporal targeting of gene expression in *Drosophila* by means of a tetracycline-dependent transactivator system," Development (1998) 125(12):2193-2202.

Beullens et al., "Inactivation of nuclear inhibitory polypeptides of protein phosphatase-1 (NIPP-1) by protein kinase A," J Biol Chem (1993) 268(18):13172-13177.

Beullens et al., "Molecular determinants of nuclear protein phosphatase-1 regulation by NIPP-1," J Biol Chem (1999) 274(20):14053-14061.

Beullens et al., "The isolation of novel inhibitory polypeptides of protein phosphatase 1 from bovine thymus nuclei," J Biol Chem (1992) 267(23):16538-16544.

Bieschke et al. "Doxycycline-Induced Transgene Expression During *Drosophila* Development and Aging," Mol Gen Genet (1998) 258(6):571-579.

Blitvich et al., Insect Molecular Biology (2002) 11(5):431-442.

Boudrez et al., "Identification of MYPT1 and NIPP1 as subunits of protein phosphatase 1 in rat liver cytosol," FEBS Letters 455 (1999) pp. 175-178.

Burcin et al., "A regulatory system for target gene expression," Frontiers in Biosc. (1998) 3:c1-7.

Cabera et al. "Expression Pattern of Ga14 Enhancer Trap Insertions Into the bric a brac Locus Generated by P Element Replacement," Genesis (2002) 34:62-65.

Carriere et al., "Reversing Insect Adaptation to Transgenic Insecticidal Plants," Proc. R. Soc. Lond. B. (2001) 268:1475-1480.

Chen et al. "The Use of Modified Tetracycline Regulatory Expression System with Reduced Basal Level to Develop and In Vivo Biopesticide Expression System," Food Sci Agricult. Chem (2000) 2(4):220-225.

Chen et al., The Journal of Biological Chemistry (1996) 271(42):25735-25737.

Davis et al. "Engineered Underdominance Allows Efficient and Economical Introgression of Traits into Pest Populations," J. Theor. Biol. (2001) 212(1):83-98.

Deng et al., "A targeted gene silencing technique shows that *Drosophila* myosin VI is required for egg chamber and imaginal disc morphogenesis," J Cell Science (1999) 112:3677-3690.

Devault et al., "Biotechnology and new integrated pest management approaches," Nature Biotechnology (1996) 14:46-49.

Egloff et al., "Structural basis for the recognition of regulatory subunits by the catalytic subunit of protein phosphatase 1," EMBO J (1997) 16(8):1876-1887.

Elick et al. "Analysis of the Cis-Acting DNA Elements Required for piggyback Transposable Element Excision," Mol. Gen. Genet. (1997) 255:605-610.

Ernst, U. "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD (1991) (Abstract Only).

Fryxell et al., "Autocidal biological control: a general strategy for insect control based on genetic transformation with a highly conserved gene," J Econ Entomol (1995) 88(5):1221-1232.

Fu et al. "Female-specific insect lethality engineered using alternative splicing", Nature Biotechnology (2007) 25(3):353-357.

Fu et al., "Female-specific flightless phenotype for mosquito control," PNAS (2010) 107(10):4550-4554.

Funaguma et al. The Bmdsx transgene including trimmed introns is sex-specifically spliced in tissues of the silkworm, *Bombyx moil*, Journal of Insect Science (online) (2005) 5(17):1-6.

Further Search Report for GB 9928181.8, dated Apr. 30, 2001.

Fussenegger et al., "Autoregulated multiscistronic expression vectors provide one-step cloning of regulated product gene expression in mammalian cells," Biotechnol Prog (1997) 13:733-740.

Fussenegger et al., "Regulated Multicistronic Expression Technology for Mammalian Metabolic Engineering," Cytotechnology (1998) 28:111-125.

Fux et al., "Novel Macrolide-Adjustable Bidirectional Expression Modules for Coordinated Expression of Two Different Transgenes in Mice," J Gene Medicine (2003) 5:1067-1079.

"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.

Gloor et al. "Targeted Gene Replacement in *Drosophila* Via P Element-Induced Gap Repair," Science (1991) 253:1110-1117.

Golovnin et al., "The su(Hw) insulator can disrupt enhancer-promoter interactions when located more than 20 kilobases away from the *Drosophila* achaete-scute complex," Mol Cell Biol (1999) 19(5):3443-3456.

Gong et al. "A dominant lethal genetic system for autocidal control of the Mediterranean fruitfly", Nature Biotechnology (2005) 23(4):453-456.

Gonzy-Treboul et al. "Enhancer-Trap Targeting at the Broad-Complex Locus of *Drosophila melanogaster*," Genes Dev (1995) 9:1137-1148.

Gossen et al., "Tetracyclines in the control of gene expression in eukaryotes," Tetracyclines I Biology, Chemistry and Medicine (2001) pp. 139-157.

Guo et al., "Species-specific signals for the splicing of a short *Drosophila* intron in vitro," Mol Cell Biol (1993) 13(2):1104-1118.

Handler et al. "A Current Prospective on Insect Gene Transformation," Insect Biochem. Mol. Biol. (2001) 31(2):111-128.

Handler, A. (2002) "Use of piggyback Transposon for Germ-Line Transformation of insects," Insect Biochem Mol Biol 32:1211-1220.

Harris et al., "Field performance of engineered male mosquitoes," Nature Biotechnology (2011) 29(11):1034-1039.

Heinrich et al. "A Repressible Female-Specific Lethal Genetic System for Making Transgenic Insect Strains Suitable for a Sterile-Release Program," Proc. Nat. Acad. Sci. USA (2000) 97:8229-8232.

Heslip et al. "Targeted Transposition at the vestigial Locus of *Drosophila melanogaster*," Genetics (1994) 138:1127-1135.

Hofmann et al. "Rapid Retroviral Delivery of Tetracycline-Inducible Genes in a Single Autoregulatory Cassette," Proc. Nat. Acad. Sci. USA (1996) 93:5185-5190.

(56) References Cited

OTHER PUBLICATIONS

Hondred et al., Plant Physiology (1999) 119:713-723.
Horn et al. "Highly sensitive, fluorescent transformation marker for Drosophil49a transgenesis" Dev Genes Evol (2000) 210:623-629.
Horn et al. "PiggyBac-Based Insertional Metagenesis and Enhancer Detection as a Tool for Functional Insect Genomics," Genetics (2003) 163(2):647-661.
Horn et al. "A Transgene-Based Embryo-Specific Lethality System for Insect Pest Management," Nat. Biotechnol (2003) 21(1):64-70.
Horn et al., "Highly sensitive, fluorescent transformation marker for *Drosophila* transgenesis," Dev Genes Evol (2000) 210:623-629.
Horn et al "Fluorescent Transformation Markers for Insect Transgenesis," Insect Biochem. Mol. Biol. (2002) 32:1221-1235.
Imai, C. "Control of Insecticide Resistance in a Field Population of Houseflies, *Musca domestica*, by Releasing Susceptible Flies," Res. Popul. Ecol. (1987) 29:129-146.
Inoue et al., "Binding of the *Drosophila* Sex-lethal gene product to the alternative splice site of transformer primary transcript," Nature (1990) 344:461-463.
International Preliminary Examination Report for PCT/GB00/04541, dated Apr. 4, 2002, 2 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2004/003263, dated Jan. 30, 2006, 6 pages.
International Preliminary Report on Patentability for PCT/GB2007/000488, date of search May 5, 2008, 11 pages.
International Search Report for PCT/GB00/04541, dated Dec. 5, 2001, 4 pages.
International Search Report for PCT/GB2004/002021, dated Oct. 6, 2004, 3 pages.
International Search Report for PCT/GB2004/002869, dated Jan. 11, 2005, 5 pages.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Johnson-Schlitz et al. "P-Element-Induced Interallelic Gene Conversion of Insertions and Deletions in *Drosophila melanogaster*," Mol Cell Biol. (1993)13:70067018.
Krafsur, "Bionomics of the face fly, *Musca autumnalis*," Annu Rev Entomol (1997) 42:503-523 (Abstract).
Lankenau et al. "Comparison of Targeted-Gene Replacement Frequencies in *Drosophila melanogaster* at the Forked and White Loci," Mol. Cell Biol. (1996)16:3535-3544.
Louis et al. "A Theoretical Model for the Regulation of Sex-Lethal, a Gene That Controls Sex Determination and Dosage Compensation in *Drosophila melanogaster*," Genetics (2003) 165:1355-1384.
Loukeris et al. "Introduction of the transposable element Minos into the germ line of *Drosophila melanogaster*," Proc Natl Acad Sci (1995) 92:9485-9489.
Munoz et al. "The AeAct-4 gene is expressed in the developing flight muscles of female Aedes aegypti", Insect Molecular Biology (2004)13(5):563-568.
Namciu et al., "Human matrix attachment regions insulate transgene expression from chromosomal position effects in *Drosophila melanogaster*," Mol Cell Biol (1998) 18(4):2382-2391.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
O'Brochta et al., "Gene vector and transposable element behavior in mosquitos," J Exp Biol (2003) 206(Pt 21):3823-3834.
Oxitec Nov. 2011 Newsletter, http://www.oxitec.com/our-news/newsletters/november-2011-newsletter/, downloaded Dec. 13, 2011, 6 pages.

Pane et al. "The transformer gene in Ceratitis capitata provides a genetic basis for selecting and remembering the sexual fate" Development (2002) 129:3715-3725.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
Phuc et al., "Late-acting dominant lethal genetic systems and mosquito control," BMC Biology (2007) 5:11, 11 pages.
PiggyBac website, http://piggybac.bio.nd.edu/, Mar. 21, 2006, 5 pp.
Raton CRC Press, pp. 219-235.
Robinson et al. "Mutations and Their Use in Insect Control," Mutation Research (2002) 511(2):113-132.
Ronaldson et al., "Two independent cis-acting elements regulate the sex- and tissue-specific expression of yp3 in *Drosophila melanogaster*," Genet Res. (1995) 66(1):9-17.
Rong et al. "Gene Targeting by Homologous Recombination in *Drosophila*," Science (2000) 288:2013-2018.
Rong et al. "A Targeted Gene Knockout in *Drosophila*," Genetics (2001)157:1307-1312.
Russ et al. "Self-Deleting Retrovirus Vectors for Gene Therapy," J. Virol. (1996) 70:4927-4932.
Saccone et al., Genetica (2002) 116:15-23.
Saccone et al. "Sex Determination in Medfly: A Molecular Approach," In; Area-Wide Control of Fruit Flies and Other Pest Insects, Tan, K.H. ed., Penerbit USM, Penag, (2000) pp. 491-496.
Scali et al. "Identification of sex-specific transcripts of the Anopheles gambiae doublesex gene", Journal of Experimental Biology (2005) 208(19):3701-3709.
Schwechheimer et al., "Transactivation of a target gene through feedforward loop activation in plants," Funct Integr Genomics (2000) 1:35-43.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report corresponding to International Application No. PCT/GB2007/000488, dated Jun. 6, 2007, 3 pages.
Search Report Corresponding to International Application No. PCT/GB2004/003263, dated Nov. 5, 2004, 3 pages.
Second Office Action for AU 17165/01, dated Mar. 21, 2006, 2 pages.
Second Office Action for CN 00818682.0, dated Jul. 28, 2006, 4 pages.
Sepp et al. "Conversion of IacZ Enhanced Trap Lines to GAL4 Lines Using Targeted Transposition in *Drosophila melanogaster*," Genetics (1999)151:1093-1101.
Shelton et al. "Field Tests on Managing Resistance to Bt-Engineered Plants", Nature Biotechnology (2000) 18(3):339-342.
Shockett et al. "A Modified Tetracycline-Regulated System Provides Autoregulatory, Inducible Gene Expression in Cultured Cells and Transgenic Mice," Proc Nat Acad Sci USA (1995) 92:6522-6526.
Simmons et al., "Field Performance of a Genetically Engineered Strain of Pink Bollworm," PLoS One (2011) 6(9):1-11.
Sondergaard et al., "Nutritional response in a *Drosophila* yolk protein gene promoter," Mol Gen Genet (1995) 248(1):25-32.
Spradling et al., "Transposition of cloned P elements into *Drosophila* germ line chromosomes," Science (1982) 218(4570):341-347.
Stadtfeld et al., "Without a trace? PiggyBac-ing toward pluripotency," Nat Methods (2009) 6(5):329-330.
Stebbins et al. "Adaptable Doxycycline-Regulated Gene Expression Systems for *Drosophila*," Gene (2001) 270:103-111.
Stebbins et al. "Tetracycline-Inducible Systems for *Drosophila*," Proc Nat Acad Sci USA (2001) 98:10775-10780.
Steiner et al. "Homologous Recombination as the Main Mechanism for DNA Integration and Cause of Rearrangements in the Filamentous Ascomycete Ashbya gossypii," Genetics (1995)140:973-987.
Thomas et al. "Insect Population Control Using Dominant, Repressible, Lethal Genetic System," Science (2000) 287:2474-2476.

(56) References Cited

OTHER PUBLICATIONS

Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Wobus et al. "A New Transposable Element in Chironomus thummi," Mol General Genet (1990) 222:311-316.
Woltjen et al., "PiggyBac transposition reprograms fibroblasts to induced pluripotent stem cells," Nature (2009) 458(7239):766-770.
Wool et al., "Genetically-Induced Susceptibility to Malathion in Tribolium Castaneum Despite Selection for Resistance," Ent. Exp. & Appl (1980) 28:183190.
Written Opinion corresponding to International Application No. PCT/GB2007/000488, parent of the present application.
Written Opinion for PCT/GB2004/002021, received Oct. 4, 2004, 5 pages.
Written Opinion for PCT/GB2004/002869, received Jan. 12, 2005, 8 pages.
Written Opinion for PCT/GB2004/003263, received Nov. 5, 2004, 5 pages.
Wu et al. "Expression of Highly Controllable Genes in Insect Cells Using a Modified Tetracycline-Regulated Gene Expression System," J. Biotechnol. (2000) 80(1):7583.
Allen et al., "Flight muscle-specific expression of act88F: GFP in transgenic Culex quinquefasciatus Say (Diptera: Culicidae)," Parasitology Int (2004) 53(4):307-314.
Allen et al., "PiggyBac transformation of the New World screwworm, *Cochliomyia hominivorax*, produces multiple distinct mutant strains," Med. Vet. Entomol (2004) 18:1-9.
Allen et al., "Stable, germ-line transformation of Culex quinquefasciatus (Diptera: Culicidae)," J Med Entomol (2001) 38(5):701-710.
Alphey et al., "Malaria control with genetically manipulated insect vectors," Science (2002) 298:119-21.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique," BMC Biology (2012) 10:51, 8 pages.
Arama et al., "Caspase activity and a specific cytochrome C are required for sperm differentiation in *Drosophila*," Dev Cell (2003) 4(5):687-97.
Barreau et al., "Post-meiotic transcription in *Drosophila* testes," Development (2008) 135(11):1897-1902.
Bauer Dumont et al., "Recurrent positive selection at bgcn, a key determinant of germ line differentiation, does not appear to be driven by simple coevolution with its partner protein bam," Mol Biol Evol (2007) 24(1):182-191.
Beall et al., "Discovery of tMAC: a *Drosophila* testis-specific meiotic arrest complex paralogous to Myb-Muv B," Genes Dev (2007) 21(8):904-919.

Berghammer et al., "A universal marker for transgenic insects," Nature (1999) 402(6760):370-371.
Beumer et al., "Efficient gene targeting in *Drosophila* with zinc-finger nucleases," Genetics (2006)172(4):2391-2403.
Bibikova et al., "Targeted chromosomal cleavage and mutagenesis in *Drosophila* using zinc-finger nucleases," Genetics (2002)161(3):1169-1175.
Black et al., "Why RIDL is not SIT," Trends Parasitol (2011) 27(8):362-370.
Brand et al., "Ectopic expression in *Drosophila*," Methods Cell Biol (1994)44:635-654.
Brand et al., "Targeted gene expression as a means of altering cell fates and generating dominant phenotypes," Development (1993) 118(2):401-415.
Burn et al., "Alternative 5C actin transcripts are localized in different patterns during *Drosophila* embryogenesis," Dev Biol (1989) 131(2):345-355.
Burt et al., "Site-specific selfish genes as tools for the control and genetic engineering of natural populations," Proc Biol Sci (2003) 270:921-928.
Caceres et al., "Mass rearing of temperature sensitive genetic sexing strains in the Mediterranean fruit fly (*Ceratitis capitata*)," Genetica (2002) 115(1):107-116.
Cagan et al., "Spermatogenesis: Borrowing the Apoptotic Machinery," Curr Biol (2003)13:R600-R602.
Catteruccia et al., "An Anopheles transgenic sexing strain for vector control," Nat Biotechnol, (2005) 23(11):1414-1417.
Catteruccia et al., "Impact of genetic manipulation on the fitness of Anopheles stephensi mosquitoes," Science (2003) 299(5610):1225-1227.
Catteruccia et al., "Stable germline transformation of the malaria mosquito *Anopheles stephensi*," Nature (2000) 405(6789):959-962.
Catteruccia et al., "Transgenic technologies to induce sterility," Malaria Journal (2009)8 (Supp2)S7.
Cenik et al., "Genome analysis reveals interplay between 5'UTR introns and nuclear mRNA export for secretory and mitochondrial genes," PLoS Genet (2011) 794:e1001366.
Cha et al., "Expression of green fluorescent protein in insect larvae and its application for heterologous protein production," Biotechnol Bioeng (1997) 56(3):239-247.
Chalfie et al., "Green fluorescent protein as a marker for gene expression," Science (1994) 263(5148):802-805.
Cheng et al., "Cellular transformation by Simian Virus 40 and Murine Polyoma Virus T antigens," Semin Cancer Biol (2009) 19(4):218-228.
Chintapalli et al., "Using FlyAtlas to identify better *Drosophila melanogaster* models of human disease," Nature Genetics (2007) 39(6)715-720.
Cho, "Enhancers," WIREs Dev Biol (2012) 1:469-478.
Definition of "pest" from the Concise Oxford American Dictionary (2006) p. 661.
Deredec et al., "The population genetics of using homing endonuclease genes in vector and pest management," Genetics (2008) 179(4):2013-2026.
Dhillon et al., "The melon fruit fly, *Bactrocera cucurbitae*: A review of its biology and management," J Insect Sci (2005) 5:40.
Flaminia et al., "Transgenic technologies to induce sterility," Malar J. (2009) 8 Suppl 2:S7.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Franz, "Recombination between homologous autosomes in medfly (*Ceratitis capitata*) males: type-1 recombination and the implications for the stability of genetic sexing strains," Genetica (2002) 116(1):73-84.
Fraser, "Insect transgenesis: current applications and future prospects," Annu Rev Entomol (2012) 57:267-289.
Fuller, "Spermatogenesis," in: The Development of *Drosophila melanogaster*, Bate et al., Cold Spring Harbor Laboratory Press (1993) pp. 71-147.

(56) References Cited

OTHER PUBLICATIONS

Fussenegger et al., "Streptogramin-based gene regulation systems for mammalian cells," Nat Biotechnol (2000) 18(11):1203-1208.
Fussenegger et al., "The impact of mammalian gene regulation concepts on functional genomic research, metabolic engineering, and advanced gene therapies," Biotechnol Prog (2001) 17(1):1-51.
Ghosh et al., "Transcription factor binding and induced transcription alter chromosomal c-myc replicator activity," Mol Cell Biol (2004) 24(23):10193-10207.
Gonczy et al., "Bag-of-marbles and benign gonial cell neoplasm act in the germline to restrict proliferation during Drosophila spermatogenesis," Development (1997) 124(21):4361-4371.
Gong et al., "Ends-out, or replacement, gene targeting in Drosophila," Proc Natl Acad Sci (USA) (2003) 100(5):2556-2561.
Gossen et al., "Studying gene function in eukaryotes by conditional gene inactivation," Annu Rev Genet (2002) 36:153-173.
Gossen et al., "Tight control of gene expression in mammalian cells by tetracycline-responsive promoters," Proc Natl Acad Sci (USA) (1992) 89(12):5547-5551.
Graham et al., "Larval diets containing dyes for tagging pink bollworm moth internally," J Econ Entomol (1971) 64:376-379.
Great Britain Application No. 1303932.6, filed Mar. 5, 2013, 42 pages.
Hagler et al., "Methods for marking insects: current techniques and future prospects," Annu. Rev. Entomol. (2001) 46:511-543.
Hagler et al., "An Alternative to conventional insect marking procedures; detection of a protein mark on pink bollworm by ELISA," Entomol Exp Appl (2002) 103(1):1-9.
Han et al., PNAS (2011) 108:9673-9678.
Handler et al., "Germline transformation of Drosophila melanogaster with the piggyBac transposon vector," Insect Mol Biol (1999) 8(4):449-457.
Handler et al., "Polyubiquitin-regulated DsRed marker for transgenic insects," BioTechniques (2001) 31:820-828.
Handler et al., "Prospects for using genetic transformation for improved SIT and new biocontrol methods," Genetics (2002) 116:137-149.
Handler et al., "The lepidopteran transposon vector, piggyBac, mediates germ-line transformation in the Mediterranean fruit fly," PNAS (1998) 95:7520-7525.
He et al., "The actin gene family in the oriental fruit fly Bactrocera dorsalis. Muscle specific actins," Insect Biochem Mol Biol (1994) 24(9):891-906.
Hiller et al., "Testis-specific TAF homologs collaborate to control a tissue-specific transcription program," Development (2004) 131:5297-5308.
Hockemeyer et al., "Genetic engineering of human pluripotent cells using TALE nucleases," Nat Biotechnol (2011) 29(8):731-734.
International Preliminary Report on Patentability for PCT/EP2014/054290, dated Sep. 8, 2015, 7 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion for PCT/GB2015/051633, dated Oct. 8, 2015, 11 pages.
International Search Report for PCT/GB2000/04541, dated Nov. 19, 2001.
Irvin et al., "Assessing fitness costs for transgenic Aedes aegypti expressing the GFP marker and transposase genes," Proc Natl Acad Sci U.S.A. (2004) 101(3):891-896.
Jattani et al., "Deficiency screen identifies a novel role for beta 2 tubulin in salivary gland and myoblast migration in the Drosophila embryo," Dev Dyn (2009) 238(4):853-863.
Jiang et al., "Tombola, a tesmin/TSO1-family protein, regulates transcriptional activation in the Drosophila male germline and physically interacts with always early," Development (2007) 134(8):1549-1559.
Jiang et al., "Transcriptional activation in Drosophila spermatogenesis involves the mutually dependent function of aly and a novel meiotic arrest gene cookie monster," Development (2003) 130(3):563-573.
Jin et al., "Engineered female-specific lethality for control of pest lepidoptera," ACS Synthetic Biology, ACS (2013) 1(3):160-66.
Kawase et al., "Gbb/Bmp signaling is essential for maintaining germline stem cells and for repressing bam transcription in the Drosophila testis," Development (2004) 131(6):1365-1375.
Kelly et al., "Drosophila MEF2 is a direct regulator of Actin57B transcription in cardiac, skeletal, and visceral muscle lineages," Mech Dev (2002) 110(1-2):39-50.
Kim et al., "Hybrid restriction enzymes: zinc finger fusions to Fok I cleavage domain," Proc Natl Acad Sci (USA) (1996) 93:1156-1160.
Klassen, "History of the Sterile Insect Technique," in: Sterile Insect Technique, Principles and Practice in Area-Wide Integrated Pest Management, Curits et al., (eds) The Netherlands, Springer (2005) pp. 3-36.
Knipling et al., "Possibilities of Insect Control or Eradication Through the Use of Sexually Sterile Males," J Econ Entomol (1955) 48:459-462.
Koukidou et al., "Germ line transformation of the olive fly Bactrocera oleae using a versatile transgenesis marker," Insect Mol Biol (2006) 15(1):95-103.
Loew et al., "Improved tet-responsive promoters with minimized background expression," BMC Biotechnology (2010) 10:81.
Loukeris et al., "Gene transfer into the medfly, Ceratitis capitata, with a Drosophila hydei transposable element," Science (1999) 270(5244):2002-2005.
Lycett et al., "Conditional expression in the malaria mosquito Anopheles stephensi with Tet-On and Tet-Off systems," Genetics (2004) 167(4):1781-1790.
Mahfouz et al., "De novo-engineered transcription activator-like effector (TALE) hybrid nuclease with novel DNA binding specificity creates double-strand breaks," Proc Natl Acad Sci (USA) (2011) 101(6):2623-2628.
Malacrida et al., "A transgenic sperm marking system in the medfly, as a tool for pest control strategies and sperm use analysis," Entomological Research (2007) 37:A56.
Marrelli et al., "Mosquito transgenesis: what is the fitness cost?" Trends Parasitol (2006) 22(5):197-202.
Mattox et al., "Alternative splicing of the sex determination gene transformer-2 is sex-specific in tile germ line but not in the soma," Genes & Development (1990) 4(5):789-805.
Mattox et al., "Autoregulation of the splicing of transcripts from the transformer-2 gene of Drosophila," Genes & Development (1991) 5:786-796.
Matz et al., "Fluorescent proteins from nonbioluminescent Anthozoa species," Nat Biotechnol (1999) 17(10):969-973.
Maynard-Smith et al., "A directed approach for engineering conditional protein stability using biologically silent small molecules," J Biol Chem (2007) 282(34):24866-24872.
Miller et al., "A TALE nuclease architecture for efficient genome editing," Nat Biotechnol (2011) 29(2):143-148.
Miller., "An improved zinc-finger nuclease architecture for highly specific genome editing," Nat Biotechnol (2007) 25(7):778-785.
Mishra, "Understanding Forest Biology," Discovery publishing house (2009) 3 pages.
Morrison et al., "Genetic Improvements to the sterile insect technique for agricultural pests," Asia Pacific J Mol Biol and Biotechnol (2010) 18(2):275-295.
Mounier et al., "Insect muscle actins differ distinctly from invertebrate and vertebrate cytoplasmic actins," J Mol Evol (1992) 34(5):406-415.
Nielsen et al., "Axoneme-specific beta-tubulin specialization: a conserved C-terminal motif specifies the central pair," Curr Biol (2001) 11(7):529-533.
Nongthomba et al., "Expression and function of the Drosophila ACT88F actin isoform is not restricted to the indirect flight muscles," Journal of Muscle Research and Cell Motility (2001) 22:111-119.

(56) References Cited

OTHER PUBLICATIONS

Ohshima et al., "Reassessment of 79B actin gene expression in the abdomen of adult *Drosophila melanogaster*," Insect Molecular Biology (1997) 6(3):227-231.
Osanai-Futahasi et al., "A visible dominant marker for insect transgenesis," Nature Communications (2012) 3:1295.
Osterwalder et al., "A conditional tissue-specific transgene expression system using inducible GAL4," Proc Natl Acad Sci (USA) (2001) 98(22):12596-12601.
Papathanos et al., "Sex separation strategies: past experience and new approaches," Malar J. (2009) 8 Supp 2:S5.
Parker, "Mass-rearing for sterile insect release," The Netherlands, Springer (2005) pp. 209-232.
Peloquin et al., "Germ-line transformation of pink bollworm (Lepidoptera: gelechiidae) mediated by the piggyBac transposable element," Insect Mol Biol (2000) 9(3):323-333.
Perera et al., "Germ-line transformation of the South American malaria vector, Anopheles albimanus, with a piggyBac/EGFP transposon vector is routine and highly efficient," Insect Mol Biol (2002) 11(4):291-297.
Perezgasga et al., "Regulation of transcription of meiotic cell cycle and terminal differentiation genes by the testis-specific Zn-finger protein matotopetli," Development (2004) 131(8):1691-1702.
Perrin et al., "The actin gene family: function follows isoform," Cytoskeleton (2010) 67(10):630-634.
Pinkerton et al., "Green fluorescent protein as a genetic marker in transgenic Aedes aegypti," Insect Mol Biol (2000) 9(1):1-10.
Prasher et al., "Primary structure of the Aequorea victoria green-fluorescent protein," Gene (1992) 111(2):229-233.
Qin et al., "Systematic comparison of constitutive promoters and the Doxycycline-inducible promoter," PLOS One (2010) 5(5):e10611.
Raja et al., "Replacement by *Drosophila melanogaster* Protamines and Mst77F of Histones during Chromatin Condensation in Late Spermatids and Role of Sesame in the Removal of These Proteins from the Male Pronucleus," (2005) Mol Cell Biol 25(14):6165-6177.
Remy et al., "Zinc-finger nucleases: a powerful tool for genetic engineering of animals," Transgenic Res (2010) 19:363-371.
Rendon et al., "Medfly (Diptera: Tephritidae) genetic sexing: large-scale field comparison of males-only and bisexual sterile fly releases in Guatemala," J Econ Entomol (2004) 97(5):1547-1553.
Robinson et al., "Ceratitis capitata—a suitable case for genetic sexing," Genetica (1982) 58(3):229-237.
Robinson et al., "Prospects for the future development and application of the sterile insect technique," The Netherlands, Springer (2005) pp. 727-760.
Robinson, "Genetic Basis of the Sterile Insect Technique," in: Sterile Insect Technique, Principles and Practice in Area-Wide Integrated Pest Management, Dyck et al., (eds.), The Netherland, Springer (2005) pp. 95-114.
Rong et al., "Targeted mutagenesis by homologous recombination in *D. melanogaster*," Genes Dev (2002) 16:1568-1581.
Roper et al., "Contribution of sequence variation in *Drosophila* actins to their incorporation into actin-based structures in vivo," Journal of Cell Science (2005) 118:3937-3948.
Rossler, "The genetics of the Mediterranean fruit fly: a "white pupae" mutant," Annals of the Entomological Society of America (1979) 72:583-585.
Rubin et al., "Genetic transformation of *Drosophila* with transposable element vectors," Science (1982) 218(4570):348-353.
Santel et al., "The *Drosophila* don Juan (dj) gene encodes a novel sperm specific protein component characterized by an unusual domain of a repetitive amino acid motif," Mech Dev (1997) 64(1-2):19-30.
Schetelig et al., "Strategy for enhanced transgenic strain development for embryonic conditional lethality in Anastrepha suspensa," Pro Natl Acad Sci (USA) (2012) 24: 9348-9353.
Shah et al., "Cardiac remodeling in *Drosophila* arises from changes in actin gene expression and from a contribution of lymph gland-like cells to the heart musculature," Mech Dev (2011) 128(3-4):222-233.
Smith et al., "Testis-specific expression of the beta2 tubulin promoter of Aedes aegypti and its application as a genetic sex-separation marker," Insect Mol Biol (2007) 16(1):16-71.
Spradling et al., "P element-mediated transformation," *Drosophila* a practical approach (1986) Chapter 8:175-197.
Tamura et al., "Germline transformation of the silkworm *Bombyx mori* L. using a piggyBac transposon-derived vector," Nat Biotechnol (2000) 18(1):81-84.
Theodoraki et al., "cDNA cloning, heat shock regulation and developmental expression of the hsp83 gene in the Mediterranean fruit fly *Ceratitis capitata*," Insect Mol Biol (2006) 15(6):839-852.
Urnov et al., "Highly efficient endogenous human gene correction using designed zinc-finger nucleases," Nature (2005) 435:646-651.
Viktorinova et al., "Comparative analysis of binary expression systems for directed gene expression in transgenic insects," Insect Biochem Mol Biol (2007) 37:246-254.
Vivinus et al., Eur. J. Biochem. (2001) 268:1908-1917.
Webster et al., Cell (1988) 52:169-178.
White-Cooper et al., "Transcription of meiotic cell cycle and terminal differentiation genes depends on a conserved chromatin associated protein, whose nuclear localisation is regulated," Development (2000) 127:5463-5473.
Wilson et al., "Position effects on eukaryotic gene expression," Annu Rev Cell Biol (1990) 6:679-714.
Wilson et al., "Sperm plasma membrane breakdown during *Drosophila* fertilization requires sneaky, an acrosomal membrane protein," Development (2006) 133(24):4871-4879.
Windbichler et al., "A synthetic homing endonuclease-based gene drive system in the human malaria mosquito," Nature (2011) 473(7346):212-215.
Windbichler et al., "Homing endonuclease mediated gene targeting in Anopheles gambiae cells and embryos," Nucleic Acids Res (2007) 35:5922-5933.
Windbichler et al., "Targeting the X chromosome during spermatogenesis induces Y chromosome transmission ratio distortion and early dominant embryo lethality in Anopheles gambiae," PLoS Genet (2008) 4(12):e1000291.
Zhao et al., "Male germ cell specification and differentiation," Dev Cell (2002) 2(5):537-547.
Zimowska et al., "The beta2-tubulin gene from three tephritid fruit fly species and use of its promoter for sperm marking," Insect Biochem Mol Biol (2009) 39(8):508-515.
Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt I Main, BRD.
Horn et al., "A transgene-based, embryo-specific lethality system for insect pest management," Nat Biotechnol (2003) 1:64-70.
Curtis et al., "Assessment of the impact of potential tetracycline exposure on the phenotype of Aedes aegypti 0X513A: Implications for field use," PLOS Negelcted Tropical Diseases (2015) 9(8):e0003999.
"GSN: AAD40186" Oct. 22, 2002 [Retrieved from the internet: http://ibis.internal.epo.org/exam/dbfetch.jsp?id=GSN:AAD40186] retrieved on Nov. 28, 2017.
"GSN: BB010346" Nov. 6, 2014 [Retrieved from the internet: http://ibis.internal.epo.org/exam/dbfetch.jsp?id=GSN:BB010346] retrieved on Nov. 28, 2017.
Morrison et al., "Engineered repressible lethality for controlling the pink bollworm, a lepidopteran pest of cotton," PLOS One (2012) 7(12):e50922.
Nene et al., "Genome sequence of Aedes aegypti, a major arbovirus vector," Science (2007) 316(5832):1718-1723.
Salvemini et al., "Genomic organization and splicing evolution of the doublesex gene, a *Drosophila* regulator of sexual differentiation, in the gengue and yellow fever mosquito *Aedes aegypti*," BMC Evolutionary Biology (2011) 11(1):41.
Timoshevskiy et al., "An intergrated linkage, chromosome, and Genome map for the Yellow Fever Mosquito *Aedes aegypti*," PLOS Negected Tropical Diseases (2013) 7(2):e2052.

(56) References Cited

OTHER PUBLICATIONS

Timoshevskiy et al., "Genomic composition and evolution of Aedes aegypti chromosomes revealed by the analysis of physically mapped supercontigs," BMC Biology (2014) 12(1):27.
International Search Report and Written Opinion for PCT/IB2017/001128, dated Dec. 13, 2017, 17 pages.
Arya et al., "Basic principles of real-time quantitative PCR," Expert Rev Mol Diagn (2005) 5(2):209-219.
May et al., "Tropical Arthropod Species, More or Less?," Science (2010) 329:41-42.
Oslen et al., "Fibroblast Growth Factor (FGF) Homologous Factors Share Structural but Not Functional Homology with FGFs," J. Biol. Chem. (2003) 278:34226-34236.
Hollenhorst et al., "Expression profiles frame the promoter specificity dilemma of the ETS family of transcription factors," Nucleic Acids Res (2004) 32(18):5693-5702.
Michiels et al., "A 14 bp promoter element directs the testis specificity of the *Drosophila* β2 tubulin gene," The EMBO Journal (1989) 8(5):1559-1565.

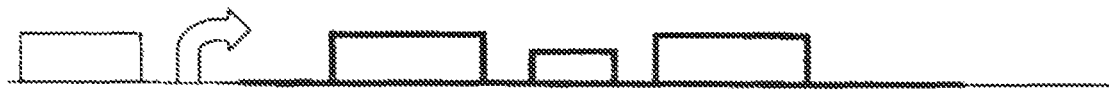

tetO₇  minimal       ORF1      IRES      ORF2
        promoter     One ORF encodes transactivator
                    other control signals not marked, e.g.
                    5'UTR, 3'UTR, intron(s), polyA

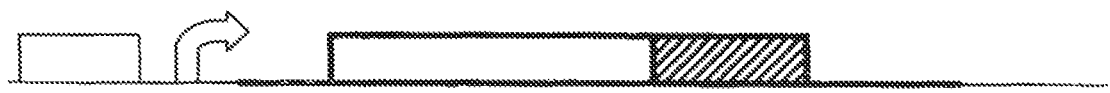

tetO₇  minimal       Fusion protein coding region
        promoter
                    other control signals not marked, e.g.
                    5'UTR, 3'UTR, intron(s), polyA Sex-specific splicing as, for
example, medfly or *Drosophila
doublesex*                Female-specific splice

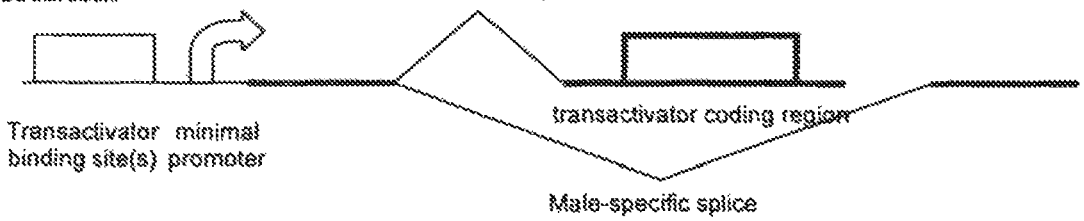

Transactivator  minimal                    transactivator coding region
binding site(s)  promoter
                                     Male-specific splice Other control signals not marked, e.g. 5'UTR,
3'UTR, intron(s), polyA Transactivator coding region:
A + C = transactivator
B = contains stop codon
or
A = DNA binding domain
B = Repression domain
C = Activation domain

Fig. 3

Potential PCR products generated:
1. If intron is not excised → ~1550 bp
2. If intron is spliced in male form (M1 or M2) → ~600 bp
3. If intron is spliced in female form → ~200 bp

```
Native:  CGTAGATTTG|GT..intron..AG|GTGAAGGCTC
LA1188:  CTACTG|GCACGT..intron..AG|GTGAAGAATA
LA3077:  AACGAAGTTG|GT..intron..AG|GTATTGAGGG
LA3097:  AGCCACCATG|GT..intron..AG|GTCAGCCGCC
```

Figure 33

| | Nit Male† | Nit Fem Jct† | Tet Male† | Tet Fem Jct† |
|---|---|---|---|---|
| 3077A | 111 | 32 | 73 | 44 |
| 3077B | 314 | 157 | 132 | 121 |
| 3077C | 161 | 116 | 60 | 84 |
| 3077D | 445 | 85 | 194 | 190 |
| 3097A | 179 | 5 | 89 | 90 |
| 3097B | 440 | 0 | 59 | 27 |
| 3097C | 172 | 0 | 46 | 44 |
| 3233A | 457 | 1 | 79 | 58 |
| 3233B | 171 | 0 | 14 | 13 |
| 3014;1217 | 136 | 0 | 48 | 10 |
| 3166;1217 | 64 | 0 | 5 | 7 |

Figure 35

|       | NT males | NTfemales | TET males | TET females |
|-------|----------|-----------|-----------|-------------|
| 3097A | 136      | 0         | 21        | 19          |
| 3097B | 295      | 11        | 14        | 11          |
| 3097C | 96       | 12        | 22        | 21          |
| 3097D | 103      | 15        | 82        | 67          |
| 3233A | 78       | 6         | 32        | 5           |

Figure 38

EXPRESSION SYSTEMS

CROSS REFERENCE TO RELATED APPLICATIONS

This application is a continuation of U.S. application Ser. No. 14/839,683, filed Aug. 28, 2015, now pending, which is a continuation of U.S. application Ser. No. 11/352,177, filed Feb. 10, 2006, now patented, which is a continuation-in-part of U.S. application Ser. No. 10/566,448, filed Apr. 18, 2006, now patented, which is the national stage entry of International Application No. PCT/GB2004/003263, filed Jul. 28, 2004, which claims the priority from GB 0317656.7, filed Jul. 28, 2003. All applications are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750402000401SeqList.txt, date recorded: Aug. 26, 2015, size: 434,690 bytes).

INTRODUCTION

The present invention relates to a gene expression system, in combination with splice control sequences, said control sequences providing a mechanism for alternative splicing.

Alternative splicing is also known as pre-mRNA splicing and involves the removal of one or more introns and ligation of the flanking exons. This reaction is catalyzed by the spliceosome, a macromolecular machine composed of five RNAs and hundreds of proteins (Jurica, M. S. & Moore, M. J. (2003) *Mol. Cell* 12, 5-14). Alternative splicing generates multiple mRNAs from a single gene, thus increasing proteome diversity (Graveley, B. R. (2001) *Trends Genet.* 17, 100-107).

Alternative splicing also plays a key role in the regulation of gene expression in many developmental processes ranging from sex determination to apoptosis (Black, D. L. (2003) *Annu. Rev. Biochem.* 72, 291-336), and defects in alternative splicing have been linked to many human disorders (Caceres, J. F. & Kornblihtt, A. R. (2002) *Trends Genet.* 18, 186-193). In general, alternative splicing is regulated by proteins that associate with the pre-mRNA and function to either enhance or repress the ability of the spliceosome to recognize the splice site(s) flanking the regulated exon (Smith, C. W. & Valcarcel, J. (2000) *Trends Biochem. Sci.* 25, 381-388).

Whether a particular alternative exon will be included or excluded from an mRNA in each cell is thought to be determined by the relative concentration of a number of positive and negative splicing regulators and the interactions of these factors with the pre-mRNA and components of the spliceosome (Smith, C. W. & Valcarcel, J. (2000) *Trends Biochem. Sci.* 25, 381-388).

Although at least 74% of human genes encode alternatively spliced mRNAs (Johnson, J. M., Castle, J., Garrett-Engele, P., Kan, Z., Loerch, P. M., Armour C. D., Santos, R., Schadt, E. E., Stoughton, R. & Shoemaker, D. D. (2003) *Science* 302, 2141-2144), relatively few splicing regulators have been identified.

SUMMARY OF THE INVENTION

The present invention provides, in a first aspect, a gene expression system comprising at least one coding sequence to be expressed in an organism, at least one promoter operably linked thereto, and at least one splice control sequence which, in cooperation with a spliceosome, mediates alternative splicing of RNA transcripts of the coding sequence, the mediation being selected from at least one of the group consisting of: sex-specific, stage-specific, germline-specific and tissue-specific mediation.

The gene expression system comprises a gene, capable of expressing a protein of interest, under the control of a promoter therefor, in combination with splice control sequences, preferably intronic sequences that control alternative splicing. Optionally, an enhancer or a transcriptional transactivator protein binding sequence is also present in the gene expression system.

The splice control sequences provide alternative splices of the at least one protein, for instance in a sex-, stage- tissue or germline-specific manner. This differential expression of the at least one protein allows the user to combine two levels of control of expression an, therefore, to express proteins in a previously unobtainable manner.

It is preferred, therefore, that alternative splicing of the RNA transcribed from the gene of interest leads to differential expression of the at least one protein in at least one of the above-mentioned specific manners.

Spliceosomes are large complexes of small nuclear RNA and protein particles (snRNPs) which assemble with pre-mRNA to achieve RNA splicing, by removing introns from eukaryotic nuclear RNAs, thereby producing mRNA which is then translated to protein in ribosomes.

The splice control sequences are preferably substantially intronic. Although it is envisaged that they may comprise a portion of exonic or coding sequence, this is not preferred according to one embodiment of the invention.

The gene expression system is capable of expressing at least one protein of interest. Said at least one protein may have a therapeutic effect or may, preferably, be a marker, for instance DsRed, Green Fluorescent Protein (GFP) or one or more of their mutants or variants, or other markers that are well known in the art.

Most preferably, the at least one protein has a lethal, deleterious or sterilizing effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

A lethal effect resulting in sterilization is particularly preferred, as this allows the organism to compete in the natural environment ("in the wild") with wild-type organisms, but the sterile insect cannot then produce offspring. In this way, the present invention achieve a similar result to techniques such as the Sterile Insect Technique (SIT) in insects, without the problems associated with SIT, such as the cost, danger to the user, and reduced competitiveness of the irradiated organism.

Preferably, the gene expression system comprises at least one positive feedback mechanism as described herein, namely at least one gene to be expressed and at least one promoter therefor, wherein a product of a gene to be expressed serves as a positive transcriptional control factor for the at least one promoter, and whereby the product, or the expression of the product, is controllable.

Preferably, the at least one protein is an apoptosis-inducing factor, such as the AIF protein described for instance in Cando et al (*Journal of Cell Science* 115, 4727-4734 (2002)) or homologues thereof. AIF homologues are found in mammals and even in invertebrates, including insects, nematodes, fungi, and plants, meaning that the AIF gene has been conserved throughout the eukaryotic kingdom.

Also preferred is Hid, the protein product of the head involution defective gene of *Drosophila melanogaster*, or Reaper (Rpr), the product of the reaper gene of *Drosophila*, or mutants thereof. Use of Hid was described by Heinrichs and Scott (*Proc. Natl Acad. Sci USA* 97, 8229-8232 (2000). Use of a mutant derivative, $Hid^{A1a5}$ was described by Horn and Wimmer (*Nature Biotechnology* 21, 64-70 (2003)). Use of a mutant derivative of Rpr, $Rpr^{KR}$, is described herein (see also White et al 1996, Wing et al., 2001, and Olson et al., 2003).

Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al., 2002, Vernooy et al., 2000) even though their own sequence is not well conserved.

Also preferred is Nipp1Dm, the *Drosophila* homologue of mammalian Nipp1 (Parker et al *Biochemical Journal* 368, 789-797 (2002); Bennett et al., *Genetics* 164, 235-245 (2003)). Nipp1Dm is another example of a protein with lethal effect if expressed at a suitable level, as would be understood by the skilled person. Indeed, many other examples of proteins with a lethal effect will be known to the person skilled in the art.

It is also preferred that the protein of interest is itself a transcriptional transactivator, such as the tTAV system described herein.

It is preferred that the promoter can be activated by environmental conditions, for instance the presence or absence of a particular factor such as tetracycline in the tet system described herein, such that the expression of the gene of interest can be easily manipulated by the skilled person. Alternatively, a preferred example of a suitable promoter is the hsp70 heat shock promoter, allowing the user to control expression by variation of the environmental temperature to which the hosts are exposed in a lab or in the field, for instance. Another preferred example of temperature control is described in Fryxell and Miller (*Journal of Economic Entomology* 88, 1221-1232 (1995)).

Also preferred as a promoter is the srya embryo-specific promoter (Horn & Wimmer (2003) from *Drosophila melanogaster*, or its homologues, or promoters from other embryo-specific or embryo-active genes, such as that of the *Drosophila* gene slow as molasses, or its homologues from other species.

It is also preferred that the genetic system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcMNPV.

The splice control mechanism allows an additional level of control of protein expression, in addition to the promoter and/or enhancer of the gene. For instance, tissue or sex-specific expression in embryos only would be extremely difficult by conventional methods. Promoters with this specificity are unknown, even in *Drosophila*. However, using combinatorial control according to the present invention, an embryo-specific promoter, for example sryα, can be combined with a suitable alternative splicing system.

It is preferred that any combination of promoter and alternative splicing mechanism is envisaged. The promoter is preferably specific to a particular protein having a short temporal or confined spatial effect.

Alternatively, it is preferred that the promoter may be specific for a broader class of proteins or a specific protein that has a long-term and/or wide system effect, such as a hormone, positive or negative growth factor, morphogen or other secreted or cell-surface signaling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e. the morphogen can still act and have an effect) beyond that life-cycle stage. Preferred examples would be the morphogen/signaling molecules Hedgehog, Wingless/WNTs, TGRß/BMPs, EGF and their homologues, which are well-known evolutionarily-conserved signalling molecules.

It is also envisaged that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germ-line- and sex-specific control.

It is also envisaged that more than one promoter, and optionally an enhancer therefor, can be used in the present system, either as alternative means for initiating transcription of the same protein or by virtue of the fact that the genetic system comprises more than one gene expression system (i.e. more than one gene and its accompanying promoter).

In a further aspect, the present invention provides a method of transformation, comprising expressing alternative splices of a protein in an organism by contacting the organism with the gene expression system and preferably inducing expression of the expression system. Methods of introduction or transformation of the gene system and induction of expression are well known in the art with respect to the relevant organism.

Also provided are organisms (i.e. transformants) transformed by the present system.

Where reference to a particular nucleotide or protein or SEQ ID NO is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences or SEQ ID NO.

DESCRIPTION OF THE FIGURES AND SEQUENCE LISTINGS

The present invention will now be described with reference to the following non-limiting Figures and Sequence Listings, wherein;

FIG. 3 shows a sex-specific system.

Figure 19:
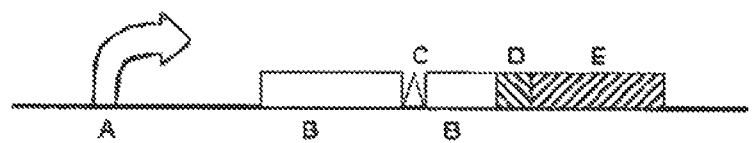

FIG. 19: One use of the P element in generating germline-specific expression of a gene of interest (Gene E). Insertion of the P element IVS3 and flanking exonic sequences upstream of an ubiquitin-Gene E fusion with allow germline-specific expression of Gene E under a germline active promoter. A—Germline active promoter; B—P-element open reading frame; C—P intron 'IVS3'; D—Ubiquitin; E—Coding region for protein of Interest e.g. tTAV.

Figure 20:
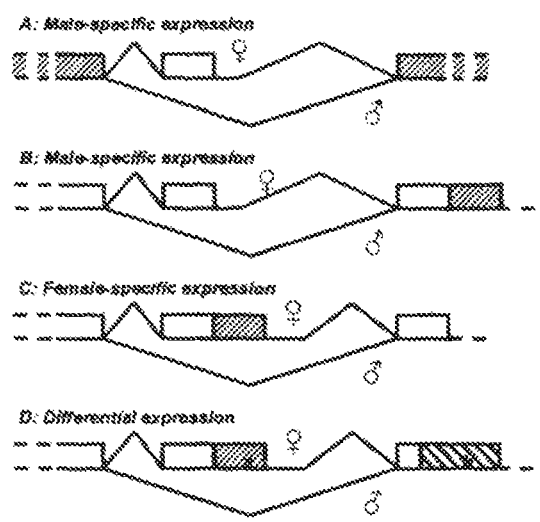

FIG. 20: Sex-specific expression using dsx. A: Intron used as Cctra intron above, but giving male-specific expression. A fragment of dsx (here the *Anopheles* version) is inserted into a heterologous coding region (shaded boxes). The intron is completely removed in males, but in females the coding region is prematurely terminated. B: An alternative approach to male-specific expression, in which a heterologous coding region is fused to a fragment of dsx. C: Female-specific expression: the heterologous coding region is inserted into the female-specific exon, either as an in-frame fusion to a fragment of Dsx, or with its own start and stop codons. D: Differential expression: designs B and C can be combined to give expression of gene a in females and b in males.

Figure 21:
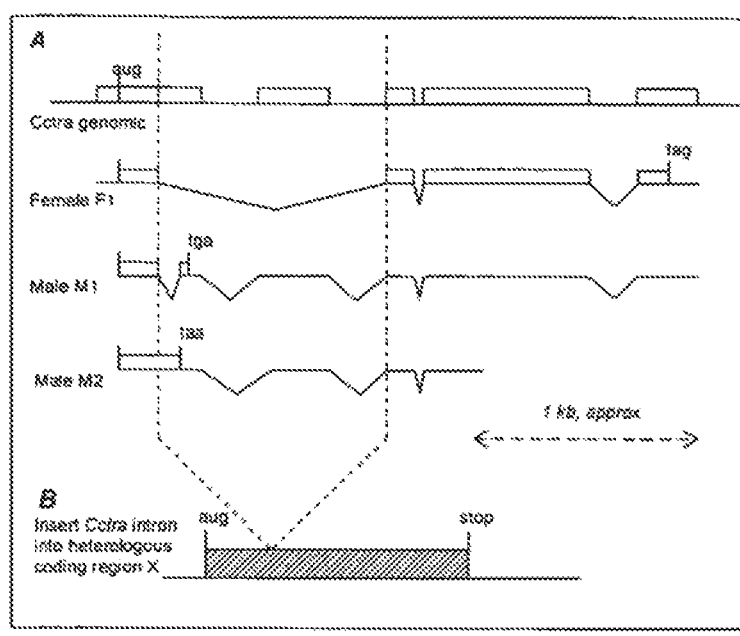

FIG. 21: Sex-specific alternative splicing of Cctra. A: Cctra is spliced in females to produce three transcripts: F1, which encodes functional Tra protein, and M1 and M2, which do not, because they include additional exons with stop codons (redrawn from Pane et al. 2002). Males produce only transcripts M1 and M2 and therefore do not produce functional Tra protein at all. B: If this intron were to function similarly in a heterologous coding region, this would similarly allow females, but not males, to produce functional protein X.

Figure 22:
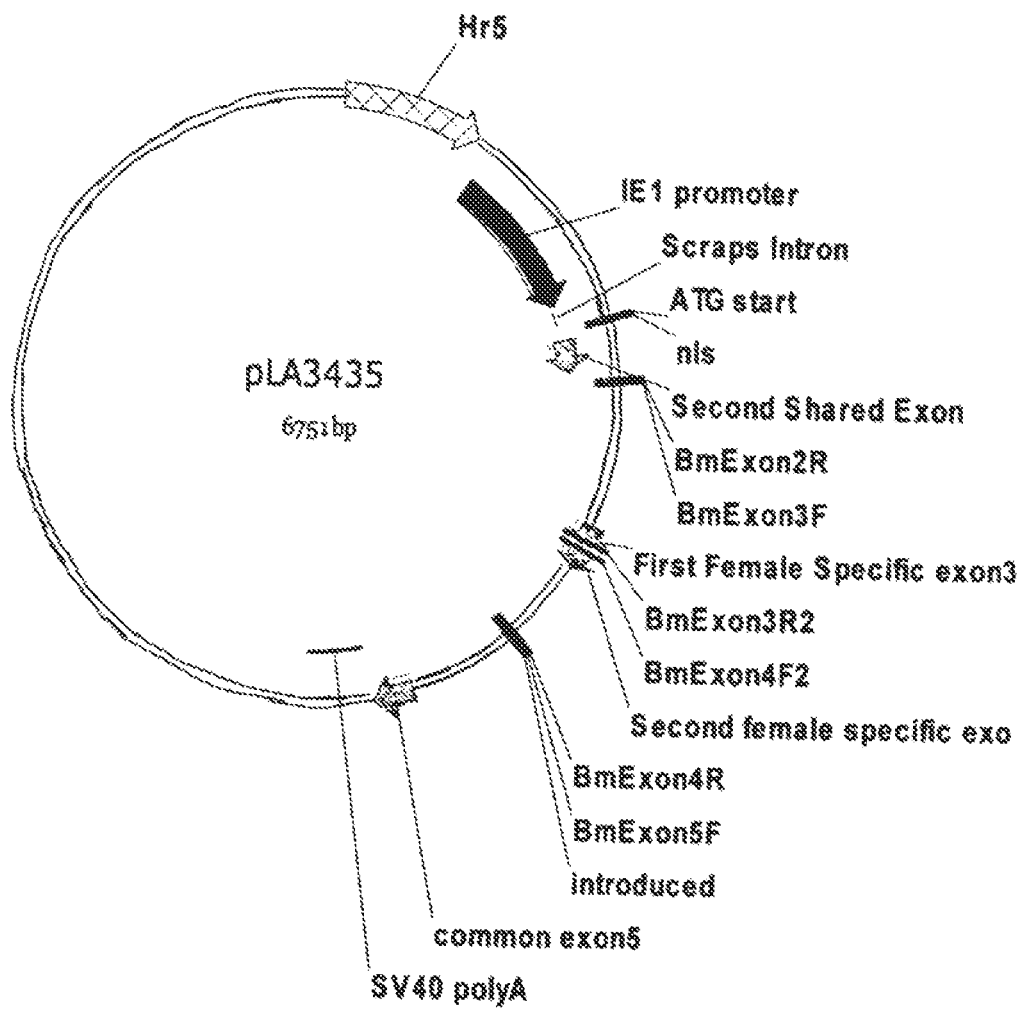

FIG. 22: Diagrammatic representation of pLA3435 construct/plasmid (SEQ ID NO. 46).

Figure 23:
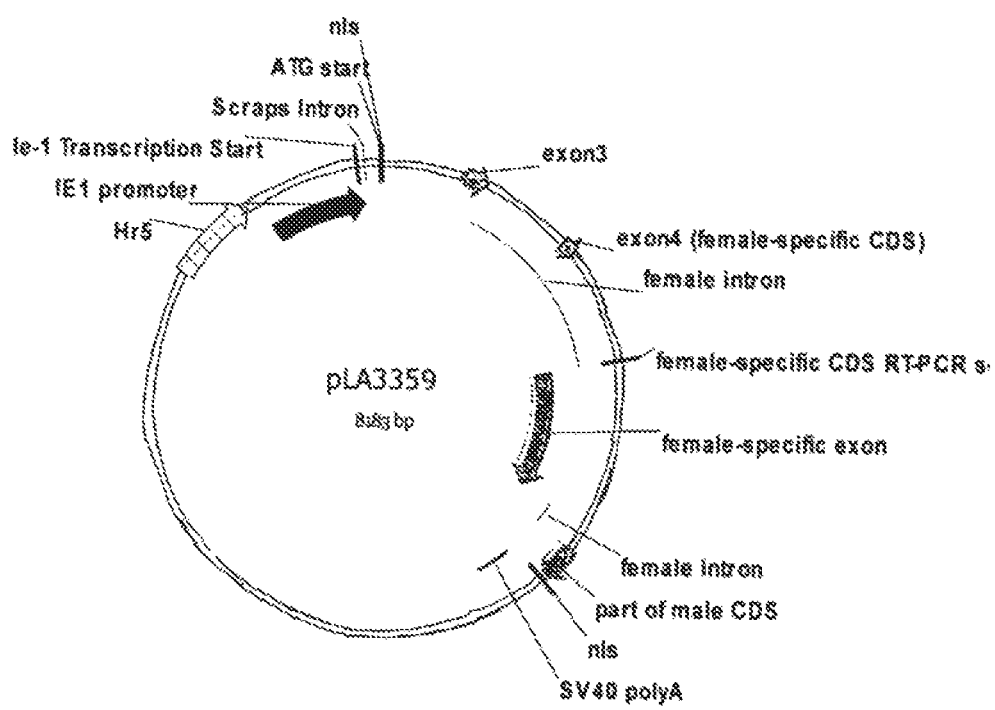

FIG. 23: Plasmid map of pLA3359 *Anopheles gambiae* dsx gene placed under the control of a Hr5-IE1 promoter for assessing splicing via transient expression.

Figure 24:
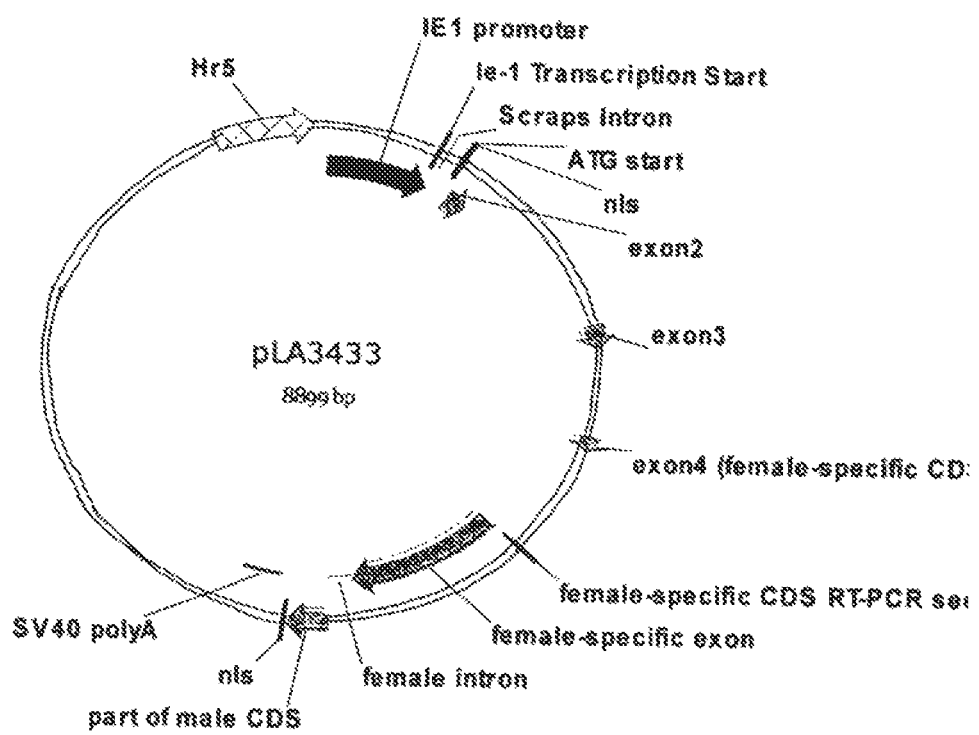

FIG. 24: pLA3433-Anopheles gambiae dsx gene placed under the control of a Hr5-IE1 promoter, with the addition of exon 2, for assessing splicing via transient expression.

Figure 25:
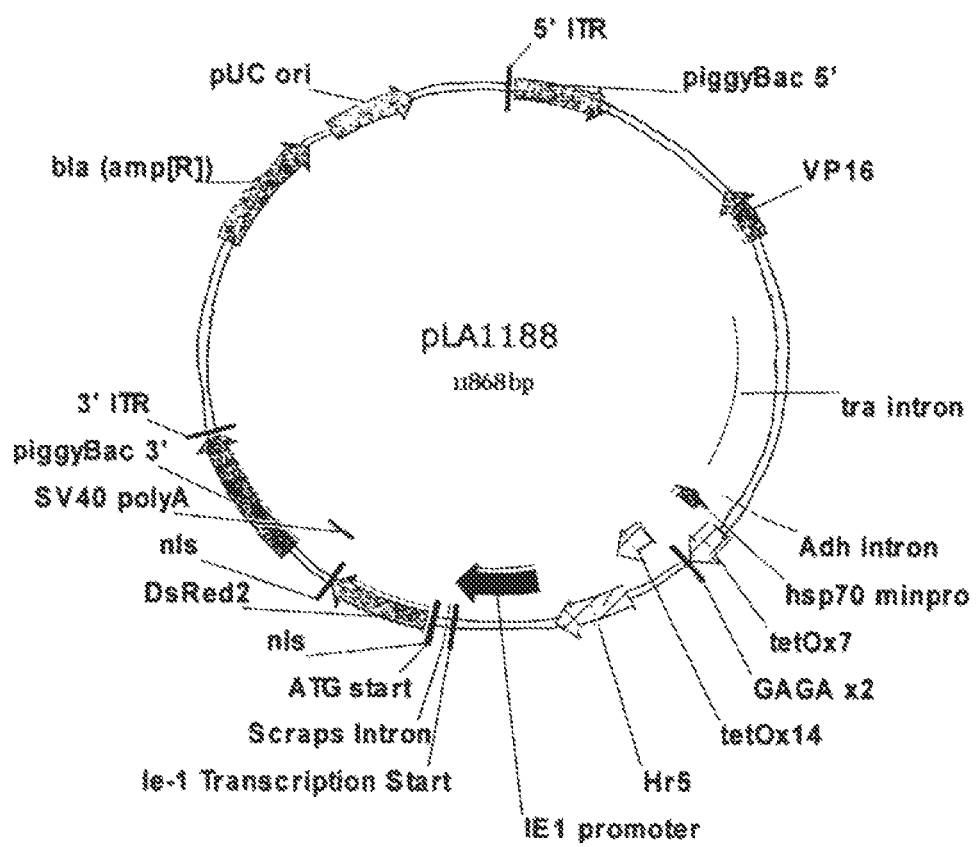

FIG. 25: Schematic representation of pLA1188 construct.

Figure 26:
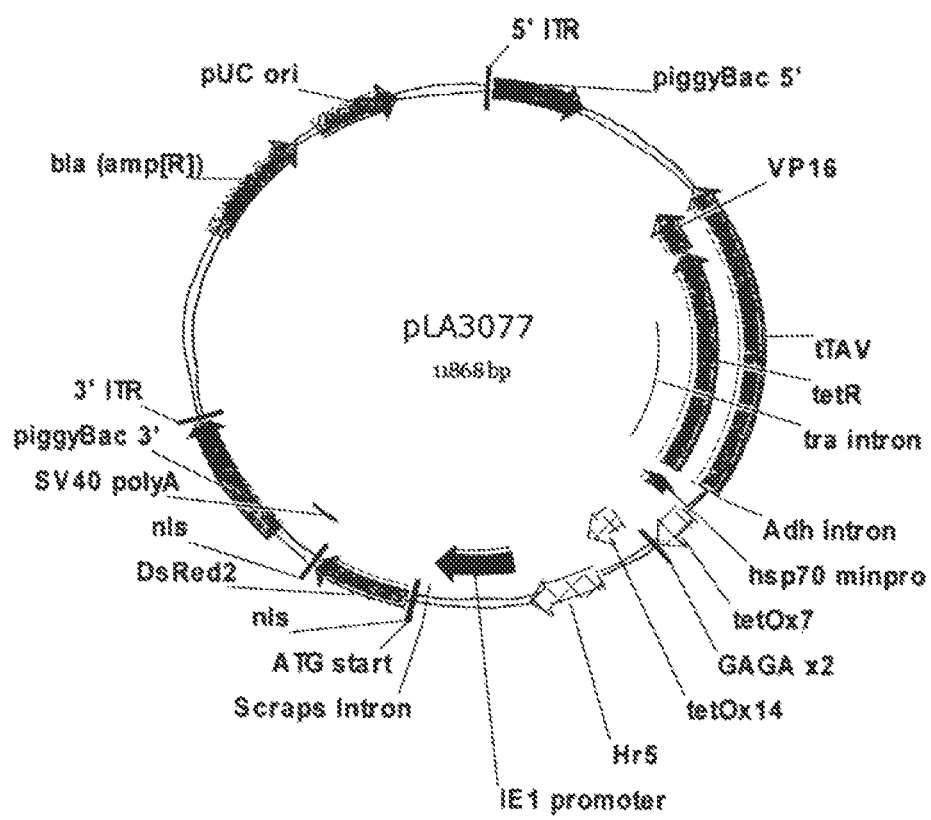

FIG. 26: Schematic diagram of pLA3077 construct.

Figure 27:
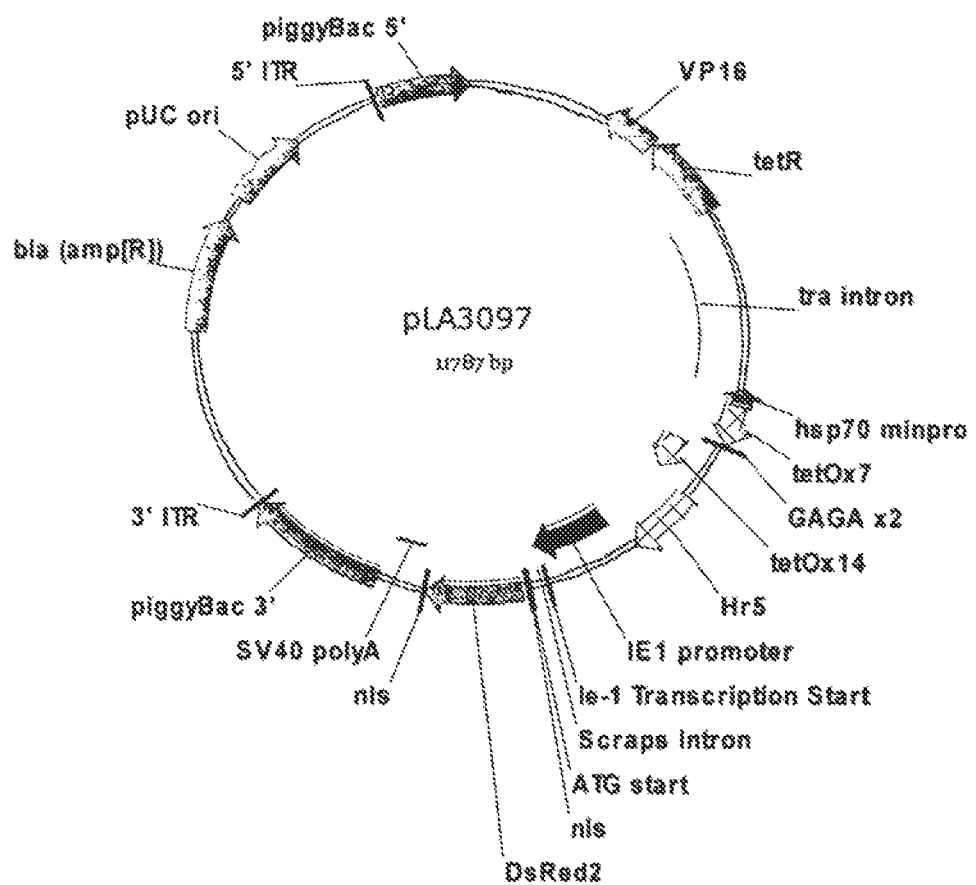

FIG. 27: Schematic diagram of pLA3097 construct.

Figure 28:
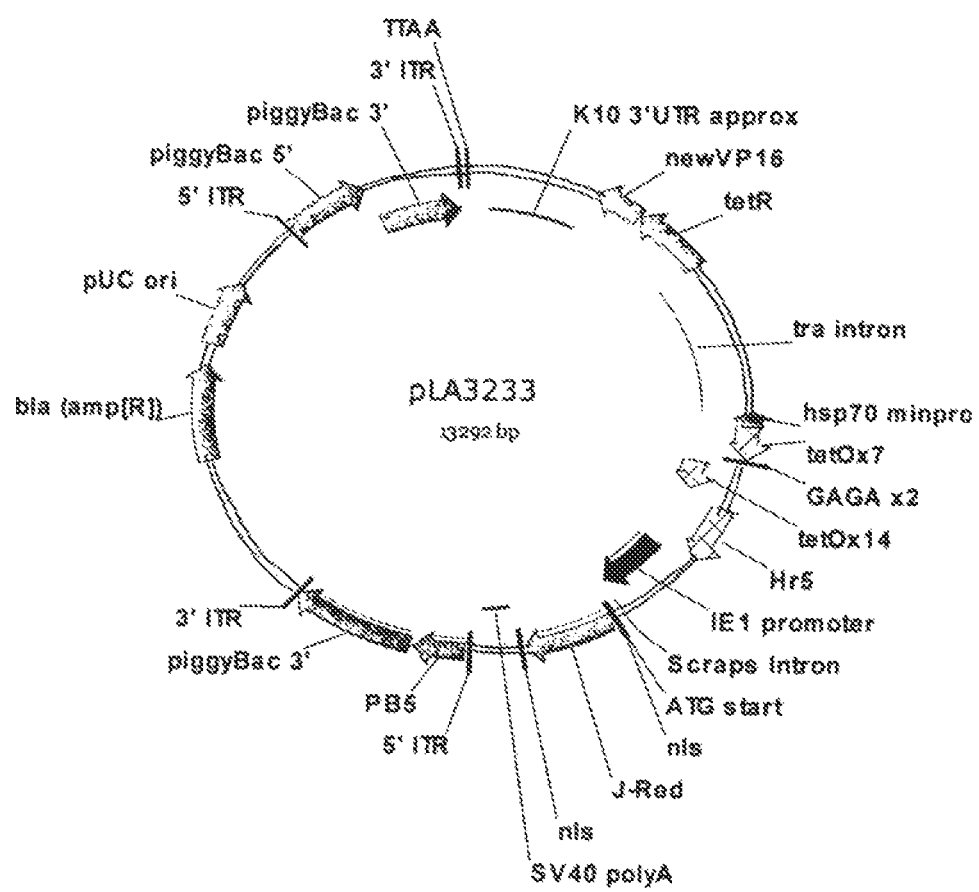

FIG. 28: Schematic diagram of pLA3233 construct.

Figure 29:
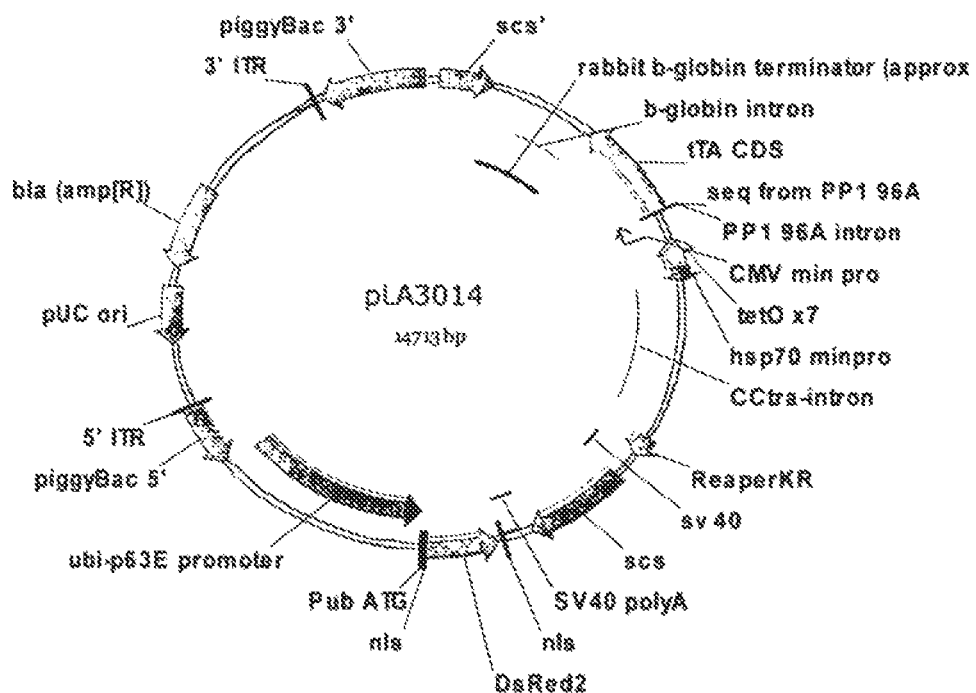

FIG. 29: Schematic diagram of pLA3014 construct.

Figure 30:
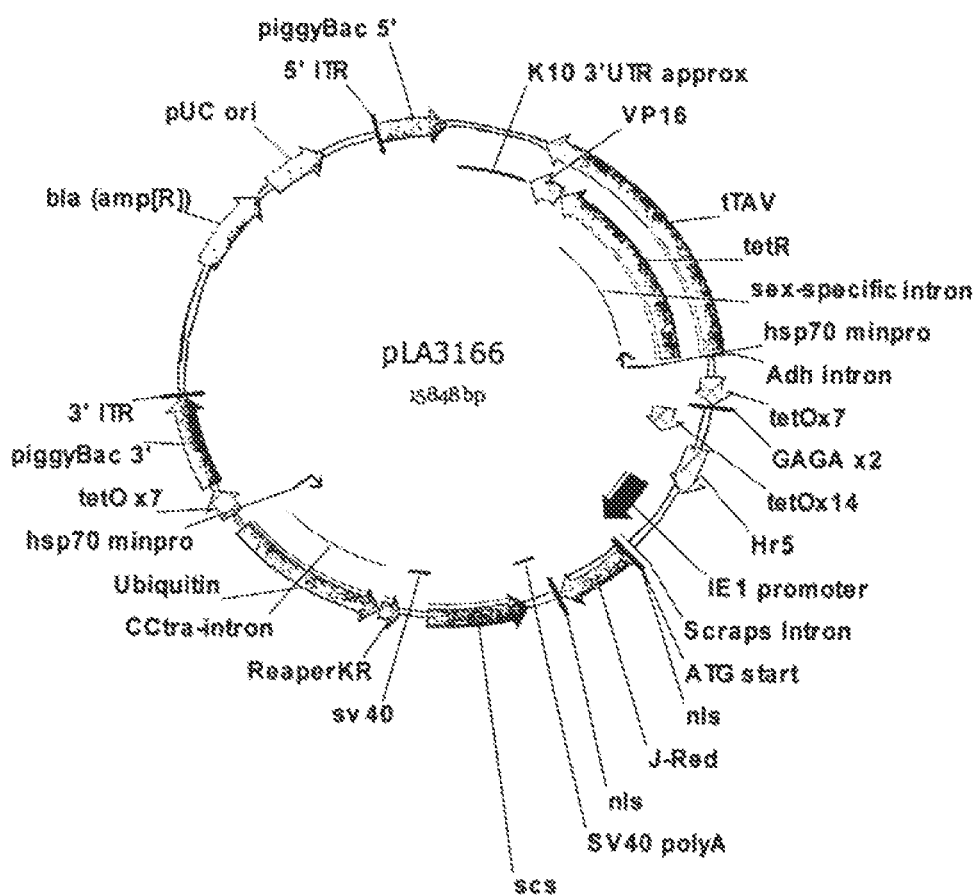

FIG. 30: Schematic diagram of pLA3166 construct.

Figure 31:
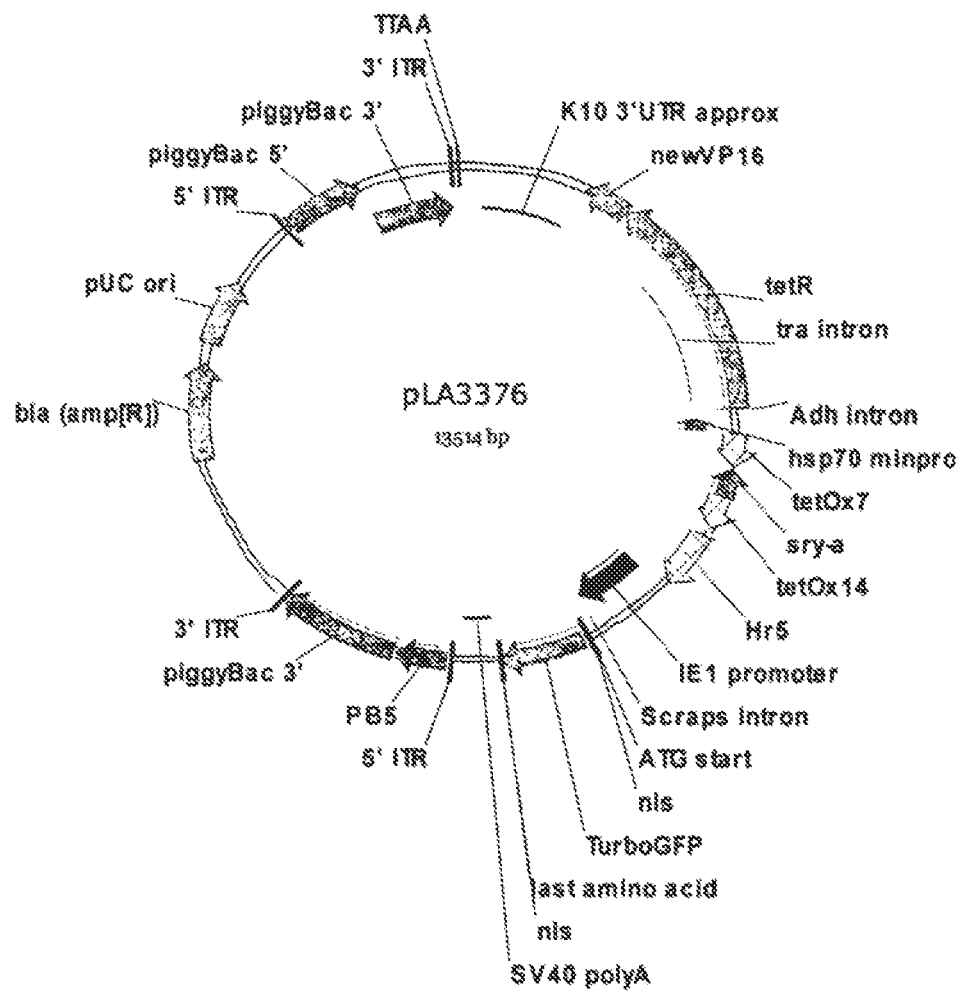

FIG. 31: Schematic diagram of pLA3376 construct.

Figure 32:
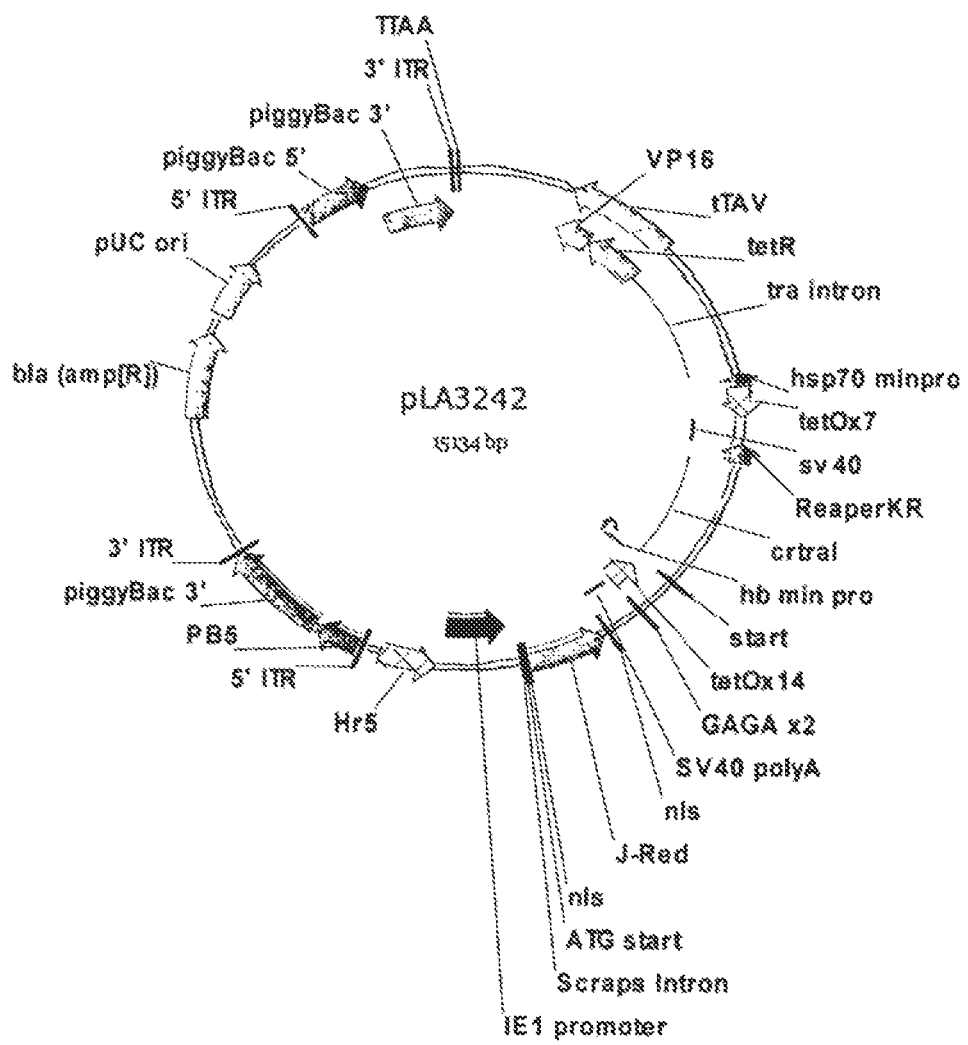

FIG. 32: Schematic diagram of pLA3242 construct.

FIG. 33: Flanking sequence of Cctra. Splicing of the Cctra intron in LA3077 and LA3097 is exactly as you would see in the native Cctra intron. Splicing in LA1188 results in the removal of 4 additional nucleotides. In all cases the introns are flanked by 5' exonic TG and 3' GT.

Figure 34:
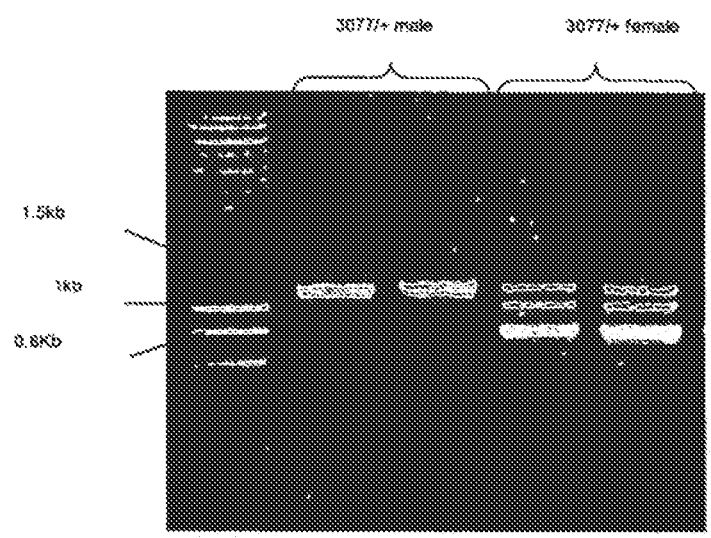

FIG. 34: Gel showing correct sex- specific splicing of intron(s) derived from CcTra (776 bp band in females) in *Ceratitis capitata* transformed with LA3077. Lane 1: Marker (SmartLadder™ from Eurogentec, bands of approx 0.8, 1.0 and 1.5 kb are indicated); Lanes 2 and 3: *Ceratitis capitata* LA3077/+ males; Lanes 4 and 5: *Ceratitis capitata* LA3077/+ females.

FIG. 35: Phenotypic data for transformed female specific constructs in *Ceratitis capitata*. Column 1: Construct designation LA#, e.g. LA3077, LA3097, LA3233, etc, is indicated by number, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 36:
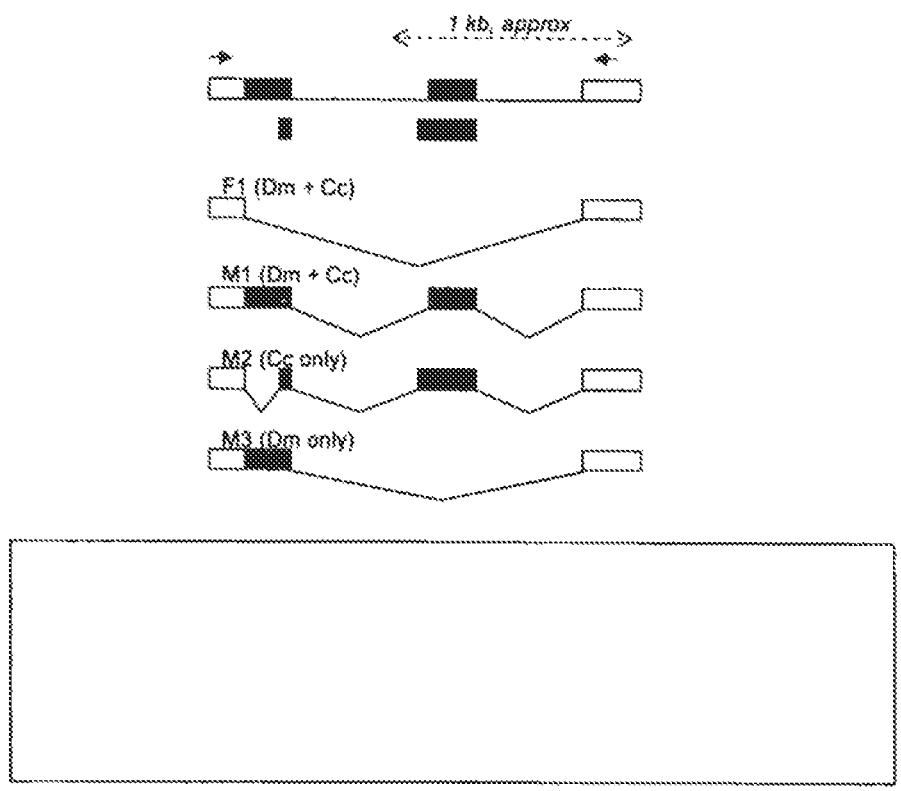

FIG. 36: Transcripts of Cctra intron constructs in *Drosophila* and *Ceratitis capitata*. The top line represents the construct DNA containing tra intron flanked by desired gene (the open box). The red box represents the male specific exons. Introns are represented by solid lines. Arrow above the first line represents the positions of the oligonucleotides used in the RT-PCR experiments. The bar indicates the scale of the figure.

Figure 37:
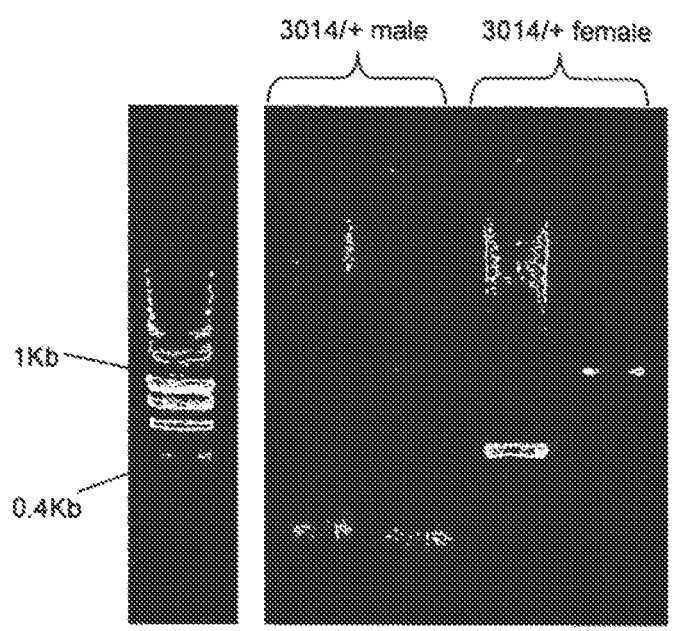

FIG. 37: Gel showing correct female specific splicing of CcTRA-derived sequence (508 bp band) in female *Ceratitis capitata* transformed with LA3014. Lane 1: Marker (SmartLadder™from Eurogentec, bands of approx 0.4 and 1.0 kb are indicated); Lane 2 *Ceratitis capitata* LA3014/+ male; Lane 4: *Ceratitis capitata* LA3014/+ female; Lanes 3 and 5: no reverse transcriptase negative controls (background bands, probably from genomic DNA, can be seen in lanes 2 and 4).

FIG. 38: Phenotypic data for transgenic *Anastrepha ludens* transformed with LA3097 or LA3233. Column 1: Construct LA# (LA3097 or LA3233) indicated, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 39:
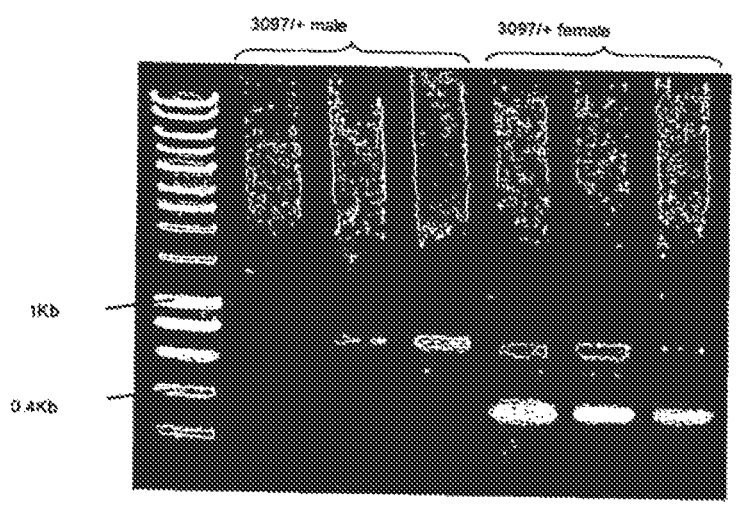

FIG. 39: Gel showing correct sex-specific splicing of CcTRA splicing (348 bp band in females) in *Anastrepha ludens* transformed with LA3097. Lane 1: Marker (SmartLadder™ from Eurogentec, bands of approx 0.4 and 1.0 kb are indicated); Lanes 2, 3 and 4: *A. ludens* LA3097/+ males; Lanes 5, 6 and 7: *A. ludens* LA3097/+ females.

Figure 40:
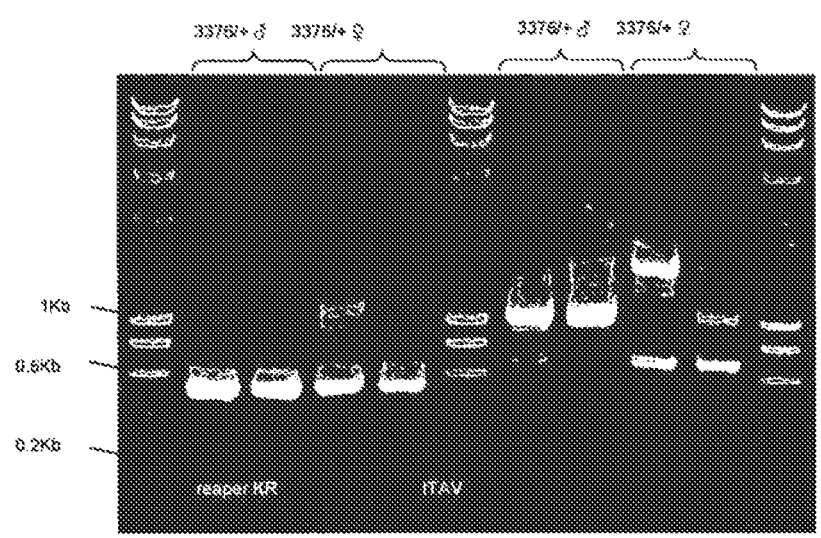

FIG. 40: Gel showing correct sex-specific splicing of BzTRA in reaperKR (200 bp band in females) and tTAV3 (670 bp band in females) regions of LA3376, in *Ceratitis capitata* transformed with LA3376. Lane 1: Marker (SmartLadder™ from Eurogentec, bands of approx 0.2, 0.6 and 1.0 kb are indicated); Lanes 2 and 3: *C. capitata* LA3376/+ males tested for splicing in reaperKR; Lanes 4 and 5: *C. capitata* LA3376/+ females tested for splicing in reaperKR; Lane 6: SmartLadder™; Lanes 7 and 8: *C. capitata* LA3376/+ males tested for splicing in tTAV; Lanes 9 and 10: *C. capitata* LA3376/+ females tested for splicing in tTAV; Lane 11: SmartLadder™.

Figure 41:
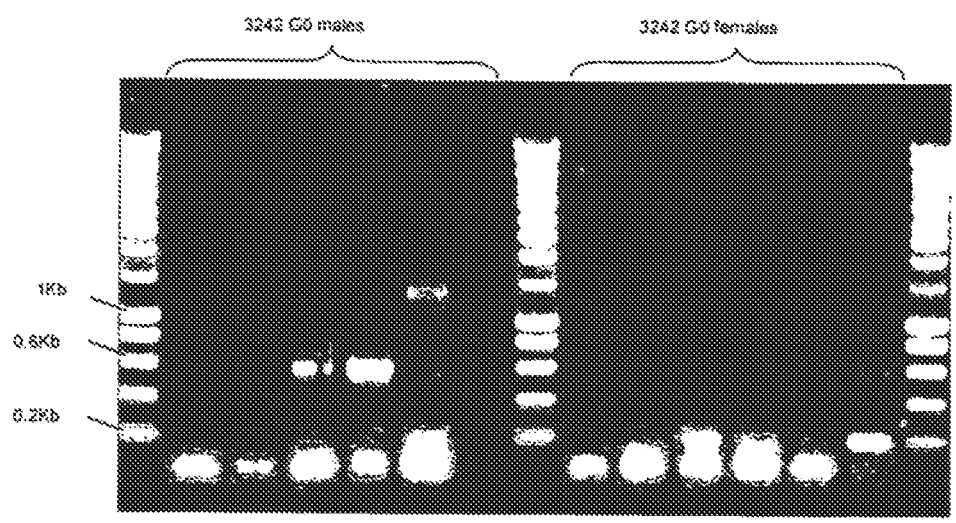

FIG. 41: Gel showing correct sex-specific CrTRA splicing in CrTRA-reaperKR (200 bp band in females) in *Ceratitis capitata* injected with LA3242. Lane 1: Marker (SmartLadder™ from Eurogentec, bands of approx 0.2, 0.6 and 1.0 kb are indicated); Lanes 2-7: *C. capitata* wild type males injected with LA3242; Lane 8: SmartLadder™;Lanes 9-14: *C. capitata* wild type females injected with LA3242; Lane 15: SmartLadder™.

Figure 15:
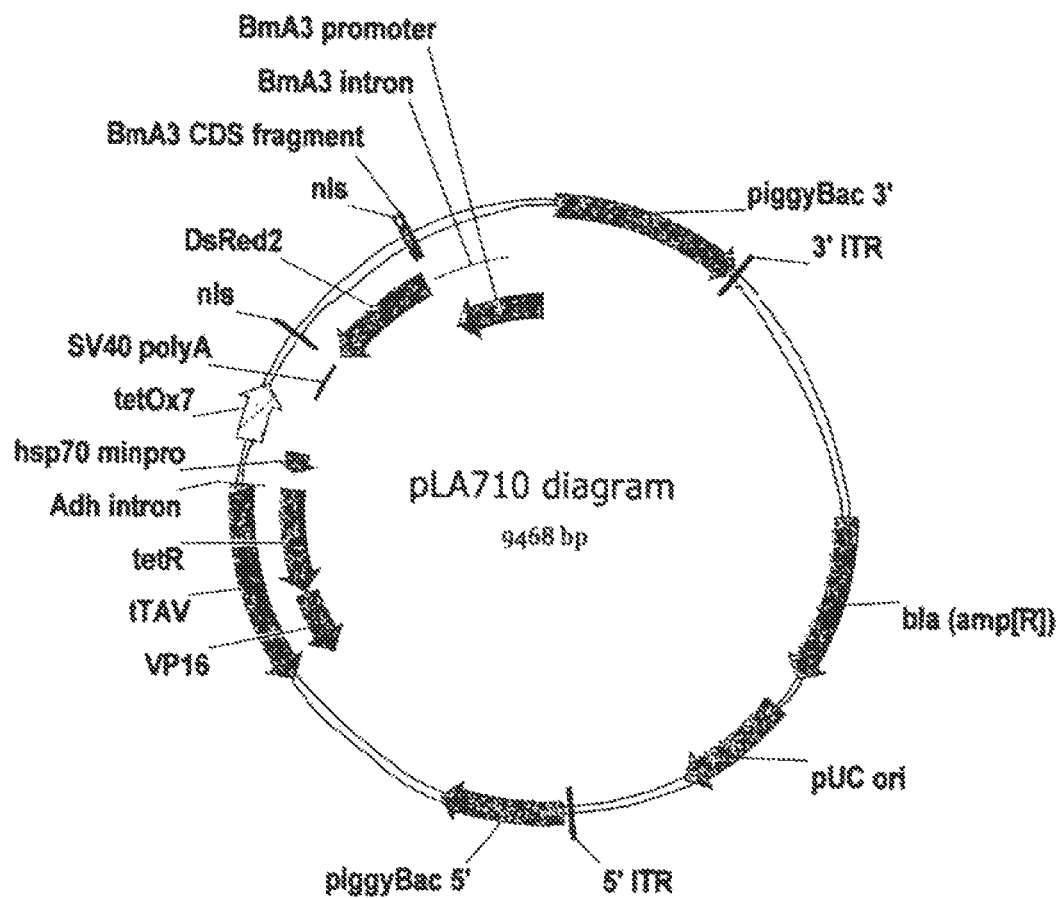
FIG. 15 is a schematic diagram of pLA710.
Figure 42:
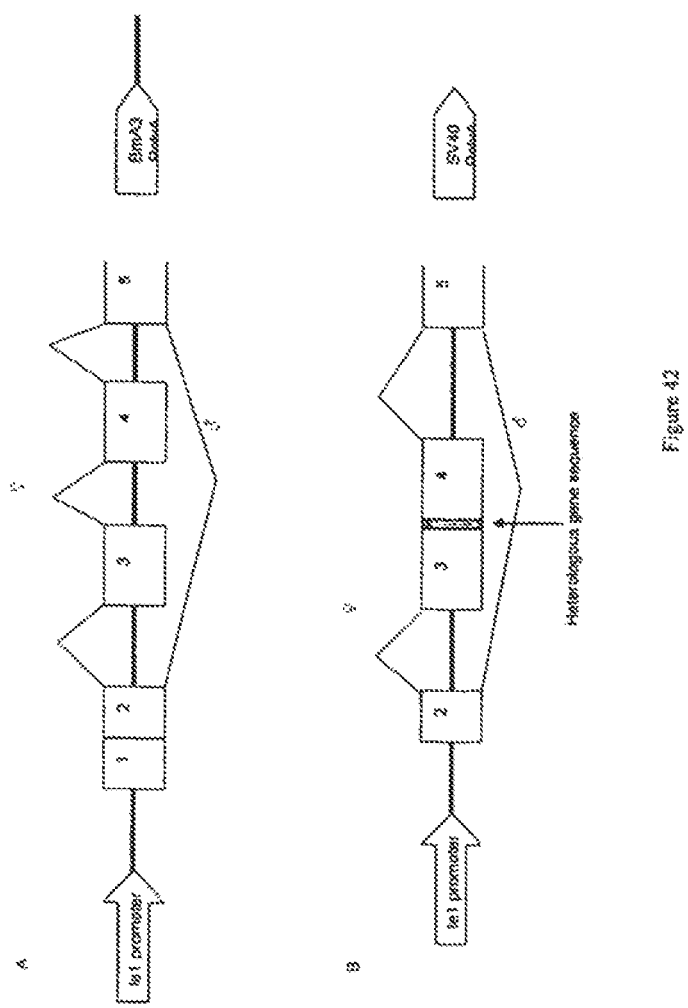

FIG. 42: Schematic representation of Bmdsx minigene constructs. Two minigene constructs derived from the *Bombyx mori* dsx gene are illustrated diagrammatically, together with the predicted alternative splicing of these constructs (female pattern shown above the construct, male pattern below). (A) is the *Bombyx mori* dsx mini-gene construct used in Funaguma et al., 2005) (B) is pLA3435. A and B differ from each other in several ways: (i) Exon 1 is excluded from pLA3435, (ii) the intron between female specific exons 3 and 4 has been removed and a short heterologous sequence has been inserted in pLA3435 (iii) Funaguma et al., use the ie1 promoter from the baculovirus BmNPV and a BmA3 3'UTR compared with pLA3435 which uses the hr5-IE1 enhancer/promoter from the baculovirus AcNPV and a 3'SV40 3'UTR. (iv) pLA3435 uses slightly longer intron sequences when compared with (A) (see FIG. 15 for sequence). Two minigene constructs derived from the *Bombyx mori* dsx gene are illustrated diagrammatically, together with the predicted alternative splicing of these constructs (female pattern shown above the construct, male pattern below).

Figure 43:
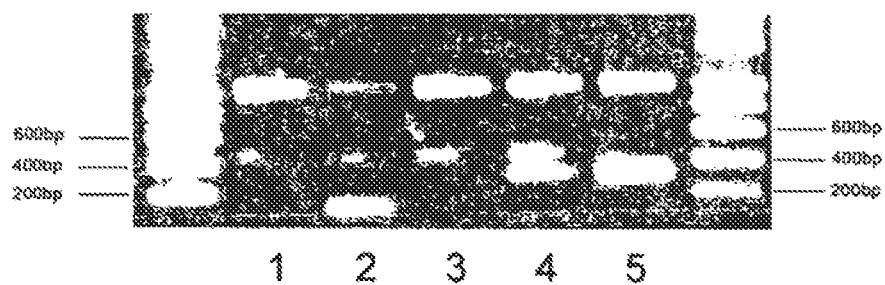

FIG. 43: Sex-specific splicing of BMdsx mini-gene construct in PBW. Analysis of transient expression from pLA3435 using RT-PCR show the presence of a 442 bp fragment (Lanes 1,2,3 and 4) in males and a 612 bp fragment in females (Lane 5), showing that the BMdsx mini-gene with a heterologous fragment inserted between exon 3 and 4 is able to splice correctly in the divergent moth, PBW. Markers are SmartLadder™ from Eurogentec; bands of approx 0.2, 0.4 and 0.6 kb are indicated FIG. 44: Sex-specific splicing of *Anopheles gambiae* dsx. Anopheles (A) shows the splicing that was reported by Scali et al 2005. However, when RT-PCR was performed using our primers (spl-agdsx-e3 (SEQ ID NO. 60) and spl-agdsx-m (SEQ ID NO. 61)) a different splicing pattern for females was revealed, represented by *Anopheles* (B).

Figure 45:
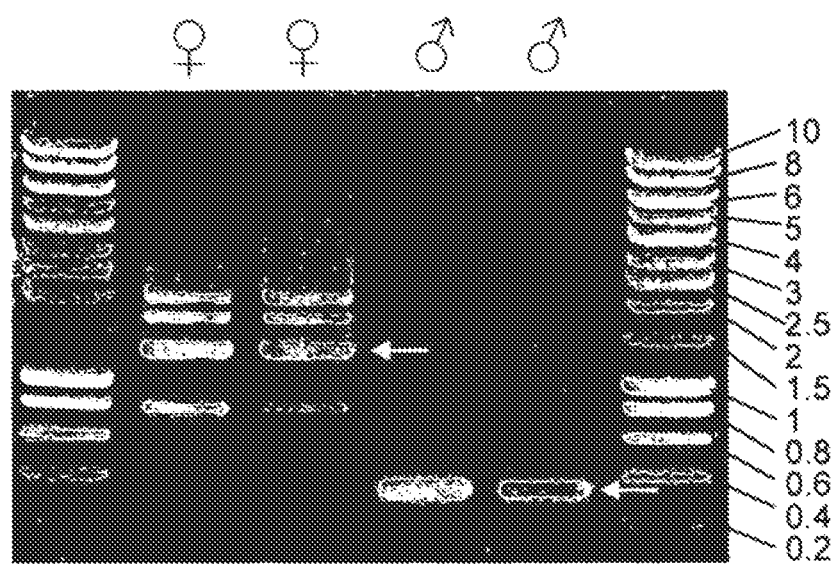

FIG. 45: Identification of male and female *Anopheles gambiae* using dsx primers. RNA was extracted from male and female *Anopheles gambiae* and the dsx transcripts were amplified by RT-PCR using the primers spl-agdsx-e3 (SEQ ID NO. 62) and spl-agdsx-m (SEQ ID NO. 63); the resulting banding pattern is shown in the gel above. The expected bands for the male and female transcripts are indicated by the white arrows, the bands have been cloned and sequenced and are identical to the predicted sequence of our version of the dsx transcript (see SEQ ID NO. 47 (LA3359) and SEQ ID NO. 48 (LA3433)). The molecular weight markers are shown in kb (SmartLadder™ from Eurogentec; sizes are approximate).

Figure 46:
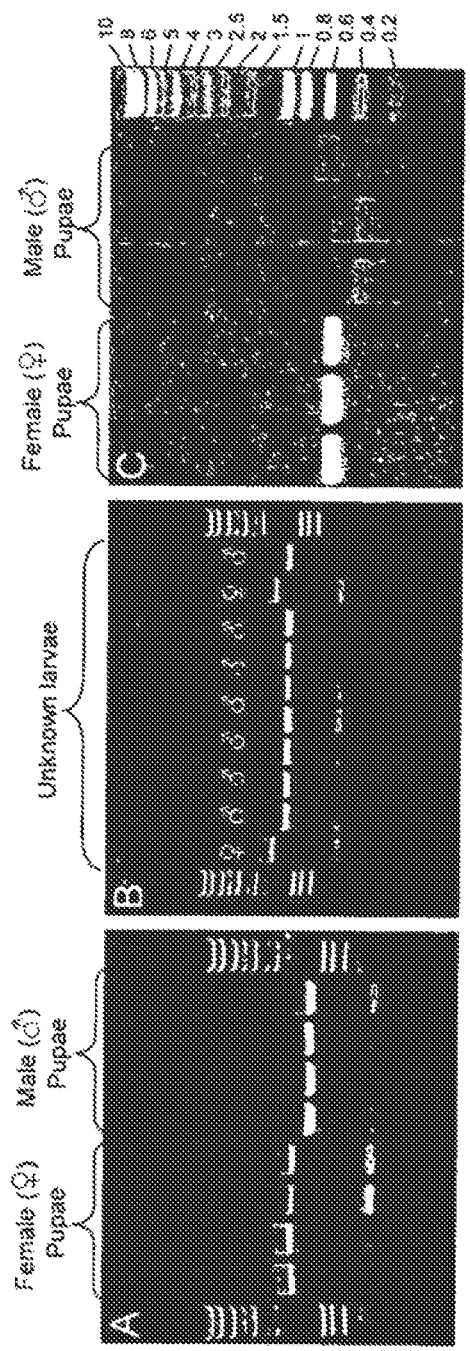

FIG. 46; Identification of male and female *Stegomyia aegypti* using dsx primers. The primers for the *Stegomyia aegypti* RT-PCR for A and B were aedesxF1 (SEQ ID NO. 64) and aedesxR5 (SEQ ID NO. 65) were tested initially on pupae, a life stage of *Stegomyia aegypti* that can be sexed conveniently and accurately; the resulting RT-PCR amplification is shown on gel image (A). The male and female pupae show a distinctive sex specific band. Then the primers were tested on RNA extractions from larvae, which can not be readily sexed by their morphology and the resulting RT-PCR amplification shown on gel image (B). The larvae show a clear banding pattern which distinguishes males from females unambiguously. Gel image (C) shows an approximately 600 bp band from RT-PCR using the primers aedessxF1 and aedesxR2 (SEQ ID NO. 66) from individual male and female pupa. Sequencing of this band showed a female specific splice variant which does not appear to possess the male shared exon to which aedesxR5 is predicted to anneal (exon 7, see FIG. 56). The molecular weight markers are shown in kb (SmartLadder™ from Eurogentec; sizes are approximate).

Figure 47:
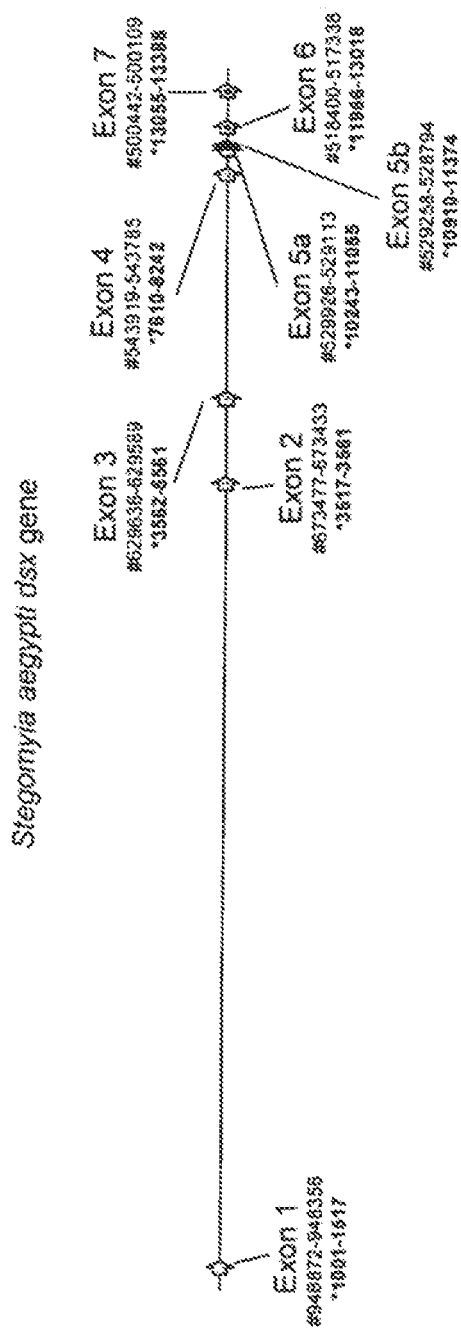

FIG. 47: Diagrammatic representation of part of the *Stegomyia aegypti* dsx gene (not to scale). A fragment of the *Stegomyia aegypti* dsx gene is represented above. Exons 5a and 5b are female specific and exon 6 is a male specific exon. Two female-specific splice variants have been found (F1 and F2) which comprise exons 1-4,5b,6 and 7 (F1) or 1-4,5a (F2); transcripts in males (M1) comprise exons 1-4,6 and 7 but not exon 5a or 5b and a transcript (C1) of 1-4 and 7 but not exons 5a, 5b or 6 is shown in males and females. The numbers for each of the exons after # relates to contig 1.370 (on the world-wide web, address broad.mit.edu/annotation/disease_vector/aedes_aegypti/), which reads in the opposite orientation, and after *relate to the nucleotide sequence shown in SEQ ID NO. 43.

Figure 12:
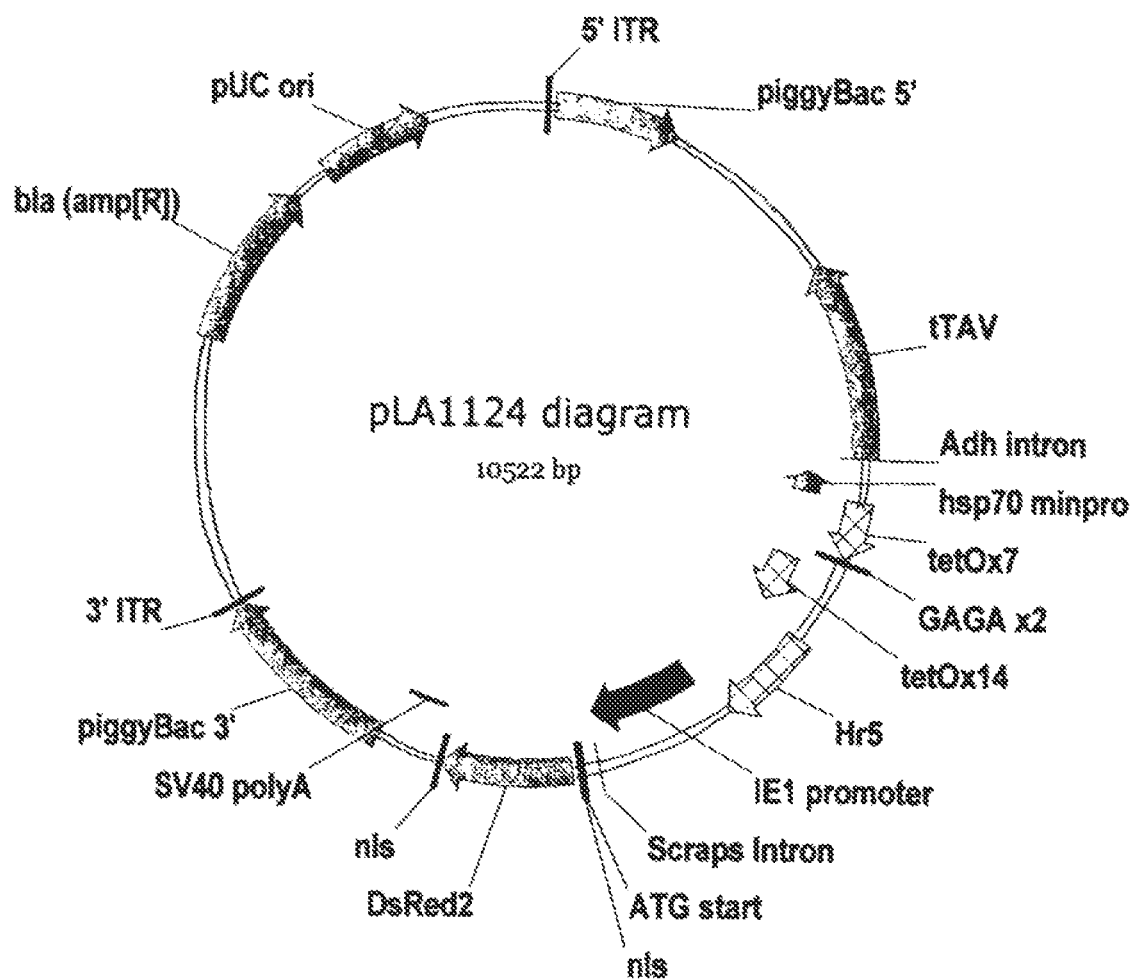
FIG. 12 is a schematic diagram of pLA1124.
Figure 48:
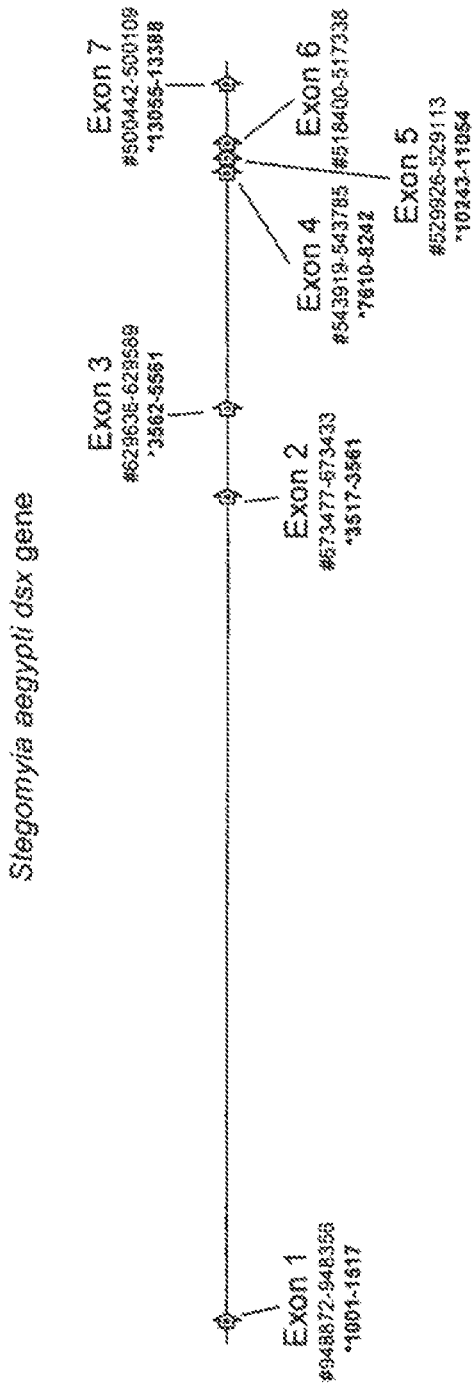

FIG. 48: Diagrammatic representation of the *Stegomyia aegypti* dsx gene. The entire *Stegomyia aegypti* dsx gene is represented above Exon 5 is the female specific exon and exon 6 is a putative male specific exon. In principle, transcripts in females comprise exons 1,2,3,4,5 and 7, and males comprise exons 1,2,3,4,6 and 7. The numbers for each of the exons after # relates to contig 1.370 (on the world-wide web, address broad.mit.edu/annotation/disease_vector/aedes_aegypti/) reading in the opposite orientation, and after * relate to FIG. 12.

Figure 49:
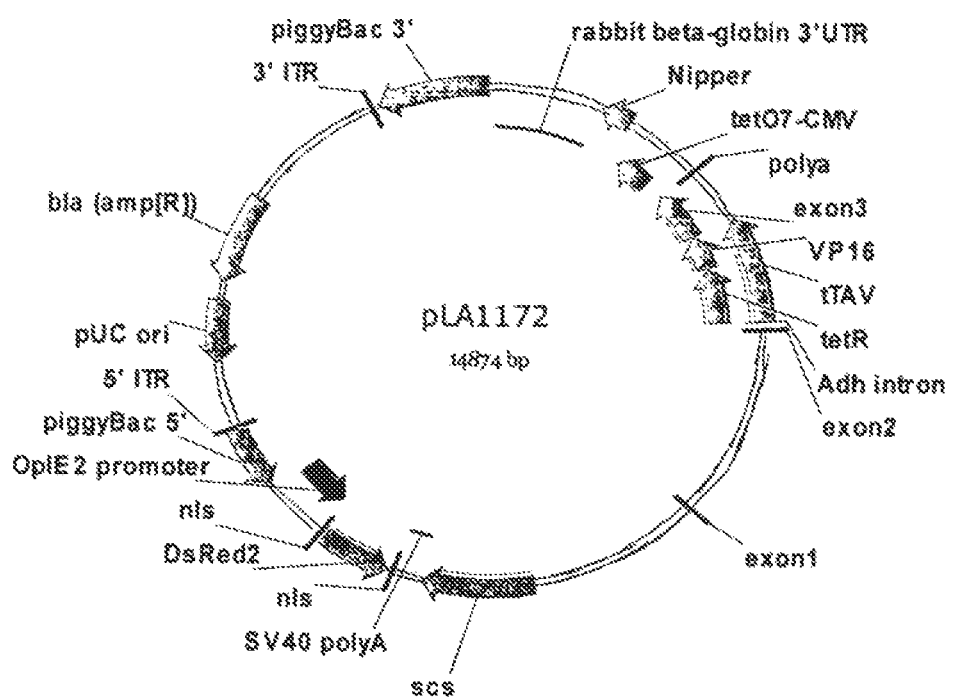

FIG. 49: Plasmid map of pLA 1172. A coding region for tTAV has been placed under the control of a fragment from the *Stegomyia aegypti* actin-4 gene (Munoz et al 2005) which includes the 5' UTR, first intron, and upstream sequences (putative promoter). The construct also contains a tetO$_7$ Nipper sequence. The construct has piggyBac ends and a DsRed2 marker for stable integration into a genome.

Figure 50:
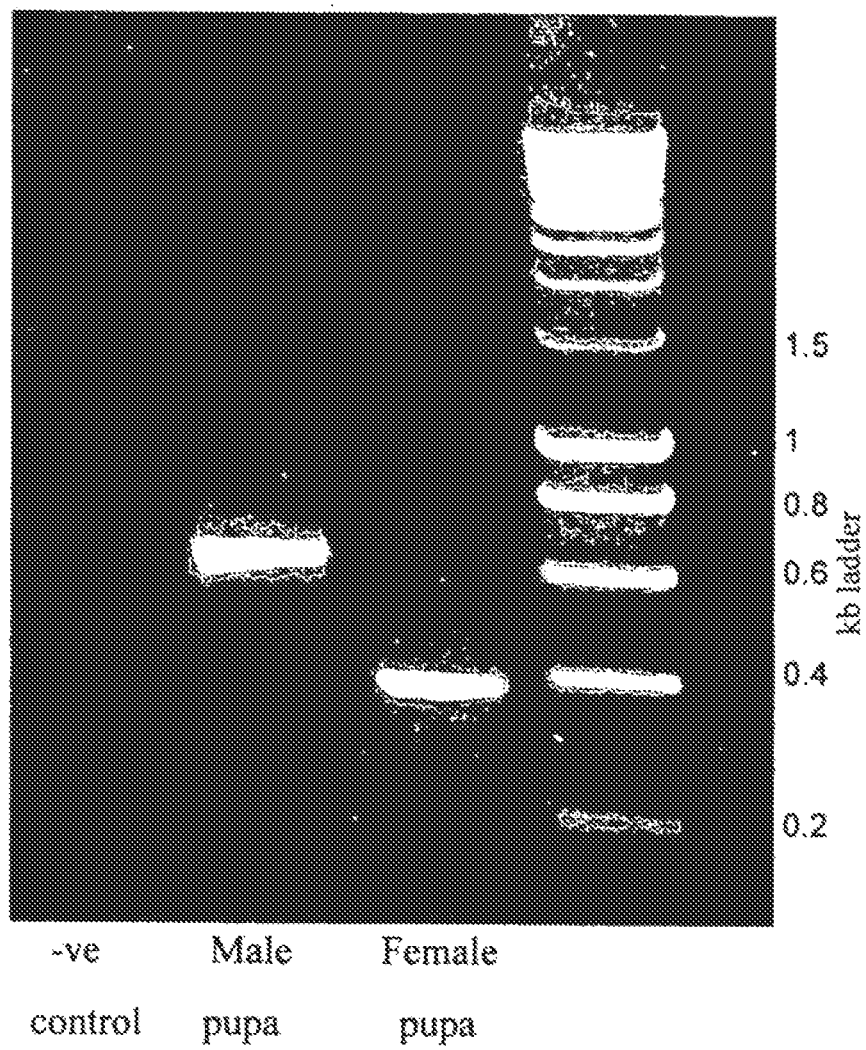

FIG. 50: Sex-specific splicing of tTAV in LA1172 (SEQ ID NO. 106) transformants. Gel image of RT-PCR of RNA extracted from LA1172 line 2 male and female pupa. The primers used were Agexon1 (SEQ ID NO. 67) and Tra (tTAV) seq+ (SEQ ID NO. 68). Sequencing of the RT-PCR bands showed the expected splicing occurring in males and females. The data shown in the above diagram is for LA1172 line 2, line 8 showed exactly the same results (data not shown). Markers are SmartLadder™ from Eurogentec; approximate sizes are indicated, in kb).

Figure 51:
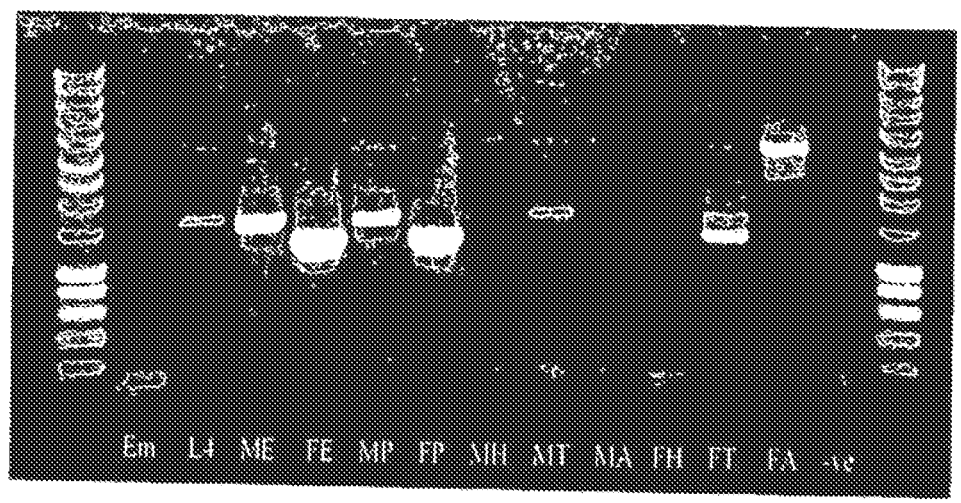

FIG. 51: RT-PCR of wild type samples, showing sex-specific splice variants of the *Stegomyia aegypti* Actin-4 gene. Gel image of RT-PCR of RNA extracted from different developmental stages, and dissections of adults, of LA1172 line 8. The primers used were Agexon1 (SEQ ID NO. 69) and Exon 3 (SEQ ID NO. 70). The gel image shows that strong expression from the Actin-4 gene only occurs at the pupal stage, and that adult expression is generally limited to the female thorax where the flight muscles are found. Table 17, below show the contents of each lane.

TABLE 17

| | |
|---|---|
| E = pool of ~100 embryos | MH = head from male adult |
| L4 = 4$^{th}$ instar larva | MT = thorax from male adult |
| ME = early male pupa (<4 hours old) | MA = abdomen from male adult |
| FE = early female pupa (<4 hours old) | FH = head from female adult |
| MP = male pupa | FT = thorax from female adult |
| FP = female pupae | FA = abdomen from female adult |
| | −ve = water control |

SEQUENCE LISTINGS

SEQ ID NOS. 1-13 and 23-33 are described in Examples 1-12.

JY2004-tTA (SEQ ID NO. 14)—sequence of the tetO$_7$-tTA region only pP[Casper-Act5C-tTA] (SEQ ID NO. 15)
pLA513 (SEQ ID NO. 16)
pLA517 (SEQ ID NO. 17)
pLA656 (SEQ ID NO. 18)
pLA670 (SEQ ID NO. 23)
pLA710 (SEQ ID NO. 19)
pLA928 (SEQ ID NO. 20)
pLA1038 (SEQ ID NO. 24)
pLA1124 (SEQ ID NO. 21)
pLA1188 (SEQ ID NO. 22)
SEQ ID NO. 34: Open reading frame of tTAV
SEQ ID NO. 35: Protein sequence of tTAV
SEQ ID NO. 36: Open reading frame of tTAV2
SEQ ID NO. 37: Protein sequence of tTAV2
SEQ ID NO. 38: Open reading frame of tTAV3
SEQ ID NO. 39: Protein sequence of tTAV3
SEQ ID NO. 40: Pink Bollworm dsx female specific sequence fragment 1
SEQ ID NO. 41: Pink Bollworm (PBW, *Pectinophora gossypiella*) dsx female specific sequence fragment 2
SEQ ID NO. 42: Pink Bollworm (PBW, *Pectinophora gossypiella*) dsx male specific sequence
SEQ ID NO. 43: Partial gene sequence of *Aedes aegypti* dsx. All exonic sequence is included, but only partial intronic sequence—see FIGS. 47 and 48 for annotation.
SEQ ID NO. 44: Codling moth (*Cydia pomonella*) dsx female gene sequence: includes a stretch of unknown nucleotides, preferably than then 100, preferably less than 50, more preferably less than 20, more preferably less than 10, and most preferably less than 5.
SEQ ID NO. 45: Codling moth (*Cydia pomonella*) dsx-male sequence.
SEQ ID NO. 46: Sequence of pLA3435—*Bombyx mori*-dsx construct/plasmid.
SEQ ID NO. 47: Sequence of pLA3359—*Anopheles gambiae* dsx construct.
SEQ ID NO. 48: Sequence of pLA3433—Agdsx (*Anopheles gambiae*)construct with exon 2 included.
SEQ ID NO. 49: Sequence of pLA1188-cctra intron construct.
SEQ ID NO. 50: Sequence of pLA3077-a Cctra intron-tTAV construct.
SEQ ID NO. 51: Sequence of pLA3097-a Cctra intron-tTAV construct.
SEQ ID NO. 52: Sequence of pLA3233-Cctra-intron-tTAV2 construct.
SEQ ID NO 53: Sequence of pLA3014-Cctra-intron-Ubiquitin-reaperKR construct.
SEQ ID NO. 54: Sequence of pLA3166-Cctra intron-Ubiquitin-reaperKR construct.
SEQ ID NO. 55: Sequence of pLA3376-Bztra intron-reaperKR and Bztra-intron-tTAV3.
SEQ ID NO. 56: Sequence of pLA3242-Crtra intron-reaperKR construct.
SEQ ID NO. 57: Partial sequence of a male transcript generated in *Drosophila melanogaster* from LA3077 transformants that differs to the sequence generated in Medfly LA3077 lines. This sequence corresponds to the M3 transcript depicted in FIG. 36.
SEQ ID NO. 58: Partial sequence of *Bactrocera zonata* tra homologue. Sequence of intron predicted to be spliced out in a female-specific transcript of *B. zonata* tra (+ 3 to + 970 bp in sequence). Exonic flanking nucleotides are at positions 1-2 and 971-972, i.e. at the 5' and 3' ends of the intronic sequence. In fact, it is worth noting that the intronic sequence is flanked on its 5' end by a Guanine nucleotide, which is thought critical for a clean exit of the intron.
SEQ ID NO 59: Partial sequence of *Ceratitis rosa* tra homologue. Sequence of intron predicted to be spliced out in a female-specific transcript of *C. rosa* tra (+ 3 to 1311 bp in sequence). Exonic flanking nucleotides are present at positions 1-2 and 1312-3. Again, it is noteworthy that the intronic sequence is flanked on its 5' end by a Guanine nucleotide, which is thought critical for a clean exit of the intron.
SEQ ID NOS. 60-70: Primers as referred to in FIGS. 44-46 and 50-51.
SEQ ID NO. 71: Pink Bollworm (PBW, *Pectinophora gossypiella*) dsx female specific fragment 3.
SEQ ID NO. 72: Open reading frame of *Drosophila melanogaster* ubiquitin.
SEQ ID NO. 73: Protein sequence of *Drosophila melanogaster* Ubiquitin.
SEQ ID NOS. 74-105 are primers as discussed below in the Examples.
SEQ ID NO. 106 is pLA1172.

DETAILED DESCRIPTION OF THE INVENTION

The key tissue for development of filarial worms in their Culex mosquito hosts is the adult female in direct flight muscle (IFM). Although it is highly desirable to express an anti-filarial effector molecule in this tissue only, no promoter with this specificity is known. The *Drosophila* IFM Actin gene Act88F is known to be expressed correctly in the IFM's of these mosquitoes (Allen et al, 2004). Therefore, as provided in the present invention, combining the Act88F Actin gene promoter with a suitable alternative splicing mechanism that is sex-specific to the female, allows expression of an effector molecule in this tissue, in females only. Accordingly, such a system is preferred.

Many examples of suitable effector molecules are known to the person skilled in the art, for example pro-apoptotic proteins, e.g. Hid and Reaper and their suitable mutant derivatives, as described above.

The above is an example of a sex-specific alternative splicing mechanism that is capable of exerting a level of male-specific or female-specific control on the expression of a gene of interest, in this case the anti-filarial effecter molecule. Further examples of sex-specific alternative splicing mechanisms are given below, but the invention also extends to tissue-specific, stage-specific, and germ-line-specific alternative splicing mechanisms. Expression with this specificity would be very useful, but extremely difficult to obtain by any other method.

Thus it is also preferred that the at least one protein differentially expressed due to alternative splicing is effective against a pathogen, i.e. is capable of reducing or preventing the transmission of a pathogen, or human, plant or livestock disease, by a non-human transmission vector. Examples are proteins having an effector function capable of preventing transmission of the malarial parasite in mosquitoes or the parasite responsible for sleeping sickness borne by the Tsetse Fly.

Preferably, the protein blocks parasite invasion or entry into the host. Beard et al. (Beard, C. B., Cordon-Rosales, C and Durvasula, R. V. (2002). Bacterial symbionts of the triatominae and their potential use in control of Chagas disease transmission. Ann. Rev. Ent. 47:123-141.) took the bacteria which live in the gut of the Kissing Bug (which transmits Chagas disease), modified it to secrete a peptide and/or protein and re-inserted the bacteria back into the Bug. This was shown to reduce transmission of the parasitic protozoan *Trypanosoma cruzi* and, therefore, the disease.

Therefore, it is envisaged that a similar approach be taken with the malaria parasite. It is known to take bacteria (*E.coli*) which live in the gut of mosquitoes (*Anopheles stephenis*) and engineer them so they express a 'killer' gene such as ricin, and an antibody which is targeted against an essential cell surface molecule of the parasite. When these genetically modified bacteria are reintroduced back into the gut of the mosquito, this resulted in a 95% reduction in the number of oocysts formed (Yoshida, S., Ioka, D., Matsuoka, H., Endo, H. and Ishii, A. (2001). Bacteria expressing single-chain immonotoxin inhibit parasite development in mosquitoes. Mol. Biochem. Parisitol. 113:89-96).

It is also preferred that two or more alternative splicing mechanisms may be combined, to give a further level of combinatorial control. So, for example, a sex-specific alternative splicing mechanism is combined with another splicing system, for example the stage-specific splicing of *Drosophila melanogaster* Mhc exon 18, as described above, to provide a transcript expressed only in embryonic and larval male (or, alternatively, female) muscles.

A wide range of alternative splicing systems will be known to the person skilled in the art. For example, the European Bioinformatics Institute of the European Molecular Biology Organization (EMBL-EBI) hosts a database of alternatively spliced genes and sequences, and computational tools for identifying such (on the world-wide web, address ebi.ac.uk/asd, and Clark and Thanaraj, 2002; Thanaraj et al., 2004). Other examples may readily be found in the literature, for example in (Black, 2003; Burset et al., 2001; Cartegni et al., 2002; Maniatis and Tasic, 2002; Pan et al., 2004; Park et al., 2004; Smith and Valcarcel, 2000; Venables, 2002, Venables, 2004) and references contained therein. Non-limiting, The present invention may use any suitable alternative splicing system, selectable by the skilled person on the basis of the combination of expression required from his common general knowledge including those described in the art discussed herein, which is hereby incorporated by reference.

The system, therefore, preferably comprises splice control sequences derived from, of rinstance AaActin-4, Dsx, Bztra or Cctra. These and other particularly preferred examples are discussed below.

By "derived" it will be understood that it is meant that the splice control sequence is a sequence from that gene. The splice control sequence itself is a sequence, usually an intron or a substantial part is intronic sequence, which is capable of regulating or mediating the alternative splicing of the pre-mRNA transcript of the coding sequence from that that particular gene.

Tissue-specific Splicing

Tissue-specific alternative splicing mechanisms are a wide spread phenomena, occurring in both the animal and plant kingdoms. Examples in plants can be found, for instance in The Plant Alternative Splicing Database, on the world-wide web, address pasdb.genomicx.org.cn, incorporated by reference.

Preferred examples of tissue-specific alternative splicing mechanisms are given below.

In rice, the KNOX family class 2 homeobox transcripts undergo tissue-specific alternative splicing. The products of these alternative splicing events are suggested to have different degrees of abilities for activation and repression of transcription of target genes in the different organs in which they are expressed (Ito et al., 2002).

In humans, tissue-specific alternative splicing occurs in the Leukocyte common antigen mRNA. The differential splicing of LCA has a functional importance to T cells, since human T4+ cells are divided into two functionally distinct sub-populations based on expression of LCA isoforms. The sequences controlling this differential splicing can be found within exon 4, which is found in B cell mRNA but not thymocyte mRNA sequences (Streuli and Saito, 1989).

The yellow fever mosquito (*Aedes aegypti*) uses alternative splicing to generate two distinct isoforms of the lipophorin receptor (LpR). This receptor is the main transport vehicle, delivering lipids through the hemolymph to various organs. One isoform (AaLpRov) is expressed exclusively in ovarian germline cells, nurse cells and oocytes throughout the previtellogenic and vitellogenic stages, where it is utilized in yolk protein uptake. In contrast the fat-body specific AaLpRfb transcript is restricted to the post-vittellogenic period where it is important in the storage of lipid, carbohydrate and protein (Seo et al., 2003).

Stage-specific Splicing

Stage-specific alternative splicing is also known in a range of organisms, and preferred examples are given below.

Stage-specific alternative splicing of the spinach and tobacco chloroplast ascorbate peroxidase (chlAPX) pre-mRNAs, generating distinct isoenzymes are important for changing the ratio and amount of chlAPX isoenzymes during germination and subsequent greening (Yoshimura et al., 2002).

*Drosophila melangaster* exhibits a diversity of functionally distinct muscle types in various tissues at different stages of development. Alternative splicing of muscle-specific contractile proteins such as myosin, actin, tropomyosin, and troponin are key in generating this functional diversity in muscle types. Myosin heavy chain (Mhc) mRNA is predicted to produce up to 480 MHC isoforms (George et al., 1989). It is expressed in not only a tissue-specific manner but also a stage specific manner. Alternative splicing of the penultimate exon18 results in its inclusion in adult indirect flight muscles and other adult muscles mRNAs, exclusion of this exon occurs in all embryonic and larval muscle Mhc mRNA (Kazzaz and Rozek, 1989, Hastings and Emerson, 1991).

Sex-specific Splicing

Sex-specific splicing is discussed elsewhere, and it will also be appreciated that sex-specific splicing also occurs in plants and examples are well-known. A preferred example is from *Marchantia polymorpha*, a liverwort. This is a sexually heteromorphic plant and displays sex-specific alternative splicing of a calcium-dependent protein kinase, a molecule involved in intracellular signaling events. In addition, tra-2 transcripts are found exclusively in the male sexual organ (Nishiyama et al., 1999 and Nishiyama et al., 2000).

Germline-specific Splicing.

Preferred examples of germline-specific alternative splicing systems are given below.

Alternative splicing of the Wilms Tumour 1 (WT1) gene results in the incorporation of three amino acids (K, T, and S) which are thought to convert WT1 from a transcription factor to a splicing factor. This splicing factor isoform is essential for male sex determination in mice (Hammes, A et al., 2001) and regulates the expression of the SRY gene.

C3G is a ubiquitously expressed guanine nucleotide-releasing protein that binds to adaptor protein SH3 domains and is involved in the processes of cell growth, differentiation and apoptosis. The germ cell and somatic forms of this molecule are tightly regulated as there is no overlap in their expression pattern (Shivakrupa, et al 1999). The somatically expressed PKCδ is cleaved by caspase 3 resulting in its deregulation. The testes-specific variant contains an extra 78 bp which results in the addition of 26 amino acids that block caspase 3 cleavage.

The *Drosophila* P element taught in Siebel et al, 1992, is particularly preferred. Under the use of this alternative splicing mechanism, a gene of interest, such as an effector molecule or a marker, for instance, can be expressed in the germline of the host under the control of an appropriate promoter. An example of this is given below and with reference to FIG. 19.

The P transposable element in *Drosophila* is 2907 bp in length and encodes an 87 kDa transposase protein, the 'full-length' canonical form. Variants are also known, especially deletion derivatives. Synthesis of a functional transposase protein is restricted to the germline. This can only occur when all introns including the third intron (IVS3) are spliced out of pre-mRNA. Splicing of IVS3 is restricted to germ-line cells and in somatic cells is prevented by the binding of a protein complex to 30 bp of regulatory sequence at the 3' end of the second to last exon (exon 2). The presence of this intron, which contains a stop codon, left unspliced, produces a 66 kDa inactive protein which acts as a repressor towards functional transposase protein.

It is preferred to use this P element to generate germline-specific expression of a gene of interest (Gene E) by placing a portion of the P element ORF containing both exonic (at least 30 bp) and intron 3 (IVS3) upstream of a ubiquitin-Gene E fusion (See FIG. 19).

An ubiquitin fusion to the gene of interest is preferred because correct splicing of IVS3 requires exonic sequence. This sequence (P-element exon/IVS3-Ubiquitin-Gene of interest) can then be placed downstream of any promoter having germline activity, or to prevent non-specific expression, a germline-specific promoter.

This germline-specific intron can preferably be used in combination with any germline-active promoter with a desired expression pattern, for example a constitutive, sex-specific or inducible promoter (such as heatshock or Gene-Switch) as described elsewhere. This could alter the expression pattern of these promoters to become germline-specific, thereby providing a level of germ-line control of protein expression in combination with another level of control, such as environmental conditions, the presence of a hormone or inducer of protein transcription and expression.

A simple method for determining whether there is sufficient flanking sequence, or the minimal flanking sequence, required for correct germline-specific splicing is provided as follows:

(1) make a construct of the form promoter-5'flanking sequence-intron-3'flanking sequence.

(2) transfect into suitable cells, e.g. by electroporation, chemical transformation, microinjection or other suitable means known to the person skilled in the art.

(3) after incubation for a suitable period of time, which will depend in part on the species and cell type, extract RNA, RT-PCR the RNA corresponding to the construct and analyse, e.g. by gel electrophoresis and/or sequencing, to determine the splicing pattern.

If this is suitable for the purpose, there is sufficient flanking sequence. If not, more flanking sequence must be included and this can be repeated. If it is desired to determine the minimum suitable flanking sequence, then make a series of deletion derivatives of the construct until this is determined.

It is particularly preferred, however, that the alternative splicing mechanism is sex-specific. This allows expression of a protein of interest in a sex-dependent manner. For instance, if the promoter and/or enhancer of the gene expression system are switched on in muscles, the inclusion of a sex-specific alternative splicing mechanism means that expression of the protein can be either in male muscles only, or, alternatively, in female muscles only.

A particularly preferred example is the sex-specific control of the tetracycline transcriptional transactivator protein, tTA, or suitable variants and mutants thereof, such as tTAV, as described herein in Example 12, and tTAV2 and tTAV3.

For instance, under the control of an alternative splicing mechanism, a functional transcriptional transactivator protein can be produced only in females, with the result that expression of the system is found only in females, such that the females are adversely affected, and may indeed die as a consequence. However, in males, a different splicing combination is achieved, such that the transcriptional transactivator protein is not expressed or is not functional, with the result that the lethal effecter gene is not expressed so that the males survive. In this way, males and females may be easily separated.

Suitable organisms under which the present system can be used include mammals such as mice, rats and farm animals. Also preferred are fish, such as salmon and trout. Plants are also preferred, but it is particularly preferred that the host organism is an insect, preferably a dipteran or tephritid. Preferably, the organism is not a human, preferably non-mammalian, preferably not a bird, preferably an invertebrate, preferably an arthropod.

In particular, it is preferred that the insect is from the Order Diptera, especially higher Diptera and particularly that it is a tephritid fruit fly, preferably Medfly (*Ceratitis capitata*), preferably Mexfly (*Anastrepha ludens*), preferably Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha oblique*). It is also particularly preferred that the host organism is a mosquito, preferably from the genera Stegomyia, Aedes, Anopheles or Culex. Particularly preferred are *Stegomyia aegyptae*, also known as *Aedes aegypti, Stegomyia albopicta* (also known as *Aedes albopictus*), *Anopheles stephensi, Anopheles albimanus* and i Anopheles gambiae.

Within Diptera, another preferred group is Calliphoridae, particularly the New world screwworm (*Cochliomyia hominivorax*), Old world screwworm (*Chrysomya bezziana*) and Australian sheep blowfly (*Lucilia cuprina*). Lepidoptera and Coleoptera are also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae. Among Coleoptera, Japanese beetle (*Popilia japonica*), White-fringed beetle (*Graphognatus* spp.), Boll weevil (*Anthonomous grandis*), corn root worm (*Diabrotica* spp) and Colorado potato beetle (*Leptinotarsa decemlineata*) are particularly preferred.

It is, as mentioned above, particularly preferred that the alternative splicing mechanism is sex-specific. Preferably, this may include the AaActin-4 mechanism, which is a gene from *Stegomyia aegypti* which shows tissue, stage and sex-specific splicing (see Act4-tTAV-LA1172, for instance in Example 20). It is also preferred that the splicing mechanism comprises at least a fragment of the *Drosophila* doublesex gene. However, it is particularly preferred that the alternative splicing mechanism is derived from the Medfly transformer gene Cctra, or from another ortholog or homolog of the *Drosophila* transformer gene, especially one derived from a tephritid fruit fly. This will be discussed in greater detail below and, although these are preferred examples, they are not limiting on the scope of the invention.

Although there a number of recent discussions in the art of combining gene expression systems with alternative splicing mechanisms to result in recombinant gene regulation, none of these groups have actually been successful in providing a construct capable of achieving this end.

In particular, Rafael et al (February 2004) disclose that "a similar approach could be achievable in any insect, including tephritids, provided that species-specific regulatory elements and lethality genes or genetic constructs are isolated. The yolk protein regulatory elements, which have been isolated from *B. tryoni*, may form the basis for female-specific expression of a transgene in this species. Alternately, the regulatory elements which control dsx sex-specific splicing may be manipulated such that the effects of a lethal gene are only observed in females of a line which carries an engineered dsx construct."

Similarly, Crisanti's and Scali's (2005) paper on the Doublesex gene derived from *Anopheles gambiae* hints that "[t]he identification of female- and male-specific transcripts of Agdsx represents an important step towards the understanding of the sex differentiation process in *A. gambiae* and will facilitate the development of genetic tools to induce male sterility or manipulate sex ratios in mosquitoes, for instance by constitutively expressing the female-specific form of dsx in the male gonads or by inducing the sex-specific splicing of a dominant lethal".

Therefore, although there is some discussion in the recent art of the need for effective systems combining alternative splicing with heterologous gene expression, these have been only *desiratum* and have not led to working examples. Indeed, Scott et al (Scott et al., 2004) try to use a composite system, comprising more than one splicing cassette, including part of *Drosophila* doublesex, but concluded that the constructs spliced in the expected "female-specific" pattern in both males and females. Accordingly, they were not able to achieve sex-specific splicing, as a single splice variant was found in both males and females.

It is preferred that the present system uses a single splicing cassette for reasons of efficiency and to avoid the risk that the function of the alternatively spliced intron is modified or compromised by heterologous sequence placed close to it.

Surprisingly, the present inventor has discovered that it is possible to provide an alternative splicing mechanism that can be used, optionally together with additional splice control sequences, in combination with a gene expression system for at least one gene or protein of interest, whereby the alternative splicing mechanism is capable of providing a level of additional control, for instance in a sex-specific or tissue-specific manner, as discussed elsewhere. Stage-specific and germ-line-specific alternative splicing mechanisms are also preferred. However, sex-specific alternative splicing mechanisms are most preferable.

Whilst it is preferred that the alternative splicing mechanism comprises at least fragments of any of the following genetic elements, selected from the group comprising 5' and/or 3' flanking sequences, exonic sequences, 5' untranslated region (UTR), the 3' untranslated region (3' UTR) and, of course, the intron, it is preferred that the alternative splicing mechanism comprises only short exonic sequences from the flanking regions surrounding the intron in its native context, preferably shorter than 50 nucleotides at each end, and particularly preferred that the alternative splicing mechanism consists entirely of the intron alone or fragments thereof, i.e. without any additional sequences from the flanking regions, the UTR's or exons which would be adjacent to the intron in its native context.

By "native context" it is meant that that the intron, for instance in its wild-type form in nature, is found in association with exon(s) and a promoter, and thus had specific sequences adjacent to it. However, it is preferred to use the intron substantially without these adjacent sequences, i.e. it may be used including only a fragment of these adjacent sequences, but is it preferred that none of the residues of these adjacent sequences are included.

However, when used according to the present invention, the intron will be surrounded by exonic sequences, which will preferably be new or heterologous sequences.

Although the Cctra intron will splice without requiring any specific exonic sequences derived from the Cctra gene, it is not obvious that this is the case for all introns. Exonic splice enhancers (ESEs) and silencers (ESSs) are prevalent in most, if not all, exons and can be important in alternative splicing (Cartegni, et al., 2002). Where exonic sequences are required for efficient operation of the alternative splicing mechanism, it is preferred that the system also include an ubiquitin protein cleavage system (Varshaysky, 2000). The ubiquitin fusion technique greatly increases the ranges and ease of application of alternative splicing as a method for controlling gene expression.

Many proteins will still function with additional amino acids fused to their amino (N) or carboxy (C) termini. This is widely used, for example to fuse an epitope tag, or a fluorescent protein, to a protein of interest, without disrupting its normal function. It is, therefore, preferred to use alternative splicing cassettes which encode one or more amino acids in all alternative splicing variants, by fusing part or all of the alternatively spliced protein to the protein of interest, typically with the alternatively spliced protein at the N-terminus.

FIG. 20 illustrates this, using dsx as example of alternative splicing. Application of this principle to other forms of alternative splicing will be clear to the person skilled in the art.

Of these, version A gives male-specific expression by inserting additional exonic material in the female, disrupting or modifying the function of the protein in females (e.g.) by addition of another protein domain, or premature termination. Version B gives male-specific expression by fusing the protein of interest to the male-specific coding sequence, as can versions C and D, though alternative configurations are also possible. In each case, this would represent the fusion of heterologous sequence to the N-terminus of the protein of interest.

Though the function of many proteins is known not to be affected by such N-terminal fusions, this is not true for all proteins. For example, many secreted or transmembrane proteins have a signal sequence that must form the N-terminus of the coding region. As another example, the proapoptotic protein Reaper is known to have a functional domain, probably involved in binding to dIAP1/Thread, which must be at the N-terminus of the protein. Fusions to the N-terminus, in some cases even of a single amino acid can, therefore, tend to inactivate Reaper (Olson et al., 2003).

However, in order to overcome the limitation of N-terminal fusions, it is particularly preferred to use amino acid or polynucleotide residues coding for at least the cleavage site portion of ubiquitin, more preferably the full protein sequence.

The nucleotide and protein sequences for ubiquitin are SEQ ID NOS 72 and 73, respectively.

It is preferred that the expression system, therefore, comprises nucleotides encoding at least the cleavage site of ubiquitin, and preferably the nucletode sequence according to SEQ ID NO. 72. This is preferably arranged such that the unbiquitin orp portion thereof is substantially N-terminal to the protein of interest, but more preferably immediately N-terminal (i.e. immediately adjacent) the protein of interest.

This arrangement will reduce the size of, or eliminate, the N-terminal fusion to the post-cleavage (mature) protein. However, in the specific case of a signal peptide, it is known that in some cases, in order to function normally, this signal must be present at the N-terminus of the primary translation product. In such a case it is preferred that the protein be expressed without a fusion N-terminal of the signal sequence.

Ubiquitin proteases will then cleave the protein of interest from the ubiquitin moiety, allowing the correct folding of the N-terminus of the downstream protein. So, if the entire fusion protein is:

Start codon–segment of alternatively spliced gene–
ubiquitin–protein of interest the protein of interest will cleaved from the ubiquitin moiety and retain normal folding and function.

Where suitable ubiquitin proteases are not constitutively expressed or expressed at a suitable level, it is preferred that the present invention comprises polynucleotides coding therefor, preferably under the control of a suitable promoter, such that expression of the ubiquitin protease is preferably linked to expression of the fusion protein.

Using this particularly preferred method, alternative splicing can be used, even if the alternative splicing requires exonic signals some distance from the intron itself, and if the specific alternative splicing strategy requires the intron to be in a translated region (and therefore requires the synthetic construct to have a significant amount of coding region derived from the source of the alternative splicing) and if the protein of interest will not tolerate fusions.

If required, several proteins could be controlled by the same regulatory system, by inserting a ubiquitin moiety between each. . In such a case, it is preferred that a stabilized mutant derivative of ubiquitin, for example ubiquitin$^{K48R}$ (Rasoulpour et al., 2003; Finley, et al., 1994), be used as the ubiquitin moiety.

Indeed, where reference is made to the term "ubiquitin" is made, it will ube inderstodd that it includes ubi$^{K48R}$ and all suitable substrates of ubiquitin. Under some circumstances, a similar effect could be obtained by using a stop codon and an internal ribosome entry sequence (IRES) to separate the coding regions.

It is also preferred to vary the level of control by using alternative splicing, e.g. the as dsx system above, to provide different C-termini for a protein. Specific signals, for instance a prenylation motif (such as—CAAX from Ras) differentially incorporated into these alternate C-termini affect protein function and/or location.

In order to differentially affect protein stability, it is preferred to incorporate signals regulating stability into the genetic system, such as PEST sequences, as are found in many rapidly degraded proteins. These sequences have been suggested to serve as signals for proteolytic degradation. From a survey of the amino acid sequences of 10 short-lived eukaryotic proteins, Rogers et al. [Science. 1986; 234:364-368] found the proteins to contain one or more regions rich in proline (P), glutamic acid (E), serine (S), and threonine (T). These regions are often flanked by positively charged amino acids.

Similarly, it is also preferred to incorporate [polynucleotides encoding RNA stability or instability signals into the genetic system according to the present invention, or signals affecting protein or RNA location, translation, for instance.

The issue of saturation is another generic objection raised in the art to the artificial use of alternative splicing to regulate gene expression. However, this is overcome by a preferred embodiment of the present invention. It is suggested in the att that the factors regulating alternative splicing are thought to be in relatively short supply, so that the alternative splicing pathway or system can be saturated if too much pre-mRNA (primary transcript) is provided (Stoss et al., 1999, Stoss 2001, Yali and Pin Ouyang., 2006).

We have, surprisingly, shown that this is not the case, in Cctra in positive feedback constructs, in that the system is not prevented from functioning as desired. For tra, the default splicing is in the male pattern; female-type splicing to give transcript F1 (FIG. 21) occurs only in the presence of a splicing complex which includes Tra and Tra-2 proteins.

Tra is expressed only in females and so this complex is present only in females. There is no reason to think that these are particularly abundant proteins. For the female-specific positive feedback system to work, i.e. to kill females, very large amounts of tTA need to be produced.

tTA is only produced from transcripts spliced in the female (F1) form, so correspondingly large amounts of this transcript have to be produced. That this is readily accomplished implies that the Tra/Tra2-dependent sex-specific splicing system is not easily saturated.

We have optimized and resynthesized the original tTA sequence for use in *Anopheles gambiae*, *Bombyx mori* and *Drosophila melanogaster* and generated the variants tTAV (SEQ ID NO. 34-DNA, SEQ ID NO. 35-protein), tTAV2 (SEQ ID NO. 36-DNA, SEQ ID NO. 37-protein) and tTAV3 (SEQ ID NO. 38-DNA and SEQ ID NO. 39-protein).

Thus, in a preferred aspect of the invention, the expression system comprises nucleotides encoding tTA or its functional variants and mutants, in particular those selected from the group consisting of: tTAV (SEQ ID NOS. 34 and 35), tTAV2 (SEQ ID NOS. 36 and 37), and tTAV3 (SEQ ID NOS. 38 and 39), being highly effective tTA variants.

It is, therefore, particularly preferred that the present invention comprises a repressible transactivator protein in combination with the alternative splicing mechanism.

Preferably this is the tet system described herein, and in particular, comprises the tTAV variants described above.

Thus, it is also particularly preferred that the genetic system is used in combination with a further control system. A preferred further control system is the positive feedback system described herein.

AaActin-4

An example of a sex-specific alternative splicing mechanism is AaActin-4. This is a gene from *Stegomyia aegypti* (formerly *Aedes aegypti*), which also shows sex-specific splicing. We have shown that a fragment of this gene, including the intron, a large amount of 5' flanking sequence and a little 3' flanking sequence, splices correctly when reintroduced into this mosquito.

There is a single publication on this gene, which does not mention sex-specific splicing (Muñoz et al., 2004). We've made transgenic mosquitoes (*Stegomyia aegypti*) carrying a fragment of this gene, which is spliced correctly, but a fragment that contained the female intron only was not correctly spliced in Medfly (spliced in the male pattern in both males and females).

It is preferred that Actin-4 is used in combination with the tTAV variant system discussed above.

Dsx and Tra

It is more preferable, however, that the alternative splicing mechanism is dependent on the transformer (tra) gene from insects such as *Drosophila* or Medfly, or its homologues. This protein acts in a complex that also comprises the product of the transformer-2 (tra-2) gene, or its homologues; this complex is involved in the genetic control of sexual differentiation (Pane et al., 2002; Saccone et al., 2002). In particular, these genes and their gene products act on the doublesex genes from *Drosophila*, and its homologues in other species; homologues of dsx are present throughout the insect world, for instance. Tra/tra-2 also act on the Medfly transformer gene which acts as an additional level of control in Medfly and similar insects including *Ceratitis rosa, Drosophila melanogaster, Bactrocera zonata*, and *Anastrepha ludens*.

When the doublesex alternative splicing mechanism is used, it is preferred that the genetic system is used in Diptera, preferably including those described above.

Particularly in the case of Dipterans, it is preferred that tra and/or tra-2 are expressed in either the male or the female host or organism.

Alternatively, it is also preferred that tra/tra-2 themselves form part of the genetic system and the respective proteins may be encoded by nucleic acids provided in a construct or constructs which form part of the genetic system according to the present invention, under the control of suitable promoters.

In this way, the skilled person will be able to separately control the expression of tra and/or tra-2 and, therefore, allow the user an additional level of spatial or temporal control, i.e. to allow the user to initiate alternative splicing at predetermined point. This could be achieved by linking the tra/tra-2 genes to a promoter, such as the hsp70 heat shock promoter, which can be initiated by high temperatures, thereby leading to expression of the tra and tra-2 proteins, which in turn allow alternative splicing to proceed, at a user-defined time and in an easily controllable manner.

For instance, this allows both and control of, for instance, the Cctra intron in species that have divergent tra (or no tra at all), by expressing tra in a particular stage- or tissue-specific manner. It also allows regulated expression in males, who would not normally express tra. However, to ensure sex-specific expression, by this mechanism, in a species that doesn't have equivalent tra, one may need to arrange differential sex-specific expression of tra, as will be apparent to the skilled person.

When using an alternative splicing mechanism comprising the doublesex mechanism, it is preferred that exonic signals from the doublesex gene are present. In this instance, it is particularly preferred that the following sequences are used:

1) the tra/tra2 binding sites (T/A)C(T/A)(T/A)C(A/G) ATCAACA (Hedley et al., 1991, Hoshijima et al., 1991, Ryner et al., 1991);

2) Medfly dsx mRNA (Genbank ID number AF435087: on the world-wide web, address ncbi.nlm.nih.gov/entrez/viewer.fcgi?db=nucleotide&val=24637185):

3) Pink boll worm dsx female specific 1 exonic sequence (SEQ ID NO. 40);

4) PBW dsx-female specific 2 sequence (SEQ ID NO. 41);

5) PBW male specific sequence (SEQ ID NO. 42);

6) Anopheles gambiae dsx gene sequence (Genbank ID number Gil 9611767);

7) Aedes aegypti dsx gene sequence (Supercontig 1.370 (on the world-wide web, address broad.mit.edu/annotation/disease_vector/aedes_aegypti/) and SEQ ID NO. 43);

8) Codling moth dsx gene sequence from females (SEQ ID NO. 44) and males (SEQ ID NO. 45).

Dsx

Where the genetic system of the present invention consists or comprises construct, it is preferred that the construct is selected from the group consisting of: LA3435 (SEQ ID NO. 46 and FIG. 22-vector map), LA3359 (SEQ ID NO. 47 and FIG. 23-vector map) and LA3433 (SEQ ID NO. 48 and FIG. 24-vector map). Dsx is also discussed in more detail elsewhere.

Tra

A particularly preferred example of an alternative splicing mechanism that is sex-specific is the transformer intron from Medfly, referred to as Cctra. This is an example of an "intron-only" alternative splicing mechanism, as it does not necessarily require the presence of exonic, 5' or 3' flanking or untranslated region sequences.

Figure 16:
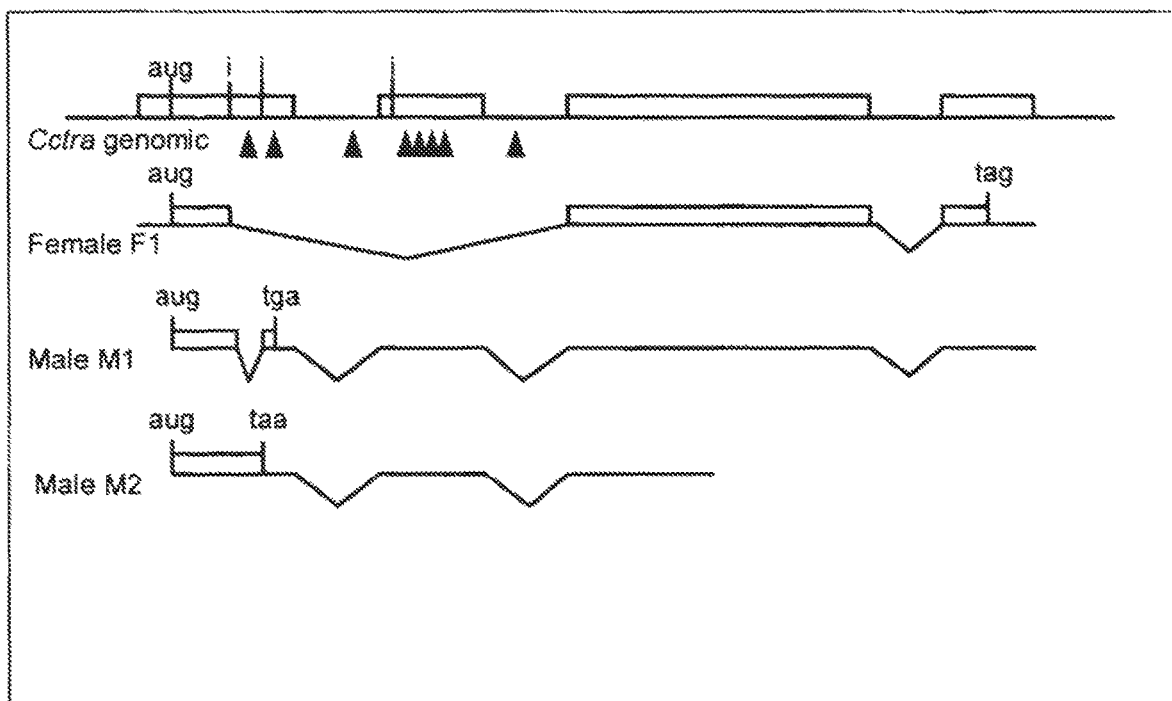
FIG. 16 illustrates the sex-specific splicing of Cctra in medfly.
Figure 17:
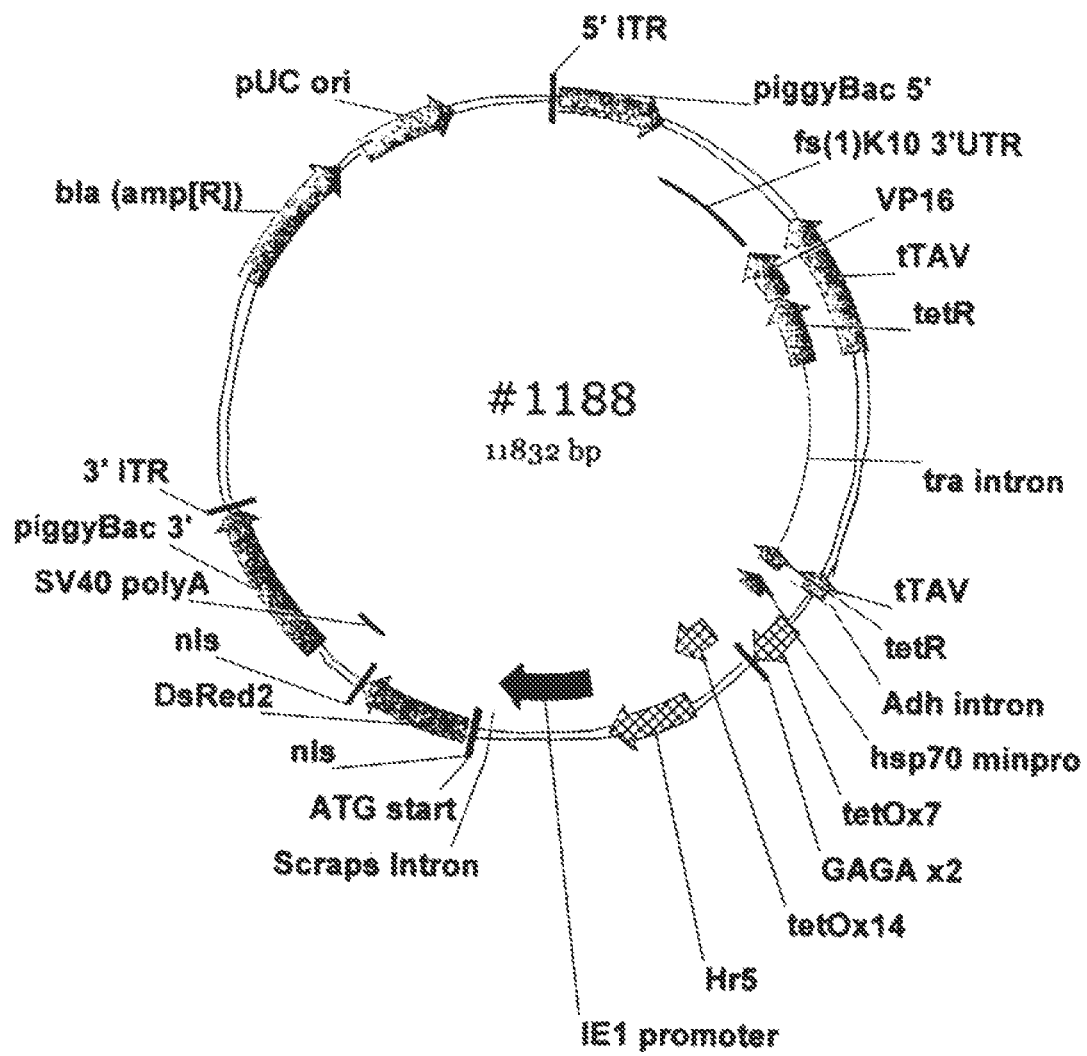
FIG. 17 is a schematic diagram of pLA1188.
Figure 18:
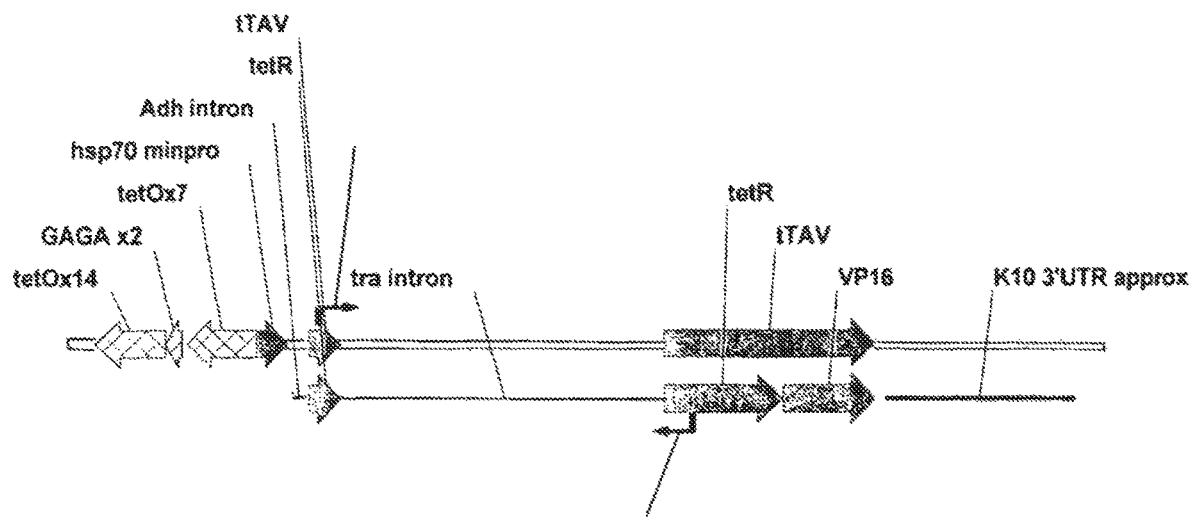
FIG. 18 illustrates sex-specific splicing in medfly.

The splicing mechanism of Cctra was first described in Pane et al (2002) as referred to in Example 12 and accompanying FIG. 16. The disclosure of Pane et al 2002 is hereby incorporated by reference.

This alternative splicing mechanism or cassette produces 3 splice variants in females, one of which is female-specific (called F1). The other two are called M1 and M2 and are also found in males. Thus, F1 is found only in females, whilst M1 and M2 are found in both males and females. Since each of the non-sex-specific transcripts (i.e. M1 and M2) contain additional exonic material with stop codons, only the female splice variant (F1) produces functional protein. Thus, where each genetic system comprises or consists of a construct, it is preferred that said construct is LA1188 and, most preferably, LA3077 or LA3097.

Although LA1188 (SEQ ID NO. 49 and FIG. 25-vector map) is functional, it is not preferred, as it can induce a frame shift.

Thus, it is particularly preferred that the construct comprises LA3077 (SEQ ID NO. 50 and FIG. 26-schematic), LA3097 (SEQ ID NO. 51 and FIG. 27-schematic), LA3233 (SEQ ID NO. 52 -sequence and FIG. 28-schematic), LA3014 (FIG. SEQ ID NO. 53 and FIG. 29-schematic), LA3166 (SEQ ID NO. 54 and FIG. 30-schematic), LA3376 (SEQ ID NO. 55 and FIG. 31-schematic) and LA3242 (SEQ ID NO. 56 and FIG. 32-schematic).

Other constructs, for instance plasmids, preferably comprise a 5' TG immediately adjacent the intronic sequence, and preferably also comprise a flanking GT sequence immediately 3' to the end of the intronic sequence. In particular, it is preferred that the intron is flanked on both 5' and 3' ends by Guanine nucleotides, in order to ensure a "clean exit" when the intron is spliced out, such that additional nucleotides are not also spliced out which may lead to a frame shift.

However, if additional nucleotides are to be excised, in the splicing process, then it is preferred that these are excised in blocks or multiples of 3, so that there is no significant frame shift.

It is most particularly preferred, however, that the intronic sequences flanked on its 5'end by a Guanine nucleotide as this is of greatest importance when seeking to ensure a clean exit. It will be apparent to the person skilled in the art that a flanking G nucleotide can be readily provided without the incorporation of specific flanking exonic sequences from the gene from which the intron is derived, by identifying suitable sequences (e.g. TGGT, 5'G, etc) within the sequence of interest (that into which the intron is to be inserted). The redundancy of the genetic code means that this can readily accomplished.

Since protein coding regions generally begin with the nucleotide sequence 5'-ATG-3', in a particularly preferred embodiment, the TG of this ATG sequence comprise the nucleotides immediately preceding the intron, for example 5'UTR-ATG-intron-GT-3'.

Within this, preferred examples place the coding sequence for either ubiquitin or tTA, or their functional mutants and or variants such as tTAV, tTAV2 or tTAV3, 3' to the intron. These are arranged so that these elements are substantially adjacent to the 3' end of the intron, more preferably the such that the coding region starts within 20 nucleotides or less of the 3' intron boundary), and most preferably, immediately adjacent the 3' end of the intron. Preferred examples of constructs according to the present invention are listed in Table 16, below.

TABLE 16

| Construct NO. (FIGS #.) | Species tra intron is from | position from ATG | tra intron is fused to- |
|---|---|---|---|
| LA3014 (29) | Medfly | +22 bp | Ubiquitin |
| LA3166 (30) | Medfly | +136 bp | Ubiquitin |
| LA3097 (27) | Medfly | +0 bp | tTAV |
| LA3077 (26) | Medfly | +61 bp | tTAV |
| LA3233 (28) | Medfly | +0 bp | tTAV2 |
| LA3376 (31) | Medfly | +0 bp | tTAV2 |
| LA3376 (31) | B. zonata | +3 bp | Reaper KR |
| LA3376 (31) | B. zonata | +0 bp | tTAV3 |
| LA3242 (32) | C. rosa | +3 bp | reaperKR |

Table 16 shows constructs which contain a tra intron. The introns were derived from from C. capitata, B. zonata or C. rosa (column 1). Said intron was inserted within the coding region such that the distance between the putative initiator ATG and the last nucleotide of the exon immediately preceding the tra intron was as should in column 2. Intron is inserted into or adjacent to coding region for either ubiquitin, tTAV or reaper$^{KR}$, as shown in column 3. These were generated and shown to successfully splice, by RT-PCR or phenotypically in Medfly and, in some cases, also either in Drosophila melanogaster (LA3077) or Anastrepha ludensi (LA3097, LA3233). In addition, the distance between the ATG and the end of the exon immediately preceeding the tra intron (assuming splicing in F1-like form) can range from 0 bp to +228 bp without adverse consequences to splicing (see Table 16, column 3).

As mentioned above when an intron is placed 5' to a protein coding region (ORF-X), it is preferred to position or use ubiquitin 3' to the intron, 5' to ORF-X, thus and providing female-specific regulation of ORF-X, whilst introducing physical separation between that sequence and the tra intron, thereby reducing the chance that sequences within ORF-X will interfere with the splicing of the tra intron.

Composite constructs and sequences are also envisaged, for example of the form:

X-ubi-Y with the alternatively spliced intron inserted between coding region X and the region encoding ubiquitin (ubi), or within the ubiquitin coding region, or between the region encoding ubiquitin and coding region Y. Thus X will be expressed irrespective of the splicing of the intron, while Y will only be expressed when the intron is spliced in a suitable form. Further configurations and arrangements of this general type will be apparent to the person skilled in the art.

Of course, it may be that the skilled person wishes to introduce a frame shift during the splicing process so that the pre-mRNA is spliced into mRNA that is not capable of being transcribed into a functional protein.

The frame-shift may be useful for a number of reasons. Firstly, as discussed above, it may be to introduce a stop codon or may otherwise result in a protein having reduced or no activity.

Alternatively, the frame-shift may be employed, in a manner similar to retro-viruses, for instance, to encode at least two different proteins from the same nucleotide sequence, by using overlapping coding sequences. One can, therefore, introduce a frame shift so that a sequence is read in one frame if the (preceding) intron is spliced in one form and a different frame if spliced in another. This allows one to get two different encoded proteins without tampering with sequence internal to the intron.

It has also been found that it is possible to employ a positive feedback mechanism both to enhance the effect of an insect promoter, as well as to control its expression.

Thus, in a further aspect, the present invention provides a gene expression system, comprising at least one gene to be expressed and at least one promoter therefor, wherein a product of a gene to be expressed serves as a positive transcriptional control factor for the at least one promoter, and whereby the product, or the expression of the product, is controllable. Preferably, the system is for expression in insects.

As used herein, the term "gene" refers to any DNA sequence that may transcribed or translated into a product, at least one such having activity or function in vivo. Such a gene will normally have at least a transcription promoter and a terminator operably associated therewith.

The product capable of positive transcriptional control may act in any suitable manner. In particular, the product may bind to an enhancer located in proximity to the promoter or promoters, thereby serving to enhance polymerase binding at the promoter, for example. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, for example, or the product may bind the inhibitor directly, thereby preventing inhibition of transcription or translation.

More preferably, the mechanism is a positive feedback mechanism, wherein the product, which may either be RNA or the translation product thereof, acts at a transcription enhancer site, normally by binding the site, thereby enhancing promoter activity. Enhancement of the promoter activity then serves to increase transcription of the gene for the product which, in turn, further serves to either lift inhibition or enhance promotion, thereby leading to a positive feedback loop.

Control of the product may be by any suitable means, and may be effective at any level. In particular, it is preferred that the control be effective either to block transcription of the control factor gene or to block translation of the RNA product thereof, or to prevent or inhibit action of the translation product of the gene.

For example, the gene product of tTA (tetracycline-repressible transcription activator) acts at the tetO operator sequence (Baron and Bujard, 2000; Gossen et al., 1994; Gossen and Bujard, 1992). Upstream of a promoter, in either orientation, tetO is capable of enhancing levels of transcription from a promoter in close proximity thereto, when bound by the product of the tTA gene. If the tTA gene is part of the cassette comprising the tetO operator together with the promoter, then positive feedback occurs when the tTA gene product is expressed.

Control of this system is readily achieved by exposure to tetracycline, which binds to the gene product and prevents transactivation at tetO.

The tTA system also has the advantage of providing stage-specific toxicity in a number of species. In particular, "squelching" is observed in the development phases of many insects, the precise phase of susceptible insects being species-dependent. Some insects may reach pupation before the larva dies, while others die early on. Susceptibility ranges from 100% fatality to a small reduction in survival rates. In general, though, adult insects appear to be immune to the squelching effect of tTA, so that it is possible to raise insects comprising a tTA positive feedback system in the presence of tetracycline, and then to release the adult insects into the wild. These insects are at little or no competitive disadvantage to the wild type, and will breed with the wild type insects, but larvae carrying the tTA positive feedback cassette will die before reaching maturity.

It is relatively straightforward to modify the tTA sequence to enhance compatibility with the desired insect species, and this has been demonstrated, in the accompanying Examples, with tTAV, which has an additional two amino acids to provide a protease site, but which is encoded by a sequence substantially changed from that of tTA in order to more closely follow *Drosophila* usage.

Accordingly, in a preferred aspect, the present invention provides a system as described, wherein at least one gene is tTA, or is a gene encoding a similar product to tTA effective to up-regulate the tetO promoter.

Thus, the present invention is useful in combination with a dominant lethal gene, allowing selective expression of the dominant lethal gene, or stage specific expression, as desired, of the lethal gene or the lethal phenotype. It will be appreciated that the dominant lethal gene does not need to be an integral part of the positive feedback mechanism, but may be part of a bicistronic cassette, for example. Use of the present invention in association with RIDL (Release of Insects carrying a Dominant Lethal) is particularly preferred.

Control of the feedback mechanism, in the case of tTA or an analogue thereof, is simply effected by the presence or absence of tetracycline, or by modulating tetracycline concentration, when the tTA gene product is used. In the case of another preferred positive feedback system, GAL4, this may be controlled by temperature, for example, thereby suppressing the effective gene, preferably a dominant lethal gene, until release of the insect.

Other mechanisms may also be employed, such as ribozymes or antisense or partially self-complementary RNA molecules, such as hairpin RNA, to inhibit or prevent expression of an activating peptide, or blocking agents that prevent binding of the activator to the enhancer site.

Such blocking agents may be expressed by the insect itself under selective conditions, or may be administered as part of the culture medium, for example.

Where the blocking, or controlling agents are produced by the insect, then it is preferred that their expression be selective, such as being sex specific. Administration of the blocking agent in the culture medium, for example, will enable suppression of the positive feedback cassette under all circumstances until release of the insect, after which stage- or sex- specific selection will occur, preferably in a succeeding generation, particularly preferably the following generation.

More preferably, the cassette comprising the positive feedback mechanism is associated with stage- or sex- specificity. For example, sex specific splicing is observed with the transformer and doublesex mechanisms seen in most insects, and can be employed to limit expression of the feedback system to a particular sex, either by employing sex specific splicing to delete all or part of the effector gene, or to incorporate a frameshift or stop codon, or to modulate RNA stability or mRNA translational efficiency, for example, or otherwise to affect expression so as to differentiate between the sexes. Targeting the females of pest species is particularly preferred.

Although it is possible to provide the effector gene in a separate location and even on a separate chromosome, it is generally preferable to link the effector gene with the feedback gene. This may be achieved either by placing the two genes in tandem, including the possibility of providing the two as a fusion product, or for example by providing each gene with its own promoter in opposite orientations but in juxtaposition to the enhancer site.

An effector gene is the gene whose expression it is desired to enhance. Where a positive feedback product is also effective as a stage-specific lethal, such as tTA in many species, then the effector and the feedback gene may be one and the same, and this is a preferred embodiment.

The effector gene will often be a lethal gene, and it is envisaged that the system of the present invention will most frequently be employed in the control of insect pest populations, particularly in combination with the RIDL technique or related method, as described hereinunder.

It is preferred to include a marker with the systems of the invention, such as DsRed, green fluorescent protein, and variants thereon, as transformation success rates in insects are extremely low, so that it is useful to be able to select in some way.

The promoter may be a large or complex promoter, but these often suffer the disadvantage of being poorly or patchily utilised when introduced into non-host insects. Accordingly, it is preferred to employ minimal promoters, such as the Hsp70 promoter which, while having a naturally somewhat low level of activity, can be substantially enhanced by a positive feedback scenario, such as by the use of tTA and tetO.

A promoter is a DNA sequence, generally directly upstream to the coding sequence, required for basal and/or regulated transcription of a gene. In particular, a promoter has sufficient information to allow initiation of transcription, generally having a transcription initiation start site and a binding site for the polymerase complex. A minimal promoter will generally have sufficient additional sequence to permit these two to be effective. Other sequence information, such as that which determines tissue specificity, for example, is usually lacking, and preferred minimal promoters are, normally as a direct result of this deficiency, substantially inactive in the absence of an active enhancer. Thus, a cistron, or system, the two terms preferably being generally interchangeable herein, of the invention will generally be inactive when the or each promoter is a minimal promoter, until a suitable enhancer or other regulatory element is de-repressed or activated, typically the gene product.

Thus, it will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from hsp70, a P minimal promoter (exemplified hereinunder as WTP-tTA), a CMV minimal promoter (exemplified hereinunder as JY2004-tTA), an Act5C-based minimal promoter, a BmA3 promoter fragment, and an Adh core promoter (Bieschke, E., Wheeler, J., and Tower, J. (1998). Doxycycline-induced transgene expression during *Drosophila* development and aging. Mol Gen Genet 258, 571-579). Act5C responds to tTA in transgenic Aedes, for example, and the invention.

Not all minimal promoters will necessarily work in all species of insect, but it is readily apparent to those skilled in the art as to how to ensure that the promoter is active. For example, a plasmid, or other vector, comprising a cistron of the invention with the minimal promoter to be tested further comprises a marker, such a gene encoding a fluorescent protein, under the control of a promoter known to work in that species, the method further comprising assaying putative transgenic individuals for expression of the marker, and wherein individuals expressing the marker are then assayed for expression of the gene under the control of the minimal promoter, such as by assaying transcribed RNA. Presence of the RNA above background levels under induced or de-repressed conditions is indicative that the minimal promoter is active in the species under investigation; absence or presence at low levels only of such RNA in non-induced or repressed conditions is indicative that the minimal promoter has low intrinsic basal activity.

We have used the following marker promoters, by way of example, only, but many more are useful and apparent to those skilled in the art:

mini-white (white promoter): WTP2-tTA, JY2004-tTA
Act5C promoter: LA513 and LA517
ubi-p63E promoter: LA656 and LA1038
BmA3 promoter: LA710
hr enhancer and ie1 promoter: LA928, LA1124 and LA1188 and all of these are useful as, or in the preparation of, minimal promoters.

It will be appreciated that a cistron or system of the invention may comprise two or more cistrons. A system may further comprise non-linked elements, such as where a second gene to be expressed is remote from the positive feedback cistron.

Figure 1:
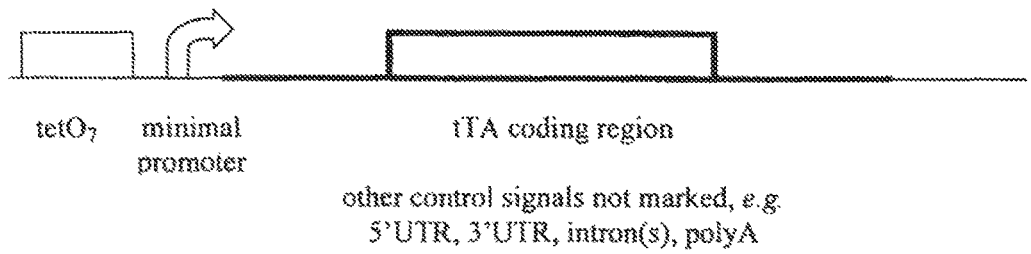
FIG. 1 shows a tetracycline-repressible transcription activator scenario.

Thus, in a preferred aspect, the present invention provides positive feedback constructs of the general form shown in accompanying FIG. 1. In this scenario, the tetracycline-repressible transcription activator (tTA) protein, when expressed, binds to the tetO operator sequence and drives expression from a nearby minimal promoter. In the configuration shown, this then drives expression of tTA, which then binds to tetO, and so on, creating a positive feedback system. This system is inhibited by tetracycline, which binds to tTA and prevents it binding tetO.

Expression is controllable, and this may be achieved by operably linking the promoter to a controllable transcription factor. As illustrated above, this may be tTA (tetracycline-repressible or tetracycline-inducible), or any other factor controllable system, such as GAL4 (which is somewhat cold-sensitive, and can be further controlled by use of GAL80 or mutants thereof), or the streptogrammin regulated expression system, for example. It will be appreciated that other binding sites for the appropriate transcription factor will depend on the transcription factor concerned, such as $UAS_{GAL4}$ (upstream activation sequence) for GAL4, for example.

Preferred systems of the present invention have high levels of induced expression, preferably available at several induced levels, with a low basal level of expression of the regulated gene but also of any other component, and preferably across a range of species. Basal levels are preferably low or substantially non-existent where expression is strongly deleterious, but acceptable levels will depend on the effect of the product. Maximum levels will not generally be an issue, as the positive feedback condition will often provide fatal levels of expression and, even where the expression product is not fatal, or associated with fatal consequences, it is likely to be expressed in far higher concentrations than most gene products.

Where a basal level of expression is desired, then a promoter sequence that does not need the presence of the enhancer may be employed, although there will then, generally, be feedback. Unless there is a cut-off level of feedback, below which the feedback product will not work, then it will be appreciated that it is preferred to keep to a minimum feedback gene expression Different constructs of the invention (described in the accompanying Examples) have varying activity, according to the components of the constructs. For example, in *Drosophila*:

WTP-tTA gives a low level of induced (non-repressed) expression

JY2004-tTA gives strong expression when not repressed, approximately equivalent to Act5C-tTA LA513 is lethal when not repressed.

The first two appear to give constitutive expression, as judged by use of a reporter gene (tRE-EGFP), this is difficult to assess for the lethal LA513, although at 10μg/ml tet, just sufficient for good survival, LA513 in *Drosophila* drives expression of a $tetO_7$-EGFP reporter gene in both the male and female germline in adults, as well as in somatic cells. This distinguishes it from Act5C, commonly used as a "ubiquitous, constitutive" promoter, which does not, in fact, express well in these cells.

The properties of these constructs are shown in Table 1, below.

TABLE 1

| | Max expression | Minimal promoter | Intron | Optimised coding region? | 3'UTR and polyA |
|---|---|---|---|---|---|
| WTP-tTA | Low | P | PP1α96A | No | fs(1)K10 |
| JY2004-tTA | High | CMV | Rabbit β-globin | No | Rabbit β-globin |
| LA513 | V. high (lethal) | Hsp70 | Adh | Yes | fs(1)K10 |

Accordingly, it will be appreciated that the induced or non-repressed expression level can be modified in a useful and predictable way by adjusting the sequence of the positive feedback system. Toxicity and/or activity of the tTA protein can be modified independently of the transcriptional and translational control signals by several approaches, e.g. use of a nuclear localisation signal, modification of the activation domain, etc. (see Fussenegger, 2001 for more examples).

The lethality of LA513 is useful, for the reasons given above, and more particularly because:

a) It provides a compact, highly effective repressible lethal gene system;

b) As it uses only simple control elements from *Drosophila* (hsp70 minimal promoter, a small intron and a terminator from fs(1)K10), it, or its expression cassette, functions across a wide phylogenetic range;

c) It has very little, if any, deleterious effect on adults, even in the absence of tetracycline. This is a highly desirable and surprising property for field use, for example in a RIDL-based control programme, as the released adults must be competitive and long-lived for full efficacy of the programme. It will be appreciated that the effect of the system of the invention could be further modified by the incorporation of an adult-effective lethal, for example in the "positive feedback—bi-directional expression" configuration described herein; and d) By its nature, "cross-talk" between various elements is minimised. This is because: (i) the core of the construct is only a single composite element, rather than the normal two in bipartite expression systems; (ii) the principal enhancer of the autoregulatory component, the tTA binding sites, is substantially active only in the absence of tetracycline and (iii) modest expression of tTA under the influence of a nearby enhancer, whether in another part of the construct or in nearby chromatin, is unlikely to be significantly deleterious.

JY2004-tTA is also useful, in the present invention.

Without being bound by theory, the mechanism by which LA513 kills embryos and early larvae, but not adults, appears to be an inherent property of its toxicity. tTA toxicity is believed to derive from "transcriptional squelching", in which high level expression of the transcriptional activator domain (in the case of tTA this is VP16 or a fragment thereof) binds elements of the transcriptional machinery and titrates them, leading to a general effect on transcription, although it may also act to saturate the ubiquitin degradation pathway. Transcriptional squelching is the effect which is thought to lead to deleterious effects in mammalian cell lines expressing tTA at high levels; in the optimised expression context of LA513 positive feedback drives tTA expression to lethal levels. However, developing stages may be more sensitive to disruption of transcription than adults: they have to express genes in a highly coordinated fashion to allow proper development, while adults may be more tolerant of disruption.

The development of LA513 heterozygotes on media with an intermediate level of tet (3 or 10 µg/ml), just sufficient for survival, showed a significant delay, relative to their wild type siblings. Parallel experiments using higher concentrations of tetracycline, e.g. 100 µg/ml, did not show any developmental delay, thereby suggesting that sub-lethal expression of tTA can adversely affect the normal development of the insects.

It is preferred that a positive feedback system show a higher on:off ratio and switch from on to off over a narrower concentration range than a conventional system, thereby allowing the use of a wider range of effector molecules. Lower-toxicity (lower specific activity) effector molecules can be used, as they can be expressed at a high level under active conditions without leading to problems of toxicity at basal levels. Conversely, more toxic (higher specific activity) ones can be used as the necessary low basal level does not preclude high levels of expression when de-repressed or induced. Since basal level of expression is only partly determined by the level of tTA, this advantage is particularly clear in the case of lower-toxicity molecules. tTA is a preferred example of a low specific activity effector molecule that can be used as a lethal in the positive feedback context of LA513, for example. The advantage of switching from on to off over a narrow concentration range is that a modest concentration of repressor can be used without risk of residual (not fully repressed) expression leading to adverse effects and potentially selecting for resistance. Conversely, for an inducible system, modest concentrations of the activator can give full expression.

Activated or de-repressed drivers are useful for expressing effector molecules. Examples of effector molecules include functional RNA's, such as hairpin RNA's, ribozymes etc., and one or more encoded proteins. It will be appreciated that, for different applications, different levels of expression are appropriate. Since the sequence-specific transcription factors used to drive the positive feedback system can also be used to express other genes in a bipartite expression system, this may be achieved by making two separate constructs, one with the driver (normally a promoter-transcription factor construct, here the positive feedback construct), the other with the gene or molecule of interest under the control of a composite promoter (binding site+ minimal promoter) responsive to the transcription factor (Bello et al., 1998; Brand et al., 1994). This is also appropriate for these positive feedback drivers. Alternatively, the two elements may be combined on the same construct. This embodiment has significant advantages for most field applications, as it very substantially reduces the risk that the two functional elements can be separated by recombination. Further, the complete expression system can be introduced with only a single transformation event, as well as meaning that insects homozygous for the system are homozygous at only one locus rather than two, which makes them easier to construct by breeding, and tends to reduce the fitness cost due to insertional mutagenesis.

Figure 2:
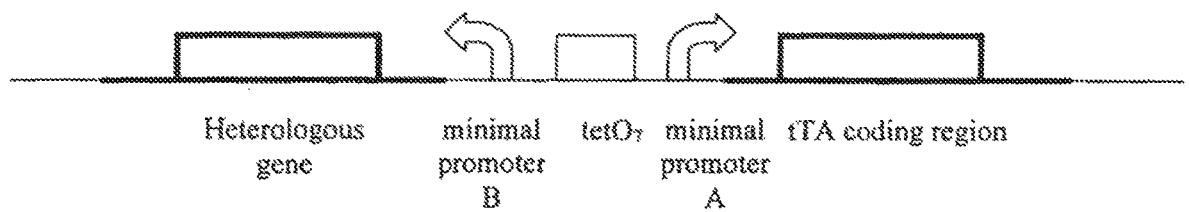
FIG. 2 shows a system of the invention using a bi-directional enhancer.

It is also possible to condense such an expression system into a more compact form, such as is illustrated in accompanying FIG. 2.

This exploits the bi-directional nature of enhancers, in this case the tetO binding site in the presence of tTA. This arrangement further allows, or facilitates, the use of insulator elements to reduce the effect of enhancers or suppressors in the adjacent chromatin: in this arrangement the entire expression cassette can be flanked by insulators. This arrangement also removes the need to duplicate the transcription factor binding sites within the construct. Such duplication is preferably avoided, as it can lead to instability through homologous recombination. For similar reasons, it is generally preferred that non-identical insulators, such as scs and scs' are used, rather than using the same one twice.

It is further possible to condense the system to provide a single transcript, either bicistronic or expressing a single polypeptide, which may potentially be further processed into more than one protein, for example by use of the ubiquitin fusion technique (Varshavsky, 2000). Each of these approaches (bi-directional expression, bicistronic expression, fusion protein with transactivator) tends to reduce the size of the construct, which in turn will tend to increase the transformation frequency and reduce the mutagenic target. Such condensation can be achieved in several ways, as shown, diagrammatically, in accompanying FIG. 3. Appropriate extensions to and variations of the arrangements shown diagrammatically will be apparent to those skilled in the art.

As an example of the utility of such a system, a general transformation marker might be constructed by using a transactivator system known to function over a wide phylogenetic range, for example those based on tetR, GAL4, lexA or AcNPV ie-1. Such a transactivator, functionally linked to a coding region for a fluorescent protein by any of the above methods (bi-directional expression, bicistronic expression, fusion protein with transactivator), would provide a genetic marker expressed in a wide range of tissues and developmental stages across a broad phylogenetic range. Such a marker would be useful not only for detecting transgenics in transformation and other lab experiments, but also for distinguishing, for example, transgenic flies from wild type flies in the field, or those caught in the field.

Another example is expression of a transposase. Integrated into the chromosomes, this would be a "jump-starter" construct, for example piggyBac transposase integrated into an insect chromosome using mariner/mos1. Such constructs are useful to remobilise piggyBac elements. A widely-applicable jump-starter should be expressed at a significant level across a wide phylogenetic range. The expression system of this invention provides this. Furthermore, such a construct (piggyBac transposase under the control of a positive feedback system of one of the above structures) would also be useful in insect transformation via transient expression (co-expression of a "helper" plasmid, the most widely-used method for insect transformation), and again would be useful and functional across a wide phylogenetic range.

It is advantageous to regulate the action of an expression system at stage-, sex- or other levels, in addition to being able to regulate the expression level by changing environmental conditions. Suitable examples are as follows:

1. Expression of a Repressor Protein.

Repressor proteins are known or can be constructed for the main expression systems, e.g. GAL80 or its mutant derivatives for the GAL4 system, tetR fused to inhibitory proteins for the tet system, etc. Another alternative is gene silencing of the transcription factor using a hairpin RNA directed against part of the expression cassette. Basal expression from the positive feedback system is rather low, therefore it can readily be suppressed by expression of such an inhibitor.

Expression of a suitable inhibitor under suitable control will tend to inhibit expression from the positive feedback expression cassette where the inhibitor is expressed. Female-specific expression, for example, can therefore be achieved by expressing an inhibitor in males.

2. Integrating Specificity into the Positive Feedback System.

Specificity can be integrated into the positive feedback system by using components that are themselves specific. For example, the hsp70 minimal promoter + SV40 intron and polyA signal combination of pUAST is known not to be expressed in the female germline of *Drosophila*, while the P minimal promoter+ P intron+ fs(1)K10 polyA signal of pUASp is so expressed (Rorth, 1998). Positive feedback expression systems can, therefore, be constructed which specifically do or do not express in this tissue, depending on the use of appropriate regulatory elements.

Figure 4:
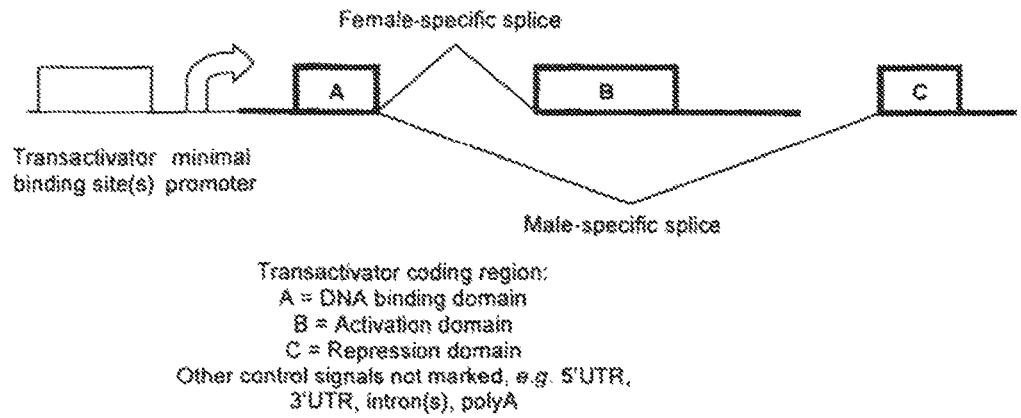
FIG. 4 shows another sex-specific system.

In another embodiment, sex-specificity can be integrated into the system by use of sex-specific splicing. The sex-specific splicing of doublesex and its homologues is a conserved regulatory mechanism and, therefore, available for use in this way across a wide phylogenetic range. Sex-specific splicing of transformer and its homologues is another alternative. The use of sex-specific splicing to integrate specificity into a positive feedback expression system can be achieved in several ways, as shown, diagrammatically, in accompanying FIG. 4. Appropriate extensions to and variations of the arrangements shown diagrammatically will be apparent to those skilled in the art.

In another configuration, a specific splice site can be inserted into the transactivator coding region so that two (or more) alternative proteins are produced in different conditions, e.g. in different cell types or in different sexes. This can be arranged so that a transcriptional activator is produced in one cell type but a transcriptional repressor is produced in another cell type. This arrangement has the advantage that it is relatively robust to inefficient (imperfect) splicing—production of a relatively low proportion of transcriptional activator in the inappropriate cell type, e.g. in male cells, will be less likely to produce the positive feedback amplification as these cells are also producing a larger amount of repressor. Discrimination in output (ratio of levels of transcriptional activator in the two cell types, or ratio of expression of a reporter or other RNA or protein functionally linked to the expression of the transcriptional activator) between the two cell types is thereby enhanced.

It will be readily apparent to those skilled in the art that any of these specific transactivator arrangements can readily be combined with any of the arrangements disclosed herein for expression of an additional protein or RNA, e.g. bi-directional expression, bi- or multi-cistronic expression, expression of a fusion protein, or combined with one or more separate expression cassettes dependent on, or partly dependent on, expression of the transactivator, either combined on the same construct or elsewhere in the genome or cell.

3. Using a Specific Effector Molecule

Specificity in phenotypic consequence can also be introduced by use of a specific effector molecule. Where a molecule, e.g. RNA or protein, expressed under the control of any of the expression systems described herein, has a specific effect only in particular cells, tissues, or sex, etc, then phenotypic specificity can be obtained with broader or less specific expression of the transactivator. For example, in the context of a RIDL-type mass-release insect population control programme, using the system to express a molecule only toxic, or preferentially toxic, to pre-adult stages, results in adults which are fully, or reasonably competitive, relative to wild type. This is desirable as the effectiveness of the programme depends on the competitiveness and longevity of the adult forms, when released into the wild. Since their internal repressor (e.g. tetracycline) concentration is likely to decline in the wild, it would be advantageous to ensure that induction (de-repression) of the expression system, as and when it occurs in adults, has a minimal negative effect on them.

As another example, sex separation, or sex-specific effects, can be achieved by expression in both males and females of a molecule with differential effects in males and females. For example, expression of the Transformer protein in male *Drosophila* will tend to transform them into females, but have no effect on females. Similarly, expression of Male specific lethal-2 (Msl-2) protein in *Drosophila* will tend to kill females, but not males (Gebauer et al., 1998; Kelley et al., 1995; Matsuo et al., 1997; Thomas et al., 2000). Conversely, expression of a partially self-complementary RNA molecule with substantial homology in its self-complementary or double-strand-forming region to ("hairpin RNA against") transformer will tend to transform genetic females into phenotypic males, while not affecting genetic males, and expression of hairpin RNA against msl-2 will tend to be lethal to males but not to females. Expression of hairpin RNA against the male- or female-specific exons of doublesex will tend to affect those sexes only, and simultaneous expression of RNA encoding the other form of doublesex (i.e. $Dsx^M$ in females or $Dsx^F$ in males) will tend to modify or enhance this effect. This simultaneous expression of a protein and a hairpin RNA molecule can readily be accomplished by combining the bicistronic or fusion protein approach described above with expression of a hairpin RNA using the bi-directional expression system also described above. Sex-, stage- or other specificity can be further added to such a system by incorporation of appropriate specific splicing or other transcriptional, translational or other post-translational control signals to either part of the system as will be apparent to the person skilled in the art.

Multi-functional hairpin RNA molecules may be constructed and are envisaged. For example, RNAi against transformer in the Mediterranean fruit fly *Ceratitis capitata* Wiedmann (medfly) will tend to transform genetic females into fertile males. For an area-wide population control program based on mass-release of such insects, it is preferable to sterilise the released flies. This can be accomplished by using a composite RNA molecule that simultaneously disrupts expression of both transformer and a gene required for spermatogenesis or embryonic or larval viability. Many such genes are known in *Drosophila* with homologues in mosquitoes or other animals. With medfly, a suitable homologue can readily be isolated, using techniques known to those skilled in the art. We prefer the use of a gene which allows the production of seminal fluid, and preferably also of sperm, to reduce the tendency of the female to re-mate after insemination by the affected male. We particularly prefer to direct this second part of the hairpin RNAi molecule against a paternal effect lethal, so that no viable progeny can be produced, or against a zygotically expressed gene required for embryonic or larval viability or development, so that progeny inheriting the construct will be affected. Other configurations are envisioned and will be readily apparent to those skilled in the art: for example expression of a female-specific lethal protein by bicistronic expression and a hairpin RNA leading to paternal-effect lethality by bi-directional expression. In common with the composite hairpin RNA against a suitable sex-determination gene and a paternal effect lethal, this allows the generation of a single-sex (male-only) population of insects, all of whose progeny die through the action of the paternal-effect lethal, irrespective of whether their progeny or mates feed on tetracycline. Thus, the present invention provides a controlled promoter, as defined, wherein the promoter is operably linked with DNA encoding an RNAi causing lethality or sterility. In this case, lethality may correspond to low fitness, such as flightless, rather than outright lethality, provided that the likelihood of breeding on is substantially reduced.

4. Using Site-Specific Recombinase(s)

Specificity can also be introduced into the positive feedback system by inserting a "stuffer" fragment which inactivates it. If this "stuffer" fragment is flanked by target sites for a suitable site-specific recombinase, then it will tend to be excised in the presence of active recombinase. Any system for selective expression of active recombinase, for example, expression of the recombinase under the control of a female-specific promoter, will therefore tend to lead to selective expression of the positive feedback system, in this case in females only. If the recombinase is expressed in somatic cells only, for example by using the method described above, then the version transmitted to the next generation includes the stuffer fragment, which can again be daughters but not sons. Conversely, if the recombinase is expressed in the genome only, provision of active recombinase will lead to offspring in which the expression system is active, from parents in which it is inactive. This can be used, for example, to generate gametes containing an active dominant lethal or sterile gene system (e.g. female-specific or non-sex-specific) for use in an insect population control strategy.

In a preferred embodiment, the stuffer fragment encodes the recombinase. This embodiment is particularly compact. In another preferred embodiment, the stuffer fragment encodes a transcriptional repressor which tends to inactivate the positive feedback expression system—this embodiment tends to reduce the basal expression of the system in the presence of the stuffer fragment.

Conversely, the system can be specifically inactivated in certain cells, or clones of cells, by introducing target sites for a suitable site-specific recombinase at suitable positions, and then expressing or introducing the appropriate active recombinase in appropriate cells, such that one or more key functional elements of the expression system are removed or disrupted by recombination between the target sites for the recombinase.

Suitable recombinase systems include cre/lox and Flp/FRT.

The present invention will now be described with reference to the following, non-limiting Examples. All references cited herein are hereby incorporated by reference.

EXAMPLES

A series of constructs was made with tTA in a positive feedback configuration, i.e. with tTA expression regulated by tTA binding to tetO. Transgenic insects carrying these constructs were obtained and their properties analysed.

tTAV

In some cases, the intention was to obtain very high levels of expression of tTA in the absence of tetracycline. In various exemplified constructs described hereinbelow, tTA expression was so high as to be lethal. As part of the process of obtaining strong expression of tTA, part of the tTA open reading frame was redesigned to express a similar protein, but with codon usage closer to the norm for *Drosophila melanogaster*, and lacking some potential cryptic splice sites present in the original nucleotide sequence. This variant tTA sequence was named tTAV (SEQ ID NO. 31, protein sequence SEQ ID NO. 32).

Example 1

WTP-tTA and JY2004-tTA in *Drosophila Melanogaster*

The tTA coding region (SEQ ID NO. 29, tTA protein sequence SEQ ID NO. 30) from pUHD15-1 (SEQ ID NO. 33, Gossen et al., 1994; Gossen and Bujard, 1992) was placed under tetO control, in a positive feedback configuration, by inserting it into pWTP2 (Bello et al., 1998) or pJY2004, a version of pJY2000 that lacks insulators (Stebbins and Yin, 2001). These constructs were named pWTP-tTA and pJY2004-tTA, respectively. A diagram of tetO$_7$-tTA region of pJY2004 is provided as accompanying FIG. 5, and is SEQ ID NO. 14.

In pWTP-tTA, the tetO$_7$ binding sites are followed by a minimal promoter from the P element, a leader sequence from *Drosophila* hsp70, a short intron from the *Drosophila*

Figure 5:
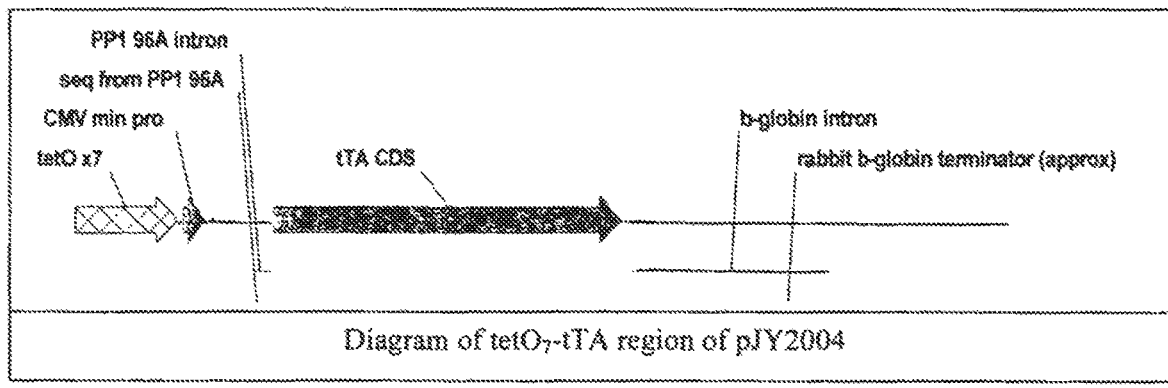
FIG. 5 is a diagram of the tetO$_7$-tTA region of pJY2004.

PP1α96A gene, the tTA coding region and a transcription terminator from *Drosophila* hsp70. In pJY2004-tTA, the minimal promoter and leader sequences are from CMV, followed by the tTA coding region and a transcription terminator from rabbit β-globin, as shown in FIG. 5.

Transgenic *Drosophila melanogaster* carrying either of these constructs were fully viable, even without dietary tetracycline. Insects doubly heterozygous for WTP-EGFP and either of these constructs were examined for green fluorescence characteristic of EGFP expression. Insects with WTP-tTA and WTP-EGFP showed very weak fluorescence only slightly above background autofluorescence. In contrast, insects with JY2004-tTA and WTP-EGFP showed strong fluorescence, similar to that seen in insects carrying EGFP under the control of the Actin5C promoter, which is widely used as a strong, constitutive promoter in *Drosophila* (e.g. Reichhart and Ferrandon, 1998). Expression of EGFP was repressed to undetectable levels when the insects were raised on diet supplemented with tetracycline to 100 µg/ml. Control insects heterozygous for either WTP-EGFP, JY2004-tTA or WTP-tTA showed no fluorescence above background whether or not they were raised on a diet containing tetracycline.

We placed tTA under the control of the Actin5C promoter, in plasmid pP [Casper-Act5C-tTA]. Transgenic flies carrying this construct and WTP-EGFP, raised on a diet lacking tetracycline, showed green fluorescence at a comparable intensity to that observed in equivalent flies with JY2004-tTA and WTP-EGFP.

These results show that positive feedback constructs can be used to give strong (JY2004-tTA) or weak (WTP-tTA), tetracycline-repressible expression from a suitable construct (here WTP-EGFP).

EGFP is widely used as a neutral reporter. We further tested JY2004-tTA flies by crossing them to flies with constructs capable of expressing proteins known or predicted to be deleterious. We inserted the central domain of Nipp1Dm (Bennett et al., 2003; Parker et al., 2002) ("nipper"), into pJY2004, to make pJY2004-nipper, and transformed *Drosophila* with this construct. We also used flies carrying tetO-hid (Heinrich and Scott, 2000). In each case, crossing to JY2004-tTA flies gave tetracycline-repressible lethality. Data from two example crosses are presented in Table 2, below.

TABLE 2

Use of positive feedback constructs to drive expression of lethal genes in *Drosophila*.

| JY2004-tTA | CyO | [tetracycline] (µg/ml) |
|---|---|---|
| Male JY2004-tTA/CyO × Female tetO-hid/tetO-hid | | |
| 0 | 15 | 0 |
| 9 | 10 | 100 |
| Male JY2004-tTA/CyO × Female JY2004-nipper/JY2004-nipper | | |
| 0 | 20 | 0 |
| 16 | 13 | 100 |

Example 2

LA513 in *Drosophila Melanogaster*

Figure 6:
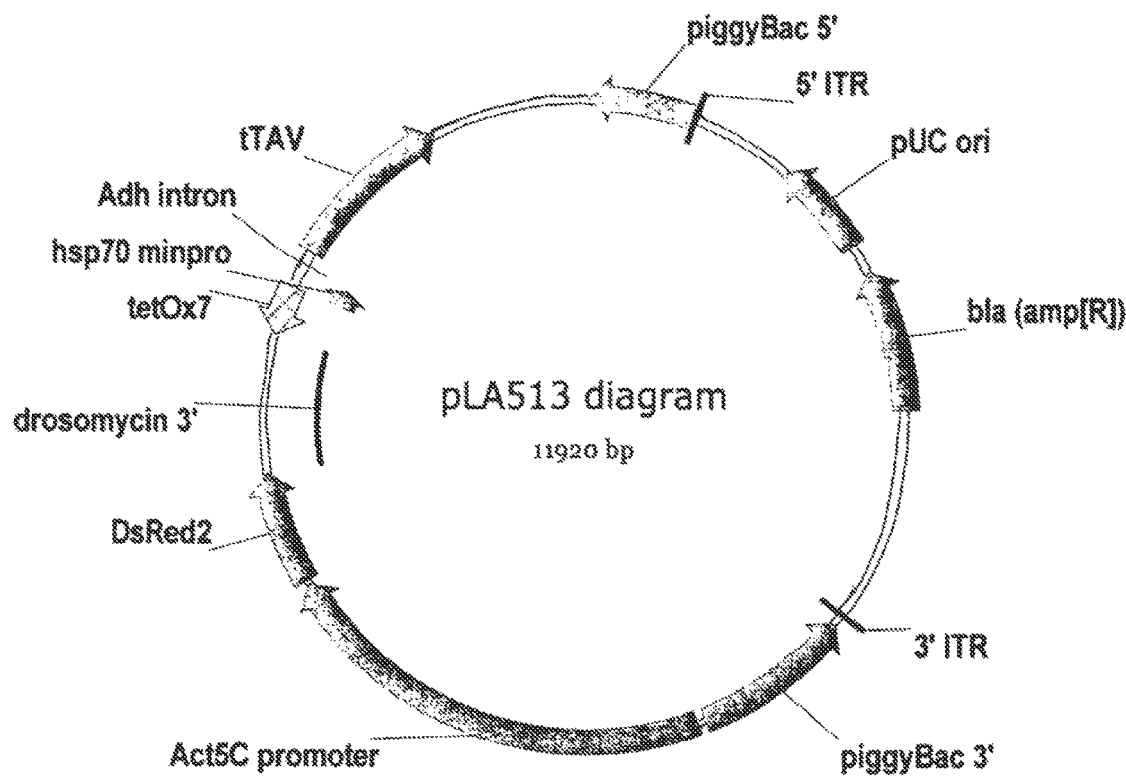
FIG. 6 is a schematic diagram of pLA513.
Figure 7:
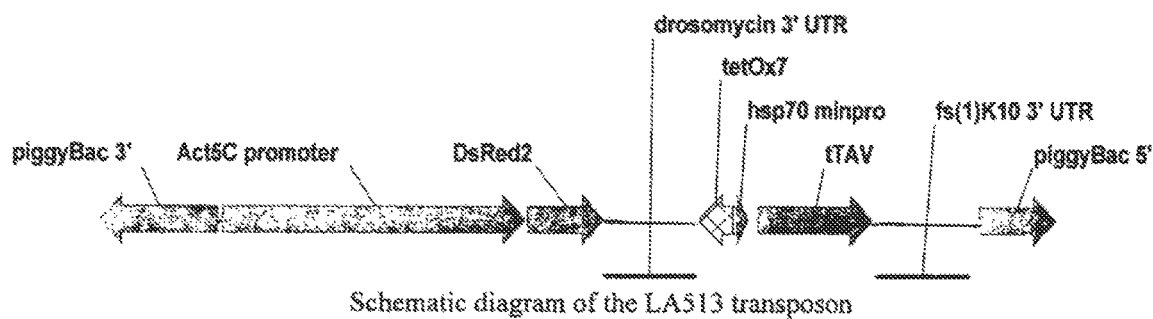
FIG. 7 is a schematic diagram of the LA513 transposon.

We made construct pLA513 (SEQ ID NO. 16, schematic diagram shown in FIG. 6), containing a non-autonomous piggyBac transposon. We generated transgenic *Drosophila melanogaster* carrying this construct by co-injection with a helper plasmid into a white-eyed strain (Handler, 2002; Handler and James, 2000). Potential transgenics were screened for fluorescence characteristic of DsRed2. 5 transgenic lines were recovered, and were designated O513, M8, M13, F23 and F24. A schematic diagram of the LA513 transposon is shown in accompanying FIG. 7.

*Drosophila melanogaster* stocks were maintained at 25° C. on yeast/sugar/maize/tetracycline medium (tetracycline (Sigma) at 100µg/ml final concentration), unless stated otherwise. All experiments were performed at 25° C.

Survival of LA513/+ Transgenics with and Without tetracycline

Heterozygous transgenics were crossed in at least triplicate to wild type on media with or without Tc (tetracycline). In the absence of any lethality, it would be expected that approximately half the progeny of such a cross would be transgenic. Progeny were scored as young adults for DsRed marker fluorescence [Matz et al., 1999] using an Olympus SZX12 microscope with fluorescence capability, and the ratio of fluorescent (transgenic) to total flies was calculated. The results are shown in Table 3, below. In these experiments, all 5 transgenic lines showed 100% lethality, in the absence of tetracycline, and good survival (i.e. fluorescent: non-fluorescent ratio -1:1), in the presence of 100 µg/ml tetracycline. Inspection of the vials showed few or no large fluorescent larvae in the absence of Tc, although many very small fluorescent larvae were present, at a time when non-fluorescent (wild type for LA513) larvae were visible at all sizes. This suggests that, in the absence of tetracycline, LA513 causes lethality at an early (embryonic and/or early larval) developmental stage.

TABLE 3

LA513 insertions are tetracycline-repressible dominant lethals

| | 0 µg/ml tetracycline | | 100 µg/ml tetracycline | | |
|---|---|---|---|---|---|
| LA513 line | # Flies | # Fluorescent | # Flies | # Fluorescent | Ratio |
| O513 | 490 | 0 | 1963 | 937 | 0.48 |
| M8 | 74 | 0 | 66 | 25 | 0.38 |
| M13 | 657 | 0 | 1838 | 892 | 0.49 |
| F23 | 473 | 0 | 1914 | 845 | 0.44 |
| F24 | 61 | 0 | 114 | 60 | 0.53 |
| Total | 1755 | 0 | 5895 | 2759 | 0.47 |

Dominant lethality could have several causes. Without being restricted by theory, it seems likely that, in the absence of tetracycline, tTAV accumulates to a relatively high concentration and that this is lethal, possibly due to transcriptional squelching, or interference with protein degradation. An alternative is that, in the absence of tetracycline, tTAV binds to tetO and acts as a long-range enhancer, perturbing the expression of genes near to the LA513 insertion. This appears unlikely, as all 5 transgenic lines gave similar results. Each of these lines was derived from a different GO injection survivor, and these lines are, therefore, likely to carry LA513 integrated at different genomic sites. We verified this by inverse PCR. Table 4, below, shows the integration sites for 3 of the lines; in each case the LA513 insertion was at a TTAA sequence, as expected from the known insertion site preference of the piggyBac transposon. As expected, the 3 insertions were indeed at 3 different sites in the *Drosophila* genome.

TABLE 4

Insertion sites of LA513 in Drosophila genome

| Line | Sequence Amplified or at Site of Integration | Predicted chromosome arm | Predicted Drosophila cytology | Nearest predicted gene |
|---|---|---|---|---|
| O513 | CacagcgcatgatgagcacaTTAAcaaaatgtagtaaaatagga (SEQ ID NO. 1) | 2L | 25F4-25F5 | CG9171 |
| M8 | GtttcgataaatattgctatTTAAaatgcttattttcaatgcta (SEQ ID NO. 2) | 2L | 26F6-26F6 | CG15160 |
| F24 | TttgttttctaacgttaaagTTAAagagagtccagccacatttt (SEQ ID NO. 3) | 2L | 21C4-21C5 | CG13691 |

Flanking sequence is shown with the TTAA insertion site capitalised. Predicted chromosome locations, and the nearest predicted gene, are also shown; these are based on the published *Drosophila* genome sequence.

Example 3

Reducing the Toxicity of tTAV

Figure 8:
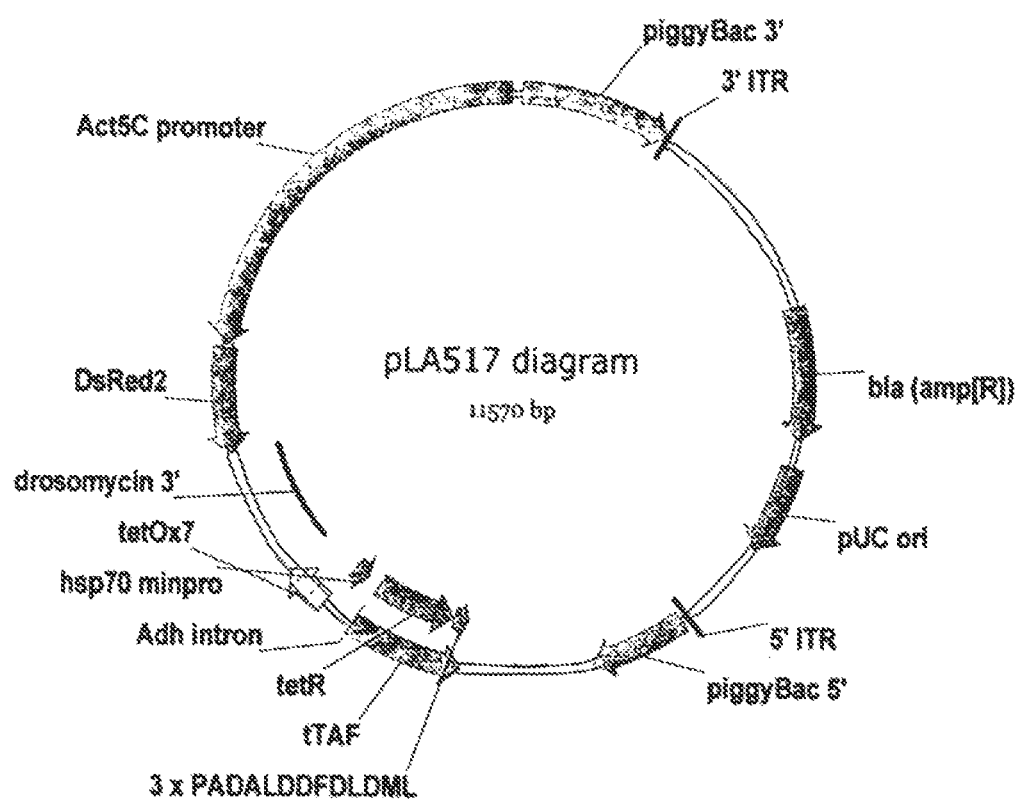
FIG. 8 is a schematic diagram of pLA517.

The toxic effect of high level expression of tTAV is thought to be due to transcriptional squelching and/or interference with ubiquitin-dependent proteolysis, via the VP16-derived section (Gossen and Bujard, 1992; Salghetti et al., 2001). We, therefore, modified tTAV by removing the VP16 section and replacing it with a synthetic sequence which encodes 3 copies of a peptide (PADALDDFDLDML) derived from VP16 (Baron and Bujard, 2000; Baron et al., 1997). This derivative was named tTAF; the resulting plasmid was named pLA517, and is SEQ ID NO. 17, and is shown, diagrammatically, in accompanying FIG. 8.

*Drosophila melanogaster* were transformed with this construct, and one transgenic line was obtained. LA513 heterozygous males were crossed to wild type (for LA513) females and the progeny scored for fluorescence (as adults). If all progeny are equally likely to survive, the expected proportion of the total progeny that are fluorescent is 50%. In the absence of tetracycline, this proportion was 32%, only a modest reduction compared with 48% when parents and progeny were raised on diet supplemented with tetracycline to 100 µg/ml. The results are shown in Table 5, below. We tested whether supplying tetracycline in the diet of the parents but not of the progeny could reduce this lethality. In this case, we observed an intermediate proportion of 0.37, indicating that maternally contributed tetracycline has a modest beneficial effect.

TABLE 5

Effect of tetracycline on the survival of LA517/+ *Drosophila* and their +/+ siblings
LA517

| Parent [Tc] µg/ml | Progeny [Tc] µg/ml | Non-Fluorescent | Fluorescent |
|---|---|---|---|
| 0 | 0 | 165 | 78 |
| 100 | 100 | 524 | 482 |
| 100 | 0 | 502 | 297 |

Since LA517, alone, had little impact on viability, unlike the closely related construct LA513, we tested whether it was capable of driving expression of a heterologous gene under tetO control. For this we used tetO-hid (Heinrich and Scott, 2000). Flies homozygous for tetO-hid were crossed with flies heterozygous for LA517. In the absence of tetracycline, only 3.4% of the adult progeny carried LA517. In the presence of 100 µg/ml tetracycline, this proportion was 42%. LA517 is, therefore, capable of driving effective expression of a heterologous gene.

TABLE 6

Effect of tetracycline on the survival of LA517/+, +/tetO-hid *Drosophila* and their +/+, +/tetO-hid siblings
TetO-Hid × LA517/+

| [Tc] | Non-Fluorescent | Fluorescent |
|---|---|---|
| 0 | 636 | 23 |
| 100 | 174 | 127 |

Example 4

Use of Analogues of tetracycline

Line F23 was used to determine whether chemical analogues of tetracycline could be used in place of tetracycline to suppress the lethality of LA513. For this purpose we tested 3 analogues at a range of concentrations from 0 to 100 µg/ml (suppliers: tetracycline and doxycycline, Sigma; 4-epi-oxytetracycline, Acros Organics; chlortetracycline Fuzhou Antibiotic Group Corp.). We calculated the concentrations required for half-maximal survival. These are shown in Table 7, below.

TABLE 7

Efficacy of Tc analogues

| Line | Tc/Analogue | Concentration for half-maximal survival, µg/ml |
|---|---|---|
| F23 | Tetracycline | 5.0 |
| F23 | Doxycycline | 3.9 |
| F23 | 7-chlortetracycline | 1.7 |
| F23 | 4-epi-oxytetracycline | 42.0 |

Example 5

Longevity of LA513/+ Adults in the Absence of tetracycline

LA513 clearly confers dominant lethality, active at an embryonic and/or early larval stage. Larvae were raised on a diet supplemented with 100 µg/ml tetracycline. After eclosion, adults were transferred to a diet lacking tetracycline. The lifespan of these adults was measured, and also of comparable $w^{1118}$ non-transgenic adults. As shown in Table 8, below, the transgenic lines showed good adult survival relative to the non-transgenic control. This suggests that stage-specificity can be obtained in this way—here LA513 is a larval/embryonic lethal, but not an adult lethal.

TABLE 8

Mean adult lifespan of LA513/+ transgenic Drosophila.

| Line | Mean post-eclosion survival time, days | Standard deviation | Number of Flies |
|---|---|---|---|
| O513 | 40.3 | 12.3 | 66 |
| M8 | 26.1 | 2.5 | 9 |
| M13 | 29.5 | 9.9 | 47 |
| F23 | 29.6 | 11.3 | 83 |
| F24 | 19.9 | 10.0 | 9 |
| $w^{1118}$ | 22.2 | 8.6 | 88 |

It is possible to explain these longevity data by postulating that larvae accumulate tetracycline by feeding, and retain this tetracycline into adulthood, so that they survive even in the absence of dietary tetracycline as adults. To examine this, flies heterozygous for LA513/+ (M13 line) were raised as larvae on various concentrations of tetracycline. After eclosion, adults were transferred to diet lacking tetracycline and the lifespan of these adults was measured, as above. As shown in Table 9, below, the concentration of dietary tetracycline as larvae had no obvious effect on subsequent adult longevity in the absence of tetracycline, implying that adult survival is not primarily due to retention of tetracycline from larval feeding. At a concentration of 1 µg/ml, no transgenics survived to adulthood, and at 3 µg/ml only about half of the expected number survived to adulthood, so that this concentration is close to the minimum for larval survival.

TABLE 9

Effect of larval tetracycline on adult longevity

| Larval tetracycline µg/ml | Mean post-eclosion survival time, days | Standard deviation | Number of Flies |
|---|---|---|---|
| 1 | — | — | — |
| 3 | 33.5 | 13.2 | 9 |
| 10 | 28.4 | 9.6 | 17 |
| 30 | 26.3 | 11.3 | 23 |
| 100 | 29.5 | 9.9 | 47 |

Another possible explanation for the survival of LA513/+ adults is that tTAV is inactive in adults, so that the positive feedback cycle does not work, and tTAV does not accumulate. We examined this by measuring the amount of tTAV mRNA by quantitative PCR following a reverse transcriptase reaction (quantitative rt-PCR, or qPCR). We used Taqman chemistry and reagents (ABI), and an ABI Prism 7000 qPCR instrument. Each sample was assayed in triplicate; data are the mean of these three assays. The 18S primers anneal to Drosophila melanogaster, Ceratitis capitata and Aedes aegypti 18S RNA, so these primers were used for all three species.

Primers Used:

| | | SEQ ID NO. |
|---|---|---|
| 18S RNA | | |
| Forward Primer: | ACGCGAGAGGTGAAATTCTTG | 4 |
| Reverse Primer: | GAAAACATCTTTGGCAAATGCTT | 5 |
| TaqMan MGB Probe: | 6-Fam-CCGTCGTAAGACTAAC-MGB | 6 |
| tTAV | | |
| Forward Primer: | CATGCCGACGCGCTAGA | 7 |
| Reverse Primer: | GTAAACATCTGCTCAAACTCGAAGTC | 8 |
| TaqMan MGB Probe: | VIC-TCGATCTGGACATGTTGG-MGB | 9 |

We found that O513 raised on 100 µg/ml tetracycline had a tTA:18S ratio of 0.00016 (larvae) and 0.00013 (adult). Adults raised as larvae on 100 µg/ml tetracycline, but then transferred to non-tetracycline diet as adults had ratios of 0.0061, 0.0047, 0.0087 and 0.011 after 1, 2, 4 and 8 days without tetracycline, respectively. This 28- to 64-fold increase in expression relative to the tetracycline-fed control indicates that the tTAV-based positive feedback expression system is functional in adults.

Example 6

LA513 in Aedes aegypti

Aedes aegypti (the yellow fever mosquito, also the major vector of urban dengue fever) were transformed with LA513. Two independent insertion lines, LA513A and LA513B, were obtained.

Males heterozygous for LA513A (reared as larvae on 30 µg/ml tetracycline) were allowed to mate with wild type females. Eggs were collected and the resulting larvae raised in normal media, or in media supplemented with tetracycline (Tc) to 30 µg/ml. The number of transgenic and non-transgenic adults resulting from these eggs was determined. Data are the sum of at least 5 experiments. Larvae were reared at a density of ≤250 individuals per litre; all the eggs in "no tetracycline" experiments were washed twice before submergence to avoid transferring tetracycline. For the "with tetracycline" experiments, the parental blood and sugar-water was supplemented with tetracycline to 30 µg/ml; for the "no tetracycline" experiments it was not. $x^2$ test for differentiation in ratio of the transgene and wild types for survival to adult: "with tetracycline", either orientation: P>0.05 ; "without tetracycline, either orientation P<0.001 (null hypothesis: genotype with respect to LA513 has no effect on survival).

LA513A is, therefore, a repressible dominant lethal, with a penetrance in these experiments of 95-97%. LA513B is also a repressible dominant lethal, with a penetrance in these experiments of 100%. The results are shown in Table 10, below.

TABLE 10

Effect of tetracycline on the survival of LA513/+ *Aedes aegypti* and their +/+ siblings.

| Parents | | Progeny | Tc as | Genotype | 1st instar larvae | 2nd | 3rd | 4th | Pupae | Adults |
|---|---|---|---|---|---|---|---|---|---|---|
| Male | Female | Egg | larvae | | | | | | | |
| LA513A/+ | +/+ | 1000 | Yes | LA513A/+ | 489 | 468 | 446 | 442 | 437 | 434 |
| | | | | Wild type | 444 | 431 | 403 | 400 | 396 | 392 |
| +/+ | LA513A/+ | 1000 | Yes | LA513A/+ | 442 | 420 | 404 | 399 | 393 | 383 |
| | | | | Wild type | 466 | 444 | 428 | 417 | 412 | 404 |
| LA513A/+ | +/+ | 540 | No | LA513A/+ | 274 | 265 | 235 | 208 | 155 | 7 |
| | | | | Wild type | 233 | 225 | 214 | 212 | 209 | 206 |
| +/+ | LA513A/+ | 497 | No | LA513A/+ | 216 | 205 | 181 | 168 | 131 | 9 |
| | | | | Wild type | 241 | 225 | 216 | 214 | 211 | 207 |
| LA513B/+ | +/+ | 377 | Yes | LA513B/+ | 161 | 153 | 147 | 141 | 139 | 131 |
| | | | | Wild type | 178 | 171 | 165 | 160 | 157 | 153 |
| +/+ | LA513B/+ | 442 | Yes | LA513B/+ | 189 | 181 | 170 | 166 | 161 | 153 |
| | | | | Wild type | 203 | 198 | 185 | 182 | 180 | 176 |
| LA513B/+ | +/+ | 188 | No | LA513B/+ | 69 | 19 | 0 | 0 | 0 | 0 |
| | | | | Wild type | 85 | 84 | 83 | 83 | 82 | 81 |
| +/+ | LA513B/+ | 240 | No | LA513B/+ | 91 | 60 | 0 | 0 | 0 | 0 |
| | | | | Wild type | 107 | 104 | 99 | 98 | 95 | 93 |

We examined the survival of LA513A/+ males that had been raised on tetracycline (30μg/ml), as larvae, but not given tetracycline as adults. We found that all males tested survived for three weeks, irrespective of genotype (LA513A/LA513A, LA513A/+ or +/+) or the presence or absence of tetracycline in their diet (N≤140 for each genotype).

We investigated the induction kinetics of tTAV in adult LA513B/+ mosquitoes after withdrawal of tetracycline, using qPCR. As shown in Table 11, below, tTAV increased in males and females following withdrawal of tetracycline. Induction of tTA expression is fairly rapid after removal of Tc, as with *Drosophila*. In each case, shifting between diets containing different levels of tetracycline provides a level of control over the expression level of genes controlled by tTA (here exemplified by tTA itself), using such a positive feedback system.

TABLE 11

Induction of tTA expression in LA513B/+ males following withdrawal of tetracycline

| Sex | Time (days) without tetracycline | tTA:18S expression ratio | tTA:18S expression relative to male with tetracycline |
|---|---|---|---|
| Male | 0 | 0.00036 | 1 |
| Female | 0 | 0.00060 | 1.7 |
| Male | 3 | 0.0043 | 12 |
| Female | 3 | 0.014 | 38 |
| Male | 4 | 0.054 | 150 |
| Female | 4 | 0.019 | 530 |
| Male | 8 | 0.012 | 34 |
| Female | 8 | 0.52 | 1500 |
| Male | 16 | 0.10 | 280 |
| Female | 16 | 0.032 | 88 |

Example 7

Tetracycline-Repressible Enhancement of a Nearby Promoter by tTAV in a Positive Feedback Configuration We observed that the fluorescent marker in LA513A and LA513B transgenic mosquitoes showed a different pattern of fluorescence in the absence of tetracycline, compared with the pattern in the presence of tetracycline. Fluorescence in the presence of tetracycline was typical of Actin5C-driven expression in mosquitoes (Catteruccia et al., 2000; Pinkerton et al., 2000), and limited largely to the swollen part of the thorax. In contrast, in the absence of tetracycline, expression was much stronger and evident substantially throughout the body of transgenic individuals. In each case, assessment of fluorescence intensity and expression pattern was made by visual observation using fluorescence microscopy.

Elevated expression of tTAV in this positive feedback situation appears, therefore, to be stimulating expression from the nearby Actin5C promoter. This is illustrated, diagrammatically, in FIG. 9. We also found that intermediate concentrations of tetracycline, just sufficient substantially to suppress the lethality of LA513, did not suppress this broader expression pattern of fluorescence. At these intermediate concentrations of tetracycline, tTAV accumulates to an intermediate level—sub-lethal, but higher than in 30 μg/ml tetracycline, and which still influences the expression of DsRed2. This again exemplifies the additional control available by modulating tetracycline concentration.

Figure 9:
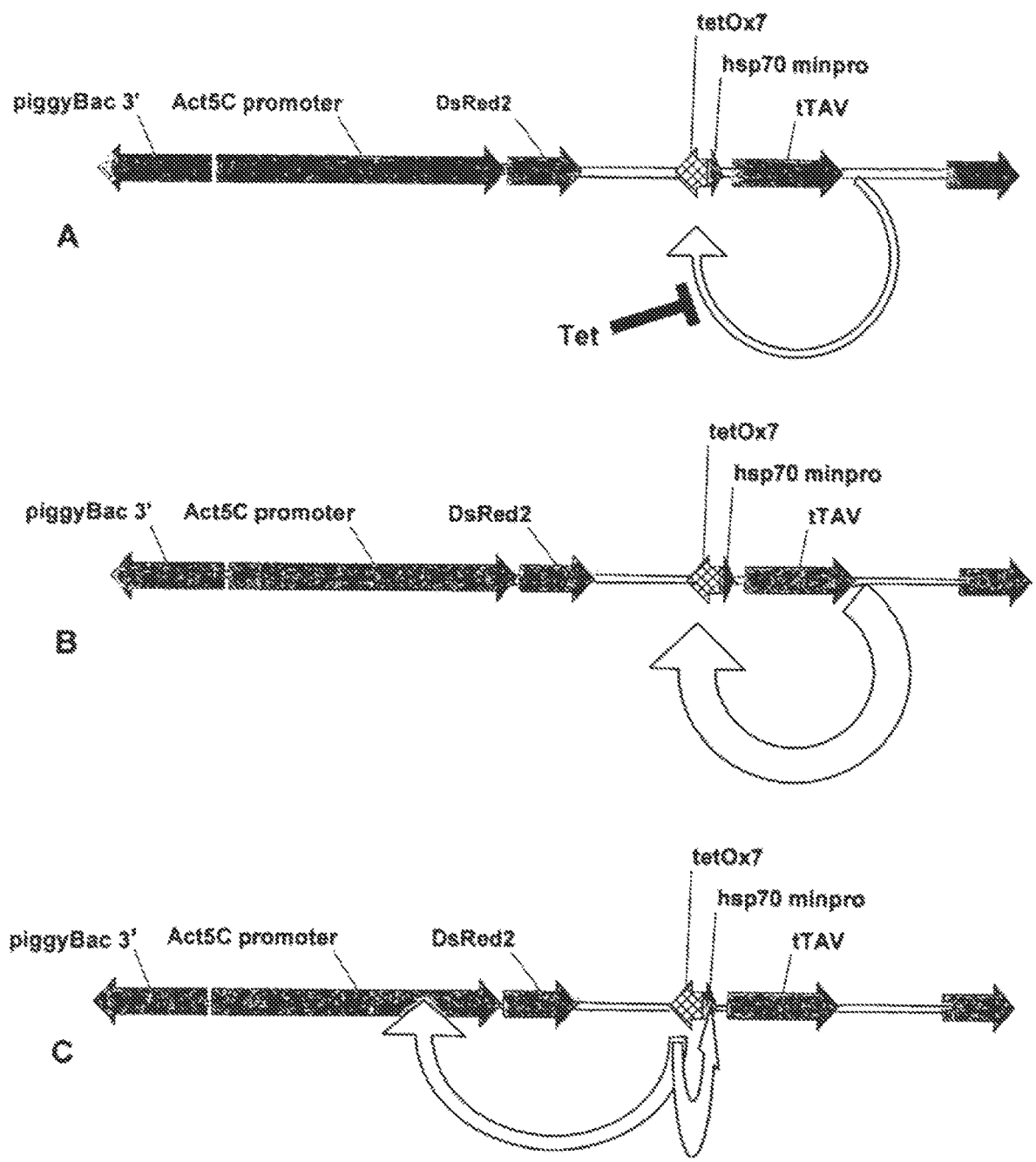
FIG. 9 illustrates the bidirectional action of tetO$_7$ in 513A and 5136 mosquitoes.

FIG. 9 illustrates the bidirectional action of tetO$_7$ in 513A and 513B mosquitoes. In 513, DsRed2 is under the transcriptional control of the *Drosophila* Actin5C promoter.
(A) In the presence of tetracycline, relatively little tTAV is produced, this binds tetracycline and has little or no effect on DsRed2 expression. DsRed2 is seen in a pattern typical of Actin5C expression in mosquitoes.
(B) In the absence of tetracycline, tTAV stimulates its own expression in a positive feedback loop.
(C) tTAV binding to the tetO sites enhances expression of both the hsp70 minimal promoter, and hence tTAV, but also the Actin5C promoter, and hence DsRed2.

Example 8

LA656, LA928 and LA1124 in *Ceratitis capitata*

Figure 10:
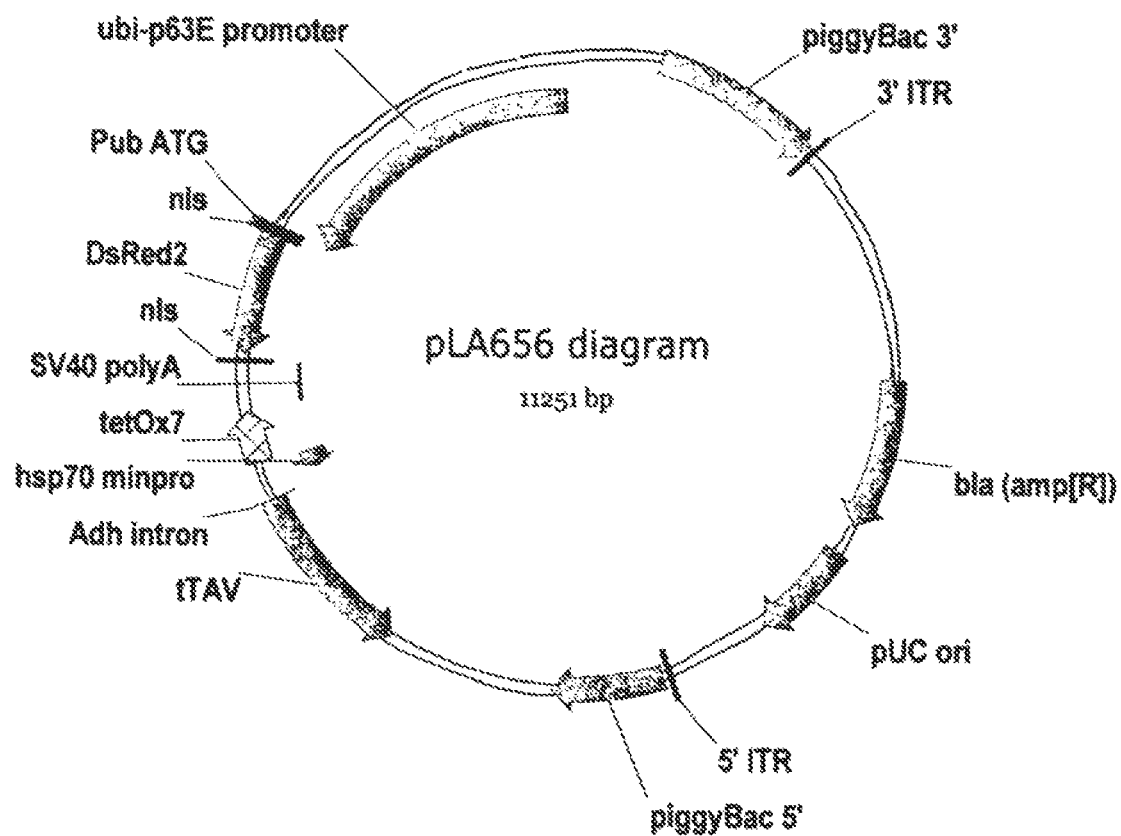
FIG. 10 is a schematic diagram of pLA656.
Figure 11:
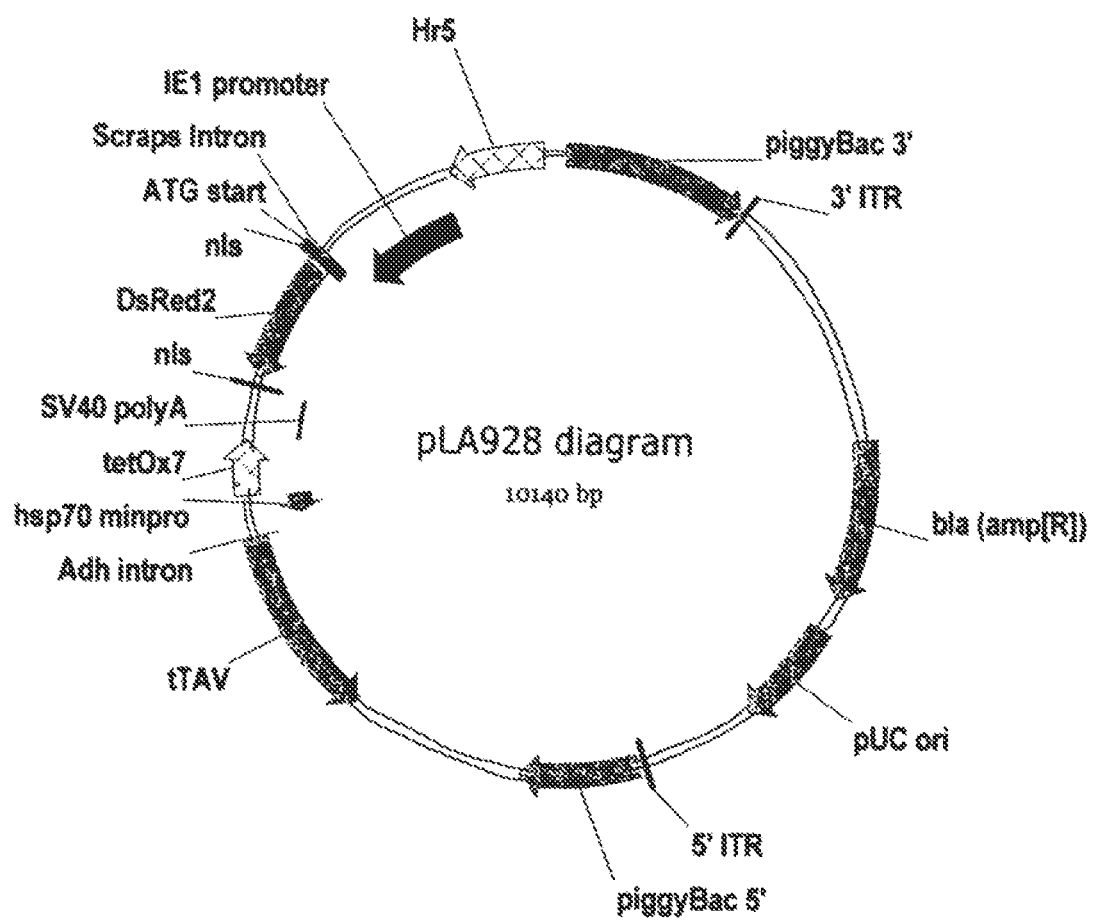
FIG. 11 is a schematic diagram of pLA928.

No transgenic lines of the Mediterranean fruit fly (medfly, *Ceratitis capitata* Wiedmann) were obtained, using pLA513, probably indicating that the Actin5C-based marker of pLA513 is inappropriate for use in medfly. This emphasises the desirability of expression constructs with a wide species range. We, therefore, modified the construct to include a polyubiquitin (ubi-p63E)-based marker instead of the Actin5C-based one of pLA513. One such construct is pLA656. We also made two additional constructs, pLA928 and pLA1124 (SEQ ID NO's 18, 20 and 21, respectively, and shown, diagrammatically, in FIGS. 10, 11 and 12), using a marker based on the hr5 enhancer and ie1 promoter from a baculovirus (*Autographica californica* nuclear polyhedrosis virus, AcMNPV). These differ in the orientation of the marker with respect to the tetO-tTAV cassette. The hr enhancer is closer to the tetO-tTAV cassette in pLA1124 than in pLA928. Furthermore, pLA1124 has 21, rather than 7, copies of tetO and additionally has a putative GAGA-factor binding region related to that of pUASp (Rorth, 1998).

One transgenic line was obtained from pLA656, three for pLA928, and three for pLA1124. These lines are assumed to have independent insertions, as they were derived from different G0 injection survivors.

wild type siblings. The survival of these wild type siblings is a good control, as they are genetically similar, and raised in the same environment. In each case, this highly penetrant dominant lethality was substantially repressed by the addition of tetracycline to 100 μg/ml. In the case of LA656 and LA928, the survival rates on intermediate concentrations of tetracycline indicated that 0.1 μg/ml was insufficient for significant viability, and that viability increased in the range 1 μg/ml to 100 μg/ml. Thus, varying the concentration of dietary tetracycline provides a convenient level of control over the expression level of genes controlled by tTAV (here exemplified by tTAV itself), using such a positive feedback system. Three additional methods, shifting between diets containing different levels of tetracycline, modifying the construct, and using position effect, are discussed elsewhere herein.

TABLE 12

Effect of tetracycline on the survival of transgenic medfly heterozygous for various constructs, and their +/+ siblings

| | Progeny [Tc] (μg/ml) | F/NF pupae | Pupal survival ratio (%) | F male | F female | NF male | NF female | Adult survival ratio (%) |
|---|---|---|---|---|---|---|---|---|
| LA656 | 0 | 84/1161 | 7 | 6 | 2 | 530 | 551 | 0.7 |
| | 0.1 | 16/423 | 4 | 0 | 0 | 205 | 177 | 0 |
| | 1 | 124/384 | 32 | 34 | 12 | 155 | 174 | 14 |
| | 3 | 258/370 | 70 | 84 | 53 | 165 | 133 | 46 |
| | 10 | 249/252 | 99 | 91 | 98 | 107 | 127 | 81 |
| | 100 | 330/307 | 107 | 151 | 150 | 134 | 148 | 107 |
| LA928m1 | 0 | 28/1499 | 1.87 | 5 | 1 | 661 | 639 | 0.46 |
| | 0.1 | 0/765 | 0 | 0 | 0 | 347 | 246 | 0 |
| | 1 | 190/256 | 74 | 62 | 59 | 119 | 101 | 55 |
| | 3 | 290/302 | 96 | 133 | 98 | 143 | 107 | 92 |
| | 10 | nd | nd | nd | nd | nd | nd | nd |
| | 100 | 222/286 | 77 | 117 | 84 | 146 | 126 | 74 |
| LA928m3 | 0 | 68/1026 | 6.6 | 13 | 4 | 489 | 449 | 1.8 |
| | 0.1 | 0/265 | 0 | 0 | 0 | 117 | 91 | 0 |
| | 1 | 358/446 | 80 | 154 | 100 | 228 | 164 | 65 |
| | 3 | 105/105 | 100 | 39 | 35 | 42 | 38 | 93 |
| | 10 | nd | nd | nd | nd | nd | nd | nd |
| | 100 | 245/245 | 100 | 109 | 121 | 117 | 108 | 100 |
| LA928f1 | 0 | 17/1331 | 1.3 | 2 | 0 | 639 | 599 | 0.16 |
| | 0.1 | 2/254 | 0.8 | 0 | 0 | 100 | 84 | 0 |
| | 1 | 461/567 | 81 | 218 | 146 | 244 | 181 | 85 |
| | 3 | 520/527 | 99 | 214 | 182 | 249 | 202 | 88 |
| | 10 | 350/399 | 91 | 139 | 112 | 131 | 159 | 87 |
| | 100 | 126/117 | 108 | 63 | 57 | 57 | 49 | 113 |
| LA1124f1 | 0 | 104/213 | 51 | 0 | 3 | 95 | 62 | 1.9 |
| | 100 | 478/536 | 89 | 218 | 208 | 205 | 203 | 104 |
| LA1124m1 | 0 | 337/437 | 77 | 2 | 1 | 176 | 207 | 0.78 |
| | 100 | 84/90 | 93 | 35 | 31 | 30 | 26 | 118 |
| LA1124m2 | 0 | 104/145 | 72 | 0 | 1 | 46 | 34 | 1.3 |
| | 100 | 77/77 | 100 | 24 | 14 | 19 | 13 | 119 |

F: fluorescent;
NF: non-fluorescent.

Males heterozygous for each line were crossed to wild type females. The progeny were raised on standard yeast/sugar/wheatgerm or yeast/sugar/maize *Drosophila* diet, supplemented with tetracycline as appropriate. The parents were raised on the same diet, supplemented with tetracycline to 100 μg/ml in the case of the transgenic males. The wild type females to which these males were mated were raised without tetracycline, to eliminate any potential maternal contribution of tetracycline. The number of transgenic and non-transgenic pupae and adults obtained from each cross was determined by scoring for DsRed2 by fluorescence microscopy.

The results of these crosses are shown in Table 12, below. In each case, in the absence of tetracycline, survival of the heterozygous transgenics was less than 2% relative to their Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals were to survive to adulthood, then this would give an "adult survival ratio" of 100%.

We further investigated the expression of tTA in these transgenic lines by quantitative (real-time) rt-PCR (qPCR). The results are given in Table 13, below.

TABLE 13

Expression levels of tTA in wild type and transgenic medfly

| Sample | tTA/18S ratio | NT/T ratio |
|---|---|---|
| Larvae | | |
| WT tet | 3.13E−06 | |
| WT NT | 2.81E−06 | |
| 656 tet | 5.80E−06 | 1.00 |
| 656 NT | 2.06E−04 | 36 |
| 670A tet | 2.71E−06 | 1.00 |
| 670A NT | 1.10E−04 | 41 |
| 670e tet | 9.70E−06 | 1.00 |
| 670e NT | 8.40E−05 | 8.7 |
| Adults | | |
| WT female | 2.83E−06 | |
| WT male | 2.16E−07 | |
| Heterozygous | | |
| 656 tet M 0 d | 5.52E−06 | 1.00 |
| 656 tet M 8 d | 1.12E−05 | 2.0 |
| 656 NT M 0 d | 4.49E−05 | 8.1 |
| 656 NT M 2 d | 2.77E−04 | 50 |
| 656 NT M 4 d | 2.22E−04 | 40 |
| 656 NT M 8 d | 9.71E−05 | 18 |
| 656 NT M 16 d | 1.49E−04 | 27 |
| 670 M tet | 4.21E−06 | 1.00 |
| 670 F tet | 2.86E−06 | 0.68 |
| 670 M NT S | 6.93E−05 | 16.45 |
| 670 F NT S | 1.92E−04 | 45.57 |
| 928Am1 F tet | 7.17E−06 | 1.00 |
| 928Am1 M tet | 8.56E−06 | 1.19 |
| 928Am1 M NT 2 d | 1.71E−04 | 23.81 |
| 928Am1 M NT 4 d | 5.36E−04 | 74.72 |
| 928Am1 M NT 8 d | 1.91E−04 | 26.66 |
| 928Am1 M NT 16 d | 1.01E−05 | 1.41 |
| 928Am1 M tet 8 d | 1.11E−06 | 0.16 |
| 928Am1 M NT S | 2.22E−04 | 31.02 |
| 928Am1 M NT S | 1.51E−04 | 21.11 |
| 928Am3 F tet | 9.09E−07 | 1.00 |
| 928Am3 M tet | 9.09E−07 | 1.00 |
| 928Am3 F NT S | 3.62E−05 | 39.85 |
| 928Am3 F NT S | 8.74E−04 | 962.07 |
| 928Am3 F NT S | 2.99E−04 | 329.32 |
| 928Am3 M NT S | 5.53E−05 | 60.83 |
| 928Am3 M NT S | 9.18E−04 | 1009.90 |
| 1124fl F tet | 2.86E−05 | 1.00 |
| 1124fl F NT 7 d | 4.11E−04 | 14.35 |
| 1124m1 M tet | 1.62E−05 | 1.00 |
| 1124m1 F NT S | 9.30E−04 | 57.55 |
| 1124m2 F tet | 8.98E−05 | 1.00 |
| 1124m2 F NT 7 d | 7.90E−04 | 8.79 |
| homozygous | | |
| 656 tet 8 d | 1.49E−05 | 1.00 |
| 656 NT 0 d | 9.23E−05 | 6.2 |
| 656 NT 2 d | 3.90E−03 | 262 |
| 656 NT 4 d | 1.92E−03 | 129 |
| 656 NT 8 d | 4.70E−03 | 316 |
| 656 NT 16 d | 8.58E−04 | 58 |

M: male;
F: female;
tet: raised on diet supplemented with tetracycline to 100 µg/ml;
NT S: raised on standard diet (0 µg/ml tetracycline);
d: days post-eclosion;
NT (n)d: raised on tet diet, then held as adults on non-tet (NT) diet for n days, as indicated;
tet (n)d: raised on tet diet, then held as adults on tet diet for n days, as indicated.

Example 9

LA670 in *Ceratitis capitata*

Figure 13:
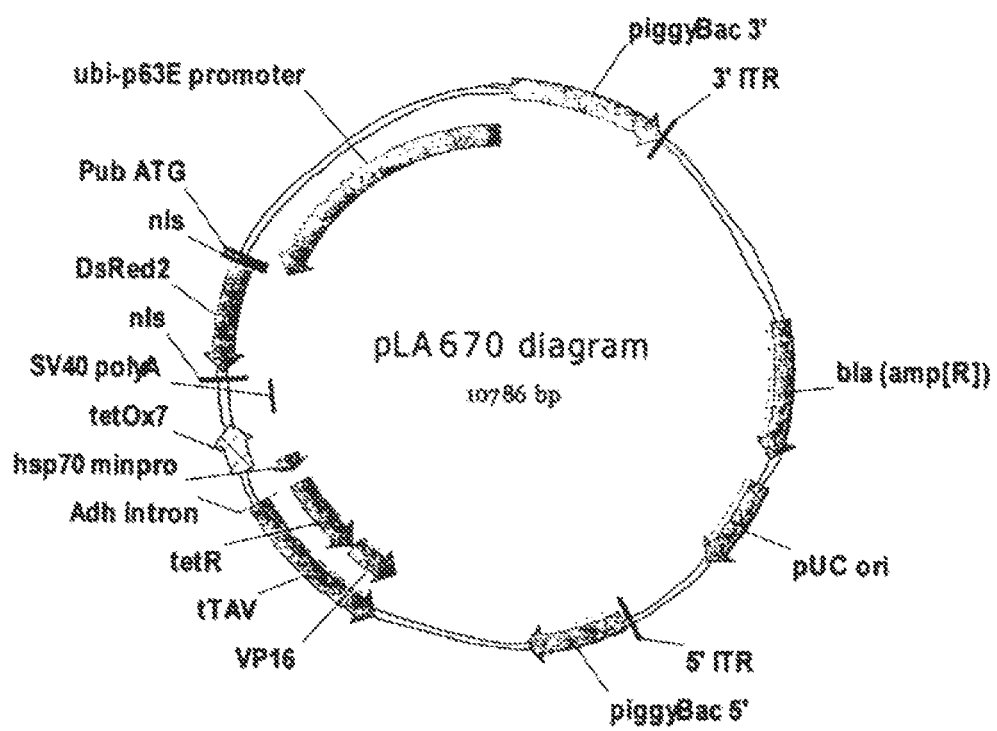
FIG. 13 is a schematic diagram of pLA670.

We obtained a single transgenic line of medfly by transformation with pLA670, a construct which closely resembles pLA656. This plasmid is illustrated in accompanying FIG. 13, and is SEQ ID NO. 23.

However, this transgenic line gave a significant number of adult transgenic progeny, even when raised as larvae on diet lacking tetracycline (Table 14). However, this LA670 insertion line does produce a readily detectable amount of tTAV mRNA in the absence of tetracycline, and this is substantially reduced by dietary tetracycline (assessed by qPCR, results shown in Table 13, above). LA670, therefore, represents a useful regulatable source of tTAV with which to drive the expression of tTAV-responsive genes. The difference in phenotype between LA656 and LA670, which are extremely similar in structure, is probably due to position effect, which is the variation in expression of transgenes depending on where they have inserted in the genome. Such variation is also shown by the variation in phenotype and tTAV expression levels between different transgenic lines with the same construct, as shown in Table 13, above. A simple method for obtaining transgenic lines carrying positive feedback constructs with different expression levels and phenotypic consequences is therefore provided, comprising generating a panel of insertion lines and screening for suitable basal and de-repressed expression levels and patterns.

TABLE 14

Effect of tetracycline on the survival of transgenic medfly heterozygous for LA670, and their +/+ siblings

| LA670 | Progeny [Tc] (µg/ml) | F/NF pupae | Pupal survival ratio (%) | F male | F female | NF male | NF female | Adult survival ratio (%) |
|---|---|---|---|---|---|---|---|---|
| | 0 | 182/220 | 83 | 72 | 35 | 102 | 103 | 52 |
| | 100 | 10/8 | 125 | 5 | 3 | 5 | 3 | 100 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals survived to adulthood, this would give an "adult survival ratio" of 100%.

Figure 14:
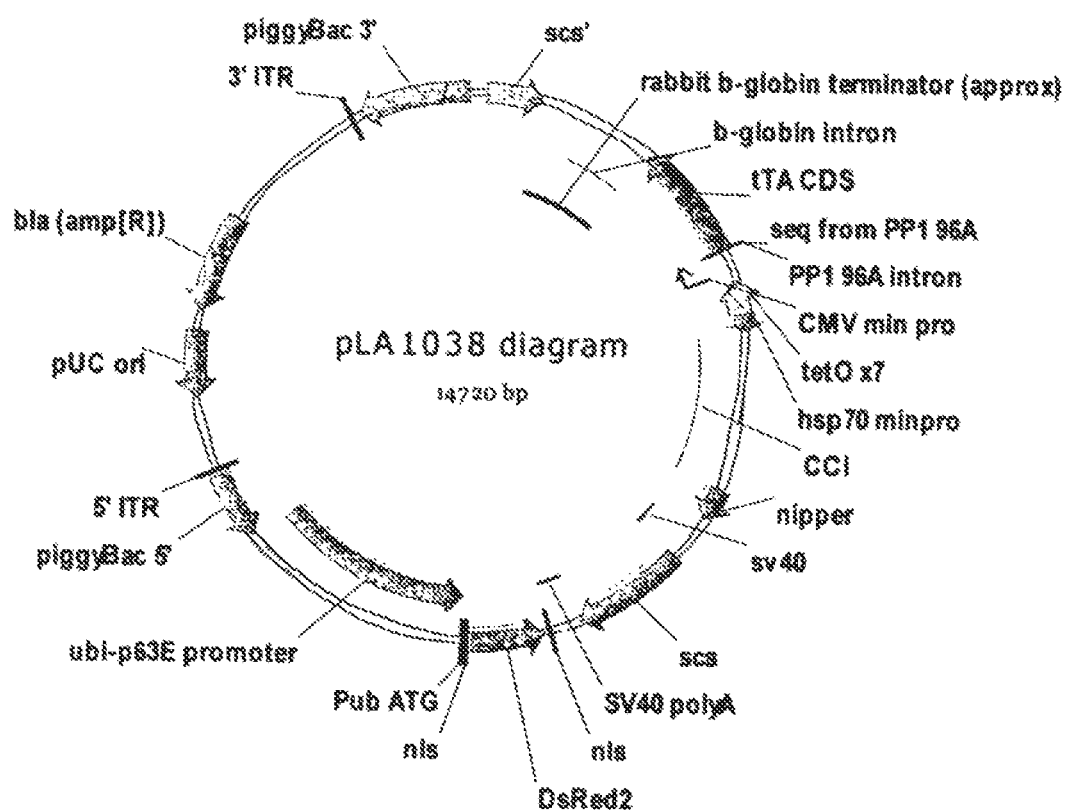
FIG. 14 is a schematic diagram of pLA1038.

We tested the ability of LA670 to drive expression of sequences placed under the transcriptional control of tetO. We analysed the expression of two potential mRNAs from pLA1038 (FIG. 14, SEQ ID NO. 24), which contains two potential tTA-responsive transcription units, divergently transcribed. These are CMV-tTA and hsp70-Cctra-nipper. PCR analysis, with controls, was performed on the expression of these transcription units in the presence and absence of pLA670. Both transcription units are expressed in the presence of pLA670. CMV-tTA is expressed at a lower, but detectable, level in LA1038/+ transgenics in the absence of LA670. hsp70-Cctra-nipper is not detectably expressed in the absence of pLA670, showing that expression is indeed driven by, and dependent on, tTAV supplied by pLA670.

Example 10

LA710 in *Pectinophora gossypiella*

*Pectinophora gossypiella* (pink bollworm, a lepidopteran) was transformed with LA710 (FIG. 15, SEQ ID NO. 19) by standard methods (Peloquin et al., 2000). Four transgenic lines were recovered. Males of these lines were crossed with females wild type for LA710. Newly hatched larvae were placed in individual 1.7 ml vials with diet, either with or without 7-chlortetracycline (40 µg/ml), and scored for fluorescence. No significant difference was observed in the numbers of transgenics surviving to adulthood relative to numbers of their wild type siblings, either with or without chlortetracycline. We conclude that LA710 does not typically lead to the accumulation of lethal levels of tTAV, even in the absence of dietary chlortetracycline.

We examined the expression of tTAV mRNA in LA710 transgenics by PCR following a reverse transcriptase reaction (rt-PCR). We found that tTAV mRNA was not detectable in chlortetracycline-fed larvae, but was detectable in larvae which had not received chlortetracycline (data not shown). This positive feedback construct LA710, therefore, provides, in these moths, a source of tTAV that can be regulated by supplying dietary chlortetracycline, and for which de-repressed expression, though readily detectable, is non-lethal. We also observed significant variation in the intensity of the band corresponding to tTAV mRNA in samples from different lines.

Example 11

LA1124 in *Pectinophora gossypiella*

*Pectinophora gossypiella* (pink bollworm, a lepidopteran) was transformed with LA1124 (FIG. 12, SEQ ID NO. 21) by standard methods (Peloquin et al., 2000). A single transgenic line was recovered. Males of this line were crossed with females wild type for LA1124. Newly hatched larvae were placed in individual 1.7 ml vials with diet, either with or without 7-chlortetracycline (40 µg/ml), and scored for fluorescence. These larvae were screened again when they had had time to develop to a late larval stage. All larvae survived, except for the fluorescent (LA1124/+) larvae on diet lacking chlortetracycline, as shown in Table 15, below.

TABLE 15

Pink bollworm: survival from early to late larval stage of LA1124/+ or their wild typ siblings, on diet with or without chlortetracycline

| 100 µg/ml chlortetracycline | | 0 µg/ml chlortetracycline | |
|---|---|---|---|
| LA1124/+ | Wild-type | LA1124/+ | Wild-type |
| 3 (0 dead) | 11 (0 dead) | 8 (8 dead) | 7 (0 dead) |

We examined the expression of tTAV mRNA in LA1124 pink bollworm by PCR following a reverse transcriptase reaction (rt-PCR). We found that tTAV mRNA was readily detectable in chlortetracycline-fed larvae, but considerably elevated in larvae which had not received chlortetracycline (data not shown). The significant basal expression of tTAV mRNA in this construct is probably due to the inclusion in LA1124 of the hr enhancer, which was included for this reason. Comparison of the structure and function of LA1124 with that of LA710 clearly illustrates that basal and maximum levels of the gene product can readily be selected by appropriate modification of the expression construct, this principle being demonstrated, here, by regulating levels of expression of a tTAV-dependent RNA (in this case the tTAV mRNA).

Example 12

Sex-Specific Expression Using Positive Feedback

It is preferred to control, by design, the expression of tTAV from a positive feedback construct, so that it can be differentially expressed in different tissues, or different developmental stages, or different sexes, for example. One application for this is in genetic sexing, in which a sexual dimorphism is induced between the two sexes and this is used as a basis for separating the two sexes. In the context of the Sterile Insect Technique, e.g. for medfly, this preferably means killing the females, most preferably at an early stage in their development. No early-acting female-specific promoters are known for medfly, which limits the potential of the two-component repressible dominant lethal system exemplified for *Drosophila* using promoters or enhancers from yolk protein genes (Heinrich and Scott, 2000; Thomas et al., 2000). It would clearly be advantageous to be able to combine the beneficial characteristics of a conditional positive feedback system with a mechanism conferring female specificity.

We, therefore, modified a non-sex-specific positive feedback construct by inserting a sex-specific intronic region from Cctra, the medfly homologue of the *Drosophila melanogaster* gene transformer (Pane et al., 2002). The sex-specific splicing of Cctra is illustrated diagrammatically in FIG. 16, which is adapted from (Pane et al., 2002)supra. FIG. 16 shows the genomic organisation of the medfly tra gene. The top line represents the genomic Cctra locus. Exons are shown as blocks; aug marks the shared start codon. The alternate splice junctions are marked i. Putative tra/tra-2 binding sites are marked with arrowheads. Transcript F1, the only one to encode functional Cctra protein, is specific to females. Transcripts M1 and M2 are found in both males and females.

Three main transcripts are produced: M1, M2 and F1. Transcript F1 is found only in females, and is the only one to encode full-length, functional Cctra protein. Transcripts M1 and M2 are found in both males and females, and include additional exonic sequence, which inserts one or more stop codons relative to transcript F1, leading to truncation of the open reading frame.

We inserted the Cctra intron into the open reading frame of tTAV, so that excision by splicing of the complete intron, in the manner of transcript F1, would reconstitute an intact tTAV coding region, but splicing in the manner of either M1 or M2 would result in a truncated protein incapable of acting as a transcriptional enhancer. The resulting plasmid, pLA1188 (FIG. 17, SEQ ID NO. 22), was injected into medfly embryos. Surviving larvae were recovered, and extracts from these larvae were analysed by rt-PCR to determine the splicing pattern of the tTAV transcript.

Female larvae yielded PCR products corresponding to the expected sizes that would result from splicing in the pattern of the endogenous Cctra gene, in other words corresponding to splicing in the Ml, M2 and F1 patterns. These data indicate that the Cctra intron can splice correctly in a heterologous context and, therefore, provides a suitable method for introducing sex-specificity into a positive feedback construct. Furthermore, since tra function is conserved across a wide phylogenetic range (Saccone et al., 2002), and other sex-specific introns are known, e.g. in the *Drosophila melanogaster* gene double-sex (dsx), which is also well conserved, this provides a general method for manipulating the expression of genes. It will be apparent to the person skilled in the art that such manipulations can alternatively, or additionally, be applied to other genes responsive to a transcriptional activator, so that sex-specific expression of a target gene can be achieved by combining non-sex-specific expression of a transcriptional activator with sex-specific expression, e.g. through splicing, of a functional RNA under the transcriptional control of the transcriptional activator. Furthermore, it will also be apparent that this provides a simple mechanism for differential expression of two, or more, different target genes, or gene products, such that one, or one group, is expressed in both sexes and the other, or other group, in only one sex. This is illustrated for medfly in FIG. 18.

The primers used were:

```
Tra(tTAV)Seq+:
                                   (SEQ ID NO: 12)
5'-CCTGCCAGGACTCGCCTTCC;
and Tra(tTAV)Seq-:
                                   (SEQ ID NO: 13)
5'-GTCATCAACTCCGCGTTGGAGC.
```

RT-PCR products of ~600 and ~200 bp were produced when cDNA derived from female medflies 1 and 2 was used as a template, representing "male" (M1 and M2) and female-specific (F1) spliced forms of mRNA respectively (data not shown). The ~200 bp product could have been produced due to contamination with tTAV DNA—the female spliced form completely removes the Cctra intron an so leads to a PCR product that is identical to that which would be obtained from any of several tTAV-containing plasmids or samples handled in the same laboratory. The ~600 bp band, in contrast, retains ~400 bp of Cctra sequence and is diagnostic of correct splicing of the construct.

In another experiment (data not shown), expression of transcripts from LA1038 in response to tTAV from LA670 was analysed by gel chromatography (data not shown), using:

A: rt-PCR for expression of CMV-tTA from LA1038 in extracts from LA1038/+ , LA670/+ double heterozygotes;
B: rt-PCR for expression of hsp70-Cctra-nipper in extracts from LA1038/+ , LA670/+ double heterozygotes; and
C: rt-PCR for expression of CMV-tTA from LA1038 in extracts from LA1038/+ heterozygotes without LA670.

All flies were raised in the absence of dietary tetracycline. In A and C, two bands were present between 200 bp and 400 bp and represent cDNA from spliced mRNA (lower molecular weight band) and genomic DNA or cDNA from unspliced message (higher molecular weight band) respectively. In B, a band at approximately 200 bp represents cDNA from mRNA spliced in the pattern of the Cctra female-specific F1 transcript, an upper band of approximately 1500 bp representing genomic DNA or cDNA from unspliced message, and bands of intermediate size representing cDNA spliced in the pattern of the Cctra non-sex-specific M1 and M2 transcripts, or non-specific bands.

Primer sequences used were:

```
hsp70-Cctra-nipper:
NIP: 5'-CATCGATGCCCAGCATTGAGATG
and

HSP: 5'-CAAGCAAAGTGAACACGTCGCTAAGCGAAAGCTA;

CMV-tTA:
CMV: 5'-GCCATCCACGCTGTTTTGACCTCCATAG
and

TTA: 5'-GCCAATACAATGTAGGCTGCTCTACAC.
```

These data (not shown) demonstrate that the hsp-Cctra-nipper section of LA1038 is shown to be correctly spliced in the female form in 6/6 females, and in the male form in 6/6 males.

Transformer

Example 13

*Ceratitis capitata* tra intron

We have prepared an insertion of a Cctra intron cassette into a synthetic open reading frame (ORF). Two versions of this splice correctly in Medfly, in other words the splicing of the Cctra intron cassette faithfully recapitulates what it would normally do in the context of the endogenous Cctra gene. This is to produce 3 (major or only) splice variants in females, one of which is female-specific (called F1), while the other two are found in both males and females (called M1 and M2). Since each of the non-sex-specific transcripts contain additional exonic material with stop codons, we have also arranged this so that only the female splice variant produces functional protein.

Each of these constructs (LA3077 and LA3097) has the Cctra intron flanked by TG and GT (to give 5'. . . TG¦intron¦GT . . . 3'. An older construct, which does not work perfectly, is LA1188. LA1188 is quite well characterized—splicing is exactly as above except that an additional 4 nucleotides are removed. The intron is in the context 5'. . . TGGCAC¦intron¦GT . . . 3'; splicing removes an additional 4 bases, i.e. 5'. . . TG¦GCACintron¦GT . . . 3' (FIG. 33).

In all cases the intron is invariant, and is simply the complete Cctra intron sequence. As is normal for introns, it begins GT and ends AG. Almost all introns start with GT, so the use of the rare alternative GC in LA1188 is surprising [GC-AG introns are a known alternative—in one large-scale survey, 0.5% of all introns were reported to use GC-AG (Burset et al., 2001), though this may be an underestimate, particularly for alternatively spliced introns, of which perhaps 5% might use GC-AG (Thanaraj and Clark, 2001)].

RT-PCR analysis was performed on LA3077, (a positive feedback construct with the CcTRA intron in the tTAV open reading frame). Transformed adult flies of both sexes were reared on diet substantially free of tetracycline ("off tetracycline") for 7 days. Flies were then collected for RNA extraction and RT PCR using primers (HSP- SEQ ID NO. 104 and VP16 SEQ ID NO. 105) were used to analyse the splicing pattern of the CcTRA intron (FIG. 34). In two female samples we found the correct splice pattern of the Cctra (776 bp, corresponding to precise removal of the Cctra intron) and saw no such band in males.

We found that LA3077 and LA3097 correspondingly gave repressible female-specific lethality. LA3077 was tested phenotypically through crossing flies heterozygous for LA3077 to wild type, on and off tetracycline. Female lethality ranged from 50 to 70%. LA3097 (a modified version of LA3077 whereby the Cctra intron immediately follows the start codon in the tTAV ORF), demonstrated a much higher level of female specific lethality, peaking at 100% (FIG. 35). The Cctra intron was also inserted in tTAV2 at the same position as LA3097, in construct LA3233, and this gave a similar phenotypic result as LA3097 (FIG. 35).

We have also prepared transformants of LA3077 in Drosophila. Phenotypically, the construct works perfectly, which is to say it is a highly effective female-specific lethal. However, sequencing of the splice variants of one of these insertions has shown that the splicing of this construct in Drosophila is not quite the same as it is in Medfly (SEQ ID NO. 57). The critical transcript, the female-specific one, is the same in both, but at least one of the non-sex-specific transcripts is different. It still incorporates extra exonic sequence, with stop codons, but the splice junctions are not quite the same (FIG. 36). This observation is extremely important in that it shows that this method (regulation of gene expression by use of alternatively spliced introns) can be used across quite a wide phylogenetic range.

A simple test to determine whether an as yet uncharacterized exonic splice regulator (such as enhancers and suppressors) may be modifying the function of the alternatively spliced intron, could include making the construct and introducing it into a target tissue, then examining its splice pattern. In many cases this will not require germline transformation, so the test can be quite rapid, for instance by transient expression in suitable tissue culture cells or in vivo. For instance, in vivo testing in insects could be achieved by delivering the DNA by microinjection. However, as the skilled person will appreciate, microinjection coupled with electroporation, or electroporation, chemical transformation, ballistic methods, for instance,have all been used in a number of various contexts and such methods of plasmid introduction and protein expression therefrom are will known in the art.

We have also recently made, and have obtained transgenics with, the Cctra intron in a different gene (LA3014) (all the above examples are in tTAV). LA3014 contains a ubiquitin-reaper$^{KR}$ fusion downstream of a Cctra intron. Phenotypic data (FIG. 35) shows that LA3014 transgenic Medfly gave repressible female-specific lethality. RT-PCR analysis on RNA extracted from adult males and females raised off tetracycline, using primers (HSP, SEQ ID NO 74) and ReaperKR (SEQ ID NO. 75), demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly (FIG. 35).

We have also recently made, and have obtained transgenics with, 'intron-only' Cctra-based constructs with the intron in a different gene (all the above examples are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above.

In order to demonstrate the phylogenetic range of the Cctra intron we generated transgenic LA3097 and LA3233 Anastrepha ludens. LA3097 and LA3233 were selected for injection into Anastrepha ludens as they demonstrated the best female specific lethality in Ceratitis capitata (see Example 13). Phenotypic data was generated for 4 independent LA3097 lines and 1 LA3233 line (see FIG. 38). Female specific lethality was generally somewhat lower in Anastrepha ludens when compared to C. capitata but reached 100% in one line.

Anastrepha ludens transformed with LA3097 and raised on tetracycline until eclosion were isolated and maintained off tetracycline for 7 days. RNA was then extracted and RT-PCR analysis was performed using primers HSP (SEQ ID NO. 76) and TETRR1 (SEQ ID NO. 77). The correct female specific (Fl-like) splice pattern was observed RNA isolated from in females (348 bp) but not from males demonstrating the function of the Cctra intron in a different species (FIG. 39)

The brightest male band and the female specific band were purified and precipitated for sequencing. The female specific transcript was found to be correctly spliced in Mexfly females as expected for LA3097:

```
LA3097:   AGCCACCATG □ □ GT . . . intron . . . AG □ GTCAGCCGCC
```

Example 14

Bactocera zonata tra intron

We isolated the tra intron from Bactocera zonata (B. zonata) (SEQ ID NO. 58) using primers ROSA1 (SEQ ID NO. 78), ROSA2 (SEQ ID NO. 79), and ROSA3 (SEQ ID NO. 80).

These primer sequences were designed based on conserved coding sequence of Ceratitis capitata and Bactrocera oleae tra homologs. Using ROSA2 and ROSA3 or ROSA1 and ROSA3 as primers, the tra intron and its flanking coding region were amplified from Bactrocera zonata genomic DNA. Then we used these PCR products as a template and amplified the tra intron fragment to make the construct-LA3376 (FIG. 31 and SEQ ID NO. 55). The primers (BZNHE- SEQ ID NO. 81 and BZR-SEQ ID NO. 82) were used for making the constructs; these primers contain additional sequences for cloning purposes. The Bztra intron in LA3376 is cloned into the ORF of tTAV3 and also of reaper$^{KR}$. Medfly transformants were generated and RNA extracted from male and female flies.

RT-PCR was then performed on both the reaper$^{KR}$ (HB-SEQ ID NO. 83) and Reaper KR- SEQ ID NO. 84) and tTAV3 (SRY- SEQ ID NO. 85) and AV3F- SEQ ID NO. 86) splice. The expected fragments of 200 bp for reaper$^{KR}$ and 670 bp for tTAV3, corresponding to splicing in a pattern equivalent to the F1 transcript of Cctra (Pane et al., 2002), were generated in females (FIG. 40).

Example 15

Isolation and Splicing of the *Ceratitis rosa* (*C. rosa*, Natal fruit fly) tra intron Primers ROSA2 (SEQ ID NO. 87) and ROSA3 (SEQ ID NO. 88) were designed based on conserved coding sequence of *Ceratitis capitata* and *Bactrocera oleae*. Using ROSA2 and ROSA3 as primers, the tra intron and its flanking coding region were amplified from *Ceratitis rosa* genomic DNA (SEQ ID NO. 59). We then used the PCR products as a template and amplified the tra intron fragment to make constructs. The primers (CRNHE-SEQ ID NO 89 and CRR SEQ ID NO 90) were used during the construction of LA3242 (SEQ ID NO. 56 and FIG. 32. LA3242 contains the *C. rosa* intron at the 5' end of the reaper$^{KR}$ ORF. *Ceratitis capitata* embryos were injected with DNA of LA3242, injected embryos were raised to adulthood on a diet substantially free of tetracycline. RNA was extracted from adult males and females; this was used as a template for RT PCR using primers HB (SEQ ID NO. 91) and ReaperKR (SEQ ID NO. 92). The expected female-specific splice band (200 bp), corresponding to splicing in the equivalent pattern to that of transcript F1 of Cctra, was observed in females and not males (FIG. 41).

Double-sex

Example 16

*Bombyx mori* dsx in PBW

The sequence of a *Bombyx mori* (silk moth) homolog of *Drosophila* Dsx (Bmdsx) has been previously described and a male- and a female-specific splice product have been identified (Suzuki et al, 2001). Both males and females use the same 3' polyA, and there are two female specific exons. One paper has suggested that the sex-specific splicing is not dependent on tra/tra2, in other words even though the pattern looks the same, the underlying mechanism may be different (Suzuki et al., 2001), though their data, principally the lack of recognisable tra-tra2 binding sites, however, is not compelling. In addition, a B. mori dsx mini-gene construct (containing exonic sequence and truncated intronic sequence) has been transformed into *B. mori* and the germline transformants show sex-specific splicing (Funaguma et al., 2005).

We have generated a Bmdsx minigene based on the sequence used in the Funaguma et al paper, with some significant changes, and injected this into the moth Pink Bollworm to ascertain if one can obtain sex-specific splicing in a divergent species. The mini-gene construct we generated does not included exon 1, which is present in both males and females. In addition, we removed the intron between exon 3 and 4 (the two female specific exons), included a heterologous sequence (containing multiple cloning sites, MCS), used the Hr5-IE1 enhancer/promoter sequence from the baculovirus AcNPV and used a 3' transcriptional termination sequence derived from SV40 (see FIG. 42 for a schematic). The individual exon/flanking intron fragments used were amplified and recombined together by PCR and ligated into a construct carrying a Hr5/IE1 enhancer promoter fragment and SV40 3'UTR (FIGS. 22 and SEQ ID NO. 22).

LA3435 was injected into pink bollworm (Pectinophora gossypiella) embryos. First instar larvae were collected after 5-7 days and analysed individually by RT-PCR (using primers 1E1 transcr- SEQ ID NO. 93 and SV40-RT-P2- SEQ ID NO. 94) to determine if BMdsx can undergo male and female specific splicing (FIG. 43). Our analysis detected the male specific band (predicted to be 442 bp) in 4 samples (Lanes 1, 2, 3 and 4) and the female specific band (predicted to be 612 bp) in 1 sample (Lane 5).

The correct splicing of *B. mori* dsx in PBW demonstrates that we can achieve (have achieved) sex-specific expression of a heterologous sequence (here, the MCS) in a Lepidopteran by utilizing an alternative splicing system. Furthermore, since this splicing system was derived from a heterologous species, this suggests that such constructs might work over a wide phylogenetic range. However, the identification of alternative splicing systems in the species of interest is also envisioned, and methods for identifying such alternative splicing systems are provided herein or will be known to the person skilled in the art. By providing a MCS in our Example (see FIG. 42), the expression of a sequence of interest, for example a coding region for a protein of interest could readily be achieved by inserting said sequence. If said sequence encoded a suitable protein, a sex-specific phenotype, for example conditional sex-specific lethality, could thereby be introduced, for example into pink bollworm.

Example 17

Isolation of Codling moth dsx

The dsx gene from Codling moth (*Cydia pomonella*) was isolated by performing 3' RACE using primers which were based on sequence alignments from *B. oleae, B. tyroni, C. capitata, D. melanogaster, B. mori* , and *A. gambiae*. RNA was isolated from a male and female codling moth and 3' RACE , to generate cDNA, was performed using the TT7T25 primer (SEQ ID NO. 95).

PCR was performed using the primers ds1c (SEQ ID NO. 96) and TT7 (SEQ ID NO. 97). Two rounds of nested PCR were then performed on the product of the first PCR using the primers codling2a (SEQ ID NO. 98) and TT7 (SEQ ID NO. 99) and the product of the second round of PCR using Codling2b (SEQ ID NO. 100) and TT7. The isolated male and female specific sequences share sequence similarity to previously isolated dsx homologues (Male-SEQ ID NO. 43 and Female- SEQ ID NO. 42).

Example 18

Isolation of PBW dsx

The dsx gene from pink bollworm was isolated by performing 3' RACE using primers which were based on sequence alignments from *B. oleae, B. tyroni, C. capitata, D. melanogaster, B. mori,* and *A. gambiae*. RNA was isolated from a male and female codling moth and 3' RACE , to generate cDNA, was performed using TT7T25 (sequence defined herein). PCR was performed using the primers Pbwdsx2 (SEQ ID NO. 101) and TT7 (SEQ ID NO. 102). Nested PCR was then performed on the product of the first PCR using the primers Pbwdsx3 (SEQ ID NO. 103) and TT7. Three female specific sequences were isolated: PBWdsx-F1 (SEQ ID NO. 40), PBWdsx-F2 (FIG. 10), and PBWdsx-F3 (SEQ ID NO. 71) and one male specific sequence (SEQ ID NO. 42). The isolated male and female specific sequences share sequence similarity to previously isolated dsx homologues.

Example 19 dsx in *Anopheles gambiae*

Figure 44:
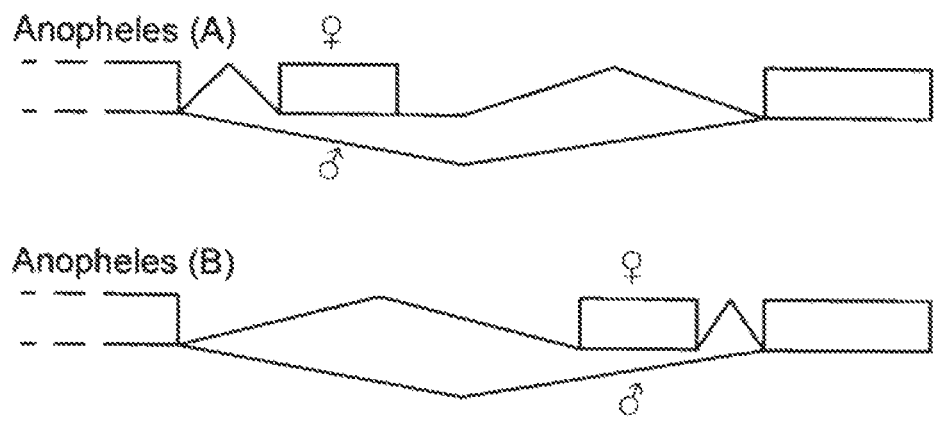

The sequence of the dsx gene of *Anopheles gambiae* has previously been described (Scali et al 2005). However, when we have tried to repeat the work described in the paper we find that there are some differences in the splicing that occurs. When we tried to repeat the amplification of the female specific transcript using primers designed from the mRNA sequence (Accession; AY903308 for female coding sequence and AY903307 for male coding sequence), the amplification failed. However, when Scali and colleagues showed that there was a shared exon, which had previously not been described, we designed primers to amplify the entire dsx transcript and gene. Using these primers and primers designed from genomic DNA sequence (Accession; GI:19611767) we find that the splicing of the female transcript is different from that described by Scali et al 2005 (FIG. 44). The transcript showed that the female exon was in a different position. There are several explanations for these differences, but the most likely are either some sort of strain difference in the *Anopheles* that we used to get the data from, or the published sequence is not from *Anopheles gambiae*, or there is more than one female isoform as shown for *Stegomyia aegypti* in Example 20.

We have also successfully used primers, designed around our version of the *Anopheles gambiae* dsx splicing, that are able to distinguish between males and females of *Anopheles gambiae* (FIG. 45). This provides good evidence that the system will be functional as a sex-specific splicing mechanism when fused to a protein of interest, such as tTAV or a killer.

The *Anopheles gambiae* dsx gene that we have isolated from genomic DNA, which has several changes in nucleotide sequence compared to the reported genomic sequence, was cloned into LA3359 (SEQ ID NO. 47) and LA3433 (SEQ ID NO. 48), schematics can be found in FIGS. 23 and FIG. 24, respectively.

Example 20 dsx in *Stegomyia aegypti*

The splicing of the gene appears to be similar to *Anopheles gambiae* dsx (Scali et al 2005). The *Stegomyia aegypti* dsx gene is illustrated diagrammatically in FIG. 47 or 48. A male-specific transcript (M1) is produced which does not include exons 5a or 5b. Two female specific splice variants (F1 and F2) have the following structure; F1 comprises exons 1-4, 5a, 6 and 7 but not 5b, F2 comprises exons 1-4 and 5b (FIG. 46). In addition, a further transcript (C1) is present in both males and females; this comprises exons 1-4 and 7, but not exons 5a, 5b or 6.

The splicing of the gene appears to be similar to *Anopheles gambiae* dsx (Scali et al 2005). The *Stegomyia aegypti* dsx gene is illustrated diagrammatically in FIG. 47 or 48. Actin 4

Example 21

*Stegomyia aegypti* Actin-4 Gene

One way to get sex-, tissue- and stage-specific expression of a gene of interest is to link it with the *Stegomyia aegypti* Actin-4 (AeAct-4) gene. This gene is only expressed in the developing flight muscles of female *Stegomyia aegypti* (Munoz et al 2004). They used in-situ hybridisation to an RNA to detect the expression profile of AeAct-4. We have taken a fragment of the *Stegomyia aegypti* Actin-4 gene, comprising a putative promoter region, an alternatively spliced intron, and a section of 5' untranslated region (UTR) and placed it in front of sequence coding for tTAV (FIG. 49) to test the function of the sex specific splicing when fused to tTAV.

We integrated LA1172 into the *Stegomyia aegypti* genome using piggyBac. Two independent lines were generated (lines 2 and 8). Both of these lines show the correct splicing of the Actin-4-tTAV gene (FIGS. 50 and 51). The Actin-4 promoter and alternatively spliced intron can therefore be used successfully to provide sex-, tissue- and stage-specific splicing of a gene of interest in *Stegomyia aegypti*.

REFERENCES PART 1

Alphey, L. (2002). Re-engineering the Sterile Insect Technique. Insect Biochem Mol Biol 32, 1243-1247.

Alphey, L., and Andreasen, M. H. (2002). Dominant lethality and insect population control. Mol Biochem Parasitol 121, 173-178.

Alphey, L., Beard, B., Billingsley, P., Coetzee, M., Crisanti, A., Curtis, C. F., Eggleston, P., Godfray, C., Hemingway, J., Jacobs-Lorena, M., et al. (2002). Malaria control with genetically modified vectors. Science 298, 119-121.

Baron, U., and Bujard, H. (2000). Tet repressor-based system for regulated gene expression in eukaryotic cells: principles and advances. Meth Enzymol 327.

Baron, U., Gossen, M., and Bujard, H. (1997). Tetracycline-controlled transcription in eukaryotes: novel transactivators with graded transactivation potential. Nucl Acids Res 25, 2723-2729.

Bello, B., Resendez-Perez, D., and Gehring, W. (1998). Spatial and temporal targeting of gene expression in *Drosophila* by means of a tetracycline-dependent transactivator system. Development 125, 2193-2202.

Benedict, M., and Robinson, A. (2003). The first releases of transgenic mosquitoes: an argument for the sterile insect technique. Trends Parasitol 19, 349-355.

Bennett, D., Szoor, B., Gross, S., Vereshchagina, N., and Alphey, L. (2003). Ectopic expression of inhibitors of Protein Phosphatase type 1 (PP1) can be used to analyse roles of PP1 in *Drosophila* development. Genetics 164, 235-245.

Berger, S. L., Cress, W. D., Cress, A., Triezenberg, S. J., and Guarente, L. (1990). Selective inhibition of activated but not basal transcription by the acidic activation domain of VP16: evidence for transcriptional adaptors. Cell 61, 1199-1208.

Berghammer, A. J., Klingler, M., and Wimmer, E. A. (1999). A universal marker for transgenic insects. Nature 402, 370-371.

Brand, A., Manoukian, A., and Perrimon, N. (1994). Ectopic expression in *Drosophila*. Meth Cell Biol 44, 635-654.

Catteruccia, F., Nolan, T., Loukeris, T., Blass, C., Savakis, C., Kafatos, F., and Crisanti, A. (2000). Stable germline transformation of the malaria mosquito *Anopheles stephensi*. Nature 405, 959-962.

Coates, C., Jasinskiene, N., Miyashiro, L., and James, A. (1998). Mariner transposition and transformation of the yellow fever mosquito, *Aedes aegypti*. Proc Natl Acad Sci USA 95, 3748-3751.

Damke, H., Gossen, M., Freundlieb, S., Bujard, H., and Schmid, S. (1995). Tightly regulated and inducible expression of dominant interfering dynamin mutant in stably transformed HeLa cells. Meth Enz 257, 209-220.

Fussenegger, M. (2001). The impact of mammalian gene regulation concepts on functional genomic research, metabolic engineering, and advanced gene therapies. Biotechnol Prog 17, 1-51.

Fussenegger, M., Mazur, X., and Bailey, J. (1998a). pTRIDENT, a novel vector family for tricistronic expression in mammalian cells. Biotech Bioeng 57, 1-10.

Fussenegger, M., Moser, S., and Bailey, J. (1998b). pQuattro vectors allow one-step transfection and auto-selection of quattrocistronic artificial mammalian operons. Cytotechnology 28, 229-235.

Gebauer, F., Merendino, L., Hentze, M. W., and Valcarcel, J. (1998). The *Drosophila* splicing regulator sex-lethal directly inhibits translation of male-specific-lethal 2 mRNA. RNA 4, 142-150.

Gill, G., and Ptashne, M. (1988). Negative effect of the transcriptional activator GAL4. Nature 334, 721-724.

Gossen, M., Bonin, A., Freundlieb, S., and Bujard, H. (1994). Inducible gene expression systems for higher eukaryotic cells. Curr Opin Biotechnol 5, 516-520.

Gossen, M., and Bujard, H. (1992). Tight control of gene expression in mammalian cells by tetracycline- responsive promoters. Proc Natl Acad Sci U S A 89, 5547-5551.

Handler, A. (2002). Use of the piggyBac transposon for germ-line transformation of insects. Insect Biochem Mol Biol 32, 1211-1220.

Handler, A., and James, A. (2000). Insect transgenesis: methods and applications (Boca Raton, CRC Press).

Heinrich, J., and Scott, M. (2000). A repressible female-specific lethal genetic system for making transgenic insect strains suitable for a sterile-release program. Proc Nat'l Acad Sci (USA) 97, 8229-8232.

Horn, C., Schmid, B., Pogoda, F., and Wimmer, E. (2002). Fluorescent transformation markers for insect transgenesis. Insect Biochem Mol Biol 32, 1221-1235.

Jasinskiene, N., Coates, C., Benedict, M., Cornel, A., Rafferty, C., James, A., and Collins, F. (1998). Stable transformation of the yellow fever mosquito, Aedes aegypti, with the Hermes element from the housefly. Proc Natl Acad Sci USA 95, 3743-3747.

Kelley, R. L., Solovyeva, I., Lyman, L. M., Richman, R., Solovyev, V., and Kuroda, M. I. (1995). Expression of msl-2 causes assembly of dosage compensation regulators on the X chromosomes and female lethality in *Drosophila*. Cell 81, 867-877.

Lobo, N., Hua-Van, A., Li, X., Nolen, B., and Fraser, M. (2002). Germ line transformation of the yellow fever mosquito, *Aedes aegypti*, mediated by transpositional insertion of a piggyBac vector. Insect Molecular Biology 11, 133-139.

Lozovsky, E., Nurminsky, D., Wimmer, E., and Hartl, D. (2002). Unexpected stability of mariner transgenes in *Drosophila*. Genetics 160, 527-535.

Matsuo, T., Takahashi, K., Kondo, S., Kaibuchi, K., and Yamamoto, D. (1997). Regulation of cone cell formation by Canoe and Ras in the developing *Drosophila* eye. Development 124, 2671-2680.

McCombs, S., and Saul, S. (1995). Translocation-based genetic sexing system for the oriental fruit-fly (Diptera, Tephritidae) based on pupal color dimorphism. Ann Ent Soc Am 88, 695-698.

Moreira, L., Wang, J., Collins, F., and Jacobs-Lorena, M. (2004). Fitness of anopheline mosquitoes expressing transgenes that inhibit Plasmodium development. Genetics 166, 1337-1341.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Parker, L., Gross, S., Beullens, M., Bollen, M., Bennett, D., and Alphey, L. (2002). Functional interaction between NIPP1 and PP1 in *Drosophila*: lethality of over-expression of NIPP1 in flies and rescue by the over-expression of PP1. Biochem J 368, 789-797.

Peloquin, J. J., Thibault, S. T., Staten, R., and Miller, T. A. (2000). Germ-line transformation of pink bollworm (Lepidoptera: gelechiidae) mediated by the piggyBac transposable element. Insect Mol Biol 9, 323-333.

Perera, O., Harrell, R., and Handler, A. (2002). Germ-line transformation of the South American malaria vector, *Anopheles albimanus*, with a piggyBac-EGFP tranposon vector is routine and highly efficient. Insect Molecular Biology 11, 291-297.

Pinkerton, A., Michel, K., O'Brochta, D., and Atkinson, P. (2000). Green fluorescent protein as a genetic marker in transgenic *Aedes aegypti*. Insect Molecular Biology 9, 1-10.

Reichhart, J., and Ferrandon, D. (1998). Green balancers. *Drosophila* Information Service 81, 201-202.

Rorth, P. (1998). Gal4 in the *Drosophila* female germline. Mech Dev 78, 113-118.

Saccone, G., Pane, A., and Polito, C. (2002). Sex determination in flies, fruitflies and butterflies. Genetica 116, 15-23.

Salghetti, S., Caudy, A., Chenoweth, J., and Tansey, W. (2001). Regulation of transcriptional activation domain function by ubiquitin. Science 293, 1651-1653.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Shockett, P., Difilippantonio, M., Hellman, N., and Schatz, D. (1995). A modified tetracycline-regulated system provides autoregulatory, inducible gene expression in cultured cells and transgenic mice. Proc Nat'l Acad Sci (USA) 92, 6522-6526.

Stebbins, M., and Yin, J. (2001). Adaptable doxycycline-regulated gene expression systems for *Drosophila*. Gene 270, 103-111.

Thomas, D., Donnelly, C., Wood, R., and Alphey, L. (2000). Insect population control using a dominant, repressible, lethal genetic system. Science 287, 2474-2476.

Varshaysky, A. (2000). Ubiquitin fusion technique and its descendants. Meth Enz 327.

REFERENCES, PART 2

Allen ML, Christensen BM. Related 2004 Flight muscle-specific expression of act88F: GFP in transgenic Culex quinquefasciatus Say (Diptera: Culicidae). Parasitol Int. 53(4):307-14.

Bennett D, Szoor B, Gross S, Vereshchagina N, Alphey L. 2003 Ectopic expression of inhibitors of protein phosphatase type 1 (PP1) can be used to analyze roles of PP1 in *Drosophila* development. Genetics. 164(1):235-45.

Black, D. (2003). Mechanisms of alternative pre-messenger RNA splicing. Annu Rev Biochem 72, 291-336.

Burset, M., Seledtsov, I., and Solovyev, V. (2001). SpliceDB: database of canonical and non-canonical splice sites in mammalian genomes. Nucleic Acids Research 29, 255-259.

Caceres JF, Kornblihtt AR. 2002 Alternative splicing: multiple control mechanisms and involvement in human disease. Trends Genet. 18(4):186-93.

Cande C, Cecconi F, Dessen P, Kroemer G. 2002 Apoptosis-inducing factor (AIF): key to the conserved caspase-independent pathways of cell death? J Cell Sci. 115(24): 4727-34.

Cartegni, L., Chew, S., and Krainer, A. (2002). Listening to silence and understanding nonsense: exonic mutations that affect splicing. Nature Reviews Genetics 3, 285-298.

Clark, F., and Thanaraj, T. (2002). Categorization and characterization of transcript-confirmed constitutively and alternatively spliced introns and exons from human. Human Molecular Genetics 11, 451-464.

Funaguma, S., Suzuki, M., Tamura, T., and Shimada, T. (2005). The Bmdsx transgene including trimmed introns is sex-specifically spliced in tissues of the silkworm, *Bombyx mori*. J Insect Sci 5, 17.

George, E. L., Ober, M. B. and Emerson Jr, C. P. (1989). Functional domains of the *Drosophila melanogaster* muscle myosin heavy-chain gene are encoded by alternatively spliced exons. Mol. Cell Biol. 9:2957-2974.

Graveley BR. 2001 Alternative splicing: increasing diversity in the proteomic world. Trends Genet. 17(2):100-7.

Hammes, A., Guo, J. K., Lutsch, G., Leheste, J. R., Landrock, D., Zeigler, U., Gubler, M.C. and Schedl, A. (2001). Two splice variants of the Wilms' Tumour 1 gene have distinct functions during sex determination and nephron formation. Cell 106:319-329.

Hastings, G. A. and Emerson Jr, C. P (1991). Myosin functional domains encoded by alternative exons are expressed in specific thoracic muscles of *Drosophila*. J. Cell Biol. 114: 263-276.

Hedley, M. L. and Maniatis (1991). Sex-specific splicing and polyadenylation of dsx pre-mRNA requires a sequence that binds specifically to a tra-2 protein in vivo. Cell 65:579-586.

Heinrich J. C. and Scott M. J. 2000 A repressible female-specific lethal genetic system for making transgenic insect strains suitable for a sterile-release program PNAS 97 (15): 8229-8232

Horn C, Wimmer E A. 2003 A transgene-based, embryo-specific lethality system for insect pest management. Nat Biotechnol. 21(1):64-70.

Hoshijima, K. K, Inoue, L., Higuchi, I., Sakamoto, H. and Shimura, Y. (1991). Control of doublesex alternative splicing by transformer and transformer-2 in *Drosophila*. Science 252:833-836.

Huang, Q., Deveraux, Q. L., Maeda, S., Salvesen, G. S., Stennicke, H. R., Hammock, B. D. and Reed, J. C. (2002). Evolutionary conservation of apoptosis mechanisms: Lepidopteran and baculoviral inhibitor of apoptosis proteins are inhibitor of mammalian caspase-9.Agricultural Sciences 97(4):1427-1432.

Ito, Y., Hirochicka, H. and Kurata, N. (2002). Organ-specific alternative transcripts of KNOX family class 2 homeobox genes of rice. Gene 288:41-47.

Johnson J M, Castle J, Garrett-Engele P, Kan Z, Loerch P M, Armour C D, Santos R, Schadt E E, Stoughton R, Shoemaker D D. 2003 Genome-wide survey of human alternative pre-mRNA splicing with exon junction microarrays. Science. 302(5653):2141-4.

Jurica M S, Moore M J. 2003 Pre-mRNA splicing: awash in a sea of proteins. *Mol Cell*. 12(1):5-14.

Kazzaz J A, Rozek CE. 1989 Tissue-specific expression of the alternately processed *Drosophila* myosin heavy-chain messenger RNAs. Dev Biol. 133(2):550-61.

Maniatis, T., and Tasic, B. (2002). Alternative pre-mRNA splicing and proteome expansion in metazoans. Nature 418, 236-243.

Muñoz, D., Jimenez, A., Marinotti, O., and James, A. (2004). The AeAct-4 gene is expressed in the developing flight muscles of females *Aedes aegypti*. Insect Molecular Biology 13, 563-568.

Nishiyama, R., Mizuno, H., Okada, S., Yamaguchi, T., Takenaka, M., Fukuzawa, H. and Ohyama, K. (1999). Two mRNA species encoding calcium-dependent protein kinases are differentially expressed in sexual organs of Marchantia polymorpha through alternative splicing. Plant Cell Physiol.40(2):205-212.

Nishiyama, R.,Yamato, K. T., Miura, K., Sakida, M., Okada, S., Kono, K., Takahama, M., Sone, T., Takenaka, M., Fukuzawa, H. and Ohyama, K. (2000). Comparison of expressed sequence tags from male and female sexual organs of Marchantia polymorpha. DNA Res. 7:165-174.

Olson, M. R., Holley, C. L., Ji Yoo, S., Huh, J. R, Hay, B. A. and Kornbluth, S. (2003). Reaper is regulated by IAP-mediated Ubiquitination. J. Biol. Chem., 278(6): 4028-4034.

Olson, M. R., Holley, C. L., Gan, E. C., Colon-Ramos, D. A., Kaplan, B. and Kornbluth, S. (2003). A GH3-like domain in reaper is required for mitochondrial localization and induction of IAP degradation. J. Biol. Chem. 278(45): 44758-44768.

Pan, Q., Shai, O., Misquitta, C., Zhang, W., Saltzman, A., Mohammad, N., Babak, T., Siu, H., Hughes, T., Morris, Q., et al. (2004). Revealing global regulatory features of mammalian alternative splicing using a quantitative microarray platform. Mol Cell 16, 929-941.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Park, J., Parisky, K., Celotto, A., Reenan, R., and Graveley, B. (2004). Identification of alternative splicing regulators by RNA interference in *Drosophila*. Proc Nat'l Acad Sci (USA) 101, 15974-15979.

Parker L, Gross S, Beullens M, Bollen M, Bennett D, Alphey L. 2002 Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1. Biochem J. 368(3): 789-97.

Raphael, K. A., Whyard, S., Shearman, D., An, X. and Frommer, M. (2004). Bactrocera tyroni and closely related pest-tephritids-molecular analysis and prospects for transgenic control strategies. Insect Biochem. Mol. Biol. 34:167-176.

Ryner, L. and Baker, B. S. (1991). Regulation of doublesex pre-mRNA processing occurs by 3'-splice site activation. Genes Dev. 5:2071-2085.

Saccone, G., Pane, A., and Polito, C. (2002). Sex determination in flies, fruitfles and butterflies. Genetica 116, 15-23.

Scali, C., Catteruccia, F., Li, Q., and Crisanti, A. (2005). Identification of sex-specific transcripts of the *Anopheles gambiae* doublesex gene. J Exp Biol 208, 3701-3709.

Scott, M., Heinrich, J., and Li, X. (2004). Progress towards the development of a transgenic strain of the Australian sheep blowfly (Lucilia cuprina) suitable for a male-only sterile release program. Insect Biochem Mol Biol 34, 185-192.

Seo, S-J., Cheon, H-M., Sun, J., Sappington, T. W. and Raikhel, A. S. (2003). Tissue- and stage-specific expression of two lipophorin receptor variants with seven and eight ligand-binding repeats in the adult mosquito. J. Biol. Chem. 278(43):41954-41962.

Siebel CW, Fresco LD, Rio DC. 1992 The mechanism of somatic inhibition of Drosophila P-element pre-mRNA splicing: multiprotein complexes at an exon pseudo-5' splice site control U1 snRNP binding. Genes Dev. 6(8): 1386-401.

Shivikrupa, Singh., R and Swarup, G. (1999). Identification of a novel splice variant of C3G which shows tissue-specific expression. DNA Cell Biol. 18: 701-708.

Smith, C., and Valcarcel, J. (2000). Alternative pre-mRNA splicing: the logic of combinatorial control. Trends Biochem Sci 25, 381-388.

Stoss, O., Stoilov, P., Hartmann, A. M., Nayler, O., and Stamm, S. (1999). The in vivo minigene approach to analyze tissue-specific splicing. Brain Research Protocols 4, 383-394.

Stoss, O., Olbrich, M, Hartmann, A. M., Konig, H., Memmott, J., Andreadis, A and Stamm, S. (2001). The STAR/GSG family protein rSLM-2 regulates the selection of alternative splice sites. J. Biol. Chem. 276(12):8665-8673.

Streuli, M. and Saito, H. (1989). Regulation of tissue-specific alternative splicing: exon-specific cis-elements govern the splicing of leukocyte common antigen pre-mRNA. EMBO J. 8(3): 787-796.

Suzuki, M., Ohbayashi, F., Mita, K., and Shimada, T. (2001). The mechanism of sex-specific splicing at the doublesex gene is different between Drosophila melanogaster and Bombyx mori. Insect Biochem Mol Biol 31, 1201-1211.

Thanaraj, T., and Clark, F. (2001). Human GC-AG alternative intron isoforms with weak donor sites show enhanced consensus at acceptor exon positions. Nucleic Acids Research 29, 2581-2593.

Thanaraj, T., Stamm, S., Clark, F., Reithoven, J., Le Texier, V., and Muilu, J. (2004). ASD: the Alternative Splicing Database. Nucleic Acids Research 32, D64-D69.

Varshaysky, A. (2000). Ubiquitin fusion technique and its descendants. Meth Enz 327.

Venables, J. (2002). Alternative splicing in the testes. Curr Opin Genet Dev 12, 615-619.

Venables JP. 2004 Aberrant and alternative splicing in cancer. Cancer Res. 64(21):7647-54.

Vernooy, S. Y., Copeland, J., Ghaboosi, N., Griffin, E. E., Yoo, S. J. and Hay, B.A. (2000). J. Cell Biol. 150(2):F69-F75.

White, K., Tahoaglu, E. and Steller, H. (1996). Cell killing by the Drosophila gene reaper. Science 271 (5250): 805-807.

Wing, J. P., Zhou, L., Schwartz, L. M. and Nambu, J. R. (2001) Distinct cell killing properties of the Drosophila reaper, head involution defective, and grim genes. Cell Death Diffn 5(11): 930-939

Yali Chiu A., and Pin Ouyang, A. B.,(2006).Loss of Pnn expression attenuates expression levels of SR family splicing factors and modulates alternative pre-mRNA splicing in vivo. Bioch. Biophys. Res. Comm.341:663-671.

Yoshimura, K., Yabuta, Y., Ishikawa, T. and Shigeoka, S. (2002). Idenitification of a cis element for tissue-specific alternative splicing of chloroplast Ascorbate Peroxidase pre-mRNA in higher plants. J. Biol.Chem 277 (43):40623-40632.

---

The invention claimed is:

1. An arthropod comprising a gene expression system comprising a coding sequence to be expressed in said arthropod, a promoter operably linked thereto, and an intronic splice control sequence, wherein the intronic splice control sequence is flanked on its 5' end by a guanine (G) nucleotide, and, in cooperation with a spliceosome, mediates alternative splicing of RNA transcripts of the coding sequence, the mediation being selected from at least one of the group consisting of sex specific, developmental stage specific, germline specific, and tissue specific mediation, wherein the coding sequence is not a sequence associated with or linked to the intronic splice control sequence in a native context, wherein the intronic splice control sequence is derived from Actin-4, dsx, or tra, and wherein the coding sequence comprises a sequence encoding a protein having a lethal, deleterious, or sterilizing effect.

2. The arthropod of claim 1, wherein said coding sequence comprises a sequence encoding a marker.

3. The arthropod of claim 1, wherein the coding sequence comprises a sequence encoding an apoptosis-inducing factor.

4. The arthropod of claim 3, wherein the apoptosis-inducing factor is selected from the group consisting of apoptosis-inducing factor (AIF), an AIF homolog, Hid, and Reaper (Rpr).

5. The arthropod of claim 1, wherein the coding sequence comprises a sequence encoding Nipp1, Nipp1Dm, or nipper.

6. The arthropod of claim 1, wherein the coding sequence comprises a sequence encoding a transcriptional transactivator protein.

7. The arthropod of claim 6, further comprising a binding sequence for the transcriptional transactivator protein.

8. The arthropod of claim 1, wherein the coding sequence comprises a sequence encoding tTA or a functional variant or mutant thereof.

9. The arthropod of claim 8, wherein the tTA or functional variant or mutant is selected from the group consisting of tTAV (SEQ ID NO. 34), tTAV2 (SEQ ID NO. 36), and tTAV3 (SEQ ID NO. 38).

10. The arthropod of claim 1, wherein the coding sequence comprises a sequence encoding a ubiquitin or a functional variant or mutant thereof.

11. The arthropod of claim 1, wherein the intronic splice control sequence is flanked on its 3' end by a Guanine (G) nucleotide.

12. The arthropod of claim 1, further comprising an enhancer.

13. The arthropod of claim 1, which is an insect.

14. The arthropod of claim 1, wherein the arthropod is an insect of the Order Diptera, Calliphoridae, Lepidoptera, or Coleoptera.

15. The arthropod of claim 14, wherein the insect is a Medfly (*Ceratitis capitata*), a Mexfly (*Anastrepha ludens*), an Oriental fruit fly (*Bactrocera dorsalis*), an Olive fruit fly (*Bactrocera oleae*), a Melon fly (*Bactrocera cucurbitae*), a Natal fruit fly (*Ceratitis rosa*), a Cherry fruit fly (*Rhagoletis cerasi*), a Queensland fruit fly (*Bactrocera tyroni*), a Peach fruit fly (*Bactrocera zonata*), a Caribbean fruit fly (*Anastrepha suspense*), a West Indian fruit fly (*Anastrepha oblique*), an *Aedes aegypti* mosquito, an *Aedes albopictus* mosquito, an *Anopheles stephensi* mosquito, an *Anopheles albimanus* mosquito, an *Anopheles gambiae* mosquito, a New world screwworm (*Cochliomyia hominivorax*), an Old world screwworm (*Chrysomya bezziana*), an Australian sheep blowfly (*Lucilia cuprina*), a codling moth (*Cydia*

*pomonella*), a silk worm (*Bombyx mori*), a pink bollworm (*Pectinophora gossypiella*), a diamondback moth (*Plutella xylostella*), a Gypsy moth (*Lymantria dispar*), a Navel Orange Worm (*Amyelois transitella*), a Peach Twig Borer (*Anarsia lineatella*), a rice stem borer (*Tryporyza incertulas*), a Japanese beetle (*Papilla japonica*), a White-fringed beetle (*Graphognatus* spp.), a Boll weevil (*Anthonomous grandis*), a corn root worm (*Diabrotica* spp.), or a Colorado potato beetle (*Leptinotarsa decemlineata*).

16. The arthropod of claim 1, wherein the intronic splice control sequence is derived from AaActin-4 (*Aedes aegypti* Actin-4), Aadsx (*Aedes aegypti* dsx), Agdsx (*Anopheles gambiae* dsx), Bmdsx (*Bombyx mori* dsx), *Cydia pomonella* dsx, *Pectinophora gossypiella* dsx, Bztra (*Bactrocera zonata* tra), Cctra (*Ceratitis rosa* tra), or Cctra (*Ceratitis capitata* tra).

17. The arthropod of claim 1, wherein the intronic splice control sequence is derived from dsx and the expression system comprises a sequence selected from the group consisting of SEQ ID NO:40, SEQ ID NO:41, SEQ ID NO:42, SEQ ID NO:43, SEQ ID NO:44, SEQ ID NO:45, and SEQ ID NO:71.

18. The arthropod of claim 1, wherein the intronic splice control sequence is derived from dsx and the expression system comprises a construct selected from the group consisting of pLA3435 (SEQ ID NO:46), pLA3359 (SEQ ID NO:47), and pLA3433 (SEQ ID NO:48).

19. The arthropod of claim 1, wherein the intronic splice control sequence is derived from Cctra (*Ceratitis capitata* tra) and the expression system comprises a construct selected from the group consisting of pLA1188 (SEQ ID NO:49), pLA3077 (SEQ ID NO:50), pLA3097 (SEQ ID NO:51), pLA3233 (SEQ ID NO:52), pLA3014 (SEQ ID NO:53), pLA3166 (SEQ ID NO:54), and pLA3242 (SEQ ID NO:56).

20. The arthropod of claim 1, wherein the intronic splice control sequence is derived from Bztra (*Bactrocera zonata* tra) and the expression system comprises a construct according to pLA3376 (SEQ ID NO:55).

21. The arthropod of claim 1, wherein the intronic splice control sequence is derived from Actin-4.

22. The arthropod of claim 1, wherein the intronic splice control sequence is derived from dsx.

23. The arthropod of claim 1, wherein the intronic splice control sequence is derived from tra.

* * * * *

SEQUENCE LISTING

<160> NUMBER OF SEQ ID NOS: 106

<210> SEQ ID NO 1
<211> LENGTH: 44
<212> TYPE: DNA
<213> ORGANISM: Drosophila sp.

<400> SEQUENCE: 1
cacagcgcat gatgagcaca ttaacaaaat gtagtaaaat agga        44

<210> SEQ ID NO 2
<211> LENGTH: 44
<212> TYPE: DNA
<213> ORGANISM: Drosophila sp.

<400> SEQUENCE: 2
gtttcgataa atattgctat ttaaaatgct tattttcaat gcta        44

<210> SEQ ID NO 3
<211> LENGTH: 44
<212> TYPE: DNA
<213> ORGANISM: Drosophila sp.

<400> SEQUENCE: 3
tttgttttct aacgttaaag ttaaagagag tccagccaca tttt        44

```
<210> SEQ ID NO 4
<211> LENGTH: 21
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 4
acgcgagagg tgaaattctt g                                           21

<210> SEQ ID NO 5
<211> LENGTH: 23
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 5
gaaaacatct ttggcaaatg ctt                                         23

<210> SEQ ID NO 6
<211> LENGTH: 16
<212> TYPE: DNA
<213> ORGANISM: Artificial Sequence
<220> FEATURE:
<223> OTHER INFORMATION: Synthetic construct, nucleotide portion of
      TaqMan MGB probe

<400> SEQUENCE: 6
ccgtcgtaag actaac                                                 16

<210> SEQ ID NO 7
<211> LENGTH: 17
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 7
catgccgacg cgctaga                                                17

<210> SEQ ID NO 8
<211> LENGTH: 26
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 8
gtaaacatct gctcaaactc gaagtc                                      26

<210> SEQ ID NO 9
<211> LENGTH: 18
<212> TYPE: DNA
<213> ORGANISM: Artificial Sequence
<220> FEATURE:
<223> OTHER INFORMATION: Synthetic construct, nucleotide portion of
      TaqMan MGB probe

<400> SEQUENCE: 9
tcgatctgga catgttgg                                               18

<210> SEQ ID NO 10
```

```
<211> LENGTH: 25
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 10
gccctcgatg gtagacccgt aattg                                          25

<210> SEQ ID NO 11
<211> LENGTH: 27
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 11
gctaaacaat ctgcaggtac cctggcg                                        27

<210> SEQ ID NO 12
<211> LENGTH: 20
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 12
cctgccagga ctcgccttcc                                                20

<210> SEQ ID NO 13
<211> LENGTH: 22
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 13
gtcatcaact ccgcgttgga gc                                             22

<210> SEQ ID NO 14
<211> LENGTH: 2556
<212> TYPE: DNA
<213> ORGANISM: Artificial Sequence
<220> FEATURE:
<223> OTHER INFORMATION: Synthetic construct, Sequence  of the tetO7-tTA
      region of JY2004-tTA

<400> SEQUENCE: 14
gcggccgcat agtcgacatt tcgagtttac cactccctat cagtgataga gaaaagtgaa    60
agtcgagttt accactccct atcagtgata gagaaaagtg aaagtcgagt ttaccactcc   120
ctatcagtga tagagaaaag tgaaagtcga gtttaccact ccctatcagt gatagagaaa   180
agtgaaagtc gagtttacca ctccctatca gtgatagaga aaagtgaaag tcgagtttac   240
cactccctat cagtgataga gaaaagtgaa agtcgagttt accactccct atcagtgata   300
gagaaaagtg aaagtcgagc tcggtacccg ggtcgaggta ggcgtgtacg gtgggaggcc   360
tatataagca gagctcgttt agtgaaccgt cagatcgcct ggagacgcca tccacgctgt   420
tttgacctcc atagaagaca ccgggaccga tccagcctcc gcggccccga attcgagctc   480
ggtacccggg gatccccgct cgagctgaat agggaattgg gaattggagc agaggtgggt   540
```

```
tcttcgcatt acactgttcg ccacaatctt gtttattcat tcgccttgca ggttgccacc    600
atggaattga gattagataa aagtaaagtg attaacagcg cattagagct gcttaatgag    660
gtcggaatcg aaggtttaac aacccgtaaa ctcgcccaga agctaggtgt agagcagcct    720
acattgtatt ggcatgtaaa aaataagcgg gctttgctcg acgccttagc cattgagatg    780
ttagataggc accatactca cttttgccct ttagaagggg aaagctggca agatttttta    840
cgtaataacg ctaaaagttt tagatgtgct tactaagtc atcgcgatgg agcaaaagta     900
catttaggta cacggcctac agaaaaacag tatgaaactc tcgaaaatca attagccttt    960
ttatgccaac aaggtttttc actagagaat gcattatatg cactcagcgc tgtggggcat   1020
tttactttag gttgcgtatt ggaagatcaa gagcatcaag tcgctaaaga agaaagggaa   1080
acacctacta ctgatagtat gccgccatta ttacgacaag ctatcgaatt atttgatcac   1140
caaggtgcag agccagcctt cttattcggc cttgaattga tcatatgcgg attagaaaaa   1200
caacttaaat gtgaaagtgg gtccgcgtac agccgcgcgc gtacgaaaaa caattacggg   1260
tctaccatcg agggcctgct cgatctcccg gacgacgacg cccccgaaga ggcggggctg   1320
gcggctccgc gcctgtcctt tctcccgcg ggacacacgc gcagactgtc gacggccccc    1380
ccgaccgatg tcagcctggg ggacgagctc cacttagacg gcgaggacgt ggcgatggcg   1440
catgccgacg cgctagacga tttcgatctg gacatgttgg gggacgggga ttccccgggt   1500
ccgggattta cccccacga ctccgccccc tacgcgctc tggatatggc cgacttcgag      1560
tttgagcaga tgtttaccga tgcccttgga attgacgagt acggtgggta gtgaaacgcg   1620
tctagagctg agaacttcag ggtgagtttg ggaccccttg attgttcttt cttttcgct    1680
attgtaaaat tcatgttata tggagggggc aaagttttca gggtgttgtt tagaatggga   1740
agatgtccct tgtatcacca tggaccctca tgataatttt gtttctttca ctttctactc   1800
tgttgacaac cattgtctcc tcttattttc ttttcatttt ctgtaacttt ttcgttaaac   1860
tttagcttgc atttgtaacg aatttttaaa ttcacttttg tttatttgtc agattgtaag   1920
tactttctct aatcactttt ttttcaaggc aatcaggta tattatattg tacttcagca    1980
cagttttaga gaacaattgt tataattaaa tgataaggta gaatatttct gcatataaat   2040
tctggctggc gtggaaatat tcttattggt agaaacaact acaccctggt catcatcctg   2100
cctttctctt tatggttaca atgatataca ctgtttgaga tgaggataaa atactctgag   2160
tccaaaccgg gcccctctgc taaccatgtt catgccttct tctctttcct acagctcctg   2220
ggcaacgtgc tggttgttgt gctgtctcat catttttggca aagaattcac tcctcaggtg   2280
caggctgcct atcagaaggt ggtggctggt gtggccaatg ccctggctca aaataccac    2340
tgagatcttt ttccctctgc caaaaattat ggggacatca tgaagcccct tgagcatctg   2400
acttctggct aataaaggaa atttatttc attgcaatag tgtgttggaa ttttttgtgt   2460
ctctcactcg aaggacata tgggagggca aatcatttaa aacatcagaa tgagtatttg    2520
gtttagagtt tggcaacata tgcccatagc ggccgc                             2556
```

<210> SEQ ID NO 15
<211> LENGTH: 12087
<212> TYPE: DNA
<213> ORGANISM: Artificial Sequence
<220> FEATURE:
<223> OTHER INFORMATION: Synthetic construct, plasmid
    pP[Casper-Act5C-tTA]

<400> SEQUENCE: 15

```
gatccatgag caattagcat gaacgttctg aaaagcgcgt ttagctctcc actacttaca    60
catattctat gctgcaatat tgaaaatcta ataaacaaaa ctaatgtaca ttaattcttc   120
agttttgaat atccttctcc tgactttctt atttagaatt aatataatac tgcatacatt   180
aatactgtaa atatgataag tacctgcaaa acactgcagc tcaagtctta atgaggttct   240
gcgatagctt agcataatta gtaacttatc gcgcagaatt ccctaatgtt cccgacctac   300
atgtacttct gatagttgcc gaggtcaaat gttgttgtat ttgtattata cctcaatatt   360
ggtatattca atatctaata gtacccaatt caattgcaaa gatagtcatt aaaaaaacct   420
aaatcacttg caaattgact tttctgccgg aaaagcaacc ttgacacaca agttaatta    480 gtttatctgg aagtcatgtg agaaatttgt aaataaaatt tttcgcagta atttaagtgg   540
gcctaatccc ttttaagcat cttggtttta cgatgacacc gcaataaggt acaactttat   600 attgttttg caatcagctt gagtctttat taggcatcag tctttctctc taagtttctt    660
cgtgcaataa atgaggttcc aaactccgta gattttcct tctttgttga atccagatcc    720
tgcaaagaaa aaagagcaaa cccctaggtc tgtccaggaa tgtattttcg tgtttgtcga   780
tcgaccatgg tctcgagagg ccttgcagcc aagctttgcg tactcgcaaa ttattaaaaa   840
taaaacttta aaaataattt cgtctaatta atattatgag ttaattcaaa ccccacggac   900
atgctaaggg ttaatcaaca atcatatcgc tgtctcactc agactcaata cgacactcag   960
aatactattc ctttcactcg cacttattgc aagcatacgt taagtggatg tctcttgccg  1020
acgggaccac cttatgttat ttcatcatgg tctggccatt ctcatcgtga gcttccgggt  1080
gctcgcatat ctggctctaa gacttcgggc ccgacgcaag gagtagccga catatatccg  1140
aaataactgc ttgtttttt ttttaccatt attaccatcg tgtttactgt ttattgcccc   1200
ctcaaaaagc taatgtaatt atatttgtgc caataaaaac aagatatgac ctatagaata  1260
caagtatttc cccttcgaac atccccacaa gtagactttg gatttgtctt ctaaccaaaa  1320
gacttacaca cctgcatacc ttacatcaaa aactcgttta tcgctacata aaacaccggg  1380
atatattttt tatatacata cttttcaaat cgcgcgccct cttcataatt cacctccacc  1440
acaccacgtt tcgtagttgc tctttcgctg tctcccaccc gctctccgca acacattcac  1500
cttttgttcg acgaccttgg agcgactgtc gttagttccg cgcgattcgg tgcggtattt  1560
cacaccgcat atggtgcact ctcagtacaa tctgctctga tgccgcatag ttaagccagc  1620
cccgacaccc gccaacaccc gctgacgcgc cctgacgggc ttgtctgctc ccggcatccg  1680
cttacagaca agctgtgacc gtctccggga gctgcatgtg tcagaggttt tcaccgtcat  1740
caccgaaacg cgcgagacga aagggcctcg tgatacgcct attttatag gttaatgtca   1800 tgataataat ggtttcttag acgtcaggtg gcacttttcg gggaaatgtg cgcggaaccc  1860
ctatttgttt attttctaa atacattcaa atatgtatcc gctcatgaga caataaccct  1920
gataaatgct tcaataatat tgaaaagga agagtatgag tattcaacat ttccgtgtcg  1980
cccttattcc ctttttgcg gcattttgcc ttcctgtttt tgctcaccca gaaacgctgg  2040
tgaaagtaaa agatgctgaa gatcagttgg gtgcacgagt gggttacatc gaactggatc  2100
tcaacagcgg taagatcctt gagagttttc gccccgaaga acgttttcca atgatgagca  2160
cttttaaagt tctgctatgt ggcgcggtat tatcccgtat tgacgccggg caagagcaac  2220
tcggtcgccg catacactat tctcagaatg acttggttga gtactcacca gtcacagaaa  2280
agcatcttac ggatggcatg acagtaagag aattatgcag tgctgccata accatgagtg  2340
ataacactgc ggccaactta cttctgacaa cgatcggagg accgaaggag ctaaccgctt  2400
```

```
ttttgcacaa catggggat catgtaactc gccttgatcg ttgggaaccg gagctgaatg    2460
aagccatacc aaacgacgag cgtgacacca cgatgcctgt agcaatggca acaacgttgc    2520
gcaaactatt aactggcgaa ctacttactc tagcttcccg gcaacaatta atagactgga    2580
tggaggcgga taaagttgca ggaccacttc tgcgctcggc ccttccggct ggctggttta    2640
ttgctgataa atctggagcc ggtgagcgtg gtctcgcgg tatcattgca gcactggggc    2700
cagatggtaa gccctcccgt atcgtagtta tctacacgac ggggagtcag gcaactatgg    2760
atgaacgaaa tagacagatc gctgagatag gtgcctcact gattaagcat tggtaactgt    2820
cagaccaagt ttactcatat atactttaga ttgatttaaa acttcatttt taatttaaaa    2880
ggatctaggt gaagatcctt tttgataatc tcatgaccaa atcccttaa cgtgagtttt    2940 cgttccactg agcgtcagac cccgtagaaa agatcaaagg atcttcttga tccttttt    3000 ttctgcgcgt aatctgctgc ttgcaaacaa aaaaaccacc gctaccagcg gtggtttgtt    3060
tgccggatca gagctacca actctttttc cgaaggtaac tggcttcagc agagcgcaga    3120
taccaaatac tgtccttcta gtgtagccgt agttaggcca ccacttcaag aactctgtag    3180
caccgcctac atacctcgct ctgctaatcc tgttaccagt ggctgctgcc agtggcgata    3240
agtcgtgtct taccgggttg gactcaagac gatagttacc ggataaggcg cagcggtcgg    3300
gctgaacggg gggttcgtgc acacagccca gcttggagcg aacgacctac accgaactga    3360
gatacctaca gcgtgagcta tgagaaagcg ccacgcttcc cgaagggaga aaggcggaca    3420
ggtatccggt aagcggcagg gtcggaacag gagagcgcac gagggagctt ccaggggaa    3480 acgcctggta tctttatagt cctgtcgggt ttcgccacct ctgacttgag cgtcgatttt    3540
tgtgatgctc gtcagggggg cggagcctat ggaaaaacgc cttcttcttg aactcgggct    3600
cggtgccagt atacctcaaa tggttgtcgt acctctcatg gttccgttac gccaacgagg    3660
gtctgctgat taaccaatgg gcggacgtgg agccgggcga aattagctgc acatcgtcga    3720
acaccacgtg ccccagttcg ggcaaggtca tcctggagac gcttaacttc tccgccgccg    3780
atctgccgct ggactacgtg ggtctggccc atgatgaaat aacataaggt ggtcccgtcg    3840
aaagccgaag cttaccgaag tatacactta aattcagtgc acgtttgctt gttgagagga    3900
aaggttgtgt gcggacgaat ttttttttga aaacattaac ccttacgtgg aataaaaaaa    3960
aatgaaatat tgcaaatttt gctgcaaagc tgtgactgga gtaaaattaa ttcacgtgcc    4020
gaagtgtgct attaagagaa aattgtggga gcagagcctt gggtgcagcc ttggtgaaaa    4080
ctcccaaatt tgtgataccc actttaatga ttcgcagtgg aaggctgcac ctgcaaaagg    4140
tcagacattt aaaaggaggc gactcaacgc agatgccgta cctagtaaag tgatagagcc    4200
tgaaccagaa aagataaaag aaggctatac cagtgggagt acacaaacag agtaagtttg    4260
aatagtaaaa aaaatcattt atgtaaacaa taacgtgact gtgcgttagg tcctgttcat    4320
tgtttaatga aaataagagc ttgagggaaa aaattcgtac tttggagtac gaatgcgtc    4380 gtttagagca gcagccgaat taattctagt tccagtgaaa tccaagcatt ttctaaatta    4440
aatgtattct tattattata gttgttattt tgatatata taacaacac tattatgccc    4500 accatttttt tgagatgcat ctacacaagg aacaaacact ggatgtcact ttcagttcaa    4560
attgtaacgc taatcactcc gaacaggtca caaaaatta ccttaaaaag tcataatatt    4620
aaattagaat aaatatagct gtgagggaaa tatatacaaa tatattggag caaataaatt    4680
gtacatacaa atatttatta ctaatttcta ttgagacgaa atgaaccact cggaaccatt    4740
```

```
tgagcgaacc gaatcgcgcg gaactaacga cagtcgctcc aaggtcgtcg aacaaaaggt    4800
gaatgtgttg cggagagcgg gtgggagaca gcgaaagagc aactacgaaa cgtggtgtgg    4860
tggaggtgaa ttatgaagag ggcgcgcgat ttgaaaagta tgtatataaa aaatatatcc    4920
cggtgtttta tgtagcgata aacgagtttt tgatgtaagg tatgcaggtg tgtaagtctt    4980
ttggttagaa gacaaatcca aagtctactt gtggggatgt tcgaagggga aatacttgta    5040
ttctataggt catatcttgt ttttattggc acaaatataa ttacattagc tttttgaggg    5100
ggcaataaac agtaaacacg atggtaataa tggtaaaaaa aaaaacaag cagttatttc     5160 ggatatatgt cggctactcc ttgcgtcggg cccgaagtct tagagccaga tatgcgagca    5220
cccggaagct cacgatgaga atggccagac ccacgtagtc cagcggcaga tcggcggcgg    5280
agaagttaag cgtctccagg atgaccttgc ccgaactggg gcacgtggtg ttcgacgatg    5340
tgcagctaat ttcgcccggc tccacgtccg cccattggtt aatcagcaga ccctcgttgg    5400
cgtaacggaa ccatgagagg tacgacaacc atttgaggta tactggcacc gagcccgagt    5460
tcaagaagaa gccgccaaag agcaggaatg gtatgataac cggcggaccc acagacagcg    5520
ccatcgaggt cgaggagctg cgcaggata ttagatatcc gaaggacgtt gacacattgg     5580
ccaccagagt gaccagcgcc aggcagttga agaagtgcag cactccggcc cgcagtccga    5640
tcatcggata ggcaatcgcc gtgaagacca gtggcactgt gagaaaaagc ggcaattcgg    5700
caatcgtttt gcccagaaag tatgtgtcac agcgataaag tcgacttcgg gcctccctca    5760
taaaaactgg cagctctgag gtgaacacct aaatcgaatc gattcattag aaagttagta    5820
aattattgaa atgcaaatgt attctaaaca tgacttacat ttatcgtggc aaagacgttt    5880
tgaaaggtca tgttggtcag gaagaggaag atggctccgt tgatattcat cacacccact    5940
tgcgtgagtt gttggcccaa aaagatgagg ccaatcaaga tggcaaccat ctgcaaatta    6000
aaatgttact cgcatctcat taatattcgc gagttaaatg aaatttattt atcttctgca    6060
aaactataaa ctatacatct cattgaaaaa aactaagaag ggtgtggaat caggcaattc    6120
tatctaaaat ctagcgaatt tgtttccaag aattgtaagc gttatatcat ttgtttccac    6180
tggaaccact caccgttgtc tgaataagtc gcacttttac gaggagtggt tccttgagca    6240
ccgacagcca ggatcgccac aggaccgccc ggaactgcat gaaccaggtg gccttgtagg    6300
tgtacccatt ctccggctgc tccagtggct tctccagatt tttggtggcc aacaactgct    6360
ccatatcccg ggctactttg ctaatggcaa aattgtcgcc atatcttggc gatccgatca    6420
cgggactcga tctcccgtcc gggcacaacg gccaacacct gtacgtaaaa gtccgccgga    6480
ttgtagttgg taggacactg gcacccacg ctggataggga gttgagatgt aatgtaatgc     6540 tagatacccct aataaacac atcgaactca ctaggaaaag aagtcgacgg cttcgctggg    6600
agtgcccaag aaagctaccc tgccctcggc catcagaagg atcttgtcaa agagctcaaa    6660
cagctcggaa gacggctgat gaatggtcag gatgacggtc ttgcccttct gcgacagctt    6720
cttcagcacc tggacgacgc tgtgggcggt aaatgagtcc agtccggagg tgggctcatc    6780
gcagatcaga agcggcggat cggttagtgc ctcggaggcg aatgccagac gcttcctttc    6840
tccgccggac agacctttca ccctgccggg cacaccgatg atcgtgtgct gacatttgct    6900
gagcgaaagc tcctggatca cctgatccac gcgggccact cgctgccgat aggtcagatg    6960
tcgtggcatc cgcaccatgg cttggaaaat caggtgttcc ctggccgtta gggagccgat    7020
aaagaggtca tcctgctgga cataggcgca cctggcctgc atctccttgg cgtccacagg    7080
ttggccattg agcagtcgca tcccggatgg cgatacttgg atgccctgcg gcgatcgaaa    7140
```

```
ggcaagggca ttcagcaggg tcgtctttcc ggcaccggaa ctgcccatca cggccaaaag    7200
ttcgcccgga taggccacgc cgcaaactga gtttcaaatt ggtaattgga ccctttatta    7260
agatttcaca cagatcagcc gactgcgaat agaaactcac cgttcttgag caaatgtttc    7320
ctgggcgccg gtatgtgtcg ctcgttgcag aatagtccgc gtgtccggtt gaccagctgc    7380
cgccatccgg agcccggctg attgaccgcc ccaaagatgt ccatattgtg ccaggcatag    7440
gtgaggttct cggctagttg gccgctccct gaaccggagt cctccggcgg actgggtggc    7500
aggagcgtgc cgtagttttt ggcctgcccg aagccctggt taatgcagct ctgcgaagcg    7560
tccgctgtca ccctgcaatg atagggatc tcaaatatca actacaagcg ttatgctcat    7620
ctaaccccga acaaaacgaa gtatcctacg aagtaggttt atactttat ttattttttg    7680 tgcatagctt aaaatatctg gttgttatat tttttgtaaa aaagaatgta gtcgaaaatg    7740
aatgccttta gatgtcttga tcatgatatg atcttaaaaa ttgtcttata tagcgagcac    7800
agctaccaga ataatctgtt tcgtgtcact atttgtttgt gcgattgcgg tttgggattt    7860
ttgtgggtcg cagttctcac gccgcagaca atttgatgtt gcaatcgcag ttcctataga    7920
tcaagtgaac ttaagatgta tgcacatgta ctactcacat tgttcagatg ctcggcagat    7980
gggtgtttgc tgcctccgcg aattaatagc tcctgatcct cttggcccat tgccgggatt    8040
tttcacactt tcccctgctt acccacccaa aaccaatcac cacccaatc actcaaaaaa    8100 caaacaaaaa taagaagcga gaggagtttt ggcacagcac tttgtgttta attgatggcg    8160
taaaccgctt ggagcttcgt cacgaaaccg ctgacaaagt gcaactgaag gcggacattg    8220
acgctaggta acgctacaaa cggtggcgaa agagatagcg gacgcagcgg cgaaagagac    8280
ggcgatattt ctgtggacag agaaggaggc aaacagcgct gactttgagt ggaatgtcat    8340
tttgagtgag aggtaatcga agaacctgg tacatcaaat acccttggat cgaagtaaat    8400
ttaaaactga tcagataagt tcaatgatat ccagtgcagt aaaaaaaaaa aatgttttt    8460 ttatctactt tccgcaaaaa tgggtttat taacttacat acatactaga attctaaaaa    8520
aaatcatgaa tggcatcaac tctgaatcaa atctttgcag atgcacctac ttctcatttc    8580
cactgtcaca tcattttcc agatctcgct gcctgttatg tgcccacaa accaagacac    8640 gttttatggc cattaaagct ggctgatcgt cgccaaacac caaatacata tcaatatgta    8700
cattcgagaa agaagcgatc aaagaagcgt cttcgggcga gtaggagaat gcggaggaga    8760
aggagaacga gctgatctag tatctctcca caatccaatg ccaactgacc aactggccat    8820
attcggagca atttgaagcc aatttccatc gcctggcgat cgctccattc ttggctatat    8880 gttttttcacc gttcccgggg ccattttcaa agactcgtcg gtaagataag attgtgtcac    8940
tcgctgtctc tcttcatttg tcgaagaatg ctgaggaatt tcgcgatgac gtcggcgagt    9000
attttgaaga atgagaataa tttgtattta tacgaaaatc agttagtgga attttctaca    9060
aaaacatgtt atctatagat aattttgttg caaaatatgt tgactatgac aaagattgta    9120
tgtatatacc tttaatgtat tctcattttc ttatgtattt ataatggcaa tgatgatact    9180
gatgatattt taagatgatg ccagaccaca ggctgatttc tgcgtctttt gccgaacgca    9240
gtgcatgtgc ggttgttgtt ttttggaata gtttcaattt tcggactgtc cgcttttgatt    9300 tcagtttctt ggcttattca aaaagcaaag taaagccaaa aaagcgagat ggcaatacca    9360
aatgcggcaa aacggtagtg gaaggaaagg ggtgcgggc agcggaagga agggtggggc    9420
ggggcgtggc ggggtctgtg gctgggcgcg acgtcaccga cgttggagcc actcctttga    9480
```

```
ccatgtgtgc gtgtgtgtat tattcgtgtc tcgccactcg ccggttgttt ttttcttttt   9540
atctcgctct ctctagcgcc atctcgtacg catgctcaac gcaccgcatg ttgccgtgtc   9600
ctttatgcgt cattttggct cgaaataggc aattatttaa acaaagatta gtcaacgaaa   9660
acgctaaaat aaataagtct acaatatggt tacttattgc catgtgtgtg cagccaacga   9720
tagcaacaaa agcaacaaca cagtggcttt ccctctttca cttttttgttt gcaagcgcgt   9780
gcgagcaaga cggcacgacc ggcaaacgca attacgctga caaagagcag acgaagtttt   9840
ggccgaaaaa catcaaggcg cctgatacga atgcatttgc aataacaatt gcgatattta   9900
atattgttta tgaagctgtt tgacttcaaa acacacaaaa aaaaaaataa acaaattat    9960
ttgaaagaga attaggaatc ggacagctta tcgttacggg ctaacagcac accgagacga  10020
aatagcttac ctgacgtcac agcctctgga agaactgccg ccaagcagac gatgcagagg  10080
acgacacata gagtagcgga gtaggccagc gtagtacgca tgtgcttgtg tgtgaggcgt  10140
ctctctcttc gtctcctgtt tgcgcaaacg catagactgc actgagaaaa tcgattacct  10200
attttttatg aatgaatatt tgcactatta ctattcaaaa ctattaagat agcaatcaca  10260
ttcaatagcc aaatactata ccacctgagc gatgcaacga aatgatcaat ttgagcaaaa  10320
atgctgcata tttaggacgg catcattata gaaatgcttc ttgctgtgta cttttctctc  10380
gtctggcagc tgtttcgccg ttattgttaa aaccggctta agttaggtgt gttttctacg  10440
actagtgatg cccctactag aagatgtgtg ttgcacaaat gtccctgaat aaccaatttg  10500
aagtgcagat agcagtaaac gtaagctaat atgaatatta tttaactgta atgttttaat  10560
atcgctggac attactaata aacccactat aaacacatgt acatatgtat gttttggcat  10620
acaatgagta gttggggaaa aaatgtgtaa aagcaccgtg accatcacag cataaagata  10680
accagctgaa gtatcgaata tgagtaaccc ccaaattgaa tcacatgccg caactgatag  10740
gacccatgga agtacactct tcatggcgat atacaagaca cacacaagca cgaacaccca  10800
gttgcggagg aaattctccg taaatgaaaa cccaatcggc gaacaattca tacccatata  10860
tggtaaaagt tttgaacgcg acttgagagc ggagagcatt gcggctgata aggttttagc  10920
gctaagcggg ctttataaaa cgggctgcgg gaccagtttt catatcacta ccgtttgagt  10980
tcttgtgctg tgtggatact cctcccgaca caaagccgct ccatcagcca gcagtcgtct  11040
aatccagaga ccccgatct  agaaccaaaa tggctagatt agataaaagt aaagtgatta  11100
acagcgcatt agagctgctt aatgaggtcg gaatcgaagg tttaacaacc cgtaaactcg  11160
cccagaagct aggtgtagag cagcctacat tgtattggca tgtaaaaaat aagcgggctt  11220
tgctcgacgc cttagccatt gagatgttag ataggcacca tactcacttt tgcccttta   11280
aaggggaaag ctggcaagat ttttacgta ataacgctaa aagttttaga tgtgcttta   11340
taagtcatcg cgatggagca aaagtacatt taggtacacg gcctacagaa aaacagtatg  11400
aaactctcga aaatcaatta gccttttat gccaacaagg tttttcacta gagaatgcat   11460
tatatgcact cagcgctgtg gggcatttta ctttaggttg cgtattggaa gatcaagagc  11520
atcaagtcgc taaagaagaa agggaaacac ctactactga tagtatgccg ccattattac  11580
gacaagctat cgaattattt gatcaccaag gtgcagagcc agccttctta ttcggccttg  11640
aattgatcat atgcggatta gaaaaacaac ttaaatgtga aagtgggtcc gcgtacagcc  11700
gcgcgcgtac gaaaaacaat tacgggtcta ccatcgaggg cctgctcgat ctcccggacg  11760
acgacgcccc cgaagaggcg gggctggcgg ctccgcgcct gtcctttctc cccgcgggac  11820
acacgcgcag actgtcgacg gccccccccga ccgatgtcag cctgggggac gagctccact  11880
```

```
tagacggcga ggacgtggcg atggcgcatg ccgacgcgct agacgatttc gatctggaca   11940
tgttggggga cggggattcc ccgggtccgg gatttacccc ccacgactcc gccccctacg   12000
gcgctctgga tatggccgac ttcgagtttg agcagatgtt taccgatgcc cttggaattg   12060
acgagtacgg tgggtagggg gcgcgag                                       12087

<210> SEQ ID NO 16
<211> LENGTH: 11920
<212> TYPE: DNA
<213> ORGANISM: Artificial Sequence
<220> FEATURE:
<223> OTHER INFORMATION: Synthetic construct, plasmid pLA513

<400> SEQUENCE: 16
gggccgatct gacaatgttc agtgcagaga ctcggctacg cctcgtggac tttgaagttg     60
accaacaatg tttattctta cctctaatag tcctctgtgg caaggtcaag attctgttag    120
aagccaatga agaacctggt tgttcaataa cattttgttc gtctaatatt tcactaccgc    180
ttgacgttgg ctgcacttca tgtacctcat ctataaacgc ttcttctgta tcgctctgga    240
cgtcatcttc acttacgtga tctgatattt cactgtcaga atcctcacca acaagctcgt    300
catcgctttg cagaagagca gagaggatat gctcatcgtc taaagaacta cccattttat    360
tatatattag tcacgatatc tataacaaga aaatatatat ataataagtt atcacgtaag    420
tagaacatga ataacaata taattatcgt atgagttaaa tcttaaaagt cacgtaaaag    480
ataatcatgc gtcattttga ctcacgcggt cgttatagtt caaaatcagt gacacttacc    540
gcattgacaa gcacgcctca cgggagctcc aagcggcgac tgagatgtcc taaatgcaca    600
gcgacggatt cgcgctattt agaaagagag agcaatattt caagaatgca tgcgtcaatt    660
ttacgcagac tatctttcta gggttaaaaa agatttgcgc tttactcgac ctaaacttta    720
aacacgtcat agaatcttcg tttgacaaaa accacattgt ggccaagctg tgtgacgcga    780
cgcgcgctaa agaatggcaa accaagtcgc gcgagcgtcg acctgcaggc atgcaagctt    840
gcatgcctgc aggtcgaaat tcgtaatcat ggtcatagct gtttcctgtg tgaaattgtt    900
atccgctcac aattccacac aacatacgag ccggaagcat aaagtgtaaa gcctggggtg    960
cctaatgagt gagctaactc acattaattg cgttgcgctc actgcccgct ttccagtcgg   1020
gaaacctgtc gtgccagctg cattaatgaa tcggccaacg cgcggggaga ggcggtttgc   1080
gtattgggcg ctcttccgct tcctcgctca ctgactcgct gcgctcggtc gttcggctgc   1140
ggcgagcggt atcagctcac tcaaaggcgg taatacggtt atccacagaa tcaggggata   1200
acgcaggaaa gaacatgtga gcaaaaggcc agcaaaaggc caggaaccgt aaaaaggccg   1260
cgttgctggc gttttccat aggctccgcc cccctgacga gcatcacaaa aatcgacgct   1320
caagtcagag gtggcgaaac ccgacaggac tataaagata ccaggcgttt ccccctggaa   1380
gctccctcgt gcgctctcct gttccgaccc tgccgcttac cggatacctg tccgcctttc   1440
tcccttcggg aagcgtggcg ctttctcaat gctcacgctg taggtatctc agttcggtgt   1500
aggtcgttcg ctccaagctg ggctgtgtgc acgaaccccc cgttcagccc gaccgctgcg   1560
ccttatccgg taactatcgt cttgagtcca acccggtaag acacgactta tcgccactgg   1620
cagcagccac tggtaacagg attagcagag cgaggtatgt aggcggtgct acagagttct   1680
tgaagtggtg gcctaactac ggctacacta aggacagat atttggtatc tgcgctctgc   1740
tgaagccagt taccttcgga aaaagagttg gtagctcttg atccggcaaa caaaccaccg   1800
```

```
ctggtagcgg tggttttttt gtttgcaagc agcagattac gcgcagaaaa aaaggatctc    1860
aagaagatcc tttgatcttt tctacggggt ctgacgctca gtggaacgaa aactcacgtt    1920
aagggatttt ggtcatgaga ttatcaaaaa ggatcttcac ctagatcctt ttaaattaaa    1980
aatgaagttt taaatcaatc taaagtatat atgagtaaac ttggtctgac agttaccaat    2040
gcttaatcag tgaggcacct atctcagcga tctgtctatt tcgttcatcc atagttgcct    2100
gactccccgt cgtgtagata actacgatac gggagggctt accatctggc cccagtgctg    2160
caatgatacc gcgagaccca cgctcaccgg ctccagattt atcagcaata aaccagccag    2220
ccggaagggc cgagcgcaga agtggtcctg caactttatc cgcctccatc cagtctatta    2280
attgttgccg ggaagctaga gtaagtagtt cgccagttaa tagtttgcgc aacgttgttg    2340
ccattgctac aggcatcgtg gtgtcacgct cgtcgtttgg tatggcttca ttcagctccg    2400
gttcccaacg atcaaggcga gttacatgat cccccatgtt gtgcaaaaaa gcggttagct    2460
ccttcggtcc tccgatcgtt gtcagaagta agttggccgc agtgttatca ctcatggtta    2520
tggcagcact gcataattct cttactgtca tgccatccgt aagatgcttt tctgtgactg    2580
gtgagtactc aaccaagtca ttctgagaat agtgtatgcg gcgaccgagt tgctcttgcc    2640
cggcgtcaat acgggataat accgcgccac atagcagaac tttaaaagtg ctcatcattg    2700
gaaaacgttc ttcggggcga aaactctcaa ggatcttacc gctgttgaga tccagttcga    2760
tgtaacccac tcgtgcaccc aactgatctt cagcatcttt tactttcacc agcgtttctg    2820
ggtgagcaaa aacaggaagg caaaatgccg caaaaaaggg aataagggcg acacggaaat    2880
gttgaatact catactcttc ctttttcaat attattgaag catttatcag ggttattgtc    2940
tcatgagcgg atacatattt gaatgtattt agaaaaataa acaataggg gttccgcgca    3000 catttccccg aaaagtgcca cctgacgtct aagaaaccat tattatcatg acattaacct    3060
ataaaaatag gcgtatcacg aggccctttc gtctcgcgcg tttcggtgat gacggtgaaa    3120
acctctgaca catgcagctc ccggagacgg tcacagcttg tctgtaagcg gatgccggga    3180
gcagacaagc ccgtcagggc gcgtcagcgg gtgttggcgg gtgtcggggc tggcttaact    3240
atgcggcatc agagcagatt gtactgagag tgcaccatat gcggtgtgaa ataccgcaca    3300
gatgcgtaag gagaaaatac cgcatcaggc gccattcgcc attcaggctg cgcaactgtt    3360
gggaagggcg atcggtgcgg gcctcttcgc tattacgcca gctggcgaaa ggggggatgtg    3420 ctgcaaggcg attaagttgg gtaacgccag ggttttccca gtcacgacgt tgtaaaacga    3480
cggccagtgc caagctttgt ttaaaatata acaaaattgt gatcccacaa aatgaagtgg    3540
ggcaaaatca ataattaat agtgtccgta aacttgttgg tcttcaactt tttgaggaac    3600
acgttggacg gcaaatccgt gactataaca caagttgatt taataatttt agccaacacg    3660
tcgggctgcg tgttttttgc cgacgcgtct gtgtacacgt tgattaactg gtcgattaaa    3720
ctgttgaaat aatttaattt ttggttcttc tttaaatctg tgatgaaatt ttttaaaata    3780
actttaaatt cttcattggt aaaaaatgcc acgttttgca acttgtgagg gtctaatatg    3840
aggtcaaact cagtaggagt tttatccaaa aagaaaaaca tgattacgtc tgtacacgaa    3900
cgcgtattaa cgcagagtgc aaagtataag agggttaaaa aatatatttt acgcaccata    3960
tacgcatcgg gttgatatcg ttaatatgga tcaatttgaa cagttgatta acgtgtctct    4020
gctcaagtct ttgatcaaaa cgcaaatcga cgaaaatgtg tcggacaata tcaagtcgat    4080
gagcgaaaaa ctaaaaaggc tagaatacga caatctcaca gacagcgttg agatatacgg    4140
tattcacgac agcaggctga ataataaaaa aattagaaac tattatttaa ccctagaaag    4200
```

```
ataatcatat tgtgacgtac gttaaagata atcatgcgta aaattgacgc atgtgtttta    4260
tcggtctgta tatcgaggtt tatttattaa tttgaataga tattaagttt tattatattt    4320
acacttacat actaataata aattcaacaa acaatttatt tatgtttatt tatttattaa    4380
aaaaaaacaa aaactcaaaa tttcttctat aaagtaacaa aacttttaaa cattctctct    4440
tttacaaaaa taaacttatt ttgtacttta aaaacagtca tgttgtatta taaaataagt    4500
aattagctta acttatacat aatagaaaca aattatactt attagtcagt cagaaacaac    4560
tttggcacat atcaatatta tgctctcgac aaataacttt tttgcatttt ttgcacgatg    4620
catttgcctt tcgccttatt ttagaggggc agtaagtaca gtaagtacgt tttttcatta    4680
ctggctcttc agtactgtca tctgatgtac caggcacttc atttggcaaa atattagaga    4740
tattatcgcg caaatatctc ttcaaagtag gagcttctaa acgcttacgc ataaacgatg    4800
acgtcaggct catgtaaagg tttctcataa atttttgcg actttggacc ttttctccct    4860
tgctactgac attatggctg tatataataa aagaatttat gcaggcaatg tttatcattc    4920
cgtacaataa tgccataggc cacctattcg tcttcctact gcaggtcatc acagaacaca    4980
tttggtctag cgtgtccact ccgcctttag tttgattata atacataacc atttgcggtt    5040
taccggtact ttcgttgata gaagcatcct catcacaaga tgataataag tataccatct    5100
tagctggctt cggtttatat gagacgagag taagggtcc gtcaaaacaa acatcgatg    5160 ttcccactgg cctggagcga ctgttttca gtacttccgg tatctcgcgt ttgtttgatc    5220
gcacggttcc cacaatggtt gcggccggcc agatttaaat gagcggccgc agatatccag    5280
tgcagtaaaa aaaaaaaatg ttttttttat ctactttccg caaaaatggg ttttattaac    5340
ttacatacat actagaattc tatattctaa aaacacaaat gatacttcta aaaaaaatca    5400
tgaatggcat caactctgaa tcaaatcttt gcagatgcac ctacttctca tttccactgt    5460
cacatcattt ttccagatct cgctgcctgt tatgtggccc acaaaccaag acacgtttta    5520
tggccattaa agctggctga tcgtcgccaa acaccaaata catatcaata tgtacattcg    5580
agaaagaagc gatcaaagaa gcgtcttcgg gcgagtagga gaatgcggag gagaaggaga    5640
acgagctgat ctagtatctc tccacaatcc aatgccaact gaccaactgg ccatattcgg    5700
agcaatttga agccaattc catcgcctgg cgatcgctcc attcttggct atatgttttt    5760
caccgttccc ggggccattt tcaaagactc gtcggtaaga taagattgtg tcactcgctg    5820
tctctcttca tttgtcgaag aatgctgagg aatttcgcga tgacgtcggc gagtattttg    5880
aagaatgaga ataatttgta tttatacgaa aatcagttag tggaattttc tacaaaaaca    5940
tgttatctat agataatttt gttgcaaaat atgttgacta tgacaaagat tgtatgtata    6000
tacctttaat gtattctcat tttcttatgt atttataatg gcaatgatga tactgatgat    6060 atttttaagat gatgccagac cacaggctga tttctgcgtc ttttgccgaa cgcagtgcat    6120
gtgcggttgt tgtttttttgg aatagtttca attttcggac tgtccgcttt gatttcagtt    6180
tcttggctta ttcaaaaagc aaagtaaagc caaaaaagcg agatggcaat accaaatgcg    6240
gcaaaacggt agtggaagga aaggggtgcg gggcagcgga aggaagggtg gggcggggcg    6300
tggcggggtc tgtggctggg cgcgacgtca ccgacgttgg agccactcct ttgaccatgt    6360
gtgcgtgtgt gtattattcg tgtctcgcca ctcgccggtt gttttttttct tttatctcg    6420 ctctctctag cgccatctcg tacgcatgct caacgcaccg catgttgccg tgtcctttat    6480
gcgtcatttt ggctcgaaat aggcaattat ttaaacaaag attagtcaac gaaaacgcta    6540
```

```
aaataaaataa gtctacaata tggttactta ttgccatgtg tgtgcagcca acgatagcaa    6600
caaaagcaac aacacagtgg ctttccctct ttcactttttt gtttgcaagc gcgtgcgagc    6660
aagacggcac gaccggcaaa cgcaattacg ctgacaaaga gcagacgaag ttttggccga    6720
aaaacatcaa ggcgcctgat acgaatgcat ttgcaataac aattgcgata tttaatattg    6780
tttatgaagc tgtttgactt caaaacacac aaaaaaaaaa ataaaacaaa ttatttgaaa    6840
gagaattagg aatcggacag cttatcgtta cgggctaaca gcacaccgag acgaaatagc    6900
ttacctgacg tcacagcctc tggaagaact gccgccaagc agacgatgca gaggacgaca    6960
catagagtag cggagtaggc cagcgtagta cgcatgtgct tgtgtgtgag gcgtctctct    7020
cttcgtctcc tgtttgcgca aacgcataga ctgcactgag aaaatcgatt acctattttt    7080
tatgaatgaa tatttgcact attactattc aaaactatta agatagcaat cacattcaat    7140
agccaaatac tataccacct gagcgatgca acgaaatgat caatttgagc aaaaatgctg    7200
catatttagg acggcatcat tatagaaatg cttcttgctg tgtacttttc tctcgtctgg    7260
cagctgtttc gccgttattg ttaaaaccgg cttaagttag gtgtgttttc tacgactagt    7320
gatgccccta ctagaagatg tgtgttgcac aaatgtccct gaataaccaa tttgaagtgc    7380
agatagcagt aaacgtaagc taatatgaat attatttaac tgtaatgttt taatatcgct    7440
ggacattact aataaaccca ctataaacac atgtacatat gtatgttttg gcatacaatg    7500
agtagttggg gaaaaaatgt gtaaaagcac cgtgaccatc acagcataaa gataaccagc    7560
tgaagtatcg aatatgagta accccccaaat tgaatcacat gccgcaactg ataggaccca    7620
tggaagtaca ctcttcatgg cgatatacaa gacacacaca agcacgaaca cccagttgcg    7680
gaggaaattc tccgtaaatg aaaacccaat cggcgaacaa ttcatacccca tatatggtaa    7740 aagttttgaa cgcgacttga gagcggagag cattgcggct gataaggttt tagcgctaag    7800
cgggctttat aaaacgggct gcgggaccag ttttcatatc actaccgttt gagttcttgt    7860
gctgtgtgga tactcctccc gacacaaagc cgctccatca gccagcagtc gtctaatcca    7920 gagacccccgg atctagaacc aaaatggcta gaatggcctc ctccgagaac gtcatcaccg    7980
agttcatgcg cttcaaggtg cgcatggagg gcaccgtgaa cggccacgag ttcgagatcg    8040
agggcgaggg cgagggccgc ccctacgagg gccacaacac cgtgaagctg aaggtgacca    8100
agggcggccc cctgcccttc gcctgggaca tcctgtcccc ccagttccag tacggctcca    8160
aggtgtacgt gaagcacccc gccgacatcc ccgactacaa gaagctgtcc ttccccgagg    8220
gcttcaagtg ggagcgcgtg atgaacttcg aggacggcgg cgtggcgacc gtgacccagg    8280
actcctccct gcaggacggc tgcttcatct acaaggtgaa gttcatcggc gtgaacttcc    8340
cctccgacgg ccccgtgatg cagaagaaga ccatgggctg ggaggcctcc accgagcgcc    8400 tgtaccccccg cgacggcgtg ctgaagggcg agacccacaa ggccctgaag ctgaaggacg    8460
gcggccacta cctggtggag ttcaagtcca tctacatggc caagaagccc gtgcagctgc    8520
ccggctacta ctacgtggac gccaagctgg acatcacctc ccacaacgag gactaccacc    8580
tcgtggagca gtacgagcgc accgagggcc gccaccacct gttcctgtga gatccatgag    8640
caattagcat gaacgttctg aaaagcgcgt ttagctctcc actacttaca catattctat    8700
gctgcaatat tgaaaatcta ataaacaaaa ctaatgtaca ttaattcttc agttttgaat    8760
atccttctcc tgactttctt atttagaatt aatataatac tgcatacatt aatactgtaa    8820
atatgataag tacctgcaaa acactgcagc tcaagtctta atgaggttct gcgatagctt    8880
agcataatta gtaacttatc gcgcagaatt ccctaatgtt cccgacctac atgtacttct    8940
```

```
gatagttgcc gaggtcaaat gttgttgtat ttgtattata cctcaatatt ggtatattca   9000
atatctaata gtacccaatt caattgcaaa gatagtcatt aaaaaaacct aaatcacttg   9060
caaattgact tttctgccgg aaaagcaacc ttgacacaca agttaattta gtttatctgg   9120
aagtcatgtg agaaatttgt aaataaaatt tttcgcagta atttaagtgg gcctaatccc   9180 tttttaagcat cttggtttta cgatgacacc gcaataaggt acaactttat attgttttg   9240 caatcagctt gagtctttat taggcatcag tctttctctc taagtttctt cgtgcaataa   9300
atgaggttcc aaactccgta gattttcct tctttgttga atccagatcc tgcaaagaaa   9360
aaagagcaaa cccctaggtc tgtccaggaa tgtatttcg tgtttgtcga tcgaccatgg   9420
tctcgagggg gggccttaat taagaggcgc gccaggtttc gactttcact tttctctatc   9480
actgataggg agtggtaaac tcgactttca cttttctcta tcactgatag ggagtggtaa   9540
actcgacttt cactttctc tatcactgat agggagtggt aaactcgact ttcactttc   9600 tctatcactg ataggggagtg gtaaactcga ctttcactttt tctctatcac tgataggag   9660 tggtaaactc gactttcact tttctctatc actgataggg agtggtaaac tcgactttca   9720
cttttctcta tcactgatag ggagtggtaa actcgaaaac gagcgccgga gtataaatag   9780
aggcgcttcg tctacggagc gacaattcaa ttcaaacaag caaagtgaac acgtcgctaa   9840
gcgaaagcta agcaaataaa caagcgcagc tgaacaagct aaacaatctg cggtaccctg   9900
gcggtaagtt gatcaaagga aacgcaaagt tttcaagaaa aacaaaact aatttgattt   9960 ataacccctt tagaaaccac catgggcagc cgcctggata agtccaaagt catcaactcc  10020
gcgttggagc tgttgaacga agttggcatt gagggactga cgacccgcaa gttggcgcag  10080
aagctgggcg tggagcagcc caccctctac tggcacgtga agaataagcg ggcgctgctg  10140
gatgccctgg ccatcgagat gctcgaccgc caccacacgc atttttgccc gttggaaggc  10200
gagtcctggc aggacttcct ccgcaataac gccaagtcgt tccgctgcgc tctgctgtcc  10260
caccgagacg gtgccaaagt ccatctcggc acgcgcccga ccgaaaagca atacgagaca  10320
ctggagaacc agctcgcgtt cctgtgccag caaggcttca gcctggaaaa tgctctctac  10380
gctctgagcg ccgtcggtca ctttaccctg ggctgcgtgc tggaggacca agagcatcaa  10440
gtcgcaaaag aggagcgcga gaccccaaca accgattcga tgcccccact gctgcgtcag  10500
gcaatcgagc tgttcgatca tcaaggagcc gagccggcat tcctgttcgg cttggagctg  10560
attatctgcg gattggaaaa gcaactgaaa tgcgagtcgg gctcgggccc cgcgtacagc  10620
cgcgcgcgta cgaaaaacaa ttacgggtct accatcgagg gcctgctcga tctcccggac  10680
gacgacgccc ccgaagaggc ggggctggcg gctccgcgcc tgtcctttct ccccgcggga  10740
cacacgcgca gactgtcgac ggcccccccg accgatgtca gctggggga cgagctccac  10800 ttagacggcg aggacgtggc gatggcgcat gccgacgcgc tagacgattt cgatctggac  10860 atgttgggggg acgggattc cccgggtccg ggatttaccc ccacgactc cgcccctac  10920 ggcgctctgg atatggccga cttcgagttt gagcagatgt ttaccgatgc ccttggaatt  10980
gacgagtacg gtgggtagtt ctagagtcga cctcgaacgt taacgttaac gtaacgttaa  11040
ctcgaggagc ttgataacat tatacctaaa cccatggtca agagtaaaca tttctgcctt  11100
tgaagttgag aacacaatta agcatcccct ggttaaacct gacattcata cttgttaata  11160
gcgccataaa catagcacca atttcgaaga aatcagttaa aagcaattag caattagcaa  11220
ttagcaataa ctctgctgac ttcaaaacga gaagagttgc aagtatttgt aaggcacagt  11280
```

-continued

```
ttatagacca ccgacggctc attagggctc gtcatgtaac taagcgcggt gaaacccaat    11340
tgaacatata gtggaattat tattatcaat ggggaagatt taaccctcag gtagcaaagt    11400
aatttaattg caaatagaga gtcctaagac taaataatat atttaaaaat ctggcccttt    11460
gaccttgctt gtcaggtgca tttgggttca atcgtaagtt gcttctatat aaacactttc    11520
cccatccccg caataatgaa gaataccgca gaataaagag agatttgcaa caaaaaataa    11580
aggcattgcg aaaactttt atggggatc attacactcg ggcctacggt tacaattccc      11640
agccacttaa gcgacaagtt tggccaacaa tccatctaat agctaatagc gcaatcactg    11700
gtaatcgcaa gagtatatag gcaatagaac ccatggattt gaccaaaggt aaccgagaca    11760
atggagaagc aagaggattt caaactgaac acccacagta ctgtgtacta ccactggcgc    11820
gtttgggagc tccaagcggc gactgagatg tcctaaatgc acagcgacgg attcgcgcta    11880
tttagaaaga gagagcaata tttcaagaaa acggcgccc                            11920

<210> SEQ ID NO 17
<211> LENGTH: 11570
<212> TYPE: DNA
<213> ORGANISM: Artificial Sequence
<220> FEATURE:
<223> OTHER INFORMATION: Synthetic construct, plasmid pLA517

<400> SEQUENCE: 17
ggccgctcat ttaaatctgg ccggccgcaa ccattgtggg aaccgtgcga tcaaacaaac      60
gcgagatacc ggaagtactg aaaaacagtc gctccaggcc agtgggaaca tcgatgtttt     120
gttttgacgg accccttact ctcgtctcat ataaaccgaa gccagctaag atggtatact     180
tattatcatc ttgtgatgag gatgcttcta tcaacgaaag taccggtaaa ccgcaaatgg     240
ttatgtatta taatcaaact aaaggcggag tggacacgct agaccaaatg tgttctgtga     300
tgacctgcag taggaagacg aataggtggc ctatggcatt attgtacgga atgataaaca     360
ttgcctgcat aaattctttt attatataca gccataatgt cagtagcaag ggagaaaagg     420
tccaaagtcg caaaaaattt atgagaaacc tttacatgag cctgacgtca tcgtttatgc     480
gtaagcgttt agaagctcct actttgaaga gatatttgcg cgataatatc tctaatattt     540
tgccaaatga agtgcctggt acatcagatg acagtactga agagccagta atgaaaaaac     600
gtacttactg tacttactgc ccctctaaaa taaggcgaaa ggcaaatgca tcgtgcaaaa     660
aatgcaaaaa agttatttgt cgagagcata atattgatat gtgccaaagt tgtttctgac     720
tgactaataa gtataatttg tttctattat gtataagtta agctaattac ttatttttata    780 atacaacatg actgttttta agtacaaaa taagtttatt tttgtaaaag agagaatgtt      840
taaaagtttt gttactttat agaagaaatt ttgagttttt gttttttttt aataaataaa     900
taaacataaa taaattgttt gttgaattta ttattagtat gtaagtgtaa atataataaa     960
acttaatatc tattcaaatt aataaataaa cctcgatata cagaccgata aaacacatgc    1020
gtcaatttta cgcatgatta tctttaacgt acgtcacaat atgattatct ttctagggtt    1080
aaataatagt ttctaatttt tttattattc agcctgctgt cgtgaatacc gtatatctca    1140
acgctgtctg tgagattgtc gtattctagc ctttttagtt tttcgctcat cgacttgata    1200
ttgtccgaca cattttcgtc gatttgcgtt ttgatcaaag acttgagcag agacacgtta    1260
atcaactgtt caaattgatc catattaacg atatcaaccc gatgcgtata tggtgcgtaa    1320
aatatatttt ttaaccctct tatacttttgc actctgcgtt aatacgcgtt cgtgtacaga   1380
cgtaatcatg ttttcttttt tggataaaac tcctactgag tttgacctca tattagaccc    1440
```

```
tcacaagttg caaaacgtgg cattttttac caatgaagaa tttaaagtta tttaaaaaa      1500 tttcatcaca gatttaaaga agaaccaaaa attaaattat ttcaacagtt taatcgacca     1560
gttaatcaac gtgtacacag acgcgtcggc aaaaaacacg cagcccgacg tgttggctaa    1620
aattattaaa tcaacttgtg ttatagtcac ggatttgccg tccaacgtgt tcctcaaaaa    1680
gttgaagacc aacaagttta cggacactat taattatttg attttgcccc acttcatttt    1740
gtgggatcac aattttgtta tattttaaac aaagcttggc actggccgtc gttttacaac    1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca    1920
gcctgaatgg cgaatggcgc ctgatgcggt attttctcct tacgcatctg tgcggtattt    1980
cacaccgcat atggtgcact ctcagtacaa tctgctctga tgccgcatag ttaagccagc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgagacga agggcctcg tgatacgcct atttttatag gttaatgtca     2220
tgataataat ggtttcttag acgtcaggtg cacttttcg gggaaatgtg cgcggaaccc     2280
ctatttgttt attttctaa atacattcaa atatgtatcc gctcatgaga caataaccct     2340
gataaatgct tcaataatat tgaaaaagga agagtatgag tattcaacat ttccgtgtcg    2400
cccttattcc cttttttgcg gcattttgcc ttcctgtttt tgctcaccca gaaacgctgg    2460
tgaaagtaaa agatgctgaa gatcagttgg gtgcacgagt gggttacatc gaactggatc    2520
tcaacagcgg taagatcctt gagagttttc gccccgaaga acgttttcca atgatgagca    2580
cttttaaagt tctgctatgt ggcgcggtat tatcccgtat tgacgccggg caagagcaac    2640
tcggtcgccg catacactat tctcagaatg acttggttga gtactcacca gtcacagaaa    2700
agcatcttac ggatggcatg acagtaagag aattatgcag tgctgccata accatgagtg    2760
ataacactgc ggccaactta cttctgacaa cgatcggagg accgaaggag ctaaccgctt    2820
ttttgcacaa catgggggat catgtaactc gccttgatcg ttgggaaccg gagctgaatg    2880
aagccatacc aaacgacgag cgtgacacca cgatgcctgt agcaatggca acaacgttgc    2940
gcaaactatt aactggcgaa ctacttactc tagcttcccg gcaacaatta atagactgga    3000
tggaggcgga taaagttgca ggaccacttc tgcgctcggc ccttccggct ggctggttta    3060
ttgctgataa atctggagcc ggtgagcgtg ggtctcgcgg tatcattgca gcactggggc    3120
cagatggtaa gccctcccgt atcgtagtta tctacacgac ggggagtcag gcaactatgg    3180
atgaacgaaa tagacagatc gctgagatag gtgcctcact gattaagcat tggtaactgt    3240
cagaccaagt ttactcatat atactttaga ttgatttaaa acttcatttt taatttaaaa    3300
ggatctaggt gaagatcctt tttgataatc tcatgaccaa aatcccttaa cgtgagtttt    3360
cgttccactg agcgtcagac cccgtagaaa agatcaaagg atcttcttga gatccttttt    3420
ttctgcgcgt aatctgctgc ttgcaaacaa aaaaaccacc gctaccagcg gtggtttgtt    3480
tgccggatca agagctacca actctttttc cgaaggtaac tggcttcagc agagcgcaga    3540
taccaaatac tgtccttcta gtgtagccgt agttaggcca ccacttcaag aactctgtag    3600
caccgcctac atacctcgct ctgctaatcc tgttaccagt ggctgctgcc agtggcgata    3660
agtcgtgtct taccgggttg gactcaagac gatagttacc ggataaggcg cagcggtcgg    3720
gctgaacggg gggttcgtgc acacagccca gcttggagcg aacgacctac accgaactga    3780
```

```
gatacctaca gcgtgagcat tgagaaagcg ccacgcttcc cgaagggaga aaggcggaca    3840
ggtatccggt aagcggcagg gtcggaacag gagagcgcac gagggagctt ccaggggggaa   3900 acgcctggta tctttatagt cctgtcgggt ttcgccacct ctgacttgag cgtcgatttt    3960
tgtgatgctc gtcaggggggg cggagcctat ggaaaaacgc cagcaacgcg ccttttttac   4020
ggttcctggc cttttgctgg ccttttgctc acatgttctt tcctgcgtta tcccctgatt    4080
ctgtggataa ccgtattacc gcctttgagt gagctgatac cgctcgccgc agccgaacga    4140
ccgagcgcag cgagtcagtg agcgaggaag cggaagagcg cccaatacgc aaaccgcctc    4200
tccccgcgcg ttggccgatt cattaatgca gctggcacga caggtttccc gactggaaag    4260
cgggcagtga gcgcaacgca attaatgtga gttagctcac tcattaggca ccccaggctt    4320
tacactttat gcttccggct cgtatgttgt gtggaattgt gagcggataa caatttcaca    4380
caggaaacag ctatgaccat gattacgaat tcgacctgc aggcatgcaa gcttgcatgc     4440
ctgcaggtcg acgctcgcgc gacttggttt gccattcttt agcgcgcgtc gcgtcacaca    4500
gcttggccac aatgtggttt ttgtcaaacg aagattctat gacgtgttta agtttaggt     4560 cgagtaaagc gcaaatcttt tttaacccta gaaagatagt ctgcgtaaaa ttgacgcatg    4620
cattcttgaa atattgctct ctcttttctaa atagcgcgaa tccgtcgctg tgcatttagg   4680
acatctcagt cgccgcttgg agctcccgtg aggcgtgctt gtcaatgcgg taagtgtcac    4740
tgattttgaa ctataacgac cgcgtgagtc aaaatgacgc atgattatct tttacgtgac    4800
ttttaagatt taactcatac gataattata ttgttatttc atgttctact tacgtgataa    4860
cttattatat atatattttc ttgttataga tatcgtgact aatatataat aaaatgggta    4920
gttctttaga cgatgagcat atcctctctg ctcttctgca aagcgatgac gagcttgttg    4980
gtgaggattc tgacagtgaa atatcagatc acgtaagtga agatgacgtc cagagcgata    5040
cagaagaagc gtttatagat gaggtacatg aagtgcagcc aacgtcaagc ggtagtgaaa    5100
tattagacga acaaaatgtt attgaacaac caggttcttc attggcttct aacagaatct    5160
tgaccttgcc acagaggact attagaggta agaataaaca ttgttggtca acttcaaagt    5220
ccacgaggcg tagccgagtc tctgcactga acattgtcag atcggcccgg gcgccgtttc    5280
ccaaacgcgc cagtggtagt acacagtact gtgggtgttc agtttgaaat cctcttgctt    5340
ctccattgtc tcggttacct ttggtcaaat ccatgggttc tattgcctat atactcttgc    5400
gattaccagt gattgcgcta ttagctatta gatggattgt tggccaaact tgtcgcttaa    5460
gtggctggga attgtaaccg taggcccgag tgtaatgatc ccccataaaa agttttcgca    5520
atgcctttat ttttttgttgc aaatctctct ttattctgcg gtattcttca ttattgcggg   5580 gatgggggaaa gtgtttatat agaagcaact tacgattgaa cccaaatgca cctgacaagc   5640
aaggtcaaag ggccagattt ttaaatatat tattagtct taggactctc tatttgcaat     5700
taaattactt tgctacctga gggttaaatc ttccccattg ataataataa ttccactata    5760
tgttcaattg ggtttcaccg cgcttagtta catgacgagc cctaatgagc cgtcggtggt    5820
ctataaactg tgccttacaa atacttgcaa ctcttctcgt tttgaagtca gcagagttat    5880
tgctaattgc taattgctaa ttgcttttaa ctgattctt cgaaattggt gctatgttta     5940
tggcgctatt aacaagtatg aatgtcaggt ttaaccaggg gatgcttaat tgtgttctca    6000
acttcaaagg cagaaatgtt tactcttgac catgggttta ggtataatgt tatcaagctc    6060
ctcgagttaa cgttacgtta acgttaacgt tcgaggtcga ctctagatta ttacagcatg    6120
tcgagatcaa agtcgtccaa agcatcagcg ggcaacatat ccaagtcaaa atcatcgaga    6180
```

```
gcgtccgccg gcagcatatc caggtcgaag tcatccaggg catcggcggg gcccgagccc    6240
gactcgcatt tcagttgctt ttccaatccg cagataatca gctccaagcc gaacaggaat    6300
gccggctcgg ctccttgatg atcgaacagc tcgattgcct gacgcagcag tgggggcatc    6360
gaatcggttg ttggggtctc gcgctcctct tttgcgactt gatgctcttg gtcctccagc    6420
acgcagccca gggtaaagtg accgacggcg ctcagagcgt agagagcatt tccaggctg     6480 aagccttgct ggcacaggaa cgcgagctgg ttctccagtg tctcgtattg cttttcggtc    6540
gggcgcgtgc cgagatggac tttggcaccg tctcggtggg acagcagagc gcagcggaac    6600
gacttggcgt tattgcggag gaagtcctgc caggactcgc cttccaacgg gcaaaaatgc    6660
gtgtggtggc ggtcgagcat ctcgatggcc agggcatcca gcagcgcccg cttattcttc    6720
acgtgccagt agagggtggg ctgctccacg cccagcttct gcgccaactt gcgggtcgtc    6780
agtccctcaa tgccaacttc gttcaacagc tccaacgcgg agttgatgac tttggactta    6840
tccaggcggc tgcccatggt ggtttctaaa ggtgttataa atcaaattag ttttgttttt    6900
tcttgaaaac tttgcgtttc ctttgatcaa cttaccgcca gggtaccgca gattgtttag    6960
cttgttcagc tgcgcttgtt tatttgctta gctttcgctt agcgacgtgt tcactttgct    7020
tgtttgaatt gaattgtcgc tccgtagacg aagcgcctct atttatactc cggcgctcgt    7080
tttcgagttt accactccct atcagtgata gagaaaagtg aaagtcgagt ttaccactcc    7140
ctatcagtga tagagaaaag tgaaagtcga gtttaccact ccctatcagt gatagagaaa    7200
agtgaaagtc gagtttacca ctccctatca gtgatagaga aagtgaaag tcgagtttac    7260 cactccctat cagtgataga gaaagtgaa agtcgagttt accactccct atcagtgata    7320
gagaaaagtg aaagtcgagt ttaccactcc ctatcagtga tagagaaaag tgaaagtcga    7380
aacctggcgc gcctcttaat taaggccccc cctcgagacc atggtcgatc gacaaacacg    7440
aaaatacatt cctggacaga cctagggggtt tgctcttttt tctttgcagg atctggattc    7500 aacaagaag gaaaaatcta cggagtttgg aacctcattt attgcacgaa gaaacttaga    7560
gagaaagact gatgcctaat aaagactcaa gctgattgca aaacaatat aaagttgtac    7620 cttattgcgg tgtcatcgta aaaccaagat gcttaaaagg gattaggccc acttaaatta    7680
ctgcgaaaaa ttttatttac aaatttctca catgacttcc agataaacta attaactttg    7740
tgtgtcaagg ttgcttttcc ggcagaaaag tcaatttgca agtgatttag gttttttaa     7800 tgactatctt tgcaattgaa ttgggtacta ttagatattg aatataccaa tattgaggta    7860
taatacaaat acaacaacat ttgacctcgg caactatcag aagtacatgt aggtcggaa     7920 cattagggaa ttctgcgcga taagttacta attatgctaa gctatcgcag aacctcatta    7980
agacttgagc tgcagtgttt tgcaggtact tatcatattt acagtattaa tgtatgcagt    8040
attatattaa ttctaaataa gaaagtcagg agaaggatat tcaaaactga agaattaatg    8100
tacattagtt ttgtttatta gattttcaat attgcagcat agaatatgtg taagtagtgg    8160
agagctaaac gcgcttttca gaacgttcat gctaattgct catggatctc acaggaacag    8220
gtggtggcgg ccctcggtgc gctcgtactg ctccacgatg gtgtagtcct cgttgtggga    8280
ggtgatgtcc agcttggcgt ccacgtagta gtagccgggc agctgcacgg gcttcttggc    8340
catgtagatg gacttgaact ccaccaggta gtggccgccg tccttcagct tcagggcctt    8400
gtgggtctcg cccttcagca cgccgtcgcg ggggtacagg cgctcggtgg aggcctccca    8460
gcccatggtc ttcttctgca tcacggggcc gtcggagggg aagttcacgc cgatgaactt    8520
```

```
caccttgtag atgaagcagc cgtcctgcag ggaggagtcc tgggtcacgg tcgccacgcc    8580
gccgtcctcg aagttcatca cgcgctccca cttgaagccc tcggggaagg acagcttctt    8640
gtagtcgggg atgtcggcgg ggtgcttcac gtacaccttg gagccgtact ggaactgggg    8700
ggacaggatg tcccaggcga agggcagggg gccgcccttg gtcaccttca gcttcacggt    8760
gttgtggccc tcgtaggggc ggccctcgcc ctcgccctcg atctcgaact cgtggccgtt    8820
cacggtgccc tccatgcgca ccttgaagcg catgaactcg gtgatgacgt tctcggagga    8880
ggccattcta gccattttgg ttctagatcc ggggtctctg gattagacga ctgctggctg    8940
atggagcggc tttgtgtcgg gaggagtatc cacacagcac aagaactcaa acggtagtga    9000
tatgaaaact ggtcccgcag cccgttttat aaagcccgct tagcgctaaa accttatcag    9060
ccgcaatgct ctccgctctc aagtcgcgtt caaaacttttt accatatatg ggtatgaatt    9120
gttcgccgat tgggttttca tttacggaga atttcctccg caactgggtg ttcgtgcttg    9180
tgtgtgtctt gtatatcgcc atgaagagtg tacttccatg ggtcctatca gttgcggcat    9240
gtgattcaat ttgggggtta ctcatattcg atacttcagc tggttatctt tatgctgtga    9300
tggtcacggt gcttttacac attttttccc caactactca ttgtatgcca aaacatacat    9360
atgtacatgt gtttatagtg ggtttattag taatgtccag cgatattaaa acattacagt    9420
taaataatat tcatattagc ttacgtttac tgctatctgc acttcaaatt ggttattcag    9480
ggacatttgt gcaacacaca tcttctagta ggggcatcac tagtcgtaga aaacacacct    9540
aacttaagcc ggttttaaca ataacggcga acagctgcc agacgagaga aaagtacaca    9600
gcaagaagca tttctataat gatgccgtcc taaatatgca gcattttgc tcaaattgat    9660
catttcgttg catcgctcag gtggtatagt atttggctat tgaatgtgat tgctatctta    9720
atagttttga atagtaatag tgcaaatatt cattcataaa aaataggtaa tcgatttttct    9780
cagtgcagtc tatgcgtttg cgcaaacagg agacgaagag agagacgcct cacacacaag    9840
cacatgcgta ctacgctggc ctactccgct actctatgtg tcgtcctctg catcgtctgc    9900
ttggcggcag ttcttccaga ggctgtgacg tcaggtaagc tatttcgtct cggtgtgctg    9960
ttagcccgta acgataagct gtccgattcc taattctctt tcaaataatt tgttttattt    10020
tttttttttgt gtgttttgaa gtcaaacagc ttcataaaca atattaaata tcgcaattgt    10080
tattgcaaat gcattcgtat caggcgcctt gatgtttttc ggccaaaact tcgtctgctc    10140
tttgtcagcg taattgcgtt tgccggtcgt gccgtcttgc tcgcacgcgc ttgcaaacaa    10200
aaagtgaaag agggaaagcc actgtgttgt tgcttttgtt gctatcgttg gctgcacaca    10260
catggcaata agtaaccata ttgtagactt atttatttta gcgttttcgt tgactaatct    10320
ttgtttaaat aattgcctat ttcgagccaa aatgacgcat aaaggacacg gcaacatgcg    10380
gtgcgttgag catgcgtacg agatggcgct agagagagcg agataaaaag aaaaaaacaa    10440
ccggcgagtg gcgagacacg aataatacac acacgcacac atggtcaaag gagtggctcc    10500
aacgtcggtg acgtcgcgcc cagccacaga ccccgccacg ccccgcccca cccttccttc    10560
cgctgccccg cacccctttc cttccactac cgttttgccg catttggtat gccatctcg    10620
cttttttggc tttactttgc tttttgaata agccaagaaa ctgaaatcaa agcggacagt    10680
ccgaaaattg aaactattcc aaaaaacaac aaccgcacat gcactgcgtt cggcaaaaga    10740
cgcagaaatc agcctgtggt ctggcatcat cttaaaatat catcagtatc atcattgcca    10800
ttataaatac ataagaaaat gagaaatcat taaaggtata tacatacaat ctttgtcata    10860
gtcaacatat tttgcaacaa aattatctat agataacatg ttttttgtaga aaattccact    10920
```

```
aactgatttt cgtataaata caaattattc tcattcttca aaatactcgc cgacgtcatc    10980
gcgaaattcc tcagcattct tcgacaaatg aagagagaca gcgagtgaca caatcttatc    11040
ttaccgacga gtctttgaaa atggccccgg gaacggtgaa aaacatatag ccaagaatgg    11100
agcgatcgcc aggcgatgga aattggcttc aaattgctcc gaatatggcc agttggtcag    11160
ttggcattgg attgtggaga gatactagat cagctcgttc tccttctcct ccgcattctc    11220
ctactcgccc gaagacgctt ctttgatcgc ttctttctcg aatgtacata ttgatatgta    11280
tttggtgttt ggcgacgatc agccagcttt aatggccata aaacgtgtct tggtttgtgg    11340
gccacataac aggcagcgag atctggaaaa atgatgtgac agtggaaatg agaagtaggt    11400
gcatctgcaa agatttgatt cagagttgat gccattcatg attttttta gaagtatcat    11460 ttgtgttttt agaatataga attctagtat gtatgtaagt aataaaacc cattttgcg     11520 gaaagtagat aaaaaaaaca tttttttttt ttactgcact ggatatctgc               11570

<210> SEQ ID NO 18
<211> LENGTH: 11251
<212> TYPE: DNA
<213> ORGANISM: Artificial Sequence
<220> FEATURE:
<223> OTHER INFORMATION: Synthetic construct, plasmid pLA656

<400> SEQUENCE: 18
cgccaggcga tggaaattgg cttcaaattg ctccgaatat ggccagttgg tcagttggca        60
ttggattgtg gagagatact agatcagctc gttctccttc tcctccgcat tctcctactc       120
gcccgaagac gcttctttga tcgcttcttt ctcgaatgta catattgata tgtatttggt       180
gtttggcgac gatcagccag ctttaatggc cataaaacgt gtcttggttt gtgggccaca       240
taacaggcag cgagatctgg aaaaatgatg tgacagtgga aatgagaagt aggtgcatct       300
gcaaagattt gattcagagt tgatgccatt catgattttt tttagaagta tcatttgtgt       360
ttttagaata tagaattcta gtatgtatgt aagttaataa aacccatttt tgcggaaagt       420
agataaaaaa aacattttt tttttttactg cactggatat ctgcggccgc tcatttaaat       480
ctggccggcc gcaaccattg tgggaaccgt gcgatcaaac aaacgcgaga taccggaagt       540
actgaaaaac agtcgctcca ggccagtggg aacatcgatg ttttgtttg acggacccct       600 tactctcgtc tcatataaac cgaagccagc taagatggta tacttattat catcttgtga       660
tgaggatgct tctatcaacg aaagtaccgg taaaccgcaa atggttatgt attataatca       720
aactaaaggc ggagtggaca cgctagacca aatgtgttct gtgatgacct gcagtaggaa       780
gacgaatagg tggcctatgg cattattgta cggaatgata acattgcct gcataaattc       840 ttttattata tacagccata atgtcagtag caagggagaa aaggtccaaa gtcgcaaaaa       900
atttatgaga aacctttaca tgagcctgac gtcatcgttt atgcgtaagc gtttagaagc       960
tcctactttg aagagatatt tgcgcgataa atatctctaat attttgccaa atgaagtgcc      1020
tggtacatca gatgacagta ctgaagagcc agtaatgaaa aaacgtactt actgtactta      1080
ctgcccctct aaaataaggc gaaaggcaaa tgcatcgtgc aaaaaatgca aaaaagttat      1140
ttgtcgagag cataatattg atatgtgcca agttgtttc tgactgacta ataagtataa      1200
tttgtttcta ttatgtataa gttaagctaa ttacttattt tataatacaa catgactgtt      1260
tttaaagtac aaaataagtt tatttttgta aagagagaa tgtttaaaag ttttgttact      1320
ttatagaaga aattttgagt ttttgttttt ttttaataaa taaataaaca taaataaatt      1380
```

```
gtttgttgaa tttattatta gtatgtaagt gtaaatataa taaaacttaa tatctattca    1440
aattaataaa taaacctcga tatacagacc gataaaacac atgcgtcaat tttacgcatg    1500
attatcttta acgtacgtca caatatgatt atctttctag ggttaaataa tagtttctaa    1560 ttttttttatt attcagcctg ctgtcgtgaa taccgtatat ctcaacgctg tctgtgagat    1620
tgtcgtattc tagcctttttt agttttttcgc tcatcgactt gatattgtcc gacacatttt    1680
cgtcgatttg cgttttgatc aaagacttga gcagagacag gttaatcaac tgttcaaatt    1740
gatccatatt aacgatatca acccgatgcg tatatggtgc gtaaaatata ttttttaacc    1800
ctcttatact ttgcactctg cgttaatacg cgttcgtgta cagacgtaat catgttttct    1860
tttttggata aaactcctac tgagtttgac ctcatattag accctcacaa gttgcaaaac    1920
gtggcatttt ttaccaatga agaatttaaa gttattttaa aaaatttcat cacagattta    1980
aagaagaacc aaaaattaaa ttatttcaac agtttaatcg accagttaat caacgtgtac    2040
acagacgcgt cggcaaaaaa cacgcagccc gacgtgttgg ctaaaattat taaatcaact    2100
tgtgttatag tcacggattt gccgtccaac gtgttcctca aaaagttgaa gaccaacaag    2160
tttacggaca ctattaatta tttgattttg ccccacttca ttttgtggga tcacaatttt    2220
gttatatttt aaacaaagct tggcactggc cgtcgtttta caacgtcgtg actgggaaaa    2280
ccctggcgtt acccaactta atcgccttgc agcacatccc cctttcgcca gctggcgtaa    2340
tagcgaagag gcccgcaccg atcgcccttc ccaacagttg cgcagcctga atggcgaatg    2400
gcgcctgatg cggtattttc tccttacgca tctgtgcggt atttcacacc gcatatggtg    2460
cactctcagt acaatctgct ctgatgccgc atagttaagc cagccccgac acccgccaac    2520
acccgctgac gcgccctgac gggcttgtct gctcccggca tccgcttaca gacaagctgt    2580
gaccgtctcc gggagctgca tgtgtcagag gttttcaccg tcatcaccga aacgcgcgag    2640
acgaaagggc ctcgtgatac gcctattttt ataggttaat gtcatgataa taatggtttc    2700
ttagacgtca ggtggcactt ttcggggaaa tgtgcgcgga acccctattt gtttattttt    2760
ctaaatacat tcaaatatgt atccgctcat gagacaataa ccctgataaa tgcttcaata    2820
atattgaaaa aggaagagta tgagtattca acatttccgt gtcgccctta ttcccttttt    2880
tgcggcattt tgccttcctg ttttgctca cccagaaacg ctggtgaaag taaaagatgc    2940
tgaagatcag ttgggtgcac gagtgggtta catcgaactg gatctcaaca gcggtaagat    3000
ccttgagagt tttcgccccg aagaacgttt tccaatgatg agcactttta aagttctgct    3060
atgtggcgcg gtattatccc gtattgacgc cgggcaagag caactcggtc gccgcataca    3120
ctattctcag aatgacttgg ttgagtactc accagtcaca gaaaagcatc ttacggatgg    3180
catgacagta agagaattat gcagtgctgc cataaccatg agtgataaca ctgcggccaa    3240
cttacttctg acaacgatcg gaggaccgaa ggagctaacc gcttttttgc acaacatggg    3300
ggatcatgta actcgccttg atcgttggga accggagctg aatgaagcca taccaaacga    3360
cgagcgtgac accacgatgc ctgtagcaat ggcaacaacg ttgcgcaaac tattaactgg    3420
cgaactactt actctagctt cccggcaaca attaatagac tggatggagg cggataaagt    3480
tgcaggacca cttctgcgct cggcccttcc ggctggctgg tttattgctg ataaatctgg    3540
agccggtgag cgtgggtctc gcggtatcat tgcagcactg gggccagatg gtaagccctc    3600
ccgtatcgta gttatctaca cgacggggag tcaggcaact atggatgaac gaaatagaca    3660
gatcgctgag ataggtgcct cactgattaa gcattggtaa ctgtcagacc aagtttactc    3720
atatatactt tagattgatt taaaacttca ttttttaattt aaaaggatct aggtgaagat    3780
```

```
ccttttttgat aatctcatga ccaaaatccc ttaacgtgag ttttcgttcc actgagcgtc      3840
agaccccgta gaaaagatca aaggatcttc ttgagatcct ttttttctgc gcgtaatctg      3900
ctgcttgcaa acaaaaaaac caccgctacc agcggtggtt tgtttgccgg atcaagagct      3960
accaactctt tttccgaagg taactggctt cagcagagcg cagataccaa atactgtcct      4020
tctagtgtag ccgtagttag gccaccactt caagaactct gtagcaccgc ctacatacct      4080
cgctctgcta atcctgttac cagtggctgc tgccagtggc gataagtcgt gtcttaccgg      4140
gttggactca agacgatagt taccggataa ggcgcagcgg tcgggctgaa cggggggttc      4200
gtgcacacag cccagcttgg agcgaacgac ctacaccgaa ctgagatacc tacagcgtga      4260
gcattgagaa agcgccacgc ttcccgaagg gagaaaggcg gacaggtatc cggtaagcgg      4320
cagggtcgga acaggagagc gcacgaggga gcttccaggg ggaaacgcct ggtatcttta      4380
tagtcctgtc gggtttcgcc acctctgact tgagcgtcga ttttttgtgat gctcgtcagg      4440 ggggcggagc ctatggaaaa acgccagcaa cgcggccttt ttacggttcc tggccttttg      4500
ctggcctttt gctcacatgt tctttcctgc gttatcccct gattctgtgg ataaccgtat      4560
taccgccttt gagtgagctg ataccgctcg ccgcagccga acgaccgagc gcagcgagtc      4620
agtgagcgag gaagcggaag agcgcccaat acgcaaaccg cctctccccg cgcgttggcc      4680
gattcattaa tgcagctggc acgacaggtt cccgactgg aaagcgggca gtgagcgcaa      4740
cgcaattaat gtgagttagc tcactcatta ggcacccag gctttacact ttatgcttcc      4800
ggctcgtatg ttgtgtggaa ttgtgagcgg ataacaattt cacacaggaa acagctatga      4860
ccatgattac gaatttcgac ctgcaggcat gcaagcttgc atgcctgcag tcgacgctc      4920 gcgcgacttg gtttgccatt cttagcgcg cgtcgcgtca cacagcttgg ccacaatgtg      4980 gttttgtca acgaagatt ctatgacgtg tttaaagttt aggtcgagta aagcgcaaat      5040 ctttttaac cctagaaaga tagtctgcgt aaaattgacg catgcattct tgaaatattg      5100
ctctctcttt ctaaatagcg cgaatccgtc gctgtgcatt taggacatct cagtcgccgc      5160
ttggagctcc cgtgaggcgt gcttgtcaat gcggtaagtg tcactgattt tgaactataa      5220
cgaccgcgtg agtcaaaatg acgcatgatt atcttttacg tgacttttaa gatttaactc      5280
atacgataat tatattgtta tttcatgttc tacttacgtg ataacttatt atatatatat      5340
tttcttgtta tagatatcgt gactaatata taataaaatg ggtagttctt tagacgatga      5400
gcatatcctc tctgctcttc tgcaaagcga tgacgagctt gttggtgagg attctgacag      5460
tgaaatatca gatcacgtaa gtgaagatga cgtccagagc gatacagaag aagcgtttat      5520
agatgaggta catgaagtgc agccaacgtc aagcggtagt gaaatattag acgaacaaaa      5580
tgttattgaa caaccaggtt cttcattggc ttctaacaga atcttgacct tgccacagag      5640
gactattaga ggtaagaata aacattgttg gtcaacttca aagtccacga ggcgtagccg      5700
agtctctgca ctgaacattg tcagatcggc ccgggcgccg tttttcttga atattgctc      5760 tctctttcta aatagcgcga atccgtcgct gtgcatttag gacatctcag tcgccgcttg      5820
gagctcccaa acgcgccagt ggtagtacac agtactgtgg gtgttcagtt tgaaatcctc      5880
ttgcttctcc attgtctcgg ttacctttgg tcaaatccat gggttctatt gcctatatac      5940
tcttgcgatt accagtgatt gcgctattag ctattagatg gattgttggc caaacttgtc      6000
gcttaagtgg ctgggaattg taaccgtagg cccgagtgta atgatccccc ataaaaagtt      6060
ttcgcaatgc ctttatttt tgttgcaaat ctctctttat tctgcggtat tcttcattat      6120
```

```
tgcggggatg gggaaagtgt ttatatagaa gcaacttacg attgaaccca aatgcacctg    6180
acaagcaagg tcaaagggcc agattttaaa atatattatt tagtcttagg actctctatt    6240
tgcaattaaa ttactttgct acctgagggt taaatcttcc ccattgataa taataattcc    6300
actatatgtt caattgggtt tcaccgcgct tagttacatg acgagcccta atgagccgtc    6360
ggtggtctat aaactgtgcc ttacaaatac ttgcaactct tctcgttttg aagtcagcag    6420
agttattgct aattgctaat tgctaattgc ttttaactga tttcttcgaa attggtgcta    6480
tgtttatggc gctattaaca agtatgaatg tcaggtttaa ccaggggatg cttaattgtg    6540
ttctcaactt caaaggcaga aatgtttact cttgaccatg ggtttaggta taatgttatc    6600
aagctcctcg agttaacgtt acgttaacgt taacgttcga ggtcgactct agaactaccc    6660
accgtactcg tcaattccaa gggcatcggt aaacatctgc tcaaactcga agtcggccat    6720
atccagagcg ccgtaggggg cggagtcgtg gggggtaaat cccggacccg gggaatcccc    6780 gtccccaac atgtccagat cgaaatcgtc tagcgcgtcg gcatgcgcca tcgccacgtc     6840
ctcgccgtct aagtggagct cgtcccccag gctgacatcg tcgggggggg ccgtcgacag    6900
tctgcgcgtg tgtcccgcgg ggagaaagga caggcgcgga gccgccagcc ccgcctcttc    6960
gggggcgtcg tcgtccggga gatcgagcag gccctcgatg gtagaccgt aattgttttt     7020 cgtacgcgcg cggctgtacg cggggcccga gcccgactcg catttcagtt gcttttccaa    7080
tccgcagata atcagctcca agccaacag gaatgccggc tcggctcctt gatgatcgaa     7140
cagctcgatt gcctgacgca gcagtggggg catcgaatcg gttgttgggg tctcgcgctc    7200
ctcttttgcg acttgatgct cttggtcctc cagcacgcag cccagggtaa agtgaccgac    7260
ggcgctcaga gcgtagagag cattttccag gctgaagcct tgctggcaca ggaacgcgag    7320
ctggttctcc agtgtctcgt attgcttttc ggtcgggcgc gtgccgagat ggactttggc    7380
accgtctcgg tgggacagca gagcgcagcg gaacgacttg gcgttattgc ggaggaagtc    7440
ctgccaggac tcgccttcca acgggcaaaa atgcgtgtgg tggcggtcga gcatctcgat    7500
ggccagggca tccagcagcg cccgcttatt cttcacgtgc cagtagaggg tgggctgctc    7560
cacgcccagc ttctgcgcca acttgcgggt cgtcagtccc tcaatgccaa cttcgttcaa    7620
cagctccaac gcggagttga tgactttgga cttatccagg cggctgccca tggtggtttc    7680
taaaggtgtt ataaatcaaa ttagttttgt ttttcttga aactttgcg tttcctttga      7740 tcaacttacc gccagggtac cgcagattgt ttagcttgtt cagctgcgct tgtttatttg    7800
cttagctttc gcttagcgac gtgttcactt tgcttgtttg aattgaattg tcgctccgta    7860
gacgaagcgc ctctatttat actccggcgc tcgttttcga gtttaccact ccctatcagt    7920
gatagagaaa agtgaaagtc gagtttacca ctccctatca gtgatagaga aaagtgaaag    7980
tcgagtttac cactccctat cagtgataga gaaaagtgaa agtcgagttt accactccct    8040
atcagtgata gagaaaagtg aaagtcgagt ttaccactcc ctatcagtga tagagaaaag    8100
tgaaagtcga gtttaccact ccctatcagt gatagagaaa agtgaaagtc gagtttacca    8160
ctccctatca gtgatagaga aaagtgaaag tcgaaacctg gcgcgcctct taattaactc    8220
gcgttaagat acattgatga gtttggacaa accacaacta gaatgcagtg aaaaaaatgc    8280
tttatttgtg aaatttgtga tgctattgct ttatttgtaa ccattataag ctgcaataaa    8340
caagttaaca acaacaattg cattcatttt atgtttcagg ttcagggggga ggtgtgggag    8400 gttttttaaa gcaagtaaaa cctctacaaa tgtggtatgg ctgattatga tcagttatct    8460
agatccggtg gatcttacgg gtcctccacc ttccgctttt tcttgggtcg agatctcagg    8520
```

```
aacaggtggt ggcggccctc ggtgcgctcg tactgctcca cgatggtgta gtcctcgttg    8580
tgggaggtga tgtccagctt ggcgtccacg tagtagtagc cgggcagctg cacgggcttc    8640
ttggccatgt agatggactt gaactccacc aggtagtggc cgccgtcctt cagcttcagg    8700
gccttgtggg tctcgccctt cagcacgccg tcgcgggggt acaggcgctc ggtggaggcc    8760
tcccagccca tggtcttctt ctgcatcacg gggccgtcgg aggggaagtt cacgccgatg    8820
aacttcacct tgtagatgaa gcagccgtcc tgcaggagg agtcctgggt cacggtcgcc     8880
acgccgccgt cctcgaagtt catcacgcgc tcccacttga agccctcggg gaaggacagc    8940
ttcttgtagt cggggatgtc ggcggggtgc ttcacgtaca ccttggagcc gtactggaac    9000
tgggggggaca ggatgtccca ggcgaagggc agggggccgc ccttggtcac cttcagcttc   9060
acggtgttgt ggccctcgta ggggcggccc tcgccctcgc cctcgatctc gaactcgtgg    9120
ccgttcacgg tgccctccat gcgcaccttg aagcgcatga actcggtgat gacgttctcg    9180
gaggaggcca tggtggcgac cggtttgcgc ttcttcttgg gtggggtggg atccccgatc    9240
tgcattttgg attattctgc gggtcaaaat agagatgtgg aaaattagta cgaaatcaaa    9300
tgagtttcgt tgaaattaca aaactattga aactaacttc ctggctgggg aataaaaatg    9360
ggaaacttat ttatcgacgc caactttgtt gagaaacccc tattaaccct ctacgaatat    9420
tggaacaaag gaaagcgaag aaacaggaac aaaggtagtt gagaaacctg ttccgttgct    9480
cgtcatcgtt ttcataatgc gagtgtgtgc atgtatatat acacagctga aacgcatgca    9540
tacacattat tttgtgtgta tatggtgacg tcacaactac taagcaataa gaaattttcc    9600
agacgtggct ttcgtttcaa gcaacctact ctatttcagc taaaaataag tggatttcgt    9660
tggtaaaata cttcaattaa gcaaagaact aactaactaa taacatgcac acaaatgctc    9720
gagtgcgttc gtgatttctc gaattttcaa atgcgtcact gcgaatttca caatttgcca    9780
ataaatcttg gcgaaaatca acacgcaagt tttatttata gatttgtttg cgttttgatg    9840
ccaattgatt gggaaaacaa gatgcgtggc tgccaatttc ttattttgta attacgtaga    9900
gcgttgaata aaaaaaaaat ggccgaacaa agaccttgaa atgcagtttt tcttgaaatt    9960
actcaacgtc ttgttgctct tattactaat tggtaacagc gagttaaaaa cttacgtttc    10020
ttgtgacttt cgagaatgtt cttttaattg tactttaatc accaacaatt aagtataaat    10080
ttttcgctga ttgcgcttta ctttctgctt gtacttgctg ctgcaaatgt caattggttt    10140
tgaaggcgac cgttcgcgaa cgctgtttat ataccttcgg tgtccgttga aaatcactaa    10200
aaaataccgt agtgttcgta acactttagt acagagaaaa aaaattgtgc cgaaatgttt    10260
ttgatacgta cgaatacctt gtattaaaat ttttttatgat ttctgtgtat cacttttttt   10320
ttgtgttttt cgtttaaact caccacagta caaaacaata aaatatttt aagacaattt     10380
caaattgaga cctttctcgt actgacttga ccggctgaat gaggatttct acctagacga    10440
cctacttctt accatgacat tgaatgcaat gccacctttg atctaaactt acaaaagtcc    10500
aaggcttgtt aggattggtg tttatttagt ttgcttttga aatagcactg tcttctctac    10560
cggctataat tttgaaactc gcagcttgac tggaaattta aaaagtaatt ctgtgtaggt    10620
aaagggtgtt ttaaagtgt gatgtgttga gcgttgcggc aacgactgct atttatgtat     10680
atattttcaa aacttattgt ttttgaagtg ttttaaatgg agctatctgg caacgctgcg    10740
cataatctta cacaagcttt tcttaatcca tttttaagtg aaatttgttt ttactctttc    10800
ggcaaataat tgttaaatcg ctttaagtgg gcttacatct ggataagtaa tgaaaacctg    10860
```

```
catattataa tattaaaaca tataatccac tgtgctttcc ccgtgtgtgg ccatatacct    10920
aaaaaagttt attttcgcag agccccgcac ggtcacacta cggttcggcg attttcgatt    10980
ttggacagta ctgattgcaa gcgcaccgaa agcaaaatgg agctggagat tttgaacgcg    11040
aagaacagca agccgtacgg caaggtgaag gtgccctccg gcgccacgcc catcggcgat    11100
ctgcgcgccc taattcacaa gaccctgaag cagaccccac acgcgaatcg ccagtcgctt    11160
cgtctggaac tgaagggcaa aagcctgaaa gatacggaca cattggaatc tctgtcgctg    11220
cgttccggcg acaagatcgg ggtaccgcga t                                   11251

<210> SEQ ID NO 19
<211> LENGTH: 9468
<212> TYPE: DNA
<213> ORGANISM: Artificial Sequence
<220> FEATURE:
<223> OTHER INFORMATION: Synthetic construct, plasmid pLA710

<400> SEQUENCE: 19
ggccgctcat ttaaatctgg ccggccgcaa ccattgtggg aaccgtgcga tcaaacaaac      60
gcgagatacc ggaagtactg aaaaacagtc gctccaggcc agtgggaaca tcgatgtttt     120
gttttgacgg acccctcact ctcgtctcat ataaaccgaa gccagctaag atggtatact     180
tattatcatc ttgtgatgag gatgcttcta tcaacgaaag taccggtaaa ccgcaaatgg     240
ttatgtatta taatcaaact aaaggcggag tggacacgct agaccaaatg tgttctgtga     300
tgacctgcag taggaagacg aataggtggc ctatggcatt attgtacgga atgataaaca     360
ttgcctgcat aaattctttt attatataca gccataatgt cagtagcaag ggagaaaagg     420
tccaaagtcg caaaaaattt atgagaaacc tttacatgag cctgacgtca tcgtttatgc     480
gtaagcgttt agaagctcct actttgaaga gatatttgcg cgataatatc tctaatattt     540
tgccaaatga agtgcctggt acatcagatg acagtactga gagccagta atgaaaaaac     600 gtacttactg tacttactgc ccctctaaaa taaggcgaaa ggcaaatgca tcgtgcaaaa     660
aatgcaaaaa agttatttgt cgagagcata atattgatat gtgccaaagt gtttctgac      720 tgactaataa gtataatttg tttctattat gtataagtta agctaattac ttattttata     780
atacaacatg actgttttta agtacaaaa taagtttatt tttgtaaaag agagaatgtt     840
taaaagtttt gttacttat agaagaaatt ttgagtttt gttttttttt aataaataaa       900
taaacataaa taaattgttt gttgaatta ttattagtat gtaagtgtaa atataataaa     960
acttaatatc tattcaaatt aataaataaa cctcgatata cagaccgata aaacacatgc    1020 gtcaattta cgcatgatta tctttaacgt acgtcacaat atgattatct ttctagggtt    1080
aaataatagt ttctaatttt tttattattc agcctgctgt cgtgaatacc gtatatctca    1140
acgctgtctg tgagattgtc gtattctagc ctttttagtt tttcgctcat cgacttgata    1200
ttgtccgaca cattttcgtc gatttgcgtt ttgatcaaag acttgagcag agacacgtta    1260
atcaactgtt caaattgatc catattaacg atatcaaccc gatgcgtata tggtgcgtaa    1320
aatatatttt ttaaccctct tatactttgc actctgcgtt aatacgcgtt cgtgtacaga    1380
cgtaatcatg ttttctttt tggataaaac tcctactgag tttgacctca tattagaccc    1440
tcacaagttg caaaacgtgg cattttttac caatgaagaa tttaaagtta ttttaaaaaa    1500
tttcatcaca gatttaaaga agaaccaaaa attaaattat tcaacagtt taatcgacca    1560 gttaatcaac gtgtacacag acgcgtcggc aaaaaacacg cagcccgacg tgttggctaa    1620
aattattaaa tcaacttgtg ttatagtcac ggatttgccg tccaacgtgt tcctcaaaaa    1680
```

```
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct attttatag gttaatgtca   2220
tgataataat ggtttcttag acgtcaggtg cacttttcg gggaaatgtg cgcggaaccc   2280
ctatttgttt attttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg cattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga tccttttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccaggggga   3900
acgcctggta tctttatagt cctgtcgggt ttcgccacct ctgacttgag cgtcgatttt   3960
tgtgatgctc gtcaggggg cggagcctat ggaaaaacgc cagcaacgcg gcctttttac   4020
```

```
ggttcctggc cttttgctgg cctttgctc acatgttctt tcctgcgtta tccctgatt      4080
ctgtggataa ccgtattacc gcctttgagt gagctgatac cgctcgccgc agccgaacga    4140
ccgagcgcag cgagtcagtg agcgaggaag cggaagagcg cccaatacgc aaaccgcctc    4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat tcgacctgc aggcatgcaa gcttgcatgc    4440
ctgcaggtcg acgctcgcgc gacttggttt gccattcttt agcgcgcgtc gcgtcacaca   4500
gcttggccac aatgtggttt tgtcaaacg aagattctat gacgtgttta agtttaggt    4560
cgagtaaagc gcaaatcttt ttaaccccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatattttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagcga acaaaatgtt attgaacaac caggttcttc attggcttct aacagaatct    5160
tgaccttgcc acagaggact attagaggta agaataaaca ttgttggtca acttcaaagt   5220
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tccccataa aaagttttcg caatgccttt atttttgtt gcaaatctct ctttattctg     5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
```

```
gggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
acccgtaatt gttttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
tgccaacttc gttcaacagc tccaacgcgg agttgatgac tttggactta ccaggcggc   7200 tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt catttatgt ttcaggttca   7920 gggggaggtg tgggaggttt tttaaagcaa gtaaacctc tacaaatgtg gtatggctga   7980
ttatgatcag ttatctagat ccggtggatc ttacgggtcc tccaccttcc gcttttctct   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag acagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
```

| | |
|---|---:|
| ggtgggatcc tcgtcgcaca tcttgaatta gtctgcaaga aaagaaaaaa aacaattcaa | 8820 |
| actacattct cattccatac attatactaa gtaaacgaca aatttatttg cgtccatcta | 8880 |
| tttagtgacg ttaaagaaaa ctgtataaga ttcataattc actgttccca atttctgttt | 8940 |
| ccgaattgat cgatgcgagt ggacactttg aaatgtgcgt ccaataaact tatttcttat | 9000 |
| ttagtagtgt ttattaacat ctgcagtaca ctaaattccg aaaaatgttt ttttttataa | 9060 |
| aaaatttcac ttcactagtt atgcaacaat tatgtaacgt aacacgttat cattagcgta | 9120 |
| ttattaaaaa aaaaaaacac tcaaacatat gtaatactta aaggtaaagg gacggagaac | 9180 |
| cttcgaaatt caaattttac aaataaataa atatgttttt ttttctttcg caattttaaa | 9240 |
| attaaaactt acatagtatt attaaataag tgacaagtac gtagatgcga atgcgcactg | 9300 |
| ttcgagcaca ccttagtaaa tgagaaccga ctcgtgagga taaactatat aaaagagccg | 9360 |
| ttatcacaat ttacacagta tcggctccag tttgtttttc caccaatcgc gggctgactc | 9420 |
| agttttgtc accatatatg gtaacgcgca cgctatcagg taccatgc | 9468 |

<210> SEQ ID NO 20
<211> LENGTH: 10140
<212> TYPE: DNA
<213> ORGANISM: Artificial Sequence
<220> FEATURE:
<223> OTHER INFORMATION: Synthetic construct, plasmid pLA928

<400> SEQUENCE: 20

| | |
|---|---:|
| ggccgctcat ttaaatctgg ccggccgcaa ccattgtggg aaccgtgcga tcaaacaaac | 60 |
| gcgagatacc ggaagtactg aaaaacagtc gctccaggcc agtgggaaca tcgatgtttt | 120 |
| gttttgacgg acccccttact ctcgtctcat ataaaccgaa gccagctaag atggtatact | 180 |
| tattatcatc ttgtgatgag gatgcttcta tcaacgaaag taccggtaaa ccgcaaatgg | 240 |
| ttatgtatta taatcaaact aaaggcggag tggacacgct agaccaaatg tgttctgtga | 300 |
| tgacctgcag taggaagacg aataggtggc ctatggcatt attgtacgga atgataaaca | 360 |
| ttgcctgcat aaattctttt attatataca gccataatgt cagtagcaag ggagaaaagg | 420 |
| tccaaagtcg caaaaaattt atgagaaacc tttacatgag cctgacgtca tcgtttatgc | 480 |
| gtaagcgttt agaagctcct actttgaaga gatatttgcg cgataatatc tctaatatttt | 540 |
| tgccaaatga agtgcctggt acatcagatg acagtactga agagccagta atgaaaaaac | 600 |
| gtacttactg tacttactgc ccctctaaaa taaggcgaaa ggcaaatgca tcgtgcaaaa | 660 |
| aatgcaaaaa agttatttgt cgagagcata atattgatat gtgccaaagt tgtttctgac | 720 |
| tgactaataa gtataatttg tttctattat gtataagtta agctaattac ttatttata | 780 |
| atacaacatg actgtttta aagtacaaaa taagtttatt tttgtaaaag agagaatgtt | 840 |
| taaaagtttt gttactttat agaagaaatt ttgagttttt gttttttttt aataaataaa | 900 |
| taaacataaa taaattgttt gttgaattta ttattagtat gtaagtgtaa atataataaa | 960 |
| acttaatatc tattcaaatt aataaataaa cctcgatata cagaccgata aaacacatgc | 1020 |
| gtcaattta cgcatgatta tctttaacgt acgtcacaat atgattatct ttctagggtt | 1080 |
| aaataatagt ttctaattt tttattattc agcctgctgt cgtgaatacc gtatatctca | 1140 |
| acgctgtctg tgagattgtc gtattctagc ctttttagtt tttcgctcat cgacttgata | 1200 |
| ttgtccgaca catttcgtc gatttgcgtt tgatcaaag acttgagcag agacacgtta | 1260 |
| atcaactgtt caaattgatc catattacg atatcaaccc gatgcgtata tggtgcgtaa | 1320 |
| aatatatttt ttaaccctct tatactttgc actctgcgtt aatacgcgtt cgtgtacaga | 1380 |

```
cgtaatcatg ttttcttttt tggataaaac tcctactgag tttgacctca tattagaccc     1440
tcacaagttg caaaacgtgg cattttttac caatgaagaa tttaaagtta ttttaaaaaa     1500
tttcatcaca gatttaaaga agaaccaaaa attaaattat ttcaacagtt taatcgacca     1560
gttaatcaac gtgtacacag acgcgtcggc aaaaaacacg cagcccgacg tgttggctaa     1620
aattattaaa tcaacttgtg ttatagtcac ggatttgccg tccaacgtgt tcctcaaaaa     1680
gttgaagacc aacaagttta cggacactat taattatttg attttgcccc acttcatttt     1740
gtgggatcac aattttgtta tattttaaac aaagcttggc actggccgtc gttttacaac     1800
gtcgtgactg ggaaaaccct ggcgttaccc aacttaatcg ccttgcagca catcccctt      1860
tcgccagctg gcgtaatagc gaagaggccc gcaccgatcg cccttcccaa cagttgcgca     1920
gcctgaatgg cgaatggcgc ctgatgcggt attttctcct tacgcatctg tgcggtattt     1980
cacaccgcat atggtgcact ctcagtacaa tctgctctga tgccgcatag ttaagccagc     2040
cccgacaccc gccaacaccc gctgacgcgc cctgacgggc ttgtctgctc ccggcatccg     2100
cttacagaca agctgtgacc gtctccggga gctgcatgtg tcagaggttt tcaccgtcat     2160
caccgaaacg cgcgagacga aagggcctcg tgatacgcct atttttatag gttaatgtca     2220
tgataataat ggtttcttag acgtcaggtg gcacttttcg gggaaatgtg cgcggaaccc     2280
ctatttgttt attttctaa atacattcaa atatgtatcc gctcatgaga caataaccct      2340
gataaatgct tcaataatat tgaaaaagga agagtatgag tattcaacat ttccgtgtcg     2400
cccttattcc cttttttgcg gcattttgcc ttcctgtttt tgctcaccca gaaacgctgg     2460
tgaaagtaaa agatgctgaa gatcagttgg gtgcacgagt gggttacatc gaactggatc     2520
tcaacagcgg taagatcctt gagagttttc gccccgaaga acgttttcca atgatgagca     2580
cttttaaagt tctgctatgt ggcgcggtat tatcccgtat tgacgccggg caagagcaac     2640
tcggtcgccg catacactat tctcagaatg acttggttga gtactcacca gtcacagaaa     2700
agcatcttac ggatggcatg acagtaagag aattatgcag tgctgccata accatgagtg     2760
ataacactgc ggccaactta cttctgacaa cgatcggagg accgaaggag ctaaccgctt     2820
ttttgcacaa catgggggat catgtaactc gccttgatcg ttgggaaccg gagctgaatg     2880
aagccatacc aaacgacgag cgtgacacca cgatgcctgt agcaatggca acaacgttgc     2940
gcaaactatt aactggcgaa ctacttactc tagcttcccg gcaacaatta atagactgga     3000
tggaggcgga taaagttgca ggaccacttc tgcgctcggc ccttccggct ggctggttta     3060
ttgctgataa atctggagcc ggtgagcgtg ggtctcgcgg tatcattgca gcactggggc     3120
cagatggtaa gccctcccgt atcgtagtta tctacacgac ggggagtcag gcaactatgg     3180
atgaacgaaa tagacagatc gctgagatag gtgcctcact gattaagcat tggtaactgt     3240
cagaccaagt ttactcatat atactttaga ttgatttaaa acttcatttt taatttaaaa     3300
ggatctaggt gaagatcctt tttgataatc tcatgaccaa aatcccttaa cgtgagtttt     3360
cgttccactg agcgtcagac cccgtagaaa agatcaaagg atcttcttga gatcctttt     3420
ttctgcgcgt aatctgctgc ttgcaaacaa aaaaaccacc gctaccagcg gtggtttgtt     3480
tgccggatca agagctacca actctttttc cgaaggtaac tggcttcagc agagcgcaga     3540
taccaaatac tgtccttcta gtgtagccgt agttaggcca ccacttcaag aactctgtag     3600
caccgcctac atacctcgct ctgctaatcc tgttaccagt ggctgctgcc agtggcgata     3660
agtcgtgtct taccgggttg gactcaagac gatagttacc ggataaggcg cagcggtcgg     3720
```

```
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccaggggaa    3900
acgcctggta tctttatagt cctgtcgggt ttcgccacct ctgacttgag cgtcgatttt   3960
tgtgatgctc gtcaggggg cggagcctat ggaaaaacgc cagcaacgcg ccttttttac    4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat tcgacctgc aggcatgcaa gcttgcatgc    4440
ctgcaggtcg acgctcgcgc gacttggttt gccattcttt agcgcgcgtc gcgtcacaca   4500
gcttggccac aatgtggttt ttgtcaaacg aagattctat gacgtgttta agtttaggt    4560
cgagtaaagc gcaaatcttt tttaaccccta gaaagatagt ctgcgtaaaa ttgacgcatg   4620
cattcttgaa atattgctct ctcttctaa atagcgcgaa tccgtcgctg tgcatttagg    4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatatttc ttgttataga tatcgtgact aatatataat aaaatgggta    4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagacga acaaaatgtt attgaacaac caggttcttc attggcttct aacagaatct   5160
tgaccttgcc acagaggact attagaggta agaataaaca ttgttggtca acttcaaagt   5220
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tcccccataa aaagttttcg caatgccttt attttttgtt gcaaatctct ctttattctg   5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
```

```
taggtataat gttatcaagc tcctcgagtt aacgttacgt taacgttaac gttcgaggtc    6180
gactctagaa ctacccaccg tactcgtcaa ttccaagggc atcggtaaac atctgctcaa    6240
actcgaagtc ggccatatcc agagcgccgt aggggcgga gtcgtggggg gtaaatcccg     6300
gacccgggga atccccgtcc cccaacatgt ccagatcgaa atcgtctagc gcgtcggcat    6360
gcgccatcgc cacgtcctcg ccgtctaagt ggagctcgtc ccccaggctg acatcggtcg    6420 gggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag    6540
acccgtaatt gttttcgta cgcgcgcggc tgtacgcggg gcccgagccc gactcgcatt     6600
tcagttgctt ttccaatccg cagataatca gctccaagcc gaacaggaat gccggctcgg    6660
ctccttgatg atcgaacagc tcgattgcct gacgcagcag tggggcatc gaatcggttg     6720 ttggggtctc gcgctcctct tttgcgactt gatgctcttg gtcctccagc acgcagccca    6780
gggtaaagtg accgacggcg ctcagagcgt agagagcatt ttccaggctg aagccttgct    6840
ggcacaggaa cgcgagctgg ttctccagtg tctcgtattg cttttcggtc gggcgcgtgc    6900
cgagatggac tttggcaccg tctcggtggg acagcagagc gcagcggaac gacttggcgt    6960
tattgcggag gaagtcctgc caggactcgc cttccaacgg gcaaaaatgc gtgtggtggc    7020
ggtcgagcat ctcgatggcc agggcatcca gcagcgcccg cttattcttc acgtgccagt    7080
agagggtggg ctgctccacg cccagcttct gcgccaactt gcgggtcgtc agtccctcaa    7140
tgccaacttc gttcaacagc tccaacgcgg agttgatgac tttggactta tccaggcggc    7200
tgcccatggt ggtttctaaa ggtgttataa atcaaattag ttttgttttt tcttgaaaac    7260
tttgcgtttc ctttgatcaa cttaccgcca gggtaccgca gattgtttag cttgttcagc    7320
tgcgcttgtt tatttgctta gctttcgctt agcgacgtgt tcactttgct tgtttgaatt    7380
gaattgtcgc tccgtagacg aagcgcctct atttatactc cggcgctcgt tttcgagttt    7440
accactccct atcagtgata gagaaaagtg aaagtcgagt ttaccactcc ctatcagtga    7500
tagagaaaag tgaaagtcga gtttaccact ccctatcagt gatagagaaa agtgaaagtc    7560
gagtttacca ctccctatca gtgatagaga aagtgaaag tcgagtttac cactccctat     7620
cagtgataga gaaagtgaa agtcgagttt accactccct atcagtgata gagaaaagtg     7680
aaagtcgagt ttaccactcc ctatcagtga tagagaaaag tgaaagtcga aacctggcgc    7740
gcctcttaat taactcgcgt taagatacat tgatgagttt ggacaaacca caactagaat    7800
gcagtgaaaa aaatgcttta tttgtgaaat ttgtgatgct attgctttat ttgtaaccat    7860
tataagctgc aataaacaag ttaacaacaa caattgcatt cattttatgt ttcaggttca    7920 ggggaggtg tggaggttt tttaaagcaa gtaaaacctc tacaaatgtg gtatggctga     7980
ttatgatcag ttatctagat ccggtggatc ttacgggtcc tccaccttcc gcttttctt    8040 gggtcgagat ctcaggaaca ggtggtggcg ccctcggtg cgctcgtact gctccacgat     8100
ggtgtagtcc tcgttgtggg aggtgatgtc cagcttggcg tccacgtagt agtagccggg    8160
cagctgcacg ggcttcttgg ccatgtagat ggacttgaac tccaccaggt agtggccgcc    8220
gtccttcagc ttcagggcct tgtgggtctc gcccttcagc acgccgtcgc gggggtacag    8280
gcgctcggtg gaggcctccc agcccatggt cttcttctgc atcacggggc cgtcggaggg    8340
gaagttcacg ccgatgaact tcaccttgta gatgaagcag ccgtcctgca gggaggagtc    8400
ctgggtcacg gtcgccacgc cgccgtcctc gaagttcatc acgcgctccc acttgaagcc    8460
```

```
ctcggggaag gacagcttct tgtagtcggg gatgtcggcg gggtgcttca cgtacacctt    8520
ggagccgtac tggaactggg gggacaggat gtcccaggcg aagggcaggg ggccgccctt    8580
ggtcaccttc agcttcacgg tgttgtggcc ctcgtagggg cggccctcgc cctcgccctc    8640
gatctcgaac tcgtggccgt tcacggtgcc ctccatgcgc accttgaagc gcatgaactc    8700
ggtgatgacg ttctcggagg aggccatggt ggcgaccggt ttgcgcttct tcttgggtgg    8760
ggtgggatct cccatggtgg cctgaatctc aacttgcacc tgaaggtagt gcagcaagga    8820
tgagcaaaag ggaagaaccc agaaaagaac gggaaaactt accccaatta gaattgcttg    8880
tcgccgccag tgtcaacttg caactgaaac aatatccaac atgaacgtca atttatactg    8940
ccctaatggc gaacacgata acaatatttc ttttattatg ccctctaaaa ccaacgcggt    9000
tatcgtttat ttattcaaat tagatataga acatccgccg acatacaatg ttaatgcaaa    9060
aacgcgtttg gtgagcggat acgaaaacag tcggccgata acattaatc tgaggtcgat     9120 aacaccgtcc ttgaacggaa cacgaggagc gtacgtgatc agctgcattc gcgcgccgcg    9180
cctttatcga gatttatttg catacaacaa gtacactgcg ccgttgggat ttgtggtaac    9240
gcgcacacat gcagagctgc aagtgtggca cattttgtct gtgcgcaaaa cctttgaagc    9300
caaaagtacg aggtccgtta cgggcatgct agcgcacacg gacaatggac ccgacaaatt    9360
ctacgccaag gatttaatga taatgtcggg caacgtatcc gttcatttta tcaataacct    9420
acaaaaatgt cgcgcgcatc acaaagacat cgatatattt aaacatttat gtcccgaact    9480
gcaaatcgat aatagtgttg tgcaacctcg agcgtccgtt tgatttaacg tatagcttgc    9540
aaatgaatta tttaattatc aatcatgttt tacgcgtaga attctacccg taaagcgagt    9600
ttagttatga gccatgtgca aacatgaca tcagctttta tttttataac aaatgacatc      9660
atttcttgat tgtgttttac acgtagaatt ctactcgtaa agcgagttca gttttgaaaa    9720
acaaatgaca tcatcttttt gattgtgctt tacaagtaga attctacccg taaatcaagt    9780
tcggttttga aaaacaaatg agtcatattg tatgatatca tattgcaaaa caaatgactc    9840
atcaatcgat cgtgcgttac acgtagaatt ctactcgtaa agcgagttta tgagccgtgt    9900
gcaaaacatg acatcatctc gatttgaaaa acaaatgaca tcatccactg atcgtgcatt    9960
acaagtagaa ttctactcgt aaagccagtt cggttatgag ccgtgtacaa acatgacat    10020 cagattatga ctcatacttg attgtgtttt acgcgtagaa ttctactcgt aaagccagtt    10080
caattttaaa aacaaatgac atcatccaaa ttaataaatg acaagcaatg ggtaccatgc    10140
```

<210> SEQ ID NO 21
<211> LENGTH: 10522
<212> TYPE: DNA
<213> ORGANISM: Artificial Sequence
<220> FEATURE:
<223> OTHER INFORMATION: Synthetic construct, plasmid pLA1124

<400> SEQUENCE: 21

```
gtggtttttg tcaaacgaag attctatgac gtgtttaaag tttaggtcga gtaaagcgca      60 aatcttttt aaccctagaa agatagtctg cgtaaaattg acgcatgcat tcttgaaata     120
ttgctctctc tttctaaata gcgcgaatcc gtcgctgtgc atttaggaca tctcagtcgc    180
cgcttggagc tcccgtgagg cgtgcttgtc aatgcggtaa gtgtcactga ttttgaacta    240
taacgaccgc gtgagtcaaa atgacgcatg attatcttt acgtgacttt taagatttaa     300
ctcatacgat aattatattg ttatttcatg ttctacttac gtgataactt attatatata    360
tattttcttg ttatagatat cgtgactaat atataataaa atgggtagtt ctttagacga    420
```

```
tgagcatatc ctctctgctc ttctgcaaag cgatgacgag cttgttggtg aggattctga   480
cagtgaaata tcagatcacg taagtgaaga tgacgtccag agcgatacag aagaagcgtt   540
tatagatgag gtacatgaag tgcagccaac gtcaagcggt agtgaaatat tagacgaaca   600
aaatgttatt gaacaaccag gttcttcatt ggcttctaac agaatcttga ccttgccaca   660
gaggactatt agaggtaaga ataaacattg ttggtcaact tcaaagtcca cgaggcgtag   720
ccgagtctct gcactgaaca ttgtcagatc ggcccgggcg ccgttttttct tgaaatattg   780
ctctctcttt ctaaatagcg cgaatccgtc gctgtgcatt taggacatct cagtcgccgc   840
ttggagctcc caaacgcgcc agtggtagta cacagtactg tgggtgttca gtttgaaatc   900
ctcttgcttc tccattgtct cggttacctt tggtcaaatc catgggttct attgcctata   960
tactcttgcg attaccagtg attgcgctat tagctattag atggattgtt ggccaaactt  1020
gtcgcttaag tggctgggaa ttgtaaccgt aggcccgagt gtaatgatcc cccataaaaa  1080
gttttcgcaa tgcctttatt ttttgttgca aatctctctt tattctgcgg tattcttcat  1140
tattgcgggg atggggaaag tgtttatata gaagcaactt acgattgaac ccaaatgcac  1200
ctgacaagca aggtcaaagg gccagatttt taaatatatt atttagtctt aggactctct  1260
atttgcaatt aaattacttt gctacctgag ggttaaatct tccccattga taataataat  1320
tccactatat gttcaattgg gtttcaccgc gcttagttac atgacgagcc ctaatgagcc  1380
gtcggtggtc tataaactgt gccttacaaa tacttgcaac tcttctcgtt ttgaagtcag  1440
cagagttatt gctaattgct aattgctaat tgcttttaac tgatttcttc gaaattggtg  1500
ctatgtttat ggcgctatta acaagtatga atgtcaggtt taaccagggg atgcttaatt  1560
gtgttctcaa cttcaaaggc agaaatgttt actcttgacc atgggtttag gtataatgtt  1620
atcaagctcc tcgagttaac gttacgttaa cgttaacgtt cgaggtcgac tctagaacta  1680
cccaccgtac tcgtcaattc caagggcatc ggtaaacatc tgctcaaact cgaagtcggc  1740
catatccaga gcgccgtagg gggcggagtc gtgggggta aatcccggac ccggggaatc  1800
cccgtccccc aacatgtcca gatcgaaatc gtctagcgcg tcggcatgcg ccatcgccac  1860
gtcctcgccg tctaagtgga gctcgtcccc caggctgaca tcggtcgggg gggccgtcga  1920
cagtctgcgc gtgtgtcccg cggggagaaa ggacaggcgc ggagccgcca gccccgcctc  1980
ttcggggcg tcgtcgtccg ggagatcgag caggccctcg atggtagacc cgtaattgtt  2040
tttcgtacgc gcgcggctgt acgcggggcc cgagcccgac tcgcatttca gttgcttttc  2100
caatccgcag ataatcagct ccaagccgaa caggaatgcc ggctcggctc cttgatgatc  2160
gaacagctcg attgcctgac gcagcagtgg gggcatcgaa tcggttgttg ggtctcgcg   2220
ctcctctttt gcgacttgat gctcttggtc ctccagcacg cagcccaggg taaagtgacc  2280
gacggcgctc agagcgtaga gagcattttc caggctgaag ccttgctggc acaggaacgc  2340
gagctggttc tccagtgtct cgtattgctt ttcggtcggg cgcgtgccga gatgggacttt  2400
ggcaccgtct cggtgggaca gcagagcgca gcggaacgac ttggcgttat tgcggaggaa  2460
gtcctgccag gactcgcctt ccaacgggca aaaatgcgtg tggtggcggt cgagcatctc  2520
gatgccaggg gcatccagca gcgcccgctt attcttcacg tgccagtaga gggtgggctg  2580
ctccacgccc agcttctgcg ccaacttgcg ggtcgtcagt ccctcaatgc caacttcgtt  2640
caacagctcc aacgcggagt tgatgacttt ggacttatcc aggcggctgc ccatggtggt  2700
ttctaaaggt gttataaatc aaattagttt tgttttttct tgaaaacttt gcgtttcctt  2760
```

```
tgatcaactt accgccaggg taccgcagat tgtttagctt gttcagctgc gcttgtttat    2820
ttgcttagct ttcgcttagc gacgtgttca ctttgcttgt ttgaattgaa ttgtcgctcc    2880
gtagacgaag cgcctctatt tatactccgg cgctcgtttt cgagtttacc actccctatc    2940
agtgatagag aaaagtgaaa gtcgagttta ccactcccta tcagtgatag agaaaagtga    3000
aagtcgagtt taccactccc tatcagtgat agagaaaagt gaaagtcgag tttaccactc    3060
cctatcagtg atagagaaaa gtgaaagtcg agtttaccac tccctatcag tgatagagaa    3120
aagtgaaagt cgagtttacc actccctatc agtgatagag aaaagtgaaa gtcgagttta    3180
ccactcccta tcagtgatag agaaaagtga agtcgaaac ctggcgcgcc ccggccatcg     3240
agaaagagag agagaagaga agagagagaa cattcgagaa agagagagag aagagaagag    3300
agagaacata ctccctatca gtgatagaga agtccctatc agtgatagag atgtccctat    3360
cagtgataga gagttcccta tcagtgatag agacgtccct atcagtgata gagaagtccc    3420
tatcagtgat agagagatcc ctatcagtga tagagatttc cctatcagtg atagagaggt    3480
ccctatcagt gatagagact tccctatcag tgatagagaa atccctatca gtgatagaga    3540
catccctatc agtgatagag aactccctat cagtgataga gacctcccta tcagtgatag    3600
agatcgatgc ggccgcatgg tacccattgc ttgtcattta ttaatttgga tgatgtcatt    3660
tgtttttaaa attgaactgg ctttacgagt agaattctac gcgtaaaaca caatcaagta    3720
tgagtcataa tctgatgtca tgttttgtac acggctcata accgaactgg ctttacgagt    3780
agaattctac ttgtaatgca cgatcagtgg atgatgtcat tgttttttca aatcgagatg    3840
atgtcatgtt ttgcacacgg ctcataaact cgctttacga gtagaattct acgtgtaacg    3900
cacgatcgat tgatgagtca tttgttttgc aatatgatat catacaatat gactcatttg    3960
tttttcaaaa ccgaacttga tttacgggta gaattctact tgtaaagcac aatcaaaaag    4020
atgatgtcat ttgttttttca aaactgaact cgctttacga gtagaattct acgtgtaaaa    4080
cacaatcaag aaatgatgtc atttgttata aaaataaaag ctgatgtcat gttttgcaca    4140
tggctcataa ctaaactcgc tttacgggta gaattctacg cgtaaaacat gattgataat    4200
taaataattc atttgcaagc tatacgttaa atcaaacgga cgctcgaggt tgcacaacac    4260
tattatcgat ttgcagttcg ggacataaat gtttaaatat atcgatgtct tgtgatgcg    4320
cgcgacattt tgtaggtta ttgataaaat gaacggatac gttgcccgac attatcatta    4380
aatccttggc gtagaatttg tcgggtccat tgtccgtgtg cgctagcatg cccgtaacgg    4440
acctcgtact tttggcttca aaggttttgc gcacagacaa aatgtgccac acttgcagct    4500
ctgcatgtgt gcgcgttacc acaaatccca acggcgcagt gtacttgttg tatgcaaata    4560
aatctcgata aaggcgcggc gcgcgaatgc agctgatcac gtacgctcct cgtgttccgt    4620
tcaaggacgg tgttatcgac ctcagattaa tgtttatcgg ccgactgttt tcgtatccgc    4680
tcaccaaacg cgttttttgca ttaacattgt atgtcggcgg atgttctata tctaatttga    4740
ataaataaac gataaccgcg ttggttttag agggcataat aaaagaaata ttgttatcgt    4800
gttcgccatt agggcagtat aaattgacgt tcatgttgga tattgtttca gttgcaagtt    4860
gacactggcg gcgacaagca attctaattg gggtaagttt tcccgttctt ttctgggttc    4920
ttcccttttg ctcatccttg ctgcactacc ttcaggtgca agttgagatt caggccacca    4980
tgggagatcc caccccaccc aagaagaagc gcaaaccggt cgccaccatg gcctcctccg    5040
agaacgtcat caccgagttc atgcgcttca aggtgcgcat ggagggcacc gtgaacggcc    5100
acgagttcga gatcgagggc gagggcgagg gccgccccta cgagggccac aacaccgtga    5160
```

```
agctgaaggt gaccaagggc ggcccnctgc ccttcgcctg ggacatcctg tccccccagt   5220
tccagtacgg ctccaaggtg tacgtgaagc accccgccga catccccgac acaagaagc    5280
tgtccttccc cgagggcttc aagtgggagc gcgtgatgaa cttcgaggac ggcggcgtgg   5340
cgaccgtgac ccaggactcc tccctgcagg acggctgctt catctacaag gtgaagttca   5400
tcggcgtgaa cttcccctcc gacggccccg tgatgcagaa gaagaccatg ggctgggagg   5460
cctccaccga gcgcctgtac ccccgcgacg gcgtgctgaa gggcgagacc cacaaggccc   5520
tgaagctgaa ggacggcggc cactacctgg tggagttcaa gtccatctac atggccaaga   5580
agcccgtgca gctgcccggc tactactacg tggacgccaa gctggacatc acctcccaca   5640
acgaggacta caccatcgtg gagcagtacg agcgcaccga gggccgccac cacctgttcc   5700
tgagatctcg acccaagaaa aagcggaagg tggaggaccc gtaagatcca ccggatctag   5760
ataactgatc ataatcagcc ataccacatt tgtagaggtt ttacttgctt taaaaaacct   5820
cccacacctc cccctgaacc tgaaacataa aatgaatgca attgttgttg ttaacttgtt   5880
tattgcagct tataatggtt acaaataaag caatagcatc acaaatttca caaataaagc   5940
atttttttca ctgcattcta gttgtggttt gtccaaactc atcaatgtat cttaacgcga   6000
gttaattaag gccgctcatt taaatctggc cggccgcaac cattgtggga accgtgcgat   6060
caaacaaacg cgagataccg gaagtactga aaaacagtcg ctccaggcca gtgggaacat   6120
cgatgttttg ttttgacgga ccccttactc tcgtctcata taaaccgaag ccagctaaga   6180
tggtatactt attatcatct tgtgatgagg atgcttctat caacgaaagt accggtaaac   6240
cgcaaatggt tatgtattat aatcaaacta aaggcggagt ggacacgcta gaccaaatgt   6300
gttctgtgat gacctgcagt aggaagacga ataggtggcc tatggcatta ttgtacggaa   6360
tgataaacat tgcctgcata aattctttta ttatatacag ccataatgtc agtagcaagg   6420
gagaaaaggt ccaaagtcgc aaaaaattta tgagaaaccct ttacatgagc ctgacgtcat   6480
cgtttatgcg taagcgttta aagctcctta ctttgaagag atatttgcgc gataatatct   6540
ctaatatttt gccaaatgaa gtgcctggta catcagatga cagtactgaa gagccagtaa   6600
tgaaaaaacg tacttactgt acttactgcc cctctaaaat aaggcgaaag gcaaatgcat   6660
cgtgcaaaaa atgcaaaaaa gttatttgtc gagagcataa tattgatatg tgccaaagtt   6720
gtttctgact gactaataag tataatttgt ttctattatg tataagttaa gctaattact   6780
tattttataa tacaacatga ctgttttaa agtacaaat aagtttattt ttgtaaaga    6840
gagaatgttt aaaagttttg ttactttata gaagaaattt tgagttttg ttttttttta    6900
ataaataaat aaacataaat aaattgtttg ttgaatttat tattagtatg taagtgtaaa   6960
tataataaaa cttaatatct attcaaatta ataaataaac ctcgatatac agaccgataa   7020
aacacatgcg tcaattttac gcatgattat ctttaacgta cgtcacaata tgattatctt   7080
tctagggtta aataatagtt tctaatttt tattattca gcctgctgtc gtgaataccg    7140
tatatctcaa cgctgtctgt gagattgtcg tattctagcc ttttttagttt ttcgctcatc   7200
gacttgatat tgtccgacac attttcgtcg atttgcgttt tgatcaaaga cttgagcaga   7260
gacacgttaa tcaactgttc aaattgatcc atattaacga tatcaacccg atgcgtatat   7320
ggtgcgtaaa atatattttt taaccctctt atactttgca ctctgcgtta atacgcgttc   7380
gtgtacagac gtaatcatgt tttcttttt ggataaaact cctactgagt ttgacctcat    7440
attagaccct cacaagttgc aaaacgtggc attttttacc aatgaagaat ttaaagttat   7500
```

```
tttaaaaaat ttcatcacag atttaaagaa gaaccaaaaa ttaaattatt tcaacagttt    7560
aatcgaccag ttaatcaacg tgtcacagaa cgcgtcggca aaaaacacgc agcccgacgt    7620
gttggctaaa attattaaat caacttgtgt tatagtcacg gatttgccgt ccaacgtgtt    7680
cctcaaaaag ttgaagacca acaagtttac ggacactatt aattatttga ttttgcccca    7740
cttcattttg tgggatcaca atttgttat atttaaaca aagcttggca ctggccgtcg    7800
ttttacaacg tcgtgactgg gaaaaccctg gcgttaccca acttaatcgc cttgcagcac    7860 atccccctt cgccagctgg cgtaatagcg aagaggcccg caccgatcgc ccttcccaac     7920
agttgcgcag cctgaatggc gaatggcgcc tgatgcggta ttttctcctt acgcatctgt    7980
gcggtatttc acaccgcata tggtgcactc tcagtacaat ctgctctgat gccgcatagt    8040
taagccagcc ccgacacccg ccaacacccg ctgacgcgcc ctgacgggct tgtctgctcc    8100
cggcatccgc ttacagacaa gctgtgaccg tctccgggag ctgcatgtgt cagaggtttt    8160
caccgtcatc accgaaacgc gcgagacgaa agggcctcgt gatacgccta ttttttatagg    8220 ttaatgtcat gataataatg gtttcttaga cgtcaggtgg cacttttcgg ggaaatgtgc    8280
gcggaacccc tatttgttta ttttctaaa tacattcaaa tatgtatccg ctcatgagac    8340
aataaccctg ataaatgctt caataatatt gaaaaggaa gagtatgagt attcaacatt    8400
tccgtgtcgc ccttattccc ttttttgcgg catttgcct tcctgttttt gctcacccag    8460
aaacgctggt gaaagtaaaa gatgctgaag atcagttggg tgcacgagtg ggttacatcg    8520
aactggatct caacagcggt aagatccttg agagttttcg ccccgaagaa cgttttccaa    8580
tgatgagcac ttttaaagtt ctgctatgtg gcgcggtatt atcccgtatt gacgccgggc    8640
aagagcaact cggtcgccgc atacactatt ctcagaatga cttggttgag tactcaccag    8700
tcacagaaaa gcatcttacg gatggcatga cagtaagaga attatgcagt gctgccataa    8760
ccatgagtga taacactgcg gccaacttac ttctgacaac gatcggagga ccgaaggagc    8820
taaccgcttt tttgcacaac atgggggatc atgtaactcg ccttgatcgt tgggaaccgg    8880
agctgaatga agccatacca aacgacgagc gtgacaccac gatgcctgta gcaatggcaa    8940
caacgttgcg caaactatta actggcgaac tacttactct agcttcccgg caacaattaa    9000
tagactggat ggaggcggat aaagttgcag gaccacttct gcgctcggcc cttccggctg    9060
gctggtttat tgctgataaa tctggagccg gtgagcgtgg gtctcgcggt atcattgcag    9120
cactggggcc agatggtaag ccctcccgta tcgtagttat ctacacgacg gggagtcagg    9180
caactatgga tgaacgaaat agacagatcg ctgagatagg tgcctcactg attaagcatt    9240
ggtaactgtc agaccaagtt tactcatata ctttagat tgatttaaaa cttcattttt    9300
aatttaaaag gatctaggtg aagatccttt ttgataatct catgaccaaa atcccttaac    9360
gtgagttttc gttccactga gcgtcagacc ccgtagaaaa gatcaaagga tcttcttgag    9420
atcctttttt tctgcgcgta atctgctgct tgcaaacaaa aaaaccaccg ctaccagcgg    9480
tggtttgttt gccggatcaa gagctaccaa ctctttttcc gaaggtaact ggcttcagca    9540
gagcgcagat accaaatact gtccttctag tgtagccgta gttaggccac cacttcaaga    9600
actctgtagc accgcctaca tacctcgctc tgctaatcct gttaccagtg gctgctgcca    9660
gtggcgataa gtcgtgtctt accgggttgg actcaagacg atagttaccg gataaggcgc    9720
agcggtcggg ctgaacgggg gttcgtgca cacagcccag cttggagcga acgacctaca    9780
ccgaactgag atacctacag cgtgagcatt gagaaagcgc cacgcttccc gaagggagaa    9840
aggcggacag gtatccggta agcggcaggg tcggaacagg agagcgcacg agggagcttc    9900
```

```
cagggggaaa cgcctggtat ctttatagtc ctgtcgggtt tcgccacctc tgacttgagc    9960
gtcgattttt gtgatgctcg tcagggggc ggagcctatg gaaaaacgcc agcaacgcgg   10020 ccttttacg gttcctggcc ttttgctggc cttttgctca catgttcttt cctgcgttat   10080
cccctgattc tgtggataac cgtattaccg cctttgagtg agctgatacc gctcgccgca   10140
gccgaacgac cgagcgcagc gagtcagtga gcgaggaagc ggaagagcgc ccaatacgca   10200
aaccgcctct ccccgcgcgt tggccgattc attaatgcag ctggcacgac aggtttcccg   10260
actggaaagc gggcagtgag cgcaacgcaa ttaatgtgag ttagctcact cattaggcac   10320
cccaggcttt acactttatg cttccggctc gtatgttgtg tggaattgtg agcggataac   10380
aatttcacac aggaaacagc tatgaccatg attacgaatt cgacctgca ggcatgcaag   10440 cttgcatgcc tgcaggtcga cgctcgcgcg acttggtttg ccattcttta gcgcgcgtcg   10500
cgtcacacag cttggccaca at                                            10522
```

<210> SEQ ID NO 22
<211> LENGTH: 11867
<212> TYPE: DNA
<213> ORGANISM: Artificial Sequence
<220> FEATURE:
<223> OTHER INFORMATION: Synthetic construct, plasmid pLA1188

<400> SEQUENCE: 22

```
gtggttttg tcaaacgaag attctatgac gtgtttaaag tttaggtcga gtaaagcgca      60
aatctttttt aaccctagaa agatagtctg cgtaaaattg acgcatgcat tcttgaaata    120
ttgctctctc tttctaaata gcgcgaatcc gtcgctgtgc atttaggaca tctcagtcgc    180
cgcttggagc tcccgtgagg cgtgcttgtc aatgcggtaa gtgtcactga ttttgaacta    240
taacgaccgc gtgagtcaaa atgacgcatg attatctttt acgtgacttt taagatttaa    300
ctcatacgat aattatattg ttatttcatg ttctacttac gtgataactt attatatata    360
tattttcttg ttatagatat cgtgactaat atataataaa atgggtagtt ctttagacga    420
tgagcatatc ctctctgctc ttctgcaaag cgatgacgag cttgttggtg aggattctga    480
cagtgaaata tcagatcacg taagtgaaga tgacgtccag agcgatacag aagaagcgtt    540
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg ccgttttttct tgaaatattg    780 ctctctcttt ctaaatagcg cgaatccgtc gctgtgcatt taggacatct cagtcgccgc    840
ttggagctcc caaacgcgcc agtggtagta cacagtactg tgggtgttca gtttgaaatc    900
ctcttgcttc tccattgtct cggttacctt tggtcaaatc catgggttct attgcctata    960
tactcttgcg attaccagtg attgcgctat tagctattag atggattgtt ggccaaactt   1020
gtcgcttaag tggctgggaa ttgtaaccgt aggcccgagt gtaatgatcc cccataaaaa   1080
gttttcgcaa tgcctttatt ttttgttgca aatctctctt tattctgcgg tattcttcat   1140
tattgcgggg atggggaaag tgtttatata gaagcaactt acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
```

```
gtcggtggtc tataaactgt gccttacaaa tacttgcaac tcttctcgtt ttgaagtcag    1440
cagagttatt gctaattgct aattgctaat tgcttttaac tgatttcttc gaaattggtg    1500
ctatgtttat ggcgctatta caagtatga atgtcaggtt taaccagggg atgcttaatt     1560
gtgttctcaa cttcaaaggc agaaatgttt actcttgacc atgggtttag gtataatgtt    1620
atcaagctcc tcgagttaac gttacgttaa cgttaacgtt cgaggtcgac tctagaacta    1680
cccaccgtac tcgtcaattc caagggcatc ggtaaacatc tgctcaaact cgaagtcggc    1740
catatccaga gcgccgtagg gggcggagtc gtgggggta aatcccggac ccggggaatc     1800
cccgtccccc aacatgtcca gatcgaaatc gtctagcgcg tcggcatgcg ccatcgccac    1860
gtcctcgccg tctaagtgga gctcgtcccc caggctgaca tcggtcgggg gggccgtcga    1920
cagtctgcgc gtgtgtcccg cggggagaaa ggacaggcgc ggagccgcca gccccgcctc    1980 ttcggggcg tcgtcgtccg ggagatcgag caggccctcg atggtagacc cgtaattgtt     2040
tttcgtacgc gcgcggctgt acgcggggcc cgagcccgac tcgcatttca gttgcttttc    2100
caatccgcag ataatcagct ccaagccgaa caggaatgcc ggctcggctc cttgatgatc    2160
gaacagctcg attgcctgac gcagcagtgg gggcatcgaa tcggttgttg gggtctcgcg    2220
ctcctctttt gcgacttgat gctcttggtc tccagcacg cagcccaggg taaagtgacc     2280
gacggcgctc agagcgtaga gagcattttc caggctgaag ccttgctggc acaggaacgc    2340
gagctggttc tccagtgtct cgtattgctt ttcggtcggg cgcgtgccga gatggacttt    2400
ggcaccgtct cggtgggaca gcagagcgca gcggaacgac ttggcgttat tgcggaggaa    2460
gtcctgccag gactcgcctt ccaacgggca aaaatgcgtg tggtggcggt cgagcatctc    2520
gatggccagg gcatccagca gcgcccgctt attcttcacc tatagatacc atagatgtat    2580
ggattagtat catatacata caaaggctat ttttgggaca tattaatatt aacaatttcc    2640
gtgatagttt tcaccatttt tgttgaatgt tacgttgaaa atttaaattt gttttaaatt    2700
aattttacca gtcatgtgtt cttaaaagtt tttatgattg aaacggcata agtggttca    2760 aaaatttatc aagaaaggct ttccttttt aaatcttatc tttttctctt aaaaatcact     2820
agtcaattca ttattaattt gttaacttga atttggaatg tctatttact ttcagataaa    2880
ttaaagcaag aaacttaata ttcgaaaaaa attgattcta aatggaattt cacttgatct    2940
tcatgtatgc atatcaattt ttatttcat tgtataataa gtttcgagtt gattgttgta     3000
atccacaggt gtcccagaga attaaattcc aaattaccca agtttattga atgttgattg    3060
tagtttcagt tgctttgttg ctgcaacaat ggcttgttga ttgtagatat tttcccttc     3120 cttggtttac ttattacata gactgaaaaa gaggtttact tttttgatac ttatgaaaaa    3180
tttctattag tgattactaa ccaatcgcta tatgttact agaaaacaaa taaactcttt     3240
acattaacat tcaataatgt ttgctctgta accgacaatt gaaggcgtta cagcaacagt    3300
aatataacta gcttcttaac cctcatctat taacccatc gtttaaaaca ctatgttaaa     3360
tggtctaaca aatctagata ctaatagatg tcttattact tagcagccac agctgcaaca    3420
tccaagacaa tttttgaaac ttcttattga gctcttggca gcagaaatgt tggtattttt    3480
cacagctttc tgaaagaccg gcaccttcct ccggttcccg tttctgaatt caagaggatt    3540
tccgaccccc aattaatccc gaaacaaata aggtatattc aaaatgatgg aaaagtcatg    3600
gctgctgacc ttatttttat tcctattgat agaatattat tcccctttta aatcactgt     3660 actaagaggt ccggctataa ttttactcac ttgtcgatta tcccatagaa tgttgattgt    3720
agttggttgc ttttccaggt gagagttgat caagtcacaa aagttagcgt gtgttgattg    3780
```

```
tagatttgaa ggtaaaataa tttttgcacc cattcatcgg gtaaaacgtt ctccatagaa      3840
tacatttcca tcgataattg ataacttatg aatttcaaag aaaaaaatat gcttttaaaa      3900
ttacgtgcca gtagagggtg ggctgctcca cgcccagctt ctgcgccaac ttgcgggtcg      3960
tcagtccctc aatgccaact tcgttcaaca gctccaacgc ggagttgatg actttggact      4020
tatccaggcg gctgcccatg gtggtttcta aaggtgttat aaatcaaatt agttttgttt      4080
tttcttgaaa actttgcgtt tcctttgatc aacttaccgc cagggtaccg cagattgttt      4140
agcttgttca gctgcgcttg tttatttgct tagctttcgc ttagcgacgt gttcactttg      4200
cttgtttgaa ttgaattgtc gctccgtaga cgaagcgcct ctatttatac tccggcgctc      4260
gttttcgagt ttaccactcc ctatcagtga tagagaaaag tgaaagtcga gtttaccact      4320
ccctatcagt gatagagaaa agtgaaagtc gagtttacca ctccctatca gtgatagaga      4380
aaagtgaaag tcgagtttac cactccctat cagtgataga gaaaagtgaa agtcgagttt      4440
accactccct atcagtgata gagaaaagtg aaagtcgagt ttaccactcc ctatcagtga      4500
tagagaaaag tgaaagtcga gtttaccact ccctatcagt gatagagaaa agtgaaagtc      4560
gaaacctggc gcgccccggc catcgagaaa gagagagaga agagaagaga gagaacattc      4620
gagaaagaga gagagaagag aagagagaga acatactccc tatcagtgat agagaagtcc      4680
ctatcagtga tagagatgtc cctatcagtg atagagagtt ccctatcagt gatagagacg      4740
tccctatcag tgatagagaa gtccctatca gtgatagaga gatccctatc agtgatagag      4800
atttccctat cagtgataga gaggtcccta tcagtgatag agacttccct atcagtgata      4860
gagaaatccc tatcagtgat agagacatcc ctatcagtga tagagaactc cctatcagtg      4920
atagagacct ccctatcagt gatagagatc gatgcggccg catggtaccc attgcttgtc      4980
atttattaat ttggatgatg tcatttgttt ttaaaattga actggcttta cgagtagaat      5040
tctacgcgta aaacacaatc aagtatgagt cataatctga tgtcatgttt tgtacacggc      5100
tcataaccga actggcttta cgagtagaat tctacttgta atgcacgatc agtggatgat      5160
gtcatttgtt tttcaaatcg agatgatgtc atgttttgca cacggctcat aaactcgctt      5220
tacgagtaga attctacgtg taacgcacga tcgattgatg agtcatttgt tttgcaatat      5280
gatatcatac aatatgactc atttgttttt caaaaccgaa cttgatttac gggtagaatt      5340
ctacttgtaa agcacaatca aaagatgat gtcatttgtt tttcaaaact gaactcgctt      5400
tacgagtaga attctacgtg taaaacacaa tcaagaaatg atgtcatttg ttataaaaat      5460
aaaagctgat gtcatgtttt gcacatggct cataactaaa ctcgctttac gggtagaatt      5520
ctacgcgtaa aacatgattg ataattaaat aattcatttg caagctatac gttaaatcaa      5580
acggacgctc gaggttgcac aacactatta tcgatttgca gttcgggaca taaatgttta      5640
aatatatcga tgtctttgtg atgcgcgcga cattttgta ggttattgat aaaatgaacg      5700
gatacgttgc ccgacattat cattaaatcc ttggcgtaga atttgtcggg tccattgtcc      5760
gtgtgcgcta gcatgcccgt aacggacctc gtacttttgg cttcaaaggt tttgcgcaca      5820
gacaaaatgt gccacacttg cagctctgca tgtgtgcgcg ttaccacaaa tcccaacggc      5880
gcagtgtact tgttgtatgc aaataaatct cgataaaggc gcggcgcgcg aatgcagctg      5940
atcacgtacg ctcctcgtgt tccgttcaag gacggtgtta tcgacctcag attaatgttt      6000
atcggccgac tgttttcgta tccgctcacc aaacgcgttt ttgcattaac attgtatgtc      6060
ggcggatgtt ctatatctaa tttgaataaa taaacgataa ccgcgttggt tttagagggc      6120
```

```
ataataaaag aaatattgtt atcgtgttcg ccattagggc agtataaatt gacgttcatg   6180
ttggatattg tttcagttgc aagttgacac tggcggcgac aagcaattct aattggggta   6240
agttttcccg ttcttttctg ggttcttccc ttttgctcat ccttgctgca ctaccttcag   6300
gtgcaagttg agattcaggc caccatggga gatcccaccc cacccaagaa gaagcgcaaa   6360
ccggtcgcca ccatggcctc ctccgagaac gtcatcaccg agttcatgcg cttcaaggtg   6420
cgcatggagg gcaccgtgaa cggccacgag ttcgagatcg agggcgaggg cgagggccgc   6480
ccctacgagg gccacaacac cgtgaagctg aaggtgacca agggcggccc cctgcccttc   6540
gcctgggaca tcctgtcccc ccagttccag tacggctcca aggtgtacgt gaagcacccc   6600
gccgacatcc ccgactacaa gaagctgtcc ttccccgagg gcttcaagtg ggagcgcgtg   6660
atgaacttcg aggacggcgg cgtggcgacc gtgacccagg actcctccct gcaggacggc   6720
tgcttcatct acaaggtgaa gttcatcggc gtgaacttcc cctccgacgg ccccgtgatg   6780
cagaagaaga ccatgggctg ggaggcctcc accgagcgcc tgtaccccg cgacggcgtg   6840
ctgaagggcg agacccacaa ggccctgaag ctgaaggacg gcggcactac cctggtggag   6900
ttcaagtcca tctacatggc caagaagccc gtgcagctgc ccggctacta ctacgtggac   6960
gccagctgg acatcaccct ccacaacgag gactacacca tcgtggagca gtacgagcgc   7020
accgagggcc gccaccacct gttcctgaga tctcgaccca agaaaaagcg gaaggtggag   7080
gacccgtaag atccaccgga tctagataac tgatcataat cagccatacc acatttgtag   7140
aggttttact tgctttaaaa aacctcccac acctccccct gaacctgaaa cataaaatga   7200
atgcaattgt tgttgttaac ttgtttattg cagcttataa tggttacaaa taagcaata   7260
gcatcacaaa tttcacaaat aaagcatttt tttcactgca ttctagttgt ggtttgtcca   7320
aactcatcaa tgtatcttaa cgcgagttaa ttaaggccgc tcatttaaat ctggccggcc   7380
gcaaccattg tgggaaccgt gcgatcaaac aaacgcgaga taccggaagt actgaaaaac   7440
agtcgctcca ggcagtggg aacatcgatg ttttgttttg acggacccct tactctcgtc   7500
tcatataaac cgaagccagc taagatggta tacttattat catcttgtga tgaggatgct   7560
tctatcaacg aaagtaccgg taaaccgcaa atggttatgt attataatca aactaaaggc   7620
ggagtggaca cgctagacca aatgtgttct gtgatgacct gcagtaggaa gacgaatagg   7680
tggcctatgg cattattgta cggaatgata acattgcct gcataaattc ttttattata   7740
tacagccata atgtcagtag caagggagaa aaggtccaaa gtcgcaaaaa atttatgaga   7800
aacctttaca tgagcctgac gtcatcgttt atgcgtaagc gtttagaagc tcctactttg   7860
aagagatatt tgcgcgataa tatctctaat attttgccaa atgaagtgcc tggtacatca   7920
gatgacagta ctgaagagcc agtaatgaaa aaacgtactt actgtactta ctgcccctct   7980
aaaataaggc gaaaggcaaa tgcatcgtgc aaaaaatgca aaaagttat tgtcgagag   8040
cataatattg atatgtgcca agttgtttc tgactgacta ataagtataa tttgtttcta   8100
ttatgtataa gttaagctaa ttacttattt tataatacaa catgactgtt tttaaagtac   8160
aaaataagtt tattttgta aaagagagaa tgtttaaaag ttttgttact ttatagaaga   8220
aattttgagt tttgtttttt tttaataaa taaataaaca taaataaatt gtttgttgaa   8280
tttattatta gtatgtaagt gtaaatataa taaaacttaa tatctattca aattaataaa   8340
taaacctcga tatacagacc gataaaacac atgcgtcaat tttacgcatg attatcttta   8400
acgtacgtca caatatgatt atctttctag ggttaaataa tagttctaa tttttttatt   8460
attcagcctg ctgtcgtgaa taccgtatat ctcaacgctg tctgtgagat tgtcgtattc   8520
```

```
tagccttttt agttttcgc tcatcgactt gatattgtcc gacacatttt cgtcgatttg   8580
cgttttgatc aaagacttga gcagagacac gttaatcaac tgttcaaatt gatccatatt   8640
aacgatatca acccgatgcg tatatggtgc gtaaaatata ttttttaacc ctcttatact   8700
ttgcactctg cgttaatacg cgttcgtgta cagacgtaat catgttttct tttttggata   8760
aaactcctac tgagtttgac ctcatattag accctcacaa gttgcaaaac gtggcatttt   8820
ttaccaatga agaatttaaa gttattttaa aaaatttcat cacagattta aagaagaacc   8880
aaaaattaaa ttatttcaac agtttaatcg accagttaat caacgtgtac acagacgcgt   8940
cggcaaaaaa cacgcagccc gacgtgttgg ctaaaattat taaatcaact tgtgttatag   9000
tcacggattt gccgtccaac gtgttcctca aaaagttgaa gaccaacaag tttacggaca   9060
ctattaatta tttgattttg ccccacttca ttttgtggga tcacaatttt gttatatttt   9120
aaacaaagct tggcactggc cgtcgtttta caacgtcgtg actgggaaaa ccctggcgtt   9180
acccaactta atcgccttgc agcacatccc cctttcgcca gctggcgtaa tagcgaagag   9240
gcccgcaccg atcgcccttc ccaacagttg cgcagcctga atggcgaatg cgcctgatg    9300 cggtattttc tccttacgca tctgtgcggt atttcacacc gcatatggtg cactctcagt   9360
acaatctgct ctgatgccgc atagttaagc cagccccgac acccgccaac acccgctgac   9420
gcgccctgac gggcttgtct gctcccggca tccgcttaca gacaagctgt gaccgtctcc   9480
gggagctgca tgtgtcagag gttttcaccg tcatcaccga aacgcgcgag acgaaagggc   9540
ctcgtgatac gcctattttt ataggttaat gtcatgataa taatggtttc ttagacgtca   9600
ggtggcactt ttcggggaaa tgtgcgcgga acccctattt gtttattttt ctaaatacat   9660
tcaaatatgt atccgctcat gagacaataa ccctgataaa tgcttcaata atattgaaaa   9720
aggaagagta tgagtattca acatttccgt gtcgccctta ttcccttttt tgcggcattt   9780
tgccttcctg ttttgctca cccagaaacg ctggtgaaag taaaagatgc tgaagatcag   9840
ttgggtgcac gagtgggtta catcgaactg gatctcaaca gcggtaagat ccttgagagt   9900
tttcgccccg aagaacgttt tccaatgatg agcactttta aagttctgct atgtggcgcg   9960
gtattatccc gtattgacgc cgggcaagag caactcggtc gccgcataca ctattctcag  10020
aatgacttgg ttgagtactc accagtcaca gaaaagcatc ttacggatgg catgacagta  10080
agagaattat gcagtgctgc cataaccatg agtgataaca ctgcggccaa cttacttctg  10140
acaacgatcg aggaccgaa ggagctaacc gcttttttgc acaacatggg ggatcatgta   10200
actcgccttg atcgttggga accggagctg aatgaagcca taccaaacga cgagcgtgac  10260
accacgatgc ctgtagcaat ggcaacaacg ttgcgcaaac tattaactgg cgaactactt  10320
actctagctt cccggcaaca attaatagac tggatggagg cggataaagt tgcaggacca  10380
cttctgcgct cggcccttcc ggctggctgg tttattgctg ataaatctgg agccggtgag  10440
cgtgggtctc gcggtatcat tgcagcactg gggccagatg gtaagccctc ccgtatcgta  10500
gttatctaca cgacggggag tcaggcaact atggatgaac gaaatagaca gatcgctgag  10560
ataggtgcct cactgattaa gcattggtaa ctgtcagacc aagtttactc atatatactt  10620
tagattgatt taaaacttca tttttaattt aaaaggatct aggtgaagat cctttttgat  10680
aatctcatga ccaaaatccc ttaacgtgag ttttcgttcc actgagcgtc agaccccgta  10740
gaaaagatca aaggatcttc ttgagatcct ttttttctgc gcgtaatctg ctgcttgcaa  10800
acaaaaaaac caccgctacc agcggtggtt tgtttgccgg atcaagagct accaactctt  10860
```

```
tttccgaagg taactggctt cagcagagcg cagataccaa atactgtcct tctagtgtag   10920
ccgtagttag gccaccactt caagaactct gtagcaccgc ctacatacct cgctctgcta   10980
atcctgttac cagtggctgc tgccagtggc gataagtcgt gtcttaccgg gttggactca   11040
agacgatagt taccggataa ggcgcagcgg tcgggctgaa cggggggttc gtgcacacag   11100
cccagcttgg agcgaacgac ctacaccgaa ctgagatacc tacagcgtga gcattgagaa   11160
agcgccacgc ttcccgaagg gagaaaggcg gacaggtatc cggtaagcgg cagggtcgga   11220
acaggagagc gcacgaggga gcttccaggg ggaaacgcct ggtatcttta tagtcctgtc   11280
gggtttcgcc acctctgact tgagcgtcga ttttgtgat gctcgtcagg ggggcggagc   11340
ctatggaaaa acgccagcaa cgcggccttt ttacggttcc tggccttttg ctggcctttt   11400
gctcacatgt tctttcctgc gttatcccct gattctgtgg ataaccgtat taccgccttt   11460
gagtgagctg ataccgctcg ccgcagccga acgaccgagc gcagcgagtc agtgagcgag   11520
gaagcggaag agcgcccaat acgcaaaccg cctctccccg cgcgttggcc gattcattaa   11580
tgcagctggc acgacaggtt tcccgactgg aaagcgggca gtgagcgcaa cgcaattaat   11640
gtgagttagc tcactcatta ggcaccccag gctttacact ttatgcttcc ggctcgtatg   11700
ttgtgtggaa ttgtgagcgg ataacaattt cacacaggaa acagctatga ccatgattac   11760
gaatttcgac ctgcaggcat gcaagcttgc atgcctgcag gtcgacgctc gcgcgacttg   11820
gtttgccatt ctttagcgcg cgtcgcgtca cacagcttgg ccacaat             11867
```

<210> SEQ ID NO 23
<211> LENGTH: 10786
<212> TYPE: DNA
<213> ORGANISM: Artificial Sequence
<220> FEATURE:
<223> OTHER INFORMATION: Synthetic construct, plasmid pLA670

<400> SEQUENCE: 23

```
ggccgctcat ttaaatctgg ccggccgcaa ccattgtggg aaccgtgcga tcaaacaaac     60
gcgagatacc ggaagtactg aaaaacagtc gctccaggcc agtgggaaca tcgatgtttt    120
gttttgacgg accccttact ctcgtctcat ataaaccgaa gccagctaag atggtatact    180
tattatcatc ttgtgatgag gatgcttcta tcaacgaaag taccggtaaa ccgcaaatgg    240
ttatgtatta taatcaaact aaaggcggag tggacacgct agaccaaatg tgttctgtga    300
tgacctgcag taggaagacg aataggtggc ctatggcatt attgtacgga atgataaaca    360
ttgcctgcat aaattctttt attatataca gccataatgt cagtagcaag ggagaaaagg    420
tccaaagtcg caaaaaattt atgagaaacc tttacatgag cctgacgtca tcgtttatgc    480
gtaagcgttt agaagctcct actttgaaga gatatttgcg cgataatatc tctaatattt    540
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttatttttata    780
atacaacatg actgttttta aagtacaaaa taagtttatt tttgtaaaag agagaatgtt    840
taaaagtttt gttactttat agaagaaatt ttgagttttt gttttttttt aataaataaa    900
taaacataaa taaattgttt gttgaattta ttattagtat gtaagtgtaa atataataaa    960
acttaatatc tattccaaatt aataaataaa cctcgtata cagaccgata aaacacatgc   1020
gtcaatttta cgcatgatta tctttaacgt acgtcacaat atgattatct ttctagggtt   1080
```

```
aaataatagt ttctaattttt tttattattc agcctgctgt cgtgaatacc gtatatctca    1140
acgctgtctg tgagattgtc gtattctagc cttttagtt tttcgctcat cgacttgata    1200
ttgtccgaca cattttcgtc gatttgcgtt ttgatcaaag acttgagcag agacacgtta    1260
atcaactgtt caaattgatc catattaacg atatcaaccc gatgcgtata tggtgcgtaa    1320
aatatatttt ttaaccctct tatactttgc actctgcgtt aatacgcgtt cgtgtacaga    1380
cgtaatcatg ttttcttttt tggataaaac tcctactgag tttgacctca tattagaccc    1440
tcacaagttg caaaacgtgg cattttttac caatgaagaa tttaaagtta ttttaaaaaa    1500
tttcatcaca gatttaaaga agaaccaaaa attaaattat ttcaacagtt taatcgacca    1560
gttaatcaac gtgtacacag acgcgtcggc aaaaaacacg cagcccgacg tgttggctaa    1620
aattattaaa tcaacttgtg ttatagtcac ggatttgccg tccaacgtgt tcctcaaaaa    1680
gttgaagacc aacaagttta cggacactat taattatttg attttgcccc acttcatttt    1740
gtgggatcac aattttgtta tattttaaac aaagcttggc actggccgtc gttttacaac    1800
gtcgtgactg ggaaaaccct ggcgttaccc aacttaatcg ccttgcagca catccccctt    1860
tcgccagctg gcgtaatagc gaagaggccc gcaccgatcg cccttcccaa cagttgcgca    1920
gcctgaatgg cgaatggcgc ctgatgcggt attttctcct tacgcatctg tgcggtattt    1980
cacaccgcat atggtgcact ctcagtacaa tctgctctga tgccgcatag ttaagccagc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgagacga agggcctcg tgatacgcct atttttatag gttaatgtca    2220
tgataataat ggtttcttag acgtcaggtg gcacttttcg gggaaatgtg cgcggaaccc    2280
ctatttgttt atttttctaa atacattcaa atatgtatcc gctcatgaga caataaccct    2340
gataaatgct tcaataatat tgaaaaagga agagtatgag tattcaacat ttccgtgtcg    2400
cccttattcc cttttttgcg gcattttgcc ttcctgtttt tgctcaccca gaaacgctgg    2460
tgaaagtaaa agatgctgaa gatcagttgg gtgcacgagt gggttacatc gaactggatc    2520
tcaacagcgg taagatcctt gagagttttc gccccgaaga acgttttcca atgatgagca    2580
cttttaaagt tctgctatgt ggcgcggtat tatcccgtat tgacgccggg caagagcaac    2640
tcggtcgccg catacactat tctcagaatg acttggttga gtactcacca gtcacagaaa    2700
agcatcttac ggatggcatg acagtaagag aattatgcag tgctgccata accatgagtg    2760
ataacactgc ggccaactta cttctgacaa cgatcggagg accgaaggag ctaaccgctt    2820
ttttgcacaa catgggggat catgtaactc gccttgatcg ttgggaaccg gagctgaatg    2880
aagccatacc aaacgacgag cgtgacacca cgatgcctgt agcaatggca acaacgttgc    2940
gcaaactatt aactggcgaa ctacttactc tagcttcccg gcaacaatta atagactgga    3000
tggaggcgga taaagttgca ggaccacttc tgcgctcggc ccttccggct ggctggttta    3060
ttgctgataa atctggagcc ggtgagcgtg ggtctcgcgg tatcattgca gcactggggc    3120
cagatggtaa gccctcccgt atcgtagtta tctacacgac ggggagtcag gcaactatgg    3180
atgaacgaaa tagacagatc gctgagatag gtgcctcact gattaagcat tggtaactgt    3240
cagaccaagt ttactcatat atactttaga ttgatttaaa acttcatttt taatttaaaa    3300
ggatctaggt gaagatcctt tttgataatc tcatgaccaa aatcccttaa cgtgagtttt    3360
cgttccactg agcgtcagac cccgtagaaa agatcaaagg atcttcttga gatccttttt    3420
```

```
ttctgcgcgt aatctgctgc ttgcaaacaa aaaaaccacc gctaccagcg gtggtttgtt    3480
tgccggatca agagctacca actctttttc cgaaggtaac tggcttcagc agagcgcaga    3540
taccaaatac tgtccttcta gtgtagccgt agttaggcca ccacttcaag aactctgtag    3600
caccgcctac atacctcgct ctgctaatcc tgttaccagt ggctgctgcc agtggcgata    3660
agtcgtgtct taccgggttg gactcaagac gatagttacc ggataaggcg cagcggtcgg    3720
gctgaacggg gggttcgtgc acacagccca gcttggagcg aacgacctac accgaactga    3780
gataccacta gcgtgagcat tgagaaagcg ccacgcttcc cgaagggaga aggcggaca    3840 ggtatccggt aagcggcagg gtcggaacag gagagcgcac gagggagctt ccaggggaa    3900 acgcctggta tctttatagt cctgtcgggt ttcgccacct ctgacttgag cgtcgatttt    3960
tgtgatgctc gtcagggggg cggagcctat ggaaaaacgc cagcaacgcg cctttttac    4020 ggttcctggc cttttgctgg ccttttgctc acatgttctt cctgcgtta tcccctgatt    4080 ctgtggataa ccgtattacc gcctttgagt gagctgatac cgctcgccgc agccgaacga    4140
ccgagcgcag cgagtcagtg agcgaggaag cggaagagcg cccaatacgc aaaccgcctc    4200
tccccgcgcg ttggccgatt cattaatgca gctggcacga caggtttccc gactggaaag    4260
cgggcagtga gcgcaacgca attaatgtga gttagctcac tcattaggca ccccaggctt    4320
tacactttat gcttccggct cgtatgttgt gtggaattgt gagcggataa caatttcaca    4380
caggaaacag ctatgaccat gattacgaat ttcgacctgc aggcatgcaa gcttgcatgc    4440
ctgcaggtcg acgctcgcgc gacttggttt gccattcttt agcgcgcgtc gcgtcacaca    4500
gcttggccac aatgtggttt ttgtcaaacg aagattctat gacgtgttta agtttaggt    4560 cgagtaaagc gcaaatcttt tttaaccctaa gaaagatagt ctgcgtaaaa ttgacgcatg    4620
cattcttgaa atattgctct ctcttttctaa atagcgcgaa tccgtcgctg tgcatttagg    4680
acatctcagt cgccgcttgg agctcccgtg aggcgtgctt gtcaatgcgg taagtgtcac    4740
tgattttgaa ctataacgac cgcgtgagtc aaaatgacgc atgattatct tttacgtgac    4800
ttttaagatt taactcatac gataattata ttgttatttc atgttctact tacgtgataa    4860
cttattatat atatatttc ttgttataga tatcgtgact aatatataat aaaatgggta    4920
gttctttaga cgatgagcat atcctctctg ctcttctgca aagcgatgac gagcttgttg    4980
gtgaggattc tgacagtgaa atatcagatc acgtaagtga agatgacgtc cagagcgata    5040
cagaagaagc gtttatagat gaggtacatg aagtgcagcc aacgtcaagc ggtagtgaaa    5100
tattagacga acaaaatgtt attgaacaac caggttcttc attggcttct aacagaatct    5160
tgaccttgcc acagaggact attagaggta agaataaaca ttgttggtca acttcaaagt    5220
ccacgaggcg tagccgagtc tctgcactga acattgtcag atcggcccgg gcgccgtttt    5280
tcttgaaata ttgctctctc tttctaaata gcgcgaatcc gtcgctgtgc atttaggaca    5340
tctcagtcgc cgcttggagc tcccaaacgc gccagtggta gtacacagta ctgtgggtgt    5400
tcagtttgaa atcctcttgc ttctccattg tctcggttac ctttggtcaa atccatgggt    5460
tctattgcct atatactctt gcgattacca gtgattgcgc tattagctat tagatggatt    5520
gttggccaaa cttgtcgctt aagtggctgg gaattgtaac cgtaggcccg agtgtaatga    5580
tcccccataa aaagttttcg caatgccttt attttttgtt gcaaatctct ctttattctg    5640
cggtattctt cattattgcg gggatgggga aagtgtttat atagaagcaa cttacgattg    5700
aacccaaatg cacctgacaa gcaaggtcaa agggccagat ttttaaatat attatttagt    5760
cttaggactc tctatttgca attaaattac tttgctacct gagggttaaa tcttccccat    5820
```

```
tgataataat aattccacta tatgttcaat tgggtttcac cgcgcttagt tacatgacga    5880
gccctaatga gccgtcggtg gtctataaac tgtgccttac aaatacttgc aactcttctc    5940
gttttgaagt cagcagagtt attgctaatt gctaattgct aattgctttt aactgatttc    6000
ttcgaaattg gtgctatgtt tatggcgcta ttaacaagta tgaatgtcag gtttaaccag    6060
gggatgctta attgtgttct caacttcaaa ggcagaaatg tttactcttg accatgggtt    6120
taggtataat gttatcaagc tcctcgagtt aacgttacgt taacgttaac gttcgaggtc    6180
gactctagaa ctacccaccg tactcgtcaa ttccagggc atcggtaaac atctgctcaa     6240
actcgaagtc ggccatatcc agagcgccgt aggggggcgga gtcgtggggg gtaaatcccg    6300
gacccgggga atccccgtcc cccaacatgt ccagatcgaa atcgtctagc gcgtcggcat    6360
gcgccatcgc cacgtcctcg ccgtctaagt ggagctcgtc ccccaggctg acatcggtcg    6420 gggggggccgt cgacagtctg cgcgtgtgtc ccgcggggag aaaggacagg cgcggagccg    6480
ccagccccgc ctcttcgggg gcgtcgtcgt ccggagatc gagcaggccc tcgatggtag     6540
acccgtaatt gttttcgta cgcgcgcggc tgtacgcggg gcccgagccc gactcgcatt     6600
tcagttgctt ttccaatccg cagataatca gctccaagcc gaacaggaat gccggctcgg    6660
ctccttgatg atcgaacagc tcgattgcct gacgcagcag tgggggcatc gaatcggttg    6720
ttggggtctc gcgctcctct tttgcgactt gatgctcttg gtcctccagc acgcagccca    6780
gggtaaagtg accgacggcg ctcagagcgt agagagcatt ttccaggctg aagccttgct    6840
ggcacaggaa cgcgagctgg ttctccagtg tctcgtattg cttttcggtc gggcgcgtgc    6900
cgagatggac tttggcaccg tctcggtggg acagcagagc gcagcggaac gacttggcgt    6960
tattgcggag gaagtcctgc caggactcgc cttccaacgg gcaaaaatgc gtgtggtggc    7020
ggtcgagcat ctcgatggcc agggcatcca gcagcgcccg cttattcttc acgtgccagt    7080
agagggtggg ctgctccacg cccagcttct gcgccaactt gcgggtcgtc agtccctcaa    7140
tgccaacttc gttcaacagc tccaacgcgg agttgatgac tttggactta tccaggcggc    7200
tgcccatggt ggtttctaaa ggtgttataa atcaaattag ttttgttttt tcttgaaaac    7260
tttgcgtttc ctttgatcaa cttaccgcca gggtaccgca gattgtttag cttgttcagc    7320
tgcgcttgtt tatttgctta gctttcgctt agcgacgtgt tcactttgct tgtttgaatt    7380
gaattgtcgc tccgtagacg aagcgcctct atttatactc cggcgctcgt tttcgagttt    7440
accactccct atcagtgata gagaaaagtg aaagtcgagt ttaccactcc ctatcagtga    7500
tagagaaaag tgaaagtcga gtttaccact ccctatcagt gatagagaaa agtgaaagtc    7560
gagtttacca ctccctatca gtgatagaga aagtgaaag tcgagtttac cactccctat     7620
cagtgataga gaaagtgaa agtcgagttt accactccct atcagtgata gagaaaagtg     7680
aaagtcgagt ttaccactcc ctatcagtga tagagaaaag tgaaagtcga acctggcgc     7740 gcctcttaat taactcgcgt taagatacat tgatgagttt ggacaaacca caactagaat    7800
gcagtgaaaa aaatgcttta tttgtgaaat ttgtgatgct attgctttat ttgtaaccat    7860
tataagctgc aataaacaag ttaacaacaa caattgcatt cattttatgt ttcaggttca    7920
gggggaggtg tgggaggttt tttaaagcaa gtaaaacctc tacaaatgtg gtatggctga    7980
ttatgatcag ttatctagat ccggtggatc ttacgggtcc tccaccttcc gcttttctct    8040
gggtcgagat ctcaggaaca ggtggtggcg cccctcggtg cgctcgtact gctccacgat    8100
ggtgtagtcc tcgttgtggg aggtgatgtc cagcttggcg tccacgtagt agtagccggg    8160
```

-continued

```
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctgcccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatcc ccgatctgca ttttggatta ttctgcgggt caaaatagag atgtggaaaa   8820
ttagtacgaa atcaaatgag tttcgttgaa attacaaaac tattgaaact aacttcctgg   8880
ctggggaata aaaatgggaa acttatttat cgacgccaac tttgttgaga accccctatt   8940
aaccctctac gaatattgga acaaaggaaa gcgaagaaac aggaacaaag gtagttgaga   9000
aacctgttcc gttgctcgtc atcgtttcca taatgcgagt gtgtgcatgt atatatacac   9060
agctgaaacg catgcataca cattattttg tgtgtatatg gtgacgtcac aactactaag   9120
caataagaaa ttttccagac gtggctttcg tttcaagcaa cctactctat ttcagctaaa   9180 ataagtgga tttcgttggt aaaatacttc aattaagcaa agaactaact aactaataac   9240
atgcacacaa atgctcgagt gcgttcgtga tttctcgaat tttcaaatgc gtcactgcga   9300
atttcacaat ttgccaataa atcttggcga aaatcaacac gcaagtttta tttatagatt   9360
tgtttgcgtt ttgatgccaa ttgattggga aaacaagatg cgtggctgcc aatttcttat   9420
tttgtaatta cgtagagcgt tgaataaaaa aaaaatggcc gaacaaagac cttgaaatgc   9480 agttttctt gaaattactc aacgtcttgt tgctcttatt actaattggt aacagcgagt   9540
taaaaactta cgtttcttgt gactttcgag aatgttcttt taattgtact ttaatcacca   9600
acaattaagt ataaattttt cgctgattgc gctttacttt ctgcttgtac ttgctgctgc   9660
aaatgtcaat tggttttgaa ggcgaccgtt cgcgaacgct gtttatatac cttcggtgtc   9720
cgttgaaaat cactaaaaaa taccgtagtg ttcgtaacac tttagtacag agaaaaaaaa   9780
ttgtgccgaa atgttttttga tacgtacgaa taccttgtat taaaattttt tatgatttct   9840
gtgtatcact tttttttgt gttttcgtt taaactcacc acagtacaaa acaataaaat   9900
atttttaaga caatttcaaa ttgagacctt tctcgtactg acttgaccgg ctgaatgagg   9960
atttctacct agacgaccta cttcttacca tgacattgaa tgcaatgcca cctttgatct  10020
aaacttacaa aagtccaagg cttgttagga ttggtgttta tttagtttgc ttttgaaata  10080
gcactgtctt ctctaccggc tataattttg aaactcgcag cttgactgga aatttaaaaa  10140
gtaattctgt gtaggtaaag ggtgttttaa aagtgtgatg tgttgagcgt tgcggcaacg  10200
actgctattt atgtatatat tttcaaaact tattgttttt gaagtgtttt aaatggagct  10260
atctggcaac gctgcgcata atcttacaca agcttttctt aatccatttt taagtgaaat  10320 ttgttttttac tctttcggca aataattgtt aaatcgcttt aagtgggctt acatctggat  10380
aagtaatgaa aacctgcata ttataatatt aaaacatata atccactgtg ctttccccgt  10440
gtgtggccat atacctaaaa aagttttattt tcgcagagcc ccgcacgtc acactacggt  10500 tcggcgattt tcgattttgg acagtactga ttgcaagcgc accgaaagca aaatggagct  10560
```

```
ggagattttg aacgcgaaga acagcaagcc gtacggcaag gtgaaggtgc cctccggcgc    10620
cacgcccatc ggcgatctgc gcgccctaat tcacaagacc ctgaagcaga ccccacacgc    10680
gaatcgccag tcgcttcgtc tggaactgaa gggcaaaagc ctgaaagata cggacacatt    10740
ggaatctctg tcgctgcgtt ccggcgacaa gatcggggta ccatgc                   10786

<210> SEQ ID NO 24
<211> LENGTH: 14720
<212> TYPE: DNA
<213> ORGANISM: Artificial Sequence
<220> FEATURE:
<223> OTHER INFORMATION: Synthetic construct, plasmid pLA1038

<400> SEQUENCE: 24
gggctatggc gcgccggacg cggcaagtct gcgagcttat atttacgtgg atctccggtg      60
tgtccatgat tcggcatcat atcataaacg acgaattcca ataaaaactt tgcttgttga     120
taacacctga tgttcagaga tgcccgataa aatcacagct gttctggttc acagtcacca     180
gaaataaaaa atattggaat tgagatgtac acaattaacg atatttataa atatcttccg     240
atagtctatc gtccggttaa tcaaaataaa gtgcgacgaa ttaacatatt ttcaaaatta     300
agacgctttg atagatgtat ttgtatagag atagaaatta aggttaaaat aacataaatg     360
ccaaagttta gagcactatt caataattct cttgatttca aattgaaata atacacaata     420
taacattttc taacactaca aagtcacgat attcttccac caaccgatag tatcgcacac     480
ttgccattcg cctcatcacg cacacgcccg cttcacaatt caaacgaacg gcattttatt     540
ttcacaggat cccgggagtc gtgaatgttt tacccaatat cgactttcat tgttaactga     600
ccaaaattgt aatctgttct gttagttgtc gagtgcctgt gccgcgatcg ctatgggcat     660
atgttgccaa actctaaacc aaatactcat tctgatgttt taaatgattt gccctcccat     720
atgtccttcc gagtgagaga cacaaaaaat tccaacacac tattgcaatg aaaataaatt     780
tcctttatta gccagaagtc agatgctcaa ggggcttcat gatgtcccca taattttggg     840
cagagggaaa aagatctcag tggtatttgt gagccagggc attggccaca ccagccacca     900
ccttctgata ggcagcctgc acctgaggag tgaattcttt gccaaaatga tgagacagca     960
caacaaccag cacgttgccc aggagctgta ggaaagagaa gaaggcatga acatggttag    1020 cagagggggcc cggtttggac tcagagtatt ttatcctcat ctcaaacagt gtatatcatt    1080
gtaaccataa agagaaaggc aggatgatga ccagggtgta gttgtttcta ccaataagaa    1140
tatttccacg ccagccagaa tttatatgca gaaatattct accttatcat ttaattataa    1200
caattgttct ctaaaactgt gctgaagtac aatataatat accctgattg ccttgaaaaa    1260
aaagtgatta gagaaagtac ttacaatctg acaaataaac aaaagtgaat ttaaaaattc    1320
gttacaaatg caagctaaag tttaacgaaa aagttacaga aaatgaaaag aaaataagag    1380
gagacaatgg ttgtcaacag agtagaaagt gaaagaaaca aaattatcat gagggtccat    1440
ggtgatacaa gggacatctt cccattctaa acaacaccct gaaaactttg cccctccat     1500 ataacatgaa ttttacaata gcgaaaaaga aagaacaatc aagggtcccc aaactcaccc    1560
tgaagttctc agctctagac gcgtttcact acccaccgta ctcgtcaatt ccaagggcat    1620
cggtaaacat ctgctcaaac tcgaagtcgg ccatatccag agcgccgtag ggggcggagt    1680 cgtgggggt aaatcccgga cccgggaat ccccgtcccc caacatgtcc agatcgaaat      1740
cgtctagcgc gtcggcatgc gccatcgcca cgtcctcgcc gtctaagtgg agctcgtccc    1800
```

```
ccaggctgac atcggtcggg ggggccgtcg acagtctgcg cgtgtgtccc gcggggagaa    1860
aggacaggcg cggagccgcc agccccgcct cttcggggc gtcgtcgtcc gggagatcga     1920
gcaggccctc gatggtagac ccgtaattgt ttttcgtacg cgcgcggctg tacgcggacc    1980
cactttcaca tttaagttgt ttttctaatc cgcatatgat caattcaagg ccgaataaga    2040
aggctggctc tgcaccttgg tgatcaaata attcgatagc ttgtcgtaat aatggcggca    2100
tactatcagt agtaggtgtt tcccttcctt ctttagcgac ttgatgctct tgatcttcca    2160
atacgcaacc taaagtaaaa tgccccacag cgctgagtgc atataatgca ttctctagtg    2220
aaaaaccttg ttggcataaa aaggctaatt gattttcgag agtttcatac tgtttttctg    2280
taggccgtgt acctaaatgt acttttgctc catcgcgatg acttagtaaa gcacatctaa    2340 aactttagc gttattacgt aaaaaatctt gccagctttc cccttctaaa gggcaaaagt     2400
gagtatggtg cctatctaac atctcaatgg ctaaggcgtc gagcaaagcc cgcttatttt    2460
ttacatgcca atacaatgta ggctgctcta cacctagctt ctgggcgagt ttacgggttg    2520
ttaaaccttc gattccgacc tcattaagca gctctaatgc gctgttaatc actttacttt    2580
tatctaatct caattccatg gtggcaacct gcaaggcgaa tgaataaaca agattgtggc    2640
gaacagtgta atgcgaagaa cccacctctg ctccaattcc caattcccta ttcagctcga    2700
gcggggatcc ccgggtaccg agctcgaatt cggggccgcg gaggctggat cggtcccggt    2760
gtcttctatg gaggtcaaaa cagcgtggat ggcgtctcca ggcgatctga cggttcacta    2820
aacgagctct gcttatatag gcctcccacc gtacacgcct acctcgaccc gggtaccgag    2880
ctcgactttc acttttctct atcactgata gggagtggta aactcgactt tcactttct    2940 ctatcactga tagggagtgg taaactcgac tttcactttt ctctatcact gatagggagt    3000
ggtaaactcg actttcactt ttctctatca ctgataggga gtggtaaact cgactttcac    3060
ttttctctat cactgatagg gagtggtaaa ctcgactttc acttttctct atcactgata    3120
gggagtggta aactcgactt tcacttttct ctatcactga tagggagtgg taaactcgaa    3180
atgtcgacta tgcggaccga gcgccggagt ataaatagag gcgcttcgtc tacggagcga    3240
caattcaatt caaacaagca aagtgaacac gtcgctaagc gaaagctaag caaataaaca    3300
agcgcagctg aacaagctaa acaatctgcg ctagccacca tggttgttat taaacgtaga    3360
tttggtaatt ttaaaagcat atttttttct ttgaaattca taagttatca attatcgatg    3420
gaaatgtatt ctatggagaa cgttttaccc gatgaatggg tgcaaaaatt attttacctt    3480
caaatctaca atcaacacac gctaactttt gtgacttgat caactctcac ctggaaaagc    3540
aaccaactac aatcaacatt ctatgggata atcgacaagt gagtaaaatt atagccggac    3600
ctcttagtac agtgtattta aaggggaat aatattctat caataggaat aaaaataagg    3660
tcagcagcca tgacttttcc atcatttga atataccta tttgtttcgg gattaattgg      3720
gggtcggaaa tcctcttgaa ttcagaaacg ggaaccggag gaaggtgccg gtctttcaga    3780
aagctgtgaa aaataccaac atttctgctg ccaagagctc aataagaagt ttcaaaaatt    3840
gtcttggatg ttgcagctgt ggctgctaag taataagaca tctattagta tctagatttg    3900
ttagaccatt taacatagtg ttttaaacga tggggttaat agatgagggt taagaagcta    3960
gttatattac tgttgctgta acgccttcaa ttgtcggtta cagagcaaac attattgaat    4020
gttaatgtaa agagtttatt tgttttctag taaacatata gcgattggtt agtaatcact    4080
aatagaaatt tttcataagt atcaaaaaag taaacctctt tttcagtcta tgtaataagt    4140
aaaccaagga aagggaaaat atctacaatc aacaagccat tgttgcagca acaaagcaac    4200
```

```
tgaaactaca atcaacattc aataaacttg ggtaatttgg aatttaattc tctgggacac    4260
ctgtggatta caacaatcaa ctcgaaactt attatacaat gtaaataaaa attgatatgc    4320
atacatgaag atcaagtgaa attccattta gaatcaattt ttttcgaata ttaagtttct    4380
tgctttaatt tatctgaaag taaatagaca ttccaaattc aagttaacaa attaataatg    4440
aattgactag tgattttaa gagaaaaaga taagatttaa aaaggaaag cctttcttga      4500 taaattttg aaccacttta tgccgtttca atcataaaaa cttttaagaa cacatgactg     4560
gtaaaattaa tttaaaacaa atttaaattt tcaacgtaac attcaacaaa aatggtgaaa    4620
actatcacgg aaattgttaa tattaatatg tcccaaaaat agcctttgta tgtatatgat    4680
actaatccat acatctatgg tatctatagg tgaaggctca aagcctctgg gcgctctcct    4740
gggcctgccc gaaagccaaa cggagcttga taatcttaca gaatacaaca cggcccacaa    4800
tcggcgcatc tcaatgctgg gcatcgatga tgataccaat atgcgaaagc aaaacgcctt    4860
gaaacaggga cggcgcactc gaaatgtcac atttaacgat gaggagattg tcatcaatcc    4920
tgaggatgtg gatcctaatg tgggacgctt caggaacttg gtacaaacca ctgtggtgcc    4980
cgccaagagg gctcgctgcg acgtcaacca ttagtgataa cgcgtctaga gctgagaact    5040
tcagggtgag tttggggacc cttgattgtt cttcttttt cgctattgta aaattcatgt     5100
tatatggagg gggcaaagtt tcagggtgt tgtttagaat gggaagatgt cccttgtatc     5160
accggtgatc ataatcagcc ataccacatt tgtagaggtt ttacttgctt taaaaaacct    5220
cccacacctc cccctgaacc tgaaacataa aatgaatgca attgttgttg ttaacttgtt    5280
tattgcagct tataatggtt acaaataaag caatagcatc acaaatttca caaataaagc    5340 attttttca ctgcattcta gttgtggttt gtccaaactc atcaatgtat cttaacgcga     5400
gtttaaacgc gtccgcatac gtccgctcac gttaagttcc gcagagagaa gttgttgaaa    5460
acataaacag aatcacttgt tgcactcttt gagaaaactg gggctattgc ggaaaaaacc    5520
aactaaaaat attgcaggtt aggggtacta cgctcgattg gcgtacggcc accactttg    5580 cgacttcact gttaaccgct accttcatag agacttttac ccgataaatg ttatgtagtt    5640
tgactttctc tgttaatcac aagaaaaaat attgtggaaa ttaaaattat ctcaaactca    5700
ataaggaaat aataatatat acacctatgt tttatagaag tcaacagtaa ataagttatt    5760
tggaaaacca ttgtagccgt ttaaataaat ctccttgagt gtgttttaaa taacggtcat    5820
taagtatatt acttggccct ctgaatttct tgaattacac cattttttga aataaatcaa    5880
tccaaaagac tacttttgg tggcaaatga actgcataaa aagtaacaaa agaaatatgt     5940
ttttgaaata acagtatagc tgaagtgtat taaaaatac cgtcatatga gcgacccgct     6000
gttaccgctt cgctgcgaat gacaaaacgg gctgagcaag aaaatggcgt agaaggcgac    6060
gaaaattcgt ttcactcgtg aagaaaacct cgataactga ggaatacagc tgggatttaa    6120
agagcatatt cgaactacaa gcagagatgt ttcctggtgg aaacggaaac gccgatttgg    6180
gctacaacaa gcatgcccac gtccatggac ttggacaaca tggccatggg cacaaccata    6240
atcacaatca gttcctgcgc agcccccacc acccccacca catttttcac tgccctccgg    6300
gggcggtcag ggcatggtga cgcccatggt agccgccggc ctgccgctcg ccatgcaggg    6360
tggcgttggc atcgattggc gcagctcgcc cagcaatgga ttaattaact cgcgttaaga    6420
tacattgatg agtttggaca aaccacaact agaatgcagt gaaaaaaatg ctttatttgt    6480
gaaatttgtg atgctattgc tttatttgta accattataa gctgcaataa acaagttaac    6540
```

| | |
|---|---|
| aacaacaatt gcattcattt tatgtttcag gttcagggg aggtgtggga ggttttttaa | 6600 |
| agcaagtaaa acctctacaa atgtggtatg gctgattatg atcagttatc tagatccggt | 6660 |
| ggatcttacg ggtcctccac cttccgcttt tcttgggtc gagatctcag gaacaggtgg | 6720 |
| tggcggccct cggtgcgctc gtactgctcc acgatggtgt agtcctcgtt gtgggaggtg | 6780 |
| atgtccagct tggcgtccac gtagtagtag ccgggcagct gcacgggctt cttggccatg | 6840 |
| tagatggact tgaactccac caggtagtgg ccgccgtcct tcagcttcag ggccttgtgg | 6900 |
| gtctcgccct tcagcacgcc gtcgcggggg tacaggcgct cggtggaggc ctcccagccc | 6960 |
| atggtcttct tctgcatcac ggggccgtcg gaggggaagt tcacgccgat gaacttcacc | 7020 |
| ttgtagatga agcagccgtc ctgcagggag gagtcctggg tcacggtcgc cacgccgccg | 7080 |
| tcctcgaagt tcatcacgcg ctcccacttg aagccctcgg ggaaggacag cttcttgtag | 7140 |
| tcggggatgt cggcggggtg cttcacgtac accttggagc cgtactggaa ctgggggac | 7200 |
| aggatgtccc aggcgaaggg caggggggccg cccttggtca ccttcagctt cacggtgttg | 7260 |
| tggccctcgt aggggcggcc ctcgcccctcg ccctcgatct cgaactcgtg gccgttcacg | 7320 |
| gtgccctcca tgcgcaccct gaagcgcatg aactcggtga tgacgttctc ggaggaggcc | 7380 |
| atggtggcga ccggtttgcg cttcttcttg ggtggggtgg gatccccgat ctgcattttg | 7440 |
| gattattctg cgggtcaaaa tagagatgtg gaaaattagt acgaaatcaa atgagtttcg | 7500 |
| ttgaaattac aaaactattg aaactaactt cctggctggg gaataaaaat gggaaactta | 7560 |
| tttatcgacg ccaactttgt tgagaaaccc ctattaaccc tctacgaata ttggaacaaa | 7620 |
| ggaaagcgaa gaaacaggaa caaaggtagt tgagaaacct gttccgttgc tcgtcatcgt | 7680 |
| tttcataatg cgagtgtgtg catgtatata tacacagctg aaacgcatgc atacacatta | 7740 |
| ttttgtgtgt atatggtgac gtcacaacta ctaagcaata agaaattttc cagacgtggc | 7800 |
| tttcgttttca agcaacctac tctatttcag ctaaaaataa gtggatttcg ttggtaaaat | 7860 |
| acttcaatta agcaaagaac taactaacta ataacatgca cacaaatgct cgagtgcgtt | 7920 |
| cgtgatttct cgaattttca aatgcgtcac tgcgaatttc acaatttgcc aataaatctt | 7980 |
| ggcgaaaatc aacacgcaag ttttatttat agatttgttt gcgttttgat gccaattgat | 8040 |
| tgggaaaaca agatgcgtgg ctgccaattt cttattttgt aattacgtag agcgttgaat | 8100 |
| aaaaaaaaaa tggccgaaca aagaccttga aatgcagttt tcttgaaat tactcaacgt | 8160 |
| cttgttgctc ttattactaa ttggtaacag cgagttaaaa acttacgttt cttgtgactt | 8220 |
| tcgagaatgt tcttttaatt gtactttaat caccaacaat taagtataaa tttttcgctg | 8280 |
| attgcgcttt actttctgct tgtacttgct gctgcaaatg tcaattggtt ttgaaggcga | 8340 |
| ccgttcgcga acgctgttta tataccttcg gtgtccgttg aaaatcacta aaaaataccg | 8400 |
| tagtgttcgt aacactttag tacagagaaa aaaaattgtg ccgaaatgtt tttgatacgt | 8460 |
| acgaatacct tgtattaaaa tttttttatga tttctgtgta tcacttttt tttgtgtttt | 8520 |
| tcgtttaaac tcaccacagt acaaaacaat aaaatatttt taagacaatt tcaaattgag | 8580 |
| acctttctcg tactgacttg accggctgaa tgaggatttc tacctagacg acctacttct | 8640 |
| taccatgaca ttgaatgcaa tgccaccttt gatctaaact tacaaaagtc caaggcttgt | 8700 |
| taggattggt gtttatttag tttgcttttg aaatagcact gtcttctcta ccggctataa | 8760 |
| ttttgaaact cgcagcttga ctggaaattt aaaaagtaat tctgtgtagg taaagggtgt | 8820 |
| tttaaaagtg tgatgtgttg agcgttgcgg caacgactgc tatttatgta tatattttca | 8880 |
| aaacttattg ttttttgaagt gttttaaatg gagctatctg gcaacgctgc gcataatctt | 8940 |

```
acacaagctt tcttaatcc attttaagt gaaatttgtt tttactcttt cggcaaataa    9000
ttgttaaatc gctttaagtg ggcttacatc tggataagta atgaaaacct gcatattata   9060
atattaaaac atataatcca ctgtgctttc ccgtgtgtg gccatatacc taaaaaagtt    9120
tattttcgca gagccccgca cggtcacact acggttcggc gattttcgat tttggacagt   9180
actgattgca agcgcaccga aagcaaaatg gagctggaga ttttgaacgc gaagaacagc   9240
aagccgtacg gcaaggtgaa ggtgccctcc ggcgccacgc ccatcggcga tctgcgcgcc   9300
ctaattcaca agaccctgaa gcagacccca cacgcgaatc gccagtcgct tcgtctggaa   9360
ctgaagggca aaagcctgaa agatacggac acattggaat ctctgtcgct gcgttccggc   9420
gacaagatcg gggtaccatg cggccgctca tttaaatctg gccggcctgg ccgatctgac   9480
aatgttcagt gcagagactc ggctacgcct cgtggacttt gaagttgacc aacaatgttt   9540
attcttacct ctaatagtcc tctgtggcaa ggtcaagatt ctgttagaag ccaatgaaga   9600
acctggttgt tcaataacat tttgttcgtc taatatttca ctaccgcttg acgttggctg   9660
cacttcatgt acctcatcta taaacgcttc ttctgtatcg ctctggacgt catcttcact   9720
tacgtgatct gatatttcac tgtcagaatc ctcaccaaca agctcgtcat cgcttttgcag  9780
aagagcagag aggatatgct catcgtctaa agaactaccc atttattat atattagtca    9840
cgatatctat aacaagaaaa tatatatata ataagttatc acgtaagtag aacatgaaat   9900
aacaatataa ttatcgtatg agttaaatct taaaagtcac gtaaaagata atcatgcgtc   9960
attttgactc acgcggtcgt tatagttcaa aatcagtgac acttaccgca ttgacaagca   10020
cgcctcacgg gagctccaag cggcgactga gatgtcctaa atgcacagcg acggattcgc   10080
gctatttaga aagagagagc aatatttcaa gaatgcatgc gtcaatttta cgcagactat   10140
cttttctaggg ttaaaaaga tttgcgcttt actcgaccta aactttaaac acgtcataga   10200
atcttcgttt gacaaaaacc acattgtggc caagctgtgt gacgcgacgc gcgctaaaga   10260
atggcaaacc aagtcgcgcg agcgtcgacc tgcaggcatg caagcttgca tgcctgcagg   10320
tcgaaattcg taatcatggt catagctgtt tcctgtgtga aattgttatc cgctcacaat   10380
tccacacaac atacgagccg gaagcataaa gtgtaaagcc tggggtgcct aatgagtgag   10440
ctaactcaca ttaattgcgt tgcgctcact gcccgctttc cagtcgggaa acctgtcgtg   10500
ccagctgcat taatgaatcg gccaacgcgc ggggagaggc ggtttgcgta ttgggcgctc   10560
ttccgcttcc tcgctcactg actcgctgcg ctcggtcgtt cggctgcggc gagcggtatc   10620
agctcactca aaggcggtaa tacggttatc cacagaatca ggggataacg caggaaagaa   10680
catgtgagca aaaggccagc aaaaggccag gaaccgtaaa aaggccgcgt tgctggcgtt   10740
tttccatagg ctccgccccc ctgacgagca tcacaaaaat cgacgctcaa gtcagaggtg   10800
gcgaaacccg acaggactat aaagatacca ggcgtttccc cctggaagct ccctcgtgcg   10860
ctctcctgtt ccgaccctgc cgcttaccgg atacctgtcc gcctttctcc cttcgggaag   10920
cgtggcgctt tctcaatgct cacgctgtag gtatctcagt tcggtgtagg tcgttcgctc   10980
caagctgggc tgtgtgcacg aaccccccgt tcagcccgac cgctgcgcct tatccggtaa   11040
ctatcgtctt gagtccaacc cggtaagaca cgacttatcg ccactggcag cagccactgg   11100
taacaggatt agcagagcga ggtatgtagg cggtgctaca gagttcttga agtggtggcc   11160
taactacggc tacactagaa ggacagtatt tggtatctgc gctctgctga agccagttac   11220
cttcggaaaa agagttggta gctcttgatc cggcaaacaa accaccgctg gtagcggtgg   11280
```

```
tttttttgtt tgcaagcagc agattacgcg cagaaaaaaa ggatctcaag aagatccttt    11340
gatcttttct acggggtctg acgctcagtg gaacgaaaac tcacgttaag ggattttggt    11400
catgagatta tcaaaaagga tcttcaccta gatcctttta aattaaaaat gaagttttaa    11460
atcaatctaa agtatatatg agtaaacttg gtctgacagt taccaatgct taatcagtga    11520
ggcacctatc tcagcgatct gtctatttcg ttcatccata gttgcctgac tccccgtcgt    11580
gtagataact acgatacggg agggcttacc atctggcccc agtgctgcaa tgataccgcg    11640
agacccacgc tcaccggctc cagatttatc agcaataaac cagccagccg aagggccga    11700 gcgcagaagt ggtcctgcaa ctttatccgc ctccatccag tctattaatt gttgccggga    11760
agctagagta agtagttcgc cagttaatag tttgcgcaac gttgttgcca ttgctacagg    11820
catcgtggtg tcacgctcgt cgtttggtat ggcttcattc agctccggtt cccaacgatc    11880
aaggcgagtt acatgatccc ccatgttgtg caaaaaagcg gttagctcct tcggtcctcc    11940
gatcgttgtc agaagtaagt tggccgcagt gttatcactc atggttatgg cagcactgca    12000
taattctctt actgtcatgc catccgtaag atgcttttct gtgactggtg agtactcaac    12060
caagtcattc tgagaatagt gtatgcggcg accgagttgc tcttgcccgg cgtcaatacg    12120
ggataatacc gcgccacata gcagaacttt aaaagtgctc atcattggaa aacgttcttc    12180
ggggcgaaaa ctctcaagga tcttaccgct gttgagatcc agttcgatgt aacccactcg    12240
tgcacccaac tgatcttcag catcttttac tttcaccagc gtttctgggt gagcaaaaac    12300
aggaaggcaa aatgccgcaa aaaagggaat aagggcgaca cggaaatgtt gaatactcat    12360
actcttcctt tttcaatatt attgaagcat ttatcagggt tattgtctca tgagcggata    12420
catatttgaa tgtatttaga aaaataaaca ataggggtt ccgcgcacat ttccccgaaa    12480
agtgccacct gacgtctaag aaaccattat tatcatgaca ttaacctata aaaataggcg    12540
tatcacgagg ccctttcgtc tcgcgcgttt cggtgatgac ggtgaaaacc tctgacacat    12600
gcagctcccg gagacggtca cagcttgtct gtaagcggat gccgggagca gacaagcccg    12660
tcagggcgcg tcagcgggtg ttggcgggtg tcggggctgg cttaactatg cggcatcaga    12720
gcagattgta ctgagagtgc accatatatg cggtgtgaaa taccgcacag atgcgtaagg    12780
agaaaatacc gcatcaggcg ccattcgcca ttcaggctgc gcaactgttg ggaagggcga    12840
tcggtgcggg cctcttcgct attacgccag ctggcgaaag gggatgtgc tgcaaggcga    12900 ttaagttggg taacgccagg gttttcccag tcacgacgtt gtaaaacgac ggccagtgcc    12960
aagctttgtt taaatataaa caaaattgtg atcccacaaa atgaagtggg gcaaaatcaa    13020
ataattaata gtgtccgtaa acttgttggt cttcaacttt ttgaggaaca cgttggacgg    13080
caaatccgtg actataacac aagttgattt aataattttta gccaacacgt cgggctgcgt    13140
gttttttgcc gacgcgtctg tgtacacgtt gattaactgg tcgattaaac tgttgaaata    13200
atttaatttt tggttcttct ttaaatctgt gatgaaattt tttaaaataa ctttaaattc    13260
ttcattggta aaaaatgcca cgttttgcaa cttgtgaggg tctaatatga ggtcaaactc    13320
agtaggagtt ttatccaaaa aagaaaacat gattacgtct gtacacgaac gcgtattaac    13380
gcagagtgca aagtataaga gggttaaaaa atatatttta cgcaccatat acgcatcggg    13440
ttgatatcgt taatatggat caatttgaac agttgattaa cgtgtctctg ctcaagtctt    13500
tgatcaaaac gcaaatcgac gaaaatgtgt cggacaatat caagtcgatg agcgaaaaac    13560
taaaaaggct agaatacgac aatctcacag acagcgttga gatatacggt attcacgaca    13620
gcaggctgaa taataaaaaa attagaaact attatttaac cctagaaaga taatcatatt    13680
```

-continued

```
gtgacgtacg ttaaagataa tcatgcgtaa aattgacgca tgtgttttat cggtctgtat    13740
atcgaggttt atttattaat ttgaatagat attaagtttt attatattta cacttacata    13800
ctaataataa attcaacaaa caatttattt atgtttattt atttattaaa aaaaaacaaa    13860
aactcaaaat ttcttctata aagtaacaaa acttttaaac attctctctt ttacaaaaat    13920
aaacttattt tgtactttaa aaacagtcat gttgtattat aaaataagta attagcttaa    13980
cttatacata atagaaacaa attatactta ttagtcagtc agaaacaact ttggcacata    14040
tcaatattat gctctcgaca aataactttt ttgcattttt tgcacgatgc atttgccttt    14100
cgccttattt tagaggggca gtaagtacag taagtacgtt ttttcattac tggctcttca    14160
gtactgtcat ctgatgtacc aggcacttca tttggcaaaa tattagagat attatcgcgc    14220
aaatatctct tcaaagtagg agcttctaaa cgcttacgca taaacgatga cgtcaggctc    14280
atgtaaaggt ttctcataaa ttttttgcga ctttggacct tttctcccctt gctactgaca    14340 ttatggctgt atataataaa agaatttatg caggcaatgt ttatcattcc gtacaataat    14400
gccataggcc acctattcgt cttcctactg caggtcatca cagaacacat ttggtctagc    14460
gtgtccactc cgcctttagt ttgattataa tacataacca tttgcggttt accggtactt    14520
tcgttgatag aagcatcctc atcacaagat gataataagt ataccatctt agctggcttc    14580
ggtttatatg agacgagagt aagggggtccg tcaaaacaaa acatcgatgt tcccactggc    14640
ctggagcgac tgttttttcag tacttccggt atctcgcgtt tgtttgatcg cacggttccc    14700
acaatggttg cggccagccc                                               14720
```

<210> SEQ ID NO 25
<211> LENGTH: 23
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 25
catcgatgcc cagcattgag atg                                              23

<210> SEQ ID NO 26
<211> LENGTH: 34
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 26
caagcaaagt gaacacgtcg ctaagcgaaa gcta                                   34

<210> SEQ ID NO 27
<211> LENGTH: 28
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 27
gccatccacg ctgttttgac ctccatag                                          28

<210> SEQ ID NO 28
<211> LENGTH: 27

```
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 28
gccaatacaa tgtaggctgc tctacac                                          27

<210> SEQ ID NO 29
<211> LENGTH: 1005
<212> TYPE: DNA
<213> ORGANISM: Artificial Sequence
<220> FEATURE:
<223> OTHER INFORMATION: Synthetic construct, coding region of tTA from
      pUHD15-1

<400> SEQUENCE: 29
atgtctagat tagataaaag taaagtgatt aacagcgcat tagagctgct taatgaggtc        60
ggaatcgaag gtttaacaac ccgtaaactc gcccagaagc taggtgtaga gcagcctaca      120
ttgtattggc atgtaaaaaa taagcgggct ttgctcgacg ccttagccat tgagatgtta      180
gataggcacc atactcactt ttgcccttta aaggggaaa gctggcaaga ttttttacgt        240
aataacgcta aagttttag atgtgcttta ctaagtcatc gcgatggagc aaaagtacat       300
ttaggtacac ggcctacaga aaacagtat gaaactctcg aaaatcaatt agccttttta       360
tgccaacaag ttttttcact agagaatgca ttatatgcac tcagcgctgt ggggcatttt      420
actttaggtt gcgtattgga agatcaagag catcaagtcg ctaaagaaga agggaaaca       480 cctactactg atagtatgcc gccattatta cgacaagcta tcgaattatt tgatcaccaa      540
ggtgcagagc cagccttctt attcggcctt gaattgatca tatgcggatt agaaaaacaa     600
cttaaatgtg aaagtgggtc cgcgtacagc cgcgcgcgta cgaaaaacaa ttacgggtct     660
accatcgagg gcctgctcga tctcccggac gacgacgccc ccgaagaggc ggggctggcg     720
gctccgcgcc tgtcctttct ccccgcggga cacacgcgca gactgtcgac ggccccccg     780 accgatgtca gcctggggga cgagctccac ttagacggcg aggacgtggc gatggcgcat    840
gccgacgcgc tagacgattt cgatctggac atgttgggg acgggattc cccgggtccg     900 ggatttaccc ccacgactc cgcccctac ggcgctctgg atatggccga cttcgagttt     960
gagcagatgt taccgatgc ccttggaatt gacgagtacg gtggg                      1005

<210> SEQ ID NO 30
<211> LENGTH: 336
<212> TYPE: PRT
<213> ORGANISM: Artificial Sequence
<220> FEATURE:
<223> OTHER INFORMATION: Synthetic construct, tTA

<400> SEQUENCE: 30

Met Gly Ser Arg Leu Asp Lys Ser Lys Val Ile Asn Ser Ala Leu Glu
 1               5                  10                  15

Leu Leu Asn Glu Val Gly Ile Glu Gly Leu Thr Thr Arg Lys Leu Ala
                20                  25                  30

Gln Lys Leu Gly Val Glu Gln Pro Thr Leu Tyr Trp His Val Lys Asn
            35                  40                  45

Lys Arg Ala Leu Leu Asp Ala Leu Ala Ile Glu Met Leu Asp Arg His
        50                  55                  60

His Thr His Phe Cys Pro Leu Glu Gly Glu Ser Trp Gln Asp Phe Leu
65                  70                  75                  80
```

Arg Asn Asn Ala Lys Ser Phe Arg Cys Ala Leu Leu Ser His Arg Asp
                 85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 31
<211> LENGTH: 1017
<212> TYPE: DNA
<213> ORGANISM: Artificial Sequence
<220> FEATURE:
<223> OTHER INFORMATION: Synthetic construct, DNA sequence of tTAV

<400> SEQUENCE: 31
atgggcagcc gcctggataa gtccaaagtc atcaactccg cgttggagct gttgaacgaa     60
gttggcattg agggactgac gacccgcaag ttggcgcaga agctgggcgt ggagcagccc    120
accctctact ggcacgtgaa gaataagcgg gcgctgctgg atgccctggc catcgagatg    180
ctcgaccgcc accacacgca ttttgcccg ttggaaggcg agtcctggca ggacttcctc    240
cgcaataacg ccaagtcgtt ccgctgcgct ctgctgtccc accgagacgg tgccaaagtc    300
catctcggca cgcgcccgac cgaaaagcaa tacgagacac tggagaacca gctcgcgttc    360
ctgtgccagc aaggcttcag cctggaaaat gctctctacg ctctgagcgc cgtcggtcac    420
tttaccctgg gctgcgtgct ggaggaccaa gagcatcaag tcgcaaaaga ggagcgcgag    480
accccaacaa ccgattcgat gccccactg ctgcgtcagg caatcgagct gttcgatcat    540
caaggagccg agccggcatt cctgttcggc ttggagctga ttatctgcgg attggaaaag    600

```
caactgaaat gcgagtcggg ctcgggcccc gcgtacagcc gcgcgcgtac gaaaaacaat    660
tacgggtcta ccatcgaggg cctgctcgat ctcccggacg acgacgcccc cgaagaggcg    720
gggctggcgg ctccgcgcct gtcctttctc cccgcgggac acacgcgcag actgtcgacg    780
gcccccccga ccgatgtcag cctggggggac gagctccact tagacggcga ggacgtggcg    840
atggcgcatg ccgacgcgct agacgatttc gatctggaca tgttggggga cggggattcc    900
ccgggtccgg gatttacccc ccacgactcc gcccccctacg cgctctgga tatggccgac    960 ttcgagtttg agcagatgtt taccgatgcc cttggaattg acgagtacgg tgggtag     1017
```

<210> SEQ ID NO 32
<211> LENGTH: 338
<212> TYPE: PRT
<213> ORGANISM: Artificial Sequence
<220> FEATURE:
<223> OTHER INFORMATION: Synthetic construct, amino acid sequence of tTAV protein

<400> SEQUENCE: 32

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285
```

-continued

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly

<210> SEQ ID NO 33
<211> LENGTH: 4455
<212> TYPE: DNA
<213> ORGANISM: Artificial Sequence
<220> FEATURE:
<223> OTHER INFORMATION: Synthetic construct, plasmid pUHD15-1

<400> SEQUENCE: 33

```
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca tagtaacgcc aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg gaggtctat     660
ataagcagag ctcgtttagt gaaccgtcag atcgcctgga gacgccatcc acgctgtttt     720
gacctccata agagacaccg ggaccgatcc agcctccgcg gccccgaatt catatgtcta     780
gattagataa agtaaagtg attaacagcg cattagagct gcttaatgag gtcggaatcg     840
aaggtttaac aacccgtaaa ctcgcccaga gctaggtgt agagcagcct acattgtatt     900
ggcatgtaaa aaataagcgg gctttgctcg acgccttagc cattgagatg ttagataggc     960
accatactca cttttgccct ttagaagggg aaagctggca agattttta cgtaataacg    1020
ctaaaagttt tagatgtgct ttactaagtc atcgcgatgg agcaaaagta catttaggta    1080
cacggcctac agaaaaacag tatgaaactc tcgaaaatca attagccttt ttatgccaac    1140
aaggttttc actagagaat gcattatatg cactcagcgc tgtgggcat tttacttag     1200
gttgcgtatt ggaagatcaa gagcatcaag tcgctaaaga agaaagggaa acacctacta    1260
ctgatagtat gccgccatta ttacgacaag ctatcgaatt atttgatcac caaggtgcag    1320
agccagcctt cttattcggc cttgaattga tcatatgcgg attagaaaaa caacttaaat    1380
gtgaaagtgg gtccgcgtac agccgcgcgc gtacgaaaaa caattacggg tctaccatcg    1440
agggcctgct cgatctcccg gacgacgacg ccccgaaga ggcggggctg gcggctccgc    1500
gcctgtcctt tctccccgcg ggacacacgc gcagactgtc gacggccccc cgaccgatg    1560
tcagcctggg ggacgagctc cacttagacg gcgaggacgt ggcgatggcg catgccgacg    1620
cgctagcga tttcgatctg gacatgttgg gggacgggga ttccccgggt ccggatttta    1680
cccccacga ctccgccccc tacggcgctc tggatatggc cgacttcgag tttgagcaga    1740
```

```
tgtttaccga tgcccttgga attgacgagt acggtgggta gggggcgcga ggatccagac   1800
atgataagat acattgatga gtttggacaa accacaacta gaatgcagtg aaaaaaatgc   1860
tttatttgtg aaatttgtga tgctattgct ttatttgtaa ccattataag ctgcaataaa   1920
caagttaaca acaacaattg cattcatttt atgtttcagg ttcagggga ggtgtgggag    1980 gttttttaaa gcaagtaaaa cctctacaaa tgtggtatgg ctgattatga tcctgcaagc   2040
ctcgtcgtct ggccggacca cgctatctgt gcaaggtccc cggacgcgcg ctccatgagc   2100
agagcgcccg ccgccgaggc aagactcggg cggcgccctg cccgtcccac caggtcaaca   2160
ggcggtaacc ggcctcttca tcgggaatgc gcgcgacctt cagcatcgcc ggcatgtccc   2220
ctggcggacg ggaagtatca gctcgaccaa gcttggcgag atttcagga gctaaggaag    2280 ctaaaatgga gaaaaaaatc actgatata ccaccgttga tatatcccaa tggcatcgta    2340
aagaacattt tgaggcattt cagtcagttg ctcaatgtac ctataaccag accgttcagc   2400
tgcattaatg aatcggccaa cgcgcgggga gaggcggttt gcgtattggg cgctcttccg   2460
cttcctcgct cactgactcg ctgcgctcgg tcgttcggct gcggcgagcg gtatcagctc   2520
actcaaaggc ggtaatacgg ttatccacag aatcagggga taacgcagga aagaacatgt   2580
gagcaaaagg ccagcaaaag gccaggaacc gtaaaaaggc cgcgttgctg gcgttttcc    2640 ataggctccg ccccctgac gagcatcaca aaatcgacg ctcaagtcag aggtggcgaa     2700
acccgacagg actataaaga taccaggcgt ttccccctgg aagctccctc gtgcgctctc   2760
ctgttccgac cctgccgctt accggatacc tgtccgcctt ctcccttcg ggaagcgtgg    2820 cgctttctca atgctcacgc tgtaggtatc tcagttcggt gtaggtcgtt cgctccaagc   2880
tgggctgtgt gcacgaaccc cccgttcagc ccgaccgctg cgccttatcc ggtaactatc   2940
gtcttgagtc caacccggta agacacgact tatcgccact ggcagcagcc actggtaaca   3000
ggattagcag agcgaggtat gtaggcggtg ctacagagtt cttgaagtgg tggcctaact   3060
acggctacac tagaaggaca gtatttggta tctgcgctct gctgaagcca gttaccttcg   3120
gaaaaagagt tggtagctct tgatccggca acaaaccac cgctggtagc ggtggttttt    3180
ttgtttgcaa gcagcagatt acgcgcagaa aaaaaggatc tcaagaagat cctttgatct   3240
tttctacggg gtctgacgct cagtggaacg aaaactcacg ttaagggatt ttggtcatga   3300
gattatcaaa aaggatcttc acctagatcc ttttaaatta aaaatgaagt tttaaatcaa   3360
tctaaagtat atatgagtaa acttggtctg acagttacca atgcttaatc agtgaggcac   3420
ctatctcagc gatctgtcta tttcgttcat ccatagttgc ctgactcccc gtcgtgtaga   3480
taactacgat acgggagggc ttaccatctg gccccagtgc tgcaatgata ccgcgagacc   3540
cacgctcacc ggctccagat ttatcagcaa taaaccagcc agccggaagg gccgagcgca   3600
gaagtggtcc tgcaacttta tccgcctcca tccagtctat taattgttgc cgggaagcta   3660
gagtaagtag ttcgccagtt aatagtttgc gcaacgttgt tgccattgct acaggcatcg   3720
tggtgtcacg ctcgtcgttt ggtatggctt cattcagctc cggttcccaa cgatcaaggc   3780
gagttacatg atcccccatg ttgtgcaaaa aagcggttag ctccttcggt cctccgatcg   3840
ttgtcagaag taagttggcc gcagtgttat cactcatggt tatggcagca ctgcataatt   3900
ctcttactgt catgccatcc gtaagatgct tttctgtgac tggtgagtac tcaaccaagt   3960
cattctgaga atagtgtatg cggcgaccga gttgctcttg cccggcgtca atacgggata   4020
ataccgcgcc acatagcaga actttaaaag tgctcatcat tggaaaacgt tcttcggggc   4080
gaaaactctc aaggatctta ccgctgttga gatccagttc gatgtaaccc actcgtgcac   4140
```

-continued

```
ccaactgatc ttcagcatct tttactttca ccagcgtttc tgggtgagca aaaacaggaa    4200
ggcaaaatgc cgcaaaaaag ggaataaggg cgacacggaa atgttgaata ctcatactct    4260 tccttttca atattattga agcatttatc agggttattg tctcatgagc ggatacatat     4320
ttgaatgtat ttagaaaaat aaacaaatag gggttccgcg cacatttccc cgaaaagtgc    4380
cacctgacgt ctaagaaacc attattatca tgacattaac ctataaaaat aggcgtatca    4440
cgaggccctt tcgtc                                                      4455
```

<210> SEQ ID NO 34
<211> LENGTH: 1014
<212> TYPE: DNA
<213> ORGANISM: Artificial Sequence
<220> FEATURE:
<223> OTHER INFORMATION: Synthetic construct, open reading frame of tTAV construct

<400> SEQUENCE: 34

```
atgggcagcc gcctggataa gtccaaagtc atcaactccg cgttggagct gttgaacgaa     60
gttggcattg agggactgac gacccgcaag ttggcgcaga agctgggcgt ggagcagccc    120
accctctact ggcacgtgaa gaataagcgg gcgctgctgg atgccctggc catcgagatg    180
ctcgaccgcc accacacgca tttttgcccg ttggaaggcg agtcctggca ggacttcctc    240
cgcaataacg ccaagtcgtt ccgctgcgct ctgctgtccc accgagacgg tgccaaagtc    300
catctcggca cgcgcccgac cgaaaagcaa tacgagacac tggagaacca gctcgcgttc    360
ctgtgccagc aaggcttcag cctggaaaat gctctctacg ctctgagcgc cgtcggtcac    420
tttaccctgg gctgcgtgct ggaggaccaa gagcatcaag tcgcaaaaga ggagcgcgag    480
accccaacaa ccgattcgat gcccccactg ctgcgtcagg caatcgagct gttcgatcat    540
caaggagccg agccggcatt cctgttcggc ttggagctga ttatctgcgg attggaaaag    600
caactgaaat gcgagtcggg ctcgggcccc gcgtacagcc gcgcgcgtac gaaaacaat     660 tacgggtcta ccatcgaggg cctgctcgat ctcccggacg acgacgcccc cgaagaggcg    720
gggctggcgg ctccgcgcct gtcctttctc ccgcgggac acacgcgcag actgtcgacg    780 gccccccga ccgatgtcag cctgggggac gagctccact agacggcga ggacgtggcg      840 atggcgcatg ccgacgcgct agacgattc gatctggaca tgttggggga cggggattcc    900
ccgggtccgg gatttacccc ccacgactcc gccccctacg gcgctctgga tatggccgac    960
ttcgagtttg agcagatgtt taccgatgcc cttggaattg acgagtacgg tggg          1014
```

<210> SEQ ID NO 35
<211> LENGTH: 338
<212> TYPE: PRT
<213> ORGANISM: Artificial Sequence
<220> FEATURE:
<223> OTHER INFORMATION: Synthetic construct, Protein sequence of tTAV

<400> SEQUENCE: 35

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60
```

```
His Thr His Phe Cys Pro Leu Glu Gly Glu Ser Trp Gln Asp Phe Leu
 65                  70                  75                  80

Arg Asn Asn Ala Lys Ser Phe Arg Cys Ala Leu Leu Ser His Arg Asp
                 85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Ala Pro Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly

<210> SEQ ID NO 36
<211> LENGTH: 1014
<212> TYPE: DNA
<213> ORGANISM: Sequence
<220> FEATURE:
<223> OTHER INFORMATION: Open reading frame of tTAV2

<400> SEQUENCE: 36
atgagccgcc tggataagtc caaagtcatc aactccgcgt tggagctgtt gaacgaagtt      60
ggcattgagg gactgacgac ccgcaagttg gcgcagaagc tgggcgtgga gcagcccacc     120
ctctactggc acgtgaagaa taagcgggcg ctgctggatg ccctggccat cgagatgctc     180
gaccgccacc acacgcattt tgcccgttg gaaggcgagt cctggcagga cttcctccgc      240
aataacgcca gtcgttccg ctgcgctctg ctgtcccacc gagacggtgc caaagtccat      300
ctcggcacgc gccgaccga aaagcaatac gagacactgg agaaccagct cgcgttcctg     360
tgccagcaag gcttcagcct ggaaaatgct ctctacgctc tgagcgccgt cggtcacttt     420
accctgggct gcgtgctgga ggaccaagag catcaagtcg caaagagga gcgcgagacc    480
```

```
ccaacaaccg attcgatgcc cccactgctg cgtcaggcaa tcgagctgtt cgatcatcaa    540
ggagccgagc cggcattcct gttcggcttg gagctgatta tctgcggatt ggaaaagcaa    600
ctgaaatgcg agtcgggctc gggccccgcc tacagccgcg cccgcaccaa gaacaactac    660
ggcagcacca tcgagggcct gctggatctg ccggatgatg atgccccgga ggaggcgggc    720
ctggccgccc cgcgcctgag cttcctgccg gccggacaca cccgccgcct gtcgaccgcc    780
ccgccgaccg acgtgagcct gggcgatgag ctgcacctgg atggcgagga tgtggcgatg    840
gcccacgccg atgccctgga cgacttcgac ctggacatgc tgggcgatgg cgatagcccg    900
ggaccgggat tcaccccgca cgatagcgcc ccctacggcg ccctggatat ggccgatttc    960
gagttcgagc agatgttcac cgacgccctg ggcatcgatg agtacggcgg ctaa         1014
```

<210> SEQ ID NO 37
<211> LENGTH: 337
<212> TYPE: PRT
<213> ORGANISM: Artificial Sequence
<220> FEATURE:
<223> OTHER INFORMATION: Synthetic construct, Protein sequence of tTAV2

<400> SEQUENCE: 37

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270
```

Leu Asp Gly Glu Asp Val Ala Met Ala His Ala Asp Ala Leu Asp Asp
            275                 280                 285

Phe Asp Leu Asp Met Leu Gly Asp Gly Asp Ser Pro Gly Pro Gly Phe
        290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly

<210> SEQ ID NO 38
<211> LENGTH: 1011
<212> TYPE: DNA
<213> ORGANISM: Artificial sequence
<220> FEATURE:
<223> OTHER INFORMATION: Synthetic construct, open reading frame of
      tTAV3

<400> SEQUENCE: 38
atgggcagcc gcctggacaa gagcaaggtg atcaacagcg ccctggagct gctgaacgaa      60
gttggtatcg agggcctgac cacccgcaag ctggcccaga gctgggcgt ggaacagccg     120
accctgtact ggcacgtgaa gaacaagcgc gccctgctgg acgccctggc catcgaaatg    180
ctggatcgcc accacaccca cttctgcccg ctggagggcg agagctggca ggatttcctg    240
cgcaacaacg ccaagagctt ccgctgcgcc ctgctgtcgc accgcgatgg cgccaaggtg    300
cacctgggca cccgcccgac cgagaagcag tacgagaccc tggagaacca gctggccttc    360
ctgtgccagc agggcttcag cctggagaac gccctgtacg ccctgagcgc cgtgggccac    420
ttcaccctgg gctgtgtgct ggaggatcag gagcaccagg tggccaagga ggagcgcgag    480
accccgacca ccgatagcat gccgccgctg ctgcgccagg ccatcgagct gttcgatcac    540
cagggcgccg agccggcctt cctgttcggc ctggagctga tcatctgcgg cctggaaaag    600
cagctgaagt gcgagagcgg cagcgcctac agccgcgccc gtaccaagaa caactatggc    660
agcaccatcg agggactgct ggacctgccg gatgacgatg ccccggagga agccggcctg    720
gccgcccccc gcctgagctt cctgcccgcc ggacacacgc gccgcctgag caccgccccg    780
ccgaccgatg tgagcctggg cgacgagctg cacctggatg gagaggatgt ggcaatggcc    840
cacgccgacg ccctggacga tttcgacctg gatatgctgg gcgatggaga tagcccggga    900
ccgggcttca cgccccacga tagcccccg tacggcgccc tggacatggc cgacttcgag    960
ttcgagcaaa tgttcaccga cgcgctgggc atcgatgagt atggcgggta g            1011

<210> SEQ ID NO 39
<211> LENGTH: 336
<212> TYPE: PRT
<213> ORGANISM: Artificial Sequence
<220> FEATURE:
<223> OTHER INFORMATION: Synthetic construct, Protein sequence of tTAV3

<400> SEQUENCE: 39

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
 50                  55                  60

His Thr His Phe Cys Pro Leu Glu Gly Glu Ser Trp Gln Asp Phe Leu
 65                  70                  75                  80

Arg Asn Asn Ala Lys Ser Phe Arg Cys Ala Leu Leu Ser His Arg Asp
                 85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
210                 215                 220

Gly Leu Leu Asp Leu Pro Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 40
<211> LENGTH: 568
<212> TYPE: DNA
<213> ORGANISM: Pectinophora gossypiella

<400> SEQUENCE: 40
gctagtggag aactgccaca aactgctgga aaagttccac tactcctggg aaatgatgcc     60
cctggtgctg gtcattctaa actacgccgg ctccgacctc gacgaggctt ctagaaaaat    120
tgatgaaggg aagatgatca tcaacagagta cgcgaggaag cacaatctga acatcttcga    180
tggccacgag ctaaggaact cgactcgcca gtacggactt aatacagta atattagttt    240 tctccaacaa cactaaacac gacataacac gctacacgca aaaatacac gagtctttaa    300 tgttttacac gctcagtaaa ttattcactt acacgcttaa ctaaaatttt acacaatcgg    360
taaaaaaata caacaattta ttatcgtaaa aattacacaa ataatgag atttaaatgt     420 cgtttaataa aataaaataa aaatagcatc gggaatatct tttcacctat tgccggagaa    480
cagtttaaat ggatactctc atttgaatca ttttaattgt agtagcattt tattttatta    540

-continued

| ttaatagcaa taagtacaca aacataaa | 568 |

<210> SEQ ID NO 41
<211> LENGTH: 610
<212> TYPE: DNA
<213> ORGANISM: Pectinophora gossypiella

<400> SEQUENCE: 41

| gtagtggaga actgccacaa actgctggaa aagttccact actcctggga aatgatgccc | 60 |
| ctggtgctgg tcattctaaa ctacgccggc tccgacctcg acgaggcttc tagaaaaatt | 120 |
| gatgaaggga agatgatcat caacgagtac gcgaggaagc acaatctgaa catcttcgat | 180 |
| ggccacgagc tgaggaactc gactcgccag tacggacttt aatacagaaa atgctgagcg | 240 |
| aaattaataa tataagtggt gtactatcgt cgtccatgaa gttattttgc gaatgatact | 300 |
| ttgttttgta tgtgctgtgt gttgtgtgga cttttgctgt gcgttgctgt ttgcgatgga | 360 |
| aggactattg tgtcgtcgcc acgctggact attcgcacat tgggtggtcc accagtggcg | 420 |
| gatgtacgag cggtcgctgt gctcgctcct ggagctgcaa gcgcgcaaag ggacgtactc | 480 |
| ggtgtgctgc tcaccccgct acgtcatcgc gcccgagtac gcgtcacacc tgttgcctct | 540 |
| gccgcttacc acgcagagat catccccgcc gcccgcgcac ttgtagcgat gcgaacctgc | 600 |
| gccgcgggaa | 610 |

<210> SEQ ID NO 42
<211> LENGTH: 449
<212> TYPE: DNA
<213> ORGANISM: Pectinophora gossypiella
<220> FEATURE:
<221> NAME/KEY: misc_feature
<222> LOCATION: (26)..(26)
<223> OTHER INFORMATION: At position 26, n is a, c, g, or t

<400> SEQUENCE: 42

| gctagtggag aactgccaca aactgntgga aaagttccac tactcctggg aaatgatgcc | 60 |
| cctggtgctg tcattctaa actacgccgg ctccgacctc gacgaggctt ctagaaaaat | 120 |
| tgatgaagca cattgggtgg tccaccagtg gcggatgtac gagcggtcgc tgtgctcgct | 180 |
| cctggagctg caagcgcgca aagggacgta ctcggtgtgc tgctcacccc gctacgtcat | 240 |
| cgcgcccgag tgcgcgtcac acctgttgcc tctgccgctt accacgcaga gatcatcccc | 300 |
| gccgcccgcg cacttgtagc gatgcgaacc tgcgccgcgg gaagtaagta ctatttcatt | 360 |
| tattattctt tttattttg gttttaaggt gctgacagac ttgaatttca agcaaatagt | 420 |
| gtctgacaaa gagctcaaaa tagacatgt | 449 |

<210> SEQ ID NO 43
<211> LENGTH: 28774
<212> TYPE: DNA
<213> ORGANISM: Aedes aegypti

<400> SEQUENCE: 43

| acagtgaaat ttgatcgatc actcatcgaa acgagatcac tttcgattga tcgtgacaat | 60 |
| ttttagaat ccatttcaca gtcgttggga ctgttgaccc tgtcactta aactagctag | 120 |
| tgagtagctt tgctctagtg aaagctaact agcactgtta aaaaatctta ggtaaagtgt | 180 |
| cagcaaccct gacaactggg ccacctcttg ccgaccataa gcaaatgaaa tcaaatggtt | 240 |
| cgctacgaag gttaattggg tttcgatcta cttcgtccta agcgctattt ttcgtcatac | 300 |

```
ggtggagaac ggctggtatt cgtttacttt agtttaccaa gcgatgcttc caattaaccc    360
aaagctagat gaagcaggat tcgcgataaa aagcagtatg cgaacttaaa atgttctact    420
acattacggc gggtattcaa atttacctgc cacataaatt tattttccaa gtataatttg    480
cgaaagctgc aatggttcat gcttgaattt tacaagatga tgtaatgccg cccataagtt    540
taaatggacg gtgtatttaa ataaaaggtt catattaaac gctttcgacg ttaccaagta    600
ccatttgtac acaaacatgt aataaaacta ttgtatttct ataaataact tcagttcaat    660
catccacttt gcacattttc accgaaatcg catggacgaa ggtaaacatg tgtttgtaca    720
ttattttgat aacataaaga tatttattga agtcaagtta gtaggtgaaa cgtgtaaaag    780
tggctttagc gtacctgctt gacgtaccga gcgaaatctg attagcggtc gactaagcca    840
taaaacttct acaattcaca aaattttgaa aaattccctc gctgccacga tactaatgca    900
ctgcatggct cgctttagac taatcgccag ctgattcggt attttgaaga tgttaagtgt    960
tttaaaactt tttaagggag cgacggtgct atgattacgt aatcaaatgt tctttctttt   1020
actttcagac caattgcaga acaagcttta tcctaatcca tctcattttg ggaacagcac   1080
tagccgcgac cattagccgt ttagtttaca agaaagaaaa tgaaagtctg gttaacgtct   1140
tgttcgaaat aggattaggt agagtaaaac ccttgtcgtg atcggcgctg gtaatcggca   1200
tctgcgtaga gaacatgttg tacttcctcg aggacgattg ctcgcgctcg cacggttctt   1260
attgctacca tggtgaaacc actagcgccg aggaagtgct agacgcatct cttgtacaac   1320
atgaaggagc tcctgctaac gagcgcgagc gtgccaagaa taacgatggt accactttgg   1380
tgatcgcggc tccttcacga taccgttgtg aaggttttct gaattgcgca tcgtctccga   1440
agggtgtgtc caggtgcatt gtctcccaac tgacctgttc ccgacaatat cgagcactaa   1500
atggcaacac ttccaaaaga cttaacgcgt agcagaggct tcccacacag gtccacgtaa   1560
cagagggttg actggacaag ggctgttata gctcgtgatt ggtttccatt agagagcagt   1620
atctcgtagt agcgtaggag agtccattag agtgcgatat tccgtgagtt tgtgtgaccg   1680
gcgatagaga agccctgacg ccaaaggtaa tctctcgtca tagagcatca tcgcatcctc   1740
tcaggtaatc tcacgctata aggcactcaa acacactggc cgctatctct cgggactgc    1800 cgcgcttcaa gacgattgta actcggaaac tgacctgatt agtacataaa aagagaccta   1860
ttgcgtaagc ttataagaaa cgagtttgtc cacacggttg gcgcgaagtt ctgctaacat   1920
tgagcctttg actggactaa tcatgtattt ttctctggat aacgcattcg aatattcttt   1980
gctcaaacag gtgtgccaac atggtttcgc aagatcgctg gatggtaaag atgtccgagg   2040
cagggtacga taaccgggcg gatggcagtg gagcttccag cagcagcctg aacccgcgaa   2100
taccaaagcg ttctagcgac ctaccatttc tacaggctcc gtccatgct attggcccgc    2160 ctaccgtcac ctcgaaggtc gtcgtcggac ttgggcgctt cgccgccgaa ctgtgcccgc   2220
tgccggaacc acggtcacaa gatcggcctg aagggacaca agcgctattg taagtatcgc   2280
aattgtacct gcgaaaagtg gcggcggctt gacacgggcg acggccttgg tgccagtgtt   2340
ctagccggac ttccctgtgt tcgcgataac attcatagcg ttaacatgga cgcttttcac   2400
ctgcctgacg gccgaacggc agcgggtcat ggccctgcag acggctctcc gaagggcgca   2460
aacccaggac gaacagcggt tgctggtaga cggagaggtg gacggactgc cggcttgccg   2520
tcgcccagta ccgggacgtc tgccgagagg cttcccgcgt ttgggtcctg cttgtcgcca   2580
acgaccatct gcctctccac cccgccgaac cggtacatag ccttcaaata ccaaaattgt   2640
ctgacctaaa agagatgatc cataattctc agcagaggtc gttgatcgac tgcgactcgt   2700
```

-continued

```
gggcggcttg gccatgtatc ggaagtttat ggttttaaca gactggattt tctctactag   2760
gtattaagag tcgtctccag caactagctg acgctgagcc ccaccggctc gatgaactcc   2820
accccgggca gctcgttggt aacgctgtcc cagcaccgaa gatcaccctg ctccgccgcg   2880
tcggtccacc ccagcgaggc ggtggccgag ctacttgagg tggggcccgt cgagcaacca   2940
ttgcgacagg gtcgtggctt ctagtgggac gaggcggcgc agccaggtgg ggtcgctccg   3000
tcagcaaaac gttgcaggta ggtgtgaggc atatctattt cgttattctc tcaatgtttg   3060
tggagaaccg gccggaattc aacatcgaag tcggtttctg agtcgttttg caacgtccat   3120
ccacactccg tatagataaa gcaataagag agttacaaac acctcttggc cggccttaag   3180
ttgtagcttc agccaaagac ttctattgat ttatgataaa tttctctcaa atgtttgcgc   3240
ggagggtgga ttttgagag ctgagtggtg tagaaacgaa atgggcatca acgttatgc    3300 aagataacta aatactattt aaagagagtt tacaaacgcg cctcccacct aaaaactctc   3360
gactcaccac atctttgctt tacccgtagt ttgcaatacg ggcgctgctt gaaacaggtt   3420
tatgttaggg gtttcctgtg tttcatacag tcaccccatt gttatgtata gcacacagat   3480
atggataaaa gttggattaa ccgcgacgaa ctttgtccaa atacaatccc caaggacac    3540 aaagtatgtc agtggggtaa caatacatat cgtgtgtcta tacctatttt caacctaatt   3600
gcagtgaata tcccatcaaa tagagttgca attgagtaga acacatttta ccaacgtata   3660
aagcatcgta atcaattata atatacttaa gcaaaataca cgtcacttat agggtagttt   3720
atctcaacgt taactcatct tgtgtaaaat ggttgcatat ttcgtagcat tagttaatat   3780
tatatgaatt cgttttatgt atggggaaat aatttgtcaa ccacattcct agaaaagttg   3840
attcatacat gtgtgctttt gaaagccata taccacatta tgtttgattc atatctctta   3900 tacccctta  ttaaacagtt ggtgtaaaga tcttttcaac taagtatgta cacacgaaaa   3960
ctttcggtat atggtgtaat acaaactaag tatagagaat taatatgagt cgatttatcg   4020
cgaaattttt caaaatgtcc tatgtaccaa tgaaagatac tctcttatct cgctctgttt   4080
tgaacataac aactgaaact attatactca gctaaatagc gctttaaaaa gttttacagg   4140
atacatggtt actttctatg agagaataga gcgagacaaa acttgtattg ttgactttga   4200
tttgggaagt ttttcactat agataaaaaa atgtccttga ctagcgtttc atacaaaaaa   4260 aaaaaaaac gcaaccaaaa atgttaatgt ggttcagtga aaaccttca aaaagtgata    4320 tctattttt  tacaggaact gatcgcaaag tatgtttttt ttttttttg cgttggtttt    4380 tacaattaca ccaagtcact ttgattaaag aggaagtaaa ctaagatagt gtctcaatgt   4440
tggataggtc atttagaaaa ggtccgcgag attggatcca taataatgat tctcctctct   4500
aactaatttc tccttcattt gattctatca cagagttaca acctatccag taaatctttt   4560
ccaggcgctc taacctaggt attattacta agaggagaga cactgatccg catctgtggg   4620
atggacaacg tttgtaattt ctatcggtat cgaaaataat cgcgcatttt cgggcgtatt   4680
ccagaaaaca acaatgaaat gtgactaggc gtagacaccc tacctgttgc aaacattaaa   4740
gatagccata gcttttatta gcgcgtaaaa gcccgcataa ggtctttgt tgttacttta    4800 atactgaagc aaatgtgcac aattttcatt acatgatatt attcaatggg gtaggtgggc   4860
gacaaaatag attcattaat gttggataat aggggcgttt tatgacttcg tttacacgtg   4920
ttaaaagtaa tgtactataa taagttaccc catccaccg ctgttttatc taagtaatta    4980
caacctatta tccccgcaaa gtcattatcc ctaaatgctc cacctcagct ggtggccccg   5040
```

```
tcagtcagtt gatcgggaaa gcagcaatca atccggagac aggtcgacct ccatcgaaca    5100
cagtaatagg gatttacgag gtggagtcga ccaccggggc agtcagtcaa ctagcccttt    5160
cgtcgttagt taggcctctg tccagctgga ggtagcttgt ggaaccgaac aacactagat    5220
gttcgatttc taacgaccga ctaagaacat cgtcggaagc gtctggttca ttcgacgagc    5280 cggaagggt tcatctttcg ccttggcttg ttgtgatcta caagctaaag attgctggct     5340
gattcttgta gcagccttcg cagaccaagt aagctgctcg gccttcccca agtagaaagc    5400
ctcgtcgtcg aacgaatagc tgctgctaca cttcgcgtcg ttatcgtcgt cggggattg    5460 gtgtttgtaa ctgcgcactc gtttatacat tgttgtttgc gagcagcagc ttgcttatcg    5520
acgacgatgt gaagcgcagc aatagcagca gcccctaac cacaaacatt gacgcgtgag    5580
caaatatgta acaacaaacg cgatcggcgg gcgctgtaac tgcctgcagt cacgcgttca    5640
ttcgcagtcg ttgtcgtagt catacacacg ccgtcgttcc tttgtatcag ctgtgtagca    5700
gctagccgcc cgcgacattg acggacgtca gtgcgcaagt aagcgtcagc aacagcatca    5760
gtatgtgtgc ggcagcaagg aaacatagtc gacacatcgt tttagtggtg ttacaacatt    5820 gagctactt ttgcgtttcg ctttcgtgct gcggcggcgg cggcgggact tcgctgcact     5880
gataggaacg gaatgcatgc aaatcaccac aatgttgtaa ctcgatgaaa aacgcaaagc    5940
gaaagcacga cgccgccgcc gccgccctga agcgacgtga ctatccttgc cttacgtacg    6000
tgctccggtt gaagagagct ctgcgccact tgtggcgggt ttcactcaaa aggcatcgtc    6060
gcgtcgcaac aaagtgcgca cattcgacgc gtaactgtaa acgaggccaa cttctctcga    6120
gacgcggtga acaccgccca aagtgagttt tccgtagcag cgcagcgttg tttcacgcgt    6180
gtaagctgcg cattgacatt gtaaatagaa agactttggt gcgtttagaa aaagggtcac    6240
aaagggtggc aagtgagtat gtatgtgagc tcatttcatt ctcgatggca ttgagacgta    6300
catttatctt tctgaaacca cgcaaatctt tttcccagtg tttcccaccg ttcactcata    6360
catacactcg agtaaagtaa gagctaccgt aactctgcat atctattctg agaacgaaag    6420
ttcaatggat gcattttatg caatgccacc ggaattttcc tatgaactgc tttcacactt    6480
cttttaagaa aattttgcag tagataagac tcttgctttc aagttaccta cgtaaaatac    6540
gttacggtgg ccttaaaagg atacttgacg aaagtgtgaa gaaaattctt ttaaaacgtc    6600
atttaattta ttcactccat ttagttctga cgtaacattc cagataacac acttcaaagt    6660
catggtcagt tcatgttgaa cgaatgtgca ccgcgatcca taaattaaat aagtgaggta    6720
aatcaagact gcattgtaag gtctattgtg tgaagtttca gtaccagtca agtacaactt    6780
gcttacacgt ggcgctaggt cgcagaacga ttccatgtct taatgtcgtc acttatcata    6840
taatcaccca gttttttgccc cacttaaaaa aacgatgtcc acttttattc tgagtttctt    6900
gcgtcttgct aaggtacaga attacagcag tgaatagtat attagtgggt caaaacggg     6960 gtgaattttt ttgctacagg tgaaaaatag actcaaagaa tctcctctct tttcagccaa    7020
ccactccagc ggaaccctg aacccggaaa catggtacca ggtgagttcg ctgttgaaat     7080
actaatttgc agaaaacata agaggagaga aaagtcggtt ggtgaggtcg ccttggggac    7140
ttgggccttt gtaccatggt ccactcaagc gacaacttta tgattaaacg tcttttgtat    7200
agaaattttg ctaccgattt accataactg gaatcgaaga caatatgact tcatcacacc    7260
agcagtaaac acggcgtaaa aatgattcat caggacccgc tctttaaaac gatggctaaa    7320
tggtattgac cttagcttct gttatactga agtagtgtgg tcgtcatttg tgccgcattt    7380
ttactaagta gtcctgggcg tcaatagccc tgttttttcca cgctcatctt gggtttcaca   7440
```

```
tcggtgaaca ccacttggag acgttttcac acaatgttca tgttcttctt tgagtaaatg    7500
agttatcggg acaaaaaggt gcgagtagaa cccaaagtgt agccacttgt ggtgaacctc    7560
tgcaaaagtg tgttacaagt acaagaagaa actcatttac aagttatgcg tggtcccgtg    7620
ctcatcaaga tagtgtgcca cacataagaa ttatcttaat tgaggccttc tgcgggccgt    7680
gagcttgttt gctacgccct ttcaatacgc accagggcac gagtagttct atcacacggt    7740
gtgtattctt aatagaatta actccggaag acgcccggca ctcgaacaaa cgatgcggga    7800
tccttggcgt tgagttttag tttctttgac agagaaagac ttttgataat ctactttctg    7860
cagctacgac ctttctctga actatttgga aaattataac aggaaccgca actcaaaatc    7920
aaagaaactg tctctttctg aaaactatta gatgaaagac gtcgatgctg gaaagagact    7980
tgataaacct tttaatattg ttatgttgac aatatttatc ccttcgatta caaaaaaact    8040
tcaagccagg gaaacatcca gtgtgaaaac actaagcggc gcactttggt tcatttcatt    8100
aatacaactg ttataaatag ggaagctaat tgttttttga agttcggtcc ctttgtaggt    8160
cacacttttg tgattcgccg cgtgaaacca agtaaagtaa cgtatcgatc actcttaatt    8220
caagatgaca aagtggttga gtagtagagt acgtggctca caatcggaag gttcttggct    8280
cgaatctcaa tgtatgctat gcatagctag tgagaattaa gttctactgt ttcaccaact    8340
catcatctca tgcaccgagt gttagccttc caagaaccga gcttagagtt acatacgata    8400
ttttaacttt ttttttattt tgtcgatcat aaacggatgc gcgactcagc attttttggca    8460 tttgaatcat gattccgagt aatcagctac aaaaacctaa aaattgaaa aaaaaataaa    8520 acagctagta tttgcctacg cgctgagtcg taaaaaccgt aaacttagta ctaaggctca    8580
ttagtcgatg ttttttggatt cgcgtgtgtt gcgttacggc aatctgactc atgatatcat    8640
gagtccaaat catggtgtat tttcataaga cgaaaacacg ctggaatcat gatatcatga    8700
gcgcacacaa cgcaatgccg ttagactgag tactatagta ctcaggttta gtaccacata    8760
aaagtattct gcttttgtgc gaccttagta ctatagtact gtaataatct tgtttttgga    8820
ttctgatttc tacccgtgca tttctaaagt ttgcaaagaa ggaagcttca aaaaacttcc    8880
aaaagcttat gttacagaag cattattaga acaaaaacct aagactaaag atgggcacgt    8940
aaagatttca aacgtttctt ccttcgaagt ttttttgaagg ttttcgaata caatgtcttc    9000
cttggaaagc ttaagttaca gcagtttccg taccagaacg ttggaaagct tatattacga    9060
aacagtaata gggtttctat gcggtggaag tgctgttata gaacctttcg aattcaatgt    9120
cgtcaaaggc atggtcttgc aacctttcga atataatgct ttgtcattat cccaaagata    9180
cgccaccttc acgacaatat tggcgtgtaa gcatttataa tacatctggg tatcatcgaa    9240
atcattagaa aaaatgcggt ataagtttca cttgaattca gatcagtgat cgattgttac    9300
accgcacatt cgtaaatatt atgtagaccc ataagtagctt tagtaatctt ttttacgcca    9360
tattcaaagt gaacttaagt ctagtcacta gctaacaatg agttcaaata gatccaaata    9420
tatgagggtg aaacgtcatt gcgatccact gtgaactgca gttgattggc cgcaatttca    9480
aaatatgtac acccgagtga tcaagtttat ctaggtttat atactcccac tttgcagtaa    9540
cgctaggtga cacttgacgt caactaaccg gcgttaaagt tttatacatg tgggctcact    9600
tctgcacggc tgttcagctg acatccttca ttgtcccagt cgttcataca aacttgcccg    9660
tcaagatcaa ggaagttggc gcttgatcaa tgttctgttt agacgtgccg acaagtcgac    9720
tgtaggaagt aacagggtca gcaagtatgt ttgaacgggc agttctagtt ccttcaaccg    9780
```

```
cgaactagtt acaagacaaa catttctttt ttcttaagta gtattgggcg ctgcggtcac   9840
ctcatttatc tttttgaaat tgtttcggaa ataatgcacg agatgcaata acggttcttg   9900
gtaaagaaaa aagaattcat cataacccgc gacgccagtg gagtaaatag aaaaacttta   9960
acaaagcctt tattacgtgc tctacgttat tgccaagaac aacatagtca tgtagaacct  10020
tacaaatgat cagaattgat ttgatcaatt catttccagc tttcaaactg acgatcgccc  10080
aatgctaccg tccatcacga ttgtatcagt acatcttgga atgtttacta gtcttaacta  10140
aactagttaa gtaaaggtcg aaagtttgac tgctagcggg ttacgatggc aggtagtgct  10200
tattccacgc actggctgtc atgttccctg ccagatttac gtagtgttct tttgtaaagg  10260
caacactgct gcactgctcc aagtcactcc aagcttcatc ataaggtgcg tgaccgacag  10320
tacaagggac ggtctaaatg catcacaaga aaacatttcc gttgtgacga cgtgacgagg  10380
ttcagtgagg ttcgaagtag tgcgagttga agcaaactgt gaaggattga tattttgaat  10440
taaatcaagc tctcgcgttg caggcagctg taacttgcca ccaagtatga tcggtcttcc  10500
acgctcaact tcgtttgaca cttcctaact ataaaactta atttagttcg agagcgcaac  10560
gtccgtcgac attgaacggt ggttcatact agccagaagg gacttcgttc cataaaaagt  10620
ggaatgctcc tcgtccgatt tccagaaaca gtcggttatg caataaaaca ggatcaggtt  10680
cgatgactct tggcgatatc ctgaagcaag gtattttttca ccttacgagg agcaggctaa  10740
aggtctttgt cagccaatac gttattttgt cctagtccaa gctactgaga accgctatag  10800
tgaattggag tcgttaccta tcccccgata aagatatcct ctcgcaattc gagggggatt  10860
aggattagaa accgtttgct gatatttgcg agatataaaa acttaacctc agcaatggat  10920 aggggggctat ttctatagga gagcgttaag ctcccccctaa tcctaatctt tggcaaacga  10980
ctataaacgc tctatatttt actaataaaa tcttcaattc gctaaaagca cttcaattct  11040
tgttttctct tctggtttca gttgaccccc atatgcgagt gcagcatcac ggaccggact  11100
tgattatttt agaagttaag cgattttcgt gaagttaaga acaaaagaga agaccaaagt  11160
caactggggg tatacgctca cgtcgtagtg cctggcctga caggaacagg tgcgtacttc  11220
cttaacttca ctatcaataa aaccgtacct cctccagtcc atcgaaacaa caataaaata  11280
ctgcaccgat cagctggaat gtccttgtcc acgcatgaag gaattgaagt gatagttatt  11340
ttggcatgga ggaggtcagg tagctttgtt gttatttat gacgtggcta gtcgaccttta  11400 ttctatcccg ggaggtccaa tcgctacaat ttatgcacat ttaattccac tggagccatg  11460
tgcgttcggg catcttatca ggcgttcggg aattgaaact aagataggc cctccaggtt  11520 agcgatgtta aatacgtgta aattaaggtg acctcggtac acgcaagccc gtagaatagt  11580
ccgcaagccc ttaactttga ttacgacctc atttgtcatt aacgggatgc attcgtacgc  11640
agtcagcgtc ttatcggcat atatgcggta gccccccgag tgacaattaa accatggagc  11700
aatgctggag taaacagtaa ttgccctacg taagcatgcg tcagtcgcag aatagccgta  11760
tatacgccat cgggggctc actgttaatt tggtacctcg cgaaaccaat ttcacagcgg  11820
tccaccaact accgaatgcg atgcattttt atacgacagt ggcgttacta ggtgcttaac  11880
atatcaaaac ttgaagctt gctttggtta agtgtcgcc aggtggttga tggcttacgc  11940
tacgtaaaaa tatgctgtca ccgcaatgat ccacgaattg tatagttttg aaccttcgaa  12000 ccttttcaaaa gcttgcaaag cttccttcca ggagcttgga aagcttcctt ccaggagctt  12060
ggaaagcttc cttccaggag cttggaaagc ttccttccag ggaaagtttt cgaacgtttc  12120
gaaggaaggt cctcgaacct ttcgaaggaa ggtcctcgaa cctttcgaag gaaggtcctc  12180
```

```
gaacctttcg aaggaaggtc gagcttggaa agcttccttc caggagcttg gaaagcttcc    12240
ttccagtagc ttggaaagct tccttccagg agcttggaaa gcttccttcc aggagcttgg    12300
ctcgaacctt tcgaaggaag gtcctcgaac ctttcgaagg aaggtcatcg aacctttcga    12360
aggaaggtcc tcgaaccttt cgaaggaagg tcctcgaacc aaagcttcct tccaggagct    12420
tggaaagctt ccttccagga gcttggaaag cttccttcca ggagcttgga agcttccttc    12480
ccaggagctt ggaaagcttc tttcgaagga aggtcctcga acctttcgaa ggaaggtcct    12540
cgaacctttc gaaggaaggt cctcgaacct tcgaaggaa ggtcctcgaa cctttcgaag    12600
cttccaggag cttggaaagc ttccttccag gagcttggaa agcttccttc caggagcttg    12660
gaaagcttcc ttccaggagc ttggaaagct tccttccagg aaggtcctc gaacctttcg    12720 aaggaaggtc ctcgaacctt tcgaaggaag gtcctcgaac ctttcgaagg aaggtcctcg    12780
aacctttcga aggaaggtcc agcttggaaa gcttccttcc aggagcttgg aaagcttcct    12840
tccaggagct tggaaagctt ccttccagga gcttggaaag cttccttcca ggagcttgga    12900
tcgaaccttt cgaaggaagg tcctcgaacc tttcgaagga aggtcctcga acctttcgaa    12960
ggaaggtcct cgaacctttc gaaggaaggt cctcgaacct aagcttcctt ccaggagctt    13020
ggaaagcttc cttccaggag cttggaaagc ttccttccag gagcttggaa agcttccttc    13080
caggagcttg gaaagcttcc ttcgaaggaa ggtcctcgaa cctttcgaag gaaggtcctc    13140
gaacctttcg aaggaaggtc ctcgaacctt tcgaaggaag gtcctcgaac ctttcgaagg    13200
ttccaggagt ggaaaagatt cctgaaaagt acttggagaa attcctcgag ttatttcagt    13260
aaagattata ctggaggaac caatggtgga atcacttgag aaggtcctca cctttctaa    13320 ggacttttca tgaacctctt taaggagctc aataaagtca tttctaatat gacctccttg    13380
gttaccacct tagtgaactc gcatttcggc agaaatccct ggcaaaatcg ctatggaaaa    13440
atccctgcaa aaaatcctgg aataatcctt gccggaatct catgaggaac tcctggtaaa    13500
cgtaaagccg tctttaggga ccgttttagc gataccttt tagggacgtt ttttaggacc    13560
ttattaggaa cggccttaga gtactccttg aggaccattt attctttaac aaatttctgt    13620
ttattttctc tacaaagtta cagctccttt accgtgccga ttggccagaa atgacccaa    13680 agactcatgg ggtacgatct taagaaattg tttaaagaca aataaaagag atgtttcaat    13740
gtcgaggaaa tggcacggct aaccggtctt tactgggggtt tctgagtacc ccatgctaga    13800
tatttctgcc aaatatactg tatgtttgtt tcttctgat atgctttaa gctcaattt    13860 cttggaatg tgagatt gttttggct ccaatatact ataaagacgg tttatatgac    13920
atacaaacaa agaaagacta tacgaaaatt cgagttaaaa gaaaccttac cacctctaaa    13980
caaaaccgga ggtatagtg tcgtagctcg tagttcgtac ctgaagtcaa ctcctcaatt    14040
cctaaatgct acaataatat ataaaatttt aggaaataac tgcaaaatat tctgaaggcc    14100
acgatcgagc atcaagcatg gacttcagtt gaggagttaa ggatttacga tgttattata    14160 tatttaaaa tcctttattg acgttttata agacttccgg atgtcttgat ctatcttgat    14220
gtatctaata tgtaatccca gaagcattct agttttttct gataatctgt gaaataagtt    14280
gtttttacga actttgactt tacagaacta gatagaacta catagattat acattagggt    14340
cttcgtaaga tcaaaaaga ctattagaca ctttattcaa caaaaatgct tgaaactgaa    14400
ttcgggattt gaggtacaag cttttcaaata tattggaggt tctgcgatat taacttcaat    14460
gaattattgg aaattagaaa tcgtcttgtg catacgggtt aagccctaaa ctccatgttc    14520
```

```
gaaagtttat ataacctcca agacgctata attgaagtta cttaataacc tttaatctttt    14580 agcagaacac gtatgcccaa aatcgatttt agtctctggt agatttcgag agggaatgtc    14640
tgaagaaatt ttctgaccta catgtgaagt attgtctgtc aaattcaaaa tattttctgt    14700
ttagctaaaa tcagagacca tctaaagctc tcccttacag acttctttaa aagactggat    14760
gtacacttca taacagacag tttaagtttt ataaaagaca aggaaattaa aattttttgg    14820
ggaaaactcg aaactccttg gatatccaag gaaacaaaaa aaaagaaat atctgaagaa    14880 gtgcatcgtc ctttttcctt tcctttaatt ttaaaaaacc ccttttgagc tttgaggaac    14940
ctataggttc ctttgttttt tttttcttta tagacttctt cacgtagcag gaaaaaggaa    15000
aattattgtt ttaattaact aatagttctg ctagaaaggt ttttggcaga accccaaaat    15060
gatattcaaa gcaactaaca gctcgatttc ccctcgtttc ttaataacaa aattaattga    15120
ttatcaagac gatctttcca aaaccgtctt tggggtttta ctataagttt cgttgattgt    15180
cgagctaaag gggagcaaag caatttcaga cgacgaactt gtcaaacgat ctcaatggct    15240
cctggagaag ctgcgatacc cctgggagat gatgcccctg atgtacgtga tactgaaagg    15300
gttaaagtct gctgcttgaa cagtttgcta gagttaccga ggacctcttc gacgctatgg    15360
ggaccctcta ctacggggac tacatgcact atgacttttcc cgccgacgga gacgtcaata    15420
aagcgcgcca acggattgac gaaggtatgg gggttcttac cggttgggac tgtttccgag    15480
gtatcgatcg ggtgtcactc gcggctgcct ctgcagttat ttcgcgcggt tgcctaactg    15540
cttccatacc cccaagaatg gccaaccctg acaaaggctc catagctagc ccacagtgag    15600
acttcctggg tgctcccatt ttgtaactgc taacgcttat tattgagttt caggacatct    15660
gggatcttcg gtcgacggag tctattccca acagtgccct tgaaggaccc acgagggtaa    15720
aacattgacg attgcgaata ataactcaaa gtcctgtaga ccctagaagc cagctgcctc    15780
agataagggt tgtcacggga ggatcaaaca ctgccatcat gcagtttccg tagcctgttg    15840
ggctacgctc cccgacttga catcccccat tcttatcaaa caacaactca aggcctgaga    15900
cctagtttgt gacggtagta cgtcaaaggc atcggacaac ccgatgcgag gggctgaact    15960 gtaggggta agaatagttt gttgttgagt tccggactct caacgagtgg tggaatttgc    16020
gcacgaagtc attggtttgt cctggtaaaa gttaaaaggg ttaactggag ggttaattga    16080
cacggtttca actgatggcc gttgctcacc accttaaacg cgtgcttcag taaccaaaca    16140
ggaccatttt caattttccc aattgacctc ccaattaact gtgccaaagt tgactaccgg    16200
ttattgacac acggatgaaa gacttgcacg cttgaccttc tgtctgtact aataaaagtt    16260
acgttggctg ggttttgggg tcataatggc cccaaaatcg aataactgtg tgcctacttt    16320
ctgaacgtgc gaactggaag acagacatga ttattttcaa tgcaaccgac ccaaaacccc    16380
agtattaccg gggttttagc aatcgtcata acttcttgaa atacaactca cgtttaagac    16440
cattcaagag tattagatca tcgtctataa tagcagattt gaaatttact tcacatttcg    16500
ttagcagtat tgaagaactt tatgttgagt gcaaattctg gtaagttctc ataatctagt    16560
agcagatatt atcgtctaaa ctttaaatga agtgtaaagc gtattgcagt gccccttgct    16620
tccacaatgg aattagttaa agtttcgaga gcattgtcaa tatcaagtgt tgttagcaaa    16680
caaatgctaa catcaagatt cataacgtca cggggaacga aggtgttacc ttaatcaatt    16740
tcaaagctct cgtaacagtt atagttcaca acaatcgttt gtttacgatt gtagttctaa    16800
actatcgatg tttgattcac atgtattcca atcagctcgt aaaaaatgga aagtggagct    16860
gatagggttg agaatcgctt catgggataa ttggaaacag tgatagctac aaactaagtg    16920
```

```
tacataaggt tagtcgagca ttttttacct ttcacctcga ctatcccaac tcttagcgaa   16980
gtaccctatt aacctttgtc ggacatgatc agaatgaaaa tcagcgtgag taaccagttg   17040
actacaaaga tgactagagt cggttaagaa aaattcaagt agggctatca ggttattgaa   17100
cctgtactag tcttactttt agtcgcactc attggtcaac tgatgtttct actgatctca   17160
gccaattctt tttaagttca tcccgatagt ccaataactt tgaaaaata tcccgaaggg   17220 ccctcatcaa ttaaaatttt gcctttggaa atgtttggca ttcaagtagc aaattttaac   17280
atactgcgat tcgatttccg aacttttat agggcttccc gggagtagtt aatttaaaa    17340 cggaaacctt tacaaaccgt aagttcatcg tttaaaattg tatgacgcta agctaaaggc   17400
caagttagtt tgaaacaaat taacttgcta cccagtgcat taaaaaggca agtaggcagc   17460
tttggaagta taaacttagc tgtgttttaa cagaagcact gttcaatcaa actttgttta   17520
attgaacgat gggtcacgta attttttccgt tcatccgtcg aaaccttcat atttgaatcg   17580
acacaaaatt gtcttcgtga cgcaagtttc aaaaattttg gtttcgaatg acaaaaaaag   17640
ttgatgttat atacgcctat tgaatgatga ttccagttga tcatttcgac aaacaaaaaa   17700
gcgttcaaag ttttaaaac caaagcttac tgttttttc aactacaata tatgcggata     17760
acttactact aaggtcaact agtaaagctg tttgtttttt gaatctcttt tgatttcaga   17820
tccaggattc aaataacatt ccgttatcag ataaagggtt aatgccacaa tcgtgtggtc   17880
cattatcccc ggaaacttca cttagagaaa actaaagtct aggtcctaag tttattgtaa   17940
ggcaatagtc tatttcccaa ttacggtgtt agcacaccag gtaataggg cctttgaagt    18000 caccgtcaca ctcgatccag atctgatgtg atctctgccg tcgggcgcct cagaagcgaa   18060
aaccacattc gcccgcgctc tccggaatta tgtcgtaaaa gtggcagtgt gagctaggtc   18120
tagactacac tagagacggc agcccgcgga gtcttcgctt ttggtgtaag cgggcgcgag   18180
aggccttaat acagcatttt taaaacttta caaccataat tattcagaac ttcgacgact   18240
gcgcgatgac ttggccgcgg tgtgcctgct tgggatggac ctccgagcac tgaaagcagt   18300
attttgaaat gttggtatta ataagtcttg aagctgctga cgcgctactg aaccggcgcc   18360
acacggacga accctacctg gaggctcgtg actttcgtca ggtttgtaca aattgaatgg   18420
gctatttgaa attaattggg ctgcgataac ttcaaagtgt gacatcaaaa tggtgtgagt   18480
tttttactgc acaaattcca ccaaacatgt ttaacttacc cgataaactt taattaaccc   18540
gacgctattg aagtttcaca ctgtagtttt accacactca aaaaatgacg tgtttaaggt   18600
agttatttcc tacttcatat caatcggagc tccaggagtg aagatccaaa ttaccaagct   18660
tggccatttc gtatgaaaaa cggcaaaatg atctttttt tcaataaagg atgaagtata    18720
gttagcctcg aggtcctcac ttctaggttt aatggttcga accggtaaag catacttttt   18780
gccgttttac tagaaaaaaa cgccagtcac tgtatctcat gatccagatg agataaaaaa   18840
gttcgagtct tcgacaaagt tgttttggaa gtcatggaca ttcttaagca aacaacttag   18900
gcggtcagtg acatagagta ctaggtctac tctattttt caagctcaga agctgtttca    18960
acaaaacctt cagtacctgt aagaattcgt tgttgaatc ttttgccact aggtggcgcc     19020
agtaagcata ttcgtcatca aacgtcaaca tcccaccgca aaatcgctag tgtttggagg   19080
ggattttaac ctccaaattg aaaacggtga tccaccgcgg tcattcgtat aagcagtagt   19140
ttgcagttgt agggtggcgt tttagcgatc acaaacctcc cctaaaattg gaggtttaac   19200
ccaaataacc tccaaatcat cacctccaag ttagttctaa tacactccgt tatatgaaat   19260
```

```
atggtggtgc gtcgatcgtc gcaagtttat cgttaaacag ggtttattgg aggtttagta    19320
gtggaggttc aatcaagatt atgtgaggca atatacttta taccaccacg cagctagcag    19380
cgttcaaata gcaatttgtc tcaataaaat gagcatttta tatcgtgata catatgagaa    19440
gatagaggtt tcaattaaaa caaatccaca tggtgtcgct aataaaattg tgcattttaa    19500
agttatttta ctcgtaaaat atagcactat gtatactctt ctatctccaa agttaatttt    19560
gtttaggtgt accacagcga ttattttaac acgtaaaatt gcgagttata tcctctgatc    19620
aagataaaat agaaaattcg attttgaat attcaattat aagagcctga ataactacaa    19680
catgtagtga atcgaaactg cgctcaatat aggagactag ttctatttta tcttttaagc    19740
taaaaactta aagttaata ttctcggact tattgatgtt gtacatcact tagctttgac    19800
atttatgacg gtttgtgaag gttacacgtc ctaagcattt ggattcaaga aaagcaagag    19860
atatgacgaa tgtaaacttt atcgtatcaa tgaagtaact taaatactgc caaacacttc    19920
caatgtgcag gattcgtaaa cctaagttct tttcgttctc tatactgctt acatttgaaa    19980
tagcatagtt acttcattga agcgtccaga acagtacaaa ccaacatcgt accgtcgtat    20040
tccactccgg tcgttgcaat atctctaggt ccaccgaaaa acactcatga ccaagatcgt    20100
tcgcaggtct tgtcatgttt ggttgtagca tggcagcata aggtgaggcc agcaacgtta    20160
tagagatcca ggtggctttt tgtgagtact ggttctagca gtcgtcgatc ttggtccacc    20220
gaaacaccga tgtccatatc gtttcgtcga acttggacca acgattcatg caactgatga    20280
caacgcggcc cccgggtcgt cagcagctag aaccaggtgg ctttgtggct acaggtatag    20340
caaagcagct tgaacctggt tgctaagtac gttgactact gttgcgccgg gggcccagca    20400
accaatatcc gaaaaatcca actgttcttc tctgcctcgc aggtcaagcc gtggtcaatg    20460
aatactcacg attgcacaat ctgaacatgt tcgacggtgt tggttatagg cttttaggt    20520 tgacaagaag agacggagcg tccagttcgg caccagttac ttatgagtgc taacgtgtta    20580
gacttgtaca agctgccaca agagttgcgc agtacgacgc gccagtccgg atgatagact    20640
ttttacacga tcagcacgac ccactgcgct gcggcaaagg tcgaaccgaa acaagaataa    20700
tctcaacgcg tcatgctgcg cggtcaggcc tactatctga aaaatgtgct agtcgtgctg    20760
ggtgacgcga cgccgtttcc agcttggctt tgttcttatt accacgaaga tcagatcgat    20820
tcgacggaag aagcaatcga atgcaaagaa gaatcggaac gaagaaaact ctaaagcatc    20880
gcatatttac aaagcataac tggtgcttct agtctagcta agctgccttc ttcgttagct    20940 tacgttctt cttagccttg cttcttttga gatttcgtag cgtataaatg tttcgtattg    21000
ggaaaacccg caagttcaaa ctagtgatta gtgtaagatg aagcaaagca gaaatgtagt    21060
atctagattt ttcgacgtta gtttacaaag ataaaaaatg cctttggggc gttcaagttt    21120
gatcactaat cacattctac ttcgtttcgt ctttacatca tagatctaaa aagctgcaat    21180
caaatgtttc tatttttttac aggttggaca tacaatcgtg ggtattcgtc tgagttcgtc    21240
acaactgcac cggaaactgt gaaacagaat agagccaacc tgtgcgcgga gaatgttgag    21300
tccaacctgt atgttagcac ccataagcag actcaagcag tgttgacgtg gcctttgaca    21360
ctttgtctta tctcggttgg acacgcgcct ttacaactc gtcattataa gcttcctag     21420 catccacggg tgaaagtcga tcgacggaag cctgcaagac tctgtcgatg ggctttcgtc    21480
ctagaagaat aagattaaac cagtaatatt cgaaggaatc gtaggtgccc actttcagct    21540
agctgccttc ggacgttctg agacagctac ccgaaagcag gatcttctta ttctaatttg    21600
ctgaaatgta ttctcccgtg gaatggtttc atttgagtaa ttctgtatct tctccttccc    21660
```

```
aattccacga acgcgacgaa ctctaataca aacaacataa gactttacat aagagggcac   21720
cttaccaaag taaactcatt aagacataga agaggaaggg ttaaggtgct tgcgctgctt   21780
gagattatgt tgttgtatt  tgaccacagt gcaaatgctg tttaacgata atagcgacat   21840
gcagccattc tggggctacc acgtgtagct ctacttgtga gacagcgttc ctaaagagtg   21900
actggtgtca cgtttacgac aaattgctat tatcgctgta cgtcggtaag accccgatgg   21960
tgcacatcga gatgaacact ctgtcgcaag gatttctcac tgaaagtgca aacaagtgat   22020
gaaaccaata gtgcaaagca agtttagagg gaaaatttaa aaaatgcaaa acagcagtag   22080
tacttaactt ttaagattgt actttcacgt ttgttcacta ctttggttat cacgtttcgt   22140
tcaaatctcc cttttaaatt ttttacgttt tgtcgtcatc atgaattgaa aattctaaca   22200
gtttcgaaag ccgaagtgtg ttccatctgc caccggaaaa aaacgacgac agcagaatca   22260
tcaacaagca acatccatcc gaaaaaatcc gggaaaccgg caaagctttc ggcttcacac   22320
aaggtagacg gtgccttttt tttgctgctg tcgtcttagt agttgttcgt tgtaggtagg   22380
cttttttagg ccctttggcc atcttcaacc aaccatccta caatctacaa accagagatt   22440
atatctcttc aatcgtttcc gacatcggtc ggtttcggtg cccaaaatga tctgataaac   22500
tagaagttgg ttggtaggat gttagatgtt tggtctctaa tatagagaag ttagcaaagg   22560
ctgtagccag ccaaagccac gggtttttact agactatttg acttatctct ctgtagcttg   22620
catgccattg cgagcgtatt ttggtagctg gccgttgcca aacggctccg acaggtactg   22680
ctattggagg ttgtgcacga tgaatagaga gacatcgaac gtacggtaac gctcgcataa   22740
aaccatcgac cggcaacggt ttgccgaggc tgtccatgac gataacctcc aacacgtgct   22800
ccacgttgag tttgcctttt gagttggaga gtgtgtcttt tcgtcatata tttggccttt   22860
tcaagggtga ttttcaggct gcgtaaagat tgtatagttt ggtgcaactc aaacggaaaa   22920
ctcaacctct cacacagaaa agcagtatat aaaccggaaa agttcccact aaaagtccga   22980
cgcatttcta acatatcaaa aaccagctaa acatattga  tgacaagttc tatttcagca   23040
ccacaaacaa gcctgttaat gtctctcacc gcaaccattg ttctgcgcgc gttataatca   23100
ttggtcgatt ttgtataact actgttcaag ataaagtcgt ggtgtttgtt cggacaatta   23160
cagagagtgg cgttggtaac aagacgcgcg caatattagt gcatagaagt ttatttctt    23220
tgggatgatt caaatattac gtgacgcaaa gtttgccaat tttagaaccc ctccctcctc   23280
cacgtaacgg cttttgtgtg cgtatcttca aataaaagaa accctactaa gtttataatg   23340
cactgcgttt caaacggtta aaatcttggg gagggaggag gtgcattgcc gaaaacacac   23400
aaaaatttaa attttgtgta tagaccgtag catttcggaa gacccctcc  cttactctgt   23460
tgagttacgt aaaatttcaa cgatcctttt gtagttctga tttttaaatt taaaacacat   23520
atctggcatc gtaaagcctt ctgggggagg gaatgagaca actcaatgca ttttaaagtt   23580
gctaggaaaa catcaagact atttatatc  agcgtgcagt gttatgaaga tatccacagt   23640
ataaaatatt atttattt   aaattctatg ctgattatca atgtgttact agtggctttt   23700
taaaatatag tcgcacgtca caatacttct ataggtgtca tattttataa taaaataaaa   23760
tttaagatac gactaatagt tacacaatga tcaccgaaaa catactcatg ttgcgagctc   23820
gatttggcgc acggggtcat ctacacctga tacctttagg gtcgttgggg gaccacttag   23880
cgtgcacgta cggacattca gtatgagtac aacgctcgag ctaaaccgcg tgccccagta   23940
gatgtggact atggaaatcc cagcaacccc ctggtgaatc gcacgtgcat gcctgtaagt   24000
```

```
aaatgttgtt caaattttt tcttaccaag acgagcactt tacaatgaca aactctggct    24060
ctgctctggc tctgctctgg ctctgctctg gctctgctct tttacaacaa gtttaaaaaa    24120
agaatggttc tgctcgtgaa atgttactgt ttgagaccga gacgagaccg agacgagacc    24180
gagacgagac cgagacgaga ggctctgctc tggctctgct ctggctctgc tctggctctg    24240
ctctggctct gctctggctc tgctctggct ctgctctggc tctgctctgg ctctgctctg    24300
ccgagacgag accgagacga gaccgagacg agaccgagac gagaccgag    24360 acgagaccga gacgagaccg agacgagacc gagacgagac gctctgctct ggctctgctc    24420
tggctctgct ctggctctgc tctggctctg ctctggctct gctctggctc tgctctggct    24480
ctgctctggc tctgctctgg cgagacgaga ccgagacgag accgagacga gaccgagacg    24540
agaccgagac gagaccgaga cgagaccgag acgagaccga gacgagaccg agacgagacc    24600
ctctgctctg caaaatgctc tggattaatt tattgctcac actcttttgc tgttggacca    24660
ctattcattt caaatcttca atatgttcct attaccccca gagacgagac gttttacgag    24720
acctaattaa ataacgagtg tgagaaaacg acaacctggt gataagtaaa gtttagaagt    24780
tatacaagga taatgggggt aacacggtcc acacggatcg atttcaacta actccactct    24840
cgtatgcata ttttgtgtat aaattttgaa taatcgaaaa gggttgctgc aaatgttaat    24900
ttgtgccagg tgtgcctagc taaagttgat tgaggtgaga gcatacgtat aaaacacata    24960
tttaaaactt attagctttt cccaacgacg tttacaatta attttttccc tctaccccct    25020
cactctgtcg ttggcgttgg aaaaaaatca ccactgcata caaaacactc attggttggg    25080
tggaaggacg gtttagcaga taaaaaaggg agatggggga gtgagacagc aaccgcaacc    25140 ttttttttagt ggtgacgtat gttttgtgag taaccaaccc accttcctgc caaatcgtct    25200
gttgctaaat tttccatatc acgctgattg atttgtgatt aaaaataaat ataaatagaa    25260
aatgaataat tcccacatgt gtttcggtat taggcaccgg caacgattta aaaggtatag    25320
tgcgactaac taaacactaa tttttatttta tatttatctt ttacttatta agggtgtaca    25380
caaagccata atccgtggcc catggggcgg cgaagtgcag acggtctag ttctcattat    25440 ttggcatcga ttggcggtca aactacaacc tccatggaga aacaggcccc atccgtactt    25500
gtaccccgcc gcttcacgtc tgccaagatc aagagtaata aaccgtagct aaccgccagt    25560
ttgatgttgg aggtacctct ttgtccgggg taggcatgaa agttattaat aaataacaat    25620
gatttgaatt tgaatcattc atgctgcggc gtggctgatt tcggtgaatt gttgttctct    25680
tagagaaaga gggggatttg tcaataatta tttattgtta ctaaacttaa acttagtaag    25740
tacgacgccg caccgactaa agccacttaa caacaagaga atctctttct cccctaaac    25800 aatttggacg agtaaataac attgaatatt acactttatg actaatcacc agtaatgaaa    25860
caacacgggt gatgatttca aaagcttcat tctaaatgca ttaaacctgc tcatttattg    25920
taacttataa tgtgaaatac tgattagtgg tcattacttt gttgtgccca ctactaaagt    25980
tttcgaagta agatttacgt tggttcactt ttggtggcag atttaaaact cttatcttcc    26040
tcttttcttc aacaggtttc acgccatcaa agacgcttgg cagccgcttc catttgcgta    26100
accaagtgaa aaccaccgtc taaattttga gaatagaagg agaaaagaag ttgtccaaag    26160
tgcggtagtt tctgcgaacc gtcggcgaag gtaaacgcat gcaaacgtat gttaacctta    26220
ggttttaatg ttaaaagtat caccaaaaat caagtcccaa gacttctgca agaatggttt    26280
atgctgaatt tattcgaaat cgtttgcata caattggaat ccaaaattac aattttcata    26340 gtggtttta gttcagggtt ctgaagacgt tcttaccaaa tacgacttaa ataagcttta    26400
```

```
ggttttatttt tcatcgaaac atgtgtgatg taggctacta ttttggtaaa accgttggca    26460
acgactgtat ttaaactcac aaaatttgaa ccaaacttat ccaaaataaa agtagctttg    26520
tacacactac atccgatgat aaaaccattt tggcaaccgt tgctgacata aatttgagtg    26580
ttttaaactt ggtttgaata aattgtaact tttaattgag taaacatagg cgaaagagag    26640
tgattcaaat gggattcgga atcgaacggt tcttctaagt aagacaaacg aaaaaaacaa    26700
ttaacattga aaattaactc atttgtatcc gctttctctc actaagttta ccctaagcct    26760
tagcttgcca agaagattca ttctgtttgc tttttttgtt ccaaacgagt caaagctgca    26820
aaaacttcaa gtttgaactg tgatatcaat gaaattaaat acgaactatg tatcaagatt    26880
acagtaaaat ttaagaaga ggtttgctca gtttcgacgt ttttgaagtt caaacttgac     26940
actatagtta ctttaattta tgcttgatac atagttctaa tgtcatttta aatttcttct    27000
ctttcaacgc atgaaacagg agggtggcaa ccgaaaagtg actgaatcaa ttgcgggtta    27060
tcattcgaga tatccagggg ttgaattgtg agaaaacttc gaaagttgcg tactttgtcc    27120
tcccaccgtt ggcttttcac tgacttagtt aacgcccaat agtaagctct ataggtcccc    27180
aacttaacac tcttttgaag ttcttcttct tattcttggc aatacgtcct cactgggata    27240
gagtctgctt cctaacttca tgttcaatga ccacttccac agttattaac tgagagcttt    27300
aagaagaaga ataagaaccg ttatgcagga gtgaccctat ctcagacgaa ggattgaagt    27360
acaagttact ggtgaaggtg tcaataattg actctcgaaa ctttgccaaa gttgccattt    27420
tcgcattcgt atatcgtgtg gcagcagtgt tgtgaaaaac tcaatttctc ataactaacg    27480
cttgagattt ttcatgcgtg gaaacggttt caacggtaaa agcgtaagca tatagcacac    27540
cgtcgtcaca acactttttg agttaaagag tattgattgc gaactctaaa aagtacgcac    27600
agttgtcaat cacgcaactc agcagtcaaa attttccaca gtatacttac acacggcaat    27660
aatttcttgc tagtctggta aaattatagt aatctttct tcaacagtta gtgcgttgag     27720
tcgtcagttt taaaggtgt catatgaatg tgtgccgtta ttaaagaacg atcagaccat     27780
tttaatatca ttagaaaaga aacgtaaaca acaaaattcg ggtttcaaga gttttttgacg   27840 ggagcaagca aaataggatt tagaattttg catgagacga agtttgaaaa ttttattgtc    27900
ttgcatttgt tgttttaagc ccaaagttct caaaaactgc cctcgttcgt tttatcctaa    27960
atcttaaaac gtactctgct tcaaacttt aaaataacag aaatttagta tcggttcaat     28020
cgaattttcg aacacaattg taggctctat ataaactaca tttattccct tattttgcca    28080
gatacaatac tcgcataact tttaaatcat agccaagtta gcttaaaagc ttgtgttaac    28140
atccgagata tatttgatgt aaataaggga ataaaacggt ctatgttatg agcgtattga    28200
tgagatctcg cctaaaaagc cattggtaac cgagtgtgta gctctttgtt tctaagccaa    28260
ttaatggacc tggatgaaaa ctatcatcac tgggaaatag actctagagc ggattttcg     28320 gtaaccattg gctcacacat cgagaaacaa agattcggtt aattacctgg acctactttt    28380
gatagtagtg acccttatc aggaggaact tgtctttatc gtagcattgt taaataacgt     28440
gtaaacccat ttgttcctc ggtagctgca agctacacac tcgattacca atggctttta    28500
tcctccttga acagaaatag catcgtaaca atttattgca catttgggta aacaaaggag   28560
ccatcgacgt tcgatgtgtg agctaatggt taccgaaaat gggcgagatc acaagttatg    28620
cgagaatact tcccgaaatc accaccttt acccttttaa ataacgaaat tactacaaac    28680
ttcgttaccc gctctagtgt tcaatacgct cttatgaagg gctttagtgg tggaaaatgg    28740
```

```
gaaaatttat tgctttaatg atgtttgaag caat                              28774
```

<210> SEQ ID NO 44
<211> LENGTH: 3399
<212> TYPE: DNA
<213> ORGANISM: Cydia pomonella
<220> FEATURE:
<221> NAME/KEY: misc_feature
<222> LOCATION: (1179)..(1184)
<223> OTHER INFORMATION: At positions 1179-1184, n, at each occurrence,
      is a or c or g or t

<400> SEQUENCE: 44

```
catcagacgg gcccaggctc aggatgaagc tagagcgcgg gcggcggacg cagggctcca      60
ccctcccggg atcgagctag atcggcctga gccgccagtg gtgaaagcgc cgaggagtcc     120
cgtgatcccg ccgccgccgc cgcgctccat gggatcggcg agctgcgact ccgttccggg     180
atcgcccggg gtatcgccgt atgcgccgaa cccgccgtcc gctccgcctc cgccgatgcc     240
gccgctcccg cctccgcaac cagtggccct ggactccctg gtagaaaact gccacaagct     300
gctggaaaaa ttccactaca gttgggagat gatgccgctc gtgctggtca tcctcaacta     360
cgccggctcc gacctggagg aggcctcgcg gaagattgac gaaggtaagt ttaaatttaa     420
gtacataaca atgcttacag acgaattgaa agggaatgtg actcggctaa tccaccagga     480
tataattttg tagagtgcgc taaagaattc tagcaacgga cgctgttatt ctgccaccgc     540
cgttgatgcc gccgtcttct gatagtgata ctttaagatc cgtatactac gctcacttcc     600
attcacttat gtcgtacgga gtattaatat gggtaaactc gcggacacga aacgattacg     660
aaaacgcaga gtacttagat tggagcaaag cccagggatt cgccgagact tttttgttac     720
ggaagattga tgaaggtaag caagttggga ctgtggcgag ttgacacatg aaacaagtca     780
aggtcacagc tggagttcca ttaaagctgg atgctaccgc tagtcatcct gaggccggct     840
ccgacttcgt gcaatgaggt attaagctgc tggaattgaa tggaatatag tggtgaaaca     900
ctactactag gtttaagcgt ttagttatat ggttgttttc ttatttttaa tttttaaatg     960
ctctgctaag ctaaaacggc waatgtctat ttttgattat aaagacttat ataaaacaac    1020
ttgtttagct tcttttkacgt cttttttgtta agctgtgccc tggttttaaa wkgggcgaac    1080
acytcacgaa taagacgtaa ttttaaaaag aaaatagata tcggccctct tggttcgcat    1140
ttatacatat gtattgctgc ccgtgcgaat gttggggann nnnnaaacag tacccctagt    1200
gtaartaaat tcgatttcga aacgtgacgt acgcgtttgc gtttagtctc mwtttgtatt    1260
ggatttagaa agagcgcgcc aagcgggacg ttttggaaac tcaaaatcct atacaaaatg    1320
agacttaacg caaasgcgtt tcgtcacgtt atgatgtcga tcaaatttac actaggggta    1380
cagaggtatt gcagtaactg tacaaatact aaactaaatt aataaattag ctaaatctaa    1440
aatatacccct tcaggcattg tactaaggat gctggcggaa ttacttgtgc gaggaagccg    1500
ccagcttttc ggtcaccatt tacgagtacg tataccaaac gcttcgttgc tgcaaaaaag    1560
tttcaacgcc aaatggtaca aaatgcttta tattgttctc tatatattat attaacacat    1620
cgttattttta acctaggtct tagttatgta caaggttaca taaaatagat gttcctagtc    1680
cattcctccg tgtatgttgt gtctattata aagcaaggct gcattttgta atcagtcaat    1740
ttcaatataa aaaagttgca tcgtttttttt ttactkttcg acaattaaat tcaagtagca    1800
aaaaataacc caccttaatt tgtcatggtc ataatgaaac aatgacaarg ttttttttat    1860
cgcccgatac atgtacgtgt tctccaaaat gcagtctccg cgccgccaag cgaacgttca    1920
```

| | |
|---|---:|
| aactgtgcga tttccgttgt ccccaggcaa aatgatcatc aacgattacg ccaggaagca | 1980 |
| taatctgaac atcttcgacg ggctcgagct gaggaactcg acacgccact ccatttcgga | 2040 |
| tggcgatgaa aaacgcccac cgcaacctaa gcaagtctca aagtaaggtt ccatttaaat | 2100 |
| catctcaaaa ccgttagaaa cactcaaaaa gaaaccaaaa ttctgttcgg aaaccgacct | 2160 |
| ttgtttttta cacacactta gaccgaattt gcaaatttta accccttatt cctaaaacta | 2220 |
| gcaatggtaa gctcggctga atttcacata caaacggagt ttcgttctca ttataaaact | 2280 |
| gcgtgttgga ttgtaatgga actttgcaca tacaatgaca tgaggtatgt ctagggctga | 2340 |
| aattagttta tacttggtat ctgaggctac ataaactaat tacagcctta gacttggagg | 2400 |
| atttaacaac tggaaacacc ttgtctgtaa ttctctgtac aacgatttta cggggagga | 2460 |
| gcaaatatgt cagttaaacg tcagtccaaa caatacatat gactattggc cgtggtattt | 2520 |
| cgacggaggg gtaataagct cttaaaggcg actccgatat gcctaatcct attgttagta | 2580 |
| caaagtttca gagcaattta gctagtcgtt ttaaaatgag agcgtaacta cgttagcttg | 2640 |
| ctcttcttcc tcctgctctt atcccacgtt atgtggggtc ggcacaacat gttcctctct | 2700 |
| tctcactcct ttctttctca tatcctcttt cacacaatcc atccatcgtt tacttacaac | 2760 |
| cgagcttgct ggggaccgtt aaggcgccgc gagttcaggt tcttctctca ctctcactct | 2820 |
| cactggtgtg agcggagcga gacagcgttt tattttcgcc ttatcgaggt tccactgtat | 2880 |
| tataaataac ttacatttat aaagacgctg taatcgataa gaagttgagt cacgcttacg | 2940 |
| tcgcttacgt actacgtata gtaacgtagc ctgccgttta caaacaatgt acggagctac | 3000 |
| aacgttgcaa gttcggtccc cacacaacac aatgtgtcat aacacattaa caacattgtt | 3060 |
| acacacccac acatacaaat ttgctaagtt gataaaagag tggtgtgtcc gacgaatcag | 3120 |
| aacatcacta acccagtcgt gatttcattt ccacagtgac cggacgaagg tggagaagtt | 3180 |
| cgaaatttaa aaaaagtgac cacatttttat ttaatagtga tgtgcaagtg atactatttt | 3240 |
| tattttgttt ttcttttgta ggaaaatgct gagcgaaata aataaatttta gtggtgtgct | 3300 |
| atcgtcatcg atgaagttgt tttgcgaatg atactatgtt cttcaagtgc tgtgttttgt | 3360 |
| ggactgtggg gtgactgttc ctgtaaataa gcttcgttg | 3399 |

<210> SEQ ID NO 45
<211> LENGTH: 996
<212> TYPE: DNA
<213> ORGANISM: Cydia pomonella

<400> SEQUENCE: 45

| | |
|---|---:|
| catcagacgg gcccaggctc aggatgaagc tagagcgcgg gcggcggacg cagggctcca | 60 |
| ccctcccggg atcgagctag atcggcctga gccgccagtg gtgaaagcgc cgaggagtcc | 120 |
| cgtgatcccg ccgccgccgc cgcgctccat gggatcggcg agctgcgact ccgttccggg | 180 |
| atcgcccggg gtatcgccgt atgcgccgca cccgccgtcc gctccgcctc cgccgatgcc | 240 |
| gccgctcccg cctccgcaac cagtggcctt ggactccctg gtagaaaact gccacaagct | 300 |
| gctggaaaaa ttccactaca gttgggagat gatgccgctc gtgctggtca tcctcaacta | 360 |
| cgccggctcc gacctggagg aggcctcgcg gaagattgac gaagcctcct gggtggtgca | 420 |
| ccagtggcgg ctgtacgagc gctcactgtg ctcgctgctg gagctgcaag cgcgcaaaga | 480 |
| gtcgttttgc tgctcgccgc gctatgtgct gtcgcgcgag tacgcgccgc acctgcccgt | 540 |
| gccgctcatg cgctcgccgc cgccagcgca cttgtagccc cacaccgcgc cgcgacagac | 600 |
| ggcgcacgag cccactgagc catctacttc ggccaaaccc gagtaggccc gaggccgacc | 660 |

```
cgagcccgac ccgagaggac ccgagtgggc tattccggac tttacctagt tttatatgtg    720
ctatacgtgt tacaacacgc atatttgtat attatcacgg acattaagtt ggagagcggt    780
taccttatct tgttaacccg gtccttgaag taattattcc cagatatatt aagaaaacca    840
gtgaatactt tgcctgatgt ataattaaca gttgttaagc aaccatgaga attatggtat    900
ttcttgtgga catgttgcag ctagaaattt catatcatcg gtgataaaat ttaaccacac    960
tgtggttggc ggaaaaccac attgtttgta atattg                             996
```

<210> SEQ ID NO 46
<211> LENGTH: 6751
<212> TYPE: DNA
<213> ORGANISM: Artificial Sequence
<220> FEATURE:
<223> OTHER INFORMATION: Synthetic construct, pLA3435-Bombyx mori-dsx construct/plasmid.
<220> FEATURE:
<221> NAME/KEY: misc_feature
<222> LOCATION: (1617)..(1622)
<223> OTHER INFORMATION: At positions 1617-1622, n, at each occurrence, is a, c, g, or t

<400> SEQUENCE: 46

```
ggccgcatgg tacccattgc ttgtcattta ttaatttgga tgatgtcatt tgttttttaaa    60 attgaactgg ctttacgagt agaattctac gcgtaaaaca caatcaagta tgagtcataa   120
tctgatgtca tgttttgtac acggctcata accgaactgg ctttacgagt agaattctac   180
ttgtaatgca cgatcagtgg atgatgtcat ttgttttttca aatcgagatg atgtcatgtt   240
ttgcacacgg ctcataaact cgctttacga gtagaattct acgtgtaacg cacgatcgat   300
tgatgagtca tttgttttgc aatatgatat catacaatat gactcatttg ttttcaaaa   360 ccgaacttga tttacgggta gaattctact tgtaaagcac aatcaaaaag atgatgtcat   420 ttgttttttca aaactgaact cgctttacga gtagaattct acgtgtaaaa cacaatcaag   480
aaatgatgtc atttgttata aaaataaaag ctgatgtcat gttttgcaca tggctcataa   540
ctaaactcgc tttacgggta gaattctacg cgtaaaacat gattgataat taaataattc   600
atttgcaagc tatacgttaa atcaaacgga cgctcgaggt tgcacaacac tattatcgat   660
ttgcagttcg ggacataaat gtttaaatat atcgatgtct tgtgatgcg cgcgacattt   720 ttgtaggtta ttgataaaat gaacggatac gttgcccgac attatcatta aatccttggc   780
gtagaatttg tcgggtccat tgtccgtgtg cgctagcatg cccgtaacgg acctcgtact   840
tttggcttca aaggttttgc gcacagacaa aatgtgccac acttgcagct ctgcatgtgt   900
gcgcgttacc acaaatccca acggcgcagt gtacttgttg tatgcaaata aatctcgata   960
aaggcgcggc gcgcgaatgc agctgatcac gtacgctcct cgtgttccgt tcaaggacgg  1020
tgttatcgac ctcagattaa tgtttatcgg ccgactgttt tcgtatccgc tcaccaaacg  1080 cgttttgca ttaacattgt atgtcggcgg atgttctata tctaatttga ataaataaac  1140
gataaccgcg ttggttttag agggcataat aaaagaaata ttgttatcgt gttcgccatt  1200
agggcagtat aaattgacgt tcatgttgga tattgtttca gttgcaagtt gacactggcg  1260
gcgacaagca attctaattg gggtaagttt tcccgttctt ttctgggttc ttcccttttg  1320
ctcatccttg ctgcactacc ttcaggtgca agttgagatt caggccacca tgggagatcc  1380 cacccaccc aagaagaagc gcaaaccggt ccgtcccctc ggagacgctt gtggagaact  1440
gtcacagact cctcgagaag ttccattact cgtgggagat gatgccgctt gtgctcgtca  1500
```

```
tcatgaacta cgcccgcagc gacttggatg aggcttcaag gaaaatctac gaaggtaccg   1560
aatgtgtaaa tacgagtgta gcgttgatta gaaaacggac attgttcgtg agtttannnn   1620
nnggtctctc tggccagcaa gacatttgaa acactgtaaa aaaattcatt gaaaaaaaag   1680
aacactgtaa tgaaaatatt ctgaatgctt aatctggtat ttcagggatt aaactgattg   1740
tgatgaaaag tgattaaact attttcttta agtaccaaat taaccgaaca ggtttgggtc   1800
tttcctttca gtaacaaaca aaatctatcg aaggtaagaa ataaacaaca ggatattttc   1860
ttttactaaa aatcaataag gagactgcac tatttcaatg ttcaacttcc tttatcgaat   1920
gcatgaaaaa tttaattgtc taaaaatcta aattactaat taacgcaaag gaacctttgc   1980
ctaaaaaaaa aaataagcta ttaaacgaat gcctaaaata cgtaacagtg ttgccagttg   2040
taaaaattgc gaatccgaga agtgcagttt cctgaaatgc ccagcgatac gaatttccta   2100
tgttagagtc ttgtccgcag ggaagatgat cgtcgacgag tacgcgagga agcacaactt   2160
gaacgtgttc gacggactag aactaaggaa ctcgacacgc caggcgcgcc ggatccggcc   2220
ggccgaaaat gctggaaatt aataatataa gtggtgtact gtcttcgtca atgaagttat   2280
tttgcgaatg atacttagtt ttacaagtgc cgtggtgtgt gttgacactt gctgtgcgat   2340
gctgtgcgaa tttcaacgga aatatttgtt gtcgtaacat tggatctatg ggtaagttta   2400
gtataataac tttactctgt tcacattagt gaaacataca tttgtaaaat ttgtgtttta   2460
ctaatgtgaa atttattttt ggaaattcac gttaacacta ttgaataaaa aaaaatcgat   2520
aatgtaattt aaaaaaaata caaaaatata gttttcgctt attgttagaa agaaaatttt   2580
acatacgcca ttttgaataa ttccttccgg gtacattggg ccctaaacca gcgatcgggg   2640
aacttttttta attattaccc taaaatattt ttatgtaagt tgatattacc gatggcgaag   2700
aacaacaaaa aaaaaacga aatcgcttct ttttagcatc tttcatatta tagaccccac   2760
gataatttta aatcacaacg attataaaga agtttcactt caatatatac ttttttactca   2820
caaaagtttc atttttaccc catttgggat aatttagccc ggttccccccc ccgaccgctg   2880
gcctaaacgt atcaccgaca atagctaaaa taacaaggta cgttcgattt gccgagctga   2940
actaacatta cacagctttg cattattcat atgtacattg cgactgaaac gtccggaccg   3000
ttacaggtta ttggatgatg catcaatggc gattgcagca gtattcgttg tgctacggag   3060
cgctggagtt gtcggcgcgc aaggatgtgg ccgcgctatg ttgcctccga gatacgtgct   3120
ggcgcccgag gtcccgccgc gtctggtgcc cctccagctg atctagataa ctgatcataa   3180
tcagccatac cacatttgta gaggttttac ttgctttaaa aaacctccca cacctccccc   3240
tgaacctgaa acataaaatg aatgcaattg ttgttgttaa cttgtttatt gcagcttata   3300
atggttacaa ataaagcaat agcatcacaa atttcacaaa taaagcattt ttttcactgc   3360
attctagttg tggtttgtcc aaactcatca atgtatctta acgcgagtta attaagtgcg   3420
cgtaaattgt aagcgttaat attttgttaa aattcgcgtt aaattttgt taaatcagct   3480
cattttttaa ccaataggcc gaaatcggca aaatccctta taaatcaaaa gaatagaccg   3540
agatagggtt gagtgttgtt ccagtttgga acaagagtcc actattaaag aacgtggact   3600
ccaacgtcaa agggcgaaaa accgtctatc agggcgatgg cccactacgt gaaccatcac   3660
cctaatcaag ttttttgggg tcgaggtgcc gtaaagcact aaatcggaac cctaaaggga   3720
gcccccgatt tagagcttga cggggaaagc cggcgaacgt ggcgagaaag gaagggaaga   3780
aagcgaaagg agcgggcgct agggcgctgg caagtgtagc ggtcacgctg cgcgtaacca   3840
ccacacccgc cgcgcttaat gcgccgctac agggcgcgtc aggtggcact tttcggggaa   3900
```

-continued

```
atgtgcgcgg aacccctatt tgtttatttt tctaaataca ttcaaatatg tatccgctca   3960
tgagacaata accctgataa atgcttcaat aatattgaaa aaggaagagt cctgaggcgg   4020
aaagaaccag ctgtggaatg tgtgtcagtt agggtgtgga aagtcccag gctccccagc    4080
aggcagaagt atgcaaagca tgcatctcaa ttagtcagca accaggtgtg aaagtcccc    4140
aggctcccca gcaggcagaa gtatgcaaag catgcatctc aattagtcag caaccatagt   4200
cccgcccta actccgccca tcccgcccct aactccgccc agttccgccc attctccgcc    4260
ccatggctga ctaattttt ttatttatgc agaggccgag gccgcctcgg cctctgagct    4320
attccagaag tagtgaggag cttttttgg aggcctaggc ttttgcaaag atcgatcaag    4380
agacaggatg aggatcgttt cgcatgattg aacaagatgg attgcacgca ggttctccgg   4440
ccgcttgggt ggagaggcta ttcggctatg actgggcaca acagacaatc ggctgctctg   4500
atgccgccgt gttccggctg tcagcgcagg ggcgcccggt tcttttgtc aagaccgacc    4560
tgtccggtgc cctgaatgaa ctgcaagacg aggcagcgcg gctatcgtgg ctggccacga   4620
cgggcgttcc ttgcgcagct gtgctcgacg ttgtcactga agcgggaagg gactggctgc   4680
tattgggcga agtgccgggg caggatctcc tgtcatctca ccttgctcct gccgagaaag   4740
tatccatcat ggctgatgca atgcggcggc tgcatacgct tgatccggct acctgcccat   4800
tcgaccacca agcgaaacat cgcatcgagc gagcacgtac tcggatggaa gccggtcttg   4860
tcgatcagga tgatctggac gaagagcatc aggggctcgc gccagccgaa ctgttcgcca   4920
ggctcaaggc gagcatgccc gacggcgagg atctcgtcgt gacccatggc gatgcctgct   4980
tgccgaatat catggtggaa aatggccgct tttctggatt catcgactgt ggccggctgg   5040
gtgtggcgga ccgctatcag gacatagcgt tggctacccg tgatattgct gaagagcttg   5100
gcggcgaatg ggctgaccgc ttcctcgtgc tttacggtat cgccgctccc gattcgcagc   5160
gcatcgcctt ctatcgcctt cttgacgagt tcttctgagc gggactctgg ggttcgaaat   5220
gaccgaccaa gcgacgccca acctgccatc acgagatttc gattccaccg ccgccttcta   5280
tgaaaggttg ggcttcggaa tcgttttccg ggacgccggc tggatgatcc tccagcgcgg   5340
ggatctcatg ctggagttct tcgcccaccc taggggagg ctaactgaaa cacgaaagga    5400
gacaataccg gaaggaaccc gcgctatgac ggcaataaaa agacagaata aaacgcacgg   5460
tgttgggtcg tttgttcata aacgcggggt tcggtcccag ggctggcact ctgtcgatac   5520
cccaccgaga ccccattggg gccaatacgc ccgcgtttct tccttttccc caccccaccc   5580
cccaagttcg ggtgaaggcc cagggctcgc agccaacgtc ggggcggcag gccctgccat   5640
agcctcaggt tactcatata actttagat tgatttaaaa cttcatttt aatttaaaag    5700
gatctaggtg aagatccttt tgataatct catgaccaaa atcccttaac gtgagttttc     5760
gttccactga gcgtcagacc ccgtagaaaa gatcaaagga tcttcttgag atccttttt     5820
tctgcgcgta atctgctgct tgcaaacaaa aaaaccaccg ctaccagcgg tggtttgttt   5880
gccggatcaa gagctaccaa ctcttttcc gaaggtaact ggcttcagca gagcgcagat    5940
accaaatact gtccttctag tgtagccgta gttaggccac cacttcaaga actctgtagc   6000
accgcctaca tacctcgctc tgctaatcct gttaccagtg gctgctgcca gtggcgataa   6060
gtcgtgtctt accgggttgg actcaagacg atagttaccg gataaggcgc agcggtcggg   6120
ctgaacgggg ggttcgtgca cacagcccag cttggagcga acgacctaca ccgaactgag   6180
atacctacag cgtgagctat gagaaagcgc cacgcttccc gaagggagaa aggcggacag   6240
```

```
gtatccggta agcggcaggg tcggaacagg agagcgcacg agggagcttc caggggggaaa    6300 cgcctggtat ctttatagtc ctgtcgggtt tcgccacctc tgacttgagc gtcgattttt    6360
gtgatgctcg tcaggggggc ggagcctatg gaaaaacgcc agcaacgcgg ccttttttacg   6420 gttcctggcc ttttgctggc cttttgctca catgttcttt cctgcgttat ccctgattc     6480 tgtggataac cgtattaccg ccatgcatta gttattaata gtaatcaatt acgggtcat     6540 tagttcatag cccatatatg gagttccgcg ttacataact tacggtaaat ggcccgcctg    6600
gctgaccgcc caacgacccc cgcccattga cgtcaataat gacgtatgtt cccatagtaa    6660
cgccaatagg gactttccat tgacgtcaat gggtggagta tttacggtaa actgcccact    6720
tggcagtaca tcaagtgtat catagcgatg c                                   6751

<210> SEQ ID NO 47
<211> LENGTH: 8183
<212> TYPE: DNA
<213> ORGANISM: Artificial Sequence
<220> FEATURE:
<223> OTHER INFORMATION: Synthetic construct, pLA3359-Anopheles gambiae
      dsx construct

<400> SEQUENCE: 47
ccggtgctgc tgttgctgat gctacgatcc tcgacagtga ttggaaacgc ctggagatgg      60
tgggaaaaaa tcaaacacaa aaacggtcct aatgaacatc gtgtgttctc attcgctgcc    120
acgattgaca ccttcgataa gacgcacata atgagctaaa ggagaggggga cagggtcttg    180 tctttgccac gagcgataag attgcaatca ctcgtgagcg tgtgctgctg ggctgaagaa    240
gaaacacttt ccacagcagt aggtgggaag tgggattgtg aacgtggca ttgaaaagaa     300 cctatttttct aaagcccgag agcccgttct cgaactggaa aacgagatgc agaagttttt   360
tattgtcccc cgccaggaaa acaaatgtat ttaatgcttt ctctgccttt tccgccccgt    420
ttcagacgac gagctagtga agcgagccca atggctgttg agaaaactcg gctaccgtg    480 ggagatgatg cccctgatgt acgtcatact gaagagcgcc gatggcgatg tacaaaaagc    540
acaccagcgg atcgacgaag gtaagctggc gatgatggtg tcgttcgaca tcactttcat    600
caccgtgtca gacatctact gtgcctagca ccggtccagt ggtcacaggg tgtagcaaaa    660
acgtgttctt ttttgcgaga gactctacct catgatgcag ctgttaagga aaggtttcag    720
atgaagacaa ttttttcctag gataatatga tcttaagtta cctgcgtatg agtgtttaac   780
attgtcgtct caactccaag gaatgtttta accgtctagg gctagtttat ttatactgtt    840
ctcattgaaa tgtcgttaaa tccaacatgt taagttagct agctcagaca cgagaagtta    900
ggagtatctg catcttgaag gtagcggcat atggtgttat gccacgttca ctgacttcaa    960
aattcgatac aaaaaaaaac aaaatcaaaa acaaaattgt gaattccgtc agccagcagc    1020
agtgaccttc aaagccttac ctttccattc atttatgttt aacacaggtc aagcggtggt    1080
caacgaatac tcacgattgc ataatctgaa catgtttgat ggcgtggagt tgcgcaatac    1140
cacccgtcag agtggatgat aaactttccg caccactgta actgtccgta tctttgtatg    1200
tgggtgtgtg tatgtgtgtt tggtgaaacg aattcaattg ttctgtgcta tttttaaatca   1260 agccgcgtgc gcaactgatg ccgataagtt caaactagtt tttaaggagt ggagagagag    1320
agccgcacca cggtacagaa gggcagcaga atgggtcggc agcctagctg cactggtgcg    1380
gtgcgtccgg cgtctcgggg ggagggcggg gaaattctag tgttaaatcg gagcagcaaa    1440 aacaaaaacag tggtcgtccc gttcaagaaa cggcctgtac acacacagaa aacactgcag    1500
```

```
catgtttgta catagtagat cctagagcag gtggtcgttg ctcctcgaac gctctggacg    1560
cacggcttcg cgcgtacttg cgtagcgttc caccgatcgt gggtattcgt actgccacaa    1620
gcccgctttc tcccatgcaa tctctgcaac caaaccaaca acaacaaca aaataccaat     1680 cgacacaatg aatcacaccc cttttgtatc atctgtatat tcttgttctt tgcgttcttt    1740
tccatgtggc ccacgccccg gcgggtacgt aattgcgtcg aaaacccga aaccccggc     1800 acatacagtg tacatacggt ttgaggacaa ctttgacctg cagcccttct ggggctgcca    1860
cgtgtagcta tacttgtgag atcgggcgcc gacggtgtaa agcgcgaatg ccgccacac    1920 agtgtgtcca ctccaacact acccctctgg aactaccccg tccagggatg caccggctcg    1980
gctcatgccc ctgcaaaaca gtccgggctc cactgtagta gctccggcgt tgctctgaga    2040
gaaggatgcc cttcgaagtg tcgaaagcgt gcattgggcg ttcaagtgtg tgtctgtgtt    2100
aggtttagcg agaaacagca gcagttgcgt gtgctgaaaa gcgaaggagt aatagagtgc    2160
ataatgaaaa tgaaaatgaa aatgaagcaa aagtagaagg cggaggagag caacctgtgt    2220
tccactagta gcgaatagtt tagtctagtt tcgtcaccaa tcaaccttcc aaccatcgtt    2280
caaccaatac ctgagtcaac atcgtcatcg ttatcgtgcc acaactttat taaaaatgaa    2340
ccttgtccgc gccaccgtag ggtgatctga ggcgaccttt cttacgggcg cgactcacat    2400
gccatcgtca ccttctccaa tcaaaaccaa cagcctgtac cgatggtgtg caattgtgcg    2460
tgcgtgtgtg ttattagcaa aaaaagagaa agagacggcg agagagagat agatcgagat    2520
cgagagtaca aaagagcagt agaaatgttc gttgtttgtt ttccgtaaca cagttgttta    2580
gccaaaatgg gaatttccaa taatcccggg ggcggggaaa tgcgggaata ctgcgtacac    2640
acatacatca atcaaaaaga aaaatccttg cgctacatca ctaccgtttg cgcggtgctg    2700
atctagagca gaccactttc cacgccattc tacaatcaat caatctgtgc agaaggtatg    2760
gtaagacggc ctttgagcga gtcacggtcg ccaccataac gccgtccgac gagggctgaa    2820
tgcgaacttt gctaatcgat tttcgcttt ctttttatcc cacccccctt tctctctctc    2880
tcttttgcac cgccccttgt aaccccaaa aaggtaaacg acacattaag acctacgaag    2940
cgctggtgaa gtcatcgctc gatccgaaca gcgaccggct gacggaagac gacgacgagg    3000
acgagaacat ctcggtgacc cgcaccaact ccaccattcg gtcgaggtcc agctcgctgt    3060
cgcggtcccg gtcctgctcg cgccaggccg aaactccccg ggccgacgat cgggccctga    3120
accttgacac caaatagatc tcgacccaag aaaaagcgga aggtggagga cccgtaagat    3180
ccaccggatc tagataactg atcataatca gccataccac atttgtagag gttttacttg    3240
ctttaaaaaa cctcccacac ctcccctga acctgaaaca taaaatgaat gcaattgttg     3300
ttgttaactt gttattgca gcttataatg gttacaaata aagcaatagc atcacaaatt    3360
tcacaaataa agcatttttt tcactgcatt ctagttgtgg tttgtccaaa ctcatcaatg    3420
tatcttaacg cgagttaatt aagtgcgcgt aaattgtaag cgttaatatt ttgttaaaat    3480
tcgcgttaaa ttttttgttaa atcagctcat ttttaacca ataggccgaa atcggcaaaa    3540
tcccttataa atcaaagaa tagaccgaga tagggttgag tgttgttcca gtttggaaca    3600
agagtccact attaaagaac gtggactcca acgtcaaagg gcgaaaaacc gtctatcagg    3660
gcgatggccc actacgtgaa ccatcaccct aatcaagttt tttggggtcg aggtgccgta    3720
aagcactaaa tcggaaccct aaagggagcc cccgatttag agcttgacgg ggaaagccgg    3780
cgaacgtggc gagaaaggaa gggaagaaag cgaaaggagc gggcgctagg gcgctggcaa    3840
gtgtagcggt cacgctgcgc gtaaccacca cacccgccgc gcttaatgcg ccgctacagg    3900
```

```
gcgcgtcagg tggcactttt cggggaaatg tgcgcggaac ccctatttgt ttatttttct    3960
aaatacattc aaatatgtat ccgctcatga gacaataacc ctgataaatg cttcaataat    4020
attgaaaaag gaagagtcct gaggcggaaa gaaccagctg tggaatgtgt gtcagttagg    4080
gtgtggaaag tccccaggct ccccagcagg cagaagtatg caaagcatgc atctcaatta    4140
gtcagcaacc aggtgtggaa agtccccagg ctccccagca ggcagaagta tgcaaagcat    4200
gcatctcaat tagtcagcaa ccatagtccc gcccctaact ccgcccatcc cgcccctaac    4260
tccgcccagt tccgcccatt ctccgcccca tggctgacta atttttttta tttatgcaga    4320
ggccgaggcc gcctcggcct ctgagctatt ccagaagtag tgaggaggct tttttggagg    4380
cctaggcttt tgcaaagatc gatcaagaga caggatgagg atcgtttcgc atgattgaac    4440
aagatggatt gcacgcaggt tctccggccg cttgggtgga gaggctattc ggctatgact    4500
gggcacaaca gacaatcggc tgctctgatg ccgccgtgtt ccggctgtca gcgcaggggc    4560
gcccggttct ttttgtcaag accgacctgt ccggtgccct gaatgaactg caagacgagg    4620
cagcgcggct atcgtggctg gccacgacgg gcgttccttg cgcagctgtg ctcgacgttg    4680
tcactgaagc gggaagggac tggctgctat tgggcgaagt gccggggcag gatctcctgt    4740
catctcacct tgctcctgcc gagaaagtat ccatcatggc tgatgcaatg cggcggctgc    4800
atacgcttga tccggctacc tgcccattcg accaccaagc gaaacatcgc atcgagcgag    4860
cacgtactcg gatggaagcc ggtcttgtcg atcaggatga tctggacgaa gagcatcagg    4920
ggctcgcgcc agccgaactg ttcgccaggc tcaaggcgag catgcccgac ggcgaggatc    4980
tcgtcgtgac ccatggcgat gcctgcttgc cgaatatcat ggtggaaaat ggccgctttt    5040
ctggattcat cgactgtggc cggctgggtg tggcggaccg ctatcaggac atagcgttgg    5100
ctacccgtga tattgctgaa gagcttggcg gcgaatgggc tgaccgcttc ctcgtgcttt    5160
acggtatcgc cgctcccgat tcgcagcgca tcgccttcta tcgccttctt gacgagttct    5220
tctgagcggg actctggggt tcgaaatgac cgaccaagcg acgcccaacc tgccatcacg    5280
agatttcgat tccaccgccg ccttctatga aaggttgggc ttcggaatcg ttttccggga    5340
cgccggctgg atgatcctcc agcgcgggga tctcatgctg gagttcttcg cccaccctag    5400
ggggaggcta actgaaacac ggaaggagac aataccggaa ggaacccgcg ctatgacggc    5460
aataaaaaga cagaataaaa cgcacggtgt tgggtcgttt gttcataaac gcggggttcg    5520
gtcccagggc tggcactctg tcgataccccа ccgagaccc cattggggcc aatacgcccg    5580
cgtttcttcc ttttccccac cccacccccc aagttcgggt gaaggcccag gctcgcagc    5640 caacgtcggg gcggcaggcc ctgccatagc ctcaggttac tcatatatac tttagattga    5700
tttaaaactt cattttaat ttaaaaggat ctaggtgaag atccttttg ataatctcat    5760 gaccaaaatc ccttaacgtg agttttcgtt ccactgagcg tcagaccccg tagaaaagat    5820
caaaggatct tcttgagatc ctttttttct gcgcgtaatc tgctgcttgc aaacaaaaaa    5880
accaccgcta ccagcggtgg tttgtttgcc ggatcaagag ctaccaactc ttttccgaa    5940 ggtaactggc ttcagcagag cgcagatacc aaatactgtc cttctagtgt agccgtagtt    6000
aggccaccac ttcaagaact ctgtagcacc gcctacatac ctcgctctgc taatcctgtt    6060
accagtggct gctgccagtg gcgataagtc gtgtcttacc gggttggact caagacgata    6120
gttaccggat aaggcgcagc ggtcgggctg aacgggggt tcgtgcacac agcccagctt    6180
ggagcgaacg acctacaccg aactgagata cctacagcgt gagctatgag aaagcgccac    6240
```

| | | | | |
|---|---|---|---|---|
| gcttcccgaa | gggagaaagg | cggacaggta | tccggtaagc | ggcagggtcg gaacaggaga | 6300 |
| gcgcacgagg | gagcttccag | ggggaaacgc | ctggtatctt | tatagtcctg tcgggtttcg | 6360 |
| ccacctctga | cttgagcgtc | gattttttgtg | atgctcgtca | ggggggcgga gcctatggaa | 6420 |
| aaacgccagc | aacgcggcct | ttttacggtt | cctggccttt | tgctggcctt ttgctcacat | 6480 |
| gttctttcct | gcgttatccc | ctgattctgt | ggataaccgt | attaccgcca tgcattagtt | 6540 |
| attaatagta | atcaattacg | gggtcattag | ttcatagccc | atatatggag ttccgcgtta | 6600 |
| cataacttac | ggtaaatggc | ccgcctggct | gaccgcccaa | cgaccccccgc ccattgacgt | 6660 |
| caataatgac | gtatgttccc | atagtaacgc | caatagggac | tttccattga cgtcaatggg | 6720 |
| tggagtattt | acggtaaact | gcccacttgg | cagtacatca | agtgtatcat agcgatgcgg | 6780 |
| ccgcatggta | cccattgctt | gtcatttatt | aatttggatg | atgtcatttg tttttaaaat | 6840 |
| tgaactggct | ttacgagtag | aattctacgc | gtaaaacaca | atcaagtatg agtcataatc | 6900 |
| tgatgtcatg | ttttgtacac | ggctcataac | cgaactggct | ttacgagtag aattctactt | 6960 |
| gtaatgcacg | atcagtggat | gatgtcattt | gttttttcaaa | tcgagatgat gtcatgtttt | 7020 |
| gcacacggct | cataaactcg | ctttacgagt | agaattctac | gtgtaacgca cgatcgattg | 7080 |
| atgagtcatt | tgttttgcaa | tatgatatca | tacaatatga | ctcatttgtt tttcaaaacc | 7140 |
| gaacttgatt | tacgggtaga | attctacttg | taaagcacaa | tcaaaaagat gatgtcattt | 7200 |
| gtttttcaaa | actgaactcg | ctttacgagt | agaattctac | gtgtaaaaca caatcaagaa | 7260 |
| atgatgtcat | ttgttataaa | aataaaagct | gatgtcatgt | tttgcacatg gctcataact | 7320 |
| aaaactcgctt | tacgggtaga | attctacgcg | taaaacatga | ttgataatta aataattcat | 7380 |
| ttgcaagcta | tacgttaaat | caaacggacg | ctcgaggttg | cacaacacta ttatcgattt | 7440 |
| gcagttcggg | acataaatgt | ttaaatatat | cgatgtctttt | gtgatgcgcg cgacattttt | 7500 |
| gtaggttatt | gataaaatga | acggatacgt | tgcccgacat | tatcattaaa tccttggcgt | 7560 |
| agaatttgtc | gggtccattg | tccgtgtgcg | ctagcatgcc | cgtaacggac ctcgtacttt | 7620 |
| tggcttcaaa | ggttttgcgc | acagacaaaa | tgtgccacac | ttgcagctct gcatgtgtgc | 7680 |
| gcgttaccac | aaatcccaac | ggcgcagtgt | acttgttgta | tgcaaataaa tctcgataaa | 7740 |
| ggcgcggcgc | gcgaatgcag | ctgatcacgt | acgctcctcg | tgttccgttc aaggacggtg | 7800 |
| ttatcgacct | cagattaatg | tttatcggcc | gactgttttc | gtatccgctc accaaacgcg | 7860 |
| tttttgcatt | aacattgtat | gtcggcggat | gttctatatc | taatttgaat aaataaacga | 7920 |
| taaccgcgtt | ggttttagag | ggcataataa | aagaaatatt | gttatcgtgt tcgccattag | 7980 |
| ggcagtataa | attgacgttc | atgttggata | ttgtttcagt | tgcaagttga cactggcggc | 8040 |
| gacaagcaat | tctaattggg | gtaagttttc | ccgttctttt | ctgggttctt ccctttttgct | 8100 |
| catccttgct | gcactacctt | caggtgcaag | ttgagattca | ggccaccatg ggagatccca | 8160 |
| ccccacccaa | gaagaagcgc | aaa | | | 8183 |

<210> SEQ ID NO 48
<211> LENGTH: 7342
<212> TYPE: DNA
<213> ORGANISM: Artificial Sequence
<220> FEATURE:
<223> OTHER INFORMATION: Synthetic construct, pLA3433-Agdsx (Anopheles gambiae) construct with exon 2 included

<400> SEQUENCE: 48
ctagtgtcga cgatgtaggt cacggtctcg aagccgcggt gcgggtgcca gggcgtgccc        60

```
ttgggctccc cgggcgcgta ctccacctca cccatctggt ccatcatgat gaacgggtcg    120
aggtggcggt agttgatccc ggcgaacgcg cggcgcaccg ggaagccctc gccctcgaaa    180
ccgctgggcg cggtggtcac ggtgagcacg ggacgtgcga cggcgtcggc gggtgcggat    240
acgcggggca gcgtcagcgg gttctcgacg gtcacggcgg gcatgtcgac cgccggcgcc    300
ttaattaact cgcgttaaga tacattgatg agtttggaca aaccacaact agaatgcagt    360
gaaaaaaatg cttttatttgt gaaatttgtg atgctattgc tttatttgta accattataa    420
gctgcaataa acaagttaac aacaacaatt gcattcattt tatgtttcag gttcaggggg    480
aggtgtggga ggttttttaa agcaagtaaa acctctacaa atgtggtatg ctgattatg     540
atcagttatc tagatccggt ggatcttacg ggtcctccac cttccgcttt tcttgggtc     600
gagatctgag tccggaatcc tcgtcgctac cgatggcgct ggtgatgcgg ggcacgctgt    660
gggcgtaggt cacctcgcgc tggcacacgt ggtcgcgctt gtcgctggtg tccctcatct    720
gcttggtgat gatggtcacg aagtgggggc cggggatctt gatggcgcgg ctgccgttga    780
aggtcatctt gctgtcgaag tgcccatca tcaggccgcc gtcggcggtg gtgaagccga     840
tgaaggccag ctggcgcacg gcgttgggc cgtggggaa catgtgggtc tcgttgggca     900
ggatgtccac cagctggtcg cgcatgatgg ggccgtcggg ctggaagccg tcgcagttca    960
cggtgatgcg gctgaccacg caggtgccgt ccagctcgta ggtgtggtgg ctggtcatgg   1020
tgccgtcgtt ctcgaagcgc acggtgcggt cgatgctcag gccctcgggg aagcactcct   1080
gggcgaagtg gctgatgccg ttggggtagc gggcgaagaa gggctcgccg tactggatca   1140
ggtggcagat gggcttccag ctcatgggca gcttgccggt ctcgcacacg gcgtgcacgt   1200
tgaagtcgcc gtgggggaac ttgctgctgc cgtcggccac gatggtgaac ttctggccgt   1260
tcacctcgcc gtcgatgaag attttgaagg tcatgtcgct ctggaacagg gcggggccgc   1320
cctctgaacc atcctcgtcc atggtggcga ccggtttgcg cttcttcttg ggtgggtgg    1380
gatccaccag agacaggttg cggcggcggt tggatggcgt gggcgcgttg gcgttgttgg   1440
accggctcat gttgtgtcgc tgtaacagat gctgttcaac tgtgtttacc agatcgttgc   1500
gggctgtatt tataggcgcg ataagcggga cgggcgcctc gtgtccggtc acgcgcatga   1560
gataacgcgc ggctgatatg gaggcgcgtc ctgttccgat aaggagttgc gtccggctgc   1620
ggttagcaac acaggaagct ggcgtcctgt cacgataaga caacactcgt ccggtccgat   1680
aatgtgattc gtacgtgaca ggacgcgacc cgataaggcc ggcctacgtg actgccgaca   1740
cgtactttt tgcactgcaa aaaggttcaa tgtgtggtag tgtatttgga gcgtatacaa    1800
cggtgtagac tatttatgta aaatagtcta cgaaacgtag agtttgtact atgtatgggc   1860
ccgcgtgcaa aagcgtgttt ttttgcagtg caaaaaagtt ggtggtgggg aggccaccga   1920
gtatggtacc atgcggccgc gtacgcgccc ggggagccca agggcacgcc ctggcacccg   1980
tccggtgctt atctagagcg cgcttggcgt aatcatggtc atagctgttt cctgtgtgaa   2040
attgttatcc gctcacaatt ccacacaaca tacgagccgg aagcataaag tgtaaagcct   2100
ggggtgccta atgagtgagc taactcacat taattgcgtt gcgctcactg cccgctttcc   2160
agtcgggaaa cctgtcgtgc cagctgcatt aatgaatcgg ccaacgcgcg gggagaggcg   2220
gtttgcgtat tgggcgctct tccgcttcct cgctcactga ctcgctgcgc tcggtcgttc   2280
ggctgcggcg agcggtatca gctcactcaa aggcggtaat acggttatcc acagaatcag   2340
gggataacgc aggaaagaac atgtgagcaa aaggccagca aaaggccagg aaccgtaaaa   2400
aggccgcgtt gctggcgttt ttccataggc tccgcccccc tgacgagcat cacaaaaatc   2460
```

```
gacgctcaag tcagaggtgg cgaaacccga caggactata aagataccag gcgtttcccc    2520
ctggaagctc cctcgtgcgc tctcctgttc cgaccctgcc gcttaccgga tacctgtccg    2580
cctttctccc ttcgggaagc gtggcgcttt ctcatagctc acgctgtagg tatctcagtt    2640
cggtgtaggt cgttcgctcc aagctgggct gtgtgcacga accccccgtt cagcccgacc    2700
gctgcgcctt atccggtaac tatcgtcttg agtccaaccc ggtaagacac gacttatcgc    2760
cactggcagc agccactggt aacaggatta gcagagcgag gtatgtaggc ggtgctacag    2820
agttcttgaa gtggtggcct aactacggct acactagaag gacagtattt ggtatctgcg    2880
ctctgctgaa gccagttacc ttcggaaaaa gagttggtag ctcttgatcc ggcaaacaaa    2940
ccaccgctgg tagcggtggt ttttttgttt gcaagcagca gattacgcgc agaaaaaaag    3000
gatctcaaga agatcctttg atcttttcta cggggtctga cgctcagtgg aacgaaaact    3060
cacgttaagg gattttggtc atgagattat caaaaaggat cttcacctag atccttttaa    3120
attaaaaatg aagttttaaa tcaatctaaa gtatatatga gtaaacttgg tctgacagtt    3180
accaatgctt aatcagtgag gcacctatct cagcgatctg tctatttcgt tcatccatag    3240
ttgcctgact ccccgtcgtg tagataacta cgatacggga gggcttacca tctggcccca    3300
gtgctgcaat gataccgcga gacccacgct caccggctcc agatttatca gcaataaacc    3360
agccagccgg aagggccgag cgcagaagtg gtcctgcaac tttatccgcc tccatccagt    3420
ctattaattg ttgccgggaa gctagagtaa gtagttcgcc agttaatagt ttgcgcaacg    3480
ttgttgccat tgctacaggc atcgtggtgt cacgctcgtc gtttggtatg gcttcattca    3540
gctccggttc ccaacgatca aggcgagtta catgatcccc catgttgtgc aaaaaagcgg    3600
ttagctcctt cggtcctccg atcgttgtca agtaagtt ggccgcagtg ttatcactca    3660
tggttatggc agcactgcat aattctctta ctgtcatgcc atccgtaaga tgcttttctg    3720
tgactggtga gtactcaacc aagtcattct gagaatagtg tatgcggcga ccgagttgct    3780
cttgcccggc gtcaatacgg gataataccg cgccacatag cagaacttta aaagtgctca    3840
tcattggaaa acgttcttcg gggcgaaaac tctcaaggat cttaccgctg ttgagatcca    3900
gttcgatgta acccactcgt gcacccaact gatcttcagc atcttttact ttcaccagcg    3960
tttctgggtg agcaaaaaca ggaaggcaaa atgccgcaaa aaagggaata agggcgacac    4020
ggaaatgttg aatactcata ctcttccttt ttcaatatta ttgaagcatt tatcagggtt    4080
attgtctcat gagcggatac atatttgaat gtatttagaa aaataaacaa ataggggttc    4140
cgcgcacatt tccccgaaaa gtgccaccta aattgtaagc gttaatattt tgttaaaatt    4200
cgcgttaaat ttttgttaaa tcagctcatt ttttaaccaa taggccgaaa tcggcaaaat    4260
cccttataaa tcaaaagaat agaccgagat agggttgagt gttgttccag tttggaacaa    4320
gagtccacta ttaaagaacg tggactccaa cgtcaaaggg cgaaaaaccg tctatcaggg    4380
cgatggccca ctacgtgaac catcacccta atcaagtttt ttggggtcga ggtgccgtaa    4440
agcactaaat cggaacccta agggagcccc cgatttagag cttgacggg gaaagccggc    4500 gaacgtggcg agaaaggaag ggaagaaagc gaaaggagcg ggcgctaggg cgctggcaag    4560
tgtagcggtc acgctgcgcg taaccaccac acccgccgcg cttaatgcgc cgctacaggg    4620
cgcgtcccat tcgccattca ggctgcgcaa ctgttgggaa gggcgatcgg tgcgggcctc    4680
ttcgctatta cgccagctgg cgaaaggggg atgtgctgca aggcgattaa gttgggtaac    4740
gccagggttt tcccagtcac gacgttgtaa aacgacggcc agtgagcgcg ctagcgttta    4800
```

```
aacgagctct aagatacatt gatgagtttg acaaaccac aactagaatg cagtgaaaaa    4860
aatgctttat ttgtgaaatt tgtgatgcta ttgctttatt tgtaaccatt ataagctgca    4920
ataaacaagt taacaacaac aattgcattc attttatgtt tcaggttcag ggggaggtgt    4980
gggaggtttt ttaaagcaag taaaacctct acaaatgtgg tatggctgat tatgatcctg    5040
cagctacgcc gctacgtctt ccgtgccgtc ctgggcgtcg tcttcgtcgt cgtcggtcgg    5100
cggcttcgcc cacgtgatcg aagcgcgctt ctcgatgggc gttccctgcc ccctgcccgt    5160
agtcgacttc gtgacaacga tcttgtctac gaagagcccg acgaacacgc gcttgtcgtc    5220
tactgacgcg cgcccccacc acgacttagg gccggtcggg tcagcgtcgg cgtcttcggg    5280
gaaccattgg tcaaggggaa gcttcggggc ttcggcggct tcaagttcgg caagccgctc    5340
ttccgcccct tgctgccgga gcgtcagcgc tgcctgttgc ttccggaagt gcttcctgcc    5400
aacgggtccg tcgtacgcgc ctgccgcgcg gtcttcgtac agctcttcaa gggcgttcag    5460
ggcgtcggcg cgctccgcaa caaggttcgc ccgttcgccg ctcttctcag gcgcctcagt    5520
gagcttgccg aagcgtcggg cggcttccca cagaagcgcc aacgtctctt cgtcgccttc    5580
ggcgtgcctg atcttgttga agatgcgttc cgcaacgaac ttgtcgagtg ccgccatgct    5640
gacgttgcac gtgccttcgt gctgcccagg tgcgacgggt cgaccacct tccggcgacg    5700 gcagcggtaa gagtccttga tcgattcttc cccgcgcttc gaagtcatga cggcgccaca    5760
ctcgcagtac agcttgtcca tggcggacag aatggcttgc ccccgggaaa gccccttgcc    5820
gcgccccctg ccgtccaacc acgcctgaag ctcataccac tcagcgggct cgatgatcgg    5880
tccgcaatca agctcgaccg gccggagcgt gatcgggtcg cgctgaatgc ggtaaccctc    5940
aatcttcgtg gtcggcgtgc cgtccggctt cttcttgtag atcacctcag cggcgaagcc    6000
cgcaatacgc gggtcccgaa ggattcgcat aacggttgcc gggtcccagg cgcttgaagc    6060
ggtcttcttc ccaatcgtct cgccccgggt cggcacggcg tcagcgtcca tgcgcttaca    6120 aagcccgtg atgctgcccg ggtgaatggc ggcttgactg cccggcttga agggaaggtg    6180
tttgtgcgtc ttgatctcac gccaccacca ccggattacg tcgggctcga actcgaaggg    6240
tccggtaagg ggagtggtcg agtgcgcaag cttgttgatg acgacattga ccattcggcc    6300
gttgcgcgtg atctccttcg tctccgaaac aagctcgaag ccgtaaggcg ccttcccgcc    6360
gacgtacccg cccaattcgc gctgaaggtt cttcgtgtcg agaatcttcg ccgacttcag    6420
cgaagattct ttgtgcgacg cgtcgagccg cataatcagg tgaatcaggt ccatgacgtt    6480
tccctgccgg aagacgcctt cctgagtgga acaatcgtc acgcccaggg cgagcaattc    6540
cgagacaatc ggaatcgcgt ccatgacctt caggcgcgag aagcgcgaca cgtcatagac    6600
aatgatcatg ttgagccgcc cggcgcggca ttcgttcagg atgcgttcga actccgggcg    6660
ctccgccgtc ccgaacgccg acgtgcccgg cgcttcgctg aaatgcccga cgaacctgaa    6720
ccggcccccg tcgcgctcga cttcgcgctg aaggtcggcc gccttgtctt cgttggcgct    6780
acgctgtgtc gctgggcttg ctgcgctcga attctcgcgc tcgcgcgact gacggtcgta    6840
agcacccgcg tacgtgtcca tggcggatcc gtgtcgctgt aacagatgct gttcaactgt    6900
gtttaccaga tcgttgcggg ctgtatttat aggcgcgata agcgggacgg gcgcctcgtg    6960
tccggtcacg cgcatgagat aacgcgcggc tgatatggag gcgcgtcctg ttccgataag    7020
gagttgcgtc cggctgcggt tagcaacaca ggaagctggc gtcctgtcac gataagacaa    7080
cactcgtccg gtccgataat gtgattcgta cgtgacagga cgcgaccgga taaggccggc    7140
ctacgtgact gccgacacgt actttttgc actgcaaaaa ggttcaatgt gtggtagtgt    7200
```

```
atttggagcg tatacaacgg tgtagactat ttatgtaaaa tagtctacga aacgtagagt    7260
ttgtactatg tatgggcccg cgtgcaaaag cgtgtttttt tgcagtgcaa aaagttggt     7320 ggtggggagg ccaccgagta ta                                              7342
```

<210> SEQ ID NO 49
<211> LENGTH: 11868
<212> TYPE: DNA
<213> ORGANISM: Artificial Sequence
<220> FEATURE:
<223> OTHER INFORMATION: Synthetic construct, pLA1188-cctra intron construct

<400> SEQUENCE: 49

```
gtggttttttg tcaaacgaag attctatgac gtgtttaaag tttaggtcga gtaaagcgca      60 aatcttttt  aaccctagaa agatagtctg cgtaaaattg acgcatgcat tcttgaaata     120
ttgctctctc tttctaaata gcgcgaatcc gtcgctgtgc atttaggaca tctcagtcgc     180
cgcttggagc tcccgtgagg cgtgcttgtc aatgcgtaa  gtgtcactga ttttgaacta     240
taacgaccgc gtgagtcaaa atgacgcatg attatctttt acgtgacttt taagatttaa     300
ctcatacgat aattatattg ttatttcatg ttctacttac gtgataactt attatatata     360
tattttcttg ttatagatat cgtgactaat atataataaa atgggtagtt ctttagacga     420
tgagcatatc ctctctgctc ttctgcaaag cgatgacgag cttgttggtg aggattctga     480
cagtgaaata tcagatcacg taagtgaaga tgacgtccag agcgatacag aagaagcgtt     540
tatagatgag gtacatgaag tgcagccaac gtcaagcggt agtgaaatat tagacgaaca     600
aaatgttatt gaacaaccag gttcttcatt ggcttctaac agaatcttga ccttgccaca     660
gaggactatt agaggtaaga ataaacattg ttggtcaact tcaaagtcca cgaggcgtag     720
ccgagtctct gcactgaaca ttgtcagatc ggcccgggcg gccgtttttc ttgaaatatt     780
gctctctctt tctaaatagc gcgaatccgt cgctgtgcat ttaggacatc tcagtcgccg     840
cttggagctc caaacgcgc  cagtggtagt acacagtact gtgggtgttc agtttgaaat     900
cctcttgctt ctccattgtc tcggttacct ttggtcaaat ccatgggttc tattgcctat     960
atactcttgc gattaccagt gattgcgcta ttagctatta gatggattgt tggccaaact    1020
tgtcgcttaa gtggctggga attgtaaccg taggcccgag tgtaatgatc ccccataaaa    1080
agttttcgca atgcctttat ttttgttgc  aaatctctct ttattctgcg gtattcttca    1140
ttattgcggg gatggggaaa gtgtttatat agaagcaact tacgattgaa cccaaatgca    1200
cctgacaagc aaggtcaaag ggccagattt taaatatat  tatttagtct taggactctc    1260
tatttgcaat taaattactt tgctacctga gggttaaatc ttccccattg ataataataa    1320
ttccactata tgttcaattg ggtttcaccg cgcttagtta catgacgagc cctaatgagc    1380
cgtcggtggt ctataaactg tgccttacaa atacttgcaa ctcttctcgt tttgaagtca    1440
gcagagttat tgctaattgc taattgctaa ttgcttttaa ctgatttctt cgaaattggt    1500
gctatgttta tggcgctatt aacaagtatg aatgtcaggt ttaaccaggg gatgcttaat    1560
tgtgttctca acttcaaagg cagaaatgtt tactcttgac catgggttta ggtataatgt    1620
tatcaagctc ctcgagttaa cgttacgtta acgttaacgt tcgaggtcga ctctagaact    1680
acccaccgta ctcgtcaatt ccaagggcat cggtaaacat ctgctcaaac tcgaagtcgg    1740
ccatatccag agcgccgtag ggggcggagt cgtgggggt  aaatcccgga cccggggaat    1800
ccccgtcccc caacatgtcc agatcgaaat cgtctagcgc gtcggcatgc gccatcgcca    1860
```

-continued

```
cgtcctcgcc gtctaagtgg agctcgtccc ccaggctgac atcggtcggg ggggccgtcg   1920
acagtctgcg cgtgtgtccc gcggggagaa aggacaggcg cggagccgcc agccccgcct   1980 cttcggggc gtcgtcgtcc gggagatcga gcaggccctc gatggtagac ccgtaattgt   2040
ttttcgtacg cgcgcggctg tacgcggggc ccgagcccga ctcgcatttc agttgctttt   2100
ccaatccgca gataatcagc tccaagccga acaggaatgc cggctcggct ccttgatgat   2160
cgaacagctc gattgcctga cgcagcagtg ggggcatcga atcggttgtt ggggtctcgc   2220
gctcctcttt tgcgacttga tgctcttggt cctccagcac gcagcccagg gtaaagtgac   2280
cgacggcgct cagagcgtag agagcatttt ccaggctgaa gccttgctgg cacaggaacg   2340
cgagctggtt ctccagtgtc tcgtattgct tttcggtcgg gcgcgtgccg agatggactt   2400
tggcaccgtc tcggtgggac agcagagcgc agcggaacga cttggcgtta ttgcggagga   2460
agtcctgcca ggactcgcct ccaacgggc aaaaatgcgt gtggtggcgg tcgagcatct   2520
cgatggccag gcatccagc agcgcccgct tattcttcac ctatagatac catagatgta   2580
tggattagta tcatatacat acaaaggcta ttttttgggac atattaatat taacaatttc   2640
cgtgatagtt ttcaccatttt tgttgaatg ttacgttgaa aatttaaatt tgttttaaat   2700 taatttacc agtcatgtgt tcttaaaagt ttttatgatt gaaacggcat aaagtggttc   2760
aaaaatttat caagaaaggc tttccttttt taaatcttat ctttttctct taaaaatcac   2820
tagtcaattc attattaatt tgttaacttg aatttggaat gtctatttac tttcagataa   2880
attaaagcaa gaaacttaat attcgaaaaa aattgattct aaatggaatt tcacttgatc   2940
ttcatgtatg catatcaatt tttatttaca ttgtataata agtttcgagt tgattgttgt   3000
aatccacagg tgtcccagag aattaaattc caaattaccc aagtttattg aatgttgatt   3060
gtagtttcag ttgctttgtt gctgcaacaa tggcttgttg attgtagata ttttcccttt   3120
ccttggttta cttattacat agactgaaaa agaggtttac ttttttgata cttatgaaaa   3180
atttctatta gtgattacta accaatcgct atatgtttac tagaaaacaa ataaactctt   3240
tacattaaca ttcaataatg tttgctctgt aaccgacaat tgaaggcgtt acagcaacag   3300
taatataact agcttcttaa ccctcatcta ttaaccccat cgtttaaaac actatgttaa   3360
atggtctaac aaatctagat actaatagat gtcttattac ttagcagcca cagctgcaac   3420
atccaagaca atttttgaaa cttcttattg agctcttggc agcagaaatg ttggtatttt   3480
tcacagcttt ctgaaagacc ggcaccttcc tccggttccc gtttctgaat tcaagaggat   3540
ttccgacccc caattaatcc cgaaacaaat aaggtatatt caaaatgatg gaaaagtcat   3600
ggctgctgac cttattttta ttcctattga tagaatatta ttccccttt aaatacactg   3660 tactaagagg tccggctata attttactca cttgtcgatt atcccataga atgttgattg   3720
tagttggttg cttttccagg tgagagttga tcaagtcaca aaagttagcg tgtgttgatt   3780
gtagatttga aggtaaaata attttttgcac ccattcatcg ggtaaaacgt tctccataga   3840
atacatttcc atcgataatt gataacttat gaatttcaaa gaaaaaaata tgcttttaaa   3900
attacgtgcc agtagagggt gggctgctcc acgcccagct tctgcgccaa cttgcgggtc   3960
gtcagtccct caatgccaac ttcgttcaac agctccaacg cggagttgat gactttggac   4020
ttatccaggc ggctgcccat ggtggtttct aaaggtgtta taaatcaaat tagttttgtt   4080
ttttcttgaa aactttgcgt ttcctttgat caacttaccg ccagggtacc gcagattgtt   4140
tagcttgttc agctgcgctt gtttatttgc ttagctttcg cttagcgacg tgttcacttt   4200
```

```
gcttgtttga attgaattgt cgctccgtag acgaagcgcc tctatttata ctccggcgct    4260
cgttttcgag tttaccactc cctatcagtg atagagaaaa gtgaaagtcg agtttaccac    4320
tccctatcag tgatagagaa aagtgaaagt cgagtttacc actccctatc agtgatagag    4380
aaaagtgaaa gtcgagttta ccactcccta tcagtgatag agaaagtgaa agtcgagtt    4440
taccactccc tatcagtgat agagaaagt gaaagtcgag tttaccactc cctatcagtg    4500
atagagaaaa gtgaaagtcg agtttaccac tccctatcag tgatagagaa aagtgaaagt    4560
cgaaacctgg cgcgccccgg ccatcgagaa agagagagag aagagaagag agagaacatt    4620
cgagaaagag agagagaaga gaagagagag aacatactcc ctatcagtga tagagaagtc    4680
cctatcagtg atagagatgt ccctatcagt gatagagagt ccctatcag tgatagagac    4740
gtccctatca gtgatagaga agtccctatc agtgatagag agatccctat cagtgataga    4800
gatttcccta tcagtgatag agaggtccct atcagtgata gagacttccc tatcagtgat    4860
agagaaatcc ctatcagtga tagagacatc cctatcagtg atagagaact ccctatcagt    4920
gatagagacc tccctatcag tgatagagat cgatgcggcc gcatggtacc cattgcttgt    4980
catttattaa tttggatgat gtcatttgtt tttaaaattg aactggcttt acgagtagaa    5040
ttctacgcgt aaaacacaat caagtatgag tcataatctg atgtcatgtt ttgtacacgg    5100
ctcataaccg aactggcttt acgagtagaa ttctacttgt aatgcacgat cagtggatga    5160
tgtcatttgt ttttcaaatc gagatgatgt catgttttgc acacggctca taaactcgct    5220
ttacgagtag aattctacgt gtaacgcacg atcgattgat gagtcatttg ttttgcaata    5280
tgatatcata caatatgact catttgtttt tcaaaaccga acttgattta cgggtagaat    5340
tctacttgta aagcacaatc aaaaagatga tgtcatttgt ttttcaaaac tgaactcgct    5400
ttacgagtag aattctacgt gtaaaacaca atcaagaaat gatgtcattt gttataaaaa    5460
taaaagctga tgtcatgttt tgcacatggc tcataactaa actcgcttta cgggtagaat    5520
tctacgcgta aacatgatt gataattaaa taattcattt gcaagctata cgttaaatca    5580
aacggacgct cgaggttgca caacactatt atcgatttgc agttcgggac ataaatgttt    5640
aaatatatcg atgtctttgt gatgcgcgcg acatttttgt aggttattga taaaatgaac    5700
ggatacgttg cccgacatta tcattaaatc cttggcgtag aatttgtcgg gtccattgtc    5760
cgtgtgcgct agcatgcccg taacggacct cgtacttttg gcttcaaagg ttttgcgcac    5820
agacaaaatg tgccacactt gcagctctgc atgtgtgcgc gttaccacaa atcccaacgg    5880
cgcagtgtac ttgttgtatg caaataaatc tcgataaagg cgcggcgcgc gaatgcagct    5940
gatcacgtac gctcctcgtg ttccgttcaa ggacggtgtt atcgacctca gattaatgtt    6000
tatcggccga ctgttttcgt atccgctcac caaacgcgtt tttgcattaa cattgtatgt    6060
cggcggatgt tctatatcta atttgaataa ataaacgata accgcgttgg ttttagaggg    6120
cataataaaa gaaatattgt tatcgtgttc gccattaggg cagtataaat tgacgttcat    6180
gttggatatt gtttcagttg caagttgaca ctggcggcga caagcaattc taattggggt    6240
aagttttccc gttctttct gggttcttcc cttttgctca tccttgctgc actaccttca    6300
ggtgcaagtt gagattcagg ccaccatggg agatcccacc ccaccaaga agaagcgcaa    6360
accggtcgcc accatggcct cctccgagaa cgtcatcacc gagttcatgc gcttcaaggt    6420
gcgcatggag ggcaccgtga acggccacga gttcgagatc gagggcgagg gcgagggccg    6480
cccctacgag ggcacaaaca ccgtgaagct gaaggtgacc aagggcggcc cctgccctt    6540
cgcctgggac atcctgtccc cccagttcca gtacggctcc aaggtgtacg tgaagcaccc    6600
```

```
cgccgacatc cccgactaca agaagctgtc cttccccgag ggcttcaagt gggagcgcgt    6660
gatgaacttc gaggacggcg gcgtggcgac cgtgacccag gactcctccc tgcaggacgg    6720
ctgcttcatc tacaaggtga agttcatcgg cgtgaacttc ccctccgacg gccccgtgat    6780
gcagaagaag accatgggct gggaggcctc caccgagcgc ctgtacccccc gcgacggcgt    6840 gctgaagggc gagacccaca aggccctgaa gctgaaggac ggcggccact acctggtgga    6900
gttcaagtcc atctacatgg ccaagaagcc cgtgcagctg cccggctact actacgtgga    6960
cgccaagctg gacatcacct cccacaacga ggactacacc atcgtggagc agtacgagcg    7020
caccgagggc cgcccaccacc tgttcctgag atctcgaccc aagaaaaagc ggaaggtgga    7080
ggacccgtaa gatccaccgg atctagataa ctgatcataa tcagccatac cacatttgta    7140
gaggttttac ttgctttaaa aaacctccca cacctccccc tgaacctgaa acataaaatg    7200
aatgcaattg ttgttgttaa cttgtttatt gcagcttata atggttacaa ataaagcaat    7260
agcatcacaa atttcacaaa taaagcattt ttttcactgc attctagttg tggtttgtcc    7320
aaactcatca atgtatctta acgcgagtta attaaggccg ctcatttaaa tctggccggc    7380
cgcaaccatt gtgggaaccg tgcgatcaaa caaacgcgag ataccggaag tactgaaaaa    7440
cagtcgctcc aggccagtgg gaacatcgat gttttgtttt gacggacccc ttactctcgt    7500
ctcatataaa ccgaagccag ctaagatggt atacttatta tcatcttgtg atgaggatgc    7560
ttctatcaac gaaagtaccg gtaaaccgca atggttatg tattataatc aaactaaagg    7620
cggagtggac acgctagacc aaatgtgttc tgtgatgacc tgcagtagga agacgaatag    7680
gtggcctatg gcattattgt acggaatgat aaacattgcc tgcataaatt cttttattat    7740
atacagccat aatgtcagta gcaagggaga aaggtccaa agtcgcaaaa aatttatgag    7800
aaacctttac atgagcctga cgtcatcgtt tatgcgtaag cgtttagaag ctcctacttt    7860
gaagagatat ttgcgcgata atatctctaa tattttgcca aatgaagtgc ctggtacatc    7920
agatgacagt actgaagagc cagtaatgaa aaaacgtact tactgtactt actgcccctc    7980
taaaataagg cgaaaggcaa atgcatcgtg caaaaaatgc aaaaaagtta tttgtcgaga    8040
gcataatatt gatatgtgcc aaagttgttt ctgactgact aataagtata atttgtttct    8100
attatgtata agttaagcta attacttatt ttataataca acatgactgt ttttaaagta    8160
caaaataagt ttattttttgt aaaagagaga atgtttaaaa gttttgttac tttatagaag    8220
aaattttgag ttttttgttt ttttaataa ataaataaac ataaataaat tgtttgttga    8280
atttattatt agtatgtaag tgtaaatata ataaacttta atatctattc aaattaataa    8340
ataaacctcg atatacagac cgataaaaca catgcgtcaa ttttacgcat gattatcttt    8400
aacgtacgtc acaatatgat tatctttcta gggttaaata atagtttcta attttttat    8460 tattcagcct gctgtcgtga ataccgtata tctcaacgct gtctgtgaga ttgtcgtatt    8520
ctagcctttt tagtttttcg ctcatcgact tgatattgtc cgacacattt tcgtcgattt    8580
gcgttttgat caaagacttg agcagagaca cgttaatcaa ctgttcaaat tgatccatat    8640
taacgatatc aacccgatgc gtatatggtg cgtaaaatat attttttaac cctcttatac    8700
tttgcactct gcgttaatac gcgttcgtgt acagacgtaa tcatgttttc ttttttggat    8760
aaaactccta ctgagtttga cctcatatta gaccctcaca agttgcaaaa cgtggcattt    8820
tttaccaatg aagaatttaa agttatttta aaaaatttca tcacagattt aaagaagaac    8880
caaaaattaa attatttcaa cagtttaatc gaccagttaa tcaacgtgta cacagacgcg    8940
```

```
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc ccctttcgcc agctggcgta atagcgaaga   9240
ggcccgcacc gatcgccctt cccaacagtt gcgcagcctg aatggcgaat ggcgcctgat   9300
gcggtatttt ctccttacgc atctgtgcgg tatttcacac cgcatatggt gcactctcag   9360
tacaatctgc tctgatgccg catagttaag ccagccccga cacccgccaa cacccgctga   9420
cgcgccctga cgggcttgtc tgctcccggc atccgcttac agacaagctg tgaccgtctc   9480
cgggagctgc atgtgtcaga ggttttcacc gtcatcaccg aaacgcgcga cgcgaaaggg   9540
cctcgtgata cgcctatttt tataggttaa tgtcatgata ataatggttt cttagacgtc   9600
aggtggcact tttcggggaa atgtgcgcgg aaccccctat tgtttatttt tctaaataca   9660
ttcaaatatg tatccgctca tgagacaata accctgataa atgcttcaat aatattgaaa   9720
aaggaagagt atgagtattc aacatttccg tgtcgccctt attccctttt ttgcggcatt   9780
ttgccttcct gtttttgctc acccagaaac gctggtgaaa gtaaaagatg ctgaagatca   9840
gttgggtgca cgagtgggtt acatcgaact ggatctcaac agcggtaaga tccttgagag   9900
ttttcgcccc gaagaacgtt ttccaatgat gagcactttt aaagttctgc tatgtggcgc   9960
ggtattatcc cgtattgacg ccgggcaaga gcaactcggt cgccgcatac actattctca  10020
gaatgacttg gttgagtact caccagtcac agaaaagcat cttacggatg gcatgacagt  10080
aagagaatta tgcagtgctg ccataaccat gagtgataac actgcggcca acttacttct  10140
gacaacgatc ggaggaccga aggagctaac cgcttttttg cacaacatgg gggatcatgt  10200
aactcgcctt gatcgttggg aaccggagct gaatgaagcc ataccaaacg acgagcgtga  10260
caccacgatg cctgtagcaa tggcaacaac gttgcgcaaa ctattaactg gcgaactact  10320
tactctagct tcccggcaac aattaataga ctggatggag gcggataaag ttgcaggacc  10380
acttctgcgc tcggcccttc cggctggctg gtttattgct gataaatctg gagccggtga  10440
gcgtgggtct cgcggtatca ttgcagcact ggggccagat ggtaagccct cccgtatcgt  10500
agttatctac acgacgggga gtcaggcaac tatggatgaa cgaaatagac agatcgctga  10560
gataggtgcc tcactgatta agcattggta actgtcagac caagtttact catatatact  10620
ttagattgat ttaaaacttc attttttaatt taaaaggatc taggtgaaga tcctttttga  10680
taatctcatg accaaaatcc cttaacgtga gttttcgttc cactgagcgt cagaccccgt  10740
agaaaagatc aaaggatctt cttgagatcc ttttttttctg cgcgtaatct gctgcttgca  10800
aacaaaaaaa ccaccgctac cagcggtggt ttgtttgccg gatcaagagc taccaactct  10860
ttttccgaag gtaactggct tcagcagagc gcagatacca atactgtcc ttctagtgta  10920
gccgtagtta ggccaccact tcaagaactc tgtagcaccg cctacatacc tcgctctgct  10980
aatcctgtta ccagtggctg ctgccagtgg cgataagtcg tgtcttaccg ggttggactc  11040
aagacgatag ttaccggata aggcgcagcg gtcgggctga acggggggtt cgtgcacaca  11100
gcccagcttg gagcgaacga cctacaccga actgagatac ctacagcgtg agcattgaga  11160
aagcgccacg cttcccgaag ggagaaaggc ggacaggtat ccggtaagcg cagggtcgg   11220
aacaggagag cgcacgaggg agcttccagg gggaaacgcc tggtatcttt atagtcctgt  11280
cgggtttcgc cacctctgac ttgagcgtcg atttttgtga tgctcgtcag ggggggcggag  11340
```

```
cctatggaaa aacgccagca acgcggcctt tttacggttc ctggccttttt gctggccttt    11400
tgctcacatg ttctttcctg cgttatcccc tgattctgtg ataaccgta ttaccgcctt    11460
tgagtgagct gataccgctc gccgcagccg aacgaccgag cgcagcgagt cagtgagcga    11520
ggaagcggaa gagcgcccaa tacgcaaacc gcctctcccc gcgcgttggc cgattcatta    11580
atgcagctgg cacgacaggt ttcccgactg gaaagcgggc agtgagcgca acgcaattaa    11640
tgtgagttag ctcactcatt aggcacccca ggctttacac tttatgcttc cggctcgtat    11700
gttgtgtgga attgtgagcg gataacaatt tcacacagga aacagctatg accatgatta    11760
cgaatttcga cctgcaggca tgcaagcttg catgcctgca ggtcgacgct cgcgcgactt    11820
ggtttgccat tctttagcgc gcgtcgcgtc acacagcttg ccacaat               11868
```

<210> SEQ ID NO 50
<211> LENGTH: 11868
<212> TYPE: DNA
<213> ORGANISM: Artificial Sequence
<220> FEATURE:
<223> OTHER INFORMATION: Synthetic construct, pLA3077-a Cctra
      intron-tTAV construct.

<400> SEQUENCE: 50

```
gtggttttttg tcaaacgaag attctatgac gtgtttaaag tttaggtcga gtaaagcgca      60
aatcttttt aaccctagaa agatagtctg cgtaaaattg acgcatgcat tcttgaaata     120
ttgctctctc tttctaaata gcgcgaatcc gtcgctgtgc atttaggaca tctcagtcgc     180
cgcttggagc tcccgtgagg cgtgcttgtc aatgcggtaa gtgtcactga ttttgaacta     240
taacgaccgc gtgagtcaaa atgacgcatg attatctttt acgtgacttt taagatttaa     300
ctcatacgat aattatattg ttatttcatg ttctacttac gtgataactt attatatata     360
tatttcttg ttatagatat cgtgactaat atataataaa atgggtagtt ctttagacga     420
tgagcatatc ctctctgctc ttctgcaaag cgatgacgag cttgttggtg aggattctga     480
cagtgaaata tcagatcacg taagtgaaga tgacgtccag agcgatacag aagaagcgtt     540
tatagatgag gtacatgaag tgcagccaac gtcaagcggt agtgaaatat tagacgaaca     600
aaatgttatt gaacaaccag gttcttcatt ggcttctaac agaatcttga ccttgccaca     660
gaggactatt agaggtaaga ataaacattg ttggtcaact tcaaagtcca cgaggcgtag     720
ccgagtctct gcactgaaca ttgtcagatc ggcccgggcg ccgttttttct tgaaatattg     780
ctctctcttt ctaaatagcg cgaatccgtc gctgtgcatt taggacatct cagtcgccgc     840
ttggagctcc caaacgcgcc agtggtagta cacagtactg tgggtgttca gtttgaaatc     900
ctcttgcttc tccattgtct cggttacctt tggtcaaatc catgggttct attgcctata     960
tactcttgcg attaccagtg attgcgctat tagctattag atggattgtt ggccaaactt    1020
gtcgcttaag tggctgggaa ttgtaaccgt aggcccgagt gtaatgatcc cccataaaaa    1080
gttttcgcaa tgccttttatt ttttgttgca aatctctctt tattctgcgg tattcttcat    1140
tattgcgggg atggggaaag tgtttatata gaagcaactt acgattgaac ccaaatgcac    1200
ctgacaagca aggtcaaagg gccagatttt taaatatatt atttagtctt aggactctct    1260
atttgcaatt aaattacttt gctacctgag ggttaaatct tccccattga taataataat    1320
tccactatat gttcaattgg gtttcaccgc gcttagttac atgacgagcc ctaatgagcc    1380
gtcggtggtc tataaactgt gccttacaaa tacttgcaac tcttctcgtt ttgaagtcag    1440
cagagttatt gctaattgct aattgctaat tgcttttaac tgatttcttc gaaattggtg    1500
```

```
ctatgtttat ggcgctatta acaagtatga atgtcaggtt taaccagggg atgcttaatt    1560
gtgttctcaa cttcaaaggc agaaatgttt actcttgacc atgggtttag gtataatgtt    1620
atcaagctcc tcgagttaac gttacgttaa cgttaacgtt cgaggtcgac tctagaacta    1680
cccaccgtac tcgtcaattc caagggcatc ggtaaacatc tgctcaaact cgaagtcggc    1740
catatccaga gcgccgtagg gggcggagtc gtgggggta aatcccggac ccggggaatc     1800
cccgtccccc aacatgtcca gatcgaaatc gtctagcgcg tcggcatgcg ccatcgccac    1860
gtcctcgccg tctaagtgga gctcgtcccc caggctgaca tcggtcgggg gggccgtcga    1920
cagtctgcgc gtgtgtcccg cggggagaaa ggacaggcgc ggagccgcca gccccgcctc    1980
ttcgggggcg tcgtcgtccg ggagatcgag caggccctcg atggtagacc cgtaattgtt    2040
tttcgtacgc gcgcggctgt acgcggggcc cgagcccgac tcgcatttca gttgcttttc    2100
caatccgcag ataatcagct ccaagccgaa caggaatgcc ggctcggctc cttgatgatc    2160
gaacagctcg attgcctgac gcagcagtgg gggcatcgaa tcggttgttg ggtctcgcg     2220 ctcctctttt gcgacttgat gctcttggtc ctccagcacg cagcccaggg taaagtgacc    2280 gacgcgctc agagcgtaga gagcattttc caggctgaag ccttgctggc acaggaacgc     2340
gagctggttc tccagtgtct cgtattgctt tcggtcggg cgcgtgccga gatggacttt     2400
ggcaccgtct cggtgggaca gcagagcgca gcggaacgac ttggcgttat tgcggaggaa    2460
gtcctgccag gactcgcctt ccaacgggca aaaatgcgtg tggtggcggt cgagcatctc    2520
gatggccagg gcatccagca gcgcccgctt attcttcacg tgccagtaga gggtgggctg    2580
ctccacgccc agcttctgcg ccaacttgcg ggtcgtcagt ccctcaatac ctatagatac    2640
catagatgta tggattagta tcatatacat acaaaggcta tttttgggac atattaatat    2700
taacaatttc cgtgatagtt ttcaccattt ttgttgaatg ttacgttgaa aatttaaatt    2760
tgttttaaat taattttacc agtcatgtgt tcttaaaagt ttttatgatt gaaacggcat    2820
aaagtggttc aaaaatttat caagaaaggc tttccttttt taaatcttat cttttttctct   2880 taaaaatcac tagtcaattc attattaatt tgttaacttg aatttggaat gtctatttac    2940
tttcagataa attaaagcaa gaaacttaat attcgaaaaa aattgattct aaatggaatt    3000
tcacttgatc ttcatgtatg catatcaatt tttatttaca ttgtataata agtttcgagt    3060
tgattgttgt aatccacagg tgtcccagag aattaaattc caaattaccc aagtttattg    3120
aatgttgatt gtagtttcag ttgctttgtt gctgcaacaa tggcttgttg attgtagata    3180
ttttcccttt ccttggttta cttattacat agactgaaaa agaggtttac tttttttgata   3240 cttatgaaaa atttctatta gtgattacta accaatcgct atatgtttac tagaaaacaa    3300
ataaactctt tacattaaca ttcaataatg tttgctctgt aaccgacaat tgaaggcgtt    3360
acagcaacag taatataact agcttcttaa ccctcatcta ttaaccccat cgtttaaaac    3420
actatgttaa atggtctaac aaatctagat actaatagat gtcttattac ttagcagcca    3480
cagctgcaac atccaagaca atttttgaaa cttcttattg agctcttggc agcagaaatg    3540
ttggtatttt tcacagcttt ctgaaagacc ggcaccttcc tccggttccc gtttctgaat    3600
tcaagaggat ttccgacccc caattaatcc cgaaacaaat aaggtatatt caaaatgatg    3660
gaaaagtcat ggctgctgac cttattttta ttcctattga tagaatatta ttcccctttt    3720
aaatacactg tactaagagg tccggctata attttactca cttgtcgatt atcccataga    3780
atgttgattg tagttggttg cttttccagg tgagagttga tcaagtcaca aaagttagcg    3840
```

```
tgtgttgatt gtagatttga aggtaaaata attttttgcac ccattcatcg ggtaaaacgt    3900
tctccataga atacatttcc atcgataatt gataacttat gaatttcaaa gaaaaaaata    3960
tgcttttaaa attaccaact tcgttcaaca gctccaacgc ggagttgatg actttggact    4020
tatccaggcg gctgcccatg gtggtttcta aaggtgttat aaatcaaatt agttttgttt    4080
tttcttgaaa actttgcgtt tcctttgatc aacttaccgc cagggtacct gcagattgtt    4140
tagcttgttc agctgcgctt gtttatttgc ttagcttttcg cttagcgacg tgttcacttt    4200
gcttgtttga attgaattgt cgctccgtag acgaagcgcc tctatttata ctccggcgct    4260
cgttttcgag tttaccactc cctatcagtg atagagaaaa gtgaaagtcg agtttaccac    4320
tccctatcag tgatagagaa aagtgaaagt cgagtttacc actccctatc agtgatagag    4380
aaaagtgaaa gtcgagttta ccactcccta tcagtgatag agaaaagtga agtcgagtt    4440 taccactccc tatcagtgat agagaaaagt gaaagtcgag tttaccactc cctatcagtg    4500
atagagaaaa gtgaaagtcg agtttaccac tccctatcag tgatagagaa aagtgaaagt    4560
cgaaacctgg cgcgccccgg ccatcgagaa agagagagag aagagaagag agaacatt    4620 cgagaaagag agagaagaga gaagagagag aacatactcc ctatcagtga tagagaagtc    4680
cctatcagtg atagagatgt ccctatcagt gatagagagt ccctatcag tgatagagac    4740 gtccctatca gtgatagaga agtccctatc agtgatagag agatccctat cagtgataga    4800
gatttcccta tcagtgatag agaggtccct atcagtgata gagacttccc tatcagtgat    4860
agagaaatcc ctatcagtga tagagacatc cctatcagtg atagagaact cccctatcagt    4920 gatagagacc tccctatcag tgatagagat cgatgcggcc gcatggtacc cattgcttgt    4980
catttattaa tttggatgat gtcatttgtt tttaaaattg aactggcttt acgagtagaa    5040
ttctacgcgt aaaacacaat caagtatgag tcataatctg atgtcatgtt ttgtacacgg    5100
ctcataaccg aactggcttt acgagtagaa ttctacttgt aatgcacgat cagtggatga    5160
tgtcatttgt ttttcaaatc gagatgatgt catgttttgc acacggctca taaactcgct    5220
ttacgagtag aattctacgt gtaacgcacg atcgattgat gagtcatttg ttttgcaata    5280
tgatatcata caatatgact catttgtttt tcaaaaccga acttgattta cgggtagaat    5340
tctacttgta aagcacaatc aaaaagatga tgtcatttgt ttttcaaaac tgaactcgct    5400
ttacgagtag aattctacgt gtaaaacaca atcaagaaat gatgtcattt gttataaaaa    5460
taaaagctga tgtcatgttt tgcacatggc tcataactaa actcgcttta cgggtagaat    5520
tctacgcgta aaacatgatt gataattaaa taattcattt gcaagctata cgttaaatca    5580
aacggacgct cgaggttgca caacactatt atcgatttgc agttcgggac ataaatgttt    5640
aaatatatcg atgtctttgt gatgcgcgcg acatttttgt aggttattga taaaatgaac    5700
ggatacgttg cccgacatta tcattaaatc cttggcgtag aatttgtcgg gtccattgtc    5760
cgtgtgcgct agcatgcccg taacggacct cgtactttg gcttcaaagg ttttgcgcac    5820
agacaaaatg tgccacactt gcagctctgc atgtgtgcgc gttaccacaa atcccaacgg    5880
cgcagtgtac ttgttgtatg caaataaatc tcgataaagg cgcggcgcgc gaatgcagct    5940
gatcacgtac gctcctcgtg ttccgttcaa ggacggtgtt atcgacctca gattaatgtt    6000
tatcggccga ctgttttcgt atccgctcac caaacgcgtt tttgcattaa cattgtatgt    6060
cggcggatgt tctatatcta atttgaataa ataaacgata accgcgttgg ttttagaggg    6120
cataataaaa gaaatattgt tatcgtgttc gccattaggg cagtataaat tgacgttcat    6180
gttggatatt gtttcagttg caagttgaca ctggcggcga caagcaattc taattggggt    6240
```

```
aagttttccc gttcttttct gggttcttcc cttttgctca tccttgctgc actaccttca   6300
ggtgcaagtt gagattcagg ccaccatggg agatcccacc ccacccaaga agaagcgcaa   6360
accggtcgcc accatggcct cctccgagaa cgtcatcacc gagttcatgc gcttcaaggt   6420
gcgcatggag ggcaccgtga acggccacga gttcgagatc gagggcgagg gcgagggccg   6480
cccctacgag ggccacaaca ccgtgaagct gaaggtgacc aagggcggcc ccctgccctt   6540
cgcctgggac atcctgtccc cccagttcca gtacggctcc aaggtgtacg tgaagcaccc   6600
cgccgacatc cccgactaca agaagctgtc cttccccgag ggcttcaagt gggagcgcgt   6660
gatgaacttc gaggacggcg gcgtggcgac cgtgacccag gactcctccc tgcaggacgg   6720
ctgcttcatc tacaaggtga agttcatcgg cgtgaacttc ccctccgacg gccccgtgat   6780
gcagaagaag accatgggct gggaggcctc caccgagcgc ctgtaccccc gcgacggcgt   6840
gctgaagggc gagacccaca aggccctgaa gctgaaggac ggcggccact acctggtgga   6900
gttcaagtcc atctacatgg ccaagaagcc cgtgcagctg cccggctact actacgtgga   6960
cgccaagctg gacatcacct cccacaacga ggactacacc atcgtggagc agtacgagcg   7020
caccgagggc cgccaccacc tgttcctgag atctcgaccc aagaaaaagc ggaaggtgga   7080
ggacccgtaa gatccaccgg atctagataa ctgatcataa tcagccatac cacatttgta   7140
gaggttttac ttgctttaaa aaacctccca cacctccccc tgaacctgaa acataaaatg   7200
aatgcaattg ttgttgttaa cttgtttatt gcagcttata atggttacaa ataaagcaat   7260
agcatcacaa atttcacaaa taaagcattt ttttcactgc attctagttg tggtttgtcc   7320
aaactcatca atgtatctta cgcgagtta  attaaggccg ctcatttaaa tctggccggc   7380
cgcaaccatt gtgggaaccg tgcgatcaaa caaacgcgag ataccggaag tactgaaaaa   7440
cagtcgctcc aggccagtgg gaacatcgat gttttgtttt gacggacccc ttactctcgt   7500
ctcatataaa ccgaagccag ctaagatggt atacttatta tcatcttgtg atgaggatgc   7560
ttctatcaac gaaagtaccg gtaaaccgca atggttatg  tattataatc aaactaaagg   7620
cggagtggac acgctagacc aaatgtgttc tgtgatgacc tgcagtagga agacgaatag   7680
gtggcctatg gcattattgt acggaatgat aaacattgcc tgcataaatt cttttattat   7740
atacagccat aatgtcagta gcaagggaga aaggtccaa  agtcgcaaaa aatttatgag   7800
aaacctttac atgagcctga cgtcatcgtt tatgcgtaag cgtttagaag ctcctacttt   7860
gaagagatat ttgcgcgata atatctctaa tattttgcca aatgaagtgc tggtacatc   7920
agatgacagt actgaagagc cagtaatgaa aaacgtact  tactgtactt actgcccctc   7980
taaaataagg cgaaggcaa  atgcatcgtg caaaaaatgc aaaaaagtta tttgtcgaga   8040
gcataatatt gatatgtgcc aaagttgttt ctgactgact aataagtata atttgtttct   8100
attatgtata agttaagcta attacttatt ttataataca acatgactgt ttttaaagta   8160
caaaataagt ttattttgt  aaagagaga atgtttaaaa gttttgttac tttatagaag   8220
aaatttgag  tttttgtttt tttttaataa ataaataaac ataaataaat tgtttgttga   8280
atttattatt agtatgtaag tgtaaatata ataaaactta atatctattc aaattaataa   8340
ataaacctcg atatacagac cgataaaaca catgcgtcaa tttacgcat  gattatcttt   8400
aacgtacgtc acaatatgat tatcttttcta gggttaaata atagtttcta atttttttat   8460
tattcagcct gctgtcgtga ataccgtata tctcaacgct gtctgtgaga ttgtcgtatt   8520
ctagcctttt tagttttttcg ctcatcgact tgatattgtc cgacacattt tcgtcgattt   8580
```

```
gcgttttgat caaagacttg agcagagaca cgttaatcaa ctgttcaaat tgatccatat   8640
taacgatatc aacccgatgc gtatatggtg cgtaaaatat attttttaac cctcttatac   8700
tttgcactct gcgttaatac gcgttcgtgt acagacgtaa tcatgttttc ttttttggat   8760
aaaactccta ctgagtttga cctcatatta gaccctcaca agttgcaaaa cgtggcattt   8820
tttaccaatg aagaatttaa agttatttta aaaaatttca tcacagattt aaagaagaac   8880
caaaaattaa attatttcaa cagtttaatc gaccagttaa tcaacgtgta cacagacgcg   8940
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc ccctttcgcc agctggcgta atagcgaaga   9240
ggcccgcacc gatcgccctt cccaacagtt gcgcagcctg aatggcgaat ggcgcctgat   9300
gcggtatttt ctccttacgc atctgtgcgg tatttcacac cgcatatggt gcactctcag   9360
tacaatctgc tctgatgccg catagttaag ccagccccga cacccgccaa cacccgctga   9420
cgcgccctga cgggcttgtc tgctcccggc atccgcttac agacaagctg tgaccgtctc   9480
cgggagctgc atgtgtcaga ggttttcacc gtcatcaccg aaacgcgcga cgcgaagggg   9540
cctcgtgata cgcctatttt tataggttaa tgtcatgata taatggtttt cttagacgtc   9600
aggtggcact tttcggggaa atgtgcgcgg aacccctatt tgtttatttt tctaaataca   9660
ttcaaatatg tatccgctca tgagacaata accctgataa atgcttcaat aatattgaaa   9720
aaggaagagt atgagtattc aacatttccg tgtcgccctt attccctttt ttgcggcatt   9780
ttgccttcct gtttttgctc acccagaaac gctggtgaaa gtaaaagatg ctgaagatca   9840
gttgggtgca cgagtgggtt acatcgaact ggatctcaac agcggtaaga tccttgagag   9900
ttttcgcccc gaagaacgtt ttccaatgat gagcactttt aaagttctgc tatgtggcgc   9960
ggtattatcc cgtattgacg ccgggcaaga gcaactcggt cgccgcatac actattctca  10020
gaatgacttg gttgagtact caccagtcac agaaaagcat cttacggatg gcatgacagt  10080
aagagaatta tgcagtgctg ccataaccat gagtgataac actgcggcca acttacttct  10140
gacaacgatc ggaggaccga aggagctaac cgcttttttg cacaacatgg ggatcatgt  10200
aactcgcctt gatcgttggg aaccggagct gaatgaagcc ataccaaacg acgagcgtga  10260
caccacgatg cctgtagcaa tggcaacaac gttgcgcaaa ctattaactg gcgaactact  10320
tactctagct tcccggcaac aattaataga ctggatggag gcggataaag ttgcaggacc  10380
acttctgcgc tcggcccttc cggctggctg gtttattgct gataaatctg gagccggtga  10440
gcgtgggtct cgcggtatca ttgcagcact ggggccagat ggtaagccct cccgtatcgt  10500
agttatctac acgacgggga gtcaggcaac tatggatgaa cgaaatagac agatcgctga  10560
gataggtgcc tcactgatta agcattggta actgtcagac caagtttact catatatact  10620
ttagattgat ttaaaacttc attttttaatt taaaaggatc taggtgaaga tcctttttga  10680
taatctcatg accaaaatcc cttaacgtga gttttcgttc cactgagcgt cagaccccgt  10740
agaaaagatc aaaggatctt cttgagatcc ttttttttctg cgcgtaatct gctgcttgca  10800
aacaaaaaaa ccaccgctac cagcggtggt ttgtttgccg gatcaagagc taccaactct  10860
ttttccgaag gtaactggct tcagcagagc gcagatacca aatactgtcc ttctagtgta  10920
gccgtagtta ggccaccact tcaagaactc tgtagcaccg cctacatacc tcgctctgct  10980
```

```
aatcctgtta ccagtggctg ctgccagtgg cgataagtcg tgtcttaccg ggttggactc    11040
aagacgatag ttaccggata aggcgcagcg gtcgggctga acgggggggtt cgtgcacaca    11100 gcccagcttg gagcgaacga cctacaccga actgagatac ctacagcgtg agcattgaga    11160
aagcgccacg cttcccgaag ggagaaaggc ggacaggtat ccggtaagcg gcagggtcgg    11220
aacaggagag cgcacgaggg agcttccagg gggaaacgcc tggtatcttt atagtcctgt    11280
cgggtttcgc cacctctgac ttgagcgtcg atttttgtga tgctcgtcag ggggcggag    11340 cctatggaaa aacgccagca acgcggcctt tttacggttc ctggccttttt gctggccttt    11400 tgctcacatg ttctttcctg cgttatcccc tgattctgtg ataaccgta ttaccgcctt    11460 tgagtgagct gataccgctc gccgcagccg aacgaccgag cgcagcgagt cagtgagcga    11520
ggaagcggaa gagcgcccaa tacgcaaacc gcctctcccc gcgcgttggc cgattcatta    11580
atgcagctgg cacgacaggt ttcccgactg gaaagcgggc agtgagcgca acgcaattaa    11640
tgtgagttag ctcactcatt aggcaccccca ggctttacac tttatgcttc cggctcgtat    11700
gttgtgtgga attgtgagcg gataacaatt tcacacagga aacagctatg accatgatta    11760
cgaatttcga cctgcaggca tgcaagcttg catgcctgca ggtcgacgct cgcgcgactt    11820
ggtttgccat tctttagcgc gcgtcgcgtc acacagcttg gccacaat                 11868

<210> SEQ ID NO 51
<211> LENGTH: 11788
<212> TYPE: DNA
<213> ORGANISM: Artificial Sequence
<220> FEATURE:
<223> OTHER INFORMATION: Synthetic construct, pLA3097-a Cctra
      intron-tTAV construct.

<400> SEQUENCE: 51
gggcggccgt ttttcttgaa atattgctct ctctttctaa atagcgcgaa tccgtcgctg       60
tgcatttagg acatctcagt cgccgcttgg agctcccaaa cgcgccagtg gtagtacaca      120
gtactgtggg tgttcagttt gaaatcctct tgcttctcca ttgtctcggt tacctttggt      180
caaatccatg ggttctattg cctatatact cttgcgatta ccagtgattg cgctattagc      240
tattagatgg attgttggcc aaacttgtcg cttaagtggc tgggaattgt aaccgtaggc      300
ccgagtgtaa tgatccccca taaaagtttt cgcaatgcc tttatttttt gttgcaaatc      360
tctctttatt ctgcggtatt cttcattatt gcggggatgg ggaaagtgtt tatatagaag      420
caacttacga ttgaacccaa atgcacctga caagcaaggt caaagggcca gattttttaaa     480 tatattattt agtcttagga ctctctattt gcaattaaat tactttgcta cctgagggtt      540
aaatcttccc cattgataat aataattcca ctatatgttc aattgggttt caccgcgctt      600
agttacatga cgagccctaa tgagccgtcg gtggtctata aactgtgcct tacaaatact      660
tgcaactctt ctcgttttga agtcagcaga gttattgcta attgctaatt gctaattgct      720
tttaactgat ttcttcgaaa ttggtgctat gtttatggcg ctattaacaa gtatgaatgt      780
caggtttaac caggggatgc ttaattgtgt tctcaacttc aaaggcagaa atgtttactc      840
ttgaccatgg gttaggtat aatgttatca agctcctcga gttaacgtta cgttaacgtt      900
aacgttcgag gtcgactcta gaactaccca ccgtactcgt caattccaag gcatcggta      960 aacatctgct caaactcgaa gtcggccata tccagagcgc cgtagggggc ggagtcgtgg     1020
ggggtaaatc ccgacccggg gaatccccg tccccaaca tgtccagatc gaaatcgtct      1080
agcgcgtcgg catgcgccat cgccacgtcc tcgccgtcta agtggagctc gtcccccagg     1140
```

```
ctgacatcgg tcggggggc cgtcgacagt ctgcgcgtgt gtcccgcggg gagaaaggac    1200
aggcgcggag ccgccagccc cgcctcttcg ggggcgtcgt cgtccgggag atcgagcagg    1260
ccctcgatgg tagacccgta attgtttttc gtacgcgcgc ggctgtacgc ggggcccgag    1320
cccgactcgc atttcagttg cttttccaat ccgcagataa tcagctccaa gccgaacagg    1380
aatgccggct cggctccttg atgatcgaac agctcgattg cctgacgcag cagtgggggc    1440
atcgaatcgg ttgttggggt ctcgcgctcc tcttttgcga cttgatgctc ttggtcctcc    1500
agcacgcagc ccagggtaaa gtgaccgacg gcgctcagag cgtagagagc attttccagg    1560
ctgaagcctt gctggcacag gaacgcgagc tggttctcca gtgtctcgta ttgcttttcg    1620
gtcgggcgcg tgccgagatg gactttggca ccgtctcggt gggacagcag agcgcagcgg    1680
aacgacttgg cgttattgcg gaggaagtcc tgccaggact cgccttccaa cgggcaaaaa    1740
tgcgtgtggt ggcggtcgag catctcgatg ccagggcat ccagcagcgc ccgcttattc    1800
ttcacgtgcc agtagagggt gggctgctcc acgcccagct tctgcgccaa cttgcgggtc    1860
gtcagtccct caatgccaac ttcgttcaac agctccaacg cggagttgat gactttggac    1920
ttatccaggc ggctgaccta tagataccat agatgtatgg attagtatca tatacataca    1980
aaggctattt ttgggacata ttaatattaa caatttccgt gatagttttc accattttg     2040 ttgaatgtta cgttgaaaat ttaaatttgt tttaaattaa ttttaccagt catgtgttct    2100
taaaagtttt tatgattgaa acggcataaa gtggttcaaa aatttatcaa gaaaggcttt    2160
ccttttttaa atcttatctt tttctcttaa aaatcactag tcaattcatt attaatttgt    2220
taacttgaat ttggaatgtc tatttacttt cagataaatt aaagcaagaa acttaatatt    2280
cgaaaaaaat tgattctaaa tggaatttca cttgatcttc atgtatgcat atcaattttt    2340
atttacattg tataataagt ttcgagttga ttgttgtaat ccacaggtgt cccagagaat    2400
taaattccaa attcccaag tttattgaat gttgattgta gtttcagttg ctttgttgct     2460
gcaacaatgg cttgttgatt gtagatattt tcccttttcct tggtttactt attacataga    2520 ctgaaaaga ggtttacttt tttgatactt atgaaaaatt tctattagtg attactaacc      2580
aatcgctata tgtttactag aaaacaaata aactctttac attaacattc ataatgttt     2640 gctctgtaac cgacaattga aggcgttaca gcaacagtaa tataactagc ttcttaaccc    2700
tcatctatta accccatcgt ttaaaacact atgttaaatg gtctaacaaa tctagatact    2760
aatagatgtc ttattactta gcagccacag ctgcaacatc caagacaatt tttgaaactt    2820
cttattgagc tcttggcagc agaaatgttg gtattttttca cagcttttctg aaagaccggc    2880 accttcctcc ggttcccgtt tctgaattca agaggatttc cgaccccaa ttaatcccga      2940 aacaaataag gtatattcaa aatgatgaa aagtcatggc tgctgacctt attttattc       3000 ctattgatag aatattattc ccctttaaa tacactgtac taagaggtcc ggctataatt     3060
ttactcactt gtcgattatc ccatagaatg ttgattgtag ttggttgctt ttccaggtga    3120
gagttgatca agtcacaaaa gttagcgtgt gttgattgta gatttgaagg taaaataatt    3180
tttgcaccca ttcatcgggt aaaacgttct ccatagaata catttccatc gataattgat    3240
aacttatgaa tttcaaagaa aaaatatgc ttttaaaatt accatggtgg ctagcgcaga      3300
ttgtttagct tgttcagctg cgcttgttta tttgcttagc tttcgcttag cgacgtgttc    3360
actttgcttg tttgaattga attgtcgctc cgtagacgaa gcgcctctat ttatactccg    3420
gcgctcgttt tcgagtttac cactccctat cagtgataga gaaagtgaa agtcgagttt      3480
```

```
accactccct atcagtgata gagaaaagtg aaagtcgagt ttaccactcc ctatcagtga    3540
tagagaaaag tgaaagtcga gtttaccact ccctatcagt gatagagaaa agtgaaagtc    3600
gagtttacca ctccctatca gtgatagaga aaagtgaaag tcgagtttac cactccctat    3660
cagtgataga gaaagtgaa agtcgagttt accactccct atcagtgata gagaaaagtg    3720
aaagtcgaaa cctggcgcgc cccggccatc gagaaagaga gagagaagag aagagagaga    3780
acattcgaga agagagaga gaagagaaga gagagaacat actccctatc agtgatagag    3840
aagtccctat cagtgataga gatgtcccta tcagtgatag agagttccct atcagtgata    3900
gagacgtccc tatcagtgat agagaagtcc ctatcagtga tagagagatc cctatcagtg    3960
atagagattt ccctatcagt gatagagagg tccctatcag tgatagagac ttccctatca    4020
gtgatagaga atccctatc agtgatagag acatccctat cagtgataga gaactcccta    4080
tcagtgatag agacctccct atcagtgata gagatcgatg cggccgcatg gtacccattg    4140
cttgtcattt attaatttgg atgatgtcat ttgtttttaa aattgaactg gctttacgag    4200
tagaattcta cgcgtaaaac acaatcaagt atgagtcata atctgatgtc atgttttgta    4260
cacggctcat aaccgaactg gctttacgag tagaattcta cttgtaatgc acgatcagtg    4320
gatgatgtca tttgttttc aaatcgagat gatgtcatgt tttgcacacg gctcataaac    4380
tcgctttacg agtagaattc tacgtgtaac gcacgatcga ttgatgagtc atttgttttg    4440
caatatgata tcatacaata tgactcattt gttttcaaa accgaacttg atttacgggt    4500
agaattctac ttgtaaagca caatcaaaaa gatgatgtca tttgttttc aaaactgaac    4560
tcgctttacg agtagaattc tacgtgtaaa acacaatcaa gaaatgatgt catttgttat    4620
aaaaataaaa gctgatgtca tgttttgcac atggctcata actaaactcg ctttacgggt    4680
agaattctac gcgtaaaaca tgattgataa ttaaataatt catttgcaag ctatacgtta    4740
aatcaaacgg acgctcgagg ttgcacaaca ctattatcga tttgcagttc gggacataaa    4800
tgtttaaata tatcgatgtc tttgtgatgc gcgcgacatt tttgtaggtt attgataaaa    4860
tgaacggata cgttgcccga cattatcatt aaatccttgg cgtagaattt gtcgggtcca    4920
ttgtccgtgt gcgctagcat gcccgtaacg gacctcgtac ttttggcttc aaaggtttg    4980
cgcacagaca aaatgtgcca cacttgcagc tctgcatgtg tgcgcgttac cacaaatccc    5040
aacggcgcag tgtacttgtt gtatgcaaat aaatctcgat aaaggcgcgg cgcgcgaatg    5100
cagctgatca cgtacgctcc tcgtgttccg ttcaaggacg gtgttatcga cctcagatta    5160
atgtttatcg gccgactgtt ttcgtatccg ctcaccaaac gcgttttgc attaacattg    5220
tatgtcggcg gatgttctat atctaatttg aataaataaa cgataaccgc gttggtttta    5280
gagggcataa taaagaaat attgttatcg tgttcgccat tagggcagta taaattgacg    5340
ttcatgttgg atattgtttc agttgcaagt tgacactggc ggcgacaagc aattctaatt    5400
ggggtaagtt ttcccgttct tttctgggtt cttcccttt gctcatcctt gctgcactac    5460
cttcaggtgc aagttgagat tcaggccacc atgggagatc ccacccccacc caagaagaag    5520
cgcaaaccgg tcgccaccat ggcctcctcc gagaacgtca tcaccgagtt catgcgcttc    5580
aaggtgcgca tggagggcac cgtgaacggc cacgagttcg agatcgaggg cgagggcgag    5640
ggccgcccct acgagggcca acaccgtg aagctgaagg tgaccaaggg cggcccctg    5700
cccttcgcct gggacatcct gtccccccag ttcagtacg ctccaaggt gtacgtgaag    5760
caccccgccg acatccccga ctacaagaag ctgtccttcc ccgagggctt caagtgggag    5820
cgcgtgatga acttcgagga cggcggcgtg gcgaccgtga cccaggactc ctccctgcag    5880
```

```
gacggctgct tcatctacaa ggtgaagttc atcggcgtga acttccctc cgacggcccc     5940
gtgatgcaga agaagaccat gggctgggag gcctccaccg agcgcctgta cccccgcgac    6000
ggcgtgctga agggcgagac ccacaaggcc ctgaagctga aggacggcgg ccactacctg    6060
gtggagttca agtccatcta catggccaag aagcccgtgc agctgcccgg ctactactac    6120
gtggacgcca agctggacat cacctcccac aacgaggact acaccatcgt ggagcagtac    6180
gagcgcaccg agggccgcca ccacctgttc ctgagatctc gacccaagaa aaagcggaag    6240
gtggaggacc cgtaagatcc accggatcta gataactgat cataatcagc cataccacat    6300
ttgtagaggt tttacttgct ttaaaaaacc tcccacacct cccctgaac ctgaaacata     6360
aaatgaatgc aattgttgtt gttaacttgt ttattgcagc ttataatggt tacaaataaa    6420
gcaatagcat cacaaatttc acaaataaag cattttttc actgcattct agttgtggtt     6480
tgtccaaact catcaatgta tcttaacgcg agttaattaa ggccgctcat ttaaatctgg    6540
ccggccgcaa ccattgtggg aaccgtgcga tcaaacaaac gcgagatacc ggaagtactg    6600
aaaaacagtc gctccaggcc agtgggaaca tcgatgtttt gttttgacgg accccttact    6660
ctcgtctcat ataaaccgaa gccagctaag atggtatact tattatcatc ttgtgatgag    6720
gatgcttcta tcaacgaaag taccggtaaa ccgcaaatgg ttatgtatta taatcaaact    6780
aaaggcggag tggacacgct agaccaaatg tgttctgtga tgacctgcag taggaagacg    6840
aataggtggc ctatggcatt attgtacgga atgataaaca ttgcctgcat aaattctttt    6900
attatataca gccataatgt cagtagcaag ggagaaaagg tccaaagtcg caaaaaattt    6960
atgagaaacc tttacatgag cctgacgtca tcgtttatgc gtaagcgttt agaagctcct    7020
actttgaaga gatatttgcg cgataatatc tctaatattt tgccaaatga agtgcctggt    7080
acatcagatg acagtactga agagccagta atgaaaaaac gtacttactg tacttactgc    7140
ccctctaaaa taaggcgaaa ggcaaatgca tcgtgcaaaa aatgcaaaaa agttatttgt    7200
cgagagcata atattgatat gtgccaaagt tgtttctgac tgactaataa gtataatttg    7260
tttctattat gtataagtta agctaattac ttattttata atacaacatg actgttttta    7320
aagtacaaaa taagtttatt tttgtaaaag agagaatgtt taaagttttt gttacttat     7380
agaagaaatt ttgagttttt gtttttttt aataaataaa taaacataaa taaattgttt     7440
gttgaattta ttattagtat gtaagtgtaa atataataaa acttaatatc tattcaaatt    7500
aataaataaa cctcgatata cagaccgata aaacacatgc gtcaatttta cgcatgatta    7560
tctttaacgt acgtcacaat atgattatct ttctagggtt aaataatagt ttctaattt     7620
tttattattc agcctgctgt cgtgaatacc gtatatctca acgctgtctg tgagattgtc    7680
gtattctagc cttttagtt tttcgctcat cgacttgata ttgtccgaca cattttcgtc     7740
gatttgcgtt ttgatcaaag acttgagcag agacacgtta atcaactgtt caaattgatc    7800
catattaacg atatcaaccc gatgcgtata tggtgcgtaa aatatatttt ttaaccctct    7860
tatactttgc actctgcgtt aatacgcgtt cgtgtacaga cgtaatcatg ttttcttttt    7920
tggataaaac tcctactgag tttgacctca tattagaccc tcacaagttg caaaacgtgg    7980
catttttttac caatgaagaa tttaaagtta ttttaaaaaa tttcatcaca gatttaaaga    8040
agaaccaaaa attaaattat ttcaacagtt taatcgacca gttaatcaac gtgtacacag    8100
acgcgtcggc aaaaaacacg cagcccgacg tgttggctaa aattattaaa tcaacttgtg    8160
ttatagtcac ggatttgccg tccaacgtgt tcctcaaaaa gttgaagacc aacaagttta    8220
```

```
cggacactat taattatttg attttgcccc acttcatttt gtgggatcac aattttgtta    8280
tattttaaac aaagcttggc actggccgtc gttttacaac gtcgtgactg ggaaaaccct    8340
ggcgttaccc aacttaatcg ccttgcagca catccccctt tcgccagctg gcgtaatagc    8400
gaagaggccc gcaccgatcg cccttcccaa cagttgcgca gcctgaatgg cgaatggcgc    8460
ctgatgcggt attttctcct tacgcatctg tgcggtattt cacaccgcat atggtgcact    8520
ctcagtacaa tctgctctga tgccgcatag ttaagccagc cccgacaccc gccaacaccc    8580
gctgacgcgc cctgacgggc ttgtctgctc ccggcatccg cttacagaca gctgtgacc    8640 gtctccggga gctgcatgtg tcagaggttt tcaccgtcat caccgaaacg cgcgagacga    8700
aagggcctcg tgatacgcct atttttatag gttaatgtca tgataataat ggtttcttag    8760
acgtcaggtg gcacttttcg gggaaatgtg cgcggaaccc ctatttgttt attttctaa    8820 atacattcaa atatgtatcc gctcatgaga caataaccct gataaatgct tcaataatat    8880
tgaaaaagga agagtatgag tattcaacat ttccgtgtcg cccttattcc cttttttgcg    8940
gcattttgcc ttcctgtttt tgctcaccca gaaacgctgg tgaaagtaaa agatgctgaa    9000
gatcagttgg gtgcacgagt gggttacatc gaactggatc tcaacagcgg taagatcctt    9060
gagagttttc gccccgaaga acgttttcca atgatgagca cttttaaagt tctgctatgt    9120
ggcgcggtat tatcccgtat tgacgccggg caagagcaac tcggtcgccg catacactat    9180
tctcagaatg acttggttga gtactcacca gtcacagaaa agcatcttac ggatggcatg    9240
acagtaagag aattatgcag tgctgccata accatgagtg ataacactgc ggccaactta    9300
cttctgacaa cgatcggagg accgaaggag ctaaccgctt ttttgcacaa catgggggat    9360
catgtaactc gccttgatcg ttgggaaccg gagctgaatg aagccatacc aaacgacgag    9420
cgtgacacca cgatgcctgt agcaatggca acaacgttgc gcaaactatt aactggcgaa    9480
ctacttactc tagcttcccg gcaacaatta atagactgga tggaggcgga taaagttgca    9540
ggaccacttc tgcgctcggc ccttccggct ggctggttta ttgctgataa atctggagcc    9600
ggtgagcgtg ggtctcgcgg tatcattgca gcactggggc cagatggtaa gccctcccgt    9660
atcgtagtta tctacacgac ggggagtcag gcaactatgg atgaacgaaa tagacagatc    9720
gctgagatag gtgcctcact gattaagcat tggtaactgt cagaccaagt ttactcatat    9780
atactttaga ttgatttaaa acttcatttt taatttaaaa ggatctaggt gaagatcctt    9840
tttgataatc tcatgaccaa aatcccttaa cgtgagtttt cgttccactg agcgtcagac    9900
cccgtagaaa agatcaaagg atcttcttga gatccttttt ttctgcgcgt aatctgctgc    9960
ttgcaaacaa aaaaaccacc gctaccagcg gtggtttgtt tgccggatca agagctacca   10020
actctttttc cgaaggtaac tggcttcagc agagcgcaga taccaaatac tgtccttcta   10080
gtgtagccgt agttaggcca ccacttcaag aactctgtag caccgcctac atacctcgct   10140
ctgctaatcc tgttaccagt ggctgctgcc agtggcgata agtcgtgtct taccgggttg   10200
gactcaagac gatagttacc ggataaggcg cagcggtcgg gctgaacggg gggttcgtgc   10260
acacagccca gcttggagcg aacgacctac accgaactga gatacctaca gcgtgagcat   10320
tgagaaagcg ccacgcttcc cgaagggaga aaggcggaca ggtatccggt aagcggcagg   10380
gtcggaacag gagagcgcac gagggagctt ccagggggaa acgcctggta tctttatagt   10440
cctgtcgggt ttcgccacct ctgacttgag cgtcgatttt tgtgatgctc gtcagggggg   10500
cggagcctat ggaaaaacgc cagcaacgcg gcctttttac ggttcctggc cttttgctgg   10560
ccttttgctc acatgttctt tcctgcgtta tcccctgatt ctgtggataa ccgtattacc   10620
```

```
gcctttgagt gagctgatac cgctcgccgc agccgaacga ccgagcgcag cgagtcagtg    10680
agcgaggaag cggaagagcg cccaatacgc aaaccgcctc tccccgcgcg ttggccgatt    10740
cattaatgca gctggcacga caggtttccc gactggaaag cgggcagtga gcgcaacgca    10800
attaatgtga gttagctcac tcattaggca ccccaggctt tacactttat gcttccggct    10860
cgtatgttgt gtggaattgt gagcggataa caatttcaca caggaaacag ctatgaccat    10920
gattacgaat tcgacctgc aggcatgcaa gcttgcatgc ctgcaggtcg acgctcgcgc    10980
gacttggttt gccattcttt agcgcgcgtc gcgtcacaca gcttggccac aatgtggttt    11040
ttgtcaaacg aagattctat gacgtgttta aagtttaggt cgagtaaagc gcaaatcttt    11100
tttaacccta gaaagatagt ctgcgtaaaa ttgacgcatg cattcttgaa atattgctct    11160
ctctttctaa atagcgcgaa tccgtcgctg tgcatttagg acatctcagt cgccgcttgg    11220
agctcccgtg aggcgtgctt gtcaatgcgg taagtgtcac tgattttgaa ctataacgac    11280
cgcgtgagtc aaaatgacgc atgattatct tttacgtgac ttttaagatt taactcatac    11340
gataattata ttgttatttc atgttctact tacgtgataa cttattatat atatattttc    11400 ttgtttataga tatcgtgact aatatataat aaaatgggta gttctttaga cgatgagcat    11460
atcctctctg ctcttctgca aagcgatgac gagcttgttg gtgaggattc tgacagtgaa    11520
atatcagatc acgtaagtga agatgacgtc cagagcgata cagaagaagc gtttatagat    11580
gaggtacatg aagtgcagcc aacgtcaagc ggtagtgaaa tattagacga caaaatgtt    11640 attgaacaac caggttcttc attggcttct aacagaatct tgaccttgcc acagaggact    11700
attagaggta agaataaaca ttgttggtca acttcaaagt ccacgaggcg tagccgagtc    11760
tctgcactga acattgtcag atcggccc                                       11788

<210> SEQ ID NO 52
<211> LENGTH: 13292
<212> TYPE: DNA
<213> ORGANISM: Artificial Sequence
<220> FEATURE:
<223> OTHER INFORMATION: Synthetic construct, pLA3233-Cctra-intron-tTAV2
      construct.

<400> SEQUENCE: 52
gggcggccgt ttttcttgaa atattgctct ctctttctaa atagcgcgaa tccgtcgctg      60
tgcatttagg acatctcagt cgccgcttgg agctcccaaa cgcgccagtg gtagtacaca     120
gtactgtggg tgttcagttt gaaatcctct tgcttctcca ttgtctcggt tacctttggt     180
caaatccatg ggttctattg cctatatact cttgcgatta ccagtgattg cgctattagc     240
tattagatgg attgttggcc aaacttgtcg cttaagtggc tgggaattgt aaccgtaggc     300
ccgagtgtaa tgatccccca taaaagtttt tcgcaatgcc tttatttttt gttgcaaatc     360
tctctttatt ctgcggtatt cttcattatt gcgggatgg ggaaagtgtt tatatagaag     420
caacttacga ttgaacccaa atgcacctga caagcaaggt caaagggcca gattttaaa     480 tatattattt agtcttagga ctctctattt gcaattaaat tactttgcta cctgagggtt     540
aaatcttccc cattgataat aataattcca ctatatgttc aattgggttt caccgcgctt     600
agttacatga cgagccctaa tgagccgtcg gtggtctata aactgtgcct tacaaatact     660
tgcaactctt ctcgtttga agtcagcaga gttattgcta attgctaatt gctaattgct     720
tttaactgat ttcttcgaaa ttggtgctat gtttatggcg ctattaacaa gtatgaatgt     780
caggtttaac caggggatgc ttaattgtgt tctcaacttc aaaggcagaa atgtttactc     840
```

```
ttgaccatgg gtttaggtat aatgttatca agctcctcga gttaacgtta cgttaacgtt    900
aacgttcgag gtcgactcta dacaccggtg ttagccgccg tactcatcga tgcccagggc    960
gtcggtgaac atctgctcga actcgaaatc ggccatatcc agggcgccgt aggggcgct    1020
atcgtgcggg gtgaatcccg gtcccgggct atcgccatcg cccagcatgt ccaggtcgaa    1080
gtcgtccagg gcatcggcgt gggccatcgc cacatcctcg ccatccaggt gcagctcatc    1140
gcccaggctc acgtcggtcg gcggggcggt cgacaggcgg cgggtgtgtc cggccggcag    1200
gaagctcagg cgcggggcgg ccaggcccgc ctcctccggg gcatcatcat ccggcagatc    1260
cagcaggccc tcgatggtgc tgccgtagtt gttcttggtg cgggcgcggc tgtaggcggg    1320
gcccgagccc gactcgcatt tcagttgctt ttccaatccg cagataatca gctccaagcc    1380
gaacaggaat gccggctcgg ctccttgatg atcgaacagc tcgattgcct gacgcagcag    1440
tgggggcatc gaatcggttg ttggggtctc gcgctcctct tttgcgactt gatgctcttg    1500
gtcctccagc acgcagccca gggtaaagtg accgacggcg ctcagagcgt agagagcatt    1560
ttccaggctg aagccttgct ggcacaggaa cgcgagctgg ttctccagtg tctcgtattg    1620
cttttcggtc gggcgcgtgc cgagatggac tttggcaccg tctcggtggg acagcagagc    1680
gcagcggaac gacttggcgt tattgcggag gaagtcctgc caggactcgc cttccaacgg    1740
gcaaaaatgc gtgtggtggc ggtcgagcat ctcgatggcc agggcatcca gcagcgcccg    1800
cttattcttc acgtgccagt agagggtggg ctgctccacg cccagcttct gcgccaactt    1860
gcgggtcgtc agtccctcaa tgccaacttc gttcaacagc tccaacgcgg agttgatgac    1920
tttggactta tccaggcggc tgacctatag ataccataga tgtatggatt agtatcatat    1980
acatacaaag gctattttg ggacatatta atattaacaa tttccgtgat agttttcacc    2040
atttttgttg aatgttacgt tgaaaattta aatttgtttt aaattaattt taccagtcat    2100
gtgttcttaa aagttttat gattgaaacg gcataaagtg gttcaaaaat ttatcaagaa    2160
aggctttcct tttttaaatc ttatcttttt ctcttaaaaa tcactagtca attcattatt    2220
aatttgttaa cttgaatttg gaatgtctat ttactttcag ataaattaaa gcaagaaact    2280
taatattcga aaaaaattga ttctaaatgg aatttcactt gatcttcatg tatgcatatc    2340
aattttttatt tacattgtat aataagtttc gagttgattg ttgtaatcca caggtgtccc    2400
agagaattaa attccaaatt acccaagttt attgaatgtt gattgtagtt tcagttgctt    2460
tgttgctgca acaatggctt gttgattgta gatattttcc ctttccttgg tttacttatt    2520
acatagactg aaaagaggt ttactttttt gatacttatg aaaaatttct attagtgatt    2580
actaaccaat cgctatatgt ttactagaaa acaaataaac tctttacatt aacattcaat    2640
aatgtttgct ctgtaaccga caattgaagg cgttacagca acagtaatat aactagcttc    2700
ttaaccctca tctattaacc ccatcgttta aaacactatg ttaaatggtc taacaaatct    2760
agatactaat agatgtctta ttacttagca gccacagctg caacatccaa gacaattttt    2820
gaaacttctt attgagctct tggcagcaga aatgttggta tttttcacag ctttctgaaa    2880
gaccggcacc ttcctccggt tcccgttct gaattcaaga ggattccga cccccaatta    2940
atcccgaaac aaataaggta tattcaaaat gatggaaaag tcatggctgc tgaccttatt    3000
tttattccta ttgatagaat attattcccc ttttaaatac actgtactaa gaggtccggc    3060
tataatttta ctcacttgtc gattatccca tagaatgttg attgtagttg ttgcttttc    3120
caggtgagag ttgatcaagt cacaaaagtt agcgtgtgtt gattgtagat ttgaaggtaa    3180
```

```
aataattttt gcacccattc atcgggtaaa acgttctcca tagaatacat ttccatcgat   3240
aattgataac ttatgaattt caaagaaaaa aatatgcttt taaaattacc atggtggcta   3300
gcgcagattg tttagcttgt tcagctgcgc ttgtttattt gcttagcttt cgcttagcga   3360
cgtgttcact ttgcttgttt gaattgaatt gtcgctccgt agacgaagcg cctctattta   3420
tactccggcg ctcgttttcg agtttaccac tccctatcag tgatagagaa aagtgaaagt   3480
cgagtttacc actccctatc agtgatagag aaaagtgaaa gtcgagttta ccactcccta   3540
tcagtgatag agaaaagtga agtcgagtt taccactccc tatcagtgat agagaaaagt   3600
gaaagtcgag tttaccactc cctatcagtg atagagaaaa gtgaaagtcg agtttaccac   3660
tccctatcag tgatagagaa aagtgaaagt cgagtttacc actccctatc agtgatagag   3720
aaaagtgaaa gtcgaaacct ggcgcgcccc ggccatcgag aaagagagag agaagagaag   3780
agagagaaca ttcgagaaag agagagagaa gagaagagag agaacatact ccctatcagt   3840
gatagagaag tccctatcag tgatagagat gtccctatca gtgatagaga gttccctatc   3900
agtgatagag acgtccctat cagtgataga gaagtcccta tcagtgatag agagatccct   3960
atcagtgata gagatttccc tatcagtgat agagaggtcc ctatcagtga tagagacttc   4020
cctatcagtg atagagaaat ccctatcagt gatagagaca tccctatcag tgatagagaa   4080
ctccctatca gtgatagaga cctccctatc agtgatagag atcgatgcgg ccgcatggta   4140
cccattgctt gtcatttatt aatttggatg atgtcatttg ttttaaaat tgaactggct    4200 ttacgagtag aattctacgc gtaaaacaca atcaagtatg agtcataatc tgatgtcatg   4260
ttttgtacac ggctcataac cgaactggct ttacgagtag aattctactt gtaatgcacg   4320
atcagtggat gatgtcattt gttttcaaa tcgagatgat gtcatgtttt gcacacggct    4380
cataaactcg ctttacgagt agaattctac gtgtaacgca cgatcgattg atgagtcatt   4440
tgttttgcaa tatgatatca tacaatatga ctcatttgtt tttcaaaacc gaacttgatt   4500
tacgggtaga attctacttg taaagcacaa tcaaaaagat gatgtcattt gttttttcaaa  4560 actgaactcg ctttacgagt agaattctac gtgtaaaaca caatcaagaa atgatgtcat   4620
ttgttataaa aataaaagct gatgtcatgt tttgcacatg gctcataact aaactcgctt   4680
tacgggtaga attctacgcg taaaacatga ttgataatta ataattcat ttgcaagcta    4740 tacgttaaat caaacggacg ctcgaggttg cacaacacta ttatcgattt gcagttcggg   4800
acataaatgt ttaaatatat cgatgtcttt gtgatgcgcg cgacattttt gtaggttatt   4860
gataaaatga acggatacgt tgcccgacat tatcattaaa tccttggcgt agaatttgtc   4920
gggtccattg tccgtgtgcg ctagcatgcc cgtaacggac ctcgtacttt tggcttcaaa   4980
ggttttgcgc acagacaaaa tgtgccacac ttgcagctct gcatgtgtgc gcgttaccac   5040
aaatcccaac ggcgcagtgt acttgttgta tgcaaataaa tctcgataaa ggcgcggcgc   5100
gcgaatgcag ctgatcacgt acgctcctcg tgttccgttc aaggacggtg ttatcgacct   5160
cagattaatg tttatcggcc gactgttttc gtatccgctc accaaacgcg ttttttgcatt  5220 aacattgtat gtcggcggat gttctatatc taatttgaat aaataaacga taaccgcgtt   5280
ggttttagag gcataataa aagaaatatt gttatcgtgt tcgccattag gcagtataa    5340 attgacgttc atgttggata ttgtttcagt tgcaagttga cactggcggc gacaagcaat   5400
tctaattggg gtaagttttc ccgttctttt ctgggttctt cccttttgct catccttgct   5460
gcactacctt caggtgcaag ttgagattca ggccaccatg ggagatccca ccccacccaa   5520
gaagaagcgc aaaccggtcg ccaccatgga cgaggatggt tcagagggcg ccccgccct    5580
```

```
gttccagagc gacatgacct tcaaaatctt catcgacggc gaggtgaacg gccagaagtt    5640
caccatcgtg gccgacggca gcagcaagtt cccccacggc gacttcaacg tgcacgccgt    5700
gtgcgagacc ggcaagctgc ccatgagctg aagcccatc tgccacctga tccagtacgg     5760
cgagcccttc ttcgcccgct accccaacgg catcagccac ttcgcccagg agtgcttccc    5820
cgagggcctg agcatcgacc gcaccgtgcg cttcgagaac gacggcacca tgaccagcca    5880
ccacacctac gagctggacg gcacctgcgt ggtcagccgc atcaccgtga actgcgacgg    5940
cttccagccc gacggcccca tcatgcgcga ccagctggtg gacatcctgc ccaacgagac    6000
ccacatgttc ccccacggcc ccaacgccgt gcgccagctg gccttcatcg gcttcaccac    6060
cgccgacggc ggcctgatga tgggccactt cgacagcaag atgaccttca cggcagccg    6120 cgccatcaag atccccggcc cccacttcgt gaccatcatc accaagcaga tgagggacac    6180
cagcgacaag cgcgaccacg tgtgccagcg cgaggtgacc tacgcccaca gcgtgccccg    6240
catcaccagc gccatcggta gcgacgagga ttccggactc agatctcgac ccaagaaaaa    6300
gcggaaggtg gaggacccgt aagatccacc ggatctagat aactgatcat aatcagccat    6360
accacatttg tagaggtttt acttgcttta aaaaacctcc cacacctccc cctgaacctg    6420
aaacataaaa tgaatgcaat tgttgttgtt aacttgttta ttgcagctta taatggttac    6480
aaataaagca atagcatcac aaatttcaca aataaagcat ttttttcact gcattctagt    6540
tgtggtttgt ccaaactcat caatgtatct taacgcgagt taattaacac cgaaatcgta    6600
attcacggca tcattacaaa atattttgac gttttggacc tcgtccctaa tgacaccata    6660
acggtggcct tgaagtatat ttaaccctag aaagatagtc tgcgtaaaat tgacgcatgc    6720
attcttgaaa tattgctctc tctttctaaa tagcgcgaat ccgtcgctgt gcatttagga    6780
catctcagtc gccgcttgga gctccgtga ggcgtgcttg tcaatgcggt aagtgtcact     6840
gattttgaac tataacgacc gcgtgagtca aaatgacgca tgattatctt ttacgtgact    6900
tttaagattt aactcatacg ataattatat tgttatttca tgttctactt acgtgataac    6960
ttattatata tatattttct tgttatagat atcgtgacta atatataata aaatgggtag    7020
ttctttagac gatgagcata tcctctctgc tcttctgcaa agcgatgacg agcttgttgg    7080
tgaggattct gacagtgaaa tatcagatca cgtaagtgaa gatgacgtcc aggaaatctg    7140
gccggccgca accattgtgg gaaccgtgcg atcaaacaaa cgcgagatac cggaagtact    7200
gaaaaacagt cgctccaggc cagtgggaac atcgatgttt tgttttgacg gaccccttac    7260
tctcgtctca tataaaccga agccagctaa gatggtatac ttattatcat cttgtgatga    7320
ggatgcttct atcaacgaaa gtaccggtaa accgcaaatg gttatgtatt ataatcaaac    7380
taaaggcgga gtgacacgc tagaccaaat gtgttctgtg atgacctgca gtaggaagac     7440
gaataggtgg cctatggcat tattgtacgg aatgataaac attgcctgca taaattcttt    7500
tattatatac agccataatg tcagtagcaa gggagaaaag gtccaaagtc gcaaaaaatt    7560
tatgagaaac ctttacatga gcctgacgtc atcgtttatg cgtaagcgtt tagaagctcc    7620
tactttgaag agatatttgc gcgataatat ctctaatatt ttgccaaatg aagtgcctgg    7680
tacatcagat gacagtactg aagagccagt aatgaaaaaa cgtacttact gtacttactg    7740
cccctctaaa ataaggcgaa aggcaaatgc atcgtgcaaa aaatgcaaaa aagttatttg    7800
tcgagagcat aatattgata tgtgccaaag ttgtttctga ctgactaata agtataattt    7860
gtttctatta tgtataagtt aagctaatta cttatttat aatacaacat gactgttttt    7920
```

```
aaagtacaaa ataagtttat ttttgtaaaa gagagaatgt ttaaaagttt tgttacttta      7980
tagaagaaat tttgagtttt tgttttttt taataaataa ataaacataa ataaattgtt       8040
tgttgaattt attattagta tgtaagtgta aatataataa aacttaatat ctattcaaat      8100
taataaataa acctcgatat acagaccgat aaaacacatg cgtcaatttt acgcatgatt      8160
atctttaacg tacgtcacaa tatgattatc tttctagggt taaataatag tttctaattt      8220
ttttattatt cagcctgctg tcgtgaatac cgtatatctc aacgctgtct gtgagattgt      8280
cgtattctag cctttttagt ttttcgctca tcgacttgat attgtccgac acattttcgt      8340
cgatttgcgt tttgatcaaa gacttgagca gagacacgtt aatcaactgt tcaaattgat      8400
ccatattaac gatatcaacc cgatgcgtat atggtgcgta aaatatattt tttaaccctc      8460
ttatactttg cactctgcgt taatacgcgt tcgtgtacag acgtaatcat gttttctttt      8520
ttggataaaa ctcctactga gtttgacctc atattagacc ctcacaagtt gcaaaacgtg      8580
gcatttttta ccaatgaaga atttaaagtt attttaaaaa atttcatcac agatttaaag      8640
aagaaccaaa aattaaatta tttcaacagt ttaatcgacc agttaatcaa cgtgtacaca      8700
gacgcgtcgg caaaaaacac gcagcccgac gtgttggcta aaattattaa atcaacttgt      8760
gttatagtca cggatttgcc gtccaacgtg ttcctcaaaa agttgaagac caacaagttt      8820
acggacacta ttaattattt gattttgccc cacttcattt tgtgggatca caattttgtt      8880
atattttaaa caaagcttgg cactggccgt cgttttacaa cgtcgtgact gggaaaaccc      8940
tggcgttacc caacttaatc gccttgcagc acatccccct ttcgccagct ggcgtaatag      9000
cgaagaggcc cgcaccgatc gcccttccca acagttgcgc agcctgaatg gcgaatggcg      9060
cctgatgcgg tattttctcc ttacgcatct gtgcggtatt tcacaccgca tatggtgcac      9120
tctcagtaca atctgctctg atgccgcata gttaagccag ccccgacacc cgccaacacc      9180
cgctgacgcg ccctgacggg cttgtctgct cccggcatcc gcttacagac aagctgtgac      9240
cgtctccggg agctgcatgt gtcagaggtt ttcaccgtca tcaccgaaac gcgcgagacg      9300
aaagggcctc gtgatacgcc tatttttata ggttaatgtc atgataataa tggtttctta      9360
gacgtcaggt ggcactttc ggggaaatgt gcgcggaacc cctatttgtt tatttttcta      9420
aatacattca aatatgtatc cgctcatgag acaataaccc tgataaatgc ttcaataata      9480
ttgaaaaagg aagagtatga gtattcaaca tttccgtgtc gcccttattc ccttttttgc      9540
ggcattttgc cttcctgttt ttgctcaccc agaaacgctg gtgaaagtaa aagatgctga      9600
agatcagttg ggtgcacgag tgggttacat cgaactggat ctcaacagcg gtaagatcct      9660
tgagagtttt cgccccgaag aacgttttcc aatgatgagc acttttaaag ttctgctatg      9720
tggcgcggta ttatcccgta ttgacgccgg gcaagagcaa ctcggtcgcc gcatacacta      9780
ttctcagaat gacttggttg agtactcacc agtcacagaa aagcatctta cggatggcat      9840
gacagtaaga gaattatgca gtgctgccat aaccatgagt gataacactg cggccaactt      9900
acttctgaca acgatcggag gaccgaagga gctaaccgct ttttttgcaca acatggggga     9960 tcatgtaact cgccttgatc gttgggaacc ggagctgaat gaagccatac caaacgacga     10020
gcgtgacacc acgatgcctg tagcaatggc aacaacgttg cgcaaactat taactggcga     10080
actacttact ctagcttccc ggcaacaatt aatagactgg atggaggcgg ataaagttgc     10140
aggaccactt ctgcgctcgg cccttccggc tggctggttt attgctgata aatctggagc     10200
cggtgagcgt gggtctcgcg gtatcattgc agcactgggg ccagatggta agccctcccg     10260
tatcgtagtt atctacacga cggggagtca ggcaactatg gatgaacgaa atagacagat     10320
```

```
cgctgagata ggtgcctcac tgattaagca ttggtaactg tcagaccaag tttactcata   10380
tatactttag attgatttaa aacttcattt ttaatttaaa aggatctagg tgaagatcct   10440
ttttgataat ctcatgacca aaatcccttaa acgtgagttt tcgttccact gagcgtcaga   10500
ccccgtagaa aagatcaaag gatcttcttg agatcctttt tttctgcgcg taatctgctg   10560
cttgcaaaca aaaaaccac cgctaccagc ggtggtttgt ttgccggatc aagagctacc   10620 aactctttt ccgaaggtaa ctggcttcag cagagcgcag ataccaaata ctgtccttct   10680
agtgtagccg tagttaggcc accacttcaa gaactctgta gcaccgccta catacctcgc   10740
tctgctaatc ctgttaccag tggctgctgc cagtggcgat aagtcgtgtc ttaccgggtt   10800
ggactcaaga cgatagttac cggataaggc gcagcggtcg ggctgaacgg ggggttcgtg   10860
cacacagccc agcttggagc gaacgaccta caccgaactg agatacctac agcgtgagca   10920
ttgagaaagc gccacgcttc ccgaagggag aaaggcggac aggtatccgg taagcggcag   10980
ggtcggaaca ggagagcgca cgagggagct tccaggggga aacgcctggt atctttatag   11040
tcctgtcggg tttcgccacc tctgacttga gcgtcgattt ttgtgatgct cgtcaggggg   11100
gcggagccta tggaaaaacg ccagcaacgc ggcctttta cggttcctgg ccttttgctg   11160 gcctttgct cacatgttct ttcctgcgtt atcccctgat tctgtggata accgtattac   11220
cgcctttgag tgagctgata ccgctcgccg cagccgaacg accgagcgca gcgagtcagt   11280
gagcgaggaa gcggaagagc gcccaatacg caaaccgcct ctccccgcgc gttggccgat   11340
tcattaatgc agctggcacg acaggtttcc cgactggaaa gcgggcagtg agcgcaacgc   11400
aattaatgtg agttagctca ctcattaggc accccaggct ttacacttta tgcttccggc   11460
tcgtatgttg tgtggaattg tgagcggata acaatttcac acaggaaaca gctatgacca   11520
tgattacgaa tttcgacctg caggcatgca agcttgcatg cctgcaggtc gacgctcgcg   11580
cgacttggtt tgccattctt tagcgcgcgt cgcgtcacac agcttggcca caatgtggtt   11640
tttgtcaaac gaagattcta tgacgtgttt aaagtttagg tcgagtaaag cgcaaatctt   11700
ttttaaccct agaaagatag tctgcgtaaa attgacgcat gcattcttga aatattgctc   11760
tctctttcta aatagcgcga atccgtcgct gtgcatttag acatctcag tcgccgcttg   11820 gagctcccgt gaggcgtgct tgtcaatgcg gtaagtgtca ctgatttga actataacga   11880 ccgcgtgagt caaaatgacg catgattatc ttttacgtga ctttttaagat ttaactcata   11940 cgataattat attgttattt catgttctac ttacgtgata acttattata tatatatttt   12000
cttgttatag atatcgtgac taatatataa taaaatgggt agttctttag acgatgagca   12060
tatcctctct gctcttctgc aaagcgatga cgagcttgtt ggtgaggatt ctgacagtga   12120
aatatcagat cacgtaagtg aagatgacgt ccagagcgat acagaagaag cgtttataga   12180
tgaggtacat gaagtgcagc aacgtcaag cggtagtgaa atattagacg aacaaaatgt   12240
tattgaacaa ccaggttctt cattggcttc taacagaatc ttgaccttgc cacagaggac   12300
tattagaggt aagaataaac attgttggtc aacttcaaag tccacgaggc gtagccgagt   12360
ctctgcactg aacattgtca gatcggcccg gcggagtgga cacgctagac caaatgtgtt   12420
ctgtgatgac ctgcagtagg aagacgaata ggtggcctat ggcattattg tacggaatga   12480
taaacattgc ctgcataaat tcttttatta tatacagcca taatgtcagt agcaagggag   12540
aaaaggtcca aagtcgcaaa aaattttatga gaaacccttta catgagcctg acgtcatcgt   12600
ttatgcgtaa gcgtttagaa gctcctactt tgaagagata tttgcgcgat aatatctcta   12660
```

| | |
|---|---:|
| atattttgcc aaatgaagtg cctggtacat cagatgacag tactgaagag ccagtaatga | 12720 |
| aaaaacgtac ttactgtact tactgcccct ctaaaataag gcgaaaggca aatgcatcgt | 12780 |
| gcaaaaaatg caaaaaagtt atttgtcgag agcataatat tgatatgtgc caaagttgtt | 12840 |
| tctgactgac taataagtat aatttgtttc tattatgtat aagttaagct aattacttat | 12900 |
| tttataatac aacatgactg tttttaaagt acaaaataag tttattttg taaagagag | 12960 |
| aatgtttaaa agttttgtta ctttatagaa gaaattttga gttttgttt tttttaata | 13020 |
| aataaataaa cataaataaa ttgtttgttg aatttattat tagtatgtaa gtgtaaatat | 13080 |
| aataaaactt aatatctatt caaattaata aataaacctc gatatacaga ccgataaaac | 13140 |
| acatgcgtca attttacgca tgattatctt taacgtacgt cacaatatga ttatctttct | 13200 |
| agggttaaaa tgaatgtaag cactttatta acgaaatctt tgggaatatt tcgctcatca | 13260 |
| gcattttatt tgagcaggag tccgagatgc cc | 13292 |

<210> SEQ ID NO 53
<211> LENGTH: 14713
<212> TYPE: DNA
<213> ORGANISM: Artificial Sequence
<220> FEATURE:
<223> OTHER INFORMATION: Synthetic construct,
pLA3014-Cctra-intron-Ubiquitin-reaperKR construct.

<400> SEQUENCE: 53

| | |
|---|---:|
| cgcgccggac gcggcaagtc tgcgagctta tatttacgtg gatctccggt gtgtccatga | 60 |
| ttcggcatca tatcataaac gacgaattcc aataaaaact ttgcttgttg ataacacctg | 120 |
| atgttcagag atgcccgata aaatcacagc tgttctggtt cacagtcacc agaaataaaa | 180 |
| aatattggaa ttgagatgta cacaattaac gatatttata aatatcttcc gatagtctat | 240 |
| cgtccggtta atcaaaataa agtgcgacga attaacatat tttcaaaatt aagacgcttt | 300 |
| gatagatgta tttgtataga gatagaaatt aaggttaaaa taacataaat gccaaagttt | 360 |
| agagcactat tcaataattc tcttgatttc aaattgaaat aatacacaat ataacatttt | 420 |
| ctaacactac aaagtcacga tattcttcca ccaaccgata gtatcgcaca cttgccattc | 480 |
| gcctcatcac gcacacgccc gcttcacaat tcaaacgaac ggcattttat tttcacagga | 540 |
| tcccgggagt cgtgaatgtt tacccaata tcgactttca ttgttaactg accaaaattg | 600 |
| taatctgttc tgttagttgt cgagtgcctg tgccgcgatc gctatgggca tatgttgcca | 660 |
| aactctaaac caaatactca ttctgatgtt ttaaatgatt tgccctccca tatgtccttc | 720 |
| cgagtgagag acacaaaaaa ttccaacaca ctattgcaat gaaaataaat ttcctttatt | 780 |
| agccagaagt cagatgctca aggggcttca tgatgtcccc ataattttg gcagagggaa | 840 |
| aaagatctca gtggtatttg tgagccaggg cattggccac accagccacc accttctgat | 900 |
| aggcagcctg cacctgagga gtgaattctt tgccaaaatg atgagacagc acaacaacca | 960 |
| gcacgttgcc caggagctgt aggaaagaga agaaggcatg aacatggtta gcagaggggc | 1020 |
| ccggtttgga ctcagagtat tttatcctca tctcaaacag tgtatatcat tgtaaccata | 1080 |
| aagagaaagg caggatgatg accagggtgt agttgtttct accaataaga atatttccac | 1140 |
| gccagccaga atttatatgc agaaatattc taccttatca tttaattata acaattgttc | 1200 |
| tctaaaactg tgctgaagta caatataata taccctgatt gccttgaaaa aaaagtgatt | 1260 |
| agagaaagta cttacaatct gacaaataaa caaagtgaa tttaaaaatt cgttacaaat | 1320 |
| gcaagctaaa gtttaacgaa aaagttacag aaaatgaaaa gaaaataaga ggagacaatg | 1380 |

```
gttgtcaaca gagtagaaag tgaaagaaac aaaattatca tgagggtcca tggtgataca    1440
agggacatct tcccattcta acaacaccc tgaaaactttt gcccctcca tataacatga    1500 attttacaat agcgaaaaag aaagaacaat caagggtccc caaactcacc ctgaagttct    1560
cagctctaga cgcgtttcac tacccaccgt actcgtcaat ccaagggca tcggtaaaca    1620 tctgctcaaa ctcgaagtcg gccatatcca gagcgccgta gggggcggag tcgtgggggg    1680
taaatcccgg acccgggaa tccccgtccc ccaacatgtc cagatcgaaa tcgtctagcg    1740
cgtcggcatg cgccatcgcc acgtcctcgc cgtctaagtg gagctcgtcc cccaggctga    1800
catcggtcgg gggggccgtc gacagtctgc gcgtgtgtcc cgcggggaga aggacaggc    1860 gcggagccgc cagccccgcc tcttcggggg cgtcgtcgtc cgggagatcg agcaggccct    1920
cgatggtaga cccgtaattg ttttcgtac gcgcgcggct gtacgcggac ccactttcac    1980
atttaagttg tttttctaat ccgcatatga tcaattcaag gccgaataag aaggctggct    2040
ctgcaccttg gtgatcaaat aattcgatag cttgtcgtaa taatggcggc atactatcag    2100
tagtaggtgt ttcccttct tctttagcga cttgatgctc ttgatcttcc aatacgcaac    2160
ctaaagtaaa atgccccaca gcgctgagtg catataatgc attctctagt gaaaaacctt    2220
gttggcataa aaaggctaat tgattttcga gagtttcata ctgttttttct gtaggccgtg    2280 tacctaaatg tacttttgct ccatcgcgat gacttagtaa agcacatcta aaacttttag    2340
cgttattacg taaaaaatct tgccagcttt cccttctaa agggcaaaag tgagtatggt    2400
gcctatctaa catctcaatg gctaaggcgt cgagcaaagc ccgcttattt tttacatgcc    2460
aatacaatgt aggctgctct acacctagct tctgggcgag tttacgggtt gttaaacctt    2520
cgattccgac ctcattaagc agctctaatg cgctgttaat cactttactt ttatctaatc    2580
tcaattccat ggtggcaacc tgcaaggcga atgaataaac aagattgtgg cgaacagtgt    2640
aatgcgaaga acccacctct gctccaattc ccaattccct attcagctcg agcggggatc    2700
cccgggtacc gagctcgaat tcggggccgc ggaggctgga tcggtcccgg tgtcttctat    2760
ggaggtcaaa acagcgtgga tggcgtctcc aggcgatctg acggttcact aaacgagctc    2820
tgcttatata ggcctcccac cgtacacgcc tacctcgacc cgggtaccga gctcgacttt    2880 cactttctc tatcactgat agggagtggt aaactcgact ttcactttc tctatcactg    2940 atagggagtg gtaaactcga cttcactttt tctctatcac tgataggag tggtaaactc    3000 gactttcact tttctctatc actgataggg agtggtaaac tcgactttca cttttctcta    3060
tcactgatag ggagtggtaa actcgacttt cactttctc tatcactgat agggagtggt    3120
aaactcgact ttcactttc tctatcactg atagggagtg gtaaactcga atgtcgact    3180 atgcggaccg agcgccggag tataaataga ggcgcttcgt ctacgagcg acaattcaat    3240 tcaaacaagc aaagtgaaca cgtcgctaag cgaaagctaa gcaaataaac aagcgcagct    3300
gaacaagcta acaatctgc gctagccacc atggttgtta ttaaacgtag atttggtaat    3360
tttaaaagca tatttttttc tttgaaattc ataagttatc aattatcgat ggaaatgtat    3420
tctatggaga acgttttacc cgatgaatgg gtgcaaaaat tattttaccct tcaaatctac    3480 aatcaacaca cgctaacttt tgtgacttga tcaactctca cctggaaaag caaccaacta    3540
caatcaacat tctatgggat aatcgacaag tgagtaaaat tatagccgga cctcttagta    3600
cagtgtattt aaaagggggaa taatattcta tcaataggaa taaaaataag gtcagcagcc    3660 atgactttc catcattttg aatataacctt atttgtttcg ggattaattg ggggtcgaa    3720 atcctcttga attcagaaac gggaaccgga ggaaggtgcc ggtctttcag aaagctgtga    3780
```

```
aaaataccaa catttctgct gccaagagct caataagaag tttcaaaaat tgtcttggat    3840
gttgcagctg tggctgctaa gtaataagac atctattagt atctagattt gttagaccat    3900
ttaacatagt gttttaaacg atggggttaa tagatgaggg ttaagaagct agttatatta    3960
ctgttgctgt aacgccttca attgtcggtt acagagcaaa cattattgaa tgttaatgta    4020
aagagtttat ttgttttcta gtaaacatat agcgattggt tagtaatcac taatagaaat    4080
ttttcataag tatcaaaaaa gtaaacctct ttttcagtct atgtaataag taaaccaagg    4140
aaagggaaaa tatctacaat caacaagcca ttgttgcagc aacaaagcaa ctgaaactac    4200
aatcaacatt caataaactt gggtaatttg gaatttaatt ctctgggaca cctgtggatt    4260
acaacaatca actcgaaact tattatacaa tgtaaataaa aattgatatg catacatgaa    4320
gatcaagtga aattccattt agaatcaatt ttttcgaat attaagtttc ttgctttaat    4380
ttatctgaaa gtaaatagac attccaaatt caagttaaca aattaataat gaattgacta    4440
gtgattttta agagaaaaag ataagattta aaaaaggaaa gcctttcttg ataaattttt    4500
gaaccacttt atgccgtttc aatcataaaa acttttaaga acacatgact ggtaaaatta    4560
atttaaaaca aatttaaatt ttcaacgtaa cattcaacaa aaatggtgaa aactatcacg    4620
gaaattgtta atattaatat gtcccaaaaa tagcctttgt atgtatatga tactaatcca    4680
tacatctatg gtatctatag gtgaaggctc aaagcctctg atgcagatct ttgtgaagac    4740
tttgaccgga aagaccatca ccctcgaggt agagccatcg gacaccattg agaatgtaaa    4800
ggccaagatt caggataagg agggaatccc cccagatcag cagcgtctga tcttcgctgg    4860
caagcaactg gaagacggac gcaccctgtc cgattacaac atccagaagg agtccaccct    4920
tcacttggtc cttcgtctcc gtggtggcgc cgtggccttc tacatcccgg atcaggccac    4980
cctgctgcgc gaggccgagc agcgcgagca gcagatcctg cgcctgcgcg agagccagtg    5040
gcgcttcctg gccaccgtgg tgctggagac cctgcgccag tacaccagct gccaccgcg    5100 caccggccgc cgcagcggcc gttaccgccg tccgagccag taacaccggt gatcataatc    5160
agccatacca catttgtaga ggttttactt gctttaaaaa acctcccaca cctcccctg    5220 aacctgaaac ataaaatgaa tgcaattgtt gttgttaact tgtttattgc agcttataat    5280
ggttacaaat aaagcaatag catcacaaat ttcacaaata aagcattttt ttcactgcat    5340
tctagttgtg gtttgtccaa actcatcaat gtatcttaac gcgagtttaa acgcgtccgc    5400
atacgtccgc tcacgttaag ttccgcagag agaagttgtt gaaaacataa acagaatcac    5460
ttgttgcact ctttgagaaa actggggcta ttgcggaaaa aaccaactaa aaatattgca    5520
ggttaggggt actacgctcg attggcgtac ggccaccact tttgcgactt cactgttaac    5580
cgctaccttc atagagactt ttacccgata aatgttatgt agtttgactt tctctgttaa    5640
tcacaagaaa aaatattgtg gaaattaaaa ttatctcaaa ctcaataagg aaataataat    5700
atatacacct atgtttttata gaagtcaaca gtaaataagt tatttggaaa accattgtag    5760
ccgtttaaat aaatctcctt gagtgtgttt taaataacgg tcattaagta tattacttgg    5820
ccctctgaat ttcttgaatt acaccatttt ttgaaataaa tcaatccaaa agactacttt    5880
ttggtggcaa atgaactgca taaaagtaa caaaagaaat atgttttga aataacagta    5940 tagctgaagt gtattaaaaa ataccgtcat atgagcgacc cgctgttacc gcttcgctgc    6000
gaatgacaaa acgggctgag caagaaaatg gcgtagaagg cgacgaaaat tcgtttcact    6060
cgtgaagaaa acctcgataa ctgaggaata cagctgggat ttaaagagca tattcgaact    6120
```

```
acaagcagag atgtttcctg gtggaaacgg aaacgccgat ttgggctaca acaagcatgc    6180
ccacgtccat ggacttggac aacatggcca tgggcacaac cataatcaca atcagttcct    6240
gcgcagcccc caccaccccc cacacatttt tcactgccct ccggggggcgg tcagggcatg    6300
gtgacgccca tggtagccgc cggcctgccg ctcgccatgc agggtggcgt tggcatcgat    6360
tggcgcagct cgcccagcaa tggattaatt aactcgcgtt aagatacatt gatgagtttg    6420
gacaaaccac aactagaatg cagtgaaaaa aatgctttat ttgtgaaatt tgtgatgcta    6480
ttgctttatt tgtaaccatt ataagctgca ataaacaagt taacaacaac aattgcattc    6540
attttatgtt tcaggttcag ggggaggtgt gggaggtttt ttaaagcaag taaaacctct    6600
acaaatgtgg tatggctgat tatgatcagt tatctagatc cggtggatct tacgggtcct    6660
ccaccttccg cttttttcttg ggtcgagatc tcaggaacag gtggtggcgg ccctcggtgc    6720
gctcgtactg ctccacgatg gtgtagtcct cgttgtggga ggtgatgtcc agcttggcgt    6780
ccacgtagta gtagccgggc agctgcacgg gcttcttggc catgtagatg gacttgaact    6840
ccaccaggta gtggccgccg tccttcagct tcagggcctt gtgggtctcg cccttcagca    6900
cgccgtcgcg ggggtacagg cgctcggtgg aggcctccca gcccatggtc ttcttctgca    6960
tcacggggcc gtcggagggg aagttcacgc cgatgaactt caccttgtag atgaagcagc    7020
cgtcctgcag ggaggagtcc tgggtcacgg tcgccacgcc gccgtcctcg aagttcatca    7080
cgcgctccca cttgaagccc tcggggaagg acagcttctt gtagtcgggg atgtcggcgg    7140
ggtgcttcac gtacaccttg agccgtact ggaactgggg ggacaggatg tcccaggcga    7200
agggcagggg gccgcccttg gtcaccttca gcttcacggt gttgtggccc tcgtaggggc    7260
ggccctcgcc ctcgccctcg atctcgaact cgtggccgtt cacggtgccc tccatgcgca    7320
ccttgaagcg catgaactcg gtgatgacgt tctcggagga ggccatggtg gcgaccggtt    7380
tgcgcttctt cttgggtggg gtgggatccc cgatctgcat tttggattat tctgcgggtc    7440
aaaatagaga tgtggaaaat tagtacgaaa tcaaatgagt ttcgttgaaa ttacaaaact    7500
attgaaacta acttcctggc tggggaataa aaatgggaaa cttatttatc gacgccaact    7560
ttgttgagaa acccctatta accctctacg aatattggaa caaggaaaag cgaagaaaca    7620
ggaacaaagg tagttgagaa acctgttccg ttgctcgtca tcgttttcat aatgcgagtg    7680
tgtgcatgta tatatacaca gctgaaacgc atgcatacac attattttgt gtgtatatgg    7740
tgacgtcaca actactaagc aataagaaat tttccagacg tggctttcgt ttcaagcaac    7800
ctactctatt tcagctaaaa ataagtggat ttcgttggta aaatacttca attaagcaaa    7860
gaactaacta actaataaca tgcacacaaa tgctcgagtg cgttcgtgat ttctcgaatt    7920
ttcaaatgcg tcactgcgaa tttcacaatt tgccaataaa tcttggcgaa atcaacacg     7980
caagttttat ttatagattt gtttgcgttt tgatgccaat tgattgggaa aacaagatgc    8040
gtggctgcca atttcttatt ttgtaattac gtagagcgtt gaataaaaaa aaaatggccg    8100
aacaaagacc ttgaaatgca gtttttcttg aaattactca acgtcttgtt gctcttatta    8160
ctaattggta acagcgagtt aaaaacttac gtttcttgtg actttcgaga atgttctttt    8220
aattgtactt aatcaccaa caattaagta taaattttttc gctgattgcg ctttactttc    8280
tgcttgtact tgctgctgca aatgtcaatt ggttttgaag gcgaccgttc gcgaacgctg    8340
tttatatacc ttcggtgtcc gttgaaaatc actaaaaaat accgtagtgt tcgtaacact    8400
ttagtacaga gaaaaaaaat tgtgccgaaa tgttttttgat acgtacgaat accttgtatt    8460
aaaatttttt atgatttctg tgtatcactt ttttttttgtg ttttttcgttt aaactcacca    8520
```

```
cagtacaaaa caataaaata tttttaagac aatttcaaat tgagacctttt ctcgtactga    8580 cttgaccggc tgaatgagga tttctaccta gacgacctac ttcttaccat gacattgaat    8640
gcaatgccac ctttgatcta aacttacaaa agtccaaggc ttgttaggat tggtgtttat    8700
ttagtttgct tttgaaatag cactgtcttc tctaccggct ataattttga aactcgcagc    8760
ttgactggaa atttaaaaag taattctgtg taggtaaagg gtgttttaaa agtgtgatgt    8820
gttgagcgtt gcggcaacga ctgctattta tgtatatatt ttcaaaactt attgtttttg    8880
aagtgtttta aatggagcta tctggcaacg ctgcgcataa tcttacacaa gcttttctta    8940
atccattttt aagtgaaatt tgtttttact ctttcggcaa ataattgtta aatcgcttta    9000
agtgggctta catctggata agtaatgaaa acctgcatat tataatatta aaacatataa    9060
tccactgtgc tttccccgtg tgtggccata tacctaaaaa agtttatttt cgcagagccc    9120
cgcacggtca cactacggtt cggcgatttt cgattttgga cagtactgat tgcaagcgca    9180
ccgaaagcaa aatggagctg agattttga acgcgaagaa cagcaagccg tacggcaagg    9240
tgaaggtgcc ctccggcgcc acgcccatcg gcgatctgcg cgccctaatt cacaagaccc    9300
tgaagcagac cccacacgcg aatcgccagt cgcttcgtct ggaactgaag ggcaaaagcc    9360
tgaaagatac ggacacattg gaatctctgt cgctgcgttc cggcgacaag atcggggtac    9420
catgcggccg ctcatttaaa tctggccggc ctggccgatc tgacaatgtt cagtgcagag    9480
actcggctac gcctcgtgga cttttgaagtt gaccaacaat gtttattctt acctctaata    9540
gtcctctgtg gcaaggtcaa gattctgtta gaagccaatg aagaacctgg ttgttcaata    9600
acattttgtt cgtctaatat ttcactaccg cttgacgttg gctgcacttc atgtacctca    9660
tctataaacg cttcttctgt atcgctctgg acgtcatctt cacttacgtg atctgatatt    9720
tcactgtcag aatcctcacc aacaagctcg tcatcgcttt gcagaagagc agagaggata    9780
tgctcatcgt ctaaagaact acccatttta ttatatatta gtcacgtatt ctataacaag    9840
aaaatatata tataataagt tatcacgtaa gtagaacatg aaataacaat ataattatcg    9900
tatgagttaa atcttaaaag tcacgtaaaa gataatcatg cgtcattttg actcacgcgg    9960
tcgttatagt tcaaaatcag tgacacttac cgcattgaca agcacgcctc acgggagctc   10020
caagcggcga ctgagatgtc ctaaatgcac agcgacggat tcgcgctatt tagaaagaga   10080
gagcaatatt tcaagaatgc atgcgtcaat tttacgcaga ctatcttcct agggttaaaa   10140
aagatttgcg ctttactcga cctaaacttt aaacacgtca tagaatcttc gtttgacaaa   10200
aaccacattg tggccaagct gtgtgacgcg acgcgcgcta aagaatggca aaccaagtcg   10260
cgcgagcgtc gacctgcagg catgcaagct tgcatgcctg caggtcgaaa ttcgtaatca   10320
tggtcatagc tgtttcctgt gtgaaattgt tatccgctca caattccaca caacatacga   10380
gccggaagca taaagtgtaa agcctggggt gcctaatgag tgagctaact cacattaatt   10440
gcgttgcgct cactgcccgc tttccagtcg ggaaacctgt cgtgccagct gcattaatga   10500
atcggccaac gcgcggggag aggcggtttg cgtattgggc gctcttccgc ttcctcgctc   10560
actgactcgc tgcgctcggt cgttcggctg cggcgagcgg tatcagctca ctcaaaggcg   10620
gtaatacggt tatccacaga atcaggggat aacgcaggaa agaacatgtg agcaaaaggc   10680
cagcaaaagg ccaggaaccg taaaaaggcc gcgttgctgg cgttttttcca taggctccgc   10740 cccccctgacg agcatcacaa aaatcgacgc tcaagtcaga ggtggcgaaa cccgacagga   10800
ctataaagat accaggcgtt tcccccctgga agctccctcg tgcgctctcc tgttccgacc   10860
```

```
ctgccgctta ccggatacct gtccgccttt ctcccttcgg gaagcgtggc gctttctcaa   10920
tgctcacgct gtaggtatct cagttcggtg taggtcgttc gctccaagct gggctgtgtg   10980
cacgaacccc ccgttcagcc cgaccgctgc gccttatccg gtaactatcg tcttgagtcc   11040
aacccggtaa gacacgactt atcgccactg gcagcagcca ctggtaacag gattagcaga   11100
gcgaggtatg taggcggtgc tacagagttc ttgaagtggt ggcctaacta cggctacact   11160
agaaggacag tatttggtat ctgcgctctg ctgaagccag ttaccttcgg aaaaagagtt   11220
ggtagctctt gatccggcaa acaaaccacc gctggtagcg gtggtttttt tgtttgcaag   11280
cagcagatta cgcgcagaaa aaaggatct caagaagatc ctttgatctt ttctacgggg   11340
tctgacgctc agtggaacga aaactcacgt taagggattt tggtcatgag attatcaaaa   11400
aggatcttca cctagatcct tttaaattaa aaatgaagtt ttaaatcaat ctaaagtata   11460
tatgagtaaa cttggtctga cagttaccaa tgcttaatca gtgaggcacc tatctcagcg   11520
atctgtctat ttcgttcatc catagttgcc tgactccccg tcgtgtagat aactacgata   11580
cgggagggct taccatctgg ccccagtgct gcaatgatac cgcgagaccc acgctcaccg   11640
gctccagatt tatcagcaat aaaccagcca gccggaaggg ccgagcgcag aagtggtcct   11700
gcaactttat ccgcctccat ccagtctatt aattgttgcc gggaagctag agtaagtagt   11760
tcgccagtta atagtttgcg caacgttgtt gccattgcta caggcatcgt ggtgtcacgc   11820
tcgtcgtttg gtatggcttc attcagctcc ggttcccaac gatcaaggcg agttacatga   11880
tcccccatgt tgtgcaaaaa agcggttagc tccttcggtc ctccgatcgt tgtcagaagt   11940
aagttggccg cagtgttatc actcatggtt atggcagcac tgcataattc tcttactgtc   12000
atgccatccg taagatgctt ttctgtgact ggtgagtact caaccaagtc attctgagaa   12060
tagtgtatgc ggcgaccgag ttgctcttgc ccggcgtcaa tacgggataa taccgcgcca   12120
catagcagaa ctttaaaagt gctcatcatt ggaaaacgtt cttcggggcg aaaactctca   12180
aggatcttac cgctgttgag atccagttcg atgtaaccca ctcgtgcacc caactgatct   12240
tcagcatctt ttactttcac cagcgtttct gggtgagcaa aaacaggaag gcaaaatgcc   12300
gcaaaaaagg gaataagggc gacacggaaa tgttgaatac tcatactctt ccttttcaa   12360
tattattgaa gcatttatca gggttattgt ctcatgagcg gatacatatt tgaatgtatt   12420
tagaaaaata aacaaatagg ggttccgcgc acatttcccc gaaaagtgcc acctgacgtc   12480
taagaaacca ttattatcat gacattaacc tataaaaata ggcgtatcac gaggcccttt   12540
cgtctcgcgc gtttcggtga tgacggtgaa aacctctgac acatgcagct cccggagacg   12600
gtcacagctt gtctgtaagc ggatgccggg agcagacaag cccgtcaggg cgcgtcagcg   12660
ggtgttggcg ggtgtcgggg ctggcttaac tatgcggcat cagagcagat tgtactgaga   12720
gtgcaccata tatgcggtgt gaaataccgc acagatgcgt aaggagaaaa taccgcatca   12780
ggcgccattc gccattcagg ctgcgcaact gttgggaagg gcgatcggtg cgggcctctt   12840
cgctattacg ccagctggcg aaaggggat gtgctgcaag gcgattaagt tgggtaacgc   12900
cagggttttc ccagtcacga cgttgtaaaa cgacggccag tgccaagctt gtttaaaat   12960
ataacaaaat tgtgatccca caaaatgaag tggggcaaaa tcaaataatt aatagtgtcc   13020
gtaaacttgt tggtcttcaa cttttgaggg aacacgttgg acggcaaatc cgtgactata   13080
acacaagttg atttaataat tttagccaac acgtcgggct gcgtgttttt tgccgacgcg   13140
tctgtgtaca cgttgattaa ctggtcgatt aaactgttga aataatttaa ttttggttc   13200
ttctttaaat ctgtgatgaa attttttaaa ataactttaa attcttcatt ggtaaaaaat   13260
```

```
gccacgtttt gcaacttgtg agggtctaat atgaggtcaa actcagtagg agttttatcc    13320
aaaaaagaaa acatgattac gtctgtacac gaacgcgtat taacgcagag tgcaaagtat    13380
aagagggtta aaaatatat tttacgcacc atatacgcat cgggttgata tcgttaatat     13440
ggatcaattt gaacagttga ttaacgtgtc tctgctcaag tctttgatca aaacgcaaat    13500
cgacgaaaat gtgtcggaca atatcaagtc gatgagcgaa aaactaaaaa ggctagaata    13560
cgacaatctc acagacagcg ttgagatata cggtattcac gacagcaggc tgaataataa    13620
aaaaattaga aactattatt taaccctaga aagataatca tattgtgacg tacgttaaag    13680
ataatcatgc gtaaaattga cgcatgtgtt ttatcggtct gtatatcgag gtttatttat    13740
taatttgaat agatattaag ttttattata tttacactta catactaata ataaattcaa    13800
caaacaattt atttatgttt atttatttat taaaaaaaaa caaaaactca aaatttcttc    13860
tataaagtaa caaaactttt aaacattctc tcttttacaa aaataaactt attttgtact    13920
ttaaaaacag tcatgttgta ttataaaata agtaattagc ttaacttata cataatagaa    13980
acaaattata cttattagtc agtcagaaac aactttggca catatcaata ttatgctctc    14040
gacaaataac ttttttgcat tttttgcacg atgcatttgc ctttcgcctt attttagagg    14100
ggcagtaagt acagtaagta cgttttttca ttactggctc ttcagtactg tcatctgatg    14160
taccaggcac ttcatttggc aaaatattag agatattatc gcgcaaatat ctcttcaaag    14220
taggagcttc taaacgctta cgcataaacg atgacgtcag gctcatgtaa aggtttctca    14280 taaattttt gcgactttgg acctttctc ccttgctact gacattatgg ctgtatataa     14340
taaaagaatt tatgcaggca atgtttatca ttccgtacaa taatgccata ggccaccttat   14400 tcgtcttcct actgcaggtc atcacagaac acatttggtc tagcgtgtcc actccgcctt    14460
tagtttgatt ataatacata accatttgcg gtttaccggt actttcgttg atagaagcat    14520
cctcatcaca agatgataat aagtatacca tcttagctgg cttcggttta tatgagacga    14580
gagtaagggg tccgtcaaaa caaaacatcg atgttcccac tggcctggag cgactgtttt    14640
tcagtacttc cggtatctcg cgtttgtttg atcgcacggt tcccacaatg gttgcggcca    14700
gcccgggcta tgg                                                      14713
```

<210> SEQ ID NO 54
<211> LENGTH: 15848
<212> TYPE: DNA
<213> ORGANISM: Artificial Sequence
<220> FEATURE:
<223> OTHER INFORMATION: Synthetic construct, pLA3166-Cctra
      intron-Ubiquitin-reaperKR construct.

<400> SEQUENCE: 54

```
gggcggccgt ttttcttgaa atattgctct ctctttctaa atagcgcgaa tccgtcgctg      60
tgcatttagg acatctcagt cgccgcttgg agctcccaaa cgcgccagtg gtagtacaca     120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaagtttt cgcaatgcc tttatttttt gttgcaaatc     360
tctctttatt ctgcggtatt cttcattatt gcgggatgg ggaaagtgtt tatatagaag     420
caacttacga ttgaacccaa atgcacctga caagcaaggt caagggcca gattttaaa      480 tatattattt agtcttagga ctctctattt gcaattaaat tactttgcta cctgagggtt    540
```

| | |
|---|---|
| aaatcttccc cattgataat aataattcca ctatatgttc aattgggttt caccgcgctt | 600 |
| agttacatga cgagccctaa tgagccgtcg gtggtctata aactgtgcct tacaaatact | 660 |
| tgcaactctt ctcgttttga agtcagcaga gttattgcta attgctaatt gctaattgct | 720 |
| tttaactgat ttcttcgaaa ttggtgctat gtttatggcg ctattaacaa gtatgaatgt | 780 |
| caggtttaac caggggatgc ttaattgtgt tctcaacttc aaaggcagaa atgtttactc | 840 |
| ttgaccatgg gtttaggtat aatgttatca agctcctcga gttaacgtta cgttaacgtt | 900 |
| aacgttcgag gtcgactcta gaactaccca ccgtactcgt caattccaag gcatcggta | 960 |
| aacatctgct caaactcgaa gtcggccata tccagagcgc cgtaggggc ggagtcgtgg | 1020 |
| ggggtaaatc ccggacccgg ggaatccccg tcccccaaca tgtccagatc gaaatcgtct | 1080 |
| agcgcgtcgg catgcgccat cgccacgtcc tcgccgtcta agtggagctc gtcccccagg | 1140 |
| ctgacatcgg tcgggggggc cgtcgacagt ctgcgcgtgt gtcccgcggg gagaaaggac | 1200 |
| aggcgcggag ccgccagccc cgcctcttcg ggcgtcgt cgtccgggag atcgagcagg | 1260 |
| ccctcgatgg tagacccgta attgtttttc gtacgcgcgc ggctgtacgc ggggcccgag | 1320 |
| cccgactcgc atttcagttg cttttccaat ccgcagataa tcagctccaa gccgaacagg | 1380 |
| aatgccggct cggctccttg atgatcgaac agctcgattg cctgacgcag cagtggggc | 1440 |
| atcgaatcgg ttgttggggt ctcgcgctcc tcttttgcga cttgatgctc ttggtcctcc | 1500 |
| agcacgcagc ccagggtaaa gtgaccgacg gcgctcagag cgtagagagc attttccagg | 1560 |
| ctgaagcctt gctggcacag gaacgcgagc tggttctcca gtgtctcgta ttgcttttcg | 1620 |
| gtcgggcgcg tgccgagatg gactttggca ccgtctcggt gggacagcag agcgcagcgg | 1680 |
| aacgacttgg cgttattgcg gaggaagtcc tggaaatggg atagatattg gtgttattgt | 1740 |
| tcatgtggca tataaaggac aagcaacaaa aaacgaacat aacatgagag atggttctga | 1800 |
| atcagaactt ctgaatatta tcctcccaaa agggttaaag tttttattaa gcatattacg | 1860 |
| ttttatacca cttccttatg taaaattttc ttcgtagttt aatatcatgt gaaatcatat | 1920 |
| ataatttcta tcgaacgttt gttcaaattg aatgatgtca ttttttgaat aattggttat | 1980 |
| aattttataa catctcccga cttcgacatg tggttggtac taatgattgc gaaatcgccc | 2040 |
| tccgagaatg agaacaaccg aggtccaccg tctggtcgag attaaaacac ttgaggagtg | 2100 |
| ctttggtgac tcgatcaata ggtacagggc tcgttgccaa caatctggcc agctggacat | 2160 |
| ccgggacctc gttccccct ggggtatcaa aattttgta gtgtaaatag tagtacactc | 2220 |
| ttaaaaataa tgaaaattac tgcggacgta attcacatta tgattgaatg acactatcat | 2280 |
| tgacatttcc cgaatcagac accatcgtat ttaaaatgtg acacaaattc acctcatttg | 2340 |
| gctcgcttct tttatgtgca tccaaaagac gtaaaatcgc atgattttt cggagtgtgt | 2400 |
| agtaagattg tcaaatttta attttaaata accagagccc ataaagcaaa gcaacactag | 2460 |
| gaaaaaaccc acaaactcaa cctgtccaaa aaaaatata acaatcaaag ttgagggaat | 2520 |
| cggggtcaaa cgtcatgtaa aaatattttt tgtaaaaacc aaaccaggaa taaatatgaa | 2580 |
| tttaatcgga aaaaattgca aaatcgcata atttaatcct ccaactgtac tttatccagc | 2640 |
| ctgttgcaga aatgatgttt aaaggttcta atctgtaatt gttattagcc ttcaatactg | 2700 |
| atgtagtatt tatttcttat tgaaacattg agagctttat tttccaaagt tgtcattttc | 2760 |
| tcattcgtat atcgtaatat gtatattcgt aaatggcaag cacaatgata cttagggtag | 2820 |
| tcaaggatat ttcaattacg aaaagatcct gaaacgaccg ggaatcgaac ccttcagcat | 2880 |

```
ggttttgctt tgtagctgct gaatctaacc actaggctga tgaagatccc atttttagggt    2940 tgcaagttct caaagagcaa gaatgccaaa atagtgtcaa aagaagccct atttgacgat    3000
atacctttta gtctctacgt taatttgcta tgataattta tcatcaatta attggcaaag    3060
cctgatgcac gaaaagatct tcttctaaaa tttcagttgt tcttttcaac acattatgta    3120
atcataaaat ttaattaata aaccttttt tttttgtaact atccacagtt gatcaggcat    3180
aatttttctg gaaagtaaag tccatattta ggttgatgtt gaataaaaaa actttcaatt    3240
cactcttctg tttcacttca gaacttacgt aatacgacat tatgcatggt gcacacggaa    3300
caggataaga cgttcacaag ggatcaacat cacatcggat cgtaatcact ggatctggaa    3360
cacatatgac gccacaagac agcacatttt acacgatcac cagacgtgaa caaggaactg    3420
gatccacaag acgtcacagg aagacggcac atttccaacg gcttcgatgg aacttttctc    3480
gagtcttttt ccaccaatca taaacaccga cctgccagga ctcgccttcc aacgggcaaa    3540
aatgcgtgtg gtggcggtcg agcatctcga tggccagggc atccagcagc gcccgcttat    3600
tcttcacgtg ccagtagagg gtgggctgct ccacgcccag cttctgcgcc aacttgcggg    3660
tcgtcagtcc ctcaatgcca acttcgttca acagctccaa cgcggagttg atgactttgg    3720
acttatccag gcggctgccc atggtggttt ctaaaggtgt tataaatcaa attagttttg    3780 tttttcttg aaaactttgc gtttcctttg atcaacttac cgccagggta ccgcagattg    3840
tttagcttgt tcagctgcgc ttgtttattt gcttagcttt cgcttagcga cgtgttcact    3900
ttgcttgttt gaattgaatt gtcgctccgt agacgaagcg cctctattta tactccggcg    3960
ctcgttttcg agtttaccac tccctatcag tgatagagaa aagtgaaagt cgagtttacc    4020
actccctatc agtgatagag aaaagtgaaa gtcgagttta ccactcccta tcagtgatag    4080
agaaaagtga agtcgagtt taccactccc tatcagtgat agagaaaagt gaaagtcgag    4140
tttaccactc cctatcagtg atagagaaaa gtgaaagtcg agtttaccac tccctatcag    4200
tgatagagaa aagtgaaagt cgagtttacc actccctatc agtgatagag aaaagtgaaa    4260
gtcgaaacct ggcgcgcccc ggccatcgag aaagagagag agaagagaag agagagaaca    4320 tcgagaaag agagagagaa gagaagagag agaacatact ccctatcagt gatagagaag    4380
tccctatcag tgatagagat gtccctatca gtgatagaga gttccctatc agtgatagag    4440
acgtccctat cagtgataga gaagtcccta tcagtgatag agatccct atcagtgata    4500 gagatttccc tatcagtgat agagaggtcc ctatcagtga tagagacttc cctatcagtg    4560
atagagaaat ccctatcagt gatagagaca tccctatcag tgatagagaa ctccctatca    4620
gtgatagaga cctccctatc agtgatagag atcgatgcgg ccgcatggta cccattgctt    4680
gtcatttatt aatttggatg atgtcatttg ttttttaaaat tgaactggct ttacgagtag    4740
aattctacgc gtaaaacaca atcaagtatg agtcataatc tgatgtcatg ttttgtacac    4800
ggctcataac cgaactggct ttacgagtag aattctactt gtaatgcacg atcagtggat    4860
gatgtcattt gttttttcaaa tcgagatgat gtcatgtttt gcacacggct cataaactcg    4920
ctttacgagt agaattctac gtgtaacgca cgatcgattg atgagtcatt tgttttgcaa    4980
tatgatatca tacaatatga ctcatttgtt tttcaaaacc gaacttgatt tacgggtaga    5040
attctacttg taaagcacaa tcaaaagat gatgtcattt gttttttcaaa actgaactcg    5100 ctttacgagt agaattctac gtgtaaaaca caatcaagaa atgatgtcat tgttataaa    5160 aataaaagct gatgtcatgt tttgcacatg gctcataact aaactcgctt tacgggtaga    5220
attctacgcg taaaacatga ttgataatta ataattcat ttgcaagcta tacgttaaat    5280
```

```
caaacggacg ctcgaggttg cacaacacta ttatcgattt gcagttcggg acataaatgt   5340
ttaaatatat cgatgtcttt gtgatgcgcg cgacatttt gtaggttatt gataaaatga   5400
acggatacgt tgcccgacat tatcattaaa tccttggcgt agaatttgtc gggtccattg   5460
tccgtgtgcg ctagcatgcc cgtaacggac ctcgtactt tggcttcaaa ggttttgcgc   5520
acagacaaaa tgtgccacac ttgcagctct gcatgtgtgc gcgttaccac aaatcccaac   5580
ggcgcagtgt acttgttgta tgcaaataaa tctcgataaa ggcgcggcgc gcgaatgcag   5640
ctgatcacgt acgctcctcg tgttccgttc aaggacggtg ttatcgacct cagattaatg   5700
tttatcggcc gactgttttc gtatccgctc accaaacgcg ttttttgcatt aacattgtat   5760
gtcggcggat gttctatatc taatttgaat aaataaacga taaccgcgtt ggttttagag   5820
ggcataataa aagaaatatt gttatcgtgt tcgccattag ggcagtataa attgacgttc   5880
atgttggata ttgtttcagt tgcaagttga cactggcggc gacaagcaat tctaattggg   5940
gtaagttttc ccgttctttt ctgggttctt cccttttgct catccttgct gcactacctt   6000
caggtgcaag ttgagattca ggccaccatg ggagatccca ccccacccaa gaagaagcgc   6060
aaaccggtcg ccaccatgga cgaggatggt tcagagggcg gccccgccct gttccagagc   6120
gacatgacct tcaaaatctt catcgacggc gaggtgaacg gccagaagtt caccatcgtg   6180
gccgacggca gcagcaagtt cccccacggc gacttcaacg tgcacgccgt gtgcgagacc   6240
ggcaagctgc ccatgagctg gaagcccatc tgccacctga tccagtacgg cgagcccttc   6300
ttcgcccgct accccaacgg catcagccac ttcgcccagg agtgcttccc cgagggcctg   6360
agcatcgacc gcaccgtgcg cttcgagaac gacggcacca tgaccagcca ccacacctac   6420
gagctggacg gcacctgcgt ggtcagccgc atcaccgtga actgcgacgg cttccagccc   6480
gacggcccca tcatgcgcga ccagctggtg gacatcctgc ccaacgagac ccacatgttc   6540
ccccacggcc ccaacgccgt gcgccagctg gccttcatcg gcttcaccac cgccgacggc   6600
ggcctgatga tgggccactt cgacagcaag atgaccttca acggcagccg cgccatcaag   6660
atccccggcc cccacttcgt gaccatcatc accaagcaga tgagggacac cagcgacaag   6720
cgcgaccacg tgtgccagcg cgaggtgacc tacgcccaca gcgtgccccg catcaccagc   6780
gccatcggta gcgacgagga ttccggactc agatctcgac ccaagaaaaa gcggaaggtg   6840
gaggacccgt aagatccacc ggatctagat aactgatcat aatcagccat accacatttg   6900
tagaggtttt acttgcttta aaaaacctcc cacacctccc cctgaacctg aaacataaaa   6960
tgaatgcaat tgttgttgtt aacttgttta ttgcagctta taatggttac aaataaagca   7020
atagcatcac aaatttcaca aataaagcat ttttttcact gcattctagt tgtggtttgt   7080
ccaaactcat caatgtatct taacgcgagt taattaatcc attgctgggc gagctgcgcc   7140
aatcgatgcc aacgccaccc tgcatggcga gcggcaggcc ggcggctacc atgggcgtca   7200
ccatgccctg accgccccg gagggcagtg aaaaatgtgt gggggtggt ggggctgcg   7260
caggaactga ttgtgattat ggttgtgccc atggccatgt tgtccaagtc catggacgtg   7320
ggcatgcttg ttgtagccca aatcggcgtt tccgtttcca ccaggaaaca tctctgcttg   7380
tagttcgaat atgctcttta aatcccagct gtattcctca gttatcgagg ttttcttcac   7440
gagtgaaacg aattttcgtc gccttctacg ccattttctt gctcagcccg ttttgtcatt   7500
cgcagcgaag cggtaacagc gggtcgctca tatgacggta ttttttaata cacttcagct   7560
atactgttat ttcaaaaaca tatttctttt gttacttttt atgcagttca tttgccacca   7620
```

```
aaaagtagtc ttttggattg atttatttca aaaaatggtg taattcaaga aattcagagg    7680
gccaagtaat atacttaatg accgttattt aaaacacact caaggagatt tatttaaacg    7740
gctacaatgg ttttccaaat aacttattta ctgttgactt ctataaaaca taggtgtata    7800
tattattatt tccttattga gtttgagata attttaattt ccacaatatt ttttcttgtg    7860
attaacagag aaagtcaaac tacataacat ttatcgggta aaagtctcta tgaaggtagc    7920
ggttaacagt gaagtcgcaa aagtggtggc cgtacgccaa tcgagcgtag taccccctaac   7980
ctgcaatatt tttagttggt ttttccgca  atagcccag  ttttctcaaa gagtgcaaca    8040
agtgattctg tttatgtttt caacaacttc tctctgcgga acttaacgtg agcggacgta    8100
tgcggacgcg tttaaactcg cgttaagata cattgatgag tttggacaaa ccacaactag    8160
aatgcagtga aaaaaatgct ttatttgtga aatttgtgat gctattgctt tatttgtaac    8220
cattataagc tgcaataaac aagttaacaa caacaattgc attcatttta tgtttcaggt    8280
tcaggggag  gtgtgggagg ttttttaaag caagtaaaac ctctacaaat gtggtatggc    8340
tgattatgat caccggtgtt actggctcgg acggcggtaa cggccgctgc ggcggccggt    8400
gcgcgggtgg cagctggtgt actggcgcag ggtctccagc accacggtgg ccaggaagcg    8460
ccactggctc tcgcgcaggc gcaggatctg ctgctcgcgc tgctcggcct cgcgcagcag    8520
ggtggcctga tccgggatgt agaaggccac ggcgccacca cggagacgaa ggaccaagtg    8580
aagggtggac tccttctgga tgttgtaatc ggacagggtg cgtccgtctt ccagttgctt    8640
acctatagat accatagatg tatggattag tatcatatac atacaaaggc tattttggg    8700
acatattaat attaacaatt tccgtgatag ttttcaccat ttttgttgaa tgttacgttg    8760
aaaatttaaa tttgttttaa attaatttta ccagtcatgt gttcttaaaa gttttatga    8820
ttgaaacggc ataagtggt  tcaaaaattt atcaagaaag ctttcctttt tttaaatctt    8880
atctttttct cttaaaaatc actagtcaat tcattattaa tttgttaact tgaatttgga    8940
atgtctattt actttcagat aaattaaagc aagaaactta atattcgaaa aaaattgatt    9000
ctaaatggaa tttcacttga tcttcatgta tgcatatcaa ttttttattta cattgtataa    9060
taagtttcga gttgattgtt gtaatccaca ggtgtcccag agaattaaat tccaaattac    9120
ccaagtttat tgaatgttga ttgtagtttc agttgctttg ttgctgcaac aatggcttgt    9180
tgattgtaga tatttttccct ttccttggtt tacttattac atagactgaa aaagaggttt    9240
actttttgtga tacttatgaa aaatttctat tagtgattac taaccaatcg ctatatgttt    9300
actagaaaac aaataaactc tttacattaa cattcaataa tgtttgctct gtaaccgaca    9360
attgaaggcg ttacagcaac agtaatataa ctagcttctt aaccctcatc tattaacccc    9420
atcgtttaaa acactatgtt aaatggtcta acaaatctag atactaatag atgtcttatt    9480
acttagcagc cacagctgca acatccaaga caatttttga aacttcttat tgagctcttg    9540
gcagcagaaa tgttggtatt tttcacagct ttctgaaaga ccggcacctt cctccggttc    9600
ccgtttctga attcaagagg attccgacc  cccaattaat cccgaaacaa ataaggtata    9660
ttcaaaatga tggaaaagtc atggctgctg accttatttt tattcctatt gatagaatat    9720
tattccccctt ttaaatacac tgtactaaga ggtccggcta taatttttact cacttgtcga    9780
ttatcccata gaatgttgat tgtagttggt tgcttttcca ggtgagagtt gatcaagtca    9840
caaaagttag cgtgtgttga ttgtagattt gaaggtaaaa taattttttgc acccattcat    9900
cgggtaaaac gttctccata gaatacattt ccatcgataa ttgataactt atgaatttca    9960
aagaaaaaaa tatgctttta aaattaccag cgaagatcag acgctgctga tctgggggga   10020
```

```
ttccctcctt atcctgaatc ttggccttta cattctcaat ggtgtccgat ggctctacct   10080
cgagggtgat ggtctttccg gtcaaagtct tcacaaagat ctgcattttg gattgctagc   10140
gcagattgtt tagcttgttc agctgcgctt gtttatttgc ttagctttcg cttagcgacg   10200
tgttcacttt gcttgtttga attgaattgt cgctccgtag acgaagcgcc tctatttata   10260
ctccggcgct cggtccgcat agtcgacatt tcgagtttac cactccctat cagtgataga   10320
gaaaagtgaa agtcgagttt accactccct atcagtgata gagaaaagtg aaagtcgagt   10380
ttaccactcc ctatcagtga tagagaaaag tgaaagtcga gtttaccact ccctatcagt   10440
gatagagaaa agtgaaagtc gagtttacca ctccctatca gtgatagaga aagtgaaag   10500 tcgagtttac cactccctat cagtgataga gaaaagtgaa agtcgagttt accactccct   10560
atcagtgata gagaaaagtg aaagtcgagc tcggtacccg ggtcgaggta ggcgtgtacg   10620
gtgggaggaa atctggccgg ccgcaaccat tgtgggaacc gtgcgatcaa acaaacgcga   10680
gataccggaa gtactgaaaa acagtcgctc caggccagtg ggaacatcga tgttttgttt   10740
tgacggaccc cttactctcg tctcatataa accgaagcca gctaagatgg tatacttatt   10800
atcatcttgt gatgaggatg cttctatcaa cgaaagtacc ggtaaaccgc aaatggttat   10860
gtattataat caaactaaag gcggagtgga cacgctagac caaatgtgtt ctgtgatgac   10920
ctgcagtagg aagacgaata ggtggcctat ggcattattg tacggaatga taaacattgc   10980
ctgcataaat tctttatta tatacagcca taatgtcagt agcaagggag aaaaggtcca   11040
aagtcgcaaa aaatttatga gaaaccttta catgagcctg acgtcatcgt ttatgcgtaa   11100
gcgtttagaa gctcctactt tgaagagata tttgcgcgat aatatctcta atattttgcc   11160
aaatgaagtg cctggtacat cagatgacag tactgaagag ccagtaatga aaaacgtac   11220 ttactgtact tactgcccct ctaaaataag gcgaaaggca aatgcatcgt gcaaaaaatg   11280
caaaaaagtt atttgtcgag agcataaatat tgatatgtgc caaagttgtt tctgactgac   11340
taataagtat aatttgtttc tattatgtat aagttaagct aattacttat tttataatac   11400
aacatgactg ttttaaagt acaaaataag tttattttg taaaagagag aatgttaaa   11460 agttttgtta cttatagaa gaaattttga gtttttgttt tttttaata aataaataaa   11520 cataaataaa ttgtttgttg aatttattat tagtatgtaa gtgtaaatat aataaaactt   11580
aatatctatt caaattaata aataaacctc gatatacaga ccgataaaac acatgcgtca   11640
attttacgca tgattatctt taacgtacgt cacaatatga ttatctttct agggttaaat   11700
aatagtttct aatttttta ttattcagcc tgctgtcgtg aataccgtat atctcaacgc   11760
tgtctgtgag attgtcgtat tctagccttt ttagttttc gctcatcgac ttgatattgt   11820
ccgacacatt ttcgtcgatt tgcgttttga tcaaagactt gagcagagac acgttaatca   11880
actgttcaaa ttgatccata ttaacgatat caacccgatg cgtatatggt gcgtaaaata   11940 tatttttaa ccctcttata ctttgcactc tgcgttaata cgcgttcgtg tacagacgta   12000
atcatgtttt cttttttgga taaaactcct actgagtttg acctcatatt agaccctcac   12060
aagttgcaaa acgtggcatt ttttaccaat gaagaattta agttatttt aaaaatttc   12120 atcacagatt taaagaagaa ccaaaaatta aattattcca acagtttaat cgaccagtta   12180
atcaacgtgt acacagacgc gtcggcaaaa acacgcagc ccgacgtgtt ggctaaaatt   12240
attaaatcaa cttgtgttat agtcacggat ttgccgtcca acgtgttcct caaaaagttg   12300
aagaccaaca agtttacgga cactattaat tatttgattt tgccccactt catttgtgg   12360
```

-continued

```
gatcacaatt ttgttatatt ttaaacaaag cttggcactg gccgtcgttt tacaacgtcg    12420
tgactgggaa aaccctggcg ttacccaact taatcgcctt gcagcacatc cccctttcgc    12480
cagctggcgt aatagcgaag aggcccgcac cgatcgccct cccaacagtt gcgcagcct    12540 gaatggcgaa tggcgcctga tgcggtattt tctccttacg catctgtgcg gtatttcaca    12600
ccgcatatgg tgcactctca gtacaatctg ctctgatgcc gcatagttaa gccagccccg    12660
acacccgcca cacccgctgg acgcgccctg acgggcttgt ctgctcccgg catccgctta    12720
cagacaagct gtgaccgtct ccgggagctg catgtgtcag aggttttcac cgtcatcacc    12780
gaaacgcgcg agacgaaagg gcctcgtgat acgcctattt ttataggtta atgtcatgat    12840
aataatggtt tcttagacgt caggtggcac ttttcgggga atgtgcgcg gaaccccctat    12900 ttgttatttt ttctaaatac attcaaatat gtatccgctc atgagacaat aaccctgata    12960
aatgcttcaa taatattgaa aaaggaagag tatgagtatt caacatttcc gtgtcgccct    13020
tattcccttt tttgcggcat tttgccttcc tgttttttgct cacccagaaa cgctggtgaa    13080
agtaaaagat gctgaagatc agttgggtgc acagtgggt tacatcgaac tggatctcaa    13140
cagcggtaag atccttgaga gttttcgccc cgaagaacgt tttccaatga tgagcacttt    13200
taaagttctg ctatgtggcg cggtattatc ccgtattgac gccgggcaag agcaactcgg    13260
tcgccgcata cactattctc agaatgactt ggttgagtac tcaccagtca cagaaaagca    13320
tcttacggat ggcatgacag taagagaatt atgcagtgct gccataacca tgagtgataa    13380
cactgcggcc aacttacttc tgacaacgat cggaggaccg aaggagctaa ccgcttttttt    13440 gcacaacatg gggggatcatg taactcgcct tgatcgttgg gaaccggagc tgaatgaagc    13500
cataccaaac gacgagcgtg acaccacgat gcctgtagca atggcaacaa cgttgcgcaa    13560
actattaact ggcgaactac ttactctagc ttcccggcaa caattaatag actggatgga    13620
ggcggataaa gttgcaggac cacttctgcg ctcggccctt ccggctggct ggtttattgc    13680
tgataaatct ggagccggtg agcgtgggtc tcgcggtatc attgcagcac tggggccaga    13740
tggtaagccc tcccgtatcg tagttatcta cacgacgggg agtcaggcaa ctatggatga    13800
acgaaataga cagatcgctg agataggtgc ctcactgatt aagcattggt aactgtcaga    13860
ccaagtttac tcatatatac tttagattga tttaaaactt cattttaat ttaaaaggat    13920 ctaggtgaag atcctttttg ataatctcat gaccaaaatc ccttaacgtg agttttcgtt    13980
ccactgagcg tcagaccccg tagaaaagat caaaggatct tcttgagatc cttttttttct    14040 gcgcgtaatc tgctgcttgc aaacaaaaaa accaccgcta ccagcggtgg tttgtttgcc    14100
ggatcaagag ctaccaactc tttttccgaa ggtaactggc ttcagcagag cgcagatacc    14160
aaatactgtc cttctagtgt agccgtagtt aggccaccac ttcaagaact ctgtagcacc    14220
gcctacatac ctcgctctgc taatcctgtt accagtggct gctgccagtg gcgataagtc    14280
gtgtcttacc gggttggact caagacgata gttaccggat aaggcgcagc ggtcgggctg    14340
aacggggggt tcgtgcacac agcccagctt ggagcgaacg acctacaccg aactgagata    14400
cctacagcgt gagcattgag aaagcgccac gcttcccgaa gggagaaagg cggacaggta    14460
tccggtaagc ggcagggtcg gaacaggaga gcgcacgagg gagcttccag ggggaaacgc    14520
ctggtatctt tatagtcctg tcgggtttcg ccacctctga cttgagcgtc gatttttgtg    14580
atgctcgtca ggggggcgga gcctatggaa aaacgccagc aacgcggcct ttttacggtt    14640
cctggccttt tgctggcctt ttgctcacat gttctttcct gcgttatccc ctgattctgt    14700
ggataaccgt attaccgcct ttgagtgagc tgataccgct cgccgcagcc gaacgaccga    14760
```

```
gcgcagcgag tcagtgagcg aggaagcgga agagcgccca atacgcaaac cgcctctccc    14820
cgcgcgttgg ccgattcatt aatgcagctg gcacgacagg tttcccgact ggaaagcggg    14880
cagtgagcgc aacgcaatta atgtgagtta gctcactcat taggcacccc aggctttaca    14940
ctttatgctt ccggctcgta tgttgtgtgg aattgtgagc ggataacaat ttcacacagg    15000
aaacagctat gaccatgatt acgaatttcg acgctcgcgc gacttggttt gccattcttt    15060
agcgcgcgtc gcgtcacaca gcttggccac aatgtggttt ttgtcaaacg aagattctat    15120
gacgtgttta agtttaggt cgagtaaagc gcaaatcttt tttaacccta gaaagatagt      15180
ctgcgtaaaa ttgacgcatg cattcttgaa atattgctct ctctttctaa atagcgcgaa    15240
tccgtcgctg tgcatttagg acatctcagt cgccgcttgg agctcccgtg aggcgtgctt    15300
gtcaatgcgg taagtgtcac tgattttgaa ctataacgac cgcgtgagtc aaaatgacgc    15360
atgattatct tttacgtgac ttttaagatt taactcatac gataattata ttgttatttc    15420
atgttctact tacgtgataa cttattatat atatattttc ttgttataga tatcgtgact    15480
aatatataat aaaatgggta gttctttaga cgatgagcat atcctctctg ctcttctgca    15540
aagcgatgac gagcttgttg gtgaggattc tgacagtgaa atatcagatc acgtaagtga    15600
agatgacgtc cagagcgata cagaagaagc gtttatagat gaggtacatg aagtgcagcc    15660
aacgtcaagc ggtagtgaaa tattagacga acaaaatgtt attgaacaac caggttcttc    15720
attggcttct aacagaatct tgaccttgcc acagaggact attagaggta agaataaaca    15780
ttgttggtca acttcaaagt ccacgaggcg tagccgagtc tctgcactga acattgtcag    15840
atcggccc                                                              15848

<210> SEQ ID NO 55
<211> LENGTH: 17802
<212> TYPE: DNA
<213> ORGANISM: Artificial Sequence
<220> FEATURE:
<223> OTHER INFORMATION: Synthetic construct, pLA3376-Bztra
      intron-reaperKR and Bztra-intron-tTAV3.

<400> SEQUENCE: 55
gggcggccgt ttttcttgaa atattgctct ctctttctaa atagcgcgaa tccgtcgctg         60
tgcatttagg acatctcagt cgccgcttgg agctcccaaa cgcgccagtg gtagtacaca       120
gtactgtggg tgttcagttt gaaatcctct tgcttctcca ttgtctcggt taccttttggt      180 caaatccatg ggttctattg cctatatact cttgcgatta ccagtgattg cgctattagc      240
tattagatgg attgttggcc aaacttgtcg cttaagtggc tgggaattgt aaccgtaggc      300
ccgagtgtaa tgatccccca taaaaagttt tcgcaatgcc tttatttttt gttgcaaatc      360
tctctttatt ctgcggtatt cttcattatt gcggggatgg ggaaagtgtt tatatagaag      420
caacttacga ttgaacccaa atgcacctga caagcaaggt caaagggcca gatttttaaa      480
tatattattt agtcttagga ctctctattt gcaattaaat tactttgcta cctgagggtt      540
aaatcttccc cattgataat aataattcca ctatatgttc aattgggttt caccgcgctt      600
agttacatga cgagccctaa tgagccgtcg gtggtctata aactgtgcct tacaaaatact    660 tgcaactctt ctcgttttga agtcagcaga gttattgcta attgctaatt gctaattgct      720
tttaactgat ttcttcgaaa ttggtgctat gtttatggcg ctattaacaa gtatgaatgt      780
caggtttaac caggggatgc ttaattgtgt tctcaacttc aaaggcagaa atgtttactc      840
ttgaccatgg gtttaggtat aatgttatca agctcctcga gttaacgtta cgttaacgtt      900
```

```
aacgttcgag gtcgactcta gacaccggtg ttagccgccg tactcatcga tgcccagggc    960
gtcggtgaac atctgctcga actcgaaatc ggccatatcc agggcgccgt aggggggcgct  1020
atcgtgcggg gtgaatcccg gtcccgggct atcgccatcg cccagcatgt ccaggtcgaa  1080
gtcgtccagg gcatcggcgt gggccatcgc cacatcctcg ccatccaggt gcagctcatc  1140
gcccaggctc acgtcggtcg gcggggcggt cgacaggcgg cgggtgtgtc cggccggcag  1200
gaagctcagg cgcggggcgg ccaggcccgc ctcctccggg gcatcatcat ccggcagatc  1260
cagcaggccc tcgatggtgc tgccgtagtt gttcttggtg cgggcgcggc tgtaggcggg  1320
gcccgagccc gactcgcatt tcagttgctt ttccaatccg cagataatca gctccaagcc  1380
gaacaggaat gccggctcgg ctccttgatg atcgaacagc tcgattgcct gacgcagcag  1440
tgggggcatc gaatcggttg ttggggtctc gcgctcctct tttgcgactt gatgctcttg  1500
gtcctccagc acgcagccca gggtaaagtg accgacggcg ctcagagcgt agagagcatt  1560
ttccaggctg aagccttgct ggcacaggaa cgcgagctgg ttctccagtg tctcgtattg  1620
cttttcggtc gggcgcgtgc cgagatggac tttggcaccg tctcggtggg acagcagagc  1680
gcagcggaac gacttggcgt tattgcggag gaagtcctgc caggactcgc cttccaacgg  1740
gcaaaaatgc gtgtggtggc ggtcgagcat ctcgatggcc agggcatcca gcagcgcccg  1800
cttattcttc acgtgccagt agagggtggg ctgctccacg cccagcttct cgccaactt   1860
gcgggtcgtc agtccctcaa tgccaacttc gttcaacagc tccaacgcgg agttgatgac  1920
tttggactta tccaggcggc tgacctatag ataccataga tgtatggatt agtatcatat  1980
acatacaaag gctattttg ggacatatta atattaacaa tttccgtgat agttttcacc    2040
attttttgttg aatgttacgt tgaaaattta aatttgtttt aaattaattt taccagtcat  2100
gtgttcttaa aagttttttat gattgaaacg gcataaagtg gttcaaaaat ttatcaagaa  2160
aggctttcct ttttaaaatc ttatcttttt ctcttaaaaa tcactagtca attcattatt  2220
aatttgttaa cttgaatttg gaatgtctat ttactttcag ataaattaaa gcaagaaact  2280
taatattcga aaaaaattga ttctaaatgg aatttcactt gatcttcatg tatgcatatc  2340
aattttatt tacattgtat aataagtttc gagttgattg ttgtaatcca caggtgtccc   2400
agagaattaa attccaaatt acccaagttt attgaatgtt gattgtagtt tcagttgctt  2460
tgttgctgca acaatggctt gttgattgta gatattttcc ctttccttgg tttacttat   2520
acatagactg aaaagaggt ttactttttt gatacttatg aaaaatttct attagtgatt   2580
actaaccaat cgctatatgt ttactagaaa acaaataaac tctttacatt aacattcaat  2640
aatgtttgct ctgtaaccga caattgaagg cgttacagca acagtaatat aactagcttc  2700
ttaaccctca tctattaacc ccatcgttta aaacactatg ttaaatggtc taacaaatct  2760
agatactaat agatgtctta ttacttagca gccacagctg caacatccaa gacaattttt  2820
gaaacttctt attgagctct tggcagcaga aatgttggta ttttttcacag ctttctgaaa 2880
gaccggcacc ttcctccggt tcccgtttct gaattcaaga ggatttccga cccccaatta  2940
atcccgaaac aaataaggta tattcaaaat gatggaaaag tcatggctgc tgaccttatt  3000
tttattccta ttgatagaat attattcccc ttttaaatac actgtactaa gaggtccggc  3060
tataatttta ctcacttgtc gattatccca tagaatgttg attgtagttg ttgcttttc   3120
caggtgagag ttgatcaagt cacaaaagtt agcgtgtgtt gattgtagat ttgaaggtaa  3180
aataattttt gcacccattc atcgggtaaa acgttctcca tagaatacat ttccatcgat  3240
```

```
aattgataac ttatgaattt caaagaaaaa aatatgcttt taaaattacc atggtggcta    3300
gcgcagattg tttagcttgt tcagctgcgc ttgtttattt gcttagcttt cgcttagcga    3360
cgtgttcact ttgcttgttt gaattgaatt gtcgctccgt agacgaagcg cctctattta    3420
tactccggcg ctcgttttcg agtttaccac tccctatcag tgatagagaa aagtgaaagt    3480
cgagtttacc actccctatc agtgatagag aaaagtgaaa gtcgagttta ccactcccta    3540
tcagtgatag agaaaagtga agtcgagtt taccactccc tatcagtgat agagaaaagt    3600
gaaagtcgag tttaccactc cctatcagtg atagagaaaa gtgaaagtcg agtttaccac    3660
tccctatcag tgatagagaa aagtgaaagt cgagtttacc actccctatc agtgatagag    3720
aaaagtgaaa gtcgaaacct gcgcgccgtt taaactcgcg ttaagataca ttgatgagtt    3780
tggacaaacc acaactagaa tgcagtgaaa aaatgctttt atttgtgaaa tttgtgatgc    3840
tattgcttta tttgtaacca ttataagctg caataaacaa gttaacaaca acaattgcat    3900 tcatttatg tttcaggttc aggggagg tgggaggtt ttttaaagca agtaaaacct    3960
ctacaaatgt ggtatggctg attatgatcg ctctagacac cggtgctacc cgccatactc    4020
atcgatgccc agcgcgtcgg tgaacatttg ctcgaactcg aagtcggcca tgtccagggc    4080
gccgtacggg gcgctatcgt ggggcgtgaa gcccggtccc gggctatctc catcgcccag    4140
catatccagg tcgaaatcgt ccagggcgtc ggcgtgggcc attgccacat cctctccatc    4200
caggtgcagc tcgtcgccca ggctcacatc ggtcggcggg gcggtgctca ggcggcgcgt    4260
gtgtccggcg ggcaggaagc tcaggcgggg ggcggccagg ccggcttcct ccggggcatc    4320
gtcatccggc aggtccagca gtccctcgat ggtgctgcca tagttgttct tggtacgggc    4380
gcggctgtag gcgctgccgc tctcgcactt cagctgcttt tccaggccgc agatgatcag    4440
ctccaggccg aacaggaagg ccggctcggc gccctggtga tcgaacagct cgatggcctg    4500
gcgcagcagc ggcggcatgc tatcggtggt cggggtctcg cgctcctcct tggccacctg    4560
gtgctcctga tcctccagca cacagcccag ggtgaagtgg cccacggcgc tcagggcgta    4620
cagggcgttc tccaggctga agccctgctg gcacaggaag gccagctggt tctccagggt    4680
ctcgtactgc ttctcggtcg ggcggtgcc caggtgcacc ttggcgccat cgcggtgcga    4740
cagcagggcg cagcggaagc tcttggcgtt gttgcgcagg aaatcctgcc agctctcgcc    4800
ctccagcggg cagaagtggg tgtggtggcg atccagcatt tcgatggcca gggcgtccag    4860
cagggcgcgc ttgttcttca cgtgccagta cagggtcggc tgttccacgc ccagcttctg    4920
ggccagcttg cgggtggtca ggccctcgat accaacttcg ttcagcagct ccagggcgct    4980
gttgatcacc ttgctcttgt ccaggcggct gacctgtgaa tacggttaat gtcactatta    5040
gtgatttata aaataaatt tgattttat atcaacaatt tttcatcgca gccttcagct    5100
ttttgttgaa taattataat gatattttt acgattcaaa tcatttaatt gttactcaac    5160
gaaataagtt taattcaaat tttaaaacaa gattatatat taagattaga ataagaaaga    5220
actttgttag attatttaat taaaaagatt aaaatttaag tctccagtca ctatttaaag    5280
atcatctttc aaacgttaaa gtgaattcaa acgagacgtt caaatttcga ttaaacagta    5340
attaactcta aatttctatc acgaattaag ttattgaata tgaaggttta tatttattta    5400
catcatctaa taggtttgag ttgattgttg taatccgcat gtgccagaag atatcaattt    5460
ccaaattgtc cgagttcatg gaatgttgat tgttgtttgt gttgctttgt aattgttgca    5520
gggagtattt atggtttgtt gattgtagta taaggctgtt tctaaaggct agaaaataat    5580
tttatttatt tgaaaataag taaatataca taatattact aacaataggt cgtcctattt    5640
```

```
tttgatattc tgcacaaatt tttaaaacac aaagattgca atactttag acactaatac    5700 tgcacactct gaaaaattat taaattattt ttaaaaactt accttaatac tttagagaaa    5760
aatattatac cgcacctttc tactttatac tcactttatt ataccagttg catgttgatt    5820
gtagttcttt gacaagaaaa tattccatat tgctccaaat tatcttggta agttgattgg    5880
tgcgtcattt gagcaagcta acaccttgtc tcatttaagt tcgcctcaag atctcatagc    5940 attttttaaat atcactatat ttagtaagta attagaatta ccatggtggt ttgctagccg    6000
ttctatcaga tgtgctccgg gaaacagaaa tgttcaacta agttctggcg gacgacgcaa    6060
cacctttata tactttgcca agcgcacagg tagaaaggac ctattttggg gattaaaaaa    6120
catctgcctg ttttattgcc atacccgcga aaattcgcga aatccgctac tttacctact    6180
ggggttcctg gaaaatgggc gaagaacggc aaagaactgg tactttccgt caataattgt    6240
ttagaagaga gagaacatac tccctatcag tgatagagaa gtccctatca gtgatagaga    6300
tgtccctatc agtgatagag agttccctat cagtgataga gacgtcccta tcagtgatag    6360
agaagtccct atcagtgata gagagatccc tatcagtgat agagatttcc ctatcagtga    6420
tagagaggtc cctatcagtg atagagactt ccctatcagt gatagagaaa tccctatcag    6480
tgatagagac atccctatca gtgatagaga actccctatc agtgatagag acctccctat    6540
cagtgataga gatcgatgcg ccgcatggt acccattgct tgtcatttat taatttggat    6600
gatgtcattt gttttaaaa ttgaactggc tttacgagta gaattctacg cgtaaaacac    6660
aatcaagtat gagtcataat ctgatgtcat gttttgtaca cggctcataa ccgaactggc    6720
tttacgagta gaattctact tgtaatgcac gatcagtgga tgatgtcatt tgttttcaa    6780 atcgagatga tgtcatgttt tgcacacggc tcataaactc gctttacgag tagaattcta    6840
cgtgtaacgc acgatcgatt gatgagtcat tgttttgca atatgatatc atacaatatg    6900
actcatttgt ttttcaaaac cgaacttgat ttacgggtag aattctactt gtaaagcaca    6960
atcaaaaaga tgatgtcatt tgttttcaa aactgaactc gctttacgag tagaattcta    7020
cgtgtaaaac acaatcaaga aatgatgtca tttgttataa aaataaaagc tgatgtcatg    7080
ttttgcacat ggctcataac taaactcgct ttacgggtag aattctacgc gtaaaacatg    7140
attgataatt aaataattca tttgcaagct atacgttaaa tcaaacggac gctcgaggtt    7200
gcacaacact attatcgatt tgcagttcgg gacataaatg tttaaatata tcgatgtctt    7260
tgtgatgcgc gcgacatttt tgtaggttat tgataaaatg aacggatacg ttgcccgaca    7320
ttatcattaa atccttggcg tagaatttgt cgggtccatt gtccgtgtgc gctagcatgc    7380
ccgtaacgga cctcgtactt ttggcttcaa aggttttgcg cacagacaaa atgtgccaca    7440
cttgcagctc tgcatgtgtg cgcgttacca caaatcccaa cggcgcagtg tacttgttgt    7500
atgcaaataa atctcgataa aggcgcggcg cgcgaatgca gctgatcacg tacgctcctc    7560
gtgttccgtt caaggacggt gttatcgacc tcagattaat gtttatcggc cgactgtttt    7620
cgtatccgct caccaaacgc gttttttgcat taacattgta tgtcggcgga tgttctatat    7680
ctaatttgaa taaataaacg ataaccgcgt tggttttaga gggcataata aaagaaatat    7740
tgttatcgtg ttcgccatta gggcagtata aattgacgtt catgttggat attgtttcag    7800
ttgcaagttg acactggcgg cgacaagcaa ttctaattgg ggtaagtttt cccgttcttt    7860
tctgggttct tccctttttgc tcatccttgc tgcactacct tcaggtgcaa gttgagattc    7920
aggccaccat gggagatccc accccaccca agaagaagcg caaaccggtc gccaccatgg    7980
```

```
agagcgacga gagcggcctg cccgccatgg agatcgagtg ccgcatcacc ggcaccctga    8040
acggcgtgga gttcgagctg gtgggcggcg gagagggcac ccccgagcag ggccgcatga    8100
ccaacaagat gaagagcacc aaaggcgccc tgaccttcag cccctacctg ctgagccacg    8160
tgatgggcta cggcttctac cacttcggca cctaccccag cggctacgag aaccccttcc    8220
tgcacgccat caacaacggc ggctacacca cacccgcat cgagaagtac gaggacggcg    8280
gcgtgctgca cgtgagcttc agctaccgct acgaggccgg ccgcgtgatc ggcgacttca    8340
aggtgatggg caccggcttc cccgaggaca gcgtgatctt caccgacaag atcatccgca    8400
gcaacgccac cgtggagcac ctgcacccca tgggcgataa cgatctggat ggcagcttca    8460
cccgcacctt cagcctgcgc gacggcggct actacagctc cgtggtggac agccacatgc    8520
acttcaagag cgccatccac cccagcatcc tgcagaacgg ggcccccatg ttcgccttcc    8580
gccgcgtgga ggaggatcac agcaacaccg agctgggcat cgtggagtac cagcacgcct    8640
tcaagacccc ggatgcagat gccggtgaag aaagatctcg acccaagaaa aagcggaagg    8700
tggaggaccc gtaagatcca ccggatctag ataactgatc ataatcagcc ataccacatt    8760
tgtagaggtt ttacttgctt taaaaaacct cccacacctc cccctgaacc tgaaacataa    8820
aatgaatgca attgttgttg ttaacttgtt tattgcagct tataatggtt acaaataaag    8880
caatagcatc acaaatttca caaataaagc attttttttca ctgcattcta gttgtggttt    8940
gtccaaactc atcaatgtat cttaacgcga gttatcgcgc tcgcgcgact gacggtcgta    9000
agcacccgcg tacgtgtcca ccccggtcac aacccttgt gtcatgtcgg cgaccctacg    9060
cccccaactg agagaactca aaggttaccc cagttgggc actactcccg aaaaccgctt    9120
ctgacctggg aaaacgtgaa gccccggggc atccgctgag ggttgccgcc ggggcttcgg    9180
tgtgtccgtc agtacttaat taacaccgaa atcgtaattc acggcatcat tacaaaatat    9240
tttgacgttt tggacctcgt ccctaatgac accataacgg tggccttgaa gtatatttaa    9300
ccctagaaag atagtctgcg taaaattgac gcatgcattc ttgaaatatt gctctctctt    9360
tctaaatagc gcgaatccgt cgctgtgcat ttaggacatc tcagtcgccg cttggagctc    9420
ccgtgaggcg tgcttgtcaa tgcggtaagt gtcactgatt ttgaactata acgaccgcgt    9480
gagtcaaaat gacgcatgat tatcttttac gtgacttta agatttaact catacgataa    9540
ttatattgtt atttcatgtt ctacttacgt gataacttat tatatatata ttttcttgtt    9600
atagatatcg tgactaatat ataataaaat gggtagttct ttagacgatg agcatatcct    9660
ctctgctctt ctgcaaagcg atgacgagct tgttggtgag gattctgaca gtgaaatatc    9720
agatcacgta agtgaagatg acgtccagga aatctggccg gccgcaacca ttgtgggaac    9780
cgtgcgatca aacaaacgcg agataccgga agtactgaaa acagtcgct ccaggccagt    9840
gggaacatcg atgttttgtt ttgacggacc ccttactctc gtctcatata aaccgaagcc    9900
agctaagatg gtatacttat tatcatcttg tgatgaggat gcttctatca acgaaagtac    9960
cggtaaaccg caaatggtta tgtattataa tcaaactaaa ggcggagtgg acacgctaga   10020
ccaaatgtgt tctgtgatga cctgcagtag gaagacgaat aggtggccta tggcattatt   10080
gtacggaata taaacattg cctgcataaa ttctttttatt atatacagcc ataatgtcag   10140
tagcaaggga gaaaaggtcc aaagtcgcaa aaaatttatg agaaaccttt acatgagcct   10200
gacgtcatcg tttatgcgta agcgtttaga agctcctact ttgaagagat atttgcgcga   10260
taatatctct aatattttgc caaatgaagt gcctggtaca tcagatgaca gtactgaaga   10320
gccagtaatg aaaaaacgta cttactgtac ttactgcccc tctaaaataa ggcgaaaggc   10380
```

```
aaatgcatcg tgcaaaaaat gcaaaaaagt tatttgtcga gagcataata ttgatatgtg   10440
ccaaagttgt ttctgactga ctaataagta taatttgttt ctattatgta taagttaagc   10500
taattactta ttttataata caacatgact gtttttaaag tacaaaataa gtttattttt   10560
gtaaaagaga gaatgtttaa aagttttgtt actttataga agaaattttg agtttttgtt   10620
tttttttaat aaataaataa acataaataa attgtttgtt gaatttatta ttagtatgta   10680
agtgtaaata taataaaact taatatctat tcaaattaat aaataaacct cgatatacag   10740
accgataaaa cacatgcgtc aattttacgc atgattatct ttaacgtacg tcacaatatg   10800
attatctttc tagggttaaa taatagtttc taatttttt attattcagc ctgctgtcgt   10860
gaataccgta tatctcaacg ctgtctgtga gattgtcgta ttctagcctt tttagttttt   10920
cgctcatcga cttgatattg tccgacacat tttcgtcgat ttgcgttttg atcaaagact   10980
tgagcagaga cacgttaatc aactgttcaa attgatccat attaacgata tcaacccgat   11040
gcgtatatgg tgcgtaaaat atattttta accctcttat actttgcact ctgcgttaat   11100
acgcgttcgt gtacagacgt aatcatgttt tctttttgg ataaaactcc tactgagttt   11160
gacctcatat tagaccctca caagttgcaa acgtggcat tttttaccaa tgaagaattt   11220
aaagttattt taaaaattt catcacagat ttaaagaaga accaaaaatt aaattatttc   11280
aacagtttaa tcgaccagtt aatcaacgtg tacacagacg cgtcggcaaa aaacacgcag   11340
cccgacgtgt tggctaaaat tattaaatca acttgtgtta tagtcacgga tttgccgtcc   11400
aacgtgttcc tcaaaaagtt gaagaccaac aagtttacgg acactattaa ttatttgatt   11460
ttgccccact tcattttgtg ggatcacaat tttgttatat tttaaacaaa gcttggcact   11520
ggccgtcgtt ttacaacgtc gtgactggga aaaccctggc gttacccaac ttaatcgcct   11580
tgcagcacat ccccctttcg ccagctggcg taatagcgaa gaggcccgca ccgatcgccc   11640
ttcccaacag ttgcgcagcc tgaatggcga atggcgcctg atgcggtatt ttctccttac   11700
gcatctgtgc ggtatttcac accgcatatg gtgcactctc agtacaatct gctctgatgc   11760
cgcatagtta agccagcccc gacacccgcc aacacccgct gacgcgccct gacgggcttg   11820
tctgctcccg gcatccgctt acagacaagc tgtgaccgtc tccgggagct gcatgtgtca   11880
gaggttttca ccgtcatcac cgaaacgcgc gagacgaaag ggcctcgtga tacgcctatt   11940
tttataggtt aatgtcatga taataatggt ttcttagacg tcaggtggca cttttcgggg   12000
aaatgtgcgc ggaacccta tttgtttatt tttctaaata cattcaaata tgtatccgct   12060
catgagacaa taaccctgat aaatgcttca ataatattga aaaggaaga gtatgagtat   12120 tcaacatttc cgtgtcgccc ttattccctt ttttgcggca ttttgccttc ctgttttgc   12180 tcacccagaa acgctggtga agtaaaaga tgctgaagat cagttgggtg cacgagtggg   12240
ttacatcgaa ctggatctca acagcggtaa gatccttgag agttttcgcc ccgaagaacg   12300
ttttccaatg atgagcactt taaagttctg ctatgtggc gcggtattat cccgtattga   12360
cgccgggcaa gagcaactcg gtcgccgcat acactattct cagaatgact tggttgagta   12420
ctcaccagtc acagaaaagc atcttacgga tggcatgaca gtaagagaat tatgcagtgc   12480
tgccataacc atgagtgata acactgcggc caacttactt ctgacaacga tcggaggacc   12540
gaaggagcta accgcttttt tgcacaacat ggggatcat gtaactcgcc ttgatcgttg   12600
ggaaccggag ctgaatgaag ccataccaaa cgacgagcgt gacaccacga tgcctgtagc   12660
aatggcaaca acgttgcgca aactattaac tggcgaacta cttactctag cttcccggca   12720
```

| | |
|---|---|
| acaattaata gactggatgg aggcggataa agttgcagga ccacttctgc gctcggccct | 12780 |
| tccggctggc tggtttattg ctgataaatc tggagccggt gagcgtgggt ctcgcggtat | 12840 |
| cattgcagca ctggggccag atggtaagcc ctcccgtatc gtagttatct acacgacggg | 12900 |
| gagtcaggca actatggatg aacgaaatag acagatcgct gagataggtg cctcactgat | 12960 |
| taagcattgg taactgtcag accaagttta ctcatatata ctttagattg atttaaaact | 13020 |
| tcatttttaa tttaaaagga tctaggtgaa gatcctttt gataatctca tgaccaaaat | 13080 |
| cccttaacgt gagttttcgt tccactgagc gtcagacccc gtagaaaaga tcaaaggatc | 13140 |
| ttcttgagat ccttttttc tgcgcgtaat ctgctgcttg caacaaaaa aaccaccgct | 13200 |
| accagcggtg gtttgtttgc cggatcaaga gctaccaact cttttccga aggtaactgg | 13260 |
| cttcagcaga gcgcagatac caaatactgt ccttctagtg tagccgtagt taggccacca | 13320 |
| cttcaagaac tctgtagcac cgcctacata cctcgctctg ctaatcctgt taccagtggc | 13380 |
| tgctgccagt ggcgataagt cgtgtcttac cgggttggac tcaagacgat agttaccgga | 13440 |
| taaggcgcag cggtcgggct gaacggggg ttcgtgcaca cagcccagct tggagcgaac | 13500 |
| gacctacacc gaactgagat acctacagcg tgagcattga aaagcgcca cgcttcccga | 13560 |
| agggagaaag gcggacaggt atccggtaag cggcagggtc ggaacaggag agcgcacgag | 13620 |
| ggagcttcca gggggaaacg cctggtatct ttatagtcct gtcgggtttc gccacctctg | 13680 |
| acttgagcgt cgatttttgt gatgctcgtc aggggggcgg agcctatgga aaaacgccaa | 13740 |
| caacgcggcc ttttacggt tcctggcctt ttgctggcct tttgctcaca tgttctttcc | 13800 |
| tgcgttatcc cctgattctg tggataaccg tattaccgcc tttgagtgag ctgataccgc | 13860 |
| tcgccgcagc cgaacgaccg agcgcagcga gtcagtgagc gaggaagcgg aagagcgccc | 13920 |
| aatacgcaaa ccgcctctcc ccgcgcgttg gccgattcat taatgcagct ggcacgacag | 13980 |
| gtttcccgac tggaaagcgg gcagtgagcg caacgcaatt aatgtgagtt agctcactca | 14040 |
| ttaggcaccc caggctttac actttatgct tccggctcgt atgttgtgtg gaattgtgag | 14100 |
| cggataacaa tttcacacag gaaacagcta tgaccatgat tacgaatttc gacctgcagg | 14160 |
| catgcaagct tgcatgcctg caggtcgacg ctcgcgcgac ttggtttgcc attctttagc | 14220 |
| gcgcgtcgcg tcacacagct tggccacaat gtggtttttg tcaaacgaag attctatgac | 14280 |
| gtgtttaaag tttaggtcga gtaaagcgca aatctttttt aaccctagaa agatagtctg | 14340 |
| cgtaaaattg acgcatgcat tcttgaaata ttgctctctc tttctaaata gcgcgaatcc | 14400 |
| gtcgctgtgc atttaggaca tctcagtcgc cgcttggagc tcccgtgagg cgtgcttgtc | 14460 |
| aatgcggtaa gtgtcactga ttttgaacta taacgaccgc gtgagtcaaa atgacgcatg | 14520 |
| attatctttt acgtgacttt taagatttaa ctcatacgat aattatattg ttatttcatg | 14580 |
| ttctacttac gtgataactt attatatata tattttcttg ttatagatat cgtgactaat | 14640 |
| atataataaa atgggtagtt ctttagacga tgagcatatc ctctctgctc ttctgcaaag | 14700 |
| cgatgacgag cttgttggtg aggattctga cagtgaaata tcagatcacg taagtgaaga | 14760 |
| tgacgtccag agcgatacag aagaagcgtt tatagatgag gtacatgaag tgcagccaac | 14820 |
| gtcaagcggt agtgaaatat tagacgaaca aatgttatt gaacaaccag gttcttcatt | 14880 |
| ggcttctaac agaatcttga ccttgccaca gaggactatt agaggtaaga ataaacattg | 14940 |
| ttggtcaact tcaaagtcca cgaggcgtag ccgagtctct gcactgaaca ttgtcagatc | 15000 |
| ggcccggcg agtggacacg ctagaccaaa tgtgttctgt gatgacctgc agtaggaaga | 15060 |
| cgaataggtg gcctatggca ttattgtacg gaatgataaa cattgcctgc ataaattctt | 15120 |

```
ttattatata cagccataat gtcagtagca agggagaaaa ggtccaaagt cgcaaaaaat    15180
ttatgagaaa cctttacatg agcctgacgt catcgtttat gcgtaagcgt ttagaagctc    15240
ctactttgaa gagatatttg cgcgataata tctctaatat tttgccaaat gaagtgcctg    15300
gtacatcaga tgacagtact gaagagccag taatgaaaaa acgtacttac tgtacttact    15360 gccctctaa  aataaggcga aaggcaaatg catcgtgcaa aaaatgcaaa aaagttattt    15420
gtcgagagca taatattgat atgtgccaaa gttgtttctg actgactaat aagtataatt    15480
tgtttctatt atgtataagt taagctaatt acttatttta taatacaaca tgactgtttt    15540
taaagtacaa aataagttta tttttgtaaa agagagaatg tttaaaagtt ttgttacttt    15600
atagaagaaa ttttgagttt ttgttttttt taataaata  aataaacata aataaattgt    15660
ttgttgaatt tattattagt atgtaagtgt aaatataata aaacttaata tctattcaaa    15720
ttaataaata aacctcgata tacagaccga taaaacacat gcgtcaattt tacgcatgat    15780
tatctttaac gtacgtcaca atatgattat ctttctaggg ttaaaatgaa tgtaagcact    15840
ttattaacga aatctttggg aatatttcgc tcatcagcat tttatttgag caggagtccg    15900
agatgcccgg ccgcgccggc catcgagaaa gagagagaga agagaagaga gagaacattc    15960
gagaaagaga gagagaagag aagagagaga acatactccc tatcagtgat agagaagtcc    16020
ctatcagtga tagagatgtc cctatcagtg atagagagtt ccctatcagt gatagagacg    16080
tccctatcag tgatagagaa gtccctatca gtgatagaga gatccctatc agtgatagag    16140
atttccctat cagtgataga gaggtcccta tcagtgatag agacttccct atcagtgata    16200
gagaaatccc tatcagtgat agagacatcc ctatcagtga tagagaactc cctatcagtg    16260
atagagacct cccctatcagt gatagagatc gatccgtcta cctgagcgat atataaacta    16320
atgcctgttg caattgttca gtcagtcacg agtttgttac cactgcgaca agctagcaac    16380
caccatggcg gtaattctaa ttacttacta aatatagtga tatttaaaaa tgctatgaga    16440
tcttgaggcg aacttaaatg agacaaggtg ttagcttgct caaatgacgc accaatcaac    16500
ttaccaagat aatttggagc aatatggaat attttcttgt caaagaacta caatcaacat    16560
gcaactggta taataaagtg agtataaagt agaaaggtgc ggtataatat ttttctctaa    16620
agtattaagg taagttttta aaaataattt aataattttt cagagtgtgc agtattagtg    16680
tctaaaagta ttgcaatctt tgtgttttaa aaatttgtgc agaatatcaa aaaataggac    16740
gacctattgt tagtaatatt atgtatattt acttattttc aaataaataa aattattttc    16800
tagcctttag aaacagcctt atactacaat caacaaacca taaatactcc ctgcaacaat    16860
tacaaagcaa cacaaacaac aatcaacatt ccatgaactc ggacaatttg gaaattgata    16920
tcttctggca catgcggatt acaacaatca actcaaacct attagatgat gtaaataaat    16980
ataaaccttc atattcaata acttaattcg tgatagaaat ttagagttaa ttactgttta    17040
atcgaaattt gaacgtctcg tttgaattca ctttaacgtt tgaaagatga tctttaaata    17100
gtgactggag acttaaattt taatcttttt aattaaataa tctaacaaag ttctttctta    17160
ttctaatctt aatatataat cttgttttaa aatttgaatt aaacttattt cgttgagtaa    17220
caattaaatg atttgaatcg taaaaaatat cattataatt attcaacaaa agctgaagg    17280 ctgcgatgaa aaattgttga tatataaatc aaatttattt ttataaatca ctaatagtga    17340
cattaaccgt attcacaggt ggccttctac atcccggatc aggccaccct gctgcgcgag    17400
gccgagcagc gcgagcagca gatcctgcgc ctgcgcgaga gccagtggcg cttcctggcc    17460
```

| | | | |
|---|---|---|---|
| accgtggtgc | tggagaccct | gcgccagtac accagctgcc acccgcgcac cggccgccgc | 17520 |
| agcggccgtt | accgccgtcc | gagccagtaa caccggtgat cataatcagc cataccacat | 17580 |
| ttgtagaggt | tttacttgct | ttaaaaaacc tcccacacct cccctgaac ctgaaacata | 17640 |
| aaatgaatgc | aattgttgtt | gttaacttgt ttattgcagc ttataatggt tacaaataaa | 17700 |
| gcaatagcat | cacaaatttc | acaaataaag catttttttc actgcattct agttgtggtt | 17760 |
| tgtccaaact | catcaatgta | tcttaacgcg agtttaggcg cg | 17802 |

<210> SEQ ID NO 56
<211> LENGTH: 15134
<212> TYPE: DNA
<213> ORGANISM: Artificial Sequence
<220> FEATURE:
<223> OTHER INFORMATION: Synthetic construct, pLA3242-Crtra
       intron-reaperKR construct.

<400> SEQUENCE: 56

| | | | |
|---|---|---|---|
| gggcggccgt | tttcttgaa | atattgctct ctctttctaa atagcgcgaa tccgtcgctg | 60 |
| tgcatttagg | acatctcagt | cgccgcttgg agctcccaaa cgcgccagtg gtagtacaca | 120 |
| gtactgtggg | tgttcagttt | gaaatcctct tgcttctcca ttgtctcggt tacctttggt | 180 |
| caaatccatg | ggttctattg | cctatatact cttgcgatta ccagtgattg cgctattagc | 240 |
| tattagatgg | attgttggcc | aaacttgtcg cttaagtggc tgggaattgt aaccgtaggc | 300 |
| ccgagtgtaa | tgatccccca | taaaagtttt tcgcaatgcc tttatttttt gttgcaaatc | 360 |
| tctctttatt | ctgcggtatt | cttcattatt gcggggatgg ggaaagtgtt tatatagaag | 420 |
| caacttacga | ttgaacccaa | atgcacctga caagcaaggt caaagggcca gatttttaaa | 480 |
| tatattattt | agtcttagga | ctctctattt gcaattaaat tactttgcta cctgagggtt | 540 |
| aaatcttccc | cattgataat | aataattcca ctatatgttc aattgggttt caccgcgctt | 600 |
| agttacatga | cgagccctaa | tgagccgtcg gtggtctata aactgtgcct tacaaatact | 660 |
| tgcaactctt | ctcgttttga | agtcagcaga gttattgcta attgctaatt gctaattgct | 720 |
| tttaactgat | ttcttcgaaa | ttggtgctat gtttatggcg ctattaacaa gtatgaatgt | 780 |
| caggtttaac | cagggggatgc | ttaattgtgt tctcaacttc aaaggcagaa atgtttactc | 840 |
| ttgaccatgg | gtttaggtat | aatgttatca agctcctcga gttaacgtta cgttaacgtt | 900 |
| aacgttcgag | gtcgactcta | gaactaccca ccgtactcgt caattccaag ggcatcggta | 960 |
| aacatctgct | caaactcgaa | gtcggccata tccagagcgc cgtagggggc ggagtcgtgg | 1020 |
| ggggtaaatc | ccggacccgg | ggaatccccg tcccccaaca tgtccagatc gaaatcgtct | 1080 |
| agcgcgtcgg | catgcgccat | cgccacgtcc tcgccgtcta agtggagctc gtcccccagg | 1140 |
| ctgacatcgg | tcgggggggc | cgtcgacagt ctgcgcgtgt gtcccgcggg gagaaaggac | 1200 |
| aggcgcggag | ccgccagccc | cgcctcttcg ggggcgtcgt cgtccgggag atcgagcagg | 1260 |
| ccctcgatgg | tagacccgta | attgttttc gtacgcgcgc ggctgtacgc ggggcccgag | 1320 |
| cccgactcgc | atttcagttg | cttttccaat ccgcagataa tcagctccaa gccgaacagg | 1380 |
| aatgccggct | cggctccttg | atgatcgaac agctcgattg cctgacgcag cagtgggggc | 1440 |
| atcgaatcgt | tgttgggggt | ctcgcgctcc tcttttgcga cttgatgctc ttggtcctcc | 1500 |
| agcacgcagc | ccagggtaaa | gtgaccgacg gcgctcagag cgtagagagc attttccagg | 1560 |
| ctgaagcctt | gctggcacag | gaacgcgagc tggttctcca gtgtctcgta ttgcttttcg | 1620 |
| gtcgggcgcg | tgccgagatg | gactttggca ccgtctcggt gggacagcag agcgcagcgg | 1680 |

```
aacgacttgg cgttattgcg gaggaagtcc tgccaggact cgccttccaa cgggcaaaaa   1740
tgcgtgtggt ggcggtcgag catctcgatg gccagggcat ccagcagcgc ccgcttattc   1800
ttcacgtgcc agtagagggt gggctgctcc acgcccagct tctgcgccaa cttgcgggtc   1860
gtcagtccct caatgccaac ttcgttcaac agctccaacg cggagttgat gactttggac   1920
ttatccaggc ggctgaccta tagataccat agatgtatgg attagtatca tatacataca   1980
aaggctattt ttgggacata ttaatattaa caatttccgt gatagttttc accattttg    2040 ttgaatgtta cgttgaaaat ttaaatttgt tttaaattaa ttttaccagt catgtgttct   2100
taaaagtttt tatgattgaa acggcataaa gtggttcaaa aatttatcaa gaaaggcttt   2160
ccttttttaa atcttatctt tttctcttaa aaatcactag tcaattcatt attaatttgt   2220
taacttgaat ttggaatgtc tatttacttt cagataaatt aaagcaagaa acttaatatt   2280
cgaaaaaaat tgattctaaa tggaatttca cttgatcttc atgtatgcat atcaattttt   2340
atttacattg tataataagt ttcgagttga ttgttgtaat ccacaggtgt cccagagaat   2400
taaattccaa attcccaag tttattgaat gttgattgta gtttcagttg ctttgttgct    2460
gcaacaatgg cttgttgatt gtagatattt tcccttcct tggtttactt attacataga    2520 ctgaaaaga ggtttacttt tttgatactt atgaaaaatt tctattagtg attactaacc    2580
aatcgctata tgtttactag aaaacaaata aactctttac attaacattc aataatgttt   2640
gctctgtaac cgacaattga aggcgttaca gcaacagtaa tataactagc ttcttaaccc   2700
tcatctatta accccatcgt ttaaaacact atgttaaatg gtctaacaaa tctagatact   2760
aatagatgtc ttattactta gcagccacag ctgcaacatc caagacaatt tttgaaactt   2820
cttattgagc tcttggcagc agaaatgttg gtattttca cagctttctg aaagaccggc    2880
accttcctcc ggttcccgtt tctgaattca agaggatttc cgaccccaa ttaatcccga    2940 aacaaataag gtatattcaa aatgatggaa aagtcatggc tgctgacctt atttttattc   3000
ctattgatag aatattattc ccctttaaa tacactgtac taagaggtcc ggctataatt    3060
ttactcactt gtcgattatc ccatagaatg ttgattgtag ttggttgctt ttccaggtga   3120
gagttgatca agtcacaaaa gttagcgtgt gttgattgta gatttgaagg taaataatt    3180 tttgcaccca ttcatcgggt aaaacgttct ccatagaata catttccatc gataattgat   3240
aacttatgaa tttcaaagaa aaaaatatgc ttttaaaatt accatggtgg ctagcgcaga   3300
ttgtttagct tgttcagctg cgcttgttta tttgcttagc tttcgcttag cgacgtgttc   3360
actttgcttg tttgaattga attgtcgctc cgtagacgaa gcgcctctat ttatactccg   3420
gcgctcgttt tcgagtttac cactccctat cagtgataga gaaagtgaa agtcgagttt    3480 accactcct atcagtgata gagaaaagtg aaagtcgagt ttaccactcc ctatcagtga    3540
tagagaaaag tgaaagtcga gtttaccact ccctatcagt gatagagaaa agtgaaagtc   3600
gagtttacca ctccctatca gtgatagaga aagtgaaag tcgagtttac cactccctat    3660
cagtgataga gaaagtgaa agtcgagttt accactccct atcagtgata gagaaaagtg   3720
aaagtcgaaa cctggcgcgc ctaaactcgc gttaagatac attgatgagt ttggacaaac   3780
cacaactaga atgcagtgaa aaaaatgctt tatttgtgaa atttgtgatg ctattgcttt   3840
atttgtaacc attataagct gcaataaaca agttaacaac aacaattgca ttcattttat   3900
gtttcaggtt caggggggagg tgtgggaggt ttttaaagc aagtaaaacc tctacaaatg   3960
tggtatggct gattatgatc accggtgtta ctggctcgga cggcggtaac ggccgctgcg   4020
gcggccggtg cgcgggtggc agctggtgta ctggcgcagg gtctccagca ccacggtggc   4080
```

```
caggaagcgc cactggctct cgcgcaggcg caggatctgc tgctcgcgct gctcggcctc    4140
gcgcagcagg gtggcctgat ccgggatgta gaaggccacc taaagatacc atggatgtat    4200
gaattagtat catatacata taaatgcttt ttttttggc atattaatgt taaaaatatc     4260
aacaatttcc gtgatagttt ttaccatttt tgttgaatgt ttactttgaa aacttaaata    4320 tttttaact aatttacca gtcatgtgtt attaaaagta tttatgaata aaactgcaag      4380
taaagcgttt caaaaattta tcaagtaaaa ctttactttt tttaaatctt aactgtcaat    4440
tcattattaa tttattaatt taaatttgca atgtctattt actttaagac aaattaaagc    4500
aagaaactaa atattcgaat caattctttt ttaaatgaaa ttttacttca tcatcatgta    4560
tgtgtgtatc aatttttatt tacattgtat aataagtttc gagttgattg ttgtaatccg    4620
caggtgtccc gaagtattaa attccgaatt cccaagttta ttgaatgttg attgtagttt    4680
cagttgtttt gttattgcaa caatggcttg ttgattggag atattttcct tttccttggt    4740
ttacttacta catagactga aaaagatgtt tgactttttt gatactattg taaaatttct    4800
attagtgatt actaaccaat cgctataagt ttaatagaaa acaaataaac tctttgcatc    4860
cagatatacc tagcttctta acccttatct attaactcca ttgcttgtaa caaatctaga    4920
tattaataga tgtctaatta cttagcaaaa cttcttttg attaagcagc cacagctgtc     4980
gattttggtc atatttaaag gaaataaatg cgtttaaaat aataattaat ataagttttg    5040
aaacttttta ctaacacttg gcagcaggaa gtaggtgttt ttcacagctt tctgaaccac    5100
cggcaccttc cccggtctcc gttgtcgag ttcagcagga tttccggccc ccaattaacc     5160
ccgaaacaaa acatgtctta ttaataaggt gtattcaaaa tagtgggaat gtcatgactg    5220
ctgaccttat ttttattcct attgtaagtg ttccggctat aattttactc acttgtccat    5280
tatcccatag aatgttatgt tgattgtagt tgtttgcttt tccaggtgag agttgatcaa    5340
gtcgcaaaag ttagcgtgtg ttgattgtag atttgaaggt aaaataattt tgtacacatt    5400
catcaggcaa aacgttctcc atcgaataaa cttccatcga taattgatag cttatgaatt    5460
tcaaaaaaaa atatgctttt aaaattaccg ccatggtggt tgctagcttg tcgcagtggt    5520
aacaaactcg tgactgactg aacaattgca acaggcatta gtttatatat cgctcaggta    5580
gacggatcga tctctatcac tgatagggag gtctctatca ctgataggga gttctctatc    5640
actgataggg atgtctctat cactgatagg gatttctcta tcactgatag ggaagtctct    5700
atcactgata gggacctctc tatcactgat agggaaatct ctatcactga tagggatctc    5760
tctatcactg atagggactt ctctatcact gataggacg tctctatcac tgataggaa     5820 ctctctatca ctgatagggga catctctatc actgataggg acttctctat cactgatagg    5880
gagtatgttc tctctcttct cttctctctc tcttttctcga atgttctctc tcttctcttc    5940
tctctctctt tctcgatggc cggcctggct taattaactc gcgttaagat acattgatga    6000
gtttggacaa accacaacta gaatgcagtg aaaaaaatgc tttatttgtg aaatttgtga    6060
tgctattgct ttatttgtaa ccattataag ctgcaataaa caagttaaca acaacaattg    6120
cattcatttt atgtttcagg ttcaggggga ggtgtgggag gttttttaaa gcaagtaaaa    6180
cctctacaaa tgtggtatgg ctgattatga tcagttatct agatccggtg gatcttacgg    6240
gtcctccacc ttccgctttt tcttgggtcg agatctgagt ccggaatcct cgtcgctacc    6300
gatggcgctg gtgatgcggg gcacgctgtg ggcgtaggtc acctcgcgct ggcacacgtg    6360
gtcgcgcttg tcgctggtgt ccctcatctg cttggtgatg atggtcacga agtgggggcc    6420
```

-continued

```
ggggatcttg atggcgcggc tgccgttgaa ggtcatcttg ctgtcgaagt ggcccatcat    6480
caggccgccg tcggcggtgg tgaagccgat gaaggccagc tggcgcacgg cgttggggcc    6540
gtgggggaac atgtgggtct cgttgggcag gatgtccacc agctggtcgc gcatgatggg    6600
gccgtcgggc tggaagccgt cgcagttcac ggtgatgcgg ctgaccacgc aggtgccgtc    6660
cagctcgtag gtgtggtggc tggtcatggt gccgtcgttc tcgaagcgca cggtgcggtc    6720
gatgctcagg ccctcgggga agcactcctg ggcgaagtgg ctgatgccgt tggggtagcg    6780
ggcgaagaag ggctcgccgt actggatcag gtggcagatg ggcttccagc tcatgggcag    6840
cttgccggtc tcgcacacgg cgtgcacgtt gaagtcgccg tggggaact tgctgctgcc    6900 gtcggccacg atggtgaact tctggccgtt cacctcgccg tcgatgaaga ttttgaaggt    6960
catgtcgctc tggaacaggg cggggccgcc ctctgaacca tcctcgtcca tggtggcgac    7020
cggtttgcgc ttcttcttgg gtggggtggg atctcccatg gtggcctgaa tctcaacttg    7080
cacctgaagg tagtgcagca aggatgagca aagggaaga acccagaaaa gaacgggaaa    7140
acttacccca attagaattg cttgtcgccg ccagtgtcaa cttgcaactg aaacaatatc    7200
caacatgaac gtcaatttat actgccctaa tggcgaacac gataacaata tttctttat    7260 tatgccctct aaaccaacg cggttatcgt ttatttattc aaattagata tagaacatcc    7320
gccgacatac aatgttaatg caaaaacgcg tttggtgagc ggatacgaaa acagtcggcc    7380
gataaacatt aatctgaggt cgataacacc gtccttgaac ggaacacgag gagcgtacgt    7440
gatcagctgc attcgcgcgc gcgcccttta tcgagattta tttgcataca caagtacac    7500 tgcgccgttg ggatttgtgg taacgcgcac acatgcagag ctgcaagtgt ggcacatttt    7560
gtctgtgcgc aaaaccttg aagccaaaag tacgaggtcc gttacgggca tgctagcgca    7620
cacggacaat ggaccegaca aattctacgc caaggattta atgataatgt cgggcaacgt    7680
atccgttcat tttatcaata acctacaaaa atgtcgcgcg catcacaaag acatcgatat    7740
atttaaacat ttatgtcccg aactgcaaat cgataatagt gttgtgcaac ctcgagcgtc    7800
cgtttgattt aacgtatagc ttgcaaatga attatttaat tatcaatcat gttttacgcg    7860
tagaattcta cccgtaaagc gagtttagtt atgagccatg tgcaaaacat gacatcagct    7920
tttattttta taacaaatga catcatttct tgattgtgtt ttacacgtag aattctactc    7980
gtaaagcgag ttcagttttg aaaaacaaat gacatcatct ttttgattgt gctttacaag    8040
tagaattcta cccgtaaatc aagttcggtt ttgaaaaaca aatgagtcat attgtatgat    8100
atcatattgc aaaacaaatg actcatcaat cgatcgtgcg ttacacgtag aattctactc    8160
gtaaagcgag tttatgagcc gtgtgcaaaa catgacatca tctcgatttg aaaaacaaat    8220
gacatcatcc actgatcgtg cattacaagt agaattctac tcgtaaagcc agttcggtta    8280
tgagccgtgt acaaaacatg acatcagatt atgactcata cttgattgtg ttttacgcgt    8340
agaattctac tcgtaaagcc agttcaattt taaaaacaaa tgacatcatc caaattaata    8400
aatgacaagc aatgggtacc atgcggccgc accgaaatcg taattcacgg catcattaca    8460
aaatattttg acgttttgga cctcgtccct aatgacacca taacggtggc cttgaagtat    8520
atttaaccct agaagatag tctgcgtaaa attgacgcat gcattcttga atattgctc    8580 tctctttcta aatagcgcga atccgtcgct gtgcatttag gacatctcag tcgccgcttg    8640
gagctcccgt gaggcgtgct tgtcaatgcg gtaagtgtca ctgattttga actataacga    8700
ccgcgtgagt caaaatgacg catgattatc ttttacgtga ctttaagat ttaactcata    8760 cgataattat attgttattt catgttctac ttacgtgata acttattata tatatatttt    8820
```

-continued

```
cttgttatag atatcgtgac taatatataa taaaatgggt agttctttag acgatgagca    8880
tatcctctct gctcttctgc aaagcgatga cgagcttgtt ggtgaggatt ctgacagtga    8940
aatatcagat cacgtaagtg aagatgacgt ccaggaaatc tggccggccg caaccattgt    9000
gggaaccgtg cgatcaaaca aacgcgagat accggaagta ctgaaaaaca gtcgctccag    9060
gccagtggga acatcgatgt tttgttttga cggacccctt actctcgtct catataaacc    9120
gaagccagct aagatggtat acttattatc atcttgtgat gaggatgctt ctatcaacga    9180
aagtaccggt aaaccgcaaa tggttatgta ttataatcaa actaaaggcg gagtggacac    9240
gctagaccaa atgtgttctg tgatgacctg cagtaggaag acgaataggt ggcctatggc    9300
attattgtac ggaatgataa acattgcctg cataaattct tttattatat acagccataa    9360
tgtcagtagc aagggagaaa aggtccaaag tcgcaaaaaa tttatgagaa acctttacat    9420
gagcctgacg tcatcgttta tgcgtaagcg tttagaagct cctactttga agagatattt    9480
gcgcgataat atctctaata ttttgccaaa tgaagtgcct ggtacatcag atgacagtac    9540
tgaagagcca gtaatgaaaa aacgtactta ctgtacttac tgcccctcta aaataaggcg    9600
aaaggcaaat gcatcgtgca aaaaatgcaa aaaagttatt tgtcgagagc ataatattga    9660
tatgtgccaa agttgtttct gactgactaa taagtataat ttgtttctat tatgtataag    9720
ttaagctaat tacttatttt ataatacaac atgactgttt ttaaagtaca aaataagttt    9780
attttttgtaa aagagagaat gtttaaaagt tttgttactt tatagaagaa attttgagtt    9840
tttgtttttt tttaataaat aaataaacat aaataaattg tttgttgaat ttattattag    9900
tatgtaagtg taaatataat aaaacttaat atctattcaa attaataaat aaacctcgat    9960
atacagaccg ataaaacaca tgcgtcaatt ttacgcatga ttatctttaa cgtacgtcac   10020
aatatgatta tctttctagg gttaaataat agtttctaat ttttttatta ttcagcctgc   10080
tgtcgtgaat accgtatatc tcaacgctgt ctgtgagatt gtcgtattct agccttttta   10140
gttttttcgct catcgacttg atattgtccg acacattttc gtcgatttgc gttttgatca   10200
aagacttgag cagagacacg ttaatcaact gttcaaattg atccatatta acgatatcaa   10260
cccgatgcgt atatggtgcg taaaatatat tttttaaccc tcttatactt tgcactctgc   10320
gttaatacgc gttcgtgtac agacgtaatc atgttttctt ttttggataa aactcctact   10380
gagtttgacc tcatattaga ccctcacaag ttgcaaaacg tggcattttt taccaatgaa   10440
gaatttaaag ttattttaaa aaatttcatc acagatttaa agaagaacca aaaattaaat   10500
tatttcaaca gttaatcga ccagttaatc aacgtgtaca cagacgcgtc ggcaaaaaac   10560
acgcagcccg acgtgttggc taaaattatt aaatcaactt gtgttatagt cacggatttg   10620
ccgtccaacg tgttcctcaa aaagttgaag accaacaagt ttacggacac tattaattat   10680
ttgattttgc cccacttcat tttgtgggat cacaattttg ttatatttta aacaaagctt   10740
ggcactggcc gtcgttttac aacgtcgtga ctgggaaaac cctggcgtta cccaacttaa   10800
tcgccttgca gcacatcccc ctttcgccag ctggcgtaat agcgaagagg cccgcaccga   10860
tcgcccttcc caacagttgc gcagcctgaa tggcgaatgg cgcctgatgc ggtatttttct   10920
ccttacgcat ctgtgcggta tttcacaccg catatggtgc actctcagta caatctgctc   10980
tgatgccgca tagttaagcc agccccgaca cccgccaaca cccgctgacg cgccctgacg   11040
ggcttgtctg ctcccggcat ccgcttacag acaagctgtg accgtctccg ggagctgcat   11100
gtgtcagagg ttttcaccgt catcaccgaa acgcgcgaga cgaaagggcc tcgtgatacg   11160
```

```
cctattttta taggttaatg tcatgataat aatggtttct tagacgtcag gtggcacttt   11220
tcggggaaat gtgcgcggaa cccctatttg tttattttc taaatacatt caaatatgta   11280
tccgctcatg agacaataac cctgataaat gcttcaataa tattgaaaaa ggaagagtat   11340
gagtattcaa catttccgtg tcgcccttat tcccttttt gcggcatttt gccttcctgt   11400
ttttgctcac ccagaaacgc tggtgaaagt aaaagatgct gaagatcagt tgggtgcacg   11460
agtgggttac atcgaactgg atctcaacag cggtaagatc cttgagagtt tcgccccga   11520 agaacgtttt ccaatgatga gcacttttaa agttctgcta tgtggcgcgg tattatcccg   11580
tattgacgcc gggcaagagc aactcggtcg ccgcatacac tattctcaga atgacttggt   11640
tgagtactca ccagtcacag aaaagcatct tacggatggc atgacagtaa gagaattatg   11700
cagtgctgcc ataaccatga gtgataaac tgcggccaac ttacttctga caacgatcgg   11760
aggaccgaag gagctaaccg ctttttttgca caacatgggg gatcatgtaa ctcgccttga   11820
tcgttgggaa ccggagctga atgaagccat accaaacgac gagcgtgaca ccacgatgcc   11880
tgtagcaatg gcaacaacgt tgcgcaaact attaactggc gaactactta ctctagcttc   11940
ccggcaacaa ttaatagact ggatggaggc ggataaagtt gcaggaccac ttctgcgctc   12000
ggcccttccg gctggctggt ttattgctga taaatctgga gccggtgagc gtgggtctcg   12060
cggtatcatt gcagcactgg ggccagatgg taagccctcc cgtatcgtag ttatctacac   12120 gacgggagt caggcaacta tggatgaacg aaatagacag atcgctgaga taggtgcctc   12180
actgattaag cattggtaac tgtcagacca agtttactca tatatacttt agattgattt   12240
aaaacttcat ttttaattta aaaggatcta ggtgaagatc cttttgata atctcatgac   12300 caaaatccct taacgtgagt tttcgttcca ctgagcgtca gaccccgtag aaaagatcaa   12360
aggatcttct tgagatcctt ttttctgcg cgtaatctgc tgcttgcaaa caaaaaaacc   12420
accgctacca gcggtggttt gtttgccgga tcaagagcta ccaactcttt ttccgaaggt   12480
aactggcttc agcagagcgc agataccaaa tactgtcctt ctagtgtagc cgtagttagg   12540
ccaccacttc aagaactctg tagcaccgcc tacatacctc gctctgctaa tcctgttacc   12600
agtggctgct gccagtggcg ataagtcgtg tcttaccggg ttggactcaa gacgatagtt   12660
accggataag gcgcagcggt cgggctgaac ggggggttcg tgcacacagc ccagcttgga   12720
gcgaacgacc tacaccgaac tgagatacct acagcgtgag cattgagaaa gcgccacgct   12780
tcccgaaggg agaaaggcgg acaggtatcc ggtaagcggc agggtcggaa caggagagcg   12840
cacgagggag cttccagggg gaaacgcctg gtatctttat agtcctgtcg gtttcgccca   12900
cctctgactt gagcgtcgat ttttgtgatg ctcgtcaggg gggcggagcc tatggaaaaa   12960
cgccagcaac gcggcctttt tacgttcct ggccttttgc tggccttttg ctcacatgtt   13020
ctttcctgcg ttatcccctg attctgtgga taaccgtatt accgcctttg agtgagctga   13080
taccgctcgc cgcagccgaa cgaccgagcg cagcgagtca gtgagcgagg aagcggaaga   13140
gcgcccaata cgcaaaccgc ctctccccgc gcgttggccg attcattaat gcagctggca   13200
cgacaggttt cccgactgga aagcgggcag tgagcgcaac gcaattaatg tgagttagct   13260
cactcattag gcaccccagg ctttacactt tatgcttccg gctcgtatgt tgtgtggaat   13320
tgtgagcgga taacaatttc acacaggaaa cagctatgac catgattacg aatttcgacc   13380
tgcaggcatg caagcttgca tgcctgcagg tcgacgctcg cgcgacttgg tttgccattc   13440
tttagcgcgc gtcgcgtcac acagcttggc cacaatgtgg ttttttgtcaa acgaagattc   13500 tatgacgtgt ttaaagttta ggtcgagtaa agcgcaaatc tttttttaacc ctagaaagat   13560
```

```
agtctgcgta aaattgacgc atgcattctt gaaatattgc tctctctttc taaatagcgc   13620
gaatccgtcg ctgtgcattt aggacatctc agtcgccgct tggagctccc gtgaggcgtg   13680
cttgtcaatg cggtaagtgt cactgatttt gaactataac gaccgcgtga gtcaaaatga   13740
cgcatgatta tcttttacgt gacttttaag atttaactca tacgataatt atattgttat   13800
ttcatgttct acttacgtga taacttatta tatatatatt ttcttgttat agatatcgtg   13860
actaatatat aataaaatgg gtagttcttt agacgatgag catatcctct ctgctcttct   13920
gcaaagcgat gacgagcttg ttggtgagga ttctgacagt gaaatatcag atcacgtaag   13980
tgaagatgac gtccagagcg atacagaaga agcgtttata tgatgaggtac atgaagtgca   14040 gccaacgtca agcggtagtg aaatattaga cgaacaaaat gttattgaac aaccaggttc   14100
ttcattggct tctaacagaa tcttgacctt gccacagagg actattagag gtaagaataa   14160
acattgttgg tcaacttcaa agtccacgag gcgtagccga gtctctgcac tgaacattgt   14220
cagatcggcc cggcggagtg gacacgctag accaaatgtg ttctgtgatg acctgcagta   14280
ggaagacgaa taggtggcct atggcattat tgtacggaat gataaacatt gcctgcataa   14340
attcttttat tatatacagc cataatgtca gtagcaaggg agaaaaggtc caaagtcgca   14400
aaaaatttat gagaaacctt tacatgagcc tgacgtcatc gtttatgcgt aagcgtttag   14460
aagctcctac tttgaagaga tatttgcgcg ataatatctc taatattttg ccaaatgaag   14520
tgcctggtac atcagatgac agtactgaag agccagtaat gaaaaaacgt acttactgta   14580
cttactgccc ctctaaaata aggcgaaagg caaatgcatc gtgcaaaaaa tgcaaaaaag   14640
ttatttgtcg agagcataat attgatatgt gccaaagttg tttctgactg actaataagt   14700
ataatttgtt tctattatgt ataagttaag ctaattactt attttataat acaacatgac   14760
tgtttttaaa gtacaaaata agtttatttt tgtaaaagag agaatgttta aaagttttgt   14820
tactttatag aagaaatttt gagtttttgt tttttttaa taaataaata aacataaata   14880
aattgtttgt tgaatttatt attagtatgt aagtgtaaat ataataaaac ttaatatcta   14940
ttcaaattaa taaataaacc tcgatataca gaccgataaa acacatgcgt caattttacg   15000
catgattatc tttaacgtac gtcacaatat gattatcttt ctagggttaa aatgaatgta   15060
agcactttat taacgaaatc tttgggaata tttcgctcat cagcatttta tttgagcagg   15120
agtccgagat gccc                                                    15134
```

<210> SEQ ID NO 57
<211> LENGTH: 1403
<212> TYPE: DNA
<213> ORGANISM: Artificial Sequence
<220> FEATURE:
<223> OTHER INFORMATION: Synthetic construct, partial sequence of a male
      transcript generated in Drosophila melanogaster from LA3077
      transformants that differs to the sequence generated in Medfly
      LA3077 lines.

<400> SEQUENCE: 57

```
ggccagatct gttgttatta aacgtagatt tggtaatttt aaaagcatat ttttttcttt     60
gaaattcata agttatcaat tatcgatgga aatgtattct atggagaacg ttttacccga    120
tgaatgggtg caaaaattat tttaccttca aatctacaat caacacacgc taactttgt    180 gacttgatca actctcacct ggaaaagcaa ccaactacaa tcaacattct atgggataat    240
cgacaagtga gtaaaattat agccggacct cttagtacag tgtatttaaa aggggaataa    300
tattctatca ataggaataa aaataaggtc agcagccatg acttttccat cattttgaat    360
```

```
atacettatt tgtttcggga ttaattgggg gtcggaaatc ctcttgaatt cagaaacggg    420
aaccggagga aggtgccggt ctttcagaaa gctgtgaaaa ataccaacat ttctgctgcc    480
aagagctcaa taagaagttt caaaaattgt cttggatgtt gcagctgtgg ctgctaagta    540
ataagacatc tattagtatc tagatttgtt agaccattta acatagtgtt ttaaacgatg    600
gggttaatag atgagggtta agaagctagt tatattactg ttgctgtaac gccttcaatt    660
gtcggttaca gagcaaacat tattgaatgt taatgtaaag agtttatttg ttttctagta    720
aacatatagc gattggttag taatcactaa tagaaatttt tcataagtat caaaaaagta    780
aacctctttt tcagtctatg taataagtaa accaaggaaa gggaaaatat ctacaatcaa    840
caagccattg ttgcagcaac aaagcaactg aaactacaat caacattcaa taaacttggg    900
taatttggaa tttaattctc tgggacacct gtggattaca acaatcaact cgaaacttat    960
tatacaatgt aaataaaaat tgatatgcat acatgaagat caagtgaaat tccatttaga   1020
atcaattttt ttcgaatatt aagtttcttg ctttaattta tctgaaagta aatagacatt   1080
ccaaattcaa gttaacaaat taataatgaa ttgactagtg atttttaaga gaaaagata    1140 agatttaaaa aaggaaagcc tttcttgata aattttttgaa ccactttatg ccgtttcaat   1200
cataaaaact tttaagaaca catgactggt aaaattaatt taaaacaaat ttaaattttc   1260
aacgtaacat tcaacaaaaa tggtgaaaac tatcacggaa attgttaata ttaatatgtc   1320
ccaaaaatag cctttgtatg tatatgatac taatccatac atctatggta tctataggtg   1380
aaggctcaaa gcctctggct agc                                          1403

<210> SEQ ID NO 58
<211> LENGTH: 972
<212> TYPE: DNA
<213> ORGANISM: Bactrocera zonata

<400> SEQUENCE: 58
cggtaattct aattacttac taaatatagt gatatttaaa aatgctatga gatcttgagg     60
cgaacttaaa tgagacaagg tgttagcttg ctcaaatgac gcaccaatca acttaccaag    120
ataatttgga gcaatatgga atattttctt gtcaaagaac tacaatcaac atgcaactgg    180
tataataaag tgagtataaa gtagaaaggt gcggtatata attttctct aaagtattaa     240 ggtaagtttt taaaaataat ttaataattt ttcagagtgt gcagtattag tgtctaaaag    300
tattgcaatc tttgtgtttt aaaaatttgt gcagaatatc aaaaaatagg acgacctatt    360
gttagtaata ttatgtatat ttacttattt tcaaataaat aaaattattt tctagccttt    420
agaaacagcc ttatactaca atcaacaaac cataaatact ccctgcaaca attacaaagc    480
aacacaaaca acaatcaaca ttccatgaac tcggacaatt tggaaattga tatcttctgg    540
cacatgcgga ttcaacaat caactcaaac ctattagatg atgtaaataa atataaacct     600
tcatattcaa taacttaatt cgtgatagaa atttagagtt aattactgtt taatcgaaat    660
ttgaacgtct cgtttgaatt cactttaacg tttgaaagat gatctttaaa tagtgactgg    720
agacttaaat tttaatcttt ttaattaaat aatctaacaa agttctttct tattctaatc    780
ttaatatata atcttgtttt aaatttgaa ttaaacttat ttcgttgagt aacaattaaa     840
tgatttgaat cgtaaaaaat atcattataa ttattcaaca aaaagctgaa ggctgcgatg    900
aaaaattgtt gatatataaa tcaaatttat ttttataaat cactaatagt gacattaacc    960
gtattcacag gt                                                       972
```

<210> SEQ ID NO 59
<211> LENGTH: 1312
<212> TYPE: DNA
<213> ORGANISM: Ceratitis rosa

<400> SEQUENCE: 59

| | | |
|---|---|---|
| tggtaattt aaaagcatat ttttttttga aattcataag ctatcaatta tcgatggaag | 60 |
| tttattcgat ggagaacgtt ttgcctgatg aatgtgtaca aaattatttt accttcaaat | 120 |
| ctacaatcaa cacacgctaa cttttgcgac ttgatcaact ctcacctgga aaagcaaaca | 180 |
| actacaatca acataacatt ctatgggata atggacaagt gagtaaaatt atagccggaa | 240 |
| cacttacaat aggaataaaa ataaggtcag cagtcatgac attcccacta ttttgaatac | 300 |
| accttattaa taagacatgt tttgtttcgg ggttaattgg gggccggaaa tcctgctgaa | 360 |
| ctccgacaac ggagaccggg gaaggtgccg gtggttcaga aagctgtgaa aaacacctac | 420 |
| ttcctgctgc caagtgttag taaaaagttt caaaacttat attaattatt attttaaacg | 480 |
| catttatttc ctttaaatat gaccaaaatc gacagctgtg gctgcttaat caaaaagaag | 540 |
| ttttgctaag taattagaca tctattaata tctagatttg ttacaagcaa tggagttaat | 600 |
| agataagggt taagaagcta ggtatatctg gatgcaaaga gtttatttgt tttctattaa | 660 |
| acttatagcg attggttagt aatcactaat agaaatttta caatagtatc aaaaaagtca | 720 |
| aacatctttt tcagtctatg tagtaagtaa accaaggaaa aggaaaatat ctccaatcaa | 780 |
| caagccattg ttgcaataac aaaacaactg aaactacaat caacattcaa taaacttggg | 840 |
| aattcggaat ttaatacttc gggacacctg cggattacaa caatcaactc gaaacttatt | 900 |
| atacaatgta aataaaaatt gatacacaca tacatgatga tgaagtaaaa tttcatttaa | 960 |
| aaaagaattg attcgaatat ttagtttctt gctttaattt gtcttaaagt aaatagacat | 1020 |
| tgcaaattta aattaataaa ttaataatga attgacagtt aagatttaaa aaaagtaaag | 1080 |
| ttttacttga taaattttg aaacgctta cttgcagttt tattcataaa tacttttaat | 1140 |
| aacacatgac tggtaaaatt agttaaaaaa tatttaagtt ttcaaagtaa acattcaaca | 1200 |
| aaaatggtaa aaactatcac ggaaattgtt gatattttta acattaatat gccaaaaaaa | 1260 |
| aaagcattta tatgtatatg atactaattc atacatccat ggtatcttta gg | 1312 |

<210> SEQ ID NO 60
<211> LENGTH: 21
<212> TYPE: DNA
<213> ORGANISM: Artificial Sequence
<220> FEATURE:
<223> OTHER INFORMATION: Synthetic construct, spl-agdsx-e3 primer

<400> SEQUENCE: 60
cgagcccaat ggctgttgga g    21

<210> SEQ ID NO 61
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 61
gtcaaggttc agggcccgat cg    22

<210> SEQ ID NO 62
<211> LENGTH: 21

```
<212> TYPE: DNA
<213> ORGANISM: Artificial Sequence
<220> FEATURE:
<223> OTHER INFORMATION: Synthetic construct, primer spl-agdsx-e3

<400> SEQUENCE: 62
cgagcccaat ggctgttgga g                                          21

<210> SEQ ID NO 63
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 63
gtcaaggttc agggcccgat cg                                         22

<210> SEQ ID NO 64
<211> LENGTH: 20
<212> TYPE: DNA
<213> ORGANISM: Artificial Sequence
<220> FEATURE:
<223> OTHER INFORMATION: Synthetic construct, aedesxF1 primer

<400> SEQUENCE: 64
tcaatggctc ctggagaagc                                            20

<210> SEQ ID NO 65
<211> LENGTH: 25
<212> TYPE: DNA
<213> ORGANISM: Artificial Sequence
<220> FEATURE:
<223> OTHER INFORMATION: Synthetic construct, aedesxR5 primer

<400> SEQUENCE: 65
accattcttg cagaagtctt gggac                                      25

<210> SEQ ID NO 66
<211> LENGTH: 19
<212> TYPE: DNA
<213> ORGANISM: Artificial Sequence
<220> FEATURE:
<223> OTHER INFORMATION: Synthetic construct, aedesxR2 primer

<400> SEQUENCE: 66
aacattctcc gcgcacagg                                             19

<210> SEQ ID NO 67
<211> LENGTH: 23
<212> TYPE: DNA
<213> ORGANISM: Artificial SeqUence
<220> FEATURE:
<223> OTHER INFORMATION: Synthetic construct, Agexon1 primer

<400> SEQUENCE: 67
gacgctcgct ctggtacagt tcg                                        23

<210> SEQ ID NO 68
<211> LENGTH: 20
<212> TYPE: DNA
<213> ORGANISM: Artificial Sequence
<220> FEATURE:
<223> OTHER INFORMATION: Synthetic construct, Tra (tTAV) seq+ primer

<400> SEQUENCE: 68
```
cctgccagga ctcgccttcc                                               20

<210> SEQ ID NO 69
<211> LENGTH: 23
<212> TYPE: DNA
<213> ORGANISM: Artificial Sequence
<220> FEATURE:
<223> OTHER INFORMATION: Synthetic construct, Agexon1 primer

<400> SEQUENCE: 69
gacgctcgct ctggtacagt tcg                                           23

<210> SEQ ID NO 70
<211> LENGTH: 26
<212> TYPE: DNA
<213> ORGANISM: Artificial Sequence
<220> FEATURE:
<223> OTHER INFORMATION: Synthetic construct, Exon 3 primer

<400> SEQUENCE: 70
gttgtcgctt tgactggcaa tgtcgc                                        26

<210> SEQ ID NO 71
<211> LENGTH: 632
<212> TYPE: DNA
<213> ORGANISM: Pectinophora gossypiella

<400> SEQUENCE: 71
gaactgccac aaactgctgg aaaagttcca ctactcctgg gaaatgatgc ccctggtgct    60
ggtcattcta aactacgccg gctccgacct cgacgaggct tctagaaaaa ttgatgaagg   120
gaagatgatc atcaacgagt acgcgaggga gcacaatctg aacatcttcg atggccacga   180
gctgaggaac tcgactcgcc agaaaatgct gagcgaaatt aataatataa gtggtgtact   240
atcgtcgtcc atgaagttat tttgcgaatg atactttgtt ttgtatgtgc tgtgtgttgt   300
gtggactttt gctgtgcgtt gctgtttgcg atggaaggac tattgtgtcg tcgccacgct   360
ggactattcg cacattgggt ggtccaccag tggcggatgt acgagcggtc gctgtgctcg   420
ctcctggagc tgcaagcgcg caaagggacg tactcggtgt gctgctcacc ccgctacgtc   480
atcgcgcccg agtacgcgtc acacctgttg cctctgccgc ttaccacgca gagatcatcc   540
ccgccgcccg cgcacttgta gcgatgcgaa cctgcgccgc gggaagcggc gcaagaaccc   600
gccgatgccc cggcgtcgtc gtcgggtgcc ac                                 632

<210> SEQ ID NO 72
<211> LENGTH: 222
<212> TYPE: DNA
<213> ORGANISM: Drosophila melanogaster

<400> SEQUENCE: 72
atgcagatct tgtgaagac tttgaccgga aagaccatca ccctcgaggt agagccatcg     60
gacaccattg agaatgtaaa ggccaagatt caggataagg agggaatccc cccagatcag   120
cagcgtctga tcttcgctgg caagcaactg gaagacggac gcaccctgtc cgattacaac   180
atccagaagg agtccaccct tcacttggtc cttcgtctcc gt                      222

<210> SEQ ID NO 73
<211> LENGTH: 74
<212> TYPE: PRT
<213> ORGANISM: Drosophila melanogaster

<400> SEQUENCE: 73

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70
```

<210> SEQ ID NO 74
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 74
caagcaaagt gaacacgtcg ctaagcgaaa gcta        34

<210> SEQ ID NO 75
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 75
gcgggtggca gctggtgtac tg        22

<210> SEQ ID NO 76
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 76
caagcaaagt gaacacgtcg ctaagcgaaa gcta        34

<210> SEQ ID NO 77
<211> LENGTH: 24
<212> TYPE: DNA
<213> ORGANISM: Artificial Sequence
<220> FEATURE:
<223> OTHER INFORMATION: Synthetic construct, primer

<400> SEQUENCE: 77
gcggaacgac ttggcgttat tgcg        24

<210> SEQ ID NO 78
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 78
ggaagggtcc ttacgctata gagcgcag        28

<210> SEQ ID NO 79
<211> LENGTH: 31

<212> TYPE: DNA
<213> ORGANISM: Artificial Sequence
<220> FEATURE:
<223> OTHER INFORMATION: Synthetic construct, primer

<400> SEQUENCE: 79
ccaggcgaag ttgttattaa gcgtagattt g                                           31

<210> SEQ ID NO 80
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 80
cgtcgctttg aaacagaggc tttgagcctt ctc                                         33

<210> SEQ ID NO 81
<211> LENGTH: 48
<212> TYPE: DNA
<213> ORGANISM: Artificial Sequence
<220> FEATURE:
<223> OTHER INFORMATION: Synthetic construct, primer

<400> SEQUENCE: 81
gctagcaacc accatggcgg taattctaat tacttactaa atatagtg                         48

<210> SEQ ID NO 82
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 82
ccgggatgta gaaggccacc tgtgaatacg gttaatgtca c                                41

<210> SEQ ID NO 83
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 83
cagtcagtca cgagtttgtt accactgcga c                                           31

<210> SEQ ID NO 84
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 84
gcgggtggca gctggtgtac tg                                                     22

<210> SEQ ID NO 85
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 85
cggagcacat ctgatagaac g                                            21

<210> SEQ ID NO 86
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 86
cgcggctgta ggcgctgccg ctc                                          23

<210> SEQ ID NO 87
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 87
ccaggcgaag ttgttattaa gcgtagattt g                                 31

<210> SEQ ID NO 88
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 88
cgtcgctttg aaacagaggc tttgagcctt ctc                               33

<210> SEQ ID NO 89
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 89
gctagcaacc accatggcgg taattttaaa agcatatttt tttttgaaat tc           52

<210> SEQ ID NO 90
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 90
ccgggatgta gaaggccacc taaagatacc atggatgtat g                      41

<210> SEQ ID NO 91
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 91
cagtcagtca cgagtttgtt accactgcga c                                 31

<210> SEQ ID NO 92
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 92
gcgggtggca gctggtgtac tg                                              22

<210> SEQ ID NO 93
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 93
gttgcaagtt gacactggcg g                                               21

<210> SEQ ID NO 94
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 94
aggtgtggga ggttttttaa agc                                             23

<210> SEQ ID NO 95
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 95
cctgtaatac gactcactat agggcgtttt tttttttttt tttttttttt tt             52

<210> SEQ ID NO 96
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 96
gcaaacggca atcagacggg cccaggctca gga                                  33

<210> SEQ ID NO 97
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 97
cctgtaatac gactcactat agggcgtt                                        28

<210> SEQ ID NO 98
<211> LENGTH: 37
<212> TYPE: DNA
<213> ORGANISM: Artificial Sequence
<220> FEATURE:
<223> OTHER INFORMATION: Synthetic construct, primer

<400> SEQUENCE: 98
gggatcgagc tagatcggcc tgagccgcca gtggtga                              37

<210> SEQ ID NO 99
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 99
cctgtaatac gactcactat agggcgtt                                    28

<210> SEQ ID NO 100
<211> LENGTH: 32
<212> TYPE: DNA
<213> ORGANISM: Artificial Sequence
<220> FEATURE:
<223> OTHER INFORMATION: Synthetic construct, primer

<400> SEQUENCE: 100
cgctccatgg gatcggcgag ctgcgactcc gt                               32

<210> SEQ ID NO 101
<211> LENGTH: 27
<212> TYPE: DNA
<213> ORGANISM: Artificial Sequence
<220> FEATURE:
<223> OTHER INFORMATION: Synthetic construct, primer

<400> SEQUENCE: 101
gcaacaacca gcggtgtccc ttgaaac                                     27

<210> SEQ ID NO 102
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 102
cctgtaatac gactcactat agggcgtt                                    28

<210> SEQ ID NO 103
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 103
gctagtggag aactgccaca aactgctg                                    28

<210> SEQ ID NO 104
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 104
caagcaaagt gaacacgtcg ctaagcgaaa gcta                             34

<210> SEQ ID NO 105
<211> LENGTH: 25
<212> TYPE: DNA
<213> ORGANISM: Artificial Sequence
<220> FEATURE:
<223> OTHER INFORMATION: Synthetic construct, primer

<400> SEQUENCE: 105
gccctcgatg gtagacccgt aattg          25

<210> SEQ ID NO 106
<211> LENGTH: 14874
<212> TYPE: DNA
<213> ORGANISM: Artificial Sequence
<220> FEATURE:
<223> OTHER INFORMATION: Synthetic construct, LA1172, including plasmid
      backbone

<400> SEQUENCE: 106
gggctggccg caaccattgt gggaaccgtg cgatcaaaca aacgcgagat accggaagta      60
ctgaaaaaca gtcgctccag gccagtggga acatcgatgt tttgttttga cggacccctt    120
actctcgtct catataaacc gaagccagct aagatggtat acttattatc atcttgtgat    180
gaggatgctt ctatcaacga aagtaccggt aaaccgcaaa tggttatgta ttataatcaa    240
actaaaggcg gagtggacac gctagaccaa atgtgttctg tgatgacctg cagtaggaag    300
acgaataggt ggcctatggc attattgtac ggaatgataa acattgcctg cataaattct    360
tttattatat acagccataa tgtcagtagc aagggagaaa aggtccaaag tcgcaaaaaa    420
tttatgagaa acctttacat gagcctgacg tcatcgttta tgcgtaagcg tttagaagct    480
cctactttga agagatattt gcgcgataat atctctaata ttttgccaaa tgaagtgcct    540
ggtacatcag atgacagtac tgaagagcca gtaatgaaaa aacgtactta ctgtacttac    600
tgcccctcta aataaggcg aaaggcaaat gcatcgtgca aaaatgcaa aaagttatt    660 tgtcgagagc ataatattga tatgtgccaa agttgtttct gactgactaa taagtataat    720
ttgtttctat tatgtataag ttaagctaat tacttatttt ataatacaac atgactgttt    780
ttaaagtaca aataagttt attttttgtaa aagagagaat gtttaaaagt tttgttactt    840
tatagaagaa atttttgagtt tttgtttttt tttaataaat aaataaacat aaataaattg    900
tttgttgaat ttattattag tatgtaagtg taaatataat aaaacttaat atctattcaa    960
attaataaat aaacctcgat atacagaccg ataaaacaca tgcgtcaatt ttacgcatga   1020
ttatctttaa cgtacgtcac aatatgatta tctttctagg gttaaataat agtttctaat   1080 tttttttatta ttcagcctgc tgtcgtgaat accgtatatc tcaacgctgt ctgtgagatt   1140
gtcgtattct agccttttta gttttttcgct catcgacttg atattgtccg acacattttc   1200
gtcgatttgc gttttgatca aagacttgag cagagacacg ttaatcaact gttcaaattg   1260
atccatatta acgatatcaa cccgatgcgt atatggtgcg taaaatatat ttttttaaccc   1320 tcttatactt tgcactctgc gttaatacgc gttcgtgtac agacgtaatc atgttttctt   1380
ttttggataa aactcctact gagtttgacc tcatattaga ccctcacaag ttgcaaaacg   1440 tggcatttt taccaatgaa gaatttaaag ttattttaaa aaatttcatc acagatttaa   1500
agaagaacca aaaattaaat tatttcaaca gtttaatcga ccagtaatc aacgtgtaca   1560 cagacgcgtc ggcaaaaaac acgcagcccg acgtgttggc taaaattatt aaatcaactt   1620
gtgttatagt cacggatttg ccgtccaacg tgttcctcaa aaagttgaag accaacaagt   1680
ttacggacac tattaattat ttgattttgc cccacttcat tttgtgggat cacaattttg   1740
ttatatttta aacaaagctt ggcactggcc gtcgttttac aacgtcgtga ctgggaaaac   1800
cctggcgtta cccaacttaa tcgccttgca gcacatcccc ctttcgccag ctggcgtaat   1860
agcgaagagg cccgcaccga tcgcccttcc caacagttgc gcagcctgaa tggcgaatgg   1920

-continued

```
cgcctgatgc ggtatttct ccttacgcat ctgtgcggta tttcacaccg catatatggt    1980
gcactctcag tacaatctgc tctgatgccg catagttaag ccagcccga cacccgccaa    2040
cacccgctga cgcgccctga cgggcttgtc tgctcccggc atccgcttac agacaagctg   2100
tgaccgtctc cgggagctgc atgtgtcaga ggttttcacc gtcatcaccg aaacgcgcga   2160
gacgaaaggg cctcgtgata cgcctatttt tataggttaa tgtcatgata ataatggttt   2220
cttagacgtc aggtggcact tttcggggaa atgtgcgcgg aacccctatt tgtttatttt   2280
tctaaataca ttcaaatatg tatccgctca tgagacaata accctgataa atgcttcaat   2340
aatattgaaa aaggaagagt atgagtattc aacatttccg tgtcgccctt attccctttt   2400
ttgcggcatt ttgccttcct gtttttgctc acccagaaac gctggtgaaa gtaaaagatg   2460
ctgaagatca gttgggtgca cgagtgggtt acatcgaact ggatctcaac agcggtaaga   2520
tccttgagag ttttcgcccc gaagaacgtt ttccaatgat gagcactttt aaagttctgc   2580
tatgtggcgc ggtattatcc cgtattgacg ccgggcaaga gcaactcggt cgccgcatac   2640
actattctca gaatgacttg gttgagtact caccagtcac agaaaagcat cttacggatg   2700
gcatgacagt aagagaatta tgcagtgctg ccataaccat gagtgataac actgcggcca   2760
acttacttct gacaacgatc ggaggaccga aggagctaac cgcttttttg cacaacatgg   2820
gggatcatgt aactcgcctt gatcgttggg aaccggagct gaatgaagcc ataccaaacg   2880
acgagcgtga caccacgatg cctgtagcaa tggcaacaac gttgcgcaaa ctattaactg   2940
gcgaactact tactctagct tcccggcaac aattaataga ctggatggag gcggataaag   3000
ttgcaggacc acttctgcgc tcggcccttc cggctggctg gtttattgct gataaatctg   3060
gagccggtga gcgtgggtct cgcggtatca ttgcagcact ggggccagat ggtaagccct   3120
cccgtatcgt agttatctac acgacgggga gtcaggcaac tatggatgaa cgaaatagac   3180
agatcgctga gataggtgcc tcactgatta agcattggta actgtcagac caagtttact   3240
catatatact ttagattgat ttaaaacttc attttaatt taaaaggatc taggtgaaga   3300
tccttttga taatctcatg accaaaatcc cttaacgtga gttttcgttc cactgagcgt   3360
cagacccgt agaaaagatc aaaggatctt cttgagatcc ttttttctg cgcgtaatct   3420
gctgcttgca acaaaaaaa ccaccgctac cagcggtggt ttgtttgccg gatcaagagc   3480
taccaactct tttccgaag gtaactggct tcagcagagc gcagatacca atactgtcc    3540
ttctagtgta gccgtagtta ggccaccact tcaagaactc tgtagcaccg cctacatacc   3600
tcgctctgct aatcctgtta ccagtggctg ctgccagtgg cgataagtcg tgtcttaccg   3660
ggttggactc aagacgatag ttaccggata aggcgcagcg gtcgggctga acggggggtt   3720
cgtgcacaca gcccagcttg gagcgaacga cctacaccga actgagatac ctacagcgtg   3780
agcattgaga aagcgccacg cttcccgaag ggagaaaggc ggacaggtat ccggtaagcg   3840
gcagggtcgg aacaggagag cgcacgaggg agcttccagg gggaaacgcc tggtatcttt   3900
atagtcctgt cgggtttcgc cacctctgac ttgagcgtcg attttgtga tgctcgtcag   3960
ggggcggag cctatggaaa aacgccagca acgcggcctt tttacggttc ctggccttt    4020
gctggccttt tgctcacatg ttctttcctg cgttatcccc tgattctgtg ataaccgta    4080
ttaccgcctt tgagtgagct gataccgctc gccgcagccg aacgaccgag cgcagcgagt   4140
cagtgagcga ggaagcggaa gagcgcccaa tacgcaaacc gcctctcccc gcgcgttggc   4200
cgattcatta atgcagctgg cacgacaggt ttcccgactg gaaagcgggc agtgagcgca   4260
```

```
acgcaattaa tgtgagttag ctcactcatt aggcacccca ggctttacac tttatgcttc    4320
cggctcgtat gttgtgtgga attgtgagcg gataacaatt tcacacagga aacagctatg    4380
accatgatta cgaatttcga cctgcaggca tgcaagcttg catgcctgca ggtcgacgct    4440
cgcgcgactt ggtttgccat tctttagcgc gcgtcgcgtc acacagcttg ccacaatgt     4500 ggttttgtc aaacgaagat tctatgacgt gtttaaagtt taggtcgagt aaagcgcaaa    4560 tctttttaa ccctagaaag atagtctgcg taaaattgac gcatgcattc ttgaaatatt     4620
gctctctctt tctaaatagc gcgaatccgt cgctgtgcat ttaggacatc tcagtcgccg    4680
cttggagctc ccgtgaggcg tgcttgtcaa tgcggtaagt gtcactgatt ttgaactata    4740
acgaccgcgt gagtcaaaat gacgcatgat tatcttttac gtgactttta agatttaact    4800
catacgataa ttatattgtt atttcatgtt ctacttacgt gataacttat tatatatata    4860
ttttcttgtt atagatatcg tgactaatat ataataaaat gggtagttct ttagacgatg    4920
agcatatcct ctctgctctt ctgcaaagcg atgacgagct tgttggtgag gattctgaca    4980
gtgaaatatc agatcacgta agtgaagatg acgtccagag cgatacagaa gaagcgttta    5040
tagatgaggt acatgaagtg cagccaacgt caagcggtag tgaaatatta gacgaacaaa    5100
atgttattga caaccaggt tcttcattgg cttctaacaa aatcttgacc ttgccacaga     5160
ggactattag aggtaagaat aaacattgtt ggtcaacttc aaagtccacg aggcgtagcc    5220
gagtctctgc actgaacatt gtcagatcgg ccaggccggc cagatttaaa tgagcggccg    5280
catggtacca tactcggtgg cctccccacc accaactttt ttgcactgca aaaaaacacg    5340
cttttgcacg cgggcccata catagtacaa actctacgtt tcgtagacta ttttacataa    5400
atagtctaca ccgttgtata cgctccaaat acactaccac acattgaacc tttttgcagt    5460
gcaaaaaagt acgtgtcggc agtcacgtag gccggcctta tcgggtcgcg tcctgtcacg    5520
tacgaatcac attatcggac cggacgagtg ttgtcttatc gtgacaggac gccagcttcc    5580
tgtgttgcta accgcagccg gacgcaactc cttatcggaa caggacgcgc ctccatatca    5640
gccgcgcgtt atctcatgcg cgtgaccgga cacgaggcgc ccgtcccgct tatcgcgcct    5700
ataaatacag cccgcaacga tctggtaaac acagttgaac agcatctgtt acagcgacac    5760
aacatgagcc ggtccaacaa cgccaacgcg cccacgccat ccaaccgccg ccgcaacctg    5820
tctctggtgg atcccacccc acccaagaag aagcgcaaac cggtcgccac catggcctcc    5880
tccgagaacg tcatcaccga gttcatgcgc ttcaaggtgc gcatggaggg caccgtgaac    5940
ggccacgagt cgagatcga gggcgagggc gagggccgcc cctacgaggg ccacaacacc    6000
gtgaagctga aggtgaccaa gggcggcccc ctgcccttcg cctgggacat cctgtccccc    6060
cagttccagt acggctccaa ggtgtacgtg aagcaccccg ccgacatccc cgactacaag    6120
aagctgtcct tccccgaggg cttcaagtgg gagcgcgtga tgaacttcga ggacggcggc    6180
gtggcgaccg tgacccagga ctcctccctg caggacggct gcttcatcta caaggtgaag    6240
ttcatcggcg tgaacttccc ctccgacggc cccgtgatgc agaagaagac catgggctgg    6300
gaggcctcca ccgagcgcct gtaccccgc gacggcgtgc tgaagggcga gacccacaag    6360
gccctgaagc tgaaggacgg cggccactac ctggtggagt tcaagtccat ctacatggcc    6420
aagaagcccg tgcagctgcc cggctactac tacgtggacg ccaagctgga catcacctcc    6480
cacaacgagg actacaccat cgtggagcag tacgagcgca ccgagggccg ccaccacctg    6540
ttcctgagat ctcgacccaa gaaaagcgg aaggtggagg acccgtaaga tccaccggat    6600
ctagataact gatcataatc agccatacca catttgtaga ggttttactt gctttaaaaa    6660
```

```
acctcccaca cctcccctg aacctgaaac ataaaatgaa tgcaattgtt gttgttaact    6720
tgtttattgc agcttataat ggttacaaat aaagcaatag catcacaaat ttcacaaata    6780
aagcattttt ttcactgcat tctagttgtg gtttgtccaa actcatcaat gtatcttaac    6840
gcgagttaat taatccattg ctgggcgagc tgcgccaatc gatgccaacg ccaccctgca    6900
tggcgagcgg caggccggcg gctaccatgg gcgtcaccat gccctgaccg ccccggagg    6960
gcagtgaaaa atgtgtgggg ggtggtgggg gctgcgcagg aactgattgt gattatggtt    7020
gtgcccatgg ccatgttgtc caagtccatg gacgtgggca tgcttgttgt agcccaaatc    7080
ggcgtttccg tttccaccag gaaacatctc tgcttgtagt tcgaatatgc tctttaaatc    7140
ccagctgtat tcctcagtta tcgagttttt cttcacgagt gaaacgaatt ttcgtcgcct    7200
tctacgccat tttcttgctc agccgttttt gtcattcgca gcgaagcggt aacagcgggt    7260
cgctcatatg acggtatttt ttaatacact tcagctatac tgttatttca aaaacatatt    7320
tcttttgtta cttttatgc agttcatttg ccaccaaaaa gtagtctttt ggattgattt    7380
atttcaaaaa atggtgtaat tcaagaaatt cagagggcca agtaatatac ttaatgaccg    7440
ttatttaaaa cacactcaag gagatttatt taaacggcta caatggtttt ccaaataact    7500
tatttactgt tgacttctat aaaacatagg tgtatatatt attatttcct tattgagttt    7560
gagataattt taatttccac aatatttttt cttgtgatta acagagaaag tcaaactaca    7620
taacatttat cgggtaaaag tctctatgaa ggtagcggtt aacagtgaag tcgcaaaagt    7680
ggtggccgta cgccaatcga gcgtagtacc cctaacctgc aatatttttta gttggttttt    7740
tccgcaatag ccccagtttt ctcaaagagt gcaacaagtg attctgttta tgttttcaac    7800
aacttctctc tgcggaactt aacgtgagcg gacgtatgcg gacgcgccat ggtttaaact    7860
cgctagcact gggaagttga cgttgatata gagccgaatt gaacttcacc gctgcttggt    7920
aattactcta caagttcatt taggagaacc ggattcgaaa gatgattttc cagcgtttag    7980
ctttcagatg gccgcataca ttttgcacca ccaaaccgaa actcactagc gtatccaatc    8040
gttcgttttt tggtgccggt gtgttacgaa cttagctat caagctaaag caatttgctc    8100
tggtcttccg tgctaaaaag aaaaaaaaac tgttttttttt ttggttttga tatttgcgct    8160
attttttactt gggccttaat tgaacaaact tttgaaagtt tccacagcga aatcgttttc    8220
gacgatgcca ttttttggtaa catttgcatt ttcttgctca aattgcttgc aaaacccgtg    8280
aaagacatta atattcgata gtgtcatcca aaatcacgaa atgattgtt gcaaaacgtt    8340
gaacaattta cacatgtaaa aaacaaccat cgattaatgt ttattcaaac ttttttacaag    8400
aagggttatt ctgatcaatg tcaccccgct gatgaatgtt accccggatt acacttctcg    8460
aaaagtggtt caaaatgcta cttgagaatt tttatctgtc aaaggaagca aattcgagtc    8520
gaattaaatg gtatagtcct gaattaggtt tccatttact tacaggtatt ccactaaata    8580
gctggaagat ttatttttaca caataatgat aattcgtacc ccaaagagtg tagccctact    8640
ttttttctctc ttttttttttt gtaaatttttc atcgctgcgt gccagcttac cgacatgtcg    8700
cgacagcata aagagcctgt caagagatga agaaaaatga caaggagtca gtggtcaggt    8760
ctctgtatca atatttgacg tcctgacttt ccaatatacc ttttccttaaa gagtagagat    8820
catgcgatac gtgaataaat atcgtttgga cttcgaaata gaacataatt taaggtagct    8880
gatcagtagt tgaacatctt cagacttctg ggacaagaag tgttttttttg ttttgtagaaa    8940
aggttttttgt taaattatat ttgtaagata attcaatgaa tatatctctg attcagtaat    9000
```

```
caatccgtac cacgcaccgt ttaagaaaca ccctgtaggt ttgcatcacg tctcagacaa    9060
aagtgtatcg atgtgcgaac actgcatacc ggcgctttgc aaataatgcc aaatttagat    9120
atgcattaca ttgtcacttc gcaaaacaca cactcccaaa tgcgtcggaa acctcacccg    9180
aacgcacgat cgtaacgcga tcgatcgccg attgattgat cggaattaac tatctcaatc    9240
gatccttcta tggactgatg catgggccgg cacttccgag tataaaaccc cggtaaaccc    9300
aaggaatcac tcacaatcgg attttgacgc tcgctctggt acagttcgat acggtctagt    9360
gaaaccgagg ataacgacga aggttttttcc ccattgatcc aggtcggtgt ttatgattgg    9420
tggaaaaaga ctcgagaaaa gttccatcga agccgttgga aatgtgccgt cttcctgtga    9480
cgtcttgtgg atccagttcc ttgttcacgt ctggtgatcg tgtaaaatgt gctgtcttgt    9540
ggcgtcatat gtgttccaga tccagtgatt acgatccgat gtgatgttga tcccttgtga    9600
acgtcttatc ctgttccgtg tgcaccatgc ataatgtcgt attacgtaag ttctgaagtg    9660
aaacagaaga gtgaattgaa agttttttta ttcaacatca acctaaatat ggactttact    9720
ttccaagaaa attatgcctg atcaactgtg gatagttaca aaaaaaaag gtttattaat     9780 taaatttat gattacataa tgtgttgaaa agaacaactg aaattttaga agaagatctt     9840
ttcgtgcatc aggctttgcc aattaattga tgataaatta tcatagcaaa ttaacgtaga    9900
gactaaaagg tatatcgtca aatagggctt cttttgacac tattttggca ttcttgctct    9960
ttgagaactt gcaaccctaa aatgggatct tcatcagcct agtggttaga ttcagcagct   10020
acaaagcaaa accatgctga agggttcgat tcccggtcgt ttcaggatct tttcgtaatt   10080
gaaatatcct tgactaccct aagtatcatt gtgcttgcca tttacgaata tacatattac   10140
gatatacgaa tgagaaaatg acaactttgg aaaataaagc tctcaatgtt tcaataagaa   10200
ataaatacta catcagtatt gaaggctaat aacaattaca gattgaaacc tttaaacatc   10260
atttctgcaa caggctggat aaagtacagt tggaggatta aattatgcga ttttgcaatt   10320
ttttccgatt aaattcatat ttattcctgg tttggttttt acaaaaaata ttttacatg    10380 acgtttgacc ccgattccct caactttgat tgttatattt tttttttggac aggttgagtt   10440 tgtgggtttt ttcctagtgt tgctttgctt tatgggctct ggttatttaa aattaaaatt   10500
tgacaatctt actacacact ccgaaaaaat catgcgattt tacgtctttt ggatgcacat   10560
aaaagaagcg agccaaatga ggtgaatttg tgtcacattt taaatacgat ggtgtctgat   10620
tcgggaaatg tcaatgatag tgtcattcaa tcataatgtg aattacgtcc gcagtaattt   10680
tcattatttt taagagtgta ctactattta cactacaaaa attttgatac ccagggggg    10740 aacgaggtcc cggatgtcca gctggccaga ttgttggcaa cgagccctgt acctattgat   10800
cgagtcacca aagcactcct caagtgtttt aatctcgacc agacggtgga cctcggttgt   10860
tctcattctc ggagggcgat tcgcaatca ttagtaccaa ccacatgtcg aagtcgggag    10920
atgttataaa attataacca attattcaaa aaatgacatc attcaatttg aacaaacgtt   10980
cgatagaaat tatatatgat ttcacatgat attaaactac gaagaaaatt ttacataagg   11040
aagtggtata aaacgtaata tgcttaataa aaactttaac ccttttggga ggataatatt   11100
cagaagttct gattcagaac catctctcat gttatgttcg ttttttgttg cttgtccttt    11160
atatgccaca tgaacaataa caccaatatc tatcccattt ccaggaccta acggaccttg   11220
aagcggcgcc aaaacgtgtg acgatgatgc tggtaccctg gcggtaagtt gatcaaagga   11280
aacgcaaagt tttcaagaaa aaacaaaact aatttgattt ataacacctt tagaaaccac   11340
catgggcagc cgcctggata agtccaaagt catcaactcc gcgttggagc tgttgaacga   11400
```

```
agttggcatt gagggactga cgacccgcaa gttggcgcag aagctgggcg tggagcagcc    11460
caccctctac tggcacgtga agaataagcg ggcgctgctg gatgccctgg ccatcgagat    11520
gctcgaccgc caccacacgc attttttgccc gttggaaggc gagtcctggc aggacttcct    11580
ccgcaataac gccaagtcgt tccgctgcgc tctgctgtcc caccgagacg gtgccaaagt    11640
ccatctcggc acgcgcccga ccgaaaagca atacgagaca ctggagaacc agctcgcgtt    11700
cctgtgccag caaggcttca gcctggaaaa tgctctctac gctctgagcg ccgtcggtca    11760 cttttaccctg ggctgcgtgc tggaggacca agagcatcaa gtcgcaaaag aggagcgcga    11820
gaccccaaca accgattcga tgcccccact gctgcgtcag gcaatcgagc tgttcgatca    11880
tcaaggagcc gagccggcat tcctgttcgg cttggagctg attatctgcg gattggaaaa    11940
gcaactgaaa tgcgagtcgg gctcgggccc cgcgtacagc cgcgcgcgta cgaaaaacaa    12000
ttacgggtct accatcgagg gcctgctcga tctcccggac gacgacgccc ccgaagaggc    12060
ggggctggcg gctccgcgcc tgtccttttct ccccgcggga cacacgcgca gactgtcgac    12120
ggcccccccg accgatgtca gcctggggga cgagctccac ttagacggcg aggacgtggc    12180
gatggcgcat gccgacgcgc tagacgattt cgatctggac atgttggggg acggggattc    12240
cccgggtccg ggatttaccc cccacgactc cgcccctac ggcgctctgg atatggccga    12300
cttcgagttt gagcagatgt ttaccgatgc ccttggaatt gacgagtacg gtgggtagtt    12360
ctagaattgt ccaccgcaag tgcttctaag ccgatcccga ttgtactgat taccataagc    12420
gacattgcca gtgaaagcga caacagcagc atcaaagtac atttgtcata ctgattcggc    12480
tactaccacc atccggaatc agcttgcatc gaacatcaaa tcacgttatt caatgtatct    12540
gtcatccagc tcagacaagt cggagctttt ccagtcgcga aaatctgcga ctccagcgga    12600
aagcaccgaa ccacagagag gactcgtatg aaagccaggg aagaaaccat cattcacctt    12660
gcagcaaata ggaaaaaaaa cggacatctt caacaaacaa aagcccatgc gctaacttgg    12720
tttaggagtt tagtgtgaca ccatgacccc gctgatgatc tttacttagc acaccataac    12780 ccacctttatg cgttcgttca tccaaaatct acaggatatc actgcagccg cgagaagaac    12840
tcgtgaacca tcctgttttc tttttttatta tattcttact tttaacttca aattattttc    12900
agtaataaaa cgtctcaaaa taataagttc ataatgagtt taattttacg gaataagaac    12960
aaccatttaa gttattaaat ccttagattt aatggaatta gattgattat atggaaccca    13020
gacttggtaa aaaataaact ccacgttaaa tttctttctg agacttaaaa ttctttcggg    13080
aaagctggga gcaattctcg caccggtgct agggccgcat agtcgacatt tcgagtttac    13140
cactccctat cagtgataga gaaaagtgaa agtcgagttt accactccct atcagtgata    13200
gagaaaagtg aaagtcgagt ttaccactcc ctatcagtga tagagaaaag tgaaagtcga    13260
gtttaccact ccctatcagt gatagagaaa agtgaaagtc gagtttacca ctccctatca    13320
gtgatagaga aaagtgaaag tcgagtttac cactccctat cagtgataga gaaaagtgaa    13380
agtcgagttt accactccct atcagtgata gagaaaagtg aaagtcgagc tcggtacccg    13440
ggtcgaggta ggcgtgtacg gtgggaggcc tatataagca gagctcgttt agtgaaccgt    13500
cagatcgcct ggagacgcca tccacgctgt tttgacctcc atagaagaca ccgggaccga    13560
tccagcctcc gcggccccga attgagctc ggtacccggg atccccgct cgaccaccat    13620 gggcgctctc ctgggcctgc ccgaaagcca aacggagctt gataatctta cagaatacaa    13680
cacggcccac aatcggcgca tctcaatgct gggcatcgat gatgatacca atatgcgaaa    13740
```

```
                                                    -continued
gcaaaacgcc ttgaaacagg gacggcgcac tcgaaatgtc acatttaacg atgaggagat  13800
tgtcatcaat cctgaggatg tggatcctaa tgtgggacgc ttcaggaact tggtacaaac  13860
cactgtggtg cccgccaaga gggctcgctg cgacgtcaac cattagtgat aacgcgtcta  13920
gctagagctg agaacttcag ggtgagtttg gggacccttg attgttcttt ctttttcgct  13980
attgtaaaat tcatgttata tggagggggc aaagttttca gggtgttgtt tagaatggga  14040
agatgtccct tgtatcacca tggaccctca tgataatttt gtttctttca ctttctactc  14100
tgttgacaac cattgtctcc tcttattttc ttttcatttt ctgtaacttt ttcgttaaac  14160
tttagcttgc atttgtaacg aattttaaa ttcacttttg tttatttgtc agattgtaag  14220
tactttctct aatcactttt ttttcaaggc aatcagggta tattatattg tacttcagca  14280
cagttttaga gaacaattgt tataattaaa tgataaggta gaatatttct gcatataaat  14340
tctggctggc gtggaaatat tcttattggt agaaacaact acaccctggt catcatcctg  14400
cctttctctt tatggttaca atgatataca ctgtttgaga tgaggataaa atactctgag  14460
tccaaaccgg gcccctctgc taaccatgtt catgccttct tctctttcct acagctcctg  14520
ggcaacgtgc tggttgttgt gctgtctcat cattttggca aagaattcac tcctcaggtg  14580
caggctgcct atcagaaggt ggtggctggt gtggccaatg ccctggctca caataccac   14640 tgagatcttt ttccctctgc caaaaattat ggggacatca tgaagcccct tgagcatctg  14700
acttctggct aataaaggaa atttattttc attgcaatag tgtgttggaa ttttttgtgt  14760
ctctcactcg gaaggacata tgggagggca aatcatttaa aacatcagaa tgagtatttg  14820
gtttagagtt tggcaacata tgcccatagc ggccctagcg gcgcgccata gccc         14874
```